US011845724B2

(12) United States Patent
Romero et al.

(10) Patent No.: US 11,845,724 B2
(45) Date of Patent: Dec. 19, 2023

(54) USP30 INHIBITORS AND USES THEREOF

(71) Applicant: Vincere Biosciences, Inc., Cambridge, MA (US)

(72) Inventors: Donna L. Romero, Chesterfield, MO (US); Michael Garrett Johnson, San Francisco, CA (US); Andrew David Lee, Jacksonville, FL (US); Bahareh Behrouz, Jacksonville, FL (US); Edward Lawrence Fritzen, Jr., Niantic, CT (US)

(73) Assignee: Vincere Biosciences, Inc., Cambridge, MA (US)

( * ) Notice: Subject to any disclaimer, the term of this patent is extended or adjusted under 35 U.S.C. 154(b) by 0 days.

(21) Appl. No.: 17/019,097

(22) Filed: Sep. 11, 2020

(65) Prior Publication Data

US 2022/0315531 A1 Oct. 6, 2022

Related U.S. Application Data

(60) Provisional application No. 63/022,165, filed on May 8, 2020, provisional application No. 62/898,820, filed on Sep. 11, 2019.

(51) Int. Cl.
| | |
|---|---|
| *C07D 205/04* | (2006.01) |
| *C07D 209/20* | (2006.01) |
| *C07C 317/36* | (2006.01) |
| *C07D 309/14* | (2006.01) |
| *C07D 309/12* | (2006.01) |
| *C07D 217/26* | (2006.01) |
| *C07D 471/04* | (2006.01) |
| *C07D 213/72* | (2006.01) |
| *C07D 333/36* | (2006.01) |
| *C07D 305/08* | (2006.01) |
| *C07D 405/12* | (2006.01) |
| *C07D 211/58* | (2006.01) |
| *C07D 307/22* | (2006.01) |

(52) U.S. Cl.
CPC .......... *C07D 205/04* (2013.01); *C07C 317/36* (2013.01); *C07D 209/20* (2013.01); *C07D 211/58* (2013.01); *C07D 213/72* (2013.01); *C07D 217/26* (2013.01); *C07D 305/08* (2013.01); *C07D 307/22* (2013.01); *C07D 309/12* (2013.01); *C07D 309/14* (2013.01); *C07D 333/36* (2013.01); *C07D 405/12* (2013.01); *C07D 471/04* (2013.01)

(58) Field of Classification Search
CPC .. C07D 205/04; C07D 209/20; C07D 211/58; C07D 213/72; C07D 217/26; C07D 305/08; C07D 307/22; C07D 309/12; C07D 309/14; C07D 333/36; C07D 405/12; C07D 471/04; C07C 317/36
USPC .................................................. 514/210.01
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 4,895,842 A * | 1/1990 | Okamoto | ............. C07D 211/16 |
| | | | 514/20.1 |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 6,552,065 B2 | 4/2003 | Remiszewski et al. | |
| 7,071,189 B2 | 7/2006 | Kawashima et al. | |
| 7,390,799 B2 | 6/2008 | Bruncko et al. | |
| 8,138,347 B2 | 3/2012 | Knight et al. | |
| 2011/0178165 A1 | 7/2011 | Estep et al. | |
| 2015/0344888 A1 | 12/2015 | Zhang et al. | |
| 2015/0368217 A1 | 12/2015 | Li et al. | |
| 2016/0090351 A1 | 3/2016 | Hedstrom et al. | |
| 2016/0347708 A1 | 12/2016 | Ebright et al. | |

FOREIGN PATENT DOCUMENTS

| | | | | |
|---|---|---|---|---|
| EP | 0166355 A2 * | 2/1986 | ........... | C07D 209/20 |
| WO | WO-2001042246 A2 | 6/2001 | | |
| WO | WO-2002088112 A1 | 11/2002 | | |
| WO | WO-2003063794 A2 | 8/2003 | | |
| WO | WO-2004019973 A1 | 3/2004 | | |
| WO | WO-2004089925 A1 | 10/2004 | | |
| WO | WO-2004106328 A1 | 12/2004 | | |
| WO | WO-2005007623 A2 | 1/2005 | | |
| WO | WO-2005113554 A2 | 12/2005 | | |
| WO | WO-2006078846 A1 | 7/2006 | | |
| WO | WO-2006122806 A2 | 11/2006 | | |
| WO | WO-2007016176 A2 | 2/2007 | | |
| WO | WO-2007044729 A2 | 4/2007 | | |
| WO | WO-2007053452 A1 | 5/2007 | | |

(Continued)

OTHER PUBLICATIONS

Debenneville et al., New Substrates for a Pancreatic Exocrine Function Test, 1972, Journal of Medicinal Chemistry, vol. 15, No. 11, 1098-1100 (Year: 1972).*
Berge et al., "Pharmaceutical salts," J Pharm Sci. 1977; 66(1): 1-19.
Bian et al., "Overexpression of parkin ameliorates dopaminergic neurodegeneration induced by 1-methyl-4-phenyl-1,2,3,6-tetrahydropyridine in mice," PLOS One. 2012; 7(6):e39953.
Billingsley et al., "Mitochondria function associated genes contribute to Parkinson's Disease risk and later age at onset," NPJ Parkinsons Dis. 2019; 5:8.

(Continued)

*Primary Examiner* — Kristin A Vajda
(74) *Attorney, Agent, or Firm* — Dechert LLP; Chad E. Davis; Gregory H. Zayia

(57) ABSTRACT

The present invention provides compounds, compositions thereof, and methods of using the same for the inhibition of USP30, and the treatment of USP30-mediated disorders.

21 Claims, No Drawings

(56) References Cited

FOREIGN PATENT DOCUMENTS

| WO | WO-2007070514 A1 | 6/2007 |
|---|---|---|
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2009114512 A1 | 9/2009 |
| WO | WO-2011090760 A1 | 7/2011 |
| WO | WO-2014141035 A2 | 9/2014 |
| WO | 2015120320 A1 | 8/2015 |
| WO | WO-2018213150 A1 | 11/2018 |
| WO | WO-2019152437 A1 | 8/2019 |

OTHER PUBLICATIONS

Bingol et al., "The mitochondrial deubiquitinase USP30 opposes parkin-mediated mitophagy," Nature. 2014; 510(7505):370-375.
Brown et al., "Mitochondria: Potential Targets for Protection in Age-Related Macular Degeneration," Adv Exp Med Biol. 2018; 1074:11-17.
Burchell et al., "The Parkinson's disease-linked proteins Fbxo7 and Parkin interact to mediate mitophagy," Nat Neurosci. 2013; 16(9):1257-1265.
Canet-Avilés et al., "The Parkinson's disease protein DJ-1 is neuroprotective due to cysteine- sulfinic acid-driven mitochondrial localization," Proc Natl Acad Sci U S A. 2004; 101(24):9103-9108.
Cornelissen et al., "Deficiency of parkin and PINK1 impairs age-dependent mitophagy in Drosophil," Elife. 2018; 7:e35878.
Coyne et al., "The business of deubiquitination—location, location, location," F1000Res. 2016; 5:F1000 Faculty Rev-163.
Fang et al., "Mitophagy inhibits amyloid-beta and tau pathology and reverses cognitive deficits in models of Alzheimer's disease," Nat Neurosci. 2019; 22(3):401-412.
Funayama et al., "CHCHD2 mutations in autosomal dominant late-onset Parkinson's disease: a genome-wide linkage and sequencing study," Lancet Neurol. 2015; 14(3):274-282.
Gersch et al., "Mechanism and regulation of the Lys6-selective deubiquitinase USP30," Nat Struct Mol Biol. 2017; 24(11):920-930.
Gooch et al., "The burden of neurological disease in the United States: A summary report and call to action," Ann Neurol. 2017; 81(4):479-484.
Hou et al., "Parkin represses 6-hydroxydopamine-induced apoptosis via stabilizing scaffold protein p62 in PC12 cells," Acta Pharmacol Sin. 2015; 36(11):1300-1307.
Ito et al., "PARK2-mediated mitophagy is involved in regulation of HBEC senescence in COPD pathogenesis," Autophagy. 2015; 11(3):547-559.
Kapogiannis et al., "Disrupted energy metabolism and neuronal circuit dysfunction in cognitive impairment and Alzheimer's disease," Lancet Neurol. 2011; 10(2):187-198.
Katsouri et al., "PPARgamma-coactivator-1 alpha gene transfer reduces neuronal loss and amyloid-beta generation by reducing beta-secretase in an Alzheimer's disease model," Proc Natl Acad Sci U S A. 2016; 113(43):12292-12297.
Kemp, "Recent Advances in the Discovery of Deubiquitinating Enzyme Inhibitors," Prog Med Chem. 2016; 55:149-192.
Kobayashi et al., "Involvement of PARK2-Mediated Mitophagy in Idiopathic Pulmonary Fibrosis Pathogenesis," J Immunol. 2016; 197(2):504-516.
Langston et al., "Chronic Parkinsonism in humans due to a product of meperidine-analog synthesis," Science. 1983; 219(4587):979-980.
Lesage et al., "Loss of VPS13C Function in Autosomal-Recessive Parkinsonism Causes Mitochondrial Dysfunction and Increases PINK1/Parkin-Dependent Mitophagy," Am J Hum Genet. 2016; 98(3):500-513.
Liang et al., "USP30 deubiquitylates mitochondrial Parkin substrates and restricts apoptotic cell death," EMBO Rep. 2015; 16(5):618-627.
Lin et al., "PINK1-parkin pathway of mitophagy protects against contrast-induced acute kidney injury via decreasing mitochondrial ROS and NLRP3 inflammasome activation," Redox Biol. 2019; 26:101254.
Lo Bianco et al., "Lentiviral vector delivery of parkin prevents dopaminergic degeneration in an alpha-synuclein rat model of Parkinson's disease," Proc Natl Acad Sci U S A. 2004; 101(50):17510-17515.
Marcassa et al., "Dual role of USP30 in controlling basal pexophagy and mitophagy," EMBO Rep. 2018;19(7):e45595.
Marras et al., "Prevalence of Parkinson's disease across North America," NPJ Parkinsons Dis, 2018, 4:21.
Mevissen et al., "Mechanisms of Deubiquitinase Specificity and Regulation," Annu Rev Biochem. 2017; 86:159-192.
Nazarko, "Pexophagy is responsible for 65% of cases of peroxisome biogenesis disorders," Autophagy. 2017; 13(5):991-994.
Niendorf et al., "Essential role of ubiquitin-specific protease 8 for receptor tyrosine kinase stability and endocytic trafficking in vivo," Mol Cell Biol. 2007; 27(13):5029-5039.
Nijman et al., "A genomic and functional inventory of deubiquitinating enzymes," Cell. 2005; 123(5):773-786.
Obeso et al., "Past, present, and future of Parkinson's disease: A special essay on the 200th Anniversary of the Shaking Palsy," Mov Disord. 2017; 32(9):1264-1310.
Paisán-Ruiz et al., "Early-onset L-dopa-responsive parkinsonism with pyramidal signs due to ATP13A2, PLA2G6, FBXO7 and spatacsin mutations," Mov Disord. 2010; 25(12):1791-1800.
Park et al., "Mitochondrial Dysfunction in Parkinson's Disease: New Mechanistic Insights and Therapeutic Perspectives," Curr Neurol Neurosci Rep. 2018; 18(5):21.
Paterna et al., "DJ-1 and Parkin modulate dopamine-dependent behavior and inhibit MPTP—induced nigral dopamine neuron loss in mice," Mol Ther. 2007; 15(4):698-704; with Erratum: Mol Ther. 2007; 15(6):1221.
Pubchem, N-(1-Anilino-1-oxo-3-phenylpropan-2-yl)benzamide, CID 349499, Mar. 26, 2005, modified Oct. 20, 2020 (11 pages).
Ramirez et al., "Defining causative factors contributing in the activation of hedgehog signaling in diffuse large B-cell lymphoma," Leuk. Res. 2012;36(10):1267-73.
Riccio et al., "Deubiquitinating enzyme USP30 maintains basal peroxisome abundance by regulating pexophagy," J Cell Biol. 2019; 218(3):798-807.
Ridge et al., "Mitochondria and Alzheimer's Disease: the Role of Mitochondrial Genetic Variation," Curr Genet Med Rep. 2018; 6(1):1-10.
Ritorto et al., "Screening of DUB activity and specificity by MALDI-TOF mass spectrometry," Nat Commun. 2014; 5:4763.
Rostovtsev et al., "A stepwise huisgen cycloaddition process: copper(I)-catalyzed regioselective "ligation" of azides and terminal alkynes," Angew Chem Int Ed Engl. 2002; 41(14):2596-99.
Ryter et al., "Mitochondrial Dysfunction as a Pathogenic Mediator of Chronic Obstructive Pulmonary Disease and Idiopathic Pulmonary Fibrosis," Ann Am Thorac Soc. 2018; 15(Suppl 4):S266-S272.
Ryu et al., "Urolithin A induces mitophagy and prolongs lifespan in C. elegans and increases muscle function in rodents," Nat Med. 2016; 22(8):879-888.
Schapira et al., "Mitochondrial complex I deficiency in Parkinson's disease," J Neurochem. 1990; 54(3):823-827.
Smith et al., "Mitochondrial dysfunction and increased glycolysis in prodromal and early Parkinson's blood cells," Mov Disord. 2018; 33(10):1580-1590.
Sun et al., "Carbohydrate and protein immobilization onto solid surfaces by sequential Diels-Alder and azide-alkyne cycloadditions," Bioconjug Chem. 2006; 17(1):52-57.
Sun et al., "The Mitochondrial Basis of Aging," Mol Cell. 2016; 61(5):654-666.
Tang et al., "PINK1-PRKN/PARK2 pathway of mitophagy is activated to protect against renal ischemia-reperfusion injury," Autophagy. 2018; 14(5):880-897.
Tsubouchi et al., "PINK1-PARK2-mediated mitophagy in COPD and IPF pathogeneses," Inflamm Regen. 2018; 38:18.

(56) References Cited

OTHER PUBLICATIONS

Vercammen et al., "Parkin protects against neurotoxicity in the 6-hydroxydopamine rat model for Parkinson's disease," Mol Ther. 2006; 14(5):716-723.
Wang et al., "Mitophagy in Acute Kidney Injury and Kidney Repair," Cells. 2020; 9(2):338.
Wang et al., "PINK1/Parkin-mediated mitophagy is activated in cisplatin nephrotoxicity to protect against kidney injury," Cell Death Dis. 2018; 9(11):1113.
Yasuda et al., "Neuronal specificity of alpha-synuclein toxicity and effect of Parkin co-expression in primates," Neuroscience. 2007; 144(2):743-753.
Yasuda et al., "Parkin-mediated protection of dopaminergic neurons in a chronic MPTP—minipump mouse model of Parkinson disease," J Neuropathol Exp Neurol. 2011; 70(8):686-697.
Ye et al., "Parkin-mediated mitophagy in mutant hAPP neurons and Alzheimer's disease patient brains," Hum Mol Genet. 2015; 24(10):2938-2951.
International Search Report and Written Opinion issued by the United States Patent and Trademark Office as International Searching Authority for International Patent Application No. PCT/US2020/050552, dated Jan. 27, 2021 (13 pages).
Pubchem, N-[4-[[4-[[(2R)Oxolan-2-yl]methylsulfamoyl]phenyl]sulfamoyl]phenyl]acetamide, CID 1025596, National Center for Biotechnology Information. Jul. 9, 2005, modified Dec. 5, 2020 (9 pages). Retrieved from the Internet: https://pubchem.ncbi.nlm.nih.gov/compound/1025596.

\* cited by examiner

USP30 INHIBITORS AND USES THEREOF

CROSS-REFERENCE TO RELATED APPLICATIONS

The present application claims priority to U.S. provisional patent application Ser. No. 62/898,820, filed Sep. 11, 2019, and U.S. provisional patent application Ser. No. 63/022,165, filed May 8, 2020, the entirety of each of which is incorporated herein by reference.

TECHNICAL FIELD OF THE INVENTION

The present invention relates to compounds and methods useful for inhibiting ubiquitin carboxyl-terminal hydrolase 30 ("USP30"), also known as deubiquitinating enzyme 30, ubiquitin thioesterase 30, or ubiquitin-specific-processing protease 30. The invention also provides pharmaceutically acceptable compositions comprising compounds of the present invention and methods of using said compositions in the treatment of various disorders.

BACKGROUND OF THE INVENTION

Parkinson's disease (PD), an age-associated neurodegenerative disorder second only to Alzheimer's disease (AD) in prevalence, affects nearly 1 million Americans with an estimated financial cost of $15 billion (Marras et al. Parkinson's Foundation PG: Prevalence of Parkinson's disease across North America. NPJ Parkinsons Dis 2018, 4:21. PMC6039505; Gooch et al. The burden of neurological disease in the United States: A summary report and call to action. Ann Neurol 2017, 81:479-484). Those numbers are anticipated to grow as the aged population world-wide increases. Although it is becoming increasingly evident that PD is a systemic disease involving a number of peripheral tissues as well as multiple brains regions and neuronal populations beyond dopaminergic neurons (Obeso et al. Past, present, and future of Parkinson's disease: A special essay on the 200th Anniversary of the Shaking Palsy. Mov Disord 2017, 32:1264-1310. PMC5685546), existing treatments for PD primarily augment dopaminergic neurotransmission to provide symptomatic benefit. The efficacy of such treatments diminish with disease progression and intolerable motor complications emerge in a significant proportion of patients. Moreover, non-motor symptoms, including cognitive deficits reflecting non-dopaminergic pathology, remain a major source of disability. Given the strengths in the rigor of prior research implicating mitochondrial deficits in PD and AD, targeting the Parkin-USP30 pathway to restore mitochondrial homeostasis as a means of slowing disease progression holds great promise for the treatment of PD and AD.

Convergent evidence—specifically, human pharmacology, genetics, and tissue pathology as well as animal model data—indicate that restoration of mitochondrial quality control, including induction of mitophagy (clearance of damaged mitochondria) and bioenergetics, holds the promise of slowing the progression of both PD (Park et al. Mitochondrial Dysfunction in Parkinson's Disease: New Mechanistic Insights and Therapeutic Perspectives. Curr Neurol Neurosci Rep 2018, 18:21. PMC5882770) as well as AD (Fang et al. Mitophagy inhibits amyloid-beta and tau pathology and reverses cognitive deficits in models of Alzheimer's disease. Nat Neurosci 2019, 22:401-412). The first evidence of mitochondrial dysfunction in PD emerged from the observation that exposure to the mitochondrial complex I inhibitor, 1-methyl-4-phenyl-1,2,3,4-tetrahydropyridine (MPTP), causes rapid parkinsonism and dopamine neuronal death (Langston et al. Chronic Parkinsonism in humans due to a product of meperidine-analog synthesis. Science 1983, 219: 979-980). Genetic studies of monogenic PD show that pathogenic mutations in genes encoding proteins participating in mitochondrial quality control, such as PINK1, PRKN, FBXO7, DJ-1, VPS13C, and CHCHD2 cause autosomal recessive, early onset parkinsonism (Canet-Aviles et al. The Parkinson's disease protein DJ-1 is neuroprotective due to cysteine-sulfinic acid-driven mitochondrial localization. Proc Natl Acad Sci USA 2004, 101:9103-9108. PMC428480; Funayama et al. CHCHD2 mutations in autosomal dominant late-onset Parkinson's disease: a genome-wide linkage and sequencing study. Lancet Neurol 2015, 14:274-282; Burchell et al. The Parkinson's disease-linked proteins Fbxo7 and Parkin interact to mediate mitophagy. Nat Neurosci 2013, 16:1257-1265. PMC3827746; Lesage et al. French Parkinson's Disease Genetics S, International Parkinson's Disease Genomics C: Loss of VPS13C Function in Autosomal-Recessive Parkinsonism Causes Mitochondrial Dysfunction and Increases PINK1/Parkin-Dependent Mitophagy. Am J Hum Genet 2016, 98:500-513. PMC4800038; Paisan-Ruiz et al. Early-onset L-dopa-responsive parkinsonism with pyramidal signs due to ATP13A2, PLA2G6, FBXO7 and spatacsin mutations. Mov Disord 2010, 25:1791-1800. PMC6005705). Importantly, Genome-Wide Association (GWA) studies of sporadic PD show that mitochondrial-function-associated genes are risk factors for sporadic, late-onset PD (Billingsley et al. International Parkinson's Disease Genomics C, Ryten M, Koks S: Mitochondria function associated genes contribute to Parkinson's Disease risk and later age at onset. NPJ Parkinsons Dis 2019, 5:8. PMC6531455). Moreover, a decrease in respiratory capacity of mitochondria has been shown in autopsied brain tissue from sporadic PD cases (Schapira et al. Mitochondrial complex I deficiency in Parkinson's disease. J Neurochem 1990, 54:823-827). Recent evidence from peripheral blood cells of early/prodromal PD cases also demonstrates mitochondrial dysfunction (Smith et al. Mitochondrial dysfunction and increased glycolysis in prodromal and early Parkinson's blood cells. Mov Disord 2018, 33:1580-1590. PMC6221131). Finally, mitochondrial complex 1 inhibitors such as MPTP or Rotenone cause retrograde degeneration of nigrostriatal dopamine neurons in animal models highlighting that these neurons with the most severe and prototypical degeneration in PD are particularly sensitive to mitochondrial dysfunction.

Abnormal mitochondrial accumulation and mitophagy deficits have been observed in other age-related diseases such as AD and with aging itself (Fang et al. 2019; Ridge and Kauwe, Mitochondria and Alzheimer's Disease: the Role of Mitochondrial Genetic Variation. Curr Genet Med Rep 2018, 6:1-10. PMC5842281). Recent work by Fang et al., demonstrates that mitophagy is reduced in the hippocampus of AD patients and that increased mitophagy is able to rescue cognitive impairment and prevent both A plaques and tau hyperphosphorylation in induced pluripotent stem cells (iPSC) and multiple animal models of AD (Fang et al. 2019). Positron Emission Tomography (PET) imaging of AD patients have suggested reduced oxidative phosphorylation and TCA cycle, while post-mortem analysis suggests a reduction in PGC1α, a transcriptional regulator of mitochondrial biogenesis and an essential part of the mitochondrial quality control cycle (Kapogiannis and Mattson, Disrupted energy metabolism and neuronal circuit dysfunction in cognitive impairment and Alzheimer's disease. Lancet Neurol 2011, 10:187-198. PMC3026092; Katsouri et al. PPARgamma-coactivator-1alpha gene transfer reduces neuronal loss and amyloid-beta generation by reducing beta-secretase in an Alzheimer's disease model. Proc Natl Acad Sci USA 2016, 113:12292-12297. PMC5087021). Transmission Electron Microscopy (TEM) analysis of mitochondrial structures in the hippocampus of post-mortem AD patients demonstrates abnormal mitochondrial morphology, altered mitophagy, and a reduction in parkin levels, which was exacerbated with disease progression (Ye et al., Parkin-mediated mitophagy in mutant hAPP neurons and Alzheimer's disease patient brains. Hum Mol Genet 2015, 24:2938-2951. PMC4406302).

Modulating mitochondrial pathways, including increasing expression of Parkin or depletion of USP30, has been shown to be protective in a variety of genetic and toxin-based animal models of PD in multiple species[2,20-27] (Bingol et al., The mitochondrial deubiquitinase USP30 opposes parkin-mediated mitophagy. Nature 2014, 510:370-375; Bian et al., Overexpression of parkin ameliorates dopaminergic neurodegeneration induced by 1-methyl-4-phenyl-1,2,3,6-tetrahydropyridine in mice. PLoS One 2012, 7:e39953. PMC3390003; Hou et al., Parkin represses 6-hydroxydopamine-induced apoptosis via stabilizing scaffold protein p62 in PC12 cells. Acta Pharmacol Sin 2015, 36:1300-1307. PMC4635325; Lo Bianco et al., Lentiviral vector delivery of parkin prevents dopaminergic degeneration in an alpha-synuclein rat model of Parkinson's disease. Proc Natl Acad Sci USA 2004, 101:17510-17515. PMC536019; Paterna et al., DJ-1 and Parkin modulate dopamine-dependent behavior and inhibit MPTP-induced nigral dopamine neuron loss in mice. Mol Ther 2007, 15:698-704; Vercammen et al., Parkin protects against neurotoxicity in the 6-hydroxydopamine rat model for Parkinson's disease. Mol Ther 2006, 14:716-723; Yasuda et al., Parkin-mediated protection of dopaminergic neurons in a chronic MPTP-minipump mouse model of Parkinson disease. J Neuropathol Exp Neurol 2011, 70:686-697; Yasuda et al., Neuronal specificity of alpha-synuclein toxicity and effect of Parkin co-expression in primates. Neuroscience 2007, 144:743-753; Liang et al., USP30 deubiquitylates mitochondrial Parkin substrates and restricts apoptotic cell death. EMBO Rep 2015, 16:618-627. PMC4428036). PINK1/Parkin-dependent linear ubiquitination of proteins on the outer mitochondrial membrane (OMM) leads to removal of damaged protein and mitochondria through fission of mitochondrial derived vesicles (MDVs) or recruitment of phagophores to begin the mitophagy process. The deubiquitinating (DUB) enzyme, USP30, is present specifically on the OMM (unlike other DUBs such as USP8, 15 and 35 implicated in mitochondrial quality control), and acts as a counterbalance to this process by specifically removing ubiquitin chains on parkin substrates. Involvement of USP30 in regulating mitophagy has been well established through functional genomic studies in mammalian, including human, cells and flies, further validating it as a promising target (Bingol et al., 2014). Without wishing to be bound by any particular theory, it is believed that USP30 inhibitors will promote the clearance of damaged mitochondria to restore mitochondrial homeostasis, attenuating the pathogenic cascade associated with PD pathogenesis.

SUMMARY OF THE INVENTION

It has now been found that compounds of this invention, and pharmaceutically acceptable compositions thereof, are effective as inhibitors of USP30. Such compounds have the general formula I:

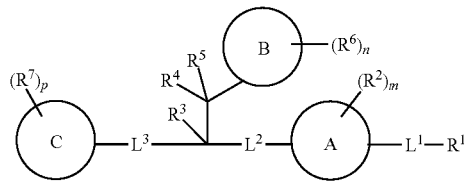

or a pharmaceutically acceptable salt thereof, wherein each variable is as defined and described herein.

In some embodiments, such compounds have the general formula I':

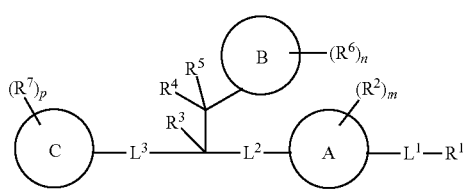

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with mitochondrial homeostasis implicating USP30. Such diseases, disorders, or conditions include those described herein.

Compounds provided by this invention are also useful for the study of USP30 in biological and pathological phenomena; the study of mitochondrial homeostasis occurring in bodily tissues; and the comparative evaluation of new USP30 inhibitors or other regulators of mitochondrial homeostasis in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of USP30.

In certain embodiments, the present invention provides a compound of formula I:

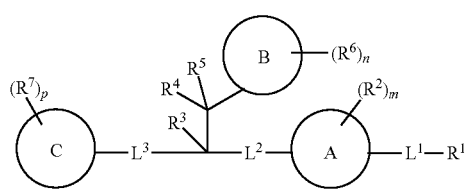

or a pharmaceutically acceptable salt thereof, wherein:
Ring A is phenyl, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

$L^1$ is a covalent bond or a $C_{1-3}$ bivalent hydrocarbon chain wherein one or two methylene units of the chain are optionally and independently replaced by —C(CF$_3$)H—, —N(R)—, —O—, —C(O)—, —OC(O)—, —C(O)O—, —C(O)N(R)—, —N(R)C(O)—, —S(O)—, —S(O)$_2$—, —S(O)N(R)—, —S(O)$_2$N(R)—, or —S(O)(R)=N—;

each R is independently hydrogen or an optionally substituted $C_{1-3}$ aliphatic group; or:
  two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur; or
  an R group and $R^1$ on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur;

$R^1$ is hydrogen or an optionally substituted group selected from $C_{1-6}$ aliphatic, a 3-8 membered saturated or partially unsaturated monocyclic carbocyclic ring, a 5-8 membered saturated or partially unsaturated bridged bicyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

each $R^2$ is independently halogen, —CF$_3$, —CN, —C(O)NHR, —NO$_2$, —NHR, —NHC(O)R, —NHS(O)$_2$R, —N(R)$_2$, or —OR, or an optionally substituted $C_{1-6}$ aliphatic group; or
  two $R^2$ on the same carbon are optionally taken together to form =O;

$L^2$ is selected from the group consisting of —C(O)N(R')—, —CH$_2$O—, —CH$_2$N(R')—, and —C(OH)(H)CH$_2$N(R')—;

R' is hydrogen or a $C_{1-3}$ aliphatic group;

$L^3$ is selected from the group consisting of —C(O)N(R")—, —OC(O)N(R")—, and —CH$_2$O—;

R" is hydrogen or a $C_{1-3}$ aliphatic group;

$R^3$ is hydrogen or $C_{1-3}$ aliphatic; or:
  $R^3$ and $R^4$ are optionally taken together with their intervening atoms to form a 3-5 membered saturated carbocyclic ring; or
  $R^3$ and $R^5$ are optionally taken together with their intervening atoms to form a 3-5 membered saturated carbocyclic ring;

$R^4$ is hydrogen or $C_{1-3}$ aliphatic;

$R^5$ is hydrogen or $C_{1-3}$ aliphatic;

Ring B is phenyl, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

each $R^6$ is independently halogen, —CN, —NO$_2$, —NHR, —N(R)$_2$, —OR, or an optionally substituted $C_{1-6}$ aliphatic group; or:
  two $R^6$ on the same carbon are optionally taken together to form =O;
  an $R^6$ group and R' group are optionally taken together with their intervening atoms to form a 5-8 membered partially unsaturated fused ring having 0-2 heteroatoms, in addition to the nitrogen, independently selected from nitrogen, oxygen or sulfur;
  an $R^6$ group and $R^3$ group are optionally taken together with their intervening atoms to form a 5-8 membered partially unsaturated spiro-fused ring having 0-2 heteroatoms independently selected from nitrogen, oxygen or sulfur; or
  an $R^6$ group and R" group are optionally taken together with their intervening atoms to form a 5-8 membered partially unsaturated fused ring having 0-2 heteroatoms, in addition to the nitrogen, independently selected from nitrogen, oxygen or sulfur;

Ring C is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

each $R^7$ is independently halogen, —CN, —NO$_2$, —NHR, —N(R)$_2$, —OR, or an optionally substituted $C_{1-6}$ aliphatic group; or
  two $R^7$ on the same carbon are optionally taken together to form =O;

each of m, n, and p is independently 0, 1, 2, 3 or 4.

In certain embodiments, the present invention provides a compound of formula I':

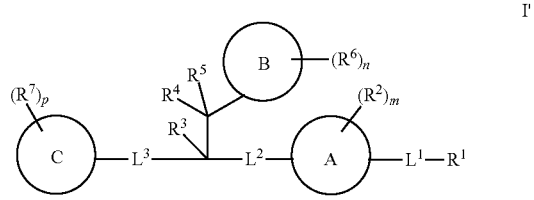

I' or a pharmaceutically acceptable salt thereof, wherein:
  Ring A is phenyl, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;

$L^1$ is a covalent bond or a $C_{1-3}$ bivalent hydrocarbon chain wherein one or two methylene units of the chain are optionally and independently replaced by —C(CF$_3$)H—, —N(R)—, —O—, —C(O)—, —OC(O)—, —C(O)O—, —C(O)N(R)—, —N(R)C(O)—, —S(O)—, —S(O)$_2$—, —S(O)N(R)—, —S(O)$_2$N(R)—, or —S(O)(R)=N—;

each R is independently hydrogen or an optionally substituted $C_{1-3}$ aliphatic group; or:
  two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur; or
  an R group and $R^1$ on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur;

$R^1$ is hydrogen or an optionally substituted group selected from $C_{1-6}$ aliphatic, a 3-8 membered saturated or partially unsaturated monocyclic carbocyclic ring, a 5-8 membered saturated or partially unsaturated bridged bicyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

each $R^2$ is independently halogen, —$CF_3$, —CN, —C(O)NHR, —$NO_2$, —NHR, —NHC(O)R, —NHS(O)$_2$R, —N(R)$_2$, or —OR, or an optionally substituted $C_{1-6}$ aliphatic group; or two $R^2$ on the same carbon are optionally taken together to form =O; or two $R^2$ groups are optionally taken together with their intervening atoms to form a 5-8 membered partially unsaturated fused ring having 0-2 heteroatoms independently selected from nitrogen, oxygen or sulfur;

$L^2$ is selected from the group consisting of —C(O)N(R')—, —$CH_2$O—, —$CH_2$N(R')—, and —C(OH)(H)$CH_2$N(R')—;

R' is hydrogen or a $C_{1-3}$ aliphatic group;

$L^3$ is selected from the group consisting of —C(O)N(R")—, —OC(O)N(R")—, and —$CH_2$O—;

R" is hydrogen or a $C_{1-3}$ aliphatic group;

$R^3$ is hydrogen or $C_{1-3}$ aliphatic; or:

$R^3$ and $R^4$ are optionally taken together with their intervening atoms to form a 3-5 membered saturated carbocyclic ring; or $R^3$ and $R^5$ are optionally taken together with their intervening atoms to form a 3-5 membered saturated carbocyclic ring;

$R^4$ is hydrogen or $C_{1-3}$ aliphatic;

$R^5$ is hydrogen or $C_{1-3}$ aliphatic;

Ring B is phenyl, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;

each $R^6$ is independently halogen, —CN, —$NO_2$, —NHR, —N(R)$_2$, —OR, or an optionally substituted $C_{1-6}$ aliphatic group; or:

two $R^6$ on the same carbon are optionally taken together to form =O;

an $R^6$ group and R' group are optionally taken together with their intervening atoms to form a 5-8 membered partially unsaturated fused ring having 0-2 heteroatoms, in addition to the nitrogen, independently selected from nitrogen, oxygen or sulfur;

an $R^6$ group and $R^3$ group are optionally taken together with their intervening atoms to form a 5-8 membered partially unsaturated spiro-fused ring having 0-2 heteroatoms independently selected from nitrogen, oxygen or sulfur; or an $R^6$ group and R" group are optionally taken together with their intervening atoms to form a 5-8 membered partially unsaturated fused ring having 0-2 heteroatoms, in addition to the nitrogen, independently selected from nitrogen, oxygen or sulfur;

Ring C is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;

each $R^7$ is independently halogen, —CN, —$NO_2$, —NHR, —N(R)$_2$, —OR, or an optionally substituted $C_{1-6}$ aliphatic group; or two $R^7$ on the same carbon are optionally taken together to form =O; or an $R^7$ group and R" group are optionally taken together with their intervening atoms to form a 5-8 membered partially unsaturated fused ring having 0-2 heteroatoms, in addition to the nitrogen, independently selected from nitrogen, oxygen or sulfur;

each of m, n, and p is independently 0, 1, 2, 3 or 4.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur.

Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

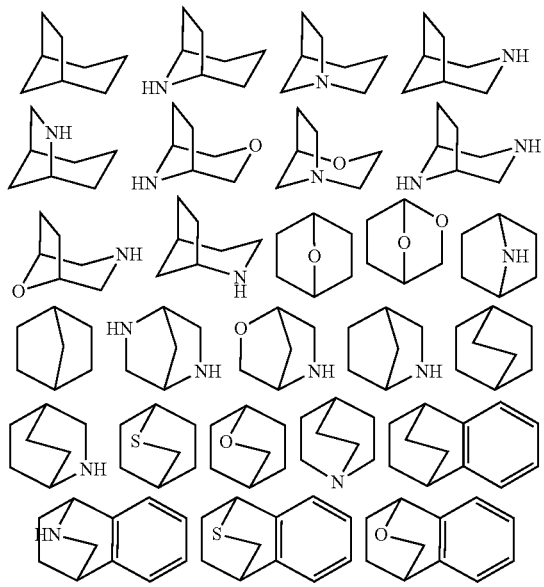

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

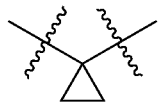

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR$^\circ$; —SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; —SiR$^\circ$$_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, R$^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits USP30 with measurable affinity. In certain embodiments, an inhibitor has an IC$_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in USP30 activity between a sample comprising a compound of the present invention, or composition thereof, and USP30, and an equivalent sample comprising USP30, in the absence of said compound, or composition thereof.

3. Description of Exemplary Embodiments

As described above, in certain embodiments, the present invention provides a compound of formula I:

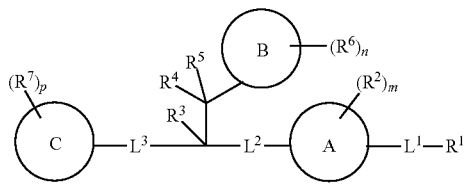

I or a pharmaceutically acceptable salt thereof, wherein:
Ring A is phenyl, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;
$L^1$ is a covalent bond or a $C_{1-3}$ bivalent hydrocarbon chain wherein one or two methylene units of the chain are optionally and independently replaced by —C(CF$_3$)H—, —N(R)—, —O—, —C(O)—, —OC(O)—, —C(O)O—, —C(O)N(R)—, —N(R)C(O)—, —S(O)—, —S(O)$_2$—, —S(O)N(R)—, —S(O)$_2$N(R)—, or —S(O)(R)=N—;
each R is independently hydrogen or an optionally substituted $C_{1-3}$ aliphatic group; or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur; or
an R group and $R^1$ on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur;
$R^1$ is hydrogen or an optionally substituted group selected from $C_{1-6}$ aliphatic, a 3-8 membered saturated or partially unsaturated monocyclic carbocyclic ring, a 5-8 membered saturated or partially unsaturated bridged bicyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;
each $R^2$ is independently halogen, —CF$_3$, —CN, —C(O)NHR, —NO$_2$, —NHR, —NHC(O)R, —NHS(O)$_2$R, —N(R)$_2$, or —OR, or an optionally substituted $C_{1-6}$ aliphatic group; or
two $R^2$ on the same carbon are optionally taken together to form =O;
$L^2$ is selected from the group consisting of —C(O)N(R')—, —CH$_2$O—, —CH$_2$N(R')—, and —C(OH)(H)CH$_2$N(R')—;
R' is hydrogen or a $C_{1-3}$ aliphatic group;
$L^3$ is selected from the group consisting of —C(O)N(R")—, —OC(O)N(R")—, and —CH$_2$O—;
R" is hydrogen or a $C_{1-3}$ aliphatic group;
$R^3$ is hydrogen or $C_{1-3}$ aliphatic; or:
$R^3$ and $R^4$ are optionally taken together with their intervening atoms to form a 3-5 membered saturated carbocyclic ring; or
$R^3$ and $R^5$ are optionally taken together with their intervening atoms to form a 3-5 membered saturated carbocyclic ring;
$R^4$ is hydrogen or $C_{1-3}$ aliphatic;
$R^5$ is hydrogen or $C_{1-3}$ aliphatic;
Ring B is phenyl, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;
each $R^6$ is independently halogen, —CN, —NO$_2$, —NHR, —N(R)$_2$, —OR, or an optionally substituted $C_{1-6}$ aliphatic group; or:

two $R^6$ on the same carbon are optionally taken together to form =O;

an $R^6$ group and R' group are optionally taken together with their intervening atoms to form a 5-8 membered partially unsaturated fused ring having 0-2 heteroatoms, in addition to the nitrogen, independently selected from nitrogen, oxygen or sulfur;

an $R^6$ group and $R^3$ group are optionally taken together with their intervening atoms to form a 5-8 membered partially unsaturated spiro-fused ring having 0-2 heteroatoms independently selected from nitrogen, oxygen or sulfur; or an $R^6$ group and R" group are optionally taken together with their intervening atoms to form a 5-8 membered partially unsaturated fused ring having 0-2 heteroatoms, in addition to the nitrogen, independently selected from nitrogen, oxygen or sulfur;

Ring C is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic ring having 0-3 heteroatoms independently selected from nitrogen, oxygen, or sulfur;

each $R^7$ is independently halogen, —CN, —$NO_2$, —NHR, —$N(R)_2$, —OR, or an optionally substituted $C_{1-6}$ aliphatic group; or two $R^7$ on the same carbon are optionally taken together to form =O;

each of m, n, and p is independently 0, 1, 2, 3 or 4.

In certain embodiments, the present invention provides a compound of formula I':

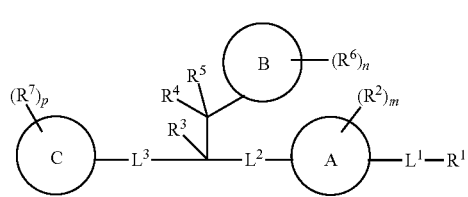

I' or a pharmaceutically acceptable salt thereof, wherein:

Ring A is phenyl, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;

$L^1$ is a covalent bond or a $C_{1-3}$ bivalent hydrocarbon chain wherein one or two methylene units of the chain are optionally and independently replaced by —C($CF_3$)H—, —N(R)—, —O—, —C(O)—, —OC(O)—, —C(O)O—, —C(O)N(R)—, —N(R)C(O)—, —S(O)—, —S(O)$_2$—, —S(O)N(R)—, —S(O)$_2$N(R)—, or —S(O)(R)=N—;

each R is independently hydrogen or an optionally substituted $C_{1-3}$ aliphatic group; or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur; or an R group and $R^1$ on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur;

$R^1$ is hydrogen or an optionally substituted group selected from $C_{1-6}$ aliphatic, a 3-8 membered saturated or partially unsaturated monocyclic carbocyclic ring, a 5-8 membered saturated or partially unsaturated bridged bicyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

each $R^2$ is independently halogen, —$CF_3$, —CN, —C(O)NHR, —$NO_2$, —NHR, —NHC(O)R, —NHS(O)$_2$R, —$N(R)_2$, or —OR, or an optionally substituted $C_{1-6}$ aliphatic group; or two $R^2$ on the same carbon are optionally taken together to form =O; or two $R^2$ groups are optionally taken together with their intervening atoms to form a 5-8 membered partially unsaturated fused ring having 0-2 heteroatoms independently selected from nitrogen, oxygen or sulfur;

$L^2$ is selected from the group consisting of —C(O)N(R')—, —$CH_2$O—, —$CH_2$N(R')—, and —C(OH)(H)$CH_2$N(R')—;

R' is hydrogen or a $C_{1-3}$ aliphatic group;

$L^3$ is selected from the group consisting of —C(O)N(R")—, —OC(O)N(R")—, and —$CH_2$O—;

R" is hydrogen or a $C_{1-3}$ aliphatic group;

$R^3$ is hydrogen or $C_{1-3}$ aliphatic; or:

$R^3$ and $R^4$ are optionally taken together with their intervening atoms to form a 3-5 membered saturated carbocyclic ring; or $R^3$ and $R^5$ are optionally taken together with their intervening atoms to form a 3-5 membered saturated carbocyclic ring;

$R^4$ is hydrogen or $C_{1-3}$ aliphatic;

$R^5$ is hydrogen or $C_{1-3}$ aliphatic;

Ring B is phenyl, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;

each $R^6$ is independently halogen, —CN, —$NO_2$, —NHR, —$N(R)_2$, —OR, or an optionally substituted $C_{1-6}$ aliphatic group; or:

two $R^6$ on the same carbon are optionally taken together to form =O;

an $R^6$ group and R' group are optionally taken together with their intervening atoms to form a 5-8 membered partially unsaturated fused ring having 0-2 heteroatoms, in addition to the nitrogen, independently selected from nitrogen, oxygen or sulfur;

an $R^6$ group and $R^3$ group are optionally taken together with their intervening atoms to form a 5-8 membered partially unsaturated spiro-fused ring having 0-2 heteroatoms independently selected from nitrogen, oxygen or sulfur; or an $R^6$ group and R" group are optionally taken together with their intervening atoms to form a 5-8 membered partially unsaturated fused ring having 0-2 heteroatoms, in addition to the nitrogen, independently selected from nitrogen, oxygen or sulfur;

Ring C is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;

each $R^7$ is independently halogen, —CN, —NO$_2$, —NHR, —N(R)$_2$, —OR, or an optionally substituted C$_{1-6}$ aliphatic group; or two $R^7$ on the same carbon are optionally taken together to form =O; or an $R^7$ group and R" group are optionally taken together with their intervening atoms to form a 5-8 membered partially unsaturated fused ring having 0-2 heteroatoms, in addition to the nitrogen, independently selected from nitrogen, oxygen or sulfur;

each of m, n, and p is independently 0, 1, 2, 3 or 4.

As defined generally above, Ring A is phenyl, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur.

In some embodiments, Ring A is phenyl. In some embodiments, Ring A is a 5-6 membered heteroaryl ring having 1-4 heteroatoms independently selected from nitrogen, oxygen, or sulfur. In some embodiments, Ring A is an 8-10 membered bicyclic aryl or heteroaryl ring having 0-3 heteroatoms independently selected from nitrogen, oxygen, or sulfur.

In some embodiments, Ring A is

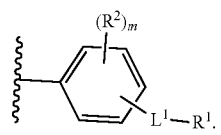

In some embodiments, Ring A is

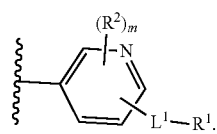

In some embodiments, Ring A is

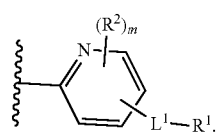

In some embodiments, Ring A is

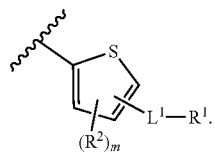

In some embodiments, Ring A is

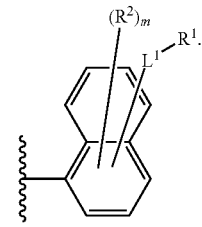

In some embodiments, Ring A is

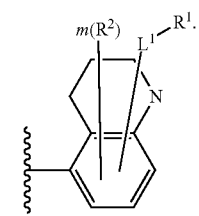

In some embodiments, Ring A is selected from those depicted in Table 1 below.

As defined generally above, $L^1$ is a covalent bond or a C$_{1-3}$ bivalent hydrocarbon chain wherein one or two methylene units of the chain are optionally and independently replaced by —C(CF$_3$)H—, —N(R)—, —O—, —C(O)—, —OC(O)—, —C(O)O—, —C(O)N(R)—, —N(R)C(O)—, —S(O)—, —S(O)$_2$—, —S(O)N(R)—, —S(O)$_2$N(R)—, or —S(O)(R)=N—.

In some embodiments, $L^1$ is a covalent bond. In some embodiments, $L^1$ is a C$_{1-3}$ bivalent hydrocarbon chain wherein one or two methylene units of the chain are optionally and independently replaced by —C(CF$_3$)H—, —N(R)—, —O—, —C(O)—, —OC(O)—, —C(O)O—, —C(O)N(R)—, —N(R)C(O)—, —S(O)—, —S(O)$_2$—, —S(O)N(R)—, —S(O)$_2$N(R)—, or —S(O)(R)=N—.

In some embodiments, $L^1$ is

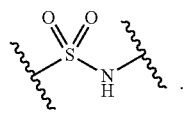 [SMILES: *NS(*)(=O)=O]

In some embodiments, $L^1$ is

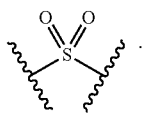

In some embodiments, $L^1$ is

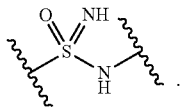 [SMILES: *NS(*)(=N)=O]

In some embodiments, $L^1$ is

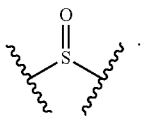

In some embodiments, $L^1$ is

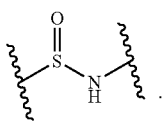 [SMILES: *NS(*)=O]

In some embodiments, $L^1$ is

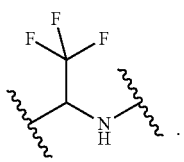 [SMILES: *NC(*)C(F)(F)F]

In some embodiments, $L^1$ is

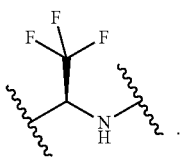 [SMILES: *N[C@@H](*)C(F)(F)F]

In some embodiments, $L^1$ is

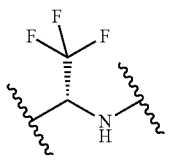

In some embodiments, $L^1$ is

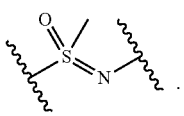 [SMILES: *N=S(*)(C)=O]

In some embodiments, $L^1$ is

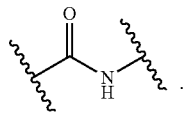

In some embodiments, when $L^1$ is $-S(O)_2N(R)-$, $R^1$ is other than hydrogen, isopropyl, t-butyl, 1-methylcyclopropyl, 1-fluoromethylcyclopropyl, 1-difluoromethylcyclopropyl, 1-trifluoromethylcyclopropyl, or 3-methyl-3-oxetanyl.

In some embodiments, $L^1$ is selected from those depicted in Table 1 below.

As defined generally above, each R is independently hydrogen or an optionally substituted $C_{1-3}$ aliphatic group; two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur; or an R group and $R^1$ on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur.

In some embodiments, R is hydrogen. In some embodiments, R is an optionally substituted $C_{1-3}$ aliphatic group. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur. In some embodiments, an R group and $R^1$ on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur.

In some embodiments, R is selected from those depicted in Table 1 below.

As defined generally above, $R^1$ is hydrogen or an optionally substituted group selected from $C_{1-6}$ aliphatic, a 3-8 membered saturated or partially unsaturated monocyclic carbocyclic ring, a 5-8 membered saturated or partially unsaturated bridged bicyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^1$ is hydrogen. In some embodiments, $R^1$ is an optionally substituted group selected from $C_{1-6}$ aliphatic, a 3-8 membered saturated or partially unsaturated monocyclic carbocyclic ring, a 5-8 membered saturated or partially unsaturated bridged bicyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^1$ is methyl. In some embodiments, $R^1$ is ethyl. In some embodiments, $R^1$ is

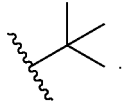

In some embodiments, R¹ is

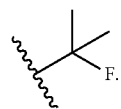

In some embodiments, R¹ is

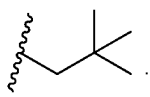 [SMILES: *CC(C)(C)C]

In some embodiments, R¹ is

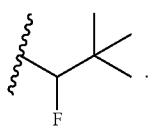

In some embodiments, R¹ is

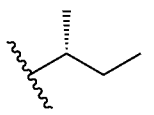

In some embodiments, R¹ is

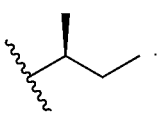 [SMILES: *[C@@H](C)CC]

In some embodiments, R¹ is

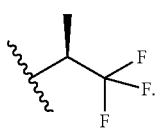 [SMILES: *[C@@H](C)C(F)(F)F]

In some embodiments, R¹ is

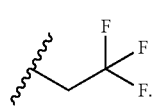

In some embodiments, R¹ is

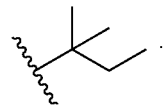 [SMILES: *C(C)(C)CC]

In some embodiments, R¹ is

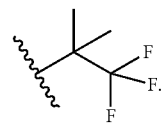 [SMILES: *C(C)(C)C(F)(F)F]

In some embodiments, R¹ is

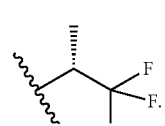

In some embodiments, R¹ is

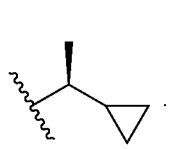 [SMILES: *[C@@H](C)C1CC1]

In some embodiments, R¹ is

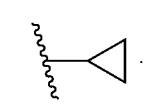

In some embodiments, R¹ is

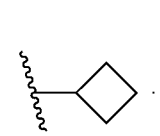

In some embodiments, R¹ is

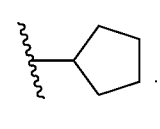

In some embodiments, R¹ is

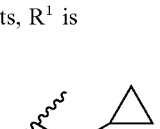

In some embodiments, R¹ is

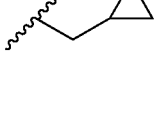

In some embodiments, R¹ is

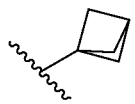

In some embodiments, R¹ is

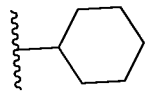

In some embodiments, R¹ is

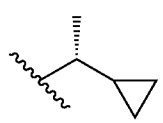

In some embodiments, R¹ is

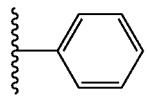

In some embodiments, R¹ is

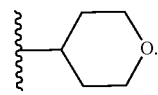

In some embodiments, R¹ is

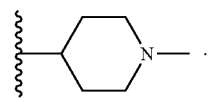 [SMILES: *C1CCN(C)CC1]

In some embodiments, R¹ is

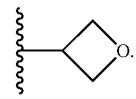

In some embodiments, R¹ is

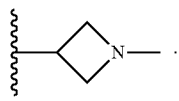 [SMILES: *C1CN(C)C1]

In some embodiments, R¹ is

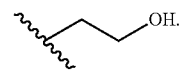 [SMILES: *CCO]

In some embodiments, R¹ is

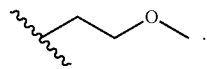 [SMILES: *CCOC]

In some embodiments, R¹ is

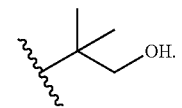 [SMILES: *C(C)(C)CO]

In some embodiments, R¹ is

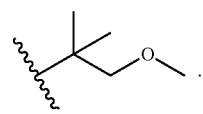 [SMILES: *C(C)(C)COC]

In some embodiments, R¹ is

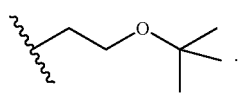 [SMILES: *CCOC(C)(C)C]

In some embodiments, R¹ is

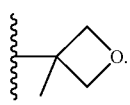 [SMILES: *C1(C)COC1]

In some embodiments, R¹ is

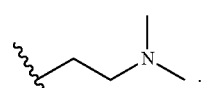

In some embodiments, R¹ is

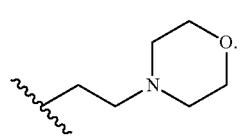 [SMILES: *CCN1CCOCC1]

In some embodiments, $R^1$ is

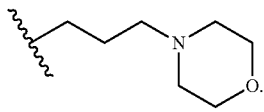 [SMILES: *CCCN1CCOCC1]

In some embodiments, $R^1$ is

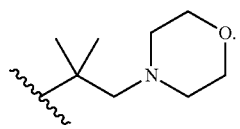 [SMILES: *C(C)(C)CN1CCOCC1]

In some embodiments, $R^1$ is

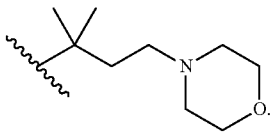 [SMILES: *C(C)(C)CCN1CCOCC1]

In some embodiments, $R^1$ is

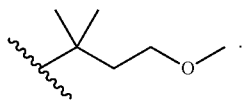 [SMILES: *C(C)(C)CCOC]

In some embodiments, $R^1$ is

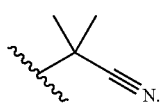 [SMILES: *C(C)(C)C#N]

In some embodiments, $R^1$ is

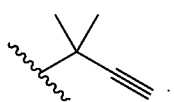

In some embodiments, $R^1$ is

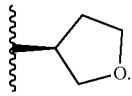

In some embodiments, $R^1$ is

In some embodiments, $R^1$ is other than hydrogen, isopropyl, t-butyl, 1-methylcyclopropyl, 1-fluoromethylcyclopropyl, 1-difluoromethylcyclopropyl, 1-trifluoromethylcyclopropyl, or 3-methyl-3-oxetanyl when $L^1$ is —S(O)$_2$N(R)—.

In some embodiments, $R^1$ is other than hydrogen or ethyl when $L^1$ is —S(O)$_2$N(R)— and Ring A is naphthyl.

In some embodiments, $R^1$ is selected from those depicted in Table 1 below.

As defined generally above, each $R^2$ is independently halogen, —CF$_3$, —CN, —C(O)NHR, —NO$_2$, —NHR, —NHC(O)R, —NHS(O)$_2$R, —N(R)$_2$, or —OR, or an optionally substituted C$_{1-6}$ aliphatic group; or two $R^2$ on the same carbon are optionally taken together to form =O; or two $R^2$ groups are optionally taken together with their intervening atoms to form a 5-8 membered partially unsaturated fused ring having 0-2 heteroatoms independently selected from nitrogen, oxygen or sulfur.

In some embodiments, $R^2$ is halogen, —CF$_3$, —CN, —C(O)NHR, —NO$_2$, —NHR, —NHC(O)R, —NHS(O)$_2$R, —N(R)$_2$, or —OR. In some embodiments, $R^2$ is an optionally substituted C$_{1-6}$ aliphatic group. In some embodiments, two $R^2$ on the same carbon are optionally taken together to form =O. In some embodiments, two $R^2$ groups are optionally taken together with their intervening atoms to form a 5-8 membered partially unsaturated fused ring having 0-2 heteroatoms independently selected from nitrogen, oxygen or sulfur.

In some embodiments, $R^2$ is methyl.

In some embodiments, $R^2$ is methoxy. In some embodiments, $R^2$ is fluoro. In some embodiments, $R^2$ is chloro. In some embodiments, $R^2$ is cyano.

In some embodiments, two $R^2$ groups are taken together with their intervening atoms to form a 6 membered partially unsaturated fused ring having 1 nitrogen. In some embodiments, two R1 groups are taken together with their intervening atoms to form

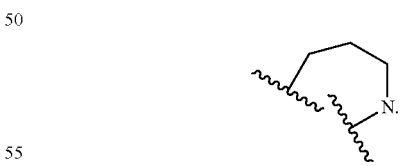

In some embodiments, $R^2$ is selected from those depicted in Table 1 below.

As defined generally above, $L^2$ is selected from the group consisting of —C(O)N(R')—, —CH$_2$O—, —CH$_2$N(R')—, and —C(OH)(H)CH$_2$N(R')—.

In some embodiments, $L^2$ is —C(O)N(R')—. In some embodiments, $L^2$ is —CH$_2$O—. In some embodiments, $L^2$ is —CH$_2$N(R')—. In some embodiments, $L^2$ is —C(OH)(H)CH$_2$N(R')—.

In some embodiments, L² is

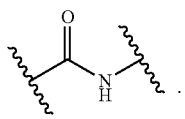 [SMILES: *NC(*)=O]

In some embodiments, L² is

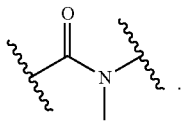 [SMILES: *C(=O)N(*)C]

In some embodiments, L² is

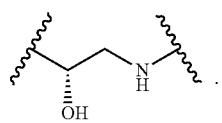 [SMILES: *NC[C@@H](*)O]

In some embodiments, L² is

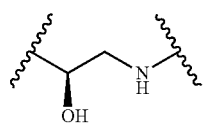

In some embodiments, L² is

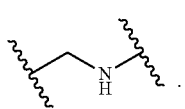

In some embodiments, L² is

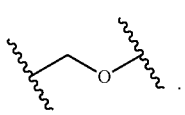

In some embodiments, L² is selected from those depicted in Table 1 below.

As defined generally above, R' is hydrogen or a $C_{1-3}$ aliphatic group.

In some embodiments, R' is hydrogen. In some embodiments, R' is a $C_{1-3}$ aliphatic group. In some embodiments, R' is methyl. In some embodiments, R' is ethyl. In some embodiments, R' is n-propyl.

In some embodiments, R' is selected from those depicted in Table 1 below.

As defined generally above, L³ is selected from the group consisting of —C(O)N(R")—, —OC(O)N(R")—, and —CH₂O—.

In some embodiments, L³ is —C(O)N(R")—. In some embodiments, L³ is —OC(O)N(R")—. In some embodiments, L³ is —CH₂O—. In some embodiments, L³ is —C(O)NH—. In some embodiments, L³ is —OC(O)NH—.

In some embodiments, L³ is

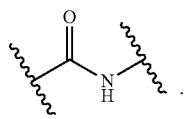 [SMILES: *NC(*)=O]

In some embodiments, L³ is

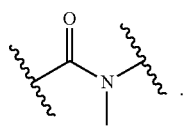 [SMILES: *C(=O)N(*)C]

In some embodiments, L³ is

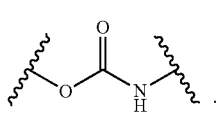

In some embodiments, L³ is

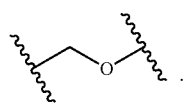

In some embodiments, L³ is

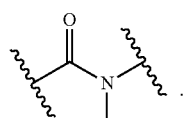

In some embodiments, L³

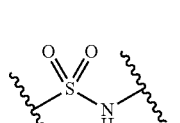

In some embodiments, L³ is selected from those depicted in Table 1 below.

As defined generally above, R" is hydrogen or a $C_{1-3}$ aliphatic group.

In some embodiments, R" is hydrogen. In some embodiments, R" is a $C_{1-3}$ aliphatic group. In some embodiments, R" is methyl. In some embodiments, R" is ethyl. In some embodiments, R" is n-propyl.

In some embodiments, R" is selected from those depicted in Table 1 below.

As defined generally above, R³ is hydrogen or $C_{1-3}$ aliphatic, or: R³ and R⁴ are optionally taken together with their intervening atoms to form a 3-5 membered saturated carbocyclic ring, or $R^3$ and $R^5$ are optionally taken together with their intervening atoms to form a 3-5 membered saturated carbocyclic ring.

In some embodiments, $R^3$ is hydrogen. In some embodiments, $R^3$ is $C_{1-3}$ aliphatic. In some embodiments, $R^3$ and $R^4$ are taken together with their intervening atoms to form a 3-5 membered saturated carbocyclic ring. In some embodiments, $R^3$ and $R^5$ are taken together with their intervening atoms to form a 3-5 membered saturated carbocyclic ring.

In some embodiments, $R^3$ and $R^4$ are taken together to form

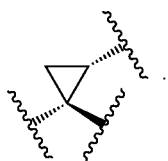

In some embodiments, $R^3$ and $R^4$ are taken together to form

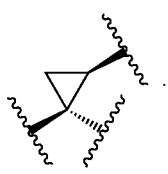

In some embodiments, $R^3$ and $R^4$ are taken together to form

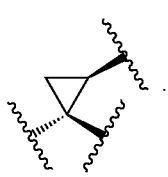

In some embodiments, $R^3$ and $R^4$ are taken together to form

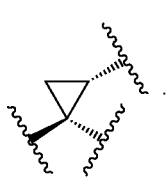

In some embodiments, $R^3$ and $R^5$ are taken together to form

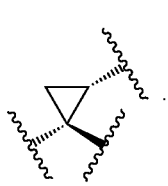

In some embodiments, $R^3$ and $R^5$ are taken together to form

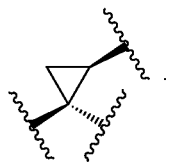

In some embodiments, $R^3$ and $R^5$ are taken together to form

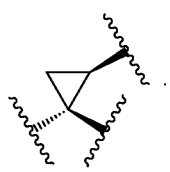

In some embodiments, $R^3$ and $R^5$ are taken together to form

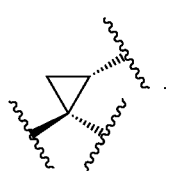

In some embodiments, $R^3$ is selected from those depicted in Table 1 below.

As defined generally above, $R^4$ is hydrogen or $C_{1-3}$ aliphatic.

In some embodiments, $R^4$ is hydrogen. In some embodiments, $R^4$ is $C_{1-3}$ aliphatic.

In some embodiments, $R^4$ is selected from those depicted in Table 1 below.

As defined generally above, $R^5$ is hydrogen or $C_{1-3}$ aliphatic.

In some embodiments, $R^5$ is hydrogen. In some embodiments, $R^5$ is $C_{1-3}$ aliphatic.

In some embodiments, $R^5$ is selected from those depicted in Table 1 below.

As defined generally above, Ring B is phenyl, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur.

In some embodiments, Ring B is phenyl. In some embodiments, Ring B is a 5-6 membered heteroaryl ring having 1-4 heteroatoms independently selected from nitrogen, oxygen, or sulfur. In some embodiments, Ring B is an 8-10 membered bicyclic aryl or heteroaryl ring having 0-3 heteroatoms independently selected from nitrogen, oxygen, or sulfur.

In some embodiments, Ring B is

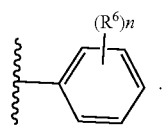

In some embodiments, Ring B is

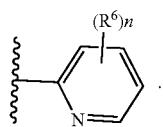

In some embodiments, Ring B is

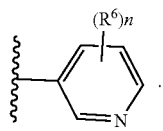

In some embodiments, Ring B is

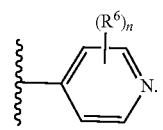

In some embodiments, Ring B is

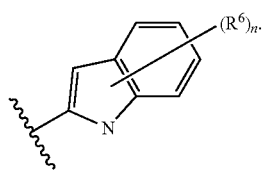

In some embodiments, Ring B is selected from those depicted in Table 1 below.

As defined generally above, each $R^6$ is independently halogen, —CN, —NO$_2$, —NHR, —N(R)$_2$, —OR, or an optionally substituted C$_{1-6}$ aliphatic group, or: two $R^6$ on the same carbon are optionally taken together to form =O; an $R^6$ group and R' group are optionally taken together with their intervening atoms to form a 5-8 membered partially unsaturated fused ring having 0-2 heteroatoms, in addition to the nitrogen, independently selected from nitrogen, oxygen or sulfur; an $R^6$ group and $R^3$ group are optionally taken together with their intervening atoms to form a 5-8 membered partially unsaturated spiro-fused ring having 0-2 heteroatoms independently selected from nitrogen, oxygen or sulfur; or an $R^6$ group and R" group are optionally taken together with their intervening atoms to form a 5-8 membered partially unsaturated fused ring having 0-2 heteroatoms, in addition to the nitrogen, independently selected from nitrogen, oxygen or sulfur.

In some embodiments, $R^6$ is halogen, —CN, —NO$_2$, —NHR, —N(R)$_2$, —OR, or an optionally substituted C$_{1-6}$ aliphatic group. In some embodiments, two $R^6$ on the same carbon are taken together to form =O. In some embodiments, an $R^6$ group and R' group are taken together with their intervening atoms to form a 5-8 membered partially unsaturated fused ring having 0-2 heteroatoms, in addition to the nitrogen, independently selected from nitrogen, oxygen or sulfur. In some embodiments, an $R^6$ group and $R^3$ group are taken together with their intervening atoms to form a 5-8 membered partially unsaturated spiro-fused ring having 0-2 heteroatoms independently selected from nitrogen, oxygen or sulfur. In some embodiments, an $R^6$ group and R" group are taken together with their intervening atoms to form a 5-8 membered partially unsaturated fused ring having 0-2 heteroatoms, in addition to the nitrogen, independently selected from nitrogen, oxygen or sulfur.

In some embodiments, $R^6$ is methyl. In some embodiments, $R^6$ is methoxy. In some embodiments, $R^6$ is fluoro.

In some embodiments, an $R^6$ group and R' group are taken together to form

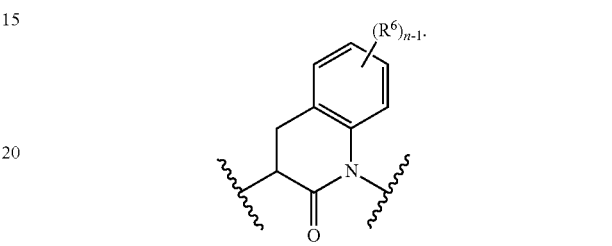

In some embodiments, an $R^6$ group and R' group are taken together to form

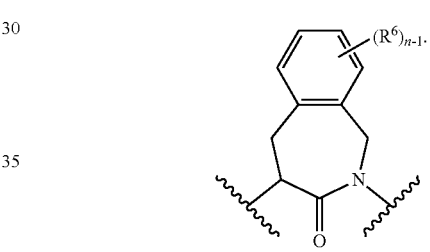

In some embodiments, an $R^6$ group and R" group are taken together to form

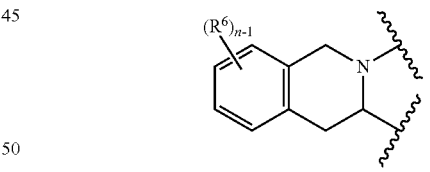

In some embodiments, an $R^6$ group and R" group are taken together to form

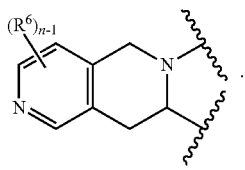

In some embodiments, an $R^6$ group and R" group are taken together to form

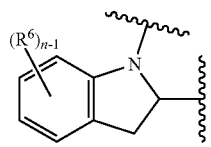

In some embodiments, an $R^6$ group and R" group are taken together to form

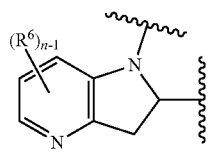

In some embodiments, an $R^6$ group and R" group are taken together to form

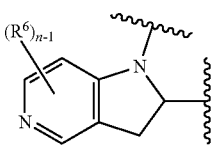

In some embodiments, an $R^6$ group and R" group are taken together to form

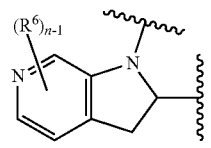

In some embodiments, an $R^6$ group and R" group are taken together to form

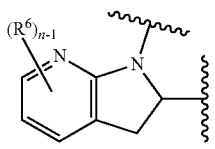

In some embodiments, an $R^6$ group and R" group are taken together to form

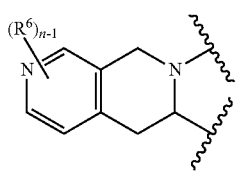

In some embodiments, an $R^6$ group and R" group are taken together to form

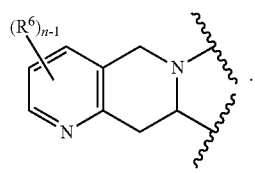

In some embodiments, an $R^6$ group and $R^3$ group are taken together to form

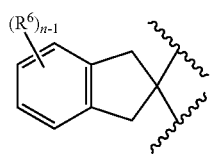

In some embodiments, an $R^6$ group and $R^3$ group are taken together to form

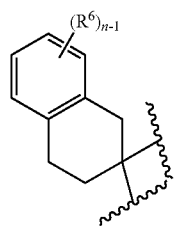

In some embodiments, $R^6$ is selected from those depicted in Table 1 below.

As defined generally above, Ring C is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur.

In some embodiments, Ring C is phenyl. In some embodiments, Ring C is a 3-8 membered saturated or partially unsaturated carbocyclic ring. In some embodiments, Ring C is a 4-7 membered saturated or partially unsaturated heterocyclic ring having 1-2 heteroatoms independently selected from nitrogen, oxygen, or sulfur. In some embodiments, Ring C is a 5-6 membered heteroaryl ring having 1-4 heteroatoms independently selected from nitrogen, oxygen, or sulfur. In some embodiments, Ring C is an 8-10 membered bicyclic aryl or heteroaryl ring having 0-3 heteroatoms independently selected from nitrogen, oxygen, or sulfur.

In some embodiments, Ring C is

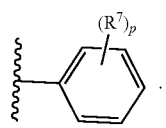

In some embodiments, Ring C is

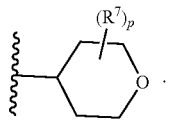

In some embodiments, Ring C is

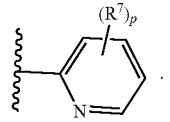

In some embodiments, Ring C is

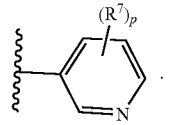

In some embodiments, Ring C is

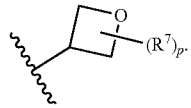

In some embodiments, Ring C is

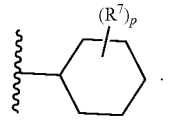

In some embodiments, Ring C is selected from those depicted in Table 1 below.

As defined generally above, $R^7$ is independently halogen, —CN, —NO$_2$, —NHR, —N(R)$_2$, —OR, or an optionally substituted $C_{1-6}$ aliphatic group, or two $R^7$ on the same carbon are optionally taken together to form =O.

As defined generally above, an $R^7$ group and R" group are optionally taken together with their intervening atoms to form a 5-8 membered partially unsaturated fused ring having 0-2 heteroatoms, in addition to the nitrogen, independently selected from nitrogen, oxygen or sulfur.

In some embodiments, $R^7$ is halogen, —CN, —NO$_2$, —NHR, —N(R)$_2$, —OR, or an optionally substituted $C_{1-6}$ aliphatic group. In some embodiments, two $R^7$ on the same carbon are optionally taken together to form =O.

In some embodiments, $R^7$ is fluoro.

In some embodiments, an $R^7$ group and R" group are taken together with their intervening atoms to form

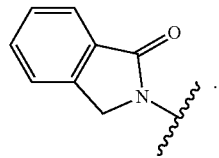 [SMILES: *N1Cc2ccccc2C1=O]

In some embodiments, an $R^7$ group and R" group are taken together with their intervening atoms to form

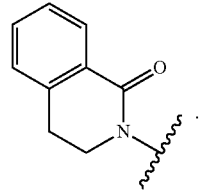 [SMILES: *N1CCc2ccccc2C1=O]

In some embodiments, $R^7$ is selected from those depicted in Table 1 below.

As defined generally above, each of m, n, and p is independently 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1 below.

In some embodiments, n is 0. In some embodiments, n is 1. In some embodiments, n is 2. In some embodiments, n is 3. In some embodiments, n is 4.

In some embodiments, n is selected from those depicted in Table 1 below.

In some embodiments, p is 0. In some embodiments, p is 1. In some embodiments, p is 2. In some embodiments, p is 3. In some embodiments, p is 4.

In some embodiments, p is selected from those depicted in Table 1 below.

In certain embodiments, the present invention provides a compound of formula I, wherein $L^2$ is —C(O)N(R)—, $L^3$ is —C(O)N(R")—, and $R^3$, $R^4$, and R are each hydrogen, thereby forming a compound of formula II:

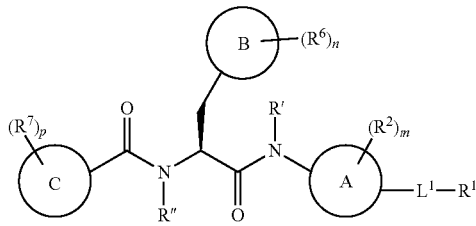

II or a pharmaceutically acceptable salt thereof, wherein each of Ring A, Ring B, Ring C, $L^1$, $R^1$, $R^2$, R, $R^7$, R', R", m, n, and p, is as defined above and described in embodiments herein, both singly and in combination.

In certain embodiments, the present invention provides a compound of formula II, wherein Ring A is phenyl, Ring B is phenyl, and Ring C is phenyl; Ring A is naphthyl, Ring B is phenyl, and Ring C is phenyl; Ring A is phenyl, Ring B is phenyl, and Ring C is cyclohexyl; or Ring A is naphthyl, Ring B is phenyl, and Ring C is cyclohexyl; thereby forming a compound of formula III-a, III-b, III-c, or III-d respectively:

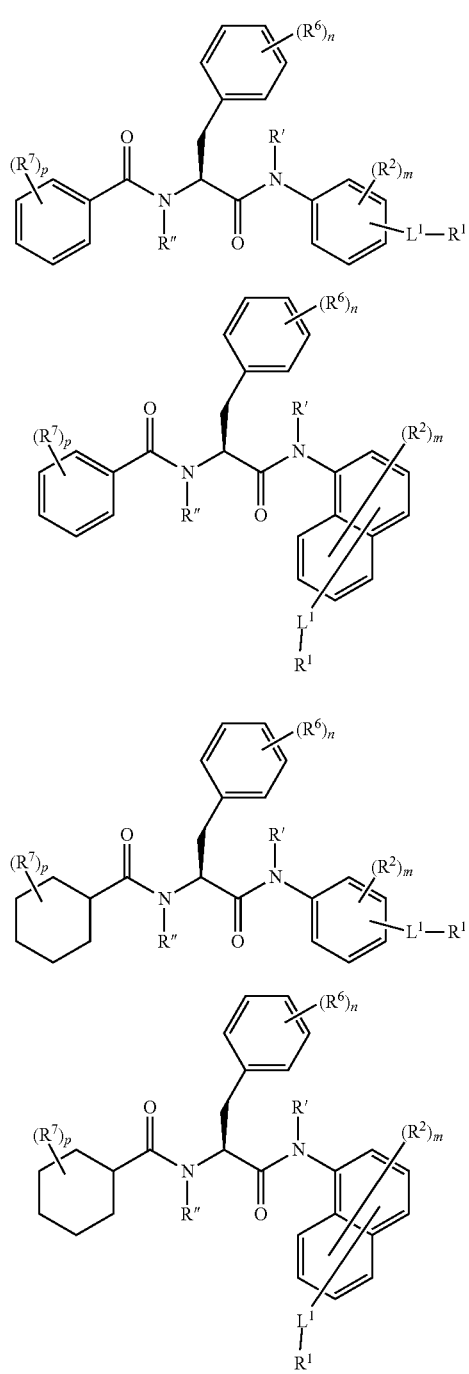

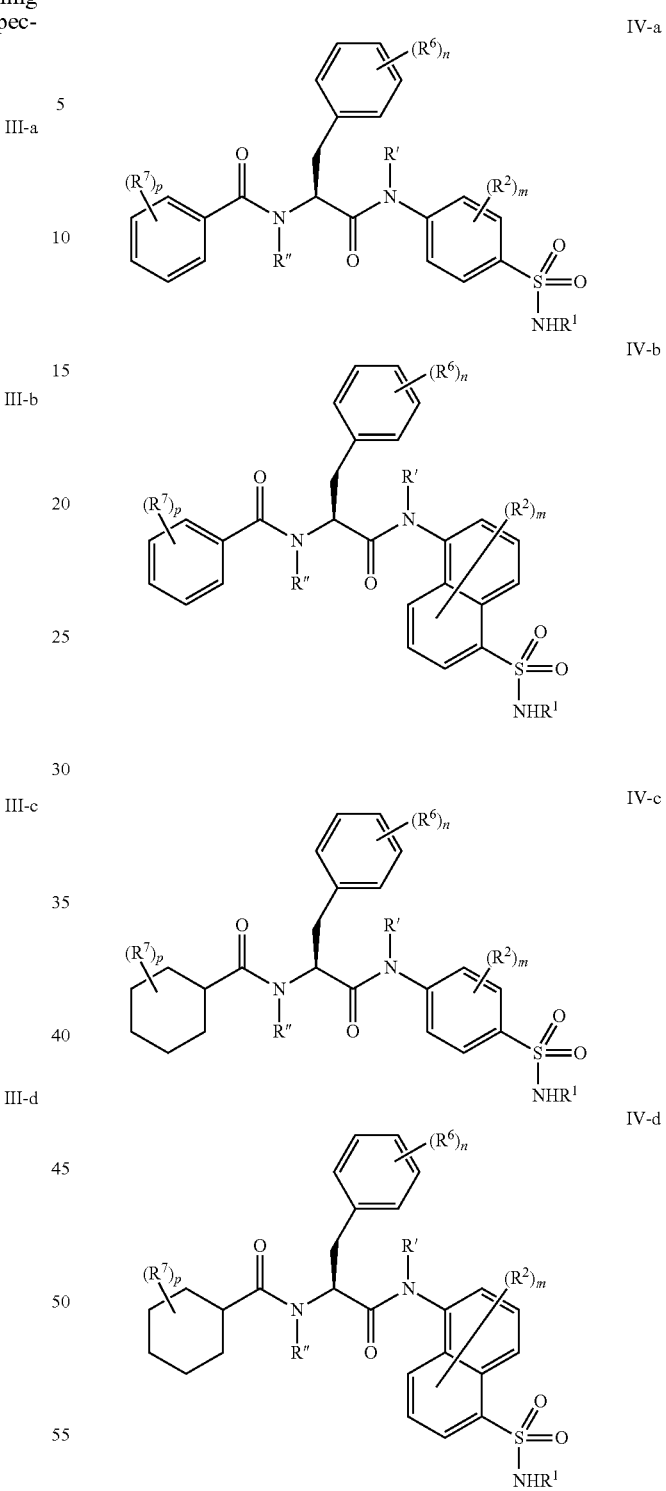

or a pharmaceutically acceptable salt thereof, wherein each of $L^1$, $R^1$, $R^2$, $R^6$, $R^7$, R', R", m, n, and p, is as defined above and described in embodiments herein, both singly and in combination.

In certain embodiments, the present invention provides a compound of formulae III-a, III-b, III-c, or III-d wherein $L^1$ are each —S(O)$_2$N(R)—, wherein the R of —S(O)$_2$N(R)— is hydrogen, thereby forming a compound of formulae IV-a, IV-b, IV-c, and IV-d respectively:

or a pharmaceutically acceptable salt thereof, wherein each of $R^1$, $R^2$, $R^6$, $R^7$, R', R", m, n, and p, is as defined above and described in embodiments herein, both singly and in combination.

In certain embodiments, the present invention provides a compound of formulae III-a, III-b, III-c, or III-d wherein $L^1$ are each —S(O)$_2$—, thereby forming a compound of formulae V-a, V-b, V-c, and V-d respectively:

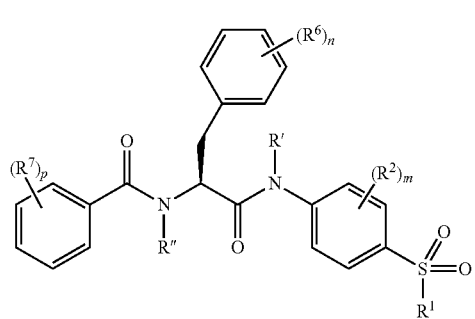

V-a

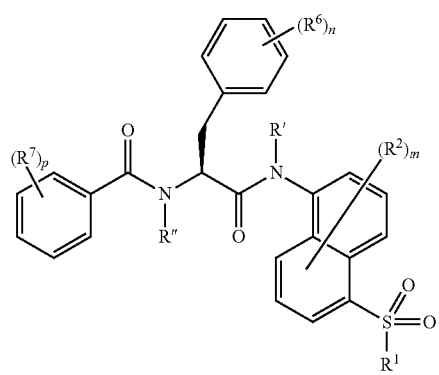

V-b

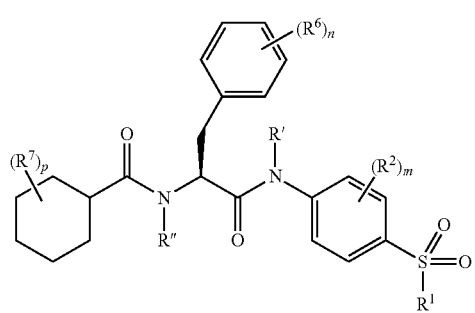

V-c

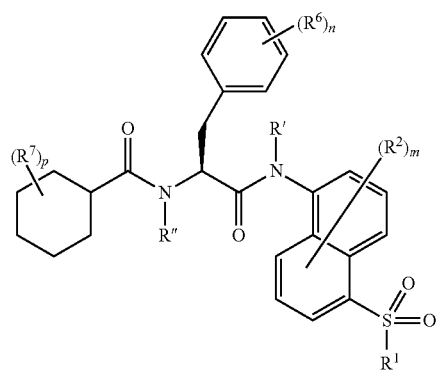

V-d

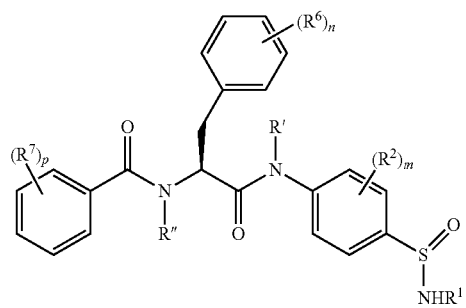

VI-a

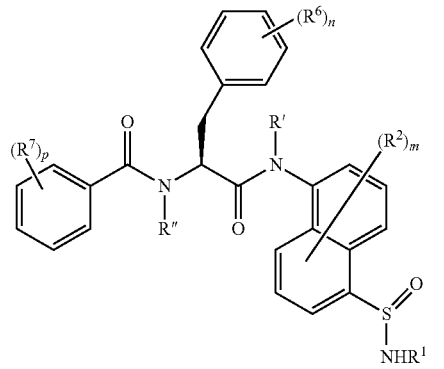

VI-b

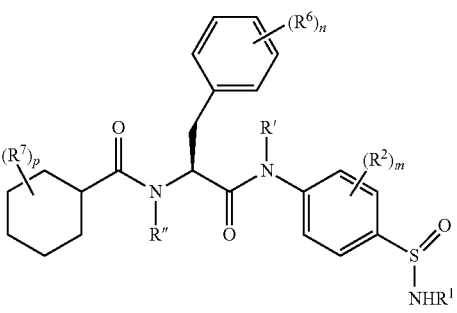

VI-c

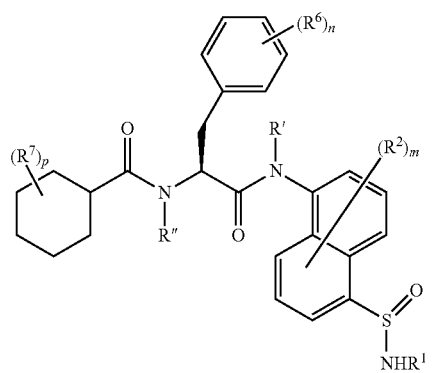

VI-d or a pharmaceutically acceptable salt thereof, wherein each of R, $R^2$, $R^6$, $R^7$, R', R", m, n, and p, is as defined above and described in embodiments herein, both singly and in combination.

In certain embodiments, the present invention provides a compound of formulae III-a, III-b, III-c, or III-d wherein L are each —S(O)N(R)—, wherein the R of —S(O)N(R)— is hydrogen, thereby forming a compound of formulae VI-a, VI-b, VI-c, and VI-d respectively:

or a pharmaceutically acceptable salt thereof, wherein each of $R^1$, $R^2$, $R^6$, $R^7$, R', R", m, n, and p, is as defined above and described in embodiments herein, both singly and in combination.

In certain embodiments, the present invention provides a compound of formulae III-a, wherein an $R^6$ group and R' group are taken together with their intervening atoms to form a 6 membered partially unsaturated fused ring, or an $R^6$ group and R" group are taken together with their intervening atoms to form a 5 membered partially unsaturated fused ring, thereby forming a compound of formulae VII-a, and VII-b respectively:

VII-a

VII-b

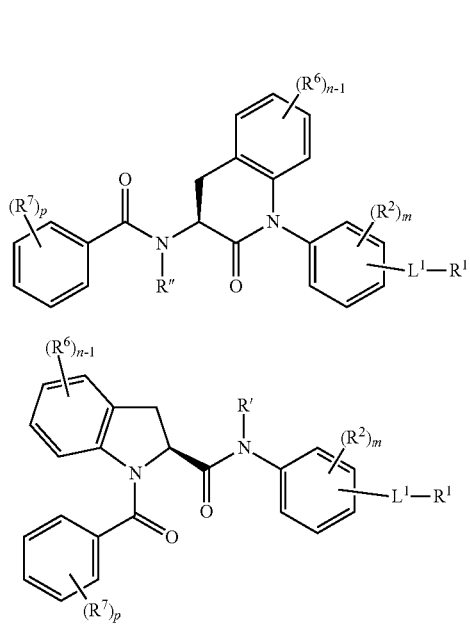

or a pharmaceutically acceptable salt thereof, wherein each of $L^1$, $R^1$, $R^2$, $R^6$, $R^7$, R', R", m, n, and p, is as defined above and described in embodiments herein, both singly and in combination.

In certain embodiments, the present invention provides a compound of formula I, wherein $L^2$ is —C(O)N(R')—, $L^3$ is —C(O)N(R")—, Ring B is phenyl, $R^4$ is hydrogen, $R^5$ is hydrogen, and an $R^6$ group and $R^3$ group are taken together with their intervening atoms to form a 5 membered partially unsaturated fused ring, thereby forming a compound of formula VIII:

VIII

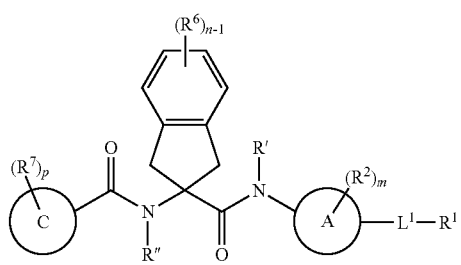

or a pharmaceutically acceptable salt thereof, wherein each of Ring A, Ring C, L, $R^1$, $R^2$, $R^6$, $R^7$, R', R", m, n, and p, is as defined above and described in embodiments herein, both singly and in combination.

In certain embodiments, the present invention provides a compound of formula I, wherein $L^2$ is —C(O)N(R')—, $L^3$ is —C(O)N(R")—, Ring B is phenyl, $R^4$ is hydrogen, $R^5$ is hydrogen, and an $R^6$ group and $R^3$ group are taken together with their intervening atoms to form a 6 membered partially unsaturated fused ring, thereby forming a compound of formula IX:

IX

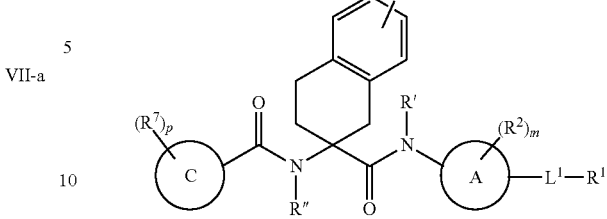

or a pharmaceutically acceptable salt thereof, wherein each of Ring A, Ring C, $L^1$, $R^1$, $R^2$, $R^6$, $R^7$, R', R", m, n, and p, is as defined above and described in embodiments herein, both singly and in combination.

In certain embodiments, the present invention provides a compound of formula I, wherein $L^2$ is —C(O)N(R')—, $L^3$ is —C(O)N(R")—, Ring B is phenyl, $R^3$ is hydrogen, $R^4$ is hydrogen, $R^5$ is hydrogen, and an $R^6$ group and R' group are taken together with their intervening atoms to form a 6 membered partially unsaturated fused ring, thereby forming a compound of formula X:

X

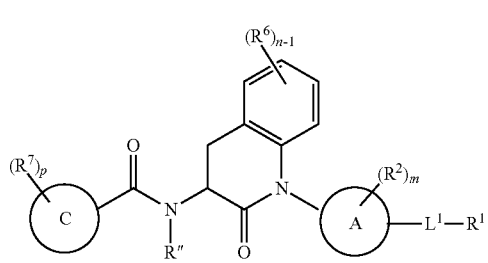

or a pharmaceutically acceptable salt thereof, wherein each of Ring A, Ring C, $L^1$, $R^1$, $R^2$, $R^6$, $R^7$, R", m, n, and p, is as defined above and described in embodiments herein, both singly and in combination.

In certain embodiments, the present invention provides a compound of formula I, wherein $L^2$ is —C(O)N(R')—, $L^3$ is —C(O)N(R")—, Ring B is phenyl, $R^3$ is hydrogen, $R^4$ is hydrogen, $R^5$ is hydrogen, and an $R^6$ group and R' group are taken together with their intervening atoms to form a 7 membered partially unsaturated fused ring, thereby forming a compound of formula XI:

XI

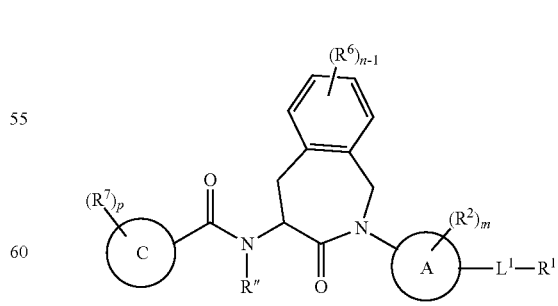

or a pharmaceutically acceptable salt thereof, wherein each of Ring A, Ring C, $L^1$, $R^1$, $R^2$, $R^6$, $R^7$, R", m, n, and p, is as defined above and described in embodiments herein, both singly and in combination.

In certain embodiments, the present invention provides a compound of formula I, wherein L² is —C(O)N(R')—, L³ is —C(O)N(R")—, Ring B is phenyl, R³ is hydrogen, R⁴ is hydrogen, R is hydrogen, and an R⁶ group and R" group are taken together with their intervening atoms to form a 5 membered partially unsaturated fused ring, thereby forming a compound of formula XII.

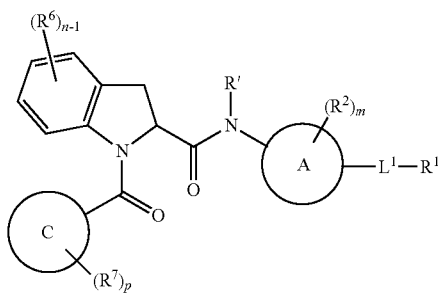

XII or a pharmaceutically acceptable salt thereof, wherein each of Ring A, Ring C, L¹, R¹, R², R⁶, R⁷, R, m, n, and p, is as defined above and described in embodiments herein, both singly and in combination.

In certain embodiments, the present invention provides a compound of formula I, wherein L² is —C(O)N(R')—, L³ is —C(O)N(R")—, Ring B is phenyl, R³ is hydrogen, R⁴ is hydrogen, R⁵ is hydrogen, and an R⁶ group and R" group are taken together with their intervening atoms to form a 6 membered partially unsaturated fused ring, thereby forming a compound of formula XIII:

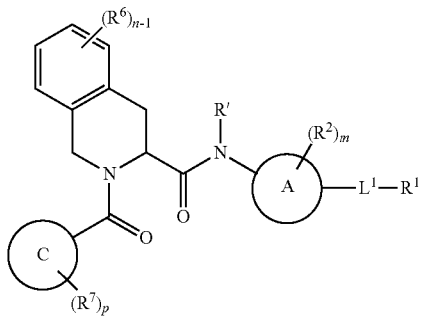

XIII or a pharmaceutically acceptable salt thereof, wherein each of Ring A, Ring C, L¹, R¹, R², R⁶, R⁷, R, m, n, and p, is as defined above and described in embodiments herein, both singly and in combination.

In certain embodiments, the present invention provides a compound of formula I, wherein L² is —C(O)N(R)—, L³ is —C(O)N(R")—, Ring C is phenyl, R³, R⁴, and R⁵ are each hydrogen, and an R⁷ group and R" group are taken together with their intervening atoms to form a 5 membered partially unsaturated fused ring or a 6 membered partially unsaturated fused ring thereby forming a compound of formula XIV-a or XIV-b:

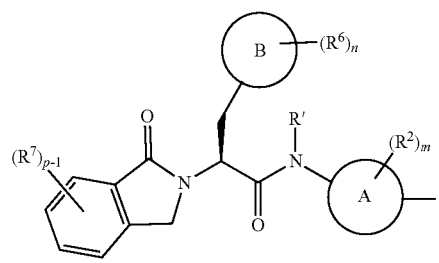

XIV-a

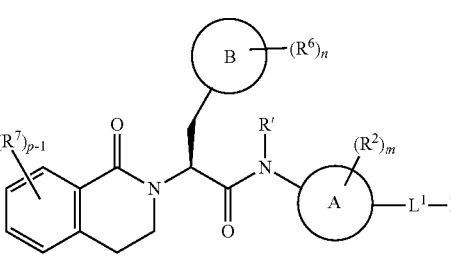

XIV-b or a pharmaceutically acceptable salt thereof, wherein each of Ring A, Ring B, L¹, R¹, R², R⁶, R⁷, R', m, n, and p, is as defined above and described in embodiments herein, both singly and in combination.

In certain embodiments, the present invention provides a compound of formula II, wherein Ring A is phenyl, Ring B is phenyl, and Ring C is 2-pyridyl; Ring A is phenyl, Ring B is phenyl, and Ring C is 3-pyridyl; Ring A is phenyl, Ring B is phenyl, and Ring C is 3-oxetanyl; or Ring A is phenyl, Ring B is 3-pyridyl, and Ring C is phenyl; thereby forming a compound of formula XV-a, XV-b, XV-c, or XV-d respectively:

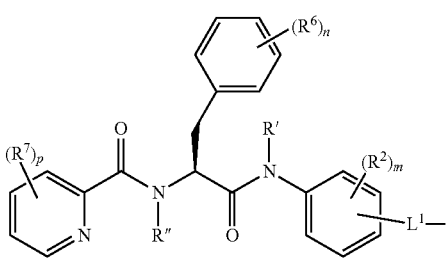

XV-a

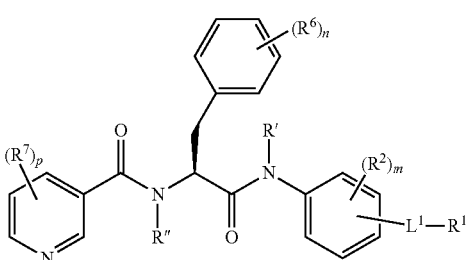

XV-b

XV-c

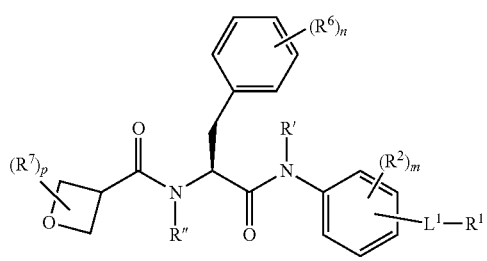

XVI-c

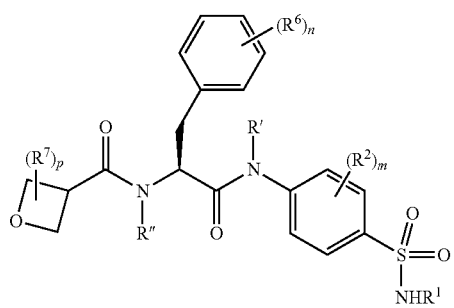

XV-d

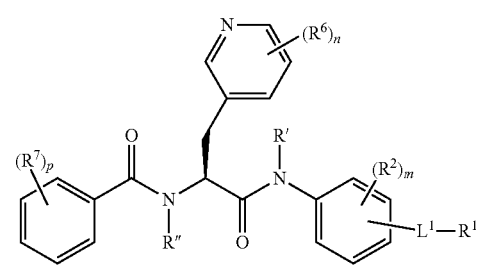

XVI-d

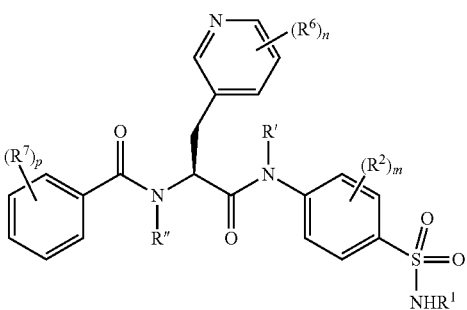

or a pharmaceutically acceptable salt thereof, wherein each of $L^1$, $R^1$, $R^2$, $R^6$, $R^7$, R', R'', m, n, and p, is as defined above and described in embodiments herein, both singly and in combination.

In certain embodiments, the present invention provides a compound of formulae XV-a, XV-b, XV-c, or XV-d wherein $L^1$ are each —S(O)$_2$N(R)—, wherein the R of —S(O)$_2$N(R)— is hydrogen, thereby forming a compound of formulae XVI-a, XVI-b, XVI-c, and XVI-d respectively:

or a pharmaceutically acceptable salt thereof, wherein each of $R^1$, $R^2$, $R^6$, $R^7$, R', R'', m, n, and p, is as defined above and described in embodiments herein, both singly and in combination.

In certain embodiments, the present invention provides a compound of formula II, wherein Ring A is 3-pyridyl, Ring B is phenyl, and Ring C is phenyl; Ring A is 2-pyridyl, Ring B is phenyl, and Ring C is phenyl; Ring A is tetrahydroquinolyl, Ring B is phenyl, and Ring C is cyclohexyl; or Ring A is tetrahydroquinolyl, Ring B is phenyl, and Ring C is phenyl; thereby forming a compound of formula XVII-a, XVII-b, XVII-c, or XVII-d respectively:

XVI-a

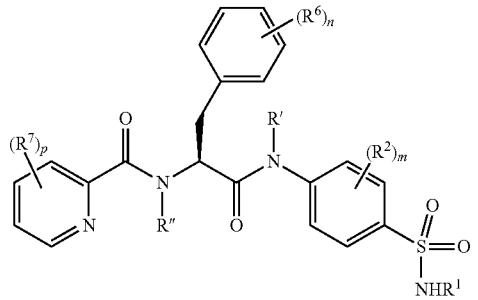

XVII-a

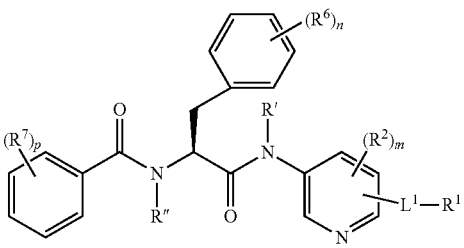

XVI-b

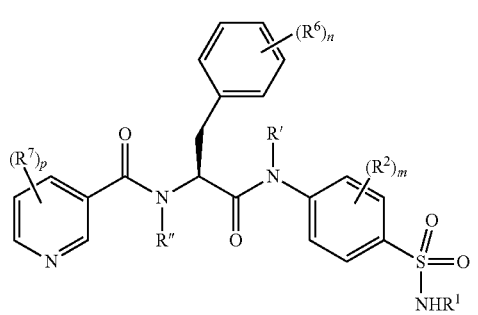

XVII-b

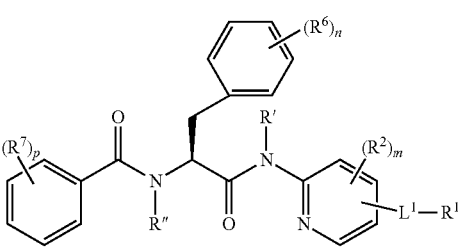

XVII-c

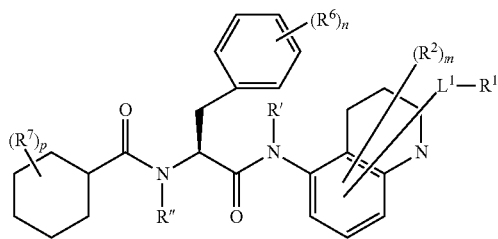

XVIII-c

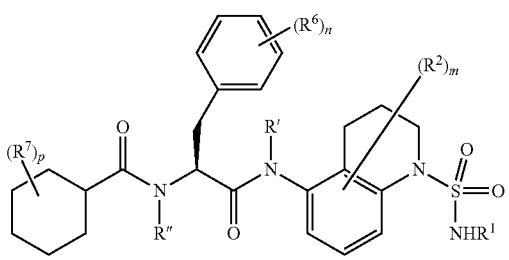

XVII-d

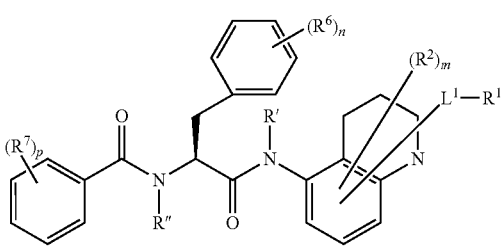

XVIII-d

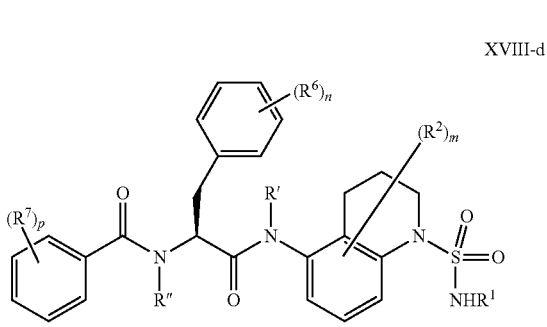

or a pharmaceutically acceptable salt thereof, wherein each of $L^1$, $R^1$, $R^2$, $R^6$, $R^7$, R', R'', m, n, and p, is as defined above and described in embodiments herein, both singly and in combination.

In certain embodiments, the present invention provides a compound of formulae XVII-a, XVII-b, XVII-c, or XVII-d wherein $L^1$ are each —S(O)$_2$N(R)—, wherein the R of —S(O)$_2$N(R)— is hydrogen, thereby forming a compound of formulae XVIII-a, XVIII-b, XVIII-c, and XVIII-d respectively:

XVIII-a

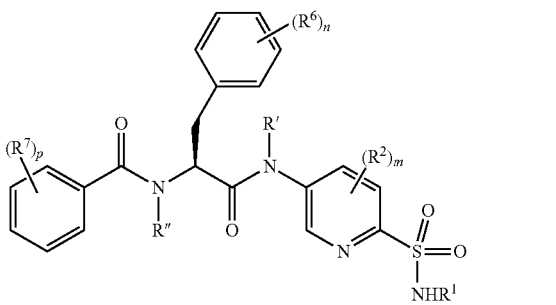

XVIII-b

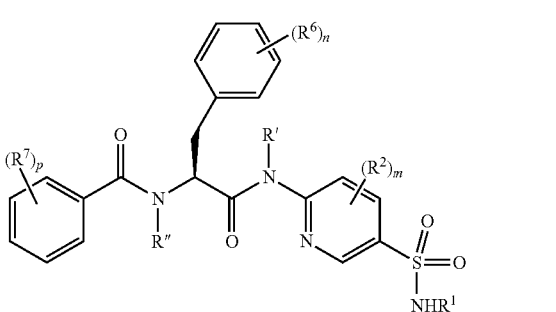

or a pharmaceutically acceptable salt thereof, wherein each of $R^1$, $R^2$, $R^6$, $R^7$, R', R'', m, n, and p, is as defined above and described in embodiments herein, both singly and in combination.

In certain embodiments, the present invention provides a compound of formula II, wherein Ring A is phenyl, Ring B is phenyl, Ring C is phenyl, $R^2$ is methoxy, and m is 1; Ring A is phenyl, Ring B is phenyl, Ring C is phenyl, $R^2$ is methoxy, and m is 1; Ring A is phenyl, Ring B is phenyl, Ring C is phenyl, $R^2$ is fluoro, and m is 1; or Ring A is phenyl, Ring B is phenyl, Ring C is phenyl, $R^2$ is fluoro, and m is 1; thereby forming a compound of formula XIX-a, XIX-b, XIX-c, or XIX-d respectively:

XIX-a

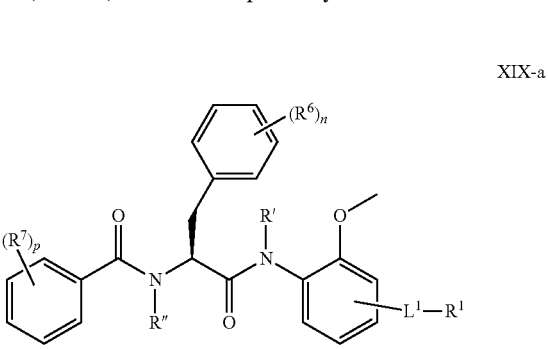

XIX-b

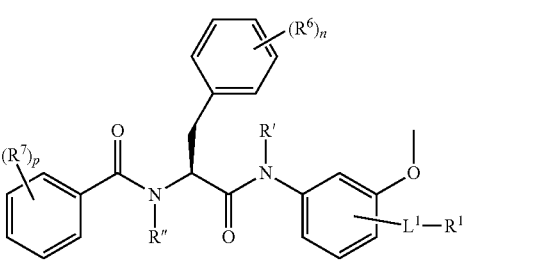

XIX-c

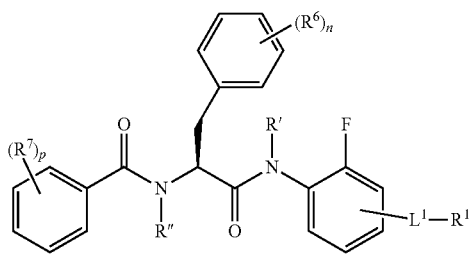

XIX-d

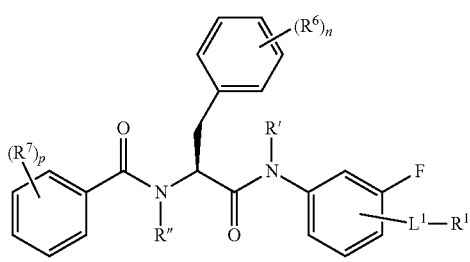

or a pharmaceutically acceptable salt thereof, wherein each of L, $R^1$, $R^6$, $R^7$, R', R", n, and p, is as defined above and described in embodiments herein, both singly and in combination.

In certain embodiments, the present invention provides a compound of formulae XIX-a, XIX-b, XIX-c, or XIX-d wherein $L^1$ are each —S(O)$_2$N(R)—, wherein the R of —S(O)$_2$N(R)— is hydrogen, thereby forming a compound of formulae XX-a, XX-b, XX-c, and XX-d respectively:

XX-a

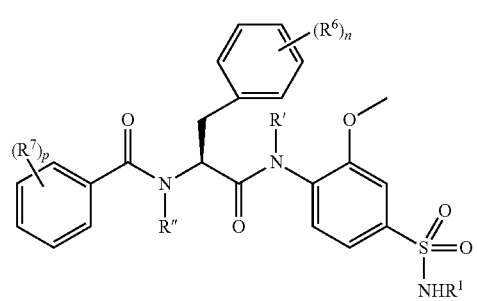

XX-b

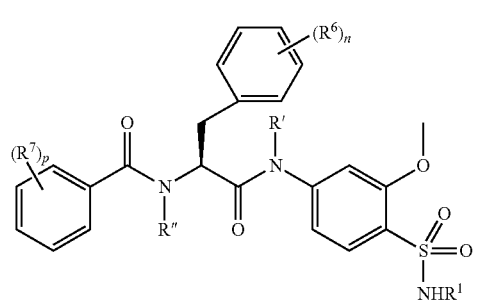

XX-c

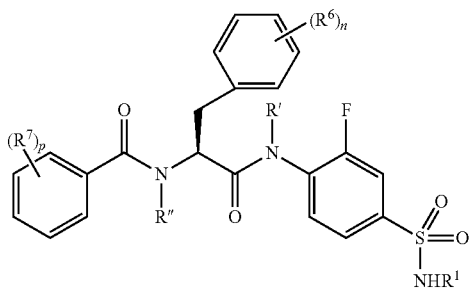

XX-d

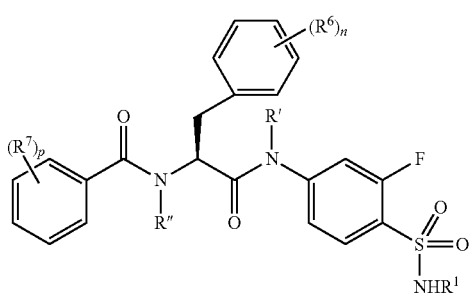

or a pharmaceutically acceptable salt thereof, wherein each of $R^1$, $R^6$, $R^7$, R', R", n, and p, is as defined above and described in embodiments herein, both singly and in combination.

In certain embodiments, the present invention provides a compound of formula II, wherein Ring A is phenyl, Ring B is 2-pyridyl, and Ring C is phenyl; thereby forming a compound of formula XXI:

XXI

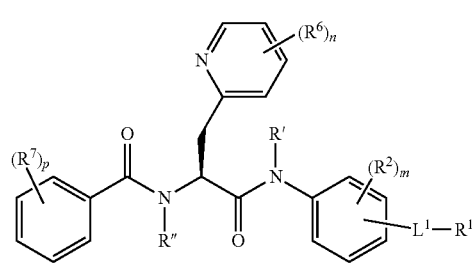

or a pharmaceutically acceptable salt thereof, wherein each of $L^1$, $R^1$, $R^2$, $R^6$, $R^7$, R', R", m, n, and p, is as defined above and described in embodiments herein, both singly and in combination.

In certain embodiments, the present invention provides a compound of formulae XXI wherein $L^1$ is —S(O)$_2$N(R)—, wherein the R of —S(O)$_2$N(R)— is hydrogen, thereby forming a compound of formulae XXII:

XXII

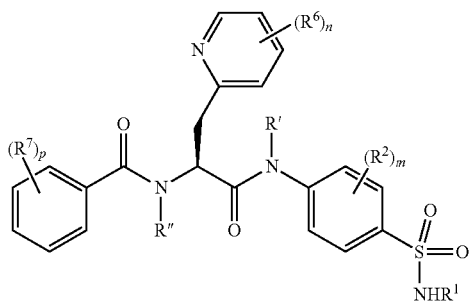

or a pharmaceutically acceptable salt thereof, wherein each of R, $R^2$, $R^6$, $R^7$, R', R", m, n, and p, is as defined above and described in embodiments herein, both singly and in combination.

In certain embodiments, the present invention provides a compound of formula II, wherein Ring A is phenyl, Ring B is phenyl, Ring C is phenyl, $R^2$ is methyl, and m is 1 or Ring A is phenyl, Ring B is phenyl, Ring C is phenyl, $R^2$ is methyl, and m is 1, thereby forming a compound of formula XXIII-a or XXIII-b respectively:

XXIII-a

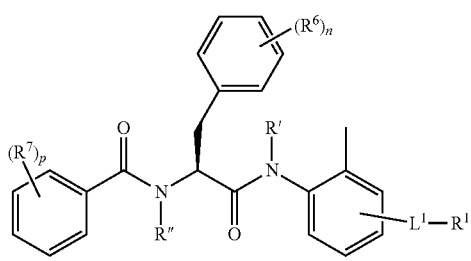

XXIII-b

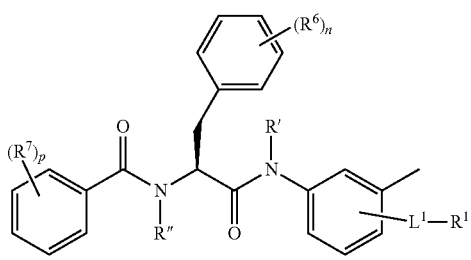

or a pharmaceutically acceptable salt thereof, wherein each of L, R, $R^6$, $R^7$, R', R", n, and p, is as defined above and described in embodiments herein, both singly and in combination.

In certain embodiments, the present invention provides a compound of formulae XXIII-a or XXIII-b wherein $L^1$ are each —S(O)$_2$N(R)—, wherein the R of —S(O)$_2$N(R)— is hydrogen, thereby forming a compound of formulae XXIV-a or XXIV-b respectively:

XXIV-a

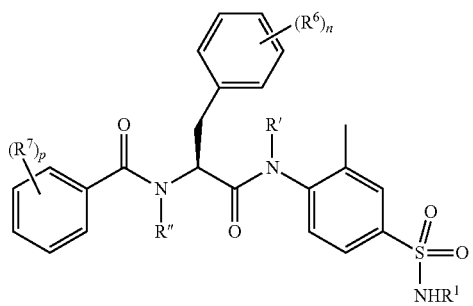

XXIV-b

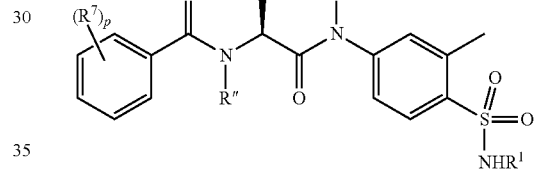

or a pharmaceutically acceptable salt thereof, wherein each of $R^1$, $R^6$, $R^7$, R', R", n, and p, is as defined above and described in embodiments herein, both singly and in combination.

In certain embodiments, the present invention provides a compound of formula II, wherein Ring A is phenyl, Ring B is phenyl, Ring C is phenyl, $R^2$ is cyano, and m is 1; Ring A is phenyl, Ring B is phenyl, Ring C is phenyl, $R^2$ is cyano, and m is 1; Ring A is phenyl, Ring B is phenyl, Ring C is phenyl, $R^2$ is chloro, and m is 1; or Ring A is phenyl, Ring B is phenyl, Ring C is phenyl, $R^2$ is chloro, and m is 1; thereby forming a compound of formula XXV-a, XXV-b, XXV-c, or XXV-d respectively:

XXV-a

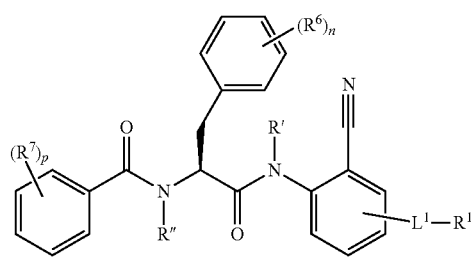

XXV-b

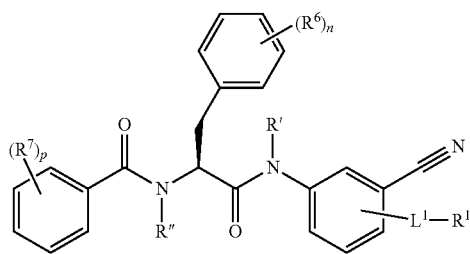

XXV-c

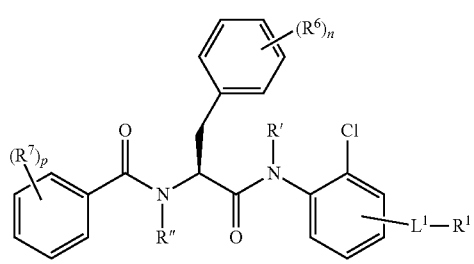

XXV-d

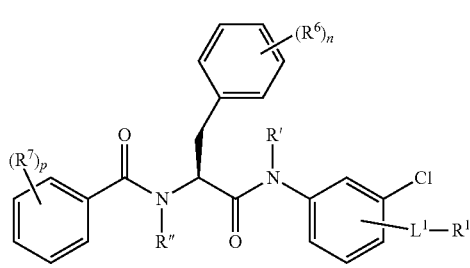

or a pharmaceutically acceptable salt thereof, wherein each of L, $R^1$, $R^6$, $R^7$, R', R", n, and p, is as defined above and described in embodiments herein, both singly and in combination.

In certain embodiments, the present invention provides a compound of formulae XXV-a, XXV-b, XXV-c, or XXV-d wherein $L^1$ are each —S(O)$_2$N(R)—, wherein the R of —S(O)$_2$N(R)— is hydrogen, thereby forming a compound of formulae XXVI-a, XXVI-b, XXVI-c, and XXVI-d respectively.

XXVI-a

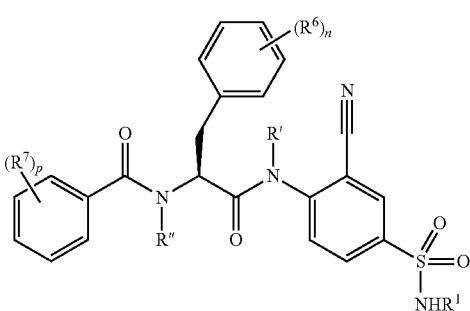

XXVI-b

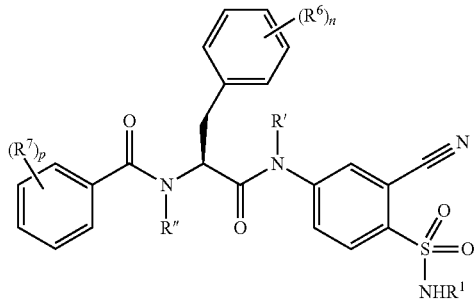

XXVI-c

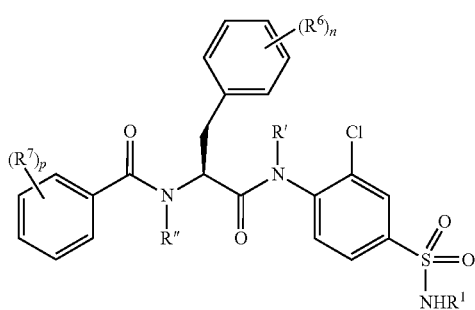

XXVI-d

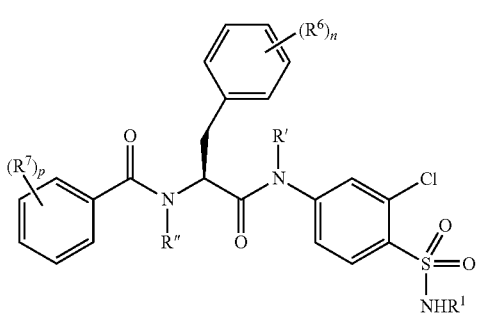

or a pharmaceutically acceptable salt thereof, wherein each of $R^1$, $R^6$, $R^7$, R', R", n, and p, is as defined above and described in embodiments herein, both singly and in combination.

Exemplary compounds of the invention are set forth in Table 1, below.

TABLE 1

Exemplary Compounds

| Compound | Structure |
|---|---|
| I-1 | 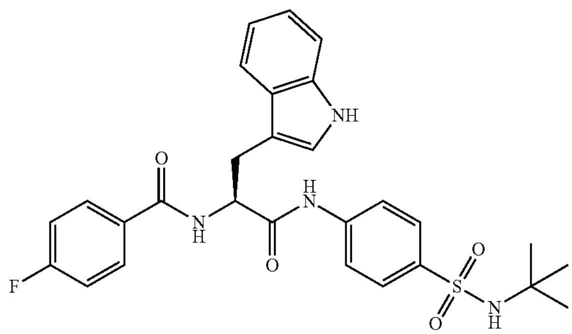 [SMILES: CC(C)(C)NS(=O)(=O)c1ccc(NC(=O)[C@H](Cc2c[nH]c3ccccc23)NC(=O)c2ccc(F)cc2)cc1] |
| I-2 | 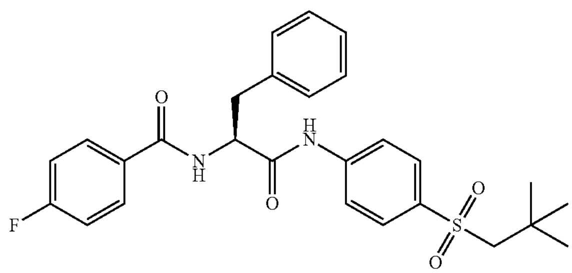 [SMILES: CC(C)(C)CS(=O)(=O)c1ccc(NC(=O)[C@H](Cc2ccccc2)NC(=O)c2ccc(F)cc2)cc1] |
| I-3 | 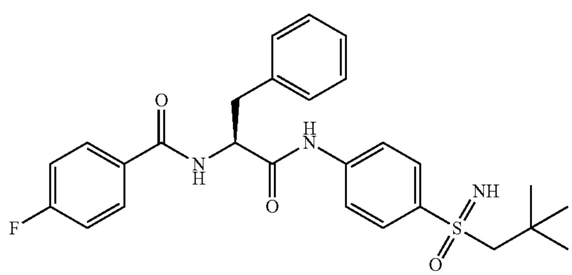 [SMILES: CC(C)(C)CS(=N)(=O)c1ccc(NC(=O)[C@H](Cc2ccccc2)NC(=O)c2ccc(F)cc2)cc1] |
| I-4 | 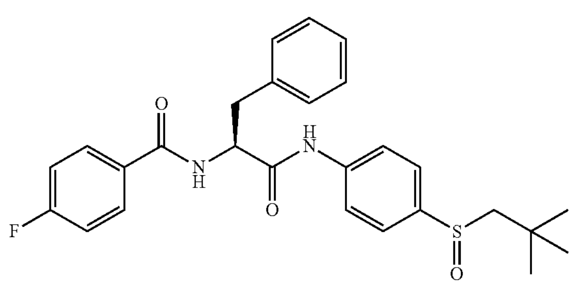 [SMILES: CC(C)(C)CS(=O)c1ccc(NC(=O)[C@H](Cc2ccccc2)NC(=O)c2ccc(F)cc2)cc1] |
| I-5 | 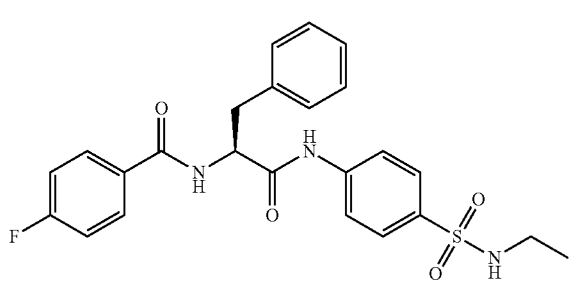 |

TABLE 1-continued

Exemplary Compounds

| Compound | Structure |
|---|---|
| I-6 | 4-fluoro-N-[(S)-1-{[4-(N-cyclopropylsulfamoyl)phenyl]carbamoyl}-2-phenylethyl]benzamide |
| I-7 | 4-fluoro-N-[(S)-1-{[4-(N-cyclobutylsulfamoyl)phenyl]carbamoyl}-2-phenylethyl]benzamide |
| I-8 | 4-fluoro-N-[(S)-1-{[4-(N-cyclopentylsulfamoyl)phenyl]carbamoyl}-2-phenylethyl]benzamide |
| I-9 | 4-fluoro-N-[(S)-1-{[4-(N-cyclopropylmethylsulfamoyl)phenyl]carbamoyl}-2-phenylethyl]benzamide |
| I-10 | 4-fluoro-N-[(S)-1-{[4-(N-(1-fluoro-2-methylpropan-2-yl)sulfamoyl)phenyl]carbamoyl}-2-phenylethyl]benzamide |

TABLE 1-continued
Exemplary Compounds
| Compound | Structure |
|---|---|
| I-11 | 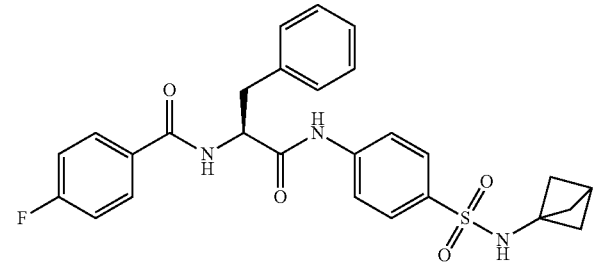 [SMILES: O=C(N[C@@H](Cc1ccccc1)C(=O)Nc1ccc(S(=O)(=O)NC23CC(C2)C3)cc1)c1ccc(F)cc1] |
| I-12 | 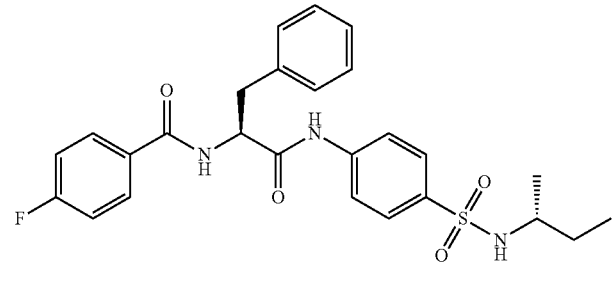 [SMILES: CC[C@@H](C)NS(=O)(=O)c1ccc(NC(=O)[C@H](Cc2ccccc2)NC(=O)c2ccc(F)cc2)cc1] |
| I-13 | 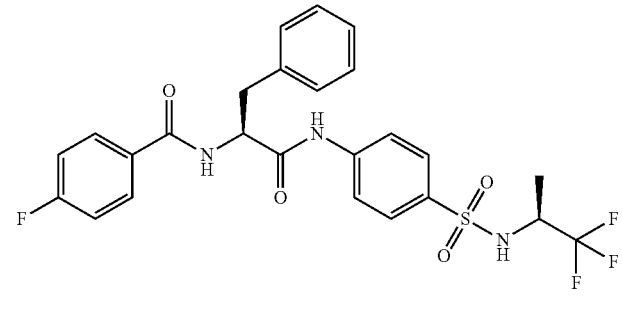 [SMILES: C[C@H](NS(=O)(=O)c1ccc(NC(=O)[C@H](Cc2ccccc2)NC(=O)c2ccc(F)cc2)cc1)C(F)(F)F] |
| I-14 | 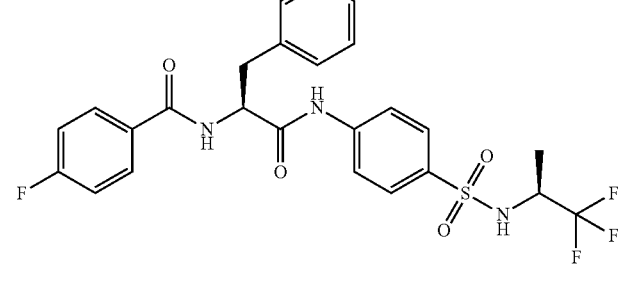 |
| I-15 | 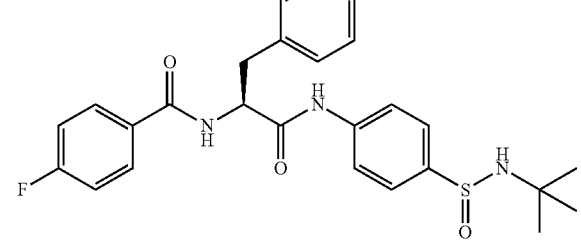 |

TABLE 1-continued

Exemplary Compounds

| Compound | Structure |
|---|---|
| I-16 | 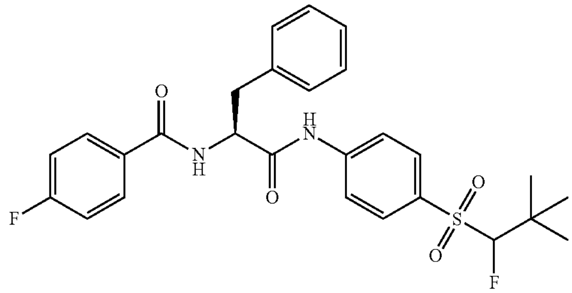 [SMILES: CC(C)(C)C(F)S(=O)(=O)c1ccc(NC(=O)[C@H](Cc2ccccc2)NC(=O)c2ccc(F)cc2)cc1] |
| I-17 | 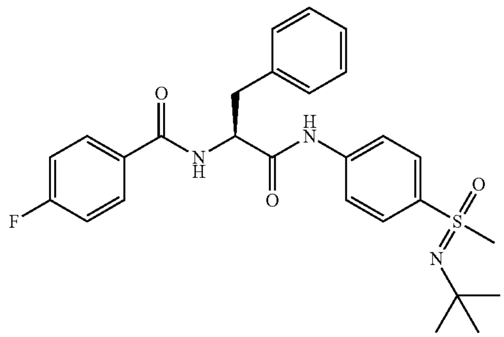 [SMILES: CC(C)(C)N=S(C)(=O)c1ccc(NC(=O)[C@H](Cc2ccccc2)NC(=O)c2ccc(F)cc2)cc1] |
| I-18 | 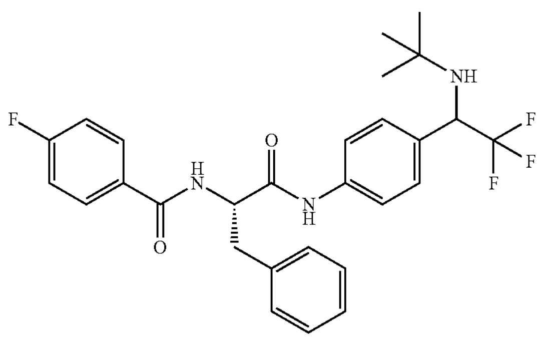 [SMILES: CC(C)(C)NC(c1ccc(NC(=O)[C@H](Cc2ccccc2)NC(=O)c2ccc(F)cc2)cc1)C(F)(F)F] |
| I-19 | 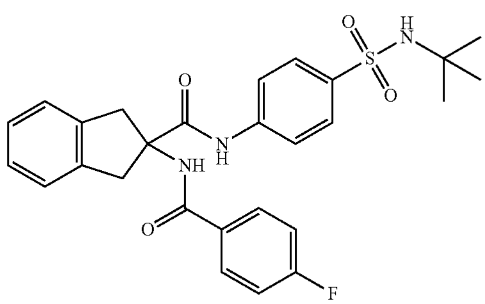 [SMILES: CC(C)(C)NS(=O)(=O)c1ccc(NC(=O)C2(NC(=O)c3ccc(F)cc3)Cc3ccccc3C2)cc1] |
| I-20 | 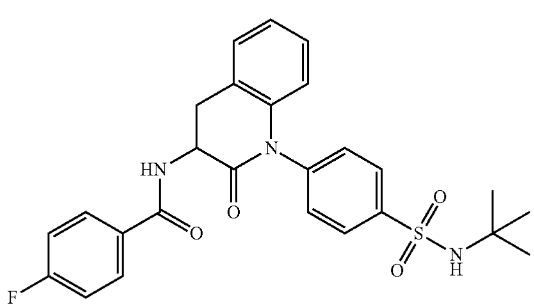 [SMILES: CC(C)(C)NS(=O)(=O)c1ccc(N2C(=O)C(NC(=O)c3ccc(F)cc3)Cc3ccccc32)cc1] |

TABLE 1-continued
Exemplary Compounds
| Compound | Structure |
| --- | --- |
| I-21 | 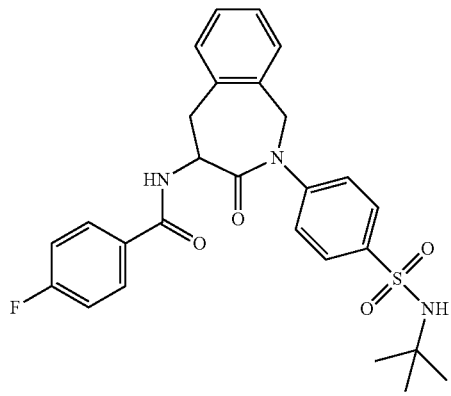 [SMILES: CC(C)(C)NS(=O)(=O)c1ccc(N2Cc3ccccc3CC(NC(=O)c3ccc(F)cc3)C2=O)cc1] |
| I-22 | 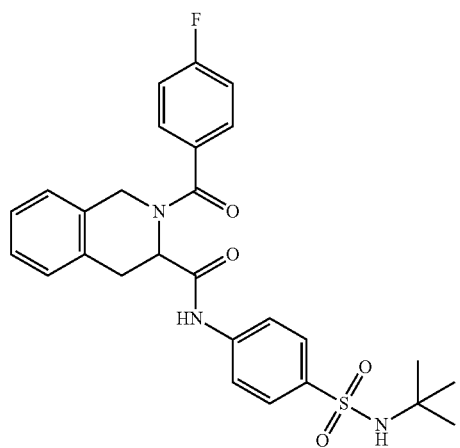 [SMILES: CC(C)(C)NS(=O)(=O)c1ccc(NC(=O)C2Cc3ccccc3CN2C(=O)c2ccc(F)cc2)cc1] |
| I-23 | 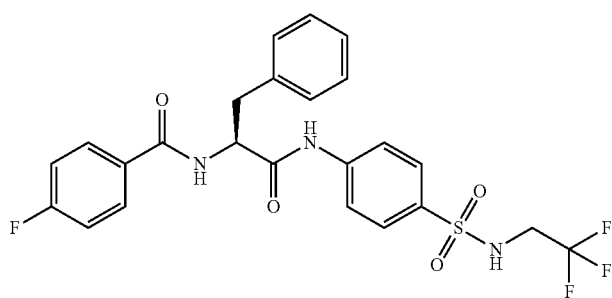 [SMILES: O=C(N[C@@H](Cc1ccccc1)C(=O)Nc1ccc(S(=O)(=O)NCC(F)(F)F)cc1)c1ccc(F)cc1] |
| I-24 | 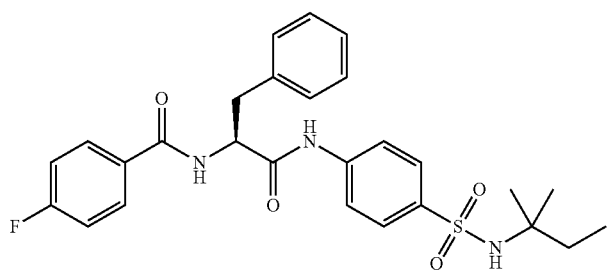 [SMILES: CCC(C)(C)NS(=O)(=O)c1ccc(NC(=O)[C@H](Cc2ccccc2)NC(=O)c2ccc(F)cc2)cc1] |

TABLE 1-continued

Exemplary Compounds

| Compound | Structure |
|---|---|
| I-25 | 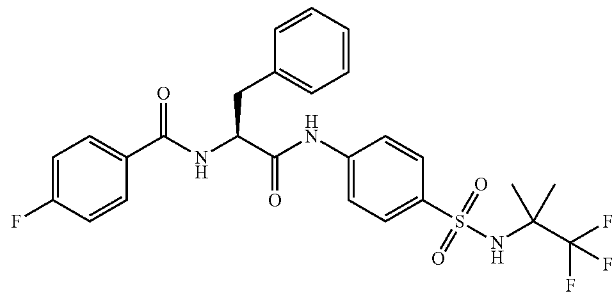 [SMILES: CC(C)(NS(=O)(=O)c1ccc(NC(=O)[C@H](Cc2ccccc2)NC(=O)c2ccc(F)cc2)cc1)C(F)(F)F] |
| I-26 | 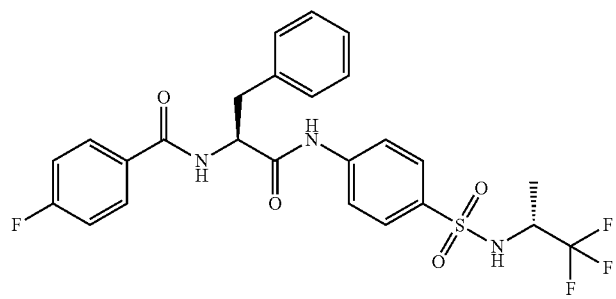 [SMILES: C[C@@H](NS(=O)(=O)c1ccc(NC(=O)[C@H](Cc2ccccc2)NC(=O)c2ccc(F)cc2)cc1)C(F)(F)F] |
| I-27 | 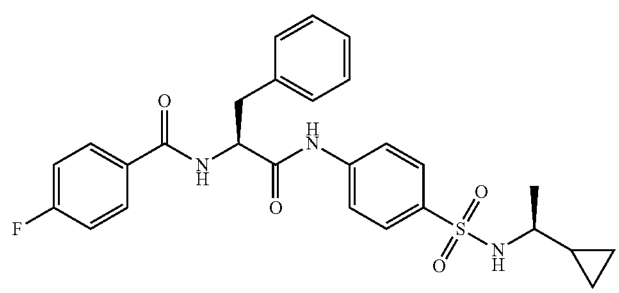 [SMILES: C[C@H](NS(=O)(=O)c1ccc(NC(=O)[C@H](Cc2ccccc2)NC(=O)c2ccc(F)cc2)cc1)C1CC1] |
| I-28 | 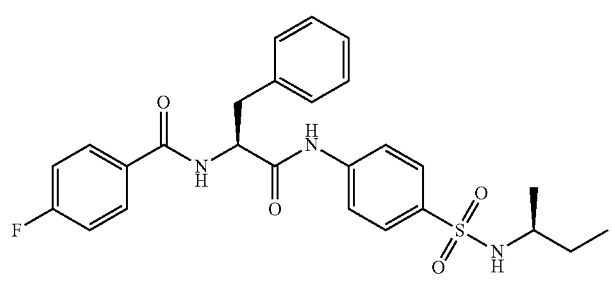 [SMILES: CC[C@H](C)NS(=O)(=O)c1ccc(NC(=O)[C@H](Cc2ccccc2)NC(=O)c2ccc(F)cc2)cc1] |
| I-29 | 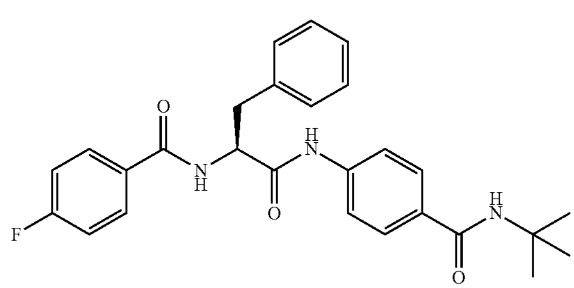 [SMILES: CC(C)(C)NC(=O)c1ccc(NC(=O)[C@H](Cc2ccccc2)NC(=O)c2ccc(F)cc2)cc1] |

TABLE 1-continued
Exemplary Compounds
| Compound | Structure |
|---|---|
| I-30 | 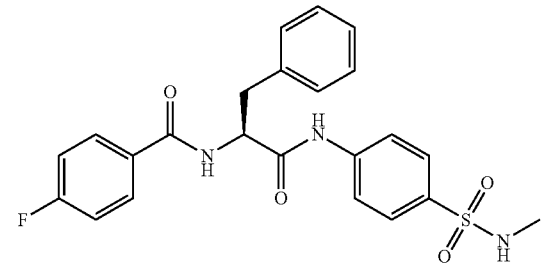 [SMILES: CNS(=O)(=O)c1ccc(NC(=O)[C@H](Cc2ccccc2)NC(=O)c2ccc(F)cc2)cc1] |
| I-31 | 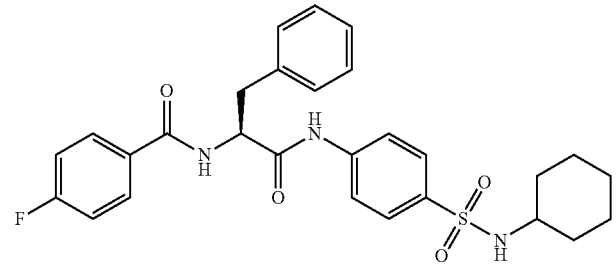 [SMILES: O=C(N[C@@H](Cc1ccccc1)C(=O)Nc1ccc(S(=O)(=O)NC2CCCCC2)cc1)c1ccc(F)cc1] |
| I-32 | 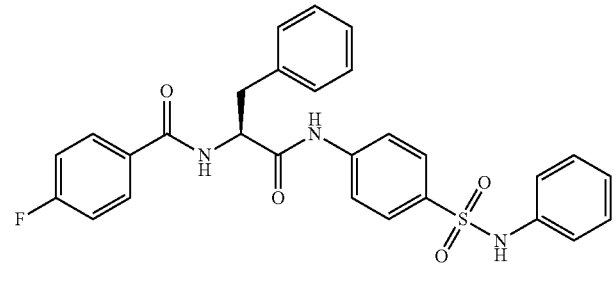 [SMILES: O=C(N[C@@H](Cc1ccccc1)C(=O)Nc1ccc(S(=O)(=O)Nc2ccccc2)cc1)c1ccc(F)cc1] |
| I-33 | 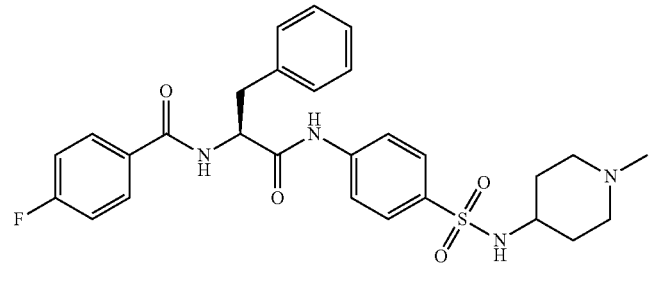 [SMILES: CN1CCC(NS(=O)(=O)c2ccc(NC(=O)[C@H](Cc3ccccc3)NC(=O)c3ccc(F)cc3)cc2)CC1] |
| I-34 | 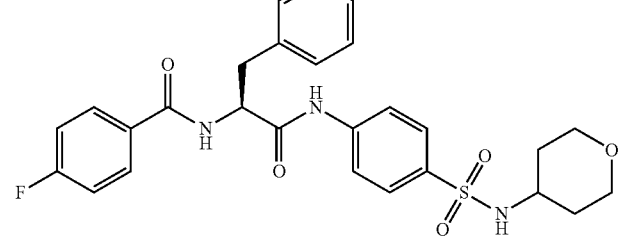 |

TABLE 1-continued

Exemplary Compounds

| Compound | Structure |
|---|---|
| I-35 | 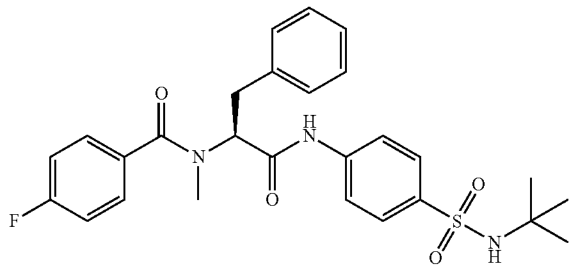 [SMILES: CN(C(=O)c1ccc(F)cc1)[C@@H](Cc1ccccc1)C(=O)Nc1ccc(S(=O)(=O)NC(C)(C)C)cc1] |
| I-36 | 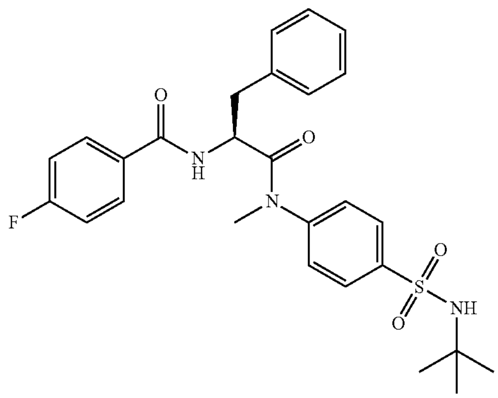 [SMILES: CN(C(=O)[C@H](Cc1ccccc1)NC(=O)c1ccc(F)cc1)c1ccc(S(=O)(=O)NC(C)(C)C)cc1] |
| I-37 | 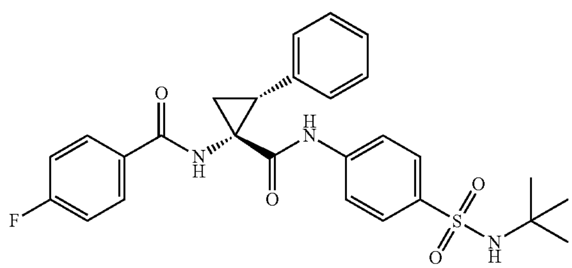 [SMILES: CC(C)(C)NS(=O)(=O)c1ccc(NC(=O)[C@@]2(NC(=O)c3ccc(F)cc3)C[C@@H]2c2ccccc2)cc1] |
| I-38 | 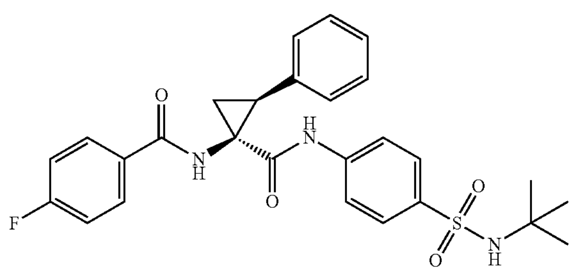 [SMILES: CC(C)(C)NS(=O)(=O)c1ccc(NC(=O)[C@]2(NC(=O)c3ccc(F)cc3)C[C@H]2c2ccccc2)cc1] |
| I-39 | 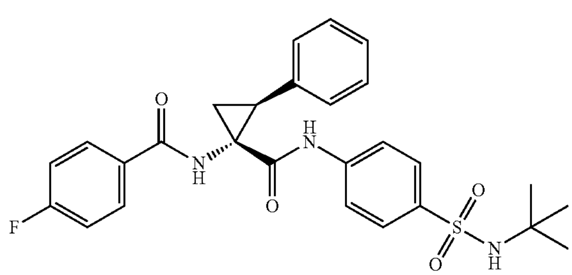 [SMILES: CC(C)(C)NS(=O)(=O)c1ccc(NC(=O)[C@@]2(NC(=O)c3ccc(F)cc3)C[C@H]2c2ccccc2)cc1] |

TABLE 1-continued

Exemplary Compounds

| Compound | Structure |
|---|---|
| I-40 | 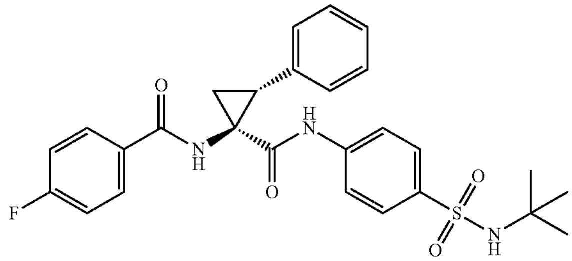 [SMILES: CC(C)(C)NS(=O)(=O)c1ccc(NC(=O)[C@]2(NC(=O)c3ccc(F)cc3)C[C@@H]2c2ccccc2)cc1] |
| I-41 | 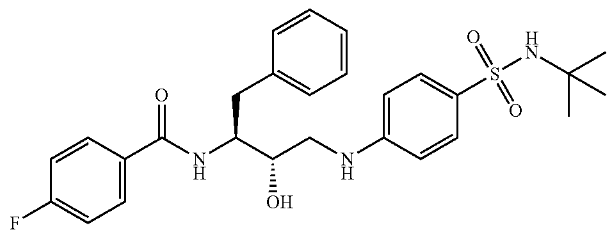 [SMILES: CC(C)(C)NS(=O)(=O)c1ccc(NC[C@H](O)[C@H](Cc2ccccc2)NC(=O)c2ccc(F)cc2)cc1] |
| I-42 | 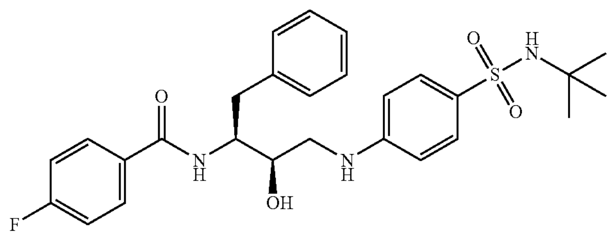 [SMILES: CC(C)(C)NS(=O)(=O)c1ccc(NC[C@@H](O)[C@H](Cc2ccccc2)NC(=O)c2ccc(F)cc2)cc1] |
| I-43 | 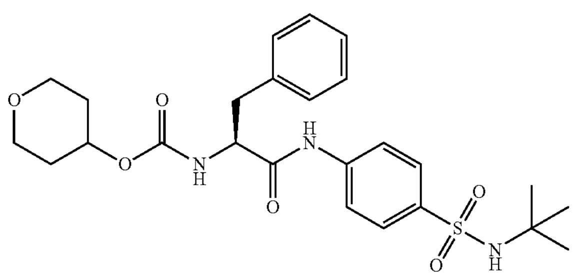 [SMILES: CC(C)(C)NS(=O)(=O)c1ccc(NC(=O)[C@H](Cc2ccccc2)NC(=O)OC2CCOCC2)cc1] |
| I-44 | 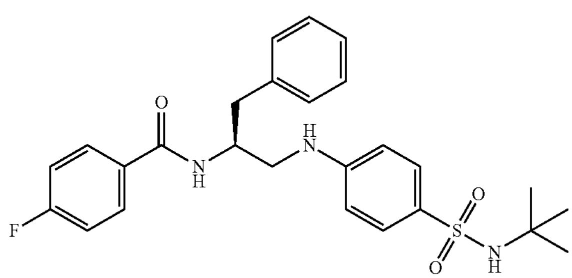 [SMILES: CC(C)(C)NS(=O)(=O)c1ccc(NC[C@H](Cc2ccccc2)NC(=O)c2ccc(F)cc2)cc1] |
| I-45 | 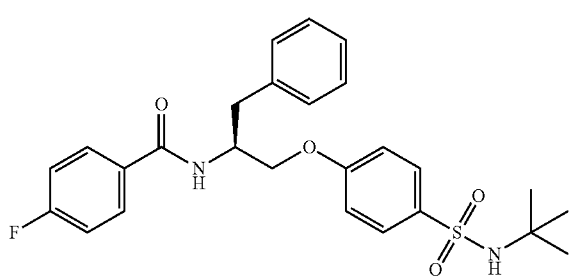 [SMILES: CC(C)(C)NS(=O)(=O)c1ccc(OC[C@H](Cc2ccccc2)NC(=O)c2ccc(F)cc2)cc1] |

TABLE 1-continued
Exemplary Compounds
| Compound | Structure |
|---|---|
| I-46 | 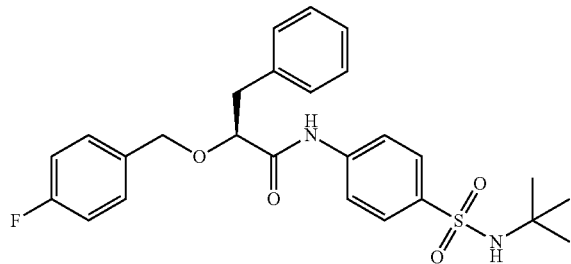 [SMILES: CC(C)(C)NS(=O)(=O)c1ccc(NC(=O)[C@H](Cc2ccccc2)OCc2ccc(F)cc2)cc1] |
| I-47 | 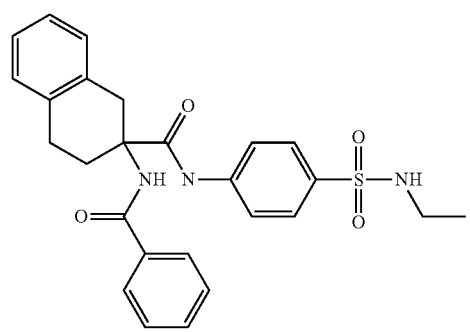 [SMILES: CCNS(=O)(=O)c1ccc(NC(=O)C2(NC(=O)c3ccccc3)CCc3ccccc3C2)cc1] |
| I-48 | 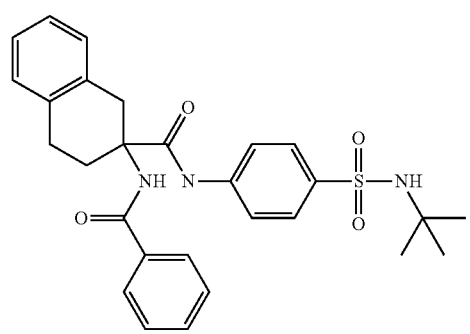 [SMILES: CC(C)(C)NS(=O)(=O)c1ccc(NC(=O)C2(NC(=O)c3ccccc3)CCc3ccccc3C2)cc1] |
| I-49 | 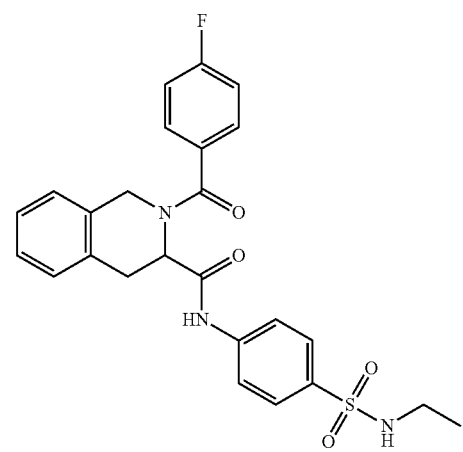 [SMILES: CCNS(=O)(=O)c1ccc(NC(=O)C2Cc3ccccc3CN2C(=O)c2ccc(F)cc2)cc1] |

TABLE 1-continued
Exemplary Compounds
| Compound | Structure |
|---|---|
| I-50 | 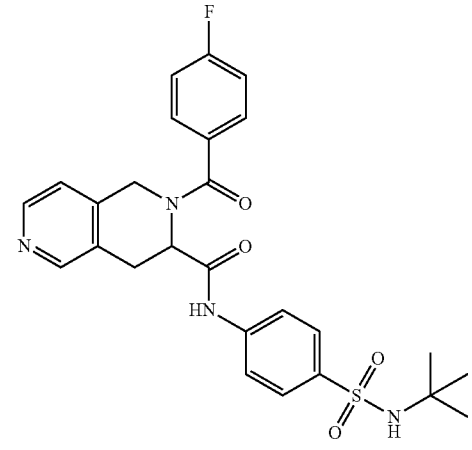 [SMILES: CC(C)(C)NS(=O)(=O)c1ccc(NC(=O)C2Cc3cnccc3CN2C(=O)c2ccc(F)cc2)cc1] |
| I-51 | 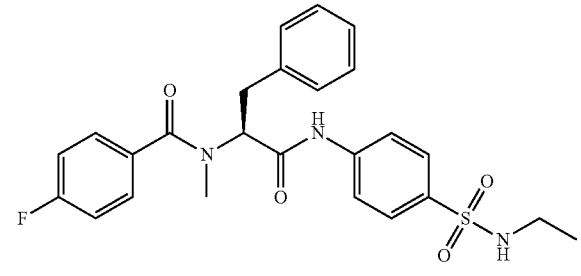 [SMILES: CCNS(=O)(=O)c1ccc(NC(=O)[C@H](Cc2ccccc2)N(C)C(=O)c2ccc(F)cc2)cc1] |
| I-52 | 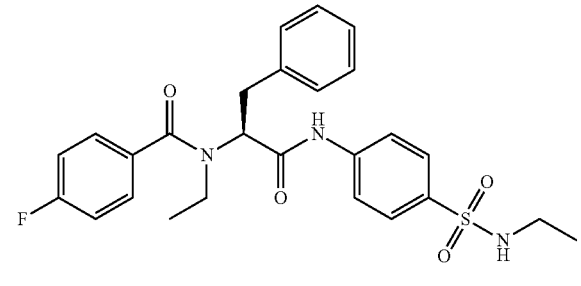 [SMILES: CCNS(=O)(=O)c1ccc(NC(=O)[C@H](Cc2ccccc2)N(CC)C(=O)c2ccc(F)cc2)cc1] |
| I-53 | 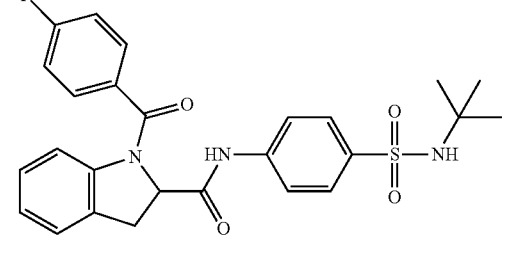 |
| I-54 | 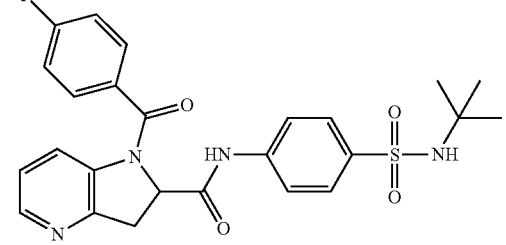 |

TABLE 1-continued

Exemplary Compounds

| Compound | Structure |
|---|---|
| I-55 | 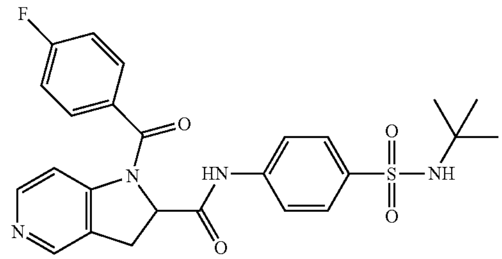 [SMILES: CC(C)(C)NS(=O)(=O)c1ccc(NC(=O)C2Cc3cnccc3N2C(=O)c2ccc(F)cc2)cc1] |
| I-56 | 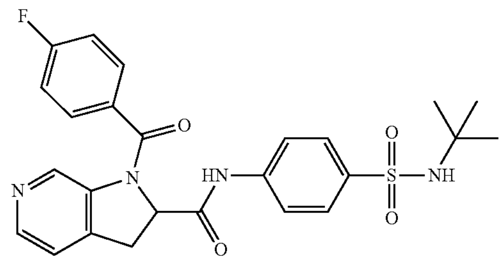 [SMILES: CC(C)(C)NS(=O)(=O)c1ccc(NC(=O)C2Cc3ccncc3N2C(=O)c2ccc(F)cc2)cc1] |
| I-57 | 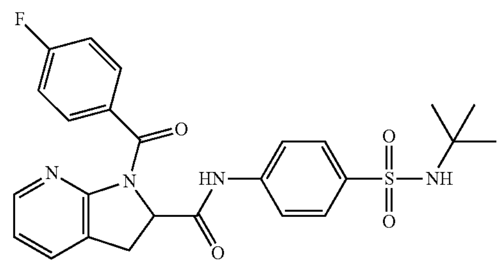 [SMILES: CC(C)(C)NS(=O)(=O)c1ccc(NC(=O)C2Cc3cccnc3N2C(=O)c2ccc(F)cc2)cc1] |
| I-58 | 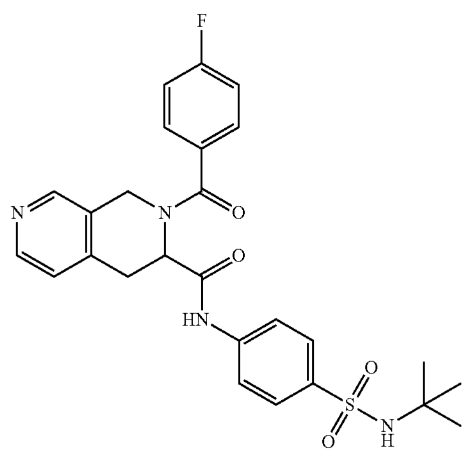 [SMILES: CC(C)(C)NS(=O)(=O)c1ccc(NC(=O)C2Cc3ccncc3CN2C(=O)c2ccc(F)cc2)cc1] |
| I-59 | 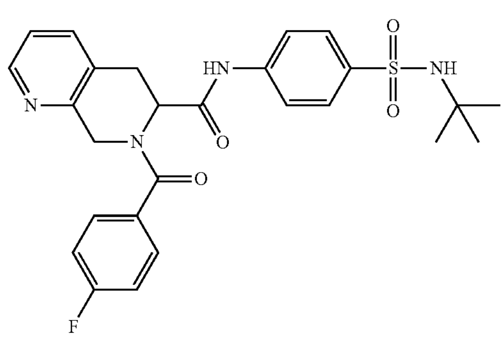 [SMILES: CC(C)(C)NS(=O)(=O)c1ccc(NC(=O)C2Cc3cccnc3CN2C(=O)c2ccc(F)cc2)cc1] |

TABLE 1-continued

Exemplary Compounds

| Compound | Structure |
|---|---|
| I-60 | 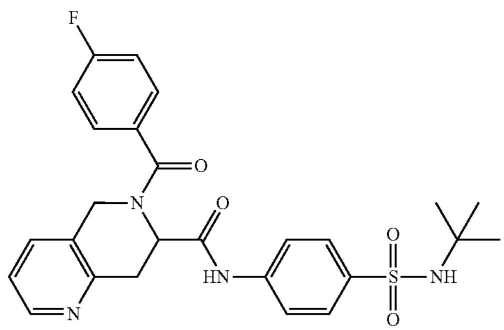 [SMILES: CC(C)(C)NS(=O)(=O)c1ccc(NC(=O)C2Cc3ncccc3CN2C(=O)c2ccc(F)cc2)cc1] |
| I-61 | 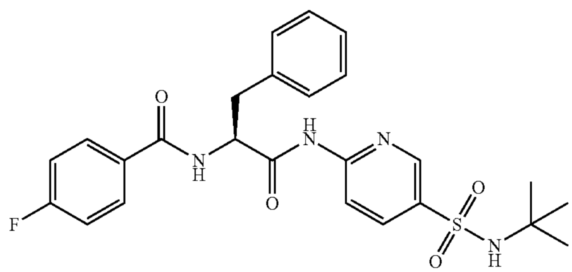 [SMILES: CC(C)(C)NS(=O)(=O)c1ccc(NC(=O)[C@H](Cc2ccccc2)NC(=O)c2ccc(F)cc2)nc1] |
| I-62 | 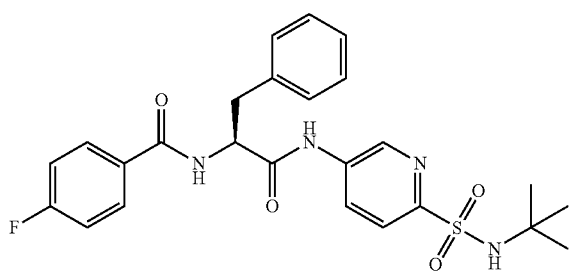 [SMILES: CC(C)(C)NS(=O)(=O)c1ccc(NC(=O)[C@H](Cc2ccccc2)NC(=O)c2ccc(F)cc2)cn1] |
| I-63 | 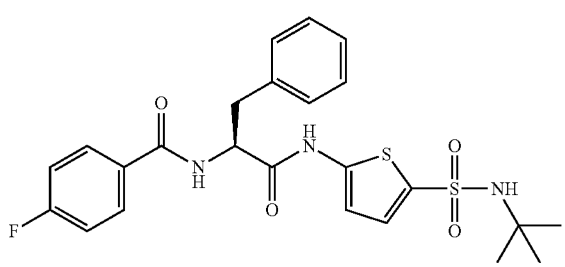 [SMILES: CC(C)(C)NS(=O)(=O)c1ccc(NC(=O)[C@H](Cc2ccccc2)NC(=O)c2ccc(F)cc2)s1] |
| I-64 | 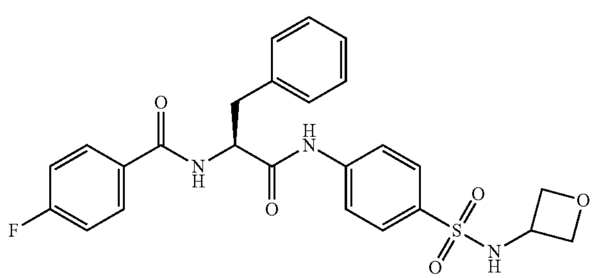 [SMILES: O=C(N[C@@H](Cc1ccccc1)C(=O)Nc1ccc(S(=O)(=O)NC2COC2)cc1)c1ccc(F)cc1] |

TABLE 1-continued

Exemplary Compounds

| Compound | Structure |
| --- | --- |
| I-65 | 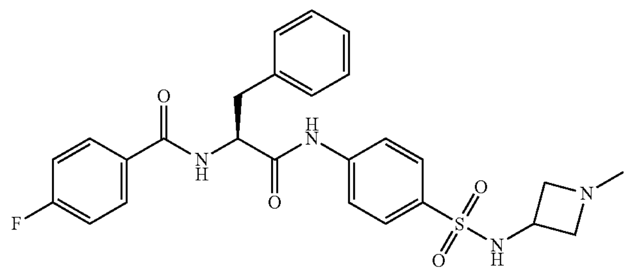 [SMILES: CN1CC(NS(=O)(=O)c2ccc(NC(=O)[C@H](Cc3ccccc3)NC(=O)c3ccc(F)cc3)cc2)C1] |
| I-66 | 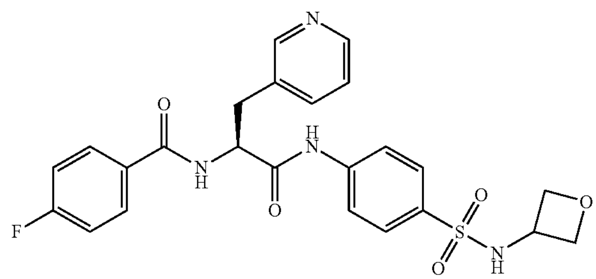 [SMILES: O=C(N[C@@H](Cc1cccnc1)C(=O)Nc1ccc(S(=O)(=O)NC2COC2)cc1)c1ccc(F)cc1] |
| I-67 | 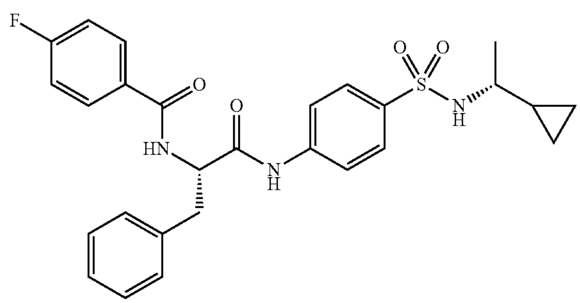 [SMILES: C[C@@H](NS(=O)(=O)c1ccc(NC(=O)[C@H](Cc2ccccc2)NC(=O)c2ccc(F)cc2)cc1)C1CC1] |
| I-68 | 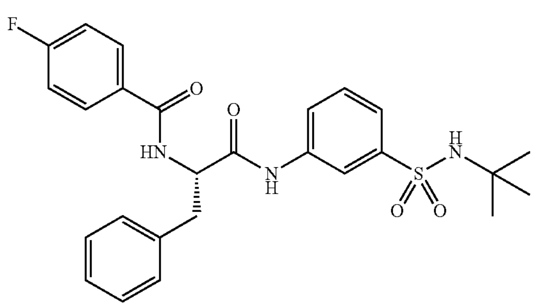 [SMILES: CC(C)(C)NS(=O)(=O)c1cccc(NC(=O)[C@H](Cc2ccccc2)NC(=O)c2ccc(F)cc2)c1] |
| I-69 | 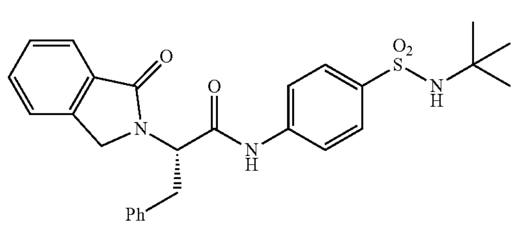 [SMILES: CC(C)(C)NS(=O)(=O)c1ccc(NC(=O)[C@H](Cc2ccccc2)N2Cc3ccccc3C2=O)cc1] |

TABLE 1-continued

Exemplary Compounds

| Compound | Structure |
|---|---|
| I-70 | 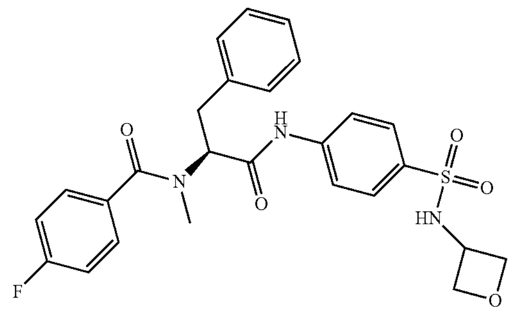 [SMILES: CN(C(=O)c1ccc(F)cc1)[C@@H](Cc1ccccc1)C(=O)Nc1ccc(S(=O)(=O)NC2COC2)cc1] |
| I-71 | 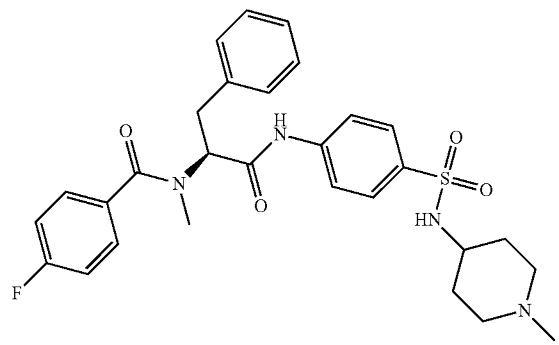 [SMILES: CN1CCC(NS(=O)(=O)c2ccc(NC(=O)[C@H](Cc3ccccc3)N(C)C(=O)c3ccc(F)cc3)cc2)CC1] |
| I-72 | 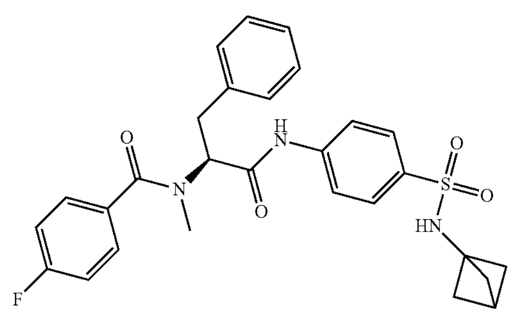 [SMILES: CN(C(=O)c1ccc(F)cc1)[C@@H](Cc1ccccc1)C(=O)Nc1ccc(S(=O)(=O)NC23CC(C2)C3)cc1] |
| I-73 | 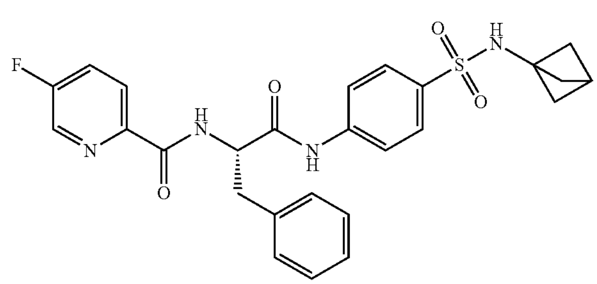 [SMILES: O=C(N[C@@H](Cc1ccccc1)C(=O)Nc1ccc(S(=O)(=O)NC23CC(C2)C3)cc1)c1ccc(F)cn1] |
| I-74 | 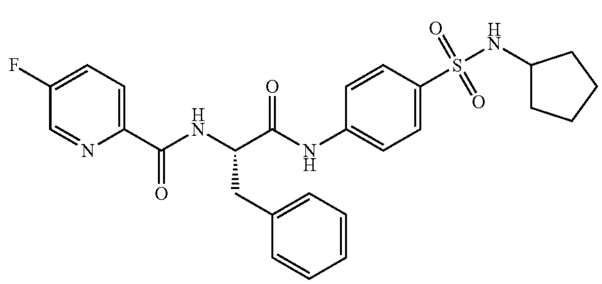 [SMILES: O=C(N[C@@H](Cc1ccccc1)C(=O)Nc1ccc(S(=O)(=O)NC2CCCC2)cc1)c1ccc(F)cn1] |

TABLE 1-continued

Exemplary Compounds

| Compound | Structure |
|---|---|
| I-75 | 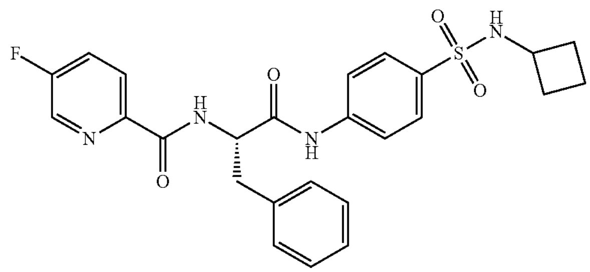 [SMILES: O=C(N[C@@H](Cc1ccccc1)C(=O)Nc1ccc(S(=O)(=O)NC2CCC2)cc1)c1ccc(F)cn1] |
| I-76 | 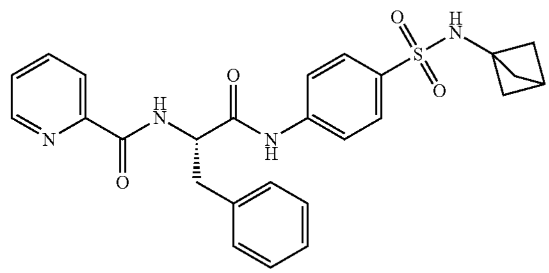 [SMILES: O=C(N[C@@H](Cc1ccccc1)C(=O)Nc1ccc(S(=O)(=O)NC23CC(C2)C3)cc1)c1ccccn1] |
| I-77 | 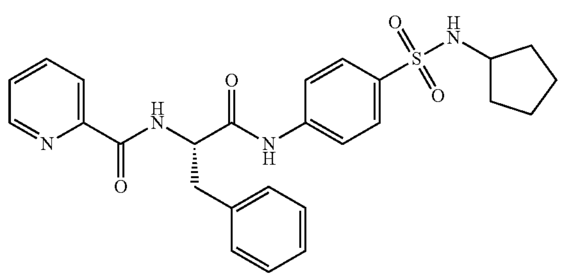 [SMILES: O=C(N[C@@H](Cc1ccccc1)C(=O)Nc1ccc(S(=O)(=O)NC2CCCC2)cc1)c1ccccn1] |
| I-78 | 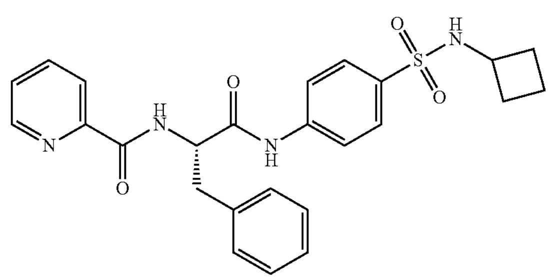 [SMILES: O=C(N[C@@H](Cc1ccccc1)C(=O)Nc1ccc(S(=O)(=O)NC2CCC2)cc1)c1ccccn1] |
| I-79 | 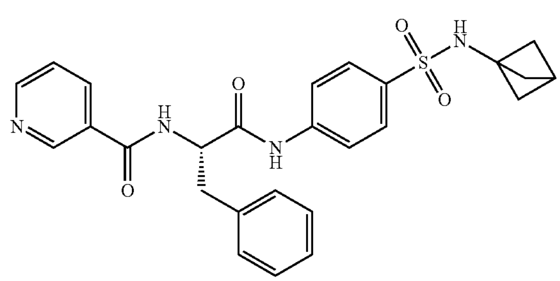 [SMILES: O=C(N[C@@H](Cc1ccccc1)C(=O)Nc1ccc(S(=O)(=O)NC23CC(C2)C3)cc1)c1cccnc1] |

TABLE 1-continued

Exemplary Compounds

| Compound | Structure |
|---|---|
| I-80 | 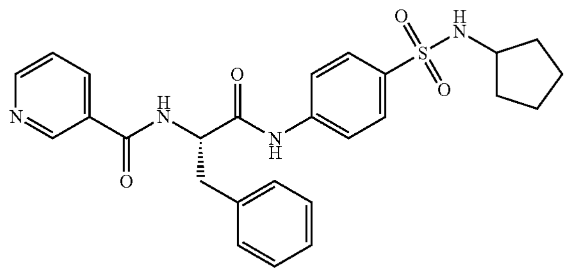 [SMILES: O=C(N[C@@H](Cc1ccccc1)C(=O)Nc1ccc(S(=O)(=O)NC2CCCC2)cc1)c1cccnc1] |
| I-81 | 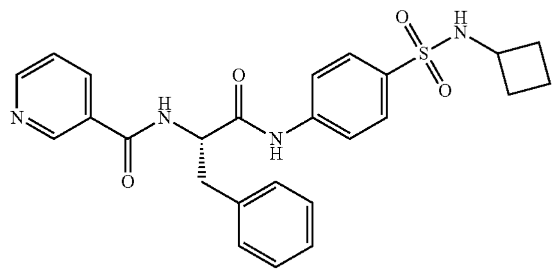 [SMILES: O=C(N[C@@H](Cc1ccccc1)C(=O)Nc1ccc(S(=O)(=O)NC2CCC2)cc1)c1cccnc1] |
| I-82 | 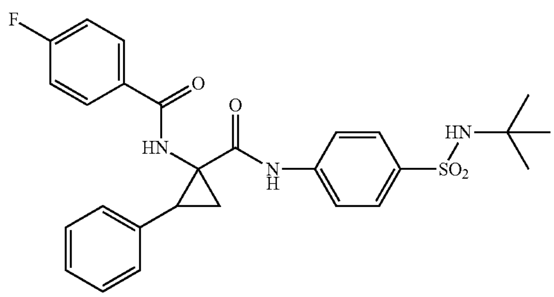 [SMILES: CC(C)(C)NS(=O)(=O)c1ccc(NC(=O)C2(NC(=O)c3ccc(F)cc3)CC2c2ccccc2)cc1] |
| I-83 | 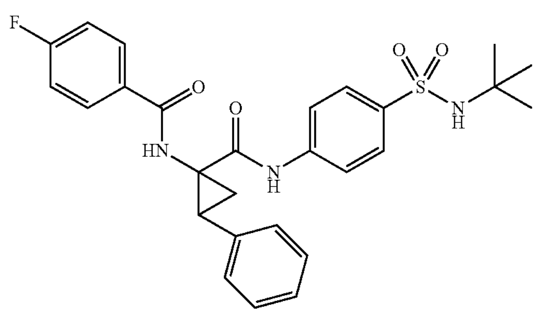 [SMILES: CC(C)(C)NS(=O)(=O)c1ccc(NC(=O)C2(NC(=O)c3ccc(F)cc3)CC2c2ccccc2)cc1] |
| I-84 | 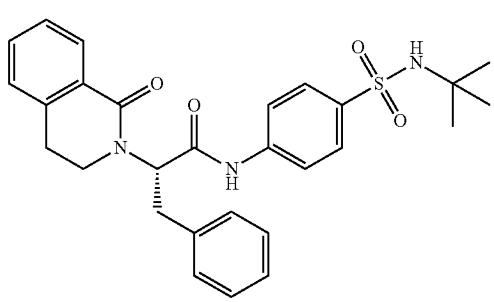 [SMILES: CC(C)(C)NS(=O)(=O)c1ccc(NC(=O)[C@H](Cc2ccccc2)N2CCc3ccccc3C2=O)cc1] |

TABLE 1-continued

Exemplary Compounds

| Compound | Structure |
|---|---|
| I-85 | 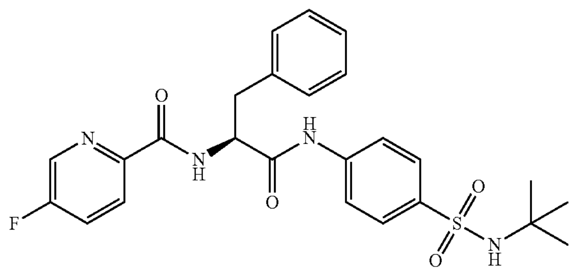 [SMILES: CC(C)(C)NS(=O)(=O)c1ccc(NC(=O)[C@H](Cc2ccccc2)NC(=O)c2ccc(F)cn2)cc1] |
| I-86 | 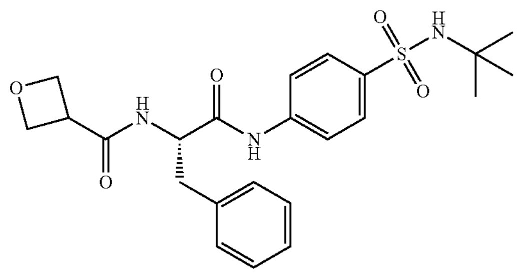 [SMILES: CC(C)(C)NS(=O)(=O)c1ccc(NC(=O)[C@H](Cc2ccccc2)NC(=O)C2COC2)cc1] |
| I-87 | 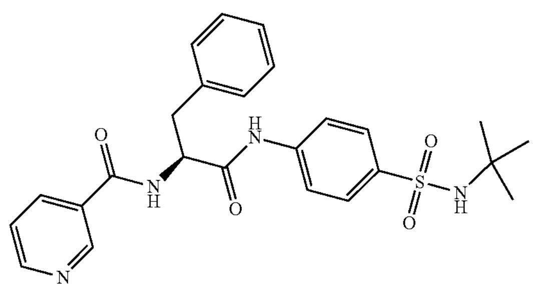 [SMILES: CC(C)(C)NS(=O)(=O)c1ccc(NC(=O)[C@H](Cc2ccccc2)NC(=O)c2cccnc2)cc1] |
| I-88 | 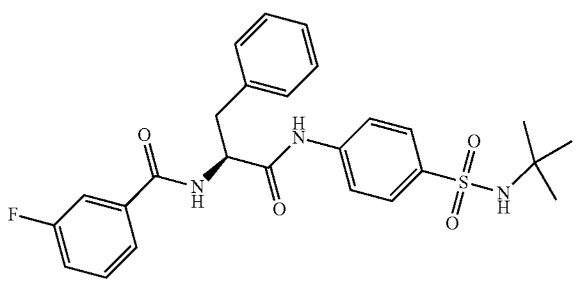 [SMILES: CC(C)(C)NS(=O)(=O)c1ccc(NC(=O)[C@H](Cc2ccccc2)NC(=O)c2cccc(F)c2)cc1] |
| I-89 | 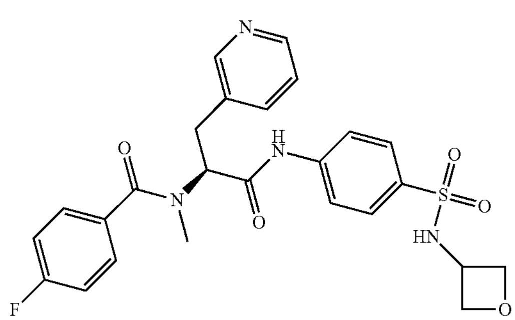 [SMILES: CN(C(=O)c1ccc(F)cc1)[C@@H](Cc1cccnc1)C(=O)Nc1ccc(S(=O)(=O)NC2COC2)cc1] |

TABLE 1-continued
Exemplary Compounds
| Compound | Structure |
|---|---|
| I-90 | 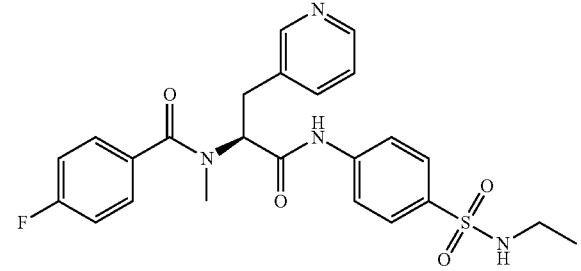 [SMILES: CCNS(=O)(=O)c1ccc(NC(=O)[C@H](Cc2cccnc2)N(C)C(=O)c2ccc(F)cc2)cc1] |
| I-91 | 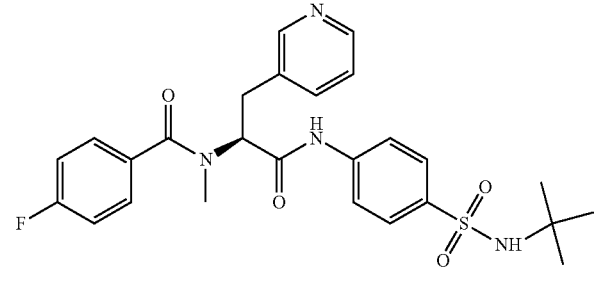 [SMILES: CN(C(=O)c1ccc(F)cc1)[C@@H](Cc1cccnc1)C(=O)Nc1ccc(S(=O)(=O)NC(C)(C)C)cc1] |
| I-92 | 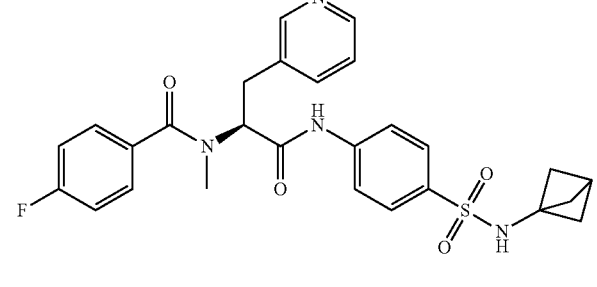 |
| I-93 | 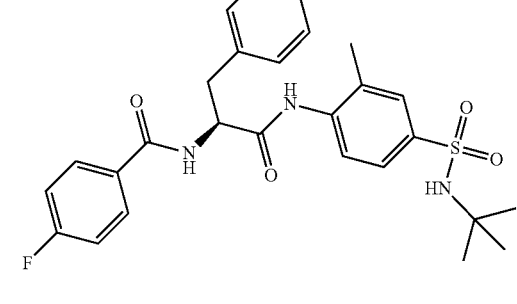 |
| I-94 | 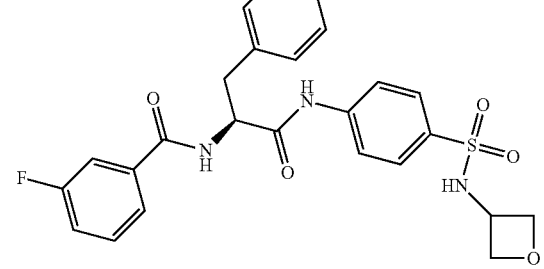 |

TABLE 1-continued

Exemplary Compounds

| Compound | Structure |
|---|---|
| I-95 | 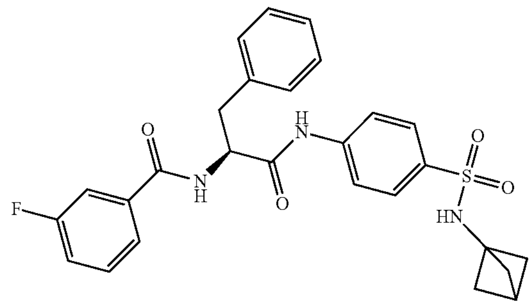 [SMILES: O=C(N[C@@H](Cc1ccccc1)C(=O)Nc1ccc(S(=O)(=O)NC23CC(C2)C3)cc1)c1cccc(F)c1] |
| I-96 | 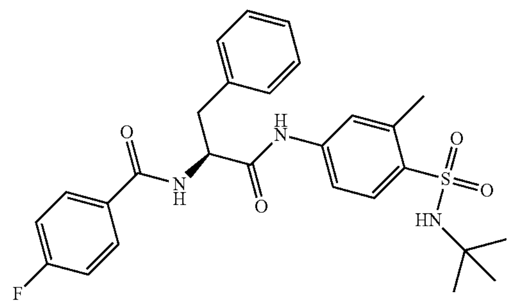 [SMILES: Cc1cc(NC(=O)[C@H](Cc2ccccc2)NC(=O)c2ccc(F)cc2)ccc1S(=O)(=O)NC(C)(C)C] |
| I-97 | 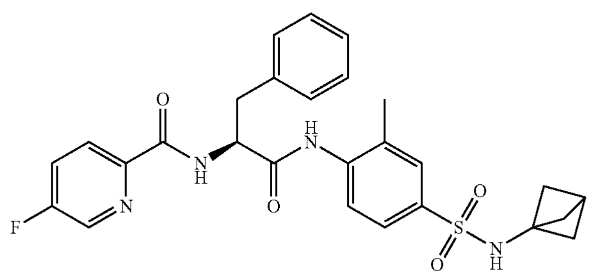 [SMILES: Cc1cc(S(=O)(=O)NC23CC(C2)C3)ccc1NC(=O)[C@H](Cc1ccccc1)NC(=O)c1ccc(F)cn1] |
| I-98 | 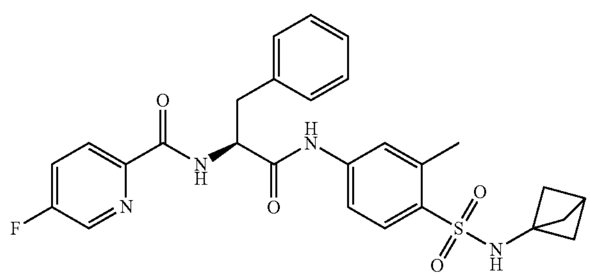 [SMILES: Cc1cc(NC(=O)[C@H](Cc2ccccc2)NC(=O)c2ccc(F)cn2)ccc1S(=O)(=O)NC12CC(C1)C2] |
| I-99 | 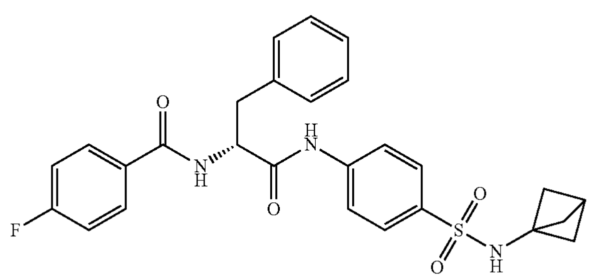 [SMILES: O=C(N[C@H](Cc1ccccc1)C(=O)Nc1ccc(S(=O)(=O)NC23CC(C2)C3)cc1)c1ccc(F)cc1] |

TABLE 1-continued

Exemplary Compounds

| Compound | Structure |
|---|---|
| I-100 | 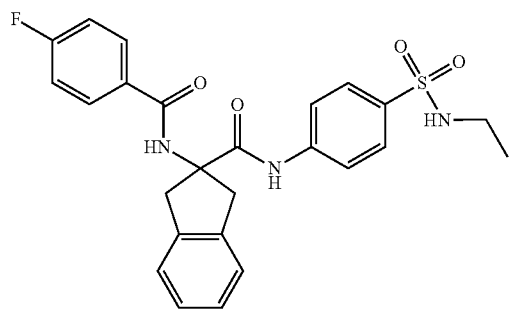 [SMILES: CCNS(=O)(=O)c1ccc(NC(=O)C2(NC(=O)c3ccc(F)cc3)Cc3ccccc3C2)cc1] |
| I-101 | 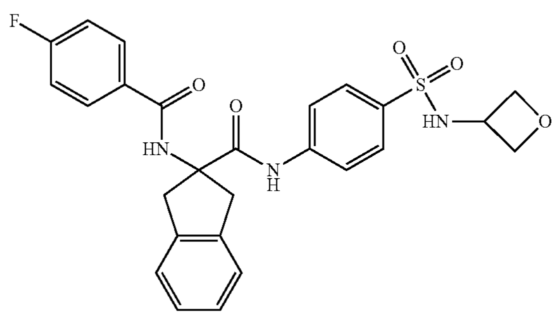 [SMILES: O=C(NC1(C(=O)Nc2ccc(S(=O)(=O)NC3COC3)cc2)Cc2ccccc2C1)c1ccc(F)cc1] |
| I-102 | 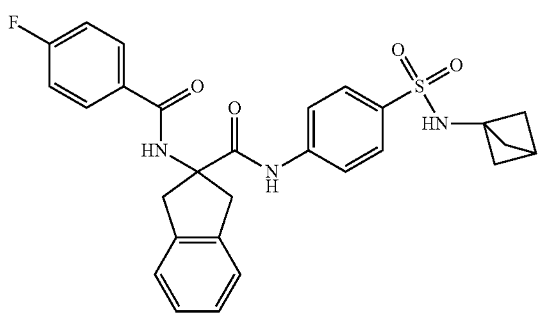 [SMILES: O=C(NC1(C(=O)Nc2ccc(S(=O)(=O)NC34CC(C3)C4)cc2)Cc2ccccc2C1)c1ccc(F)cc1] |
| I-103 | 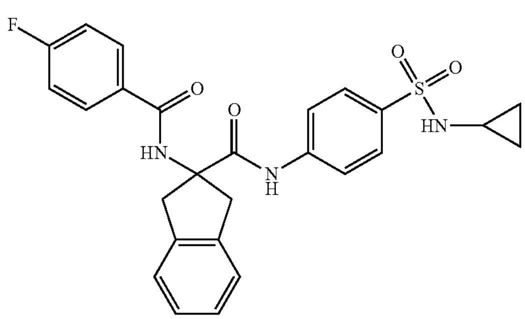 [SMILES: O=C(NC1(C(=O)Nc2ccc(S(=O)(=O)NC3CC3)cc2)Cc2ccccc2C1)c1ccc(F)cc1] |
| I-104 | 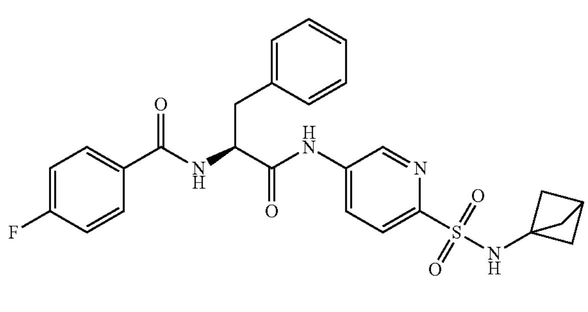 [SMILES: O=C(N[C@@H](Cc1ccccc1)C(=O)Nc1ccc(S(=O)(=O)NC23CC(C2)C3)nc1)c1ccc(F)cc1] |

TABLE 1-continued

Exemplary Compounds

| Compound | Structure |
|---|---|
| I-105 | 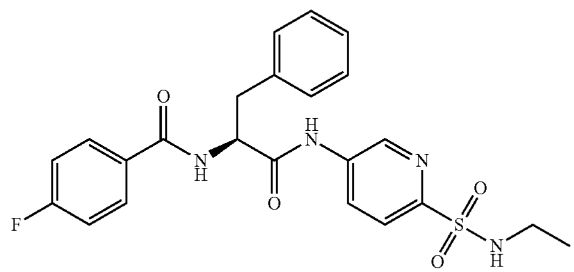 [SMILES: CCNS(=O)(=O)c1ccc(NC(=O)[C@H](Cc2ccccc2)NC(=O)c2ccc(F)cc2)cn1] |
| I-106 | 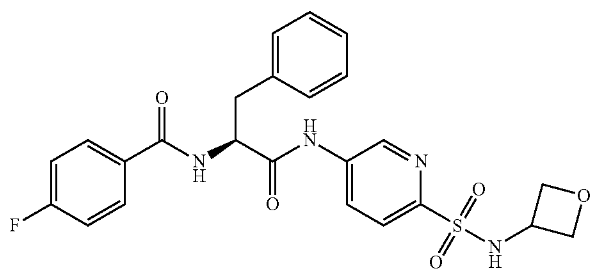 [SMILES: O=C(N[C@@H](Cc1ccccc1)C(=O)Nc1ccc(S(=O)(=O)NC2COC2)nc1)c1ccc(F)cc1] |
| I-107 | 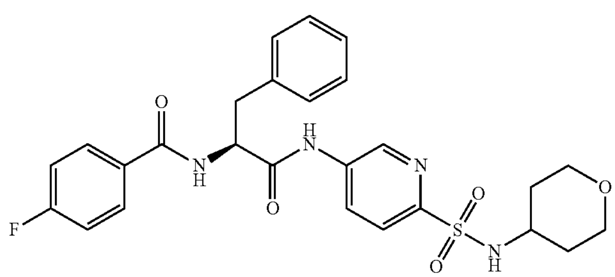 [SMILES: O=C(N[C@@H](Cc1ccccc1)C(=O)Nc1ccc(S(=O)(=O)NC2CCOCC2)nc1)c1ccc(F)cc1] |
| I-108 | 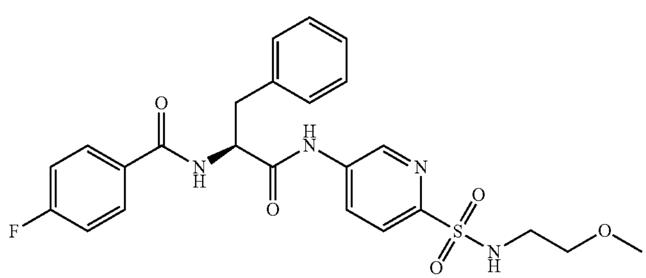 [SMILES: COCCNS(=O)(=O)c1ccc(NC(=O)[C@H](Cc2ccccc2)NC(=O)c2ccc(F)cc2)cn1] |
| I-109 | 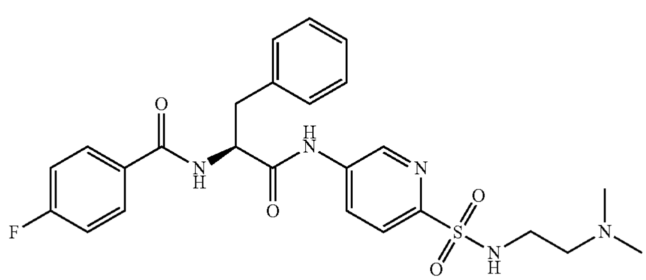 [SMILES: CN(C)CCNS(=O)(=O)c1ccc(NC(=O)[C@H](Cc2ccccc2)NC(=O)c2ccc(F)cc2)cn1] |

TABLE 1-continued
Exemplary Compounds
| Compound | Structure |
|---|---|
| I-110 | 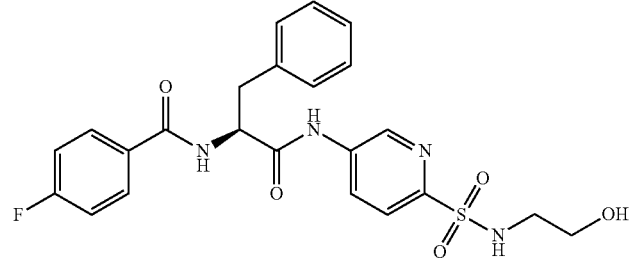 [SMILES: O=C(N[C@@H](Cc1ccccc1)C(=O)Nc1ccc(S(=O)(=O)NCCO)nc1)c1ccc(F)cc1] |
| I-111 | 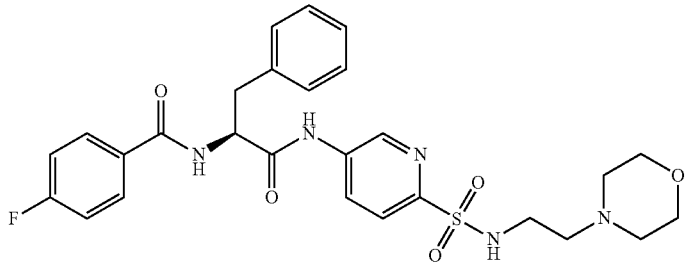 [SMILES: O=C(N[C@@H](Cc1ccccc1)C(=O)Nc1ccc(S(=O)(=O)NCCN2CCOCC2)nc1)c1ccc(F)cc1] |
| I-112 | 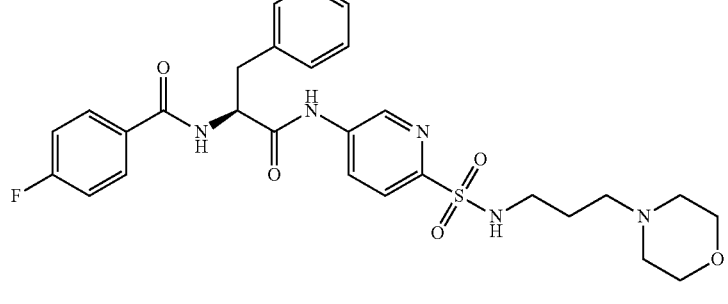 |
| I-113 | 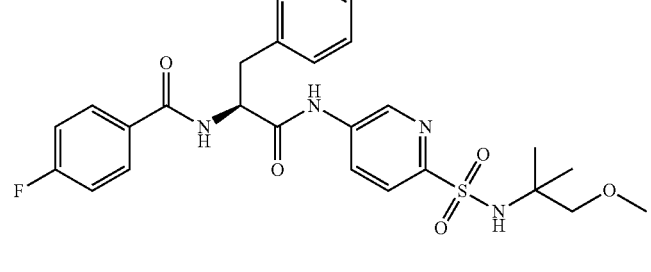 |
| I-114 | 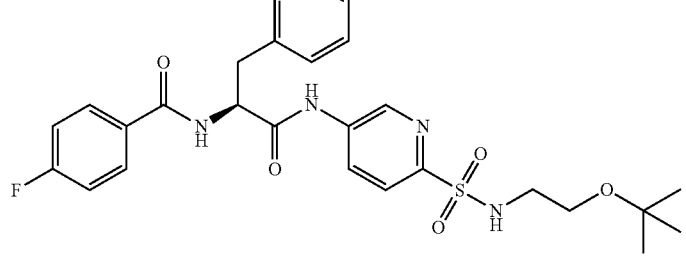 |

TABLE 1-continued

Exemplary Compounds

| Compound | Structure |
|---|---|
| I-115 | 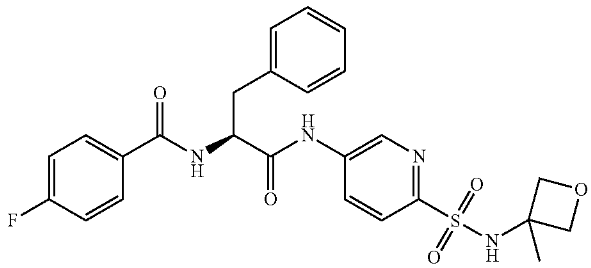 [SMILES: CC1(NS(=O)(=O)c2ccc(NC(=O)[C@H](Cc3ccccc3)NC(=O)c3ccc(F)cc3)cn2)COC1] |
| I-116 | 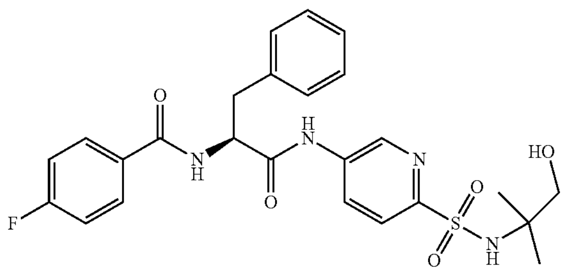 [SMILES: CC(C)(CO)NS(=O)(=O)c1ccc(NC(=O)[C@H](Cc2ccccc2)NC(=O)c2ccc(F)cc2)cn1] |
| I-117 | 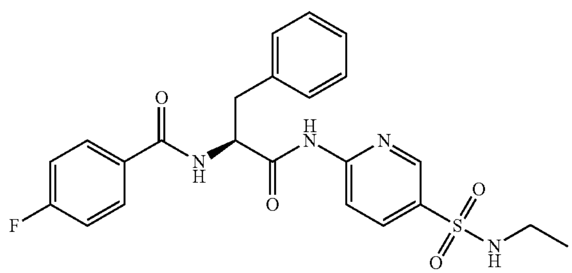 |
| I-118 | 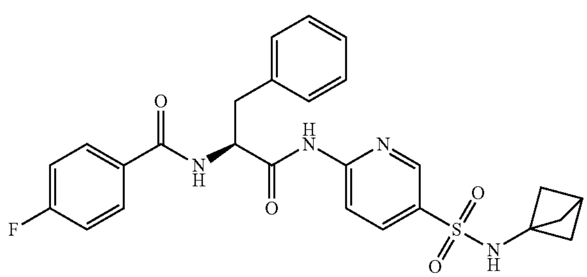 [SMILES: O=C(N[C@@H](Cc1ccccc1)C(=O)Nc1ccc(S(=O)(=O)NC23CC(C2)C3)cn1)c1ccc(F)cc1] |
| I-119 | 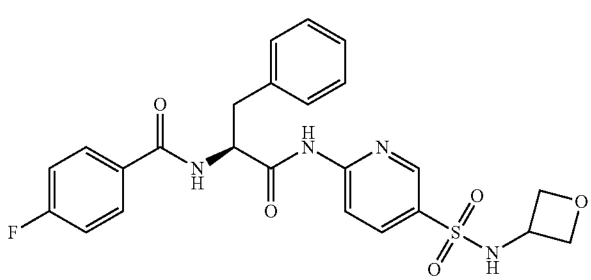 [SMILES: O=C(N[C@@H](Cc1ccccc1)C(=O)Nc1ccc(S(=O)(=O)NC2COC2)cn1)c1ccc(F)cc1] |

TABLE 1-continued
Exemplary Compounds
| Compound | Structure |
|---|---|
| I-120 | 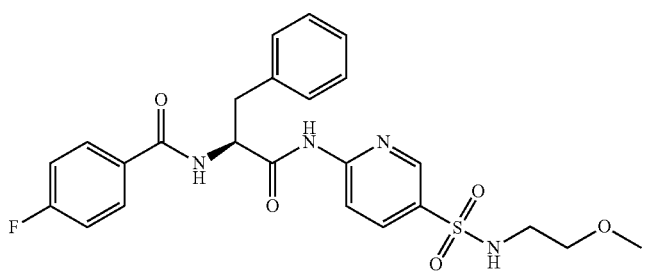 [SMILES: COCCNS(=O)(=O)c1ccc(NC(=O)[C@H](Cc2ccccc2)NC(=O)c2ccc(F)cc2)nc1] |
| I-121 | 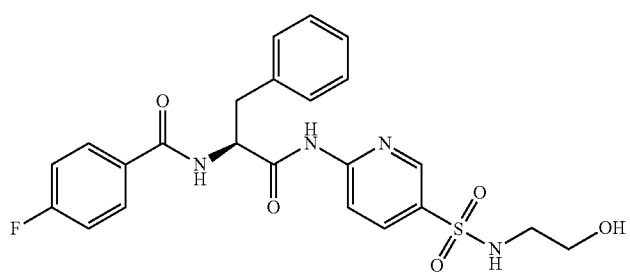 [SMILES: O=C(N[C@@H](Cc1ccccc1)C(=O)Nc1ccc(S(=O)(=O)NCCO)cn1)c1ccc(F)cc1] |
| I-122 | 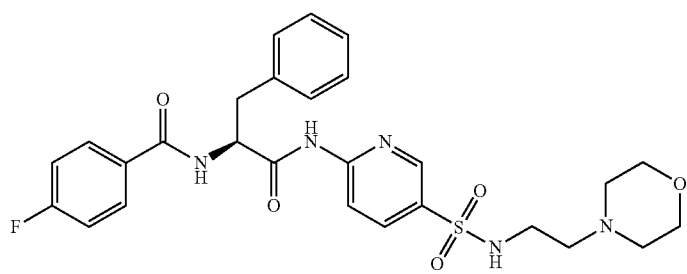 [SMILES: O=C(N[C@@H](Cc1ccccc1)C(=O)Nc1ccc(S(=O)(=O)NCCN2CCOCC2)cn1)c1ccc(F)cc1] |
| I-123 | 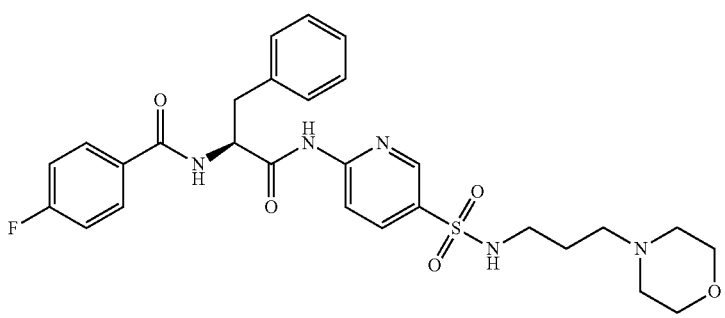 [SMILES: O=C(N[C@@H](Cc1ccccc1)C(=O)Nc1ccc(S(=O)(=O)NCCCN2CCOCC2)cn1)c1ccc(F)cc1] |
| I-124 | 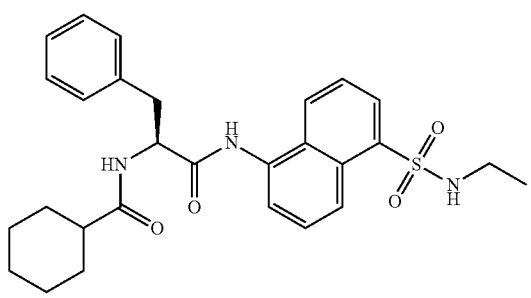 [SMILES: CCNS(=O)(=O)c1cccc2c(NC(=O)[C@H](Cc3ccccc3)NC(=O)C3CCCCC3)cccc12] |

TABLE 1-continued
Exemplary Compounds
| Compound | Structure |
|---|---|
| I-125 | 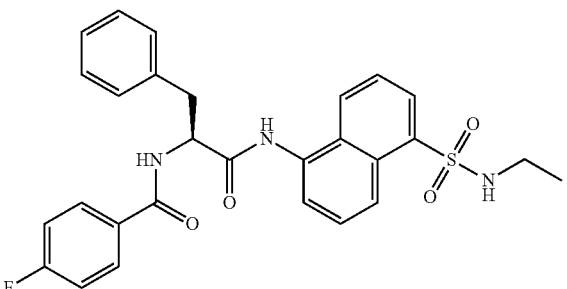 |
| I-126 | 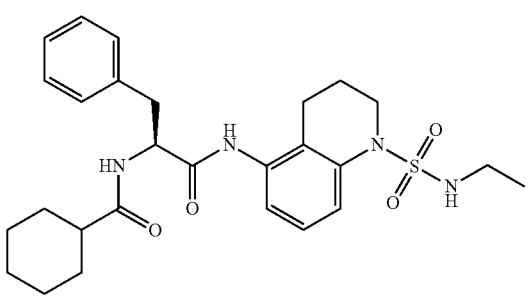 [SMILES: CCNS(=O)(=O)N1CCCc2c(NC(=O)[C@H](Cc3ccccc3)NC(=O)C3CCCCC3)cccc21] |
| I-127 | 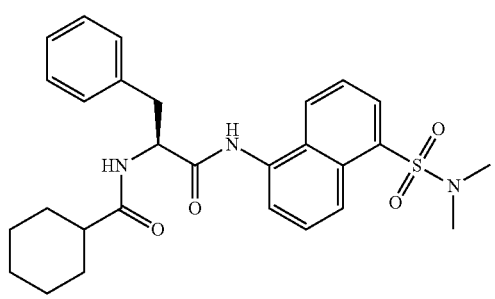 [SMILES: CN(C)S(=O)(=O)c1cccc2c(NC(=O)[C@H](Cc3ccccc3)NC(=O)C3CCCCC3)cccc12] |
| I-128 | 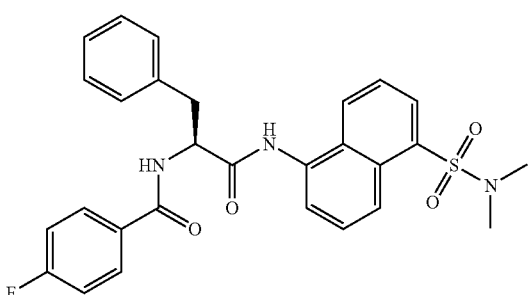 |
| I-129 | 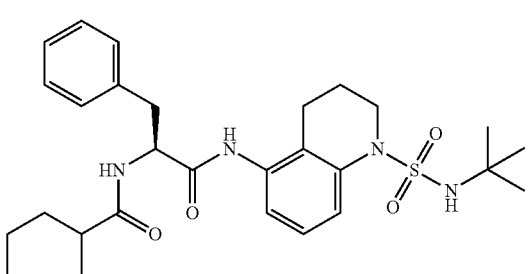 |

TABLE 1-continued

Exemplary Compounds

| Compound | Structure |
| --- | --- |
| I-130 | 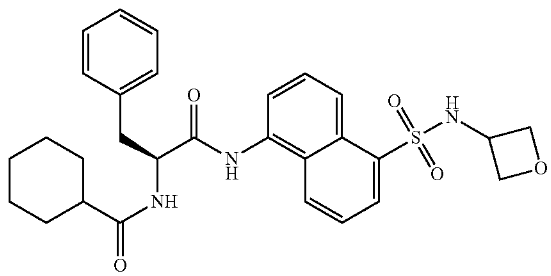 [SMILES: O=C(N[C@@H](Cc1ccccc1)C(=O)Nc1cccc2c(S(=O)(=O)NC3COC3)cccc12)C1CCCCC1] |
| I-131 | 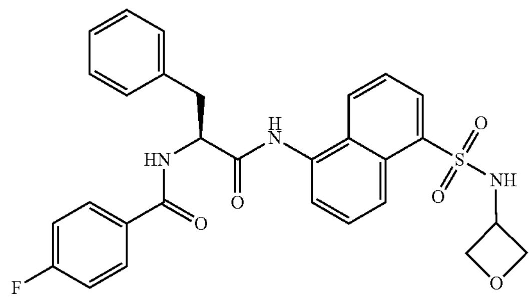 [SMILES: O=C(N[C@@H](Cc1ccccc1)C(=O)Nc1cccc2c(S(=O)(=O)NC3COC3)cccc12)c1ccc(F)cc1] |
| I-132 | 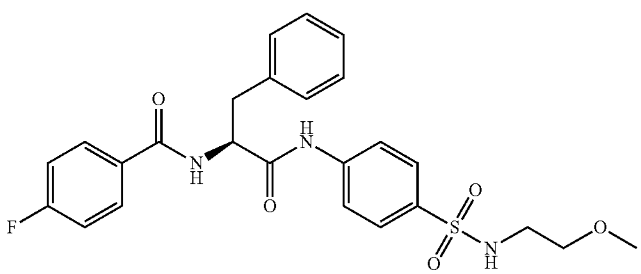 [SMILES: COCCNS(=O)(=O)c1ccc(NC(=O)[C@H](Cc2ccccc2)NC(=O)c2ccc(F)cc2)cc1] |
| I-133 | 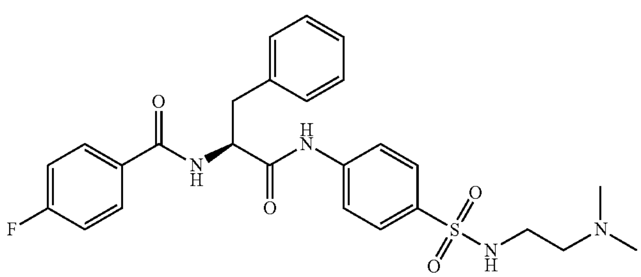 [SMILES: CN(C)CCNS(=O)(=O)c1ccc(NC(=O)[C@H](Cc2ccccc2)NC(=O)c2ccc(F)cc2)cc1] |
| I-134 | 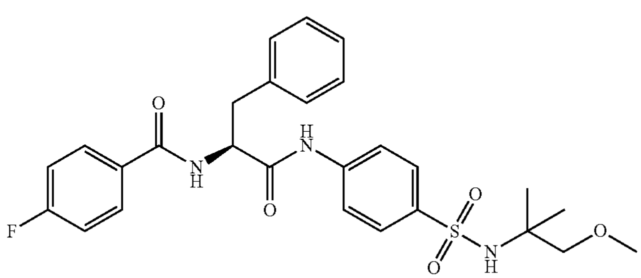 [SMILES: COCC(C)(C)NS(=O)(=O)c1ccc(NC(=O)[C@H](Cc2ccccc2)NC(=O)c2ccc(F)cc2)cc1] |

TABLE 1-continued

Exemplary Compounds

| Compound | Structure |
|---|---|
| I-135 | 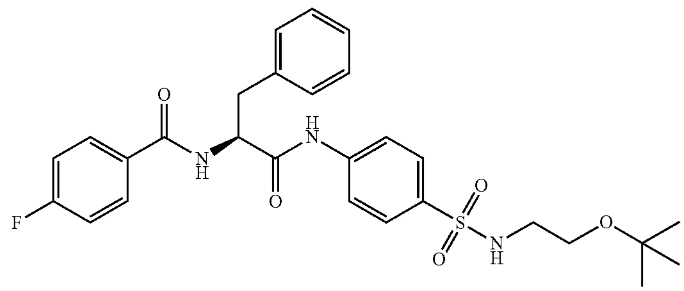 |
| I-136 | 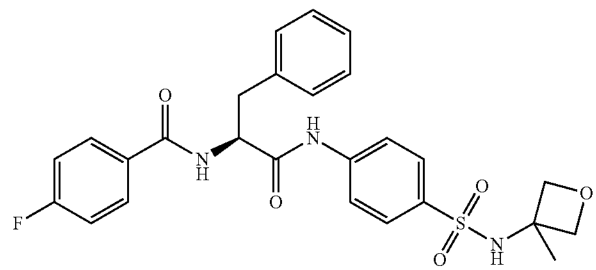 [SMILES: CC1(NS(=O)(=O)c2ccc(NC(=O)[C@H](Cc3ccccc3)NC(=O)c3ccc(F)cc3)cc2)COC1] |
| I-137 | 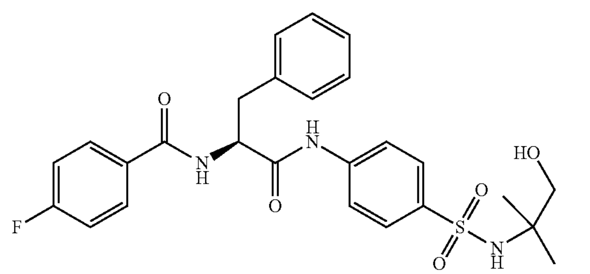 [SMILES: CC(C)(CO)NS(=O)(=O)c1ccc(NC(=O)[C@H](Cc2ccccc2)NC(=O)c2ccc(F)cc2)cc1] |
| I-138 | 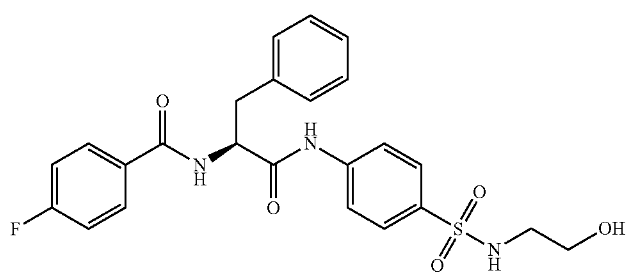 |
| I-139 | 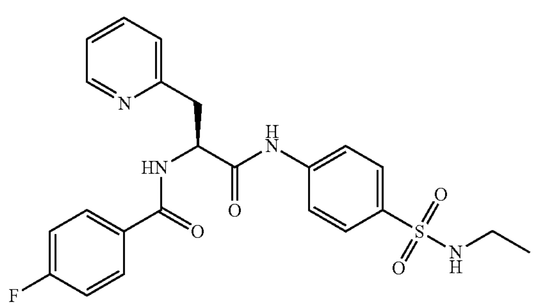 [SMILES: CCNS(=O)(=O)c1ccc(NC(=O)[C@H](Cc2ccccn2)NC(=O)c2ccc(F)cc2)cc1] |

TABLE 1-continued

Exemplary Compounds

| Compound | Structure |
|---|---|
| I-140 | 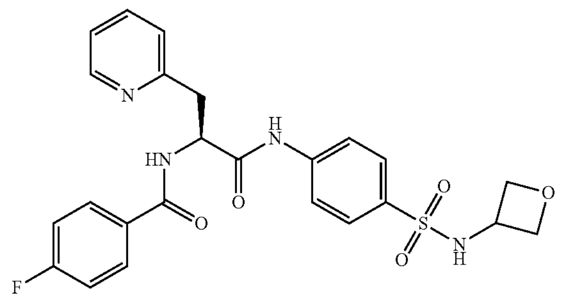 [SMILES: O=C(N[C@@H](Cc1ccccn1)C(=O)Nc1ccc(S(=O)(=O)NC2COC2)cc1)c1ccc(F)cc1] |
| I-141 | 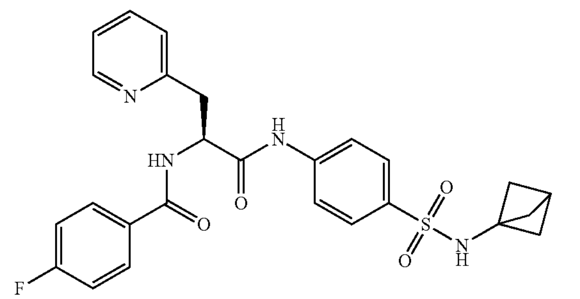 [SMILES: O=C(N[C@@H](Cc1ccccn1)C(=O)Nc1ccc(S(=O)(=O)NC23CC(C2)C3)cc1)c1ccc(F)cc1] |
| I-142 | 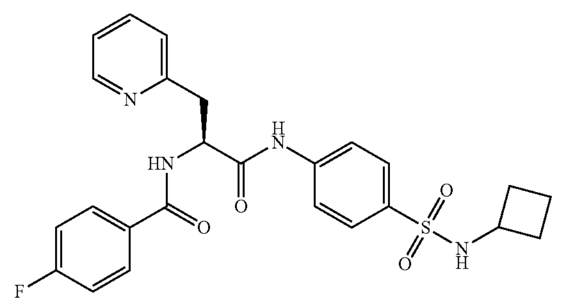 [SMILES: O=C(N[C@@H](Cc1ccccn1)C(=O)Nc1ccc(S(=O)(=O)NC2CCC2)cc1)c1ccc(F)cc1] |
| I-143 | 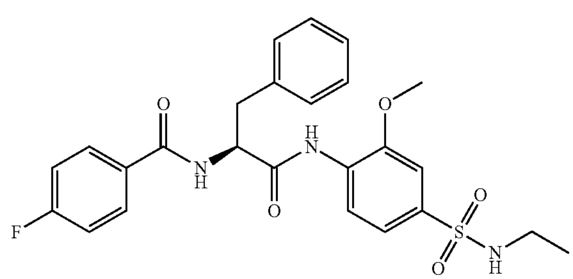 [SMILES: CCNS(=O)(=O)c1ccc(NC(=O)[C@H](Cc2ccccc2)NC(=O)c2ccc(F)cc2)c(OC)c1] |
| I-144 | 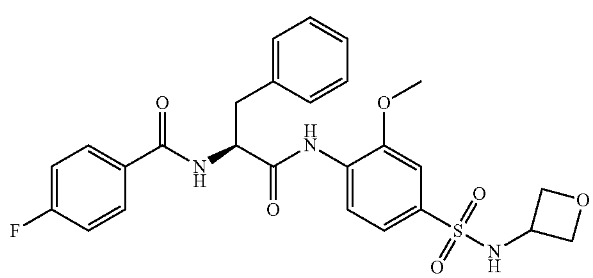 |

TABLE 1-continued

Exemplary Compounds

| Compound | Structure |
|---|---|
| I-145 | 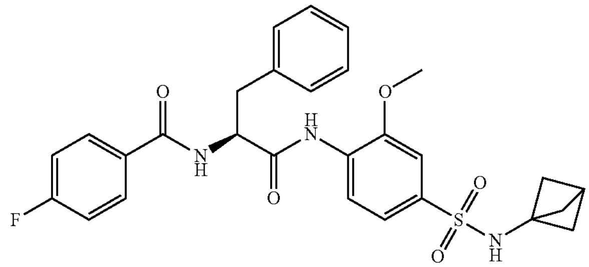 [SMILES: COc1cc(S(=O)(=O)NC23CC(C2)C3)ccc1NC(=O)[C@H](Cc1ccccc1)NC(=O)c1ccc(F)cc1] |
| I-146 | 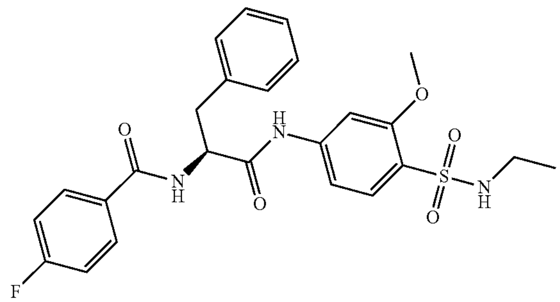 [SMILES: CCNS(=O)(=O)c1ccc(NC(=O)[C@H](Cc2ccccc2)NC(=O)c2ccc(F)cc2)cc1OC] |
| I-147 | 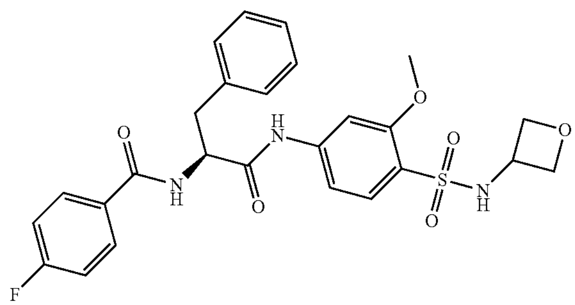 [SMILES: COc1cc(NC(=O)[C@H](Cc2ccccc2)NC(=O)c2ccc(F)cc2)ccc1S(=O)(=O)NC1COC1] |
| I-148 | 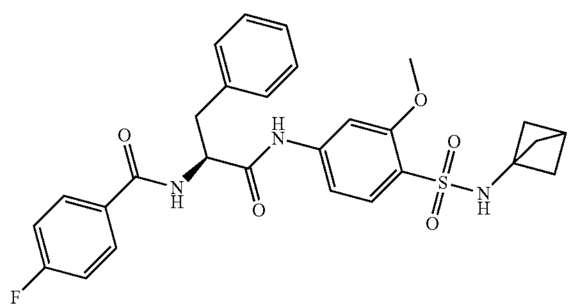 [SMILES: COc1cc(NC(=O)[C@H](Cc2ccccc2)NC(=O)c2ccc(F)cc2)ccc1S(=O)(=O)NC12CC(C1)C2] |
| I-149 | 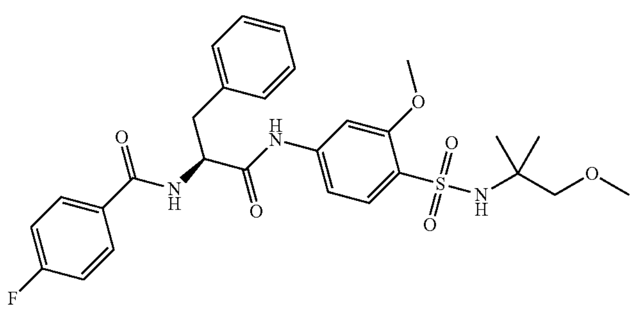 [SMILES: COCC(C)(C)NS(=O)(=O)c1ccc(NC(=O)[C@H](Cc2ccccc2)NC(=O)c2ccc(F)cc2)cc1OC] |

TABLE 1-continued

Exemplary Compounds

| Compound | Structure |
|---|---|
| I-150 | 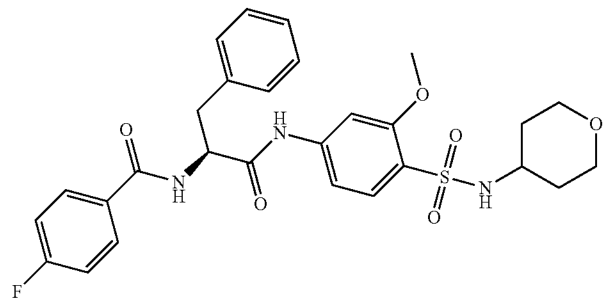 [SMILES: COc1cc(NC(=O)[C@H](Cc2ccccc2)NC(=O)c2ccc(F)cc2)ccc1S(=O)(=O)NC1CCOCC1] |
| I-151 | 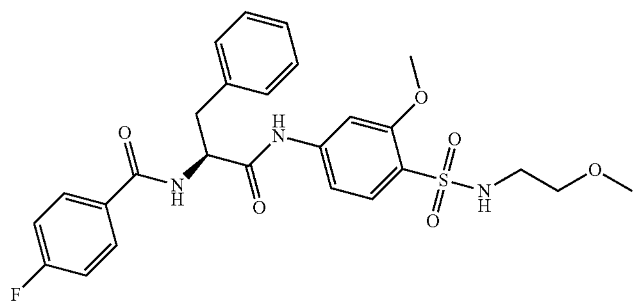 [SMILES: COCCNS(=O)(=O)c1ccc(NC(=O)[C@H](Cc2ccccc2)NC(=O)c2ccc(F)cc2)cc1OC] |
| I-152 | 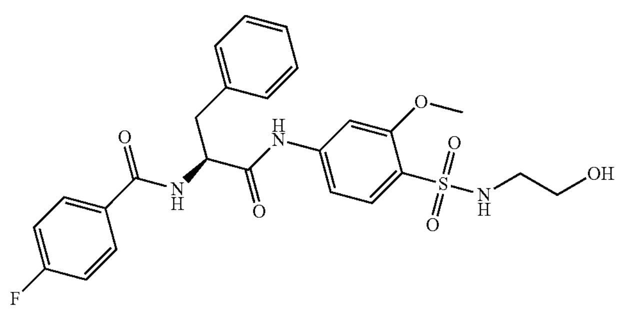 [SMILES: COc1cc(NC(=O)[C@H](Cc2ccccc2)NC(=O)c2ccc(F)cc2)ccc1S(=O)(=O)NCCO] |
| I-153 | 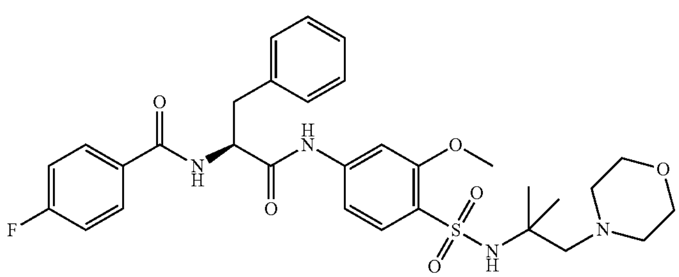 [SMILES: COc1cc(NC(=O)[C@H](Cc2ccccc2)NC(=O)c2ccc(F)cc2)ccc1S(=O)(=O)NC(C)(C)CN1CCOCC1] |
| I-154 | 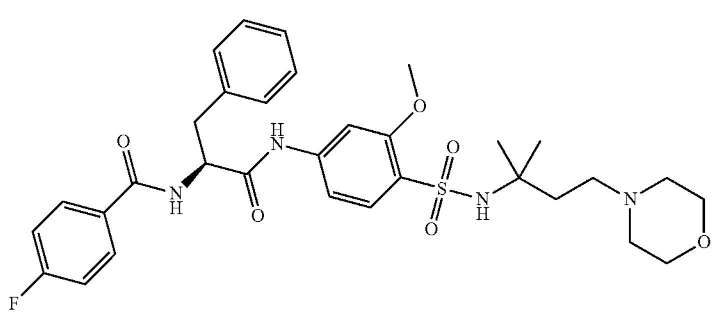 [SMILES: COc1cc(NC(=O)[C@H](Cc2ccccc2)NC(=O)c2ccc(F)cc2)ccc1S(=O)(=O)NC(C)(C)CCN1CCOCC1] |

TABLE 1-continued
Exemplary Compounds
| Compound | Structure |
|---|---|
| I-155 | 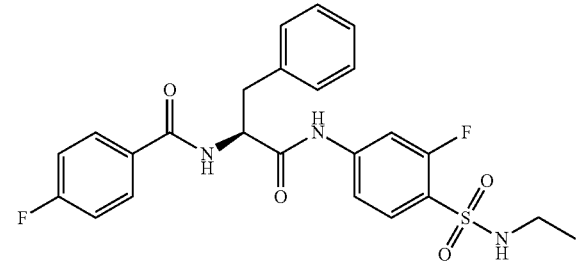 [SMILES: CCNS(=O)(=O)c1ccc(NC(=O)[C@H](Cc2ccccc2)NC(=O)c2ccc(F)cc2)cc1F] |
| I-156 | 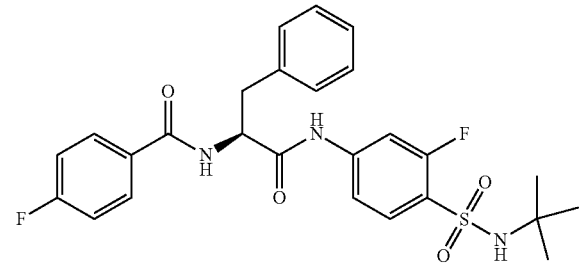 [SMILES: CC(C)(C)NS(=O)(=O)c1ccc(NC(=O)[C@H](Cc2ccccc2)NC(=O)c2ccc(F)cc2)cc1F] |
| I-157 | 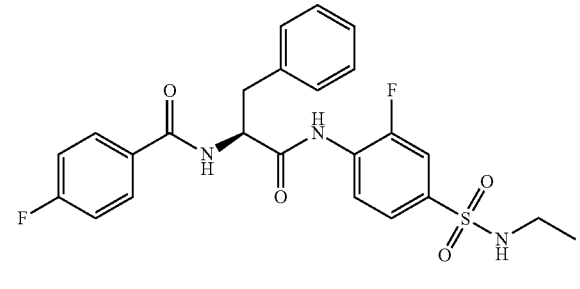 |
| I-158 | 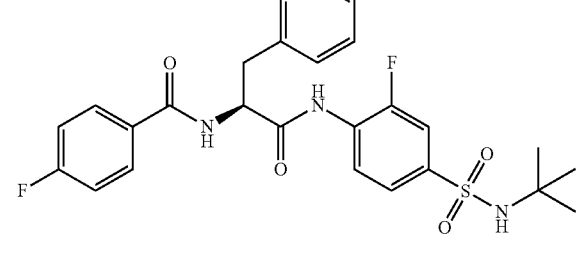 |
| I-159 | 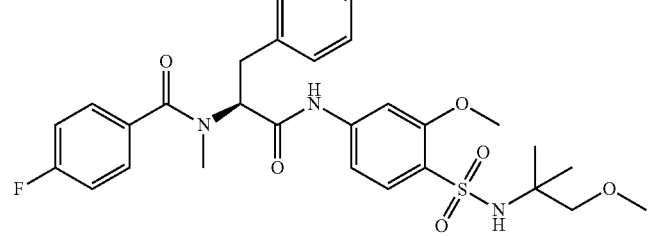 |

TABLE 1-continued

Exemplary Compounds

| Compound | Structure |
|---|---|
| I-160 | 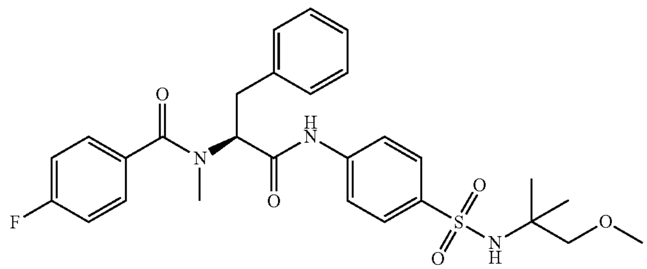 [SMILES: COCC(C)(C)NS(=O)(=O)c1ccc(NC(=O)[C@H](Cc2ccccc2)N(C)C(=O)c2ccc(F)cc2)cc1] |
| I-161 | 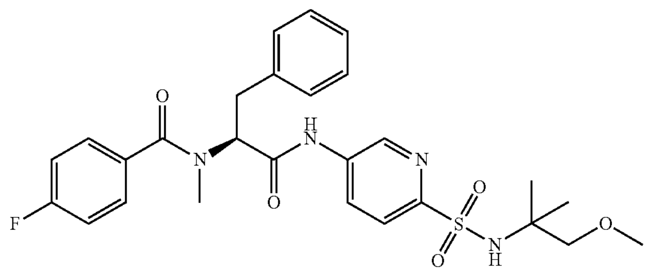 [SMILES: COCC(C)(C)NS(=O)(=O)c1ccc(NC(=O)[C@H](Cc2ccccc2)N(C)C(=O)c2ccc(F)cc2)cn1] |
| I-162 | 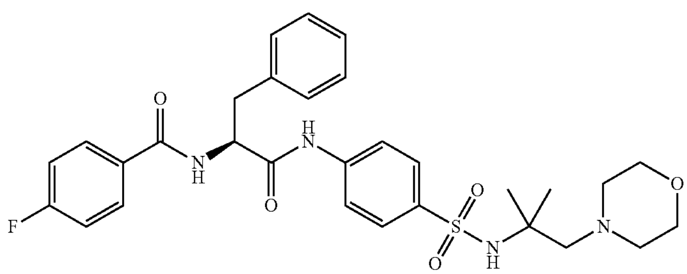 [SMILES: CC(C)(CN1CCOCC1)NS(=O)(=O)c1ccc(NC(=O)[C@H](Cc2ccccc2)NC(=O)c2ccc(F)cc2)cc1] |
| I-163 | 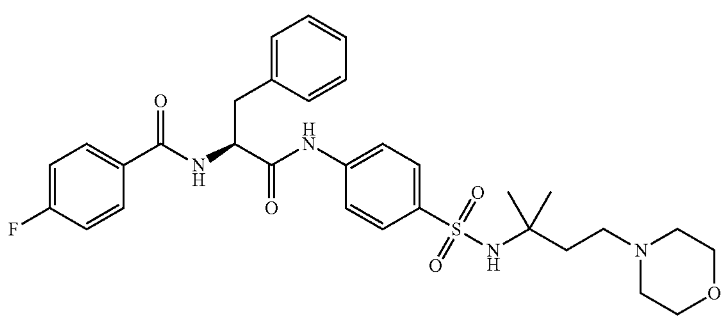 [SMILES: CC(C)(CCN1CCOCC1)NS(=O)(=O)c1ccc(NC(=O)[C@H](Cc2ccccc2)NC(=O)c2ccc(F)cc2)cc1] |
| I-165 | 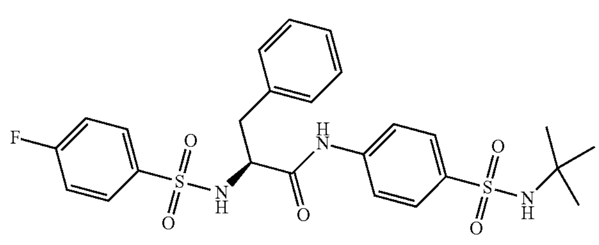 [SMILES: CC(C)(C)NS(=O)(=O)c1ccc(NC(=O)[C@H](Cc2ccccc2)NS(=O)(=O)c2ccc(F)cc2)cc1] |

TABLE 1-continued
Exemplary Compounds
| Compound | Structure |
|---|---|
| I-166 | 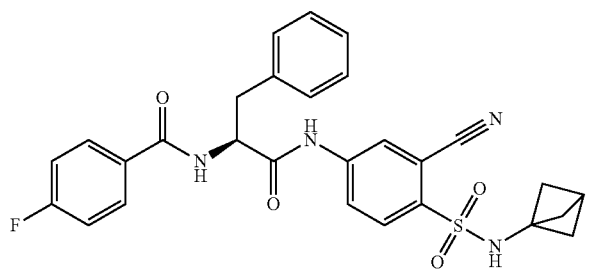 [SMILES: N#Cc1cc(NC(=O)[C@H](Cc2ccccc2)NC(=O)c2ccc(F)cc2)ccc1S(=O)(=O)NC12CC(C1)C2] |
| I-167 | 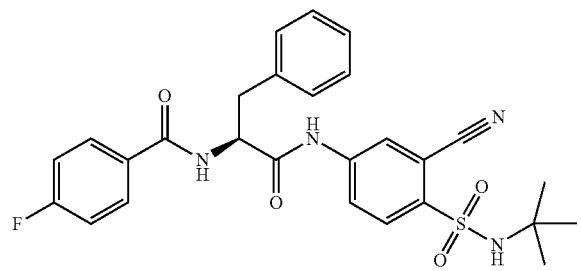 [SMILES: CC(C)(C)NS(=O)(=O)c1ccc(NC(=O)[C@H](Cc2ccccc2)NC(=O)c2ccc(F)cc2)cc1C#N] |
| I-168 | 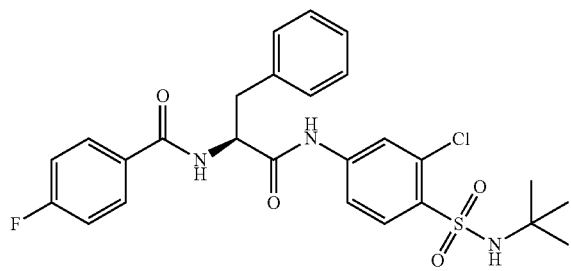 [SMILES: CC(C)(C)NS(=O)(=O)c1ccc(NC(=O)[C@H](Cc2ccccc2)NC(=O)c2ccc(F)cc2)cc1Cl] |
| I-169 | 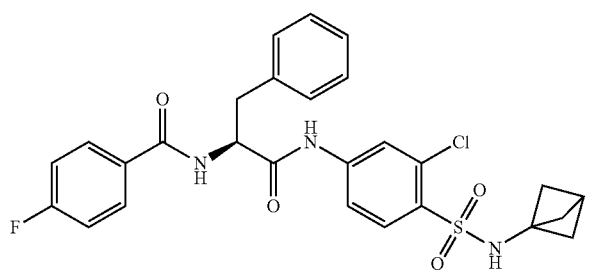 [SMILES: O=C(N[C@@H](Cc1ccccc1)C(=O)Nc1ccc(S(=O)(=O)NC23CC(C2)C3)c(Cl)c1)c1ccc(F)cc1] |
| I-170 | 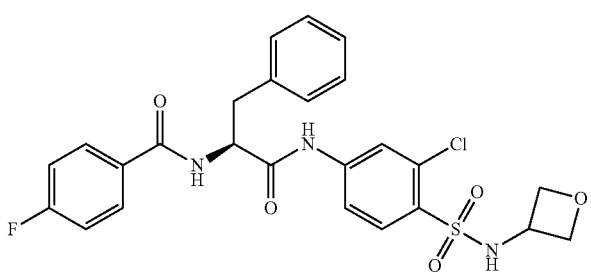 [SMILES: O=C(N[C@@H](Cc1ccccc1)C(=O)Nc1ccc(S(=O)(=O)NC2COC2)c(Cl)c1)c1ccc(F)cc1] |

TABLE 1-continued
Exemplary Compounds
| Compound | Structure |
|---|---|
| I-171 | 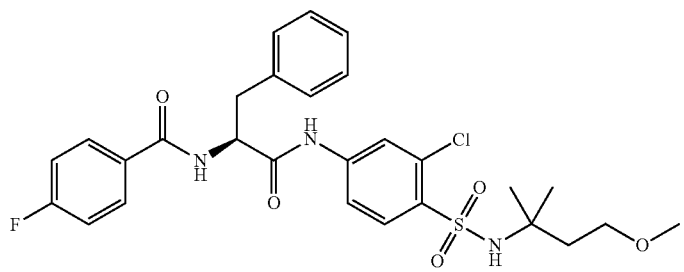 [SMILES: COCCC(C)(C)NS(=O)(=O)c1ccc(NC(=O)[C@H](Cc2ccccc2)NC(=O)c2ccc(F)cc2)cc1Cl] |
| I-172 | 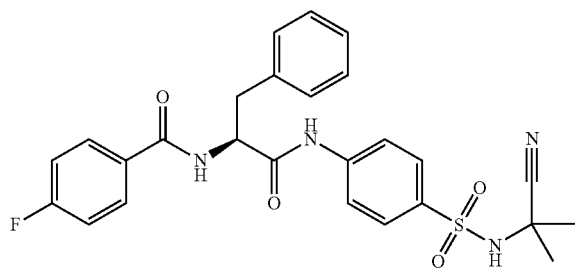 [SMILES: CC(C)(C#N)NS(=O)(=O)c1ccc(NC(=O)[C@H](Cc2ccccc2)NC(=O)c2ccc(F)cc2)cc1] |
| I-173 | 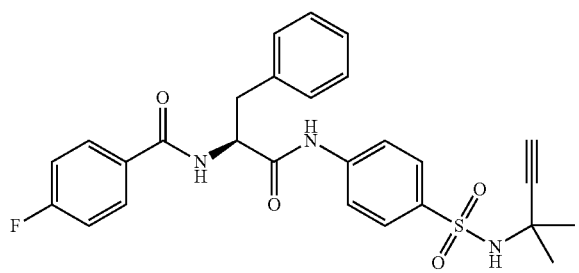 [SMILES: C#CC(C)(C)NS(=O)(=O)c1ccc(NC(=O)[C@H](Cc2ccccc2)NC(=O)c2ccc(F)cc2)cc1] |
| I-174 | 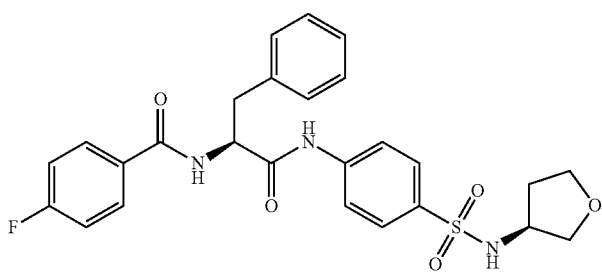 [SMILES: O=C(N[C@@H](Cc1ccccc1)C(=O)Nc1ccc(S(=O)(=O)N[C@H]2CCOC2)cc1)c1ccc(F)cc1] |
| I-175 | 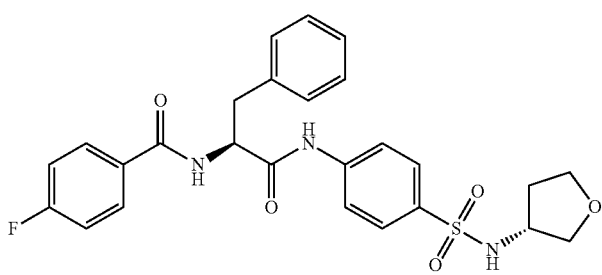 [SMILES: O=C(N[C@@H](Cc1ccccc1)C(=O)Nc1ccc(S(=O)(=O)N[C@@H]2CCOC2)cc1)c1ccc(F)cc1] |

TABLE 1-continued
Exemplary Compounds
| Compound | Structure |
|---|---|
| I-176 | 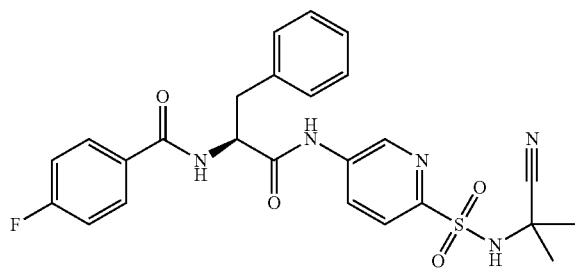 [SMILES: CC(C)(C#N)NS(=O)(=O)c1ccc(NC(=O)[C@H](Cc2ccccc2)NC(=O)c2ccc(F)cc2)cn1] |
| I-177 | 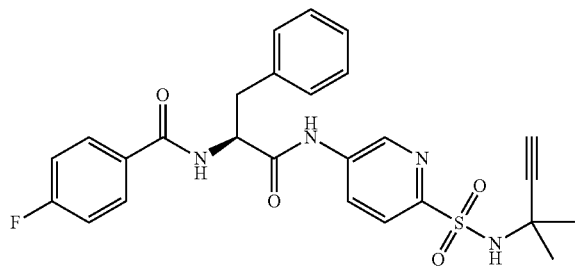 [SMILES: C#CC(C)(C)NS(=O)(=O)c1ccc(NC(=O)[C@H](Cc2ccccc2)NC(=O)c2ccc(F)cc2)cn1] |
| I-178 | 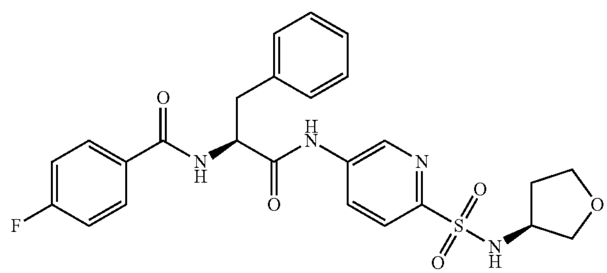 [SMILES: O=C(N[C@@H](Cc1ccccc1)C(=O)Nc1ccc(S(=O)(=O)N[C@H]2CCOC2)nc1)c1ccc(F)cc1] |
| I-179 | 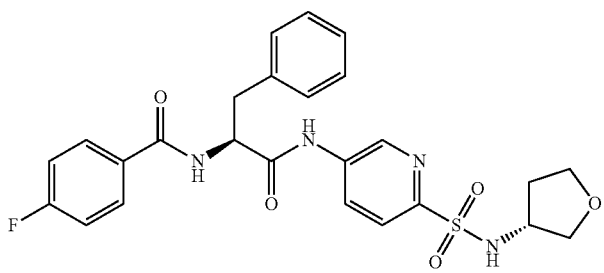 [SMILES: O=C(N[C@@H](Cc1ccccc1)C(=O)Nc1ccc(S(=O)(=O)N[C@@H]2CCOC2)nc1)c1ccc(F)cc1] |
| I-180 | 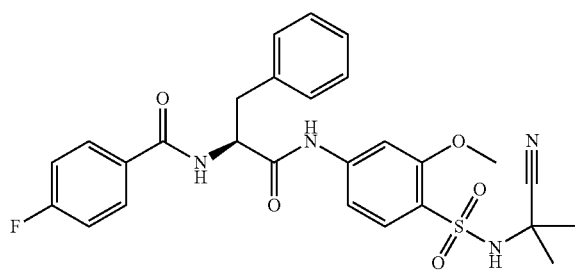 [SMILES: COc1cc(NC(=O)[C@H](Cc2ccccc2)NC(=O)c2ccc(F)cc2)ccc1S(=O)(=O)NC(C)(C)C#N] |

TABLE 1-continued
Exemplary Compounds
| Compound | Structure |
|---|---|
| I-181 | 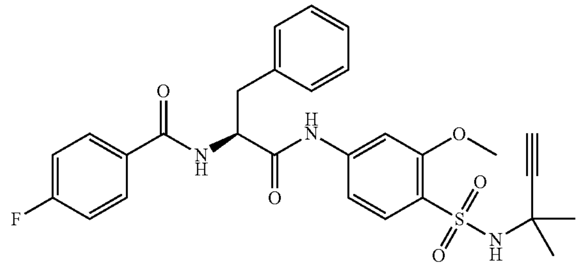 [SMILES: C#CC(C)(C)NS(=O)(=O)c1ccc(NC(=O)[C@H](Cc2ccccc2)NC(=O)c2ccc(F)cc2)cc1OC] |
| I-182 | 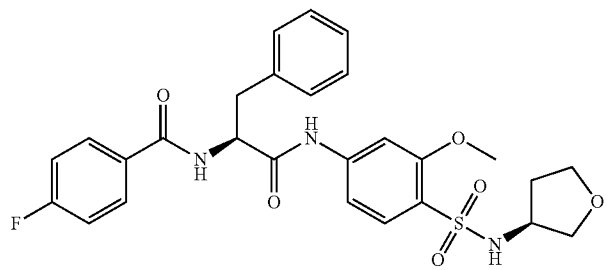 [SMILES: COc1cc(NC(=O)[C@H](Cc2ccccc2)NC(=O)c2ccc(F)cc2)ccc1S(=O)(=O)N[C@H]1CCOC1] |
| I-183 | 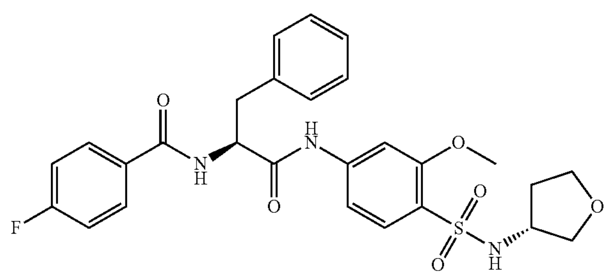 [SMILES: COc1cc(NC(=O)[C@H](Cc2ccccc2)NC(=O)c2ccc(F)cc2)ccc1S(=O)(=O)N[C@@H]1CCOC1] |
In some embodiments, the method employs a compound set forth in Table 1, above, or a pharmaceutically acceptable salt thereof.
TABLE 1-1
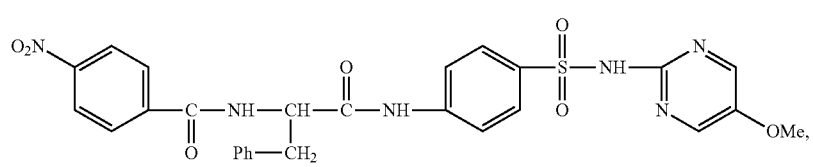 [SMILES: COc1cnc(NS(=O)(=O)c2ccc(NC(=O)C(Cc3ccccc3)NC(=O)c3ccc([N+](=O)[O-])cc3)cc2)nc1]

TABLE 1-1-continued
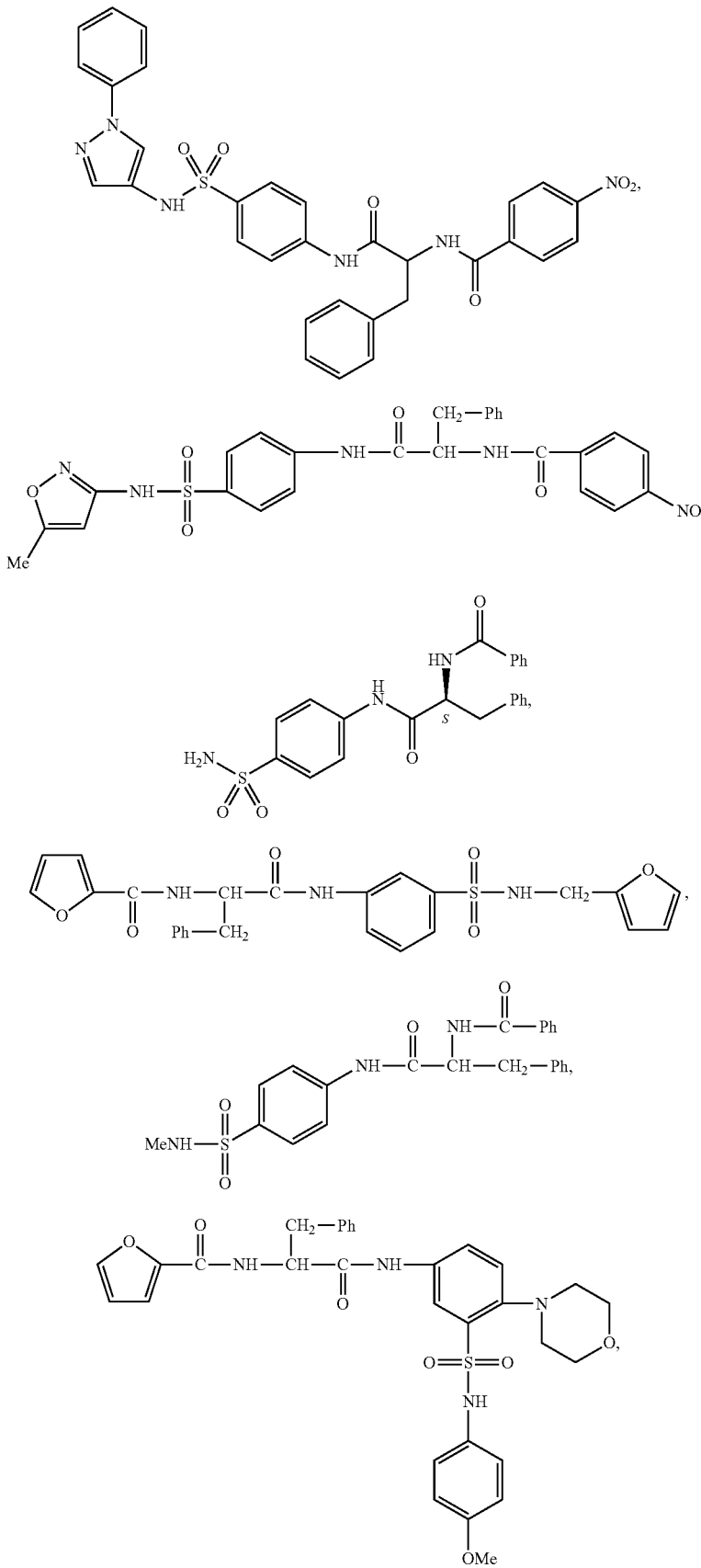

TABLE 1-1-continued
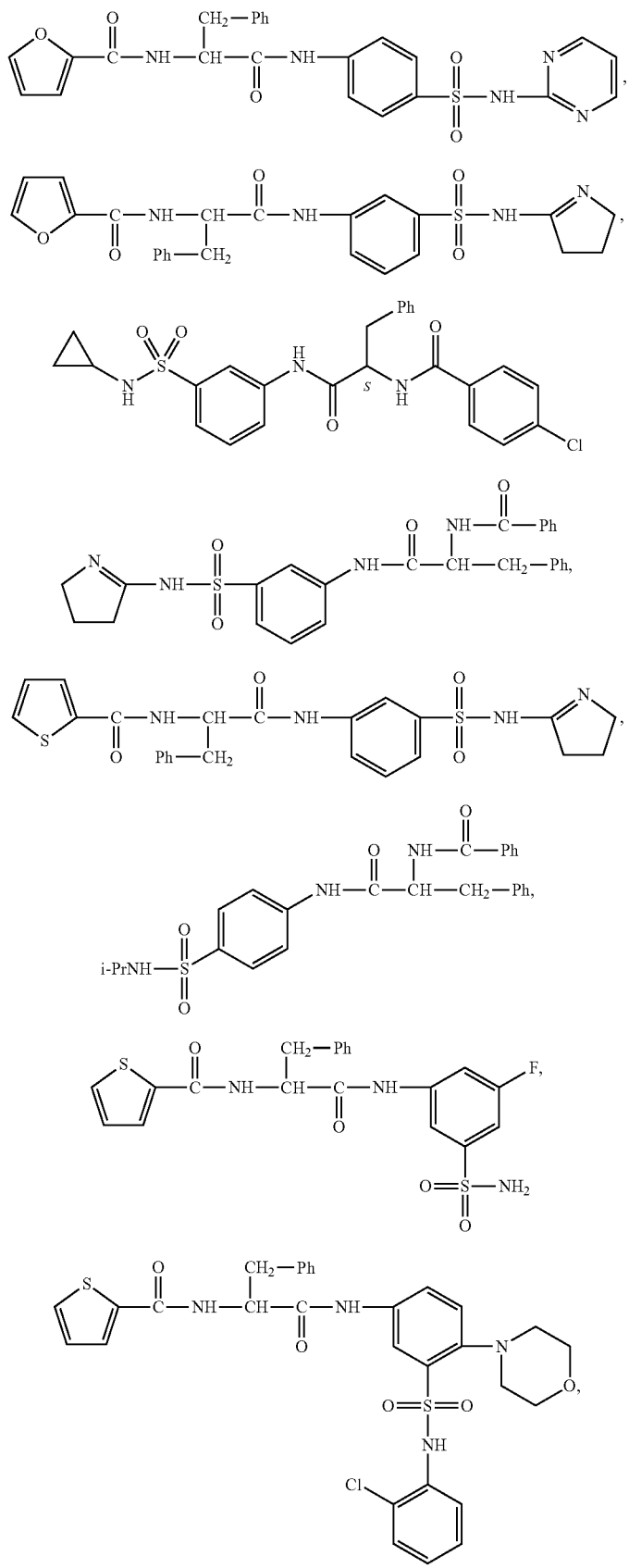

TABLE 1-1-continued
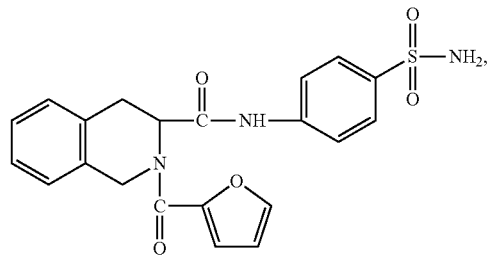 [SMILES: NS(=O)(=O)c1ccc(NC(=O)C2Cc3ccccc3CN2C(=O)c2ccco2)cc1]
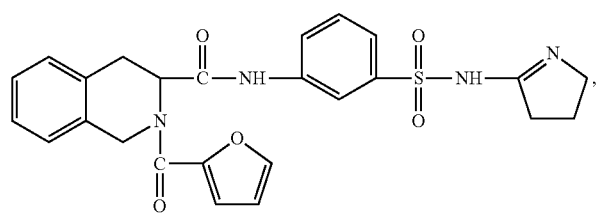 [SMILES: O=C(Nc1cccc(S(=O)(=O)NC2=NCCC2)c1)C1Cc2ccccc2CN1C(=O)c1ccco1]
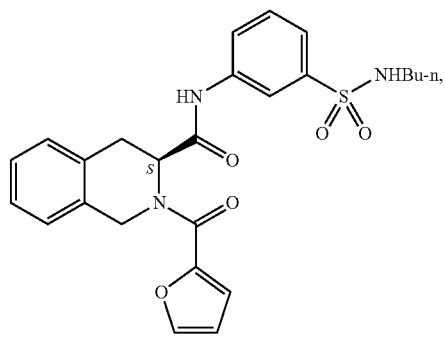
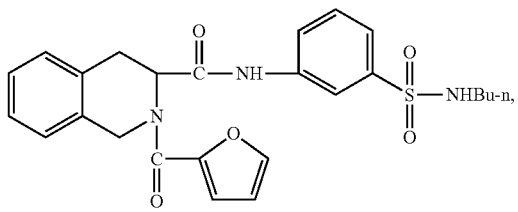
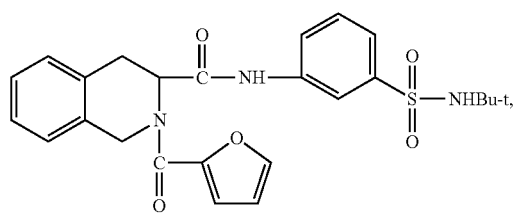
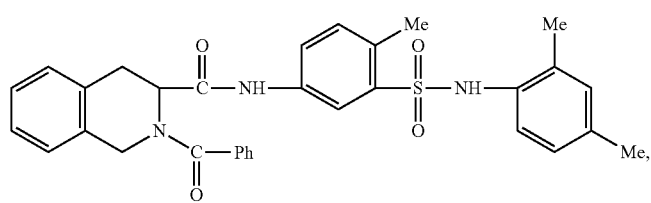 [SMILES: Cc1ccc(NS(=O)(=O)c2cc(NC(=O)C3Cc4ccccc4CN3C(=O)c3ccccc3)ccc2C)c(C)c1]

TABLE 1-1-continued

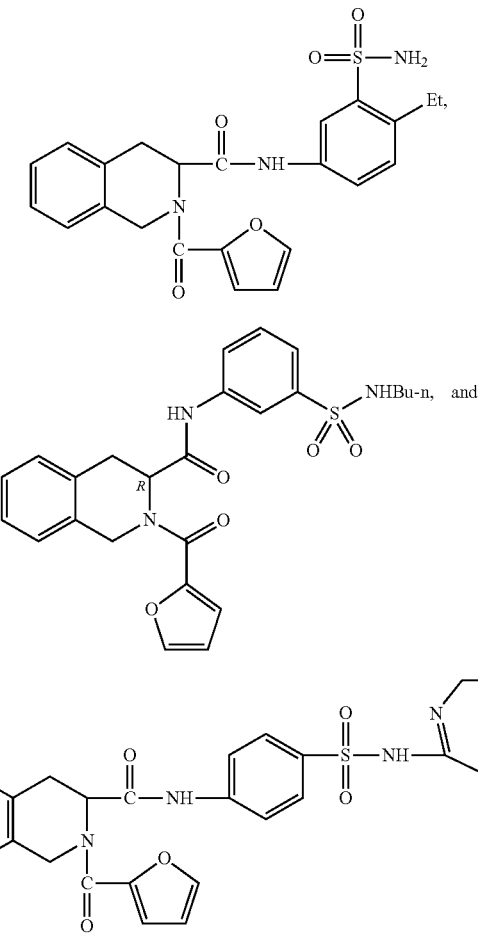

In certain embodiments, the present invention provides a compound other than one selected from those depicted in Table 1-1, above, or a pharmaceutically acceptable salt thereof.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit USP30 in a biological sample or in a patient. In certain embodiments, the amount of compound in compositions of this invention is such that is effective to measurably inhibit USP30 in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of USP30.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of USP30.

USP30, a deubiquitinase (DUB) localized to mitochondria and peroxisomes is an antagonist of Parkin-mediated mitophagy and of PEX2-mediated pexophagy. USP30, through its deubiquitinase activity, counteracts ubiquitination and degradation of damaged mitochondria, and inhibition of USP30 rescues mitophagy defects caused by mutant Parkin. Further, inhibition of USP30 decreases oxidative stress and provides protection against the mitochondrial toxin, rotenone. Since damaged mitochondria are more likely to accumulate Parkin, USP30 inhibition should preferentially clear unhealthy mitochondria. USP30 inhibition may beneficially increase rates of basal mitophagy, increase production of mitochondrial derived vesicles, arrest mitochondrial fission and trafficking, and generally improve mitochondrial quality control mechanisms. In addition to neurons (such as substantia nigra neurons, which are especially vulnerable to mitochondria dysfunction in Parkinson's disease), long-lived metabolically active cells such as cardiomyocytes also rely on an efficient mitochondria quality control system. In this context, Parkin has been shown to protect cardiomyocytes against ischemia/reperfusion injury through activating mitophagy and clearing damaged mitochondria in response to ischemic stress. Thus, inhibitors of USP30 are provided for use in treating a conditions involving mitochondrial defects, including neurological conditions, cardiac conditions, and systemic conditions. Deubiquinating enzymes function to oppose the action of the ubiquitinating enzymes in post-translational modification of cellular proteins. These conditions collectively represent examples of age related disorders and symptoms of natural aging suggesting further utility of USP30 inhibition to slow the process of aging and occurrence of age related disease. USP30 is a deubiquitinase that is localized to mitochondria and has been shown in expression studies to oppose the action of Parkin-mediated ubiquination and clearance of damaged mitochondria while also opposing basal ubiquitination by ligases such as MUL1 and MARCH5. USP30 that is localized to persoxisomes has been shown to oppose ubiquitination by PEX E3 ligases and induction of selective autophagy.

In particular, disclosed herein are methods for modulating the activity of USP30 for the treatment of diseases, developmental delays, and symptoms related to mitochondrial dysfunction. For example, the disclosed compounds and compositions are useful in the treatment of mitochondrial diseases, such as Alpers's Disease, CPEO-Chronic progressive external ophthalmoplegia, Kearns-Sayra Syndrome (KSS), Leber Hereditary Optic Neuropathy (LHON), MELAS—Mitochondrial myopathy, encephalomyopathy, lactic acidosis, and strokelike episodes, MERRF—Myoclonic epilepsy and ragged-red fiber disease, NARP-neurogenic muscle weakness, ataxia, retinitis pigmentosa, and Pearson Syndrome. Additionally, the disclosed compounds and compositions are useful in the treatment of other USP30-related diseases, such as chronic obstructive pulmonary disease (COPD) and idiopathic pulmonary fibrosis (IPF) (Tsubouchi K, Araya J, Kuwano K. PINK1-PARK2-mediated mitophagy in COPD and IPF pathogeneses. *Inflamm Regen.* 2018; 38:18. Published 2018 Oct. 24. doi:10.1186/s41232-018-0077-6; Kobayashi K, Araya J, Minagawa S, et al. Involvement of PARK2-Mediated Mitophagy in Idiopathic Pulmonary Fibrosis Pathogenesis. *J Immunol.* 2016; 197(2):504-516. doi:10.4049/jimmunol.1600265; Ryter S W, Rosas I O, Owen C A, et al. Mitochondrial Dysfunction as a Pathogenic Mediator of Chronic Obstructive Pulmonary Disease and Idiopathic Pulmonary Fibrosis. *Ann Am Thorac Soc.* 2018; 15(Suppl 4):S266-S272. doi:10.1513/AnnalsATS.201808-585MG; and Ito S, Araya J, Kurita Y, et al. PARK2-mediated mitophagy is involved in regulation of HBEC senescence in COPD pathogenesis. *Autophagy.* 2015; 11(3):547-559. doi:10.1080/15548627.2015.1017190). Alternatively, the disclosed compounds and compositions are useful in the treatment of other USP30-related diseases, such as cardiovascular disease, kidney disease, pulmonary fibrosis, ophthalmic conditions, cancer, cognitive disease, and other related conditions (Lin Q, Li S, Jiang N, et al. PINK1-parkin pathway of mitophagy protects against contrast-induced acute kidney injury via decreasing mitochondrial ROS and NLRP3 inflammasome activation. *Redox Biol.* 2019; 26:101254. doi:10.1016/j.redox.2019.101254; Wang Y, Cai J, Tang C, Dong Z. Mitophagy in Acute Kidney Injury and Kidney Repair. *Cells.* 2020; 9(2):338. Published 2020 Feb. 1. doi:10.3390/cells9020338; Wang Y, Tang C, Cai J, et al. PINK1/Parkin-mediated mitophagy is activated in cisplatin nephrotoxicity to protect against kidney injury. *Cell Death Dis.* 2018; 9(11):1113. Published 2018 Nov. 1. doi:10.1038/s41419-018-1152-2; and Tang C, Han H, Yan M, et al. PINK1-PRKN/PARK2 pathway of mitophagy is activated to protect against renal ischemia-reperfusion injury. *Autophagy.* 2018; 14(5):880-897. doi:10.1080/15548627.2017.1405880). Disclosed compounds are useful in the treatment of peroxisome related diseases such as Ataxia-telangiectasia mutated, Heimler syndrome, Infantile refsum disease, Neonatal adrenoleukodystrophy, Rhizomelic chondrodysplasia punctate, White matter dementia, Zellweger syndrome, and Zellweger spectrum disorders (Riccio et al. Deubiquitinating enzyme USP30 maintains basal peroxisome abundance by regulating pexophagy. *J Cell Biol.* 2019; 218(3):798-807. doi:10.1083/jcb.201804172; Marcassa et al. Dual role of USP30 in controlling basal pexophagy and mitophagy. *EMBO Rep.* 2018; 19(7):e45595. doi:10.15252/embr.201745595; and Nazarko T Y. Pexophagy is responsible for 65% of cases of peroxisome biogenesis disorders. *Autophagy.* 2017; 13(5): 991-994. doi:10.1080/15548627.2017.1291480).

Methods of treating a USP30-related disease or condition in a subject are disclosed. The methods can include administering to the subject an effective amount of one or more compounds or compositions provided herein. In one embodiment, the USP30-related disease is a mitochondrial disease. Examples of mitochondrial diseases include, but are not limited to, Alpers's Disease, CPEO-Chronic progressive external ophthalmoplegia, Kearns-Sayra Syndrome (KSS), Leber Hereditary Optic Neuropathy (LHON), MELAS—Mitochondrial myopathy, encephalomyopathy, lactic acidosis, and stroke-like episodes, MERRF—Myoclonic epilepsy and ragged-red fiber disease, NARP-neurogenic muscle weakness, ataxia, and retinitis pigmentosa, and Pearson Syndrome. In other embodiments, the USP30-related disease is a vascular disease (such as a cardiovascular disease or any disease that would benefit from increasing vascularization in tissues exhibiting impaired or inadequate blood flow). In other embodiments, the USP30-related disease is a muscular disease, such as a muscular dystrophy. Examples of muscular dystrophy include but are not limited to Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy. In other embodiments, the USP30-related disease is a form of pulmonary fibrosis. In other embodiments, the USP30-related disease is natural aging or an age-related disease (Sun N, Youle R J, Finkel T. The Mitochondrial Basis of Aging. *Mol Cell.* 2016; 61(5):654-666. doi: 10.1016/j.molcel.2016.01.028; Cornelissen T, Vilain S, Vints K, Gounko N, Verstreken P, Vandenberghe W. Deficiency of parkin and PINK1 impairs age-dependent mitophagy in *Drosophila. Elife.* 2018; 7:e35878. Published 2018 May 29. doi:10.7554/eLife.35878; Ryu D, Mouchiroud L, Andreux P A, et al. Urolithin A induces mitophagy and prolongs lifespan in *C. elegans* and increases muscle function in rodents. *Nat Med.* 2016; 22(8):879-888. doi:

10.1038/nm.4132; Brown E E, Lewin A S, Ash J D. Mitochondria: Potential Targets for Protection in Age-Related Macular Degeneration. *Adv Exp Med Biol.* 2018; 1074:11-17. doi:10.1007/978-3-319-75402-4_2; and Ito et al. 2015).

In some embodiments, the USP30-related disease or condition is a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome.

In other embodiments, the USP30-related disease is a metabolic disease. Examples of metabolic diseases include but are not limited to obesity, hypertriglyceridemia, hyperlipidemia, hypoalphalipoproteinemia, hypercholesterolemia, dyslipidemia, Syndrome X, and Type II diabetes mellitus.

In yet other embodiments, the USP30-related disease is a muscle structure disorder. Examples of a muscle structure disorders include, but are not limited to, Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In still other embodiments, the USP30-related disease is a neuronal activation disorder. Examples of neuronal activation disorders include, but are not limited to, amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder. In other embodiments, the USP30-related disease is a muscle fatigue disorder.

Examples of muscle fatigue disorders include, but are not limited to chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy.

In some embodiments, the USP30-related disease is a muscle mass disorder.

Examples of muscle mass disorders include, but are not limited to, cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In other embodiments, the USP30-related disease is a beta oxidation disease.

Examples of beta oxidation diseases include, but are not limited to, systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD).

In some embodiments, the USP30-related disease is a vascular disease. Examples of vascular diseases include, but are not limited to, peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In other embodiments, the USP30-related disease is an ocular vascular disease.

Examples of ocular vascular diseases include, but are not limited to, age-related macular degeneration (AMD), stargardt disease, hypertensive retinopathy, diabetic retinopathy, retinopathy, macular degeneration, retinal haemorrhage, and glaucoma.

In yet other embodiments, the USP30-related disease is a muscular eye disease.

Examples of muscular eye diseases include, but are not limited to, strabismus (crossed eye/wandering eye/walleye ophthalmoparesis), progressive external ophthalmoplegia, esotropia, exotropia, a disorder of refraction and accommodation, hypermetropia, myopia, astigmatism, anisometropia, presbyopia, a disorders of accommodation, or internal ophthalmoplegia. In yet other embodiments, the USP30-related disease is a metabolic disease.

Examples of metabolic disorders include, but are not limited to, hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, non-alcoholic fatty liver disease (NAFLD), nonalcoholic steatohepatitis (NASH), thrombus, Parkinson's disease, Alzheimer's disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In still other embodiments, the USP30-related disease is cancer. Examples of cancer include, but are not limited to, cancers of the colon, large intestine, skin, breast, prostate, ovary, and/or lung.

In other embodiments, the USP30-related disease is an ischemic injury. Examples of ischemic injuries include, but are not limited to, cardiac ischemia, such as myocardial infarction; brain ischemia (e.g., acute ischemic stroke; chronic ischemic of the brain, such as vascular dementia; and transient ischemic attack (TIA); bowel ischemia, such as ischemic colitis; limb ischemia, such as acute arm or leg ischemia; subcutaneous ischemia, such as cyanosis or gangrene; and ischemic organ injury, such as ischemic renal injury (IRI).

In still other embodiments, the USP30-related disease is a renal disease. Examples of renal diseases include, but are not limited to, glomerulonephritis, glomerulosclerosis, nephrotic syndrome, hypertensive nephrosclerosis, acute nephritis, recurrent hematuria, persistent hematuria, chronic nephritis, rapidly progressive nephritis, acute kidney injury (also known as acute renal failure), chronic renal failure, diabetic nephropathy, or Bartter's syndrome.

Even though USP30 inhibitors are known in the art, there is a continuing need to provide novel inhibitors having more effective or advantageous pharmaceutically relevant properties. For example, compounds with increased activity, selectivity over other deubiquitinating enzymes (DUBs) such as USP8, USP15, and USP16, and ADMET (absorption, distribution, metabolism, excretion, and/or toxicity) properties. Thus, in some embodiments, the present invention provides inhibitors of USP30 which show selectivity over other DUBs.

USP8 is a DUB within the same phylogenic tree as USP30, localizes to mitochondria and mediates K6-linked deubiquitination (Kemp M: Recent Advances in the Discovery of Deubiquitinating Enzyme Inhibitors. Prog Med Chem 2016, 55:149-192). USP8 can also deubiquitinate parkin, thus it may impact the mitophagy pathway. Furthermore, embryonic lethality resulting from USP8 knockout (Niendorf et al., Essential role of ubiquitin-specific protease 8 for receptor tyrosine kinase stability and endocytic trafficking in vivo. Mol Cell Biol 2007, 27:5029-5039. PMC1951504) suggests USP8 inhibition may have detrimental toxicity. USP15 also localizes to mitochondria and can alter parkin-mediated mitophagy (Coyne and Wing, The business of deubiquitination—location, location, location. F1000Res 2016, 5. PMC4755399). USP16 is similar to USP30 in that they both lack an aspartate as part of their catalytic triad (Gersch et al, Mechanism and regulation of the Lys6-selective deubiquitinase USP30. Nat Struct Mol Biol 2017, 24:920-930. PMC5757785; Nijman et al., A genomic and functional inventory of deubiquitinating enzymes. Cell 2005, 123:773-786; Mevissen and Komander, Mechanisms of Deubiquitinase Specificity and Regulation. Annu Rev Biochem 2017, 86:159-192) and knockout of this gene is embryonic lethal.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of USP30 and are therefore useful for treating one or more disorders associated with activity of USP30. Thus, in certain embodiments, the present invention provides a method for treating a USP30-mediated disorder comprising the step of administering to a patient in need thereof a compound of the present invention, or pharmaceutically acceptable composition thereof.

As used herein, the term "USP30-mediated" disorders, diseases, and/or conditions as used herein means any disease or other deleterious condition in which USP30 is known to play a role. Accordingly, another embodiment of the present invention relates to treating or lessening the severity of one or more diseases in which USP30 is known to play a role.

Furthermore, the invention provides the use of a compound according to the definitions herein, or a pharmaceutically acceptable salt, or a hydrate or solvate thereof for the preparation of a medicament for the treatment of a USP30-mediated disorder.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I or formula I' and one or more additional therapeutic agents. The therapeutic agent may be administered together with a compound of formula I or formula I', or may be administered prior to or following administration of a compound of formula I or formula I'. Suitable therapeutic agents are described in further detail below. In certain embodiments, a compound of formula I or formula I' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I or formula I' may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I or formula I' and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I or formula I' and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I or formula I' and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I or formula I' and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I or formula I' and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I or formula I' and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I or formula I' and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I or formula I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I or formula I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I or formula I' and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I or formula I' and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I or formula I' and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I or formula I' and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I or formula I' and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with ceil death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I or formula I' and a P3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleredoma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I or formula I' and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments the present invention provides a method of treating or lessening the severity of a disease comprising administering to a patient in need thereof a compound of formula I or formula I' and a parkin activator, wherein the disease is an inflamatory disorder, an autoimmune disorder, a proliferative disorder, an endocrine disorder, a neurological disorder, or a disorder associated with transplantation. In some embodiments, the disorder is a neurological disorder. In some embodiments, the disorder is Parkinson's disease. In some embodiments, the disorder is Alzheimer's disease.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting USP30 activity in a biological sample comprising the step of contacting said biological sample with a compound of this invention, or a composition comprising said compound.

According to another embodiment, the invention relates to a method of inhibiting USP30 activity in a biological sample comprising the step of contacting said biological sample with a compound of this invention, or a composition comprising said compound. In certain embodiments, the invention relates to a method of irreversibly inhibiting USP30, or a mutant thereof, activity in a biological sample comprising the step of contacting said biological sample with a compound of this invention, or a composition comprising said compound.

In another embodiment, the invention provides a method of selectively inhibiting USP30 over one or more DUBs. In some embodiments, a compound of the present invention is more than 2-fold selective over USP8, USP15, and/or USP16. In some embodiments, a compound of the present invention is more than 5-fold selective over USP8, USP15, and/or USP16. In some embodiments, a compound of the present invention is more than 10-fold selective over USP8, USP15, and/or USP16. In some embodiments, a compound of the present invention is more than 50-fold selective over USP8, USP15, and/or USP16. In some embodiments, a compound of the present invention is more than 100-fold selective over USP8, USP15, and/or USP16.

The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Inhibition of USP30 activity in a biological sample is useful for a variety of purposes that are known to one of skill in the art. Examples of such purposes include, but are not limited to biological assays.

Another embodiment of the present invention relates to a method of inhibiting USP30 activity in a patient comprising the step of administering to said patient a compound of the present invention, or a composition comprising said compound.

According to another embodiment, the invention relates to a method of inhibiting activity of USP30 in a patient comprising the step of administering to said patient a compound of the present invention, or a composition comprising said compound. According to certain embodiments, the invention relates to a method of reversibly or irreversibly inhibiting USP30 activity in a patient comprising the step of administering to said patient a compound of the present invention, or a composition comprising said compound. In other embodiments, the present invention provides a method for treating a disorder mediated by USP30 in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal©); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to, the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxo™ Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-R, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, P3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; sis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH—1 (Shenayng Pharmaceutical University), obatoclax (and analogs thereof, see WO2004106328), 5-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, 5-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (ParkeDavis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1: (S)-4-fluoro-N-(1-(4-(2,2-Dimethylpropyl sulfonyl)phenylamino)-1-oxo-3-phenylpropan-2-yl)benzamide, I-2

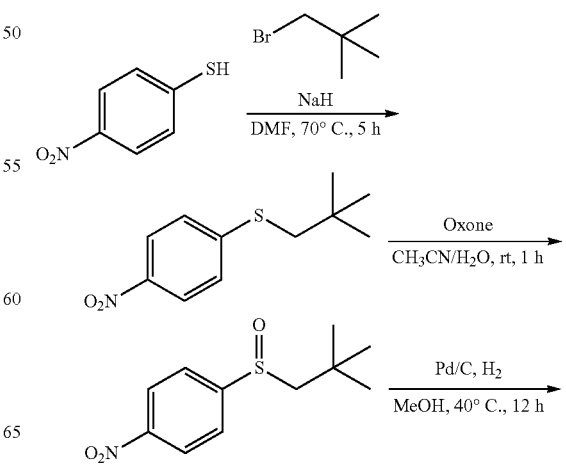

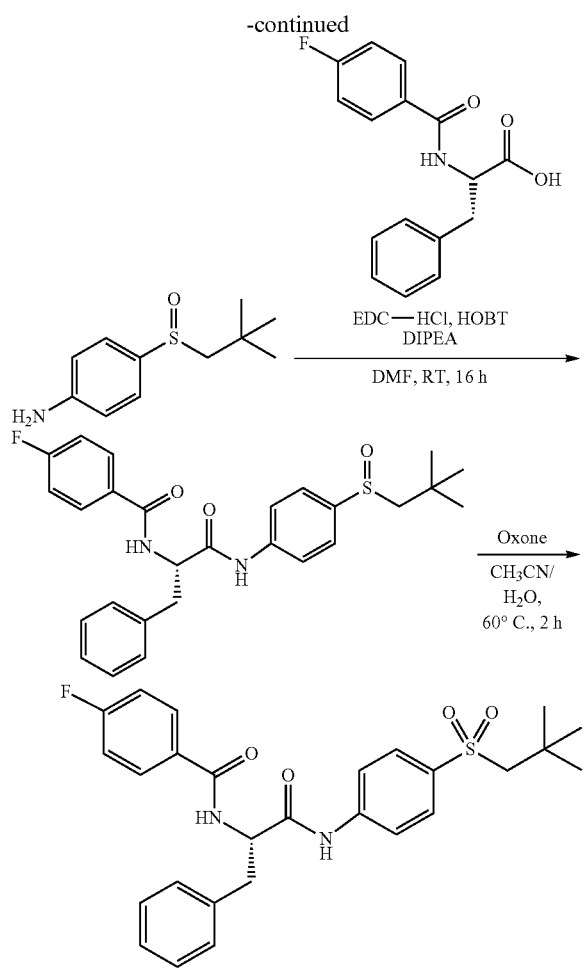

Preparation of
1-(2,2-Dimethyl-propylsulfanyl)-4-nitro-benzene

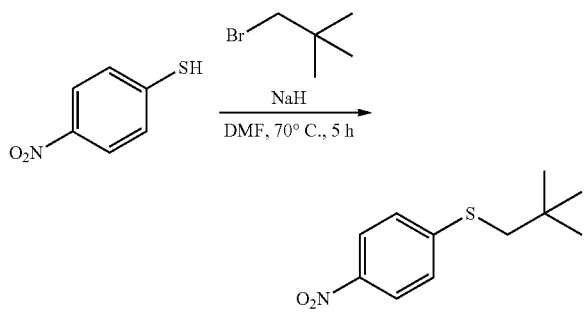

To a solution of 1.5 g of 4-nitrobenzenethiol (9.67 mmol, 1.00 eq.), and 1.89 g 1-bromo-2,2-dimethylpropane (12.58 mmol, 1.30 eq.) dissolved in 30 mL anhydrous N,N-dimethylformamide at room temperature was added 1.16 g sodium hydride (60 wt. % dispersion in mineral oil; 29.0 mmol, 3.00 eq.) all at once. The reaction was stirred at 70° C. for 5 hours. Then poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. Purification by column chromatography (silica gel, petroleum ether:ethyl acetate (1:3, v:v)) afforded 1.6 g 1-(2,2-dimethyl-propylsulfanyl)-4-nitro-benzene as a yellow solid (73% yield). MS (ESI$^+$) m/z 226 [M+H]$^+$.

Preparation of
1-(2,2-Dimethyl-propylsulfinyl)-4-nitrobenzene

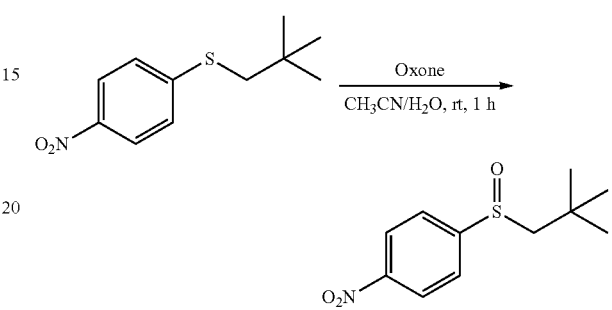

Oxone (1.02 g, 1.65 mmol, 0.50 eq.) was added all at once to a solution of 0.75 g of 1-(2,2-dimethyl-propylsulfanyl)-4-nitro-benzene (3.30 mmol, 1.00 eq.) dissolved in 30 mL acetonitrile:water (5:1). The reaction mixture was stirred at room temperature for 1 hour then it was poured into 50 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. Purification by column chromatography (silica gel, dichloromethane:methanol (20:1, v:v)) afforded 0.70 g 1-(2,2-dimethyl-propylsulfinyl)-4-nitrobenzene as a yellow solid (87% yield). MS (ESI$^+$) m/z 242 [M+H]$^+$.

Preparation of
4-(2,2-Dimethyl-propylsulfinyl)aniline

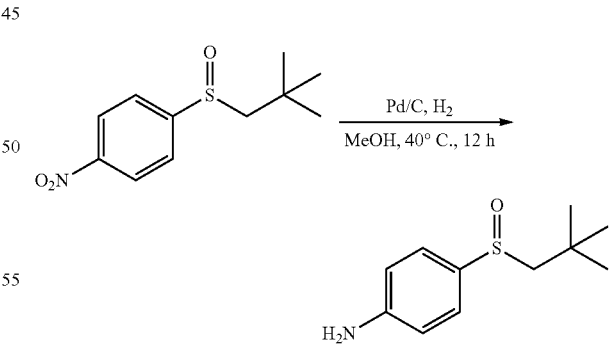

To a solution of 0.30 g 1-(2,2-dimethyl-propylsulfinyl)-4-nitrobenzene (1.24 mmol, 1.00 eq.) in methanol was added palladium on activated carbon (50 mg wet catalyst, 10 wt. % palladium dry basis). The mixture was placed under hydrogen gas via balloon and stirred at 40° C. for 12 hours. The mixture was filtered and the filtrate concentrated in vacuo. Purification by column chromatography (silica gel, petroleum ether:ethyl acetate (3:1, v:v)) to afford 187 mg 4-(2, 2-dimethyl-propylsulfinyl)aniline as a white solid (71% yield). MS (ESI+) m/z 212 [M+H]+.

Preparation of 4-Fluoro-N-((2S)-1-(4-(2,2-dimethyl-propylsulfinyl)phenylamino)-1-oxo-3-phenylpropan-2-yl)benzamide

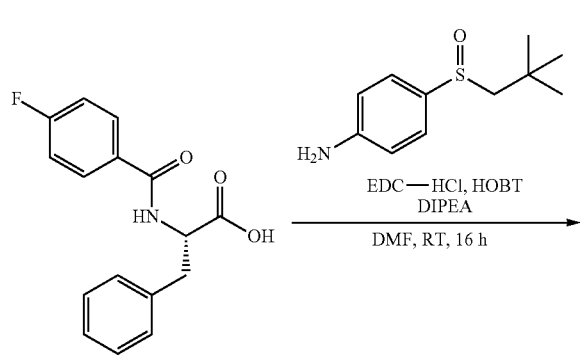

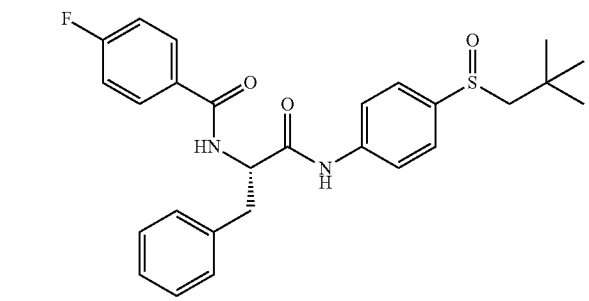

To a solution of 187 mg 4-(2,2-dimethyl-propylsulfinyl) aniline (0.88 mmol, 1.00 eq.) and 254 mg (4-fluorobenzoyl)-L-phenylalanine (0.88 mmol, 1.00 eq.) dissolved in 5 mL anhydrous N,N-dimethylformamide at room temperature was added 185 mg N-(3-Dimethylaminopropyl)-N'-ethylcarbodiimide hydrochloride (0.96 mmol, 1.10 eq.), 131 mg 1-hydroxybenzotriazole (0.96 mmol, 1.10 eq.), and 227 mg N,N-diisopropylethylamine (1.76 mmol, 2.00 eq.) in succession. Then the reaction mixture was stirred at room temperature for 16 hours and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. Purification by column chromatography (silica gel, dichloromethane:ethyl acetate (2:1, v:v)) afforded 150 mg 4-fluoro-N-((2S)-1-(4-(2,2-dimethyl-propyl sulfinyl)phenylamino)-1-oxo-3-phenylpropan-2-yl)benzamide as a white solid (35% yield). MS (ESI+) m/z 481 [M+H]+.

Preparation of(S)-4-Fluoro-N-(1-(4-(2,2-dimethyl-propylsulfonyl)phenylamino)-1-oxo-3-phenylpropan-2-yl)benzamide, I-2

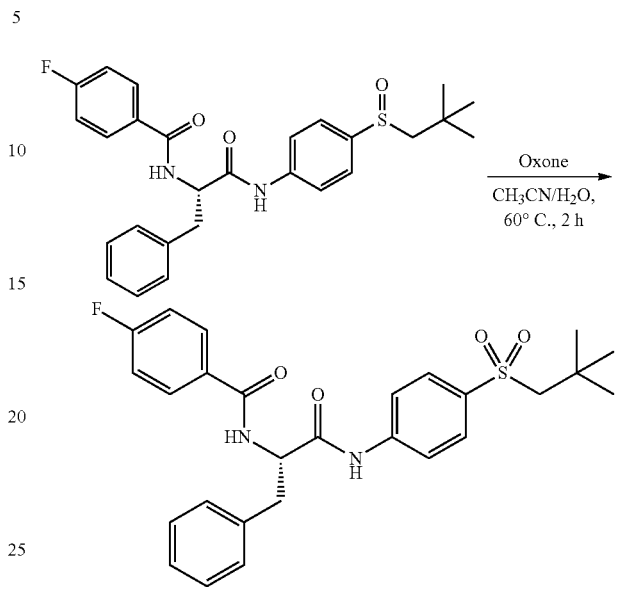

To a solution of 100 mg 4-fluoro-N-((2S)-1-(4-(2,2-dimethyl-propylsulfinyl)phenylamino)-1-oxo-3-phenylpropan-2-yl)benzamide (0.20 mmol, 1.00 eq.) dissolved in 15 mL acetonitrile:water (5:1), 128 mg oxone (0.20 mmol, 1.00 eq.) was added all at once. The reaction mixture was stirred at 60° C. for 1 hour then it was poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. Purification by preparative scale-HPLC afforded 70 mg (S)-4-fluoro-N-(1-(4-(2,2-dimethyl-propyl sulfonyl)phenylamino)-1-oxo-3-phenylpropan-2-yl)benzamide (I-2) as a white solid (68% yield). MS (ESI+) m/z 497 [M+H]+, 1H NMR (400 MHz, d6-DMSO) δ 10.69 (s, 1H), 8.90 (d, J=7.9 Hz, 1H), 7.89 (dd, J=8.8, 5.5 Hz, 2H), 7.83 (s, 4H), 7.39 (d, J=7.4 Hz, 2H), 7.33-7.21 (m, 4H), 7.16 (t, J=7.3 Hz, 1H), 4.91-4.70 (m, 1H), 3.20 (s, 2H), 3.18-3.04 (m, 2H), 1.03 (s, 9H).

Example 2a: (S)-N-(1-(4-(N-Ethylsulfamoyl)phenylamino)-1-oxo-3-phenylpropan-2-yl)-4-fluorobenzamide, I-5

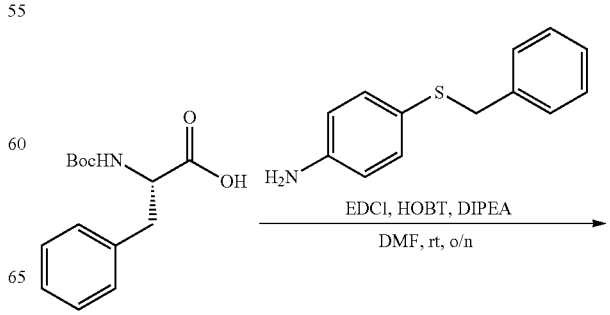

172

Preparation of (S)-tert-Butyl 1-(4-(benzylthio)phenylamino)-1-oxo-3-phenylpropan-2-ylcarbamate

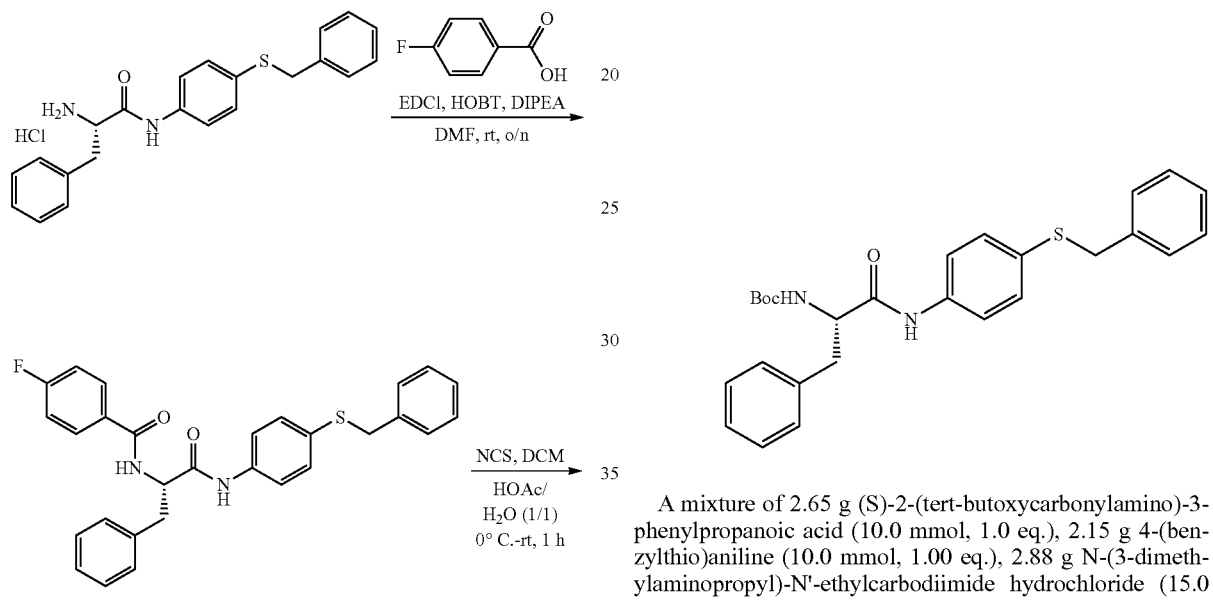

A mixture of 2.65 g (S)-2-(tert-butoxycarbonylamino)-3-phenylpropanoic acid (10.0 mmol, 1.0 eq.), 2.15 g 4-(benzylthio)aniline (10.0 mmol, 1.00 eq.), 2.88 g N-(3-dimethylaminopropyl)-N'-ethylcarbodiimide hydrochloride (15.0 mmol, 1.50 eq.), 1.62 g 1-hydroxybenzotriazole (12.0 mmol, 1.2 eq.) and 2.58 g N,N-diisopropylethylamine (20.0 mmol, 2.00 eq.) in 20 mL N,N-dimethylformamide was stirred at room temperature overnight. The mixture was diluted with 100 mL ethyl acetate and washed with 3×100 mL volumes of water. The organic phase was concentrated and the residue was purified by column chromatography on silica gel (petroleum ether:ethyl acetate (5:1, v:v)) to yield 3.70 g (S)-tert-butyl 1-(4-(benzylthio)phenylamino)-1-oxo-3-phenylpropan-2-ylcarbamate as a light yellow solid (80% yield). MS (ESI$^+$) m/z 463.1 [M+H]$^+$.

Preparation of (S)-2-Amino-N-(4-(benzylthio)phenyl)-3-phenylpropanamide, Hydrochloride

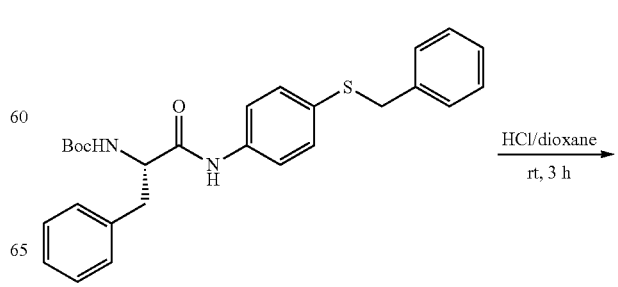

171

-continued

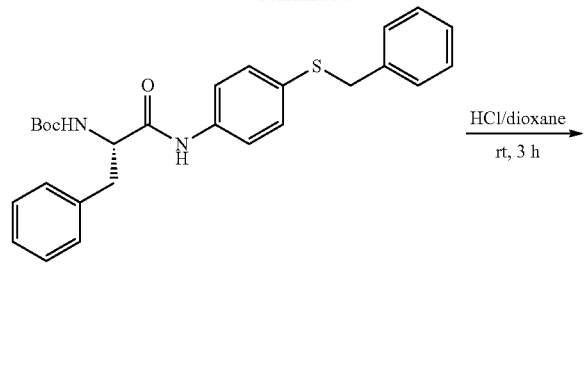

-continued

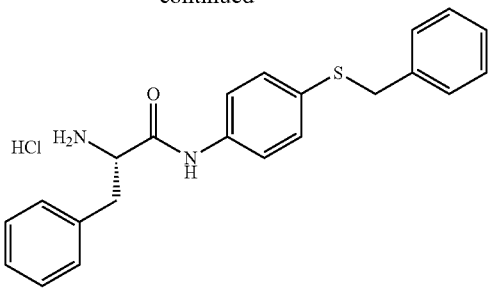

2.31 g (S)-tert-butyl1-(4-(benzylthio)phenylamino)-1-oxo-3-phenylpropan-2-ylcarbamate (5.00 mmol, 1.00 eq.) was dissolved in 20 mL hydrochloric acid in dioxane (4.0 M HCl) and stirred at room temperature for 3 hours. The mixture was concentrated to afford 1.81 g (S)-2-amino-N-(4-(benzylthio)phenyl)-3-phenylpropanamide, hydrochloride as a light yellow solid (100% yield). MS (ESI$^+$) m/z 363.1 [M+H]$^+$.

Preparation of (S)-N-(1-(4-(Benzylthio)phenylamino)-1-oxo-3-phenylpropan-2-yl)-4-fluorobenzamide

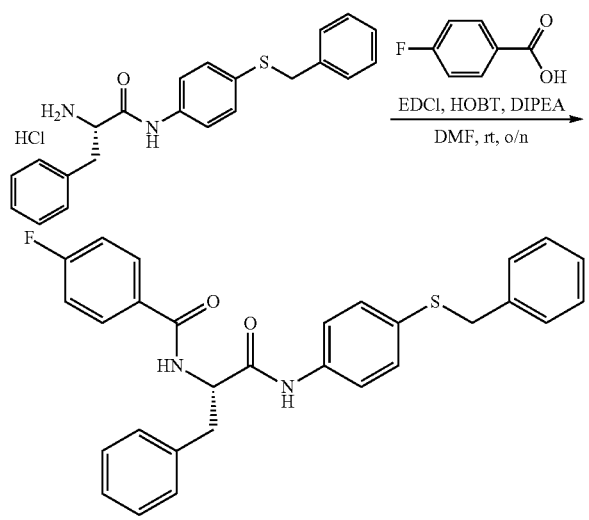

A mixture of 3.62 g (S)-2-amino-N-(4-(benzylthio)phenyl)-3-phenylpropanamide, hydrochloride (10.0 mmol, 1.00 eq.), 1.40 g 4-fluorobenzoic acid (10.0 mmol, 1.0 eq.), 2.88 g N-(3-dimethylaminopropyl)-N'-ethylcarbodiimide hydrochloride (15.0 mmol, 1.50 eq.), 1.62 g 1-hydroxybenzotriazole (12.0 mmol, 1.2 eq.) and 2.58 g N,N-diisopropylethylamine (20.0 mmol, 2.00 eq.) in 30 mL N,N-dimethylformamide was stirred at room temperature overnight. The reaction was diluted with 100 mL ethyl acetate and washed with 3×100 mL volumes of water. The organic phase was concentrated and the residue was purified by column chromatography on silica gel (petroleum ether: ethyl acetate (5:1, v:v)) to give 3.87 g (S)-N-(1-(4-(benzylthio)phenylamino)-1-oxo-3-phenylpropan-2-yl)-4-fluorobenzamide as a light yellow solid (80% yield). MS (ESI$^+$) m/z 363.1 [M+H]$^+$.

Preparation of (S)-4-(2-(4-Fluorobenzamido)-3-phenylpropanamido)benzene-1-sulfonyl Chloride

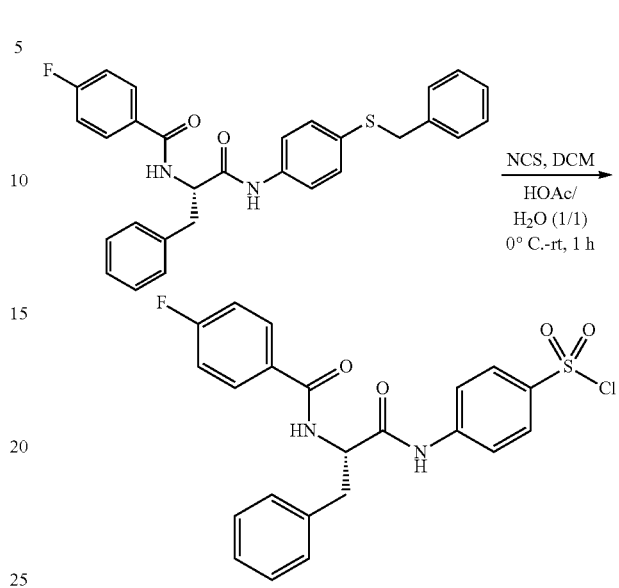

To a solution of 2.42 g (S)-N-(1-(4-(benzylthio)phenylamino)-1-oxo-3-phenylpropan-2-yl)-4-fluorobenzamide (5.00 mmol, 1.00 equiv), 60 mg acetic acid (1.0 mmol, 0.2 equiv) and 18-mg water (1.0 mmol, 0.2 equiv) in 30 mL dichloromethane was added 2.66 g N-chlorosuccinimide (20.0 mmol, 4.00 equiv) at 0° C. The mixture was stirred at room temperature for 1 hour and washed with 3×20 mL volumes of water. The organic phase was concentrated to give 1.61 g (S)-4-(2-(4-fluorobenzamido)-3-phenylpropanamido)benzene-1-sulfonyl chloride as a white solid (70% yield). MS (ESI$^+$) m/z 461.1 [M+H]$^+$.

Preparation of (S)-N-(1-(4-(N-Ethylsulfamoyl)phenylamino)-1-oxo-3-phenylpropan-2-yl)-4-fluorobenzamide, I-5


To a mixture of 50 mg ethanamine (1.1 mmol, 5.0 eq.) and 142 mg N,N-diisopropylethylamine (1.10 mmol, 5.00 eq.) in 10 mL dichloromethane was added 100 mg (S)-4-(2-(4-fluorobenzamido)-3-phenylpropanamido)benzene-1-sulfonyl chloride (0.22 mmol, 1.00 eq.). The mixture was stirred at room temperature for 1 hour and concentrated in vacuo. The residue was purified by preparative scale-HPLC to give 25.0 mg (S)-N-(1-(4-(N-ethylsulfamoyl)phenylamino)-1-oxo-3-phenylpropan-2-yl)-4-fluorobenzamide (I-5) as a white solid (24% yield). MS (ESI$^+$) m/z 470.1 [M+H]$^+$; $^1$H NMR (400 MHz, d$_6$-DMSO) δ 10.60 (s, 1H), 8.85 (d, J=7.8 Hz, 1H), 7.87 (dt, J=17.6, 8.8 Hz, 2H), 7.83-7.66 (m, 4H), 7.41 (dd, J=12.7, 6.7 Hz, 3H), 7.31-7.20 (m, 4H), 7.16 (t, J=7.3 Hz, 1H), 4.91-4.70 (m, 1H), 3.19-2.99 (m, 2H), 2.80-2.66 (m, 2H), 0.93 (t, J=7.2 Hz, 3H).

Example 2b: (S)-4-Fluoro-N-(1-(4-(N-(1-fluoro-2-methylpropan-2-yl)sulfamoyl)phenylamino)-1-oxo-3-phenylpropan-2-yl)benzamide, I-10

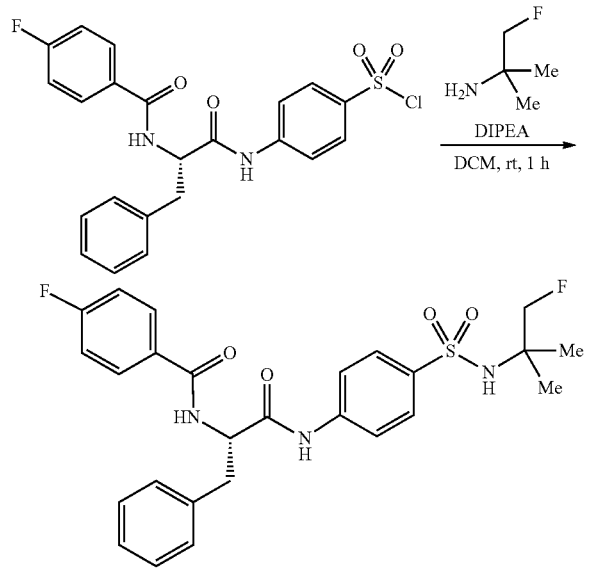

Preparation of (S)-4-Fluoro-N-(1-(4-(N-(1-fluoro-2-methylpropan-2-yl)sulfamoyl)phenylamino)-1-oxo-3-phenylpropan-2-yl)benzamide, I-10

To a mixture of 100 mg 1-fluoro-2-methylpropan-2-amine (1.10 mmol, 5.00 eq.) and 142 mg N,N-diisopropylethylamine (1.10 mmol, 5.00 eq.) in 10 mL dichloromethane was added 100 mg (S)-4-(2-(4-fluorobenzamido)-3-phenylpropanamido)benzene-1-sulfonyl chloride (0.22 mmol, 1.00 eq.). The mixture was stirred at room temperature for 1 hour and concentrated in vacuo. The residue was purified by preparative scale-HPLC to give 25.0 mg (S)-4-fluoro-N-(1-(4-(N-(1-fluoro-2-methylpropan-2-yl)sulfamoyl)phenylamino)-1-oxo-3-phenylpropan-2-yl)benzamide (I-10) as a white solid (22% yield). MS (ESI$^+$) m/z 516.1 [M+H]$^+$; $^1$H NMR (400 MHz, d$_6$-DMSO) δ 10.59 (s, 1H), 8.86 (d, J=7.9 Hz, 1H), 7.96-7.80 (m, 2H), 7.76 (s, 4H), 7.66 (s, 1H), 7.39 (d, J=7.2 Hz, 2H), 7.33-7.21 (m, 4H), 7.16 (t, J=7.3 Hz, 1H), 5.00-4.62 (m, 1H), 4.21 (s, 1H), 4.09 (s, 1H), 3.11 (qd, J=13.7, 7.6 Hz, 2H), 1.04 (d, J=1.8 Hz, 6H).

Example 2c: (S)-N-(1-(4-(N-Bicyclo[1.1.1]pentan-1-ylsulfamoyl)phenylamino)-1-oxo-3-phenylpropan-2-yl)-4-fluorobenzamide, I-11


Preparation of (S)-N-(1-(4-(N-Bicyclo[1.1.1]pentan-1-ylsulfamoyl)phenylamino)-1-oxo-3-phenylpropan-2-yl)-4-fluorobenzamide, I-11

To the mixture of 91.3 mg bicyclo[1.1.1]pentan-1-amine (1.10 mmol, 5.00 eq.) and 142 mg N,N-diisopropylethylamine (1.10 mmol, 5.00 eq.) in 10 mL dichloromethane was added 100 mg (S)-4-(2-(4-fluorobenzamido)-3-phenylpropanamido)benzene-1-sulfonyl chloride (0.22 mmol, 1.0 eq.). The mixture was stirred at room temperature for 1 hour and concentrated in vacuo. The residue was purified by preparative scale-HPLC to give 25.0 mg (S)-N-(1-(4-(N-bicyclo[1.1.1]pentan-1-ylsulfamoyl)phenylamino)-1-oxo-3-phenylpropan-2-yl)-4-fluorobenzamide (I-11) as a white solid (22% yield). MS (ESI$^+$) m/z 508.1 [M+H]$^+$; $^1$H NMR (400 MHz, d$_6$-DMSO) δ 10.60 (s, 1H), 8.87 (d, J=7.9 Hz, 1H), 8.46 (s, 1H), 7.95-7.83 (m, 2H), 7.76 (dd, J=22.1, 8.9 Hz, 2H), 7.42 (dd, J=21.9, 10.1 Hz, 2H), 7.34-7.20 (m, 4H), 7.16 (t, J=7.3 Hz, 1H), 4.92-4.70 (m, 1H), 3.11 (qd, J=13.7, 7.7 Hz, 2H), 2.24 (s, 1H), 1.68 (s, 6H).

Example 2d: (S)-4-fluoro-N-(1-(4-(N-oxetan-3-ylsulfamoyl)phenylamino)-1-oxo-3-phenylpropan-2-yl)benzamide, I-64

Preparation of (S)-4-fluoro-N-(1-(4-(N-oxetan-3-ylsulfamoyl)phenylamino)-1-oxo-3-phenylpropan-2-yl)benzamide, I-64



I-64


To a mixture of 198 mg oxetan-3-amine (2.71 mmol, 5.0 equiv) and 350 mg N,N-diisopropylethylamine (2.71 mmol, 5.00 equiv) in 10 mL dichloromethane was added 250 mg (S)-4-(2-(4-fluorobenzamido)-3-phenylpropanamido)benzene-1-sulfonyl chloride (0.54 mmol, 1.00 equiv). The mixture was stirred at room temperature for 2 hours and concentrated in vacuo. The compound was purified by reversed phase preparative HPLC on a Gilson GX-281. A concentrated solution of crude product dissolved in DMSO was injected in 800 uL volumes onto a 10 um C18 reversed phase XBridge 19 mm diameter×250 mm length column eluting with a gradient of 45-95% acetonitrile in water with 10 mmol/liter ammonium carbonate. Peaks were detected by UV absorbance at 214 nm and 254 nm and fractions collected by 1 mV threshold trigger on the 214 nm channel. Fractions containing product were combined, concentrated and lyophilized to afford 80 mg (S)-4-fluoro-N-(1-(4-(N-oxetan-3-ylsulfamoyl)phenylamino)-1-oxo-3-phenylpropan-2-yl)benzamide (I-64) as a white solid (30% yield). MS (ESI$^+$) m/z 498 [M+H]$^+$. $^1$H NMR (400 MHz, DMSO) δ 10.64 (s, 1H), 8.89 (d, J=8.0 Hz, 1H), 8.43 (s, 1H), 7.94-7.87 (m, 2H), 7.81 (d, J=8.2 Hz, 2H), 7.73 (d, J=8.4 Hz, 2H), 7.41 (d, J=7.7 Hz, 2H), 7.29 (dd, J=14.3, 7.4 Hz, 4H), 7.18 (t, J=7.3 Hz, 1H), 4.82 (d, J=13.7 Hz, 1H), 4.49 (t, J=6.7 Hz, 2H), 4.36 (s, 1H), 4.24 (t, J=6.2 Hz, 2H), 3.21-3.02 (m, 2H)

Example 2e: (S)-N-(1-(4-(N-cyclopropylsulfamoyl)phenylamino)-1-oxo-3-phenylpropan-2-yl)-4-fluorobenzamide, I-6

Preparation of (S)-N-(1-(4-(N-cyclopropylsulfamoyl)phenylamino)-1-oxo-3-phenylpropan-2-yl)-4-fluorobenzamide To a mixture of 63 mg cyclopropanamine (1.1 mmol, 5.0 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 500 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 2 mV threshold trigger on the 214 nm channel. Fractions containing product were combined, concentrated and lyophilized to afford 50.0 mg (S)-N-(1-(4-(N-cyclopropylsulfamoyl)phenylamino)-1-oxo-3-phenylpropan-2-yl)-4-fluorobenzamide (I-6) as a white solid (48% yield). MS (ESI$^+$) m/z 482 [M+H]$^+$; $^1$H NMR (400 MHz, d$_6$-DMSO) δ 10.62 (s, 1H), 8.86 (d, J=7.9 Hz, 1H), 7.88 (dd, J=8.8, 5.6 Hz, 2H), 7.84-7.66 (m, 5H), 7.46-7.33 (m, 2H), 7.33-7.21 (m, 4H), 7.16 (t, J=7.3 Hz, 1H), 4.82 (td, J=9.9, 5.0 Hz, 1H), 3.20-2.97 (m, 2H), 2.06 (d, J=4.0 Hz, 1H), 0.48-0.39 (m, 2H), 0.36-0.24 (m, 2H).

Example 2f: (S)-N-(1-(4-(N-cyclobutylsulfamoyl)phenylamino)-1-oxo-3-phenylpropan-2-yl)-4-fluorobenzamide, I-7

Preparation of (S)-N-(1-(4-(N-cyclobutylsulfamoyl)phenylamino)-1-oxo-3-phenylpropan-2-yl)-4-fluorobenzamide

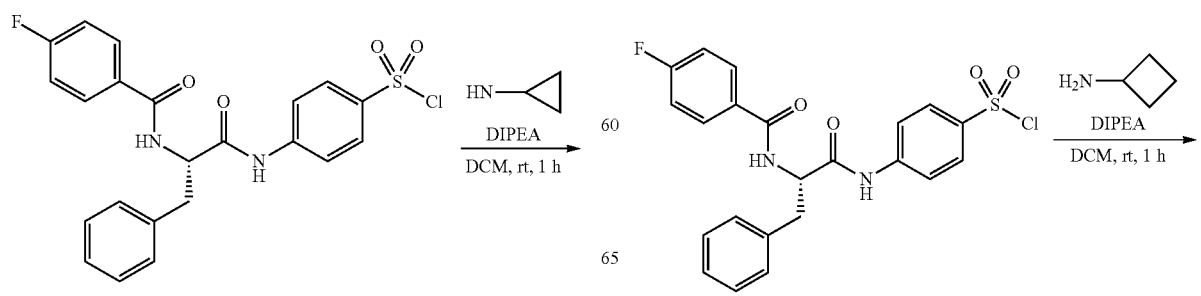

179


I-7

To a mixture of 78 mg cyclobutanamine (1.1 mmol, 5.0 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 850 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 6 mV threshold trigger on the 214 nm channel. Fractions containing product were combined, concentrated and lyophilized to afford 35.0 mg (S)-N-(1-(4-(N-cyclobutylsulfamoyl)phenylamino)-1-oxo-3-phenylpropan-2-yl)-4-fluorobenzamide (I-7) as a white solid (32% yield). MS (ESI$^+$) m/z 496 [M+H]$^+$; $^1$H NMR (400 MHz, d$_6$-DMSO) δ 10.59 (s, 1H), 8.86 (d, J=7.9 Hz, 1H), 7.88 (dd, J=8.8, 5.6 Hz, 2H), 7.82 (d, J=8.7 Hz, 1H), 7.77 (d, J=8.9 Hz, 2H), 7.70 (d, J=8.9 Hz, 2H), 7.39 (d, J=7.3 Hz, 2H), 7.31-7.20 (m, 4H), 7.16 (t, J=7.3 Hz, 1H), 4.86-4.76 (m, 1H), 3.64-3.49 (m, 1H), 3.19-3.00 (m, 2H), 1.86 (m, 2H), 1.75-1.56 (m, 2H), 1.55-1.33 (m, 2H).

Example 2g: (S)-N-(1-(4-(N-cyclopentylsulfamoyl)phenylamino)-1-oxo-3-phenylpropan-2-yl)-4-fluorobenzamide, I-8

Preparation of (S)-N-(1-(4-(N-cyclopentylsulfamoyl)phenylamino)-1-oxo-3-phenylpropan-2-yl)-4-fluorobenzamide

180


I-8

To a mixture of 94 mg cyclopentanamine (1.1 mmol, 5.0 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 950 uL volumes onto a 10 um C18 reversed phase Waters X-SELECT 19 mm diameter×250 mm length column eluting with a gradient of 53-95% acetonitrile in water with 10 mmol/liter ammonium carbonate. Peaks were detected by UV absorbance at 214 nm and 254 nm and fractions collected by 4 mV threshold trigger on the 214 nm channel. Fractions containing product were combined, concentrated and lyophilized to afford 30.0 mg (S)-N-(1-(4-(N-cyclopentylsulfamoyl)phenylamino)-1-oxo-3-phenylpropan-2-yl)-4-fluorobenzamide (I-8) as a white solid (27% yield). MS (ESI$^+$) m/z 510 [M+H]$^+$; $^1$H NMR (400 MHz, d$_6$-DMSO) δ 10.60 (s, 1H), 8.86 (d, J=7.9 Hz, 1H), 7.89 (dd, J=8.8, 5.5 Hz, 2H), 7.75 (dd, J=20.3, 8.9 Hz, 4H), 7.49 (t, J=9.2 Hz, 1H), 7.39 (d, J=7.3 Hz, 2H), 7.32-7.22 (m, 4H), 7.16 (t, J=7.3 Hz, 1H), 4.87-4.76 (m, 1H), 3.40-3.32 (m, 1H), 3.20-2.99 (m, 2H), 1.51 (m, 4H), 1.40-1.15 (m, 4H).

Example 2h: (S)-4-fluoro-N-(1-(4-(N-(1-methylazetidin-3-yl)sulfamoyl)phenylamino)-1-oxo-3-phenylpropan-2-yl)benzamide, I-65

Preparation of (S)-4-fluoro-N-(1-(4-(N-(1-methylazetidin-3-yl)sulfamoyl)phenylamino)-1-oxo-3-phenylpropan-2-yl)benzamide, I-65


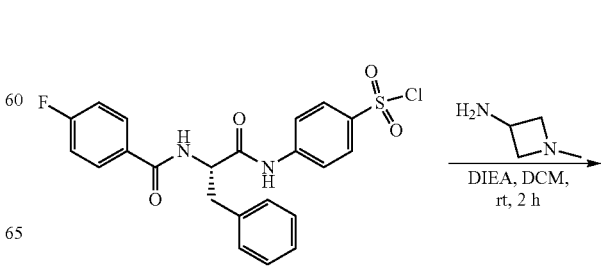

-continued

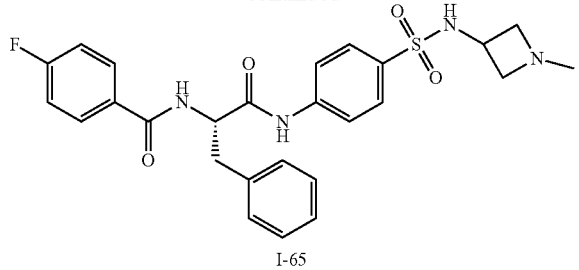

I-65

To a mixture of 233 mg 1-methylazetidin-3-amine (2.71 mmol, 5.0 equiv) and 350 mg N,N-diisopropylethylamine (2.71 mmol, 5.00 equiv) in 10 mL dichloromethane was added 250 mg (S)-4-(2-(4-fluorobenzamido)-3-phenylpropanamido)benzene-1-sulfonyl chloride (0.54 mmol, 1.00 equiv). The mixture was stirred at room temperature for 2 hours and concentrated in vacuo. The compound was purified by reversed phase preparative HPLC on a Gilson GX-281. A concentrated solution of crude product dissolved in DMSO was injected in 500 uL volumes onto a 10 um C18 reversed phase Waters X-SELECT 19 mm diameter×250 mm length column eluting with a gradient of 38-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 30 mg (S)-4-fluoro-N-(1-(4-(N-(1-methylazetidin-3-yl)sulfamoyl) phenylamino)-1-oxo-3-phenylpropan-2-yl)benzamide (I-65) as a white solid (11% yield). MS (ESI$^+$) m/z 511 [M+H]$^+$. $^1$H NMR (400 MHz, d$_6$-DMSO) δ 10.64 (s, 1H), 8.90 (d, J=7.7 Hz, 1H), 8.03 (s, 1H), 7.94-7.87 (m, 2H), 7.80 (d, J=8.6 Hz, 2H), 7.73 (d, J=8.4 Hz, 2H), 7.41 (d, J=7.4 Hz, 2H), 7.29 (dd, J=14.2, 7.4 Hz, 4H), 7.18 (t, J=7.1 Hz, 1H), 4.84 (s, 1H), 3.65 (s, 1H), 3.25 (s, 2H), 3.17-3.09 (m, 2H), 2.55 (t, J=6.9 Hz, 2H), 2.08 (s, 3H).

Example 2i: (S)-N-(1-(4-(N-(cyclopropylmethyl) sulfamoyl)phenylamino)-1-oxo-3-phenylpropan-2-yl)-4-fluorobenzamide, I-9

Preparation of (S)-N-(1-(4-(N-(cyclopropylmethyl) sulfamoyl)phenylamino)-1-oxo-3-phenylpropan-2-yl)-4-fluorobenzamide -continued

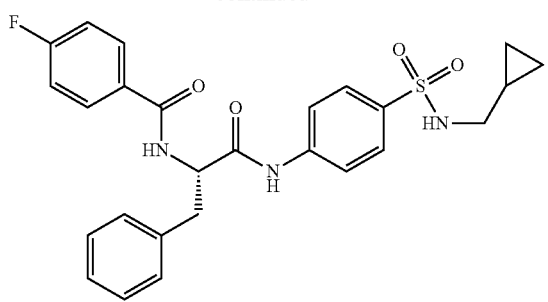

I-9

To a mixture of 78 mg cyclopropylmethanamine (1.1 mmol, 5.0 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 800 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 4 mV threshold trigger on the 214 nm channel. Fractions containing product were combined, concentrated and lyophilized to afford 30.0 mg (S)-N-(1-(4-(N-(cyclopropylmethyl)sulfamoyl)phenylamino)-1-oxo-3-phenylpropan-2-yl)-4-fluorobenzamide (I-9) as a white solid (28% yield). MS (ESI$^+$) m/z 496 [M+H]$^+$; $^1$H NMR (400 MHz, d$_6$-DMSO) δ 10.59 (s, 1H), 8.85 (d, J=7.8 Hz, 1H), 7.88 (dd, J=8.8, 5.5 Hz, 2H), 7.75 (dd, J=21.2, 8.9 Hz, 4H), 7.59 (t, J=5.9 Hz, 1H), 7.39 (d, J=7.3 Hz, 2H), 7.33-7.21 (m, 4H), 7.16 (t, J=7.3 Hz, 1H), 4.82 (td, J=10.0, 5.2 Hz, 1H), 3.20-2.96 (m, 2H), 2.61 (dd, J=16.2, 9.8 Hz, 2H), 0.90-0.67 (m, 1H), 0.42-0.18 (m, 2H), 0.04 (q, J=4.5 Hz, 2H).

Example 2j: N-((S)-1-((4-(N-((R)-sec-butyl)sulfamoyl)phenyl)amino)-1-oxo-3-phenylpropan-2-yl)-4-fluorobenzamide, I-12

Preparation of N-((S)-1-((4-(N-((R)-sec-butyl)sulfamoyl)phenyl)amino)-1-oxo-3-phenylpropan-2-yl)-4-fluorobenzamide, I-12

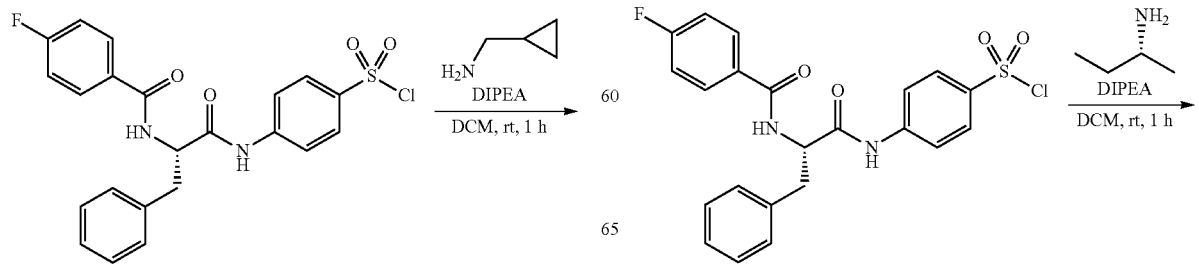

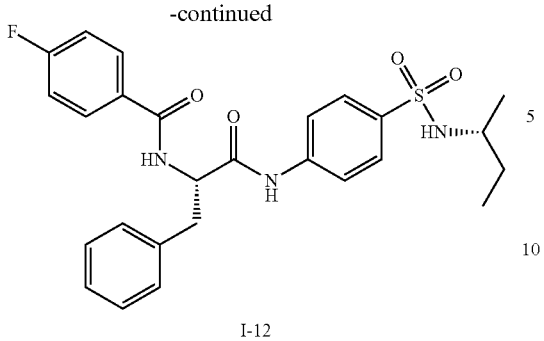

I-12

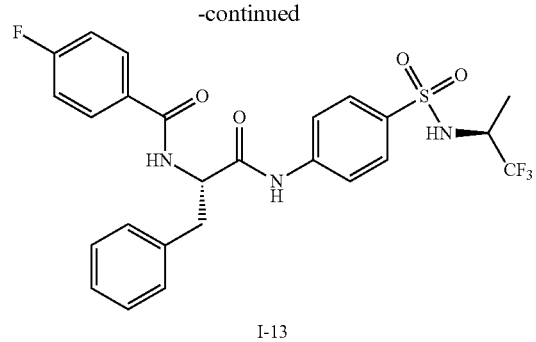

I-13

To the mixture of 80 mg (R)-butan-2-amine (1.10 mmol, 5.00 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.0 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 700 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 5 mV threshold trigger on the 214 nm channel. Fractions containing product were combined, concentrated and lyophilized to afford 40.0 mg N-((S)-1-((4-(N-((R)-sec-butyl)sulfamoyl)phenyl)amino)-1-oxo-3-phenylpropan-2-yl)-4-fluorobenzamide (I-12) as a white solid (37% yield). MS (ESI$^+$) m/z 498 [M+H]$^+$; $^1$H NMR (400 MHz, d$_6$-DMSO) δ 10.58 (s, 1H), 8.86 (d, J=7.9 Hz, 1H), 7.93-7.84 (m, 2H), 7.75 (q, J=8.9 Hz, 4H), 7.39 (d, J=7.5 Hz, 3H), 7.32-7.22 (m, 4H), 7.16 (t, J=7.3 Hz, 1H), 4.86-4.76 (m, 1H), 3.22-2.90 (m, 3H), 1.27 (p, J=7.3 Hz, 2H), 0.84 (d, J=6.6 Hz, 3H), 0.69 (t, J=7.4 Hz, 3H).

Example 2k: 4-fluoro-N-((S)-1-oxo-3-phenyl-1-(4-(N-((S)-1,1,1-trifluoropropan-2-yl)sulfamoyl)phenylamino)propan-2-yl)benzamide, I-13

Preparation of 4-fluoro-N-((S)-1-oxo-3-phenyl-1-(4-(N-((S)-1,1,1-trifluoropropan-2-yl)sulfamoyl)phenylamino)propan-2-yl)benzamide, I-13

To the mixture of 124 mg (S)-1,1,1-trifluoropropan-2-amine (1.10 mmol, 5.00 equiv) in 10 mL pyridine was added 100 mg (S)-4-(2-(4-fluorobenzamido)-3-phenylpropanamido)benzene-1-sulfonyl chloride (0.22 mmol, 1.0 equiv). The mixture was stirred at room temperature overnight and concentrated in vacuo. The compound was purified by reversed phase preparative HPLC on a Gilson GX-281. A concentrated solution of crude product dissolved in DMSO was injected in 700 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 20.0 mg 4-fluoro-N-((S)-1-oxo-3-phenyl-1-(4-(N-((S)-1,1,1-trifluoropropan-2-yl)sulfamoyl)phenylamino)propan-2-yl)benzamide (I-13) as a white solid (17% yield). MS (ESI$^+$) m/z 538 [M+H]$^+$; $^1$H NMR (400 MHz, d$_6$-DMSO) δ 10.63 (s, 1H), 8.87 (d, J=7.9 Hz, 1H), 8.36 (s, 1H), 7.95-7.84 (m, 2H), 7.84-7.72 (m, 4H), 7.39 (d, J=7.2 Hz, 2H), 7.33-7.20 (m, 4H), 7.16 (t, J=7.3 Hz, 1H), 4.87-4.75 (m, 1H), 4.26-3.69 (m, 1H), 3.11 (qd, J=13.6, 7.5 Hz, 2H), 0.95 (d, J=6.9 Hz, 3H).

Example 21: N-((S)-1-(4-(N-((R)-1-cyclopropylethyl)sulfamoyl)phenylamino)-1-oxo-3-phenylpropan-2-yl)-4-fluorobenzamide, I-67

Preparation of N-((S)-1-(4-(N-((R)-1-cyclopropylethyl)sulfamoyl)phenylamino)-1-oxo-3-phenylpropan-2-yl)-4-fluorobenzamide, I-67

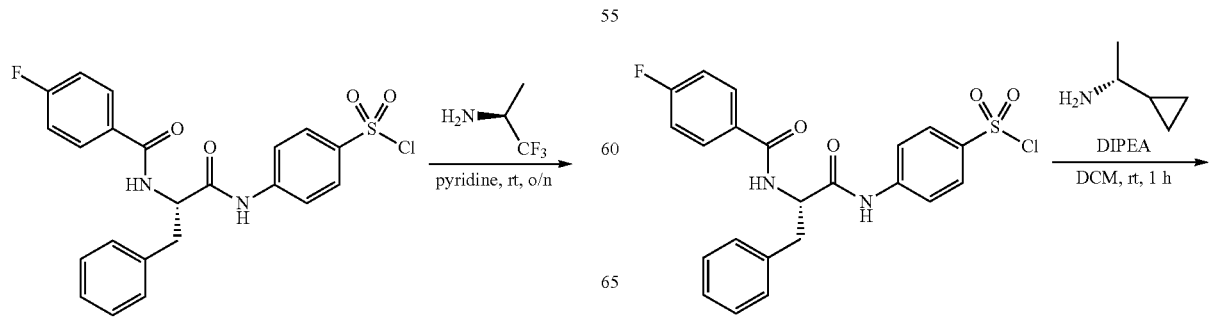

185

-continued

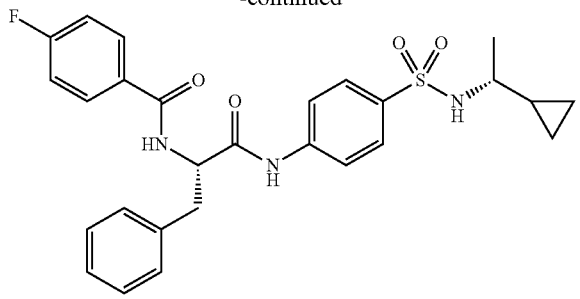

I-67

To the mixture of 94 mg (R)-1-cyclopropylethanamine (1.10 mmol, 5.00 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.0 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 700 uL volumes onto a 10 um C18 reversed phase Waters X-SELECT 19 mm diameter×250 mm length column eluting with a gradient of 55-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 50.0 mg N-((S)-1-(4-(N-((R)-1-cyclopropylethyl)sulfamoyl)phenylamino)-1-oxo-3-phenylpropan-2-yl)-4-fluorobenzamide (I-67) as a white solid (44% yield). MS (ESI$^+$) m/z 510 [M+H]$^+$; $^1$H NMR (400 MHz, d$_6$-DMSO) δ 10.57 (s, 1H), 8.86 (d, J=7.9 Hz, 1H), 7.93-7.82 (m, 2H), 7.74 (q, J=9.0 Hz, 4H), 7.54 (d, J=7.7 Hz, 1H), 7.39 (d, J=7.2 Hz, 2H), 7.33-7.19 (m, 4H), 7.16 (t, J=7.3 Hz, 1H), 4.87-4.75 (m, 1H), 3.10 (qd, J=13.7, 7.6 Hz, 2H), 2.55 (dd, J=14.3, 7.4 Hz, 1H), 0.92 (d, J=6.6 Hz, 3H), 0.80-0.60 (m, 1H), 0.38-0.24 (m, 1H), 0.24-0.13 (m, 1H), 0.09 (td, J=9.4, 5.0 Hz, 1H), −0.08 (td, J=9.5, 5.0 Hz, 1H).

Example 2m: (S)-4-fluoro-N-(1-oxo-3-phenyl-1-(4-(N-(2,2,2-trifluoroethyl)sulfamoyl)phenylamino)propan-2-yl)benzamide, I-23

Preparation of (S)-4-fluoro-N-(1-oxo-3-phenyl-1-(4-(N-(2,2,2-trifluoroethyl)sulfamoyl)phenylamino)propan-2-yl)benzamide, I-23

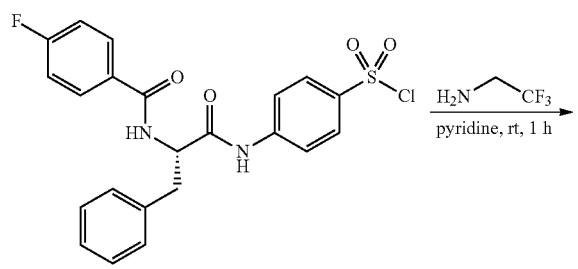

186

-continued

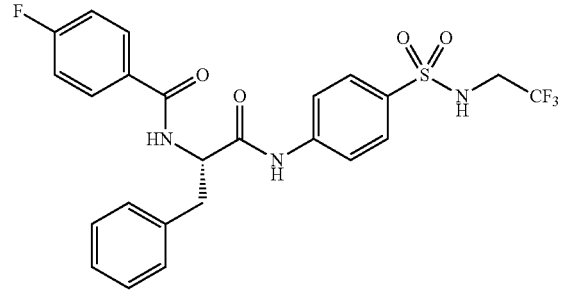

I-23

To the mixture of 109 mg 2,2,2-trifluoroethanamine (1.10 mmol, 5.00 equiv) in 10 mL pyridine was added 100 mg (S)-4-(2-(4-fluorobenzamido)-3-phenylpropanamido)benzene-1-sulfonyl chloride (0.22 mmol, 1.0 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 500 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 1 mV threshold trigger on the 214 nm channel. Fractions containing product were combined, concentrated and lyophilized to afford 60.0 mg (S)-4-fluoro-N-(1-oxo-3-phenyl-1-(4-(N-(2,2,2-trifluoroethyl)sulfamoyl)phenylamino)propan-2-yl)benzamide (I-23) as a white solid (53% yield). MS (ESI$^+$) m/z 524 [M+H]$^+$; $^1$H NMR (400 MHz, d$_6$-DMSO) δ 10.62 (s, 1H), 8.86 (d, J=7.8 Hz, 1H), 8.49 (t, J=6.8 Hz, 1H), 7.88 (dd, J=8.7, 5.6 Hz, 2H), 7.83-7.72 (m, 4H), 7.39 (d, J=7.3 Hz, 2H), 7.32-7.21 (m, 4H), 7.16 (t, J=7.3 Hz, 1H), 4.82 (td, J=9.9, 5.1 Hz, 1H), 3.72-3.52 (m, 2H), 3.18-2.97 (m, 2H).

Example 2n: (S)-4-fluoro-N-(1-oxo-1-(4-(N-tert-pentylsulfamoyl)phenylamino)-3-phenylpropan-2-yl)benzamide, I-24

Preparation of (S)-4-fluoro-N-(1-oxo-1-(4-(N-tert-pentylsulfamoyl)phenylamino)-3-phenylpropan-2-yl)benzamide, I-24

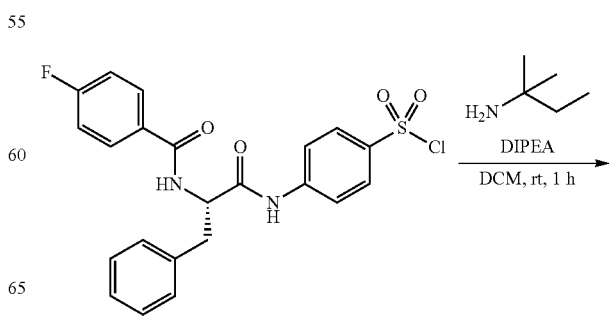

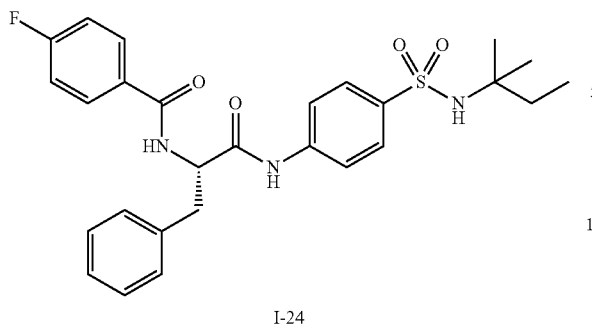

I-24

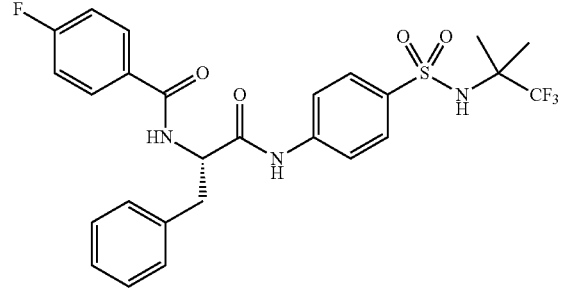

I-25

To the mixture of 96 mg 2-methylbutan-2-amine (1.10 mmol, 5.00 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.0 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 700 uL volumes onto a 10 um C18 reversed phase XBridge 19 mm diameter×250 mm length column eluting with a gradient of 45-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 40.0 mg (S)-4-fluoro-N-(1-oxo-1-(4-(N-tert-pentylsulfamoyl)phenylamino)-3-phenylpropan-2-yl)benzamide (I-24) as a white solid (35% yield). MS (ESI$^+$) m/z 512 [M+H]$^+$; $^1$H NMR (400 MHz, d$_6$-DMSO) δ 10.57 (s, 1H), 8.86 (d, J=7.9 Hz, 1H), 7.88 (dd, J=8.7, 5.6 Hz, 2H), 7.75 (s, 4H), 7.39 (d, J=7.3 Hz, 2H), 7.32-7.20 (m, 5H), 7.16 (t, J=7.3 Hz, 1H), 4.81 (td, J=9.9, 4.9 Hz, 1H), 3.21-2.99 (m, 2H), 1.40 (q, J=7.4 Hz, 2H), 0.99 (s, 6H), 0.72 (t, J=7.4 Hz, 3H).

Example 2o: (S)-4-fluoro-N-(1-oxo-3-phenyl-1-(4-(N-(1,1,1-trifluoro-2-methylpropan-2-yl)sulfamoyl)phenylamino)propan-2-yl)benzamide, I-25

Preparation of (S)-4-fluoro-N-(1-oxo-3-phenyl-1-(4-(N-(1,1,1-trifluoro-2-methylpropan-2-yl)sulfamoyl)phenylamino)propan-2-yl)benzamide, I-25

To the mixture of 140 mg 1,1,1-trifluoro-2-methylpropan-2-amine (1.10 mmol, 5.00 equiv) in 10 mL pyridine was added 100 mg (S)-4-(2-(4-fluorobenzamido)-3-phenylpropanamido)benzene-1-sulfonyl chloride (0.22 mmol, 1.0 equiv). The mixture was stirred at room temperature for overnight and concentrated in vacuo. The compound was purified by reversed phase preparative HPLC on a Gilson GX-281. A concentrated solution of crude product dissolved in DMSO was injected in 500 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 20.0 mg (S)-4-fluoro-N-(1-oxo-3-phenyl-1-(4-(N-(1,1,1-trifluoro-2-methylpropan-2-yl)sulfamoyl)phenylamino)propan-2-yl)benzamide (I-25) as a white solid (17% yield). MS (ESI$^+$) m/z 552 [M+H]$^+$; $^1$H NMR (400 MHz, d$_6$-DMSO) δ 10.63 (s, 1H), 8.87 (d, J=7.9 Hz, 1H), 8.31 (s, 1H), 7.88 (dd, J=8.8, 5.5 Hz, 2H), 7.78 (q, J=9.0 Hz, 4H), 7.39 (d, J=7.3 Hz, 2H), 7.32-7.21 (m, 4H), 7.16 (t, J=7.3 Hz, 1H), 4.87-4.76 (m, 1H), 3.20-3.00 (m, 2H), 1.23 (s, 6H).

Example 2p: 4-fluoro-N-((S)-1-oxo-3-phenyl-1-(4-(N-((R)-1,1,1-trifluoropropan-2-yl)sulfamoyl)phenylamino)propan-2-yl)benzamide, I-26

Preparation of 4-fluoro-N-((S)-1-oxo-3-phenyl-1-(4-(N-((R)-1,1,1-trifluoropropan-2-yl)sulfamoyl)phenylamino)propan-2-yl)benzamide, I-26

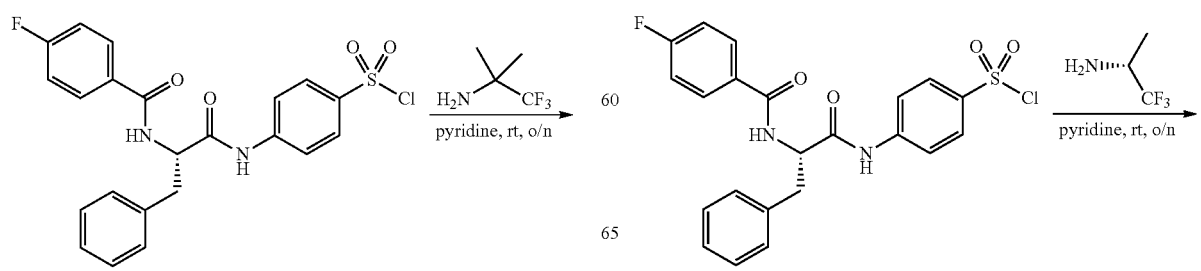

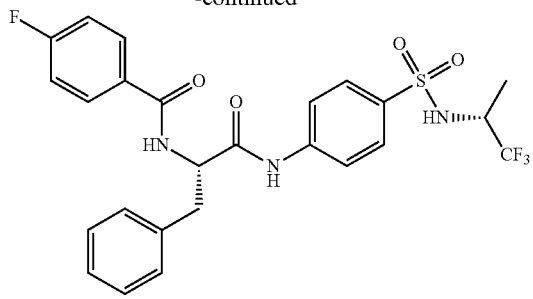

I-26

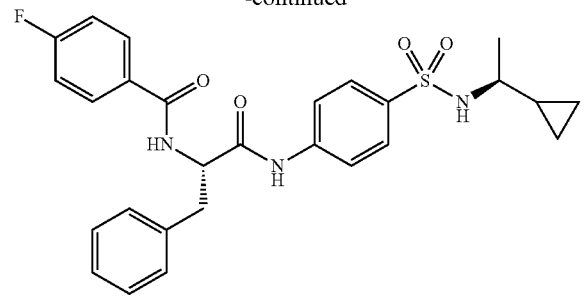

I-27

To the mixture of 124 mg (R)-1,1,1-trifluoropropan-2-amine (1.10 mmol, 5.00 equiv) in 10 mL pyridine was added 100 mg (S)-4-(2-(4-fluorobenzamido)-3-phenylpropanamido)benzene-1-sulfonyl chloride (0.22 mmol, 1.0 equiv). The mixture was stirred at room temperature overnight and concentrated in vacuo. The compound was purified by reversed phase preparative HPLC on a Gilson GX-281. A concentrated solution of crude product dissolved in DMSO was injected in 300 uL volumes onto a 10 um C18 reversed phase XBridge 19 mm diameter×250 mm length column eluting with a gradient of 43-95% acetonitrile in water with 10 mmol/liter ammonium carbonate. Peaks were detected by UV absorbance at 214 nm and 254 nm and fractions collected by 6 mV threshold trigger on the 214 nm channel. Fractions containing product were combined, concentrated and lyophilized to afford 15.0 mg 4-fluoro-N-((S)-1-oxo-3-phenyl-1-(4-(N-((R)-1,1,1-trifluoropropan-2-yl)sulfamoyl)phenylamino)propan-2-yl)benzamide (1-26) as a white solid (13% yield). MS (ESI$^+$) m/z 538 [M+H]$^+$; $^1$H NMR (400 MHz, d$_6$-DMSO) δ 10.63 (s, 1H), 8.87 (d, J=7.9 Hz, 1H), 8.35 (s, 1H), 7.93-7.84 (m, 2H), 7.84-7.78 (m, 4H), 7.39 (d, J=7.2 Hz, 2H), 7.32-7.21 (m, 4H), 7.16 (t, J=7.3 Hz, 1H), 4.87-4.75 (m, 1H), 3.98 (dt, J=14.5, 7.2 Hz, 1H), 3.20-2.98 (m, 2H), 0.95 (d, J=6.9 Hz, 3H).

Example 2q: N-((S)-1-(4-(N-((S)-1-cyclopropylethyl)sulfamoyl)phenylamino)-1-oxo-3-phenylpropan-2-yl)-4-fluorobenzamide, I-27

Preparation of N-((S)-1-(4-(N-((S)-1-cyclopropylethyl)sulfamoyl)phenylamino)-1-oxo-3-phenylpropan-2-yl)-4-fluorobenzamide, I-27

To the mixture of 94 mg (S)-1-cyclopropylethanamine (1.10 mmol, 5.00 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.0 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 700 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 25.0 mg N-((S)-1-(4-(N-((S)-1-cyclopropylethyl)sulfamoyl)phenylamino)-1-oxo-3-phenylpropan-2-yl)-4-fluorobenzamide (I-27) as a white solid (22% yield). MS (ESI$^+$) m/z 510 [M+H]$^+$; $^1$H NMR (400 MHz, d$_6$-DMSO) δ 10.57 (s, 1H), 8.86 (d, J=7.9 Hz, 1H), 7.93-7.84 (m, 2H), 7.74 (q, J=9.0 Hz, 4H), 7.55 (d, J=7.7 Hz, 1H), 7.39 (d, J=7.2 Hz, 2H), 7.34-7.21 (m, 4H), 7.16 (t, J=7.3 Hz, 1H), 4.82 (td, J=10.1, 5.1 Hz, 1H), 3.22-2.99 (m, 2H), 2.54 (dt, J=13.6, 6.8 Hz, 1H), 0.93 (d, J=6.6 Hz, 3H), 0.81-0.61 (m, 1H), 0.36-0.24 (m, 1H), 0.24-0.13 (m, 1H), 0.09 (td, J=9.3, 5.0 Hz, 1H), −0.05-−0.19 (m, 1H).

Example 2r: N-((S)-1-((4-(N-((S)-sec-butyl)sulfamoyl)phenyl)amino)-1-oxo-3-phenylpropan-2-yl)-4-fluorobenzamide, I-28

Preparation of N-((S)-1-((4-(N-((S)-sec-butyl)sulfamoyl)phenyl)amino)-1-oxo-3-phenylpropan-2-yl)-4-fluorobenzamide, I-28

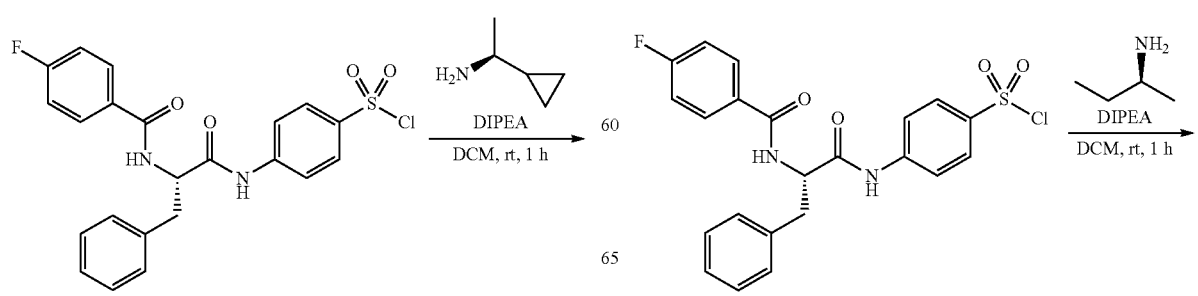

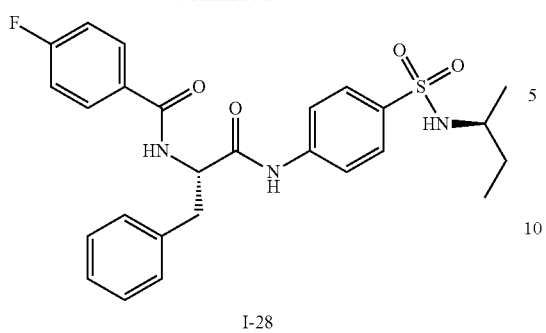

I-28

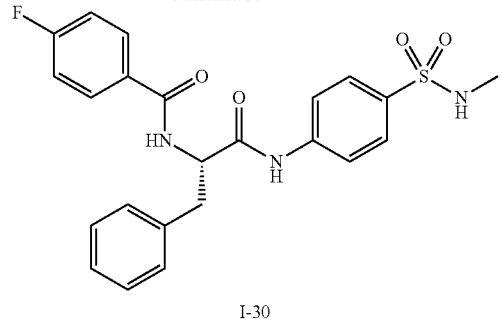

I-30

To the mixture of 80 mg (S)-butan-2-amine (1.10 mmol, 5.00 equiv) and 142 mg N,N-diisopropylethylamine (1.10 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.0 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 900 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 25.0 mg N-((S)-1-((4-(N-((S)-sec-butyl)sulfamoyl)phenyl)amino)-1-oxo-3-phenylpropan-2-yl)-4-fluorobenzamide (I-28) as a white solid (23% yield). MS (ESI$^+$) m/z 498 [M+H]$^+$; $^1$H NMR (400 MHz, d$_6$-DMSO) δ 10.60 (s, 1H), 8.88 (d, J=7.8 Hz, 1H), 7.91 (dd, J=8.8, 5.5 Hz, 2H), 7.77 (q, J=8.9 Hz, 4H), 7.41 (d, J=7.6 Hz, 3H), 7.35-7.22 (m, 4H), 7.18 (t, J=7.4 Hz, 1H), 4.88-4.79 (m, 1H), 3.09 (dtd, J=20.6, 13.8, 5.8 Hz, 3H), 1.29 (p, J=7.3 Hz, 2H), 0.86 (d, J=6.6 Hz, 3H), 0.71 (t, J=7.4 Hz, 3H).

Example 2s: (S)-4-fluoro-N-(1-(4-(N-methylsulfamoyl)phenylamino)-1-oxo-3-phenylpropan-2-yl)benzamide, I-30

Preparation of (S)-4-fluoro-N-(1-(4-(N-methylsulfamoyl)phenylamino)-1-oxo-3-phenylpropan-2-yl)benzamide, I-30

To a mixture of 34 mg methanamine (1.08 mmol, 5.0 equiv) and 139 mg N,N-diisopropylethylamine (1.08 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 2 hours and concentrated in vacuo. The compound was purified by reversed phase preparative HPLC on a Gilson GX-281. A concentrated solution of crude product dissolved in DMSO was injected in 600 uL volumes onto a 10 um C18 reversed phase Waters X-SELECT 19 mm diameter×250 mm length column eluting with a gradient of 44-95% acetonitrile in water with 10 mmol/liter ammonium carbonate. Peaks were detected by UV absorbance at 214 nm and 254 nm and fractions collected by 5 mV threshold trigger on the 214 nm channel. Fractions containing product were combined, concentrated and lyophilized to afford 40 mg (S)-4-fluoro-N-(1-(4-(N-methylsulfamoyl)phenylamino)-1-oxo-3-phenylpropan-2-yl)benzamide (I-30) as a white solid (40% yield). MS (ESI$^+$) m/z 456[M+H]$^+$. $^1$H NMR (400 MHz, d$_6$-DMSO) δ 10.61 (s, 1H), 8.86 (d, J=7.9 Hz, 1H), 7.88 (dd, J=8.9, 5.5 Hz, 2H), 7.80 (d, J=8.9 Hz, 2H), 7.71 (d, J=8.9 Hz, 2H), 7.39 (d, J=7.1 Hz, 2H), 7.28 (ddd, J=11.5, 9.2, 3.7 Hz, 5H), 7.17 (t, J=7.3 Hz, 1H), 4.82 (dd, J=15.3, 7.6 Hz, 1H), 3.17-3.02 (m, 2H), 2.37 (d, J=5.0 Hz, 3H).

Example 2t: (S)-N-(1-(4-(N-cyclohexylsulfamoyl)phenylamino)-1-oxo-3-phenylpropan-2-yl)-4-fluorobenzamide, I-31

Preparation of (S)-N-(1-(4-(N-cyclohexylsulfamoyl)phenylamino)-1-oxo-3-phenylpropan-2-yl)-4-fluorobenzamide, I-31

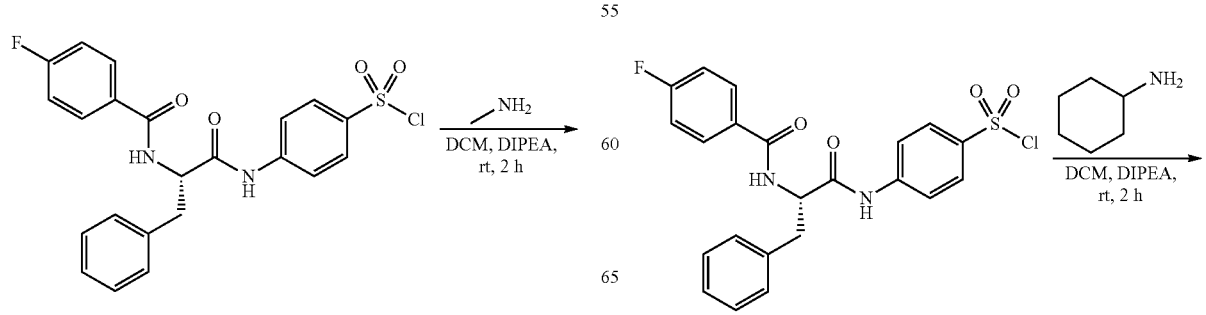

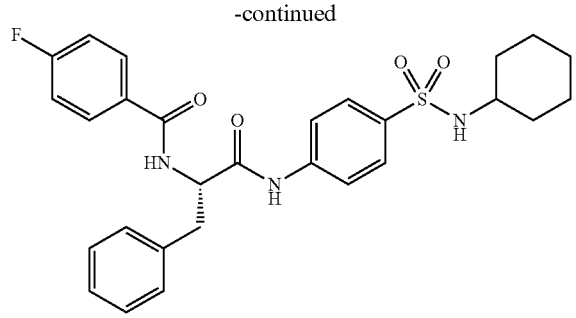

I-31

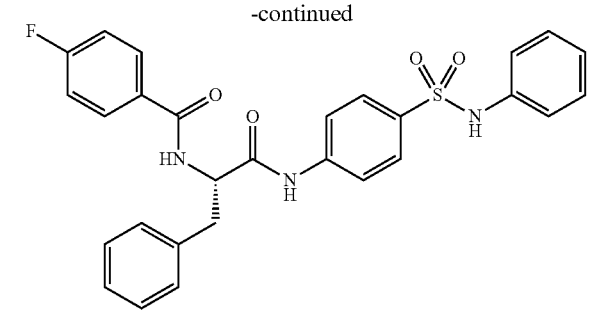

I-32

To a mixture of 108 mg cyclohexanamine (1.08 mmol, 5.0 equiv) and 139 mg N,N-diisopropylethylamine (1.08 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 2 hours and concentrated in vacuo. The compound was purified by reversed phase preparative HPLC on a Gilson GX-281. A concentrated solution of crude product dissolved in DMSO was injected in 800 uL volumes onto a 10 um C18 reversed phase Waters X-SELECT 19 mm diameter×250 mm length column eluting with a gradient of 58-95% acetonitrile in water with 10 mmol/liter ammonium carbonate. Peaks were detected by UV absorbance at 214 nm and 254 nm and fractions collected by 6 mV threshold trigger on the 214 nm channel. Fractions containing product were combined, concentrated and lyophilized to afford 44 mg (S)-N-(1-(4-(N-cyclohexylsulfamoyl)phenylamino)-1-oxo-3-phenylpropan-2-yl)-4-fluorobenzamide (I-31) as a white solid (39% yield). MS (ESI$^+$) m/z 524 [M+H]$^+$. $^1$H NMR (400 MHz, d$_6$-DMSO) δ 10.59 (s, 1H), 8.86 (d, J=7.9 Hz, 1H), 7.88 (dd, J=8.9, 5.5 Hz, 2H), 7.75 (q, J=9.1 Hz, 4H), 7.50 (d, J=7.4 Hz, 1H), 7.39 (d, J=7.1 Hz, 2H), 7.34-7.21 (m, 4H), 7.16 (t, J=7.4 Hz, 1H), 4.81 (m, 1H), 3.19-3.00 (m, 2H), 2.87 (s, 1H), 1.66-1.33 (m, 5H), 1.04 (m, 5H).

To a mixture of 100 mg aniline (1.08 mmol, 5.0 equiv) and 139 mg N,N-diisopropylethylamine (1.08 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 2 hours and concentrated in vacuo. The compound was purified by reversed phase preparative HPLC on a Gilson GX-281. A concentrated solution of crude product dissolved in DMSO was injected in 775 uL volumes onto a 10 um C18 reversed phase Waters X-SELECT 19 mm diameter×250 mm length column eluting with a gradient of 53-95% acetonitrile in water with 10 mmol/liter ammonium carbonate. Peaks were detected by UV absorbance at 214 nm and 254 nm and fractions collected by 6 mV threshold trigger on 214 nm channel. Fractions containing product were combined, concentrated and lyophilized to afford 20 mg (S)-4-fluoro-N-(1-oxo-3-phenyl-1-(4-(N-phenylsulfamoyl)phenylamino)propan-2-yl)benzamide (I-32) as a white solid (18% yield). MS (ESI$^+$) m/z 518 [M+H]$^+$. $^1$H NMR (400 MHz, d$_6$-DMSO) δ 10.58 (s, 1H), 10.14 (s, 1H), 8.84 (d, J=7.9 Hz, 1H), 7.92-7.81 (m, 2H), 7.69 (q, J=9.1 Hz, 4H), 7.37 (d, J=7.2 Hz, 2H), 7.31-7.09 (m, 7H), 7.08-7.00 (m, 2H), 6.98 (t, J=7.3 Hz, 1H), 4.84-4.73 (m, 1H), 3.16-2.98 (m, 2H).

Example 2u: (S)-4-fluoro-N-(1-oxo-3-phenyl-1-(4-(N-phenylsulfamoyl)phenylamino)propan-2-yl)benzamide, I-32

Preparation of (S)-4-fluoro-N-(1-oxo-3-phenyl-1-(4-(N-phenylsulfamoyl)phenylamino)propan-2-yl)benzamide, I-32

Example 2v: (S)-4-fluoro-N-(1-(4-(N-(1-methylpiperidin-4-yl)sulfamoyl)phenylamino)-1-oxo-3-phenylpropan-2-yl)benzamide, I-33

Preparation of (S)-4-fluoro-N-(1-(4-(N-(1-methylpiperidin-4-yl)sulfamoyl)phenylamino)-1-oxo-3-phenylpropan-2-yl)benzamide, I-33

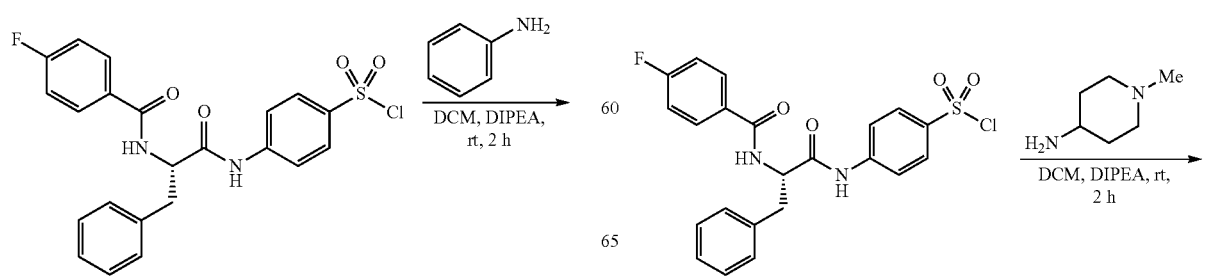

-continued

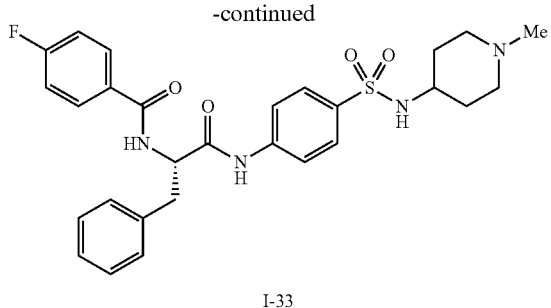

I-33

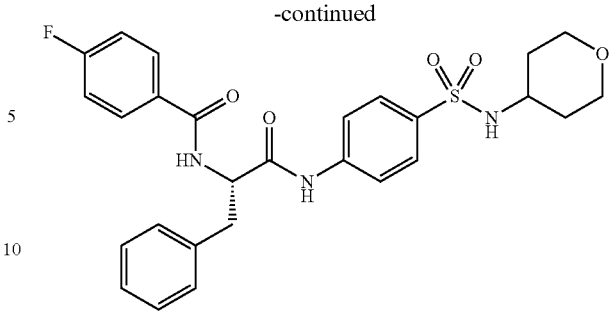

I-34

To a mixture of 123 mg 1-methylpiperidin-4-amine (1.08 mmol, 5.0 equiv) and 139 mg N,N-diisopropylethylamine (1.08 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 2 hours and concentrated in vacuo. The compound was purified by reversed phase preparative HPLC on a Gilson GX-281. A concentrated solution of crude product dissolved in DMSO was injected in 1000 uL volumes onto a 10 um C18 reversed phase Waters X-SELECT 19 mm diameter× 250 mm length column eluting with a gradient of 40-95% acetonitrile in water with 10 mmol/liter ammonium carbonate. Peaks were detected by UV absorbance at 214 nm and 254 nm and fractions collected by 5 mV threshold trigger on the 214 nm channel. Fractions containing product were combined, concentrated and lyophilized to afford 28 mg (S)-4-fluoro-N-(1-(4-(N-(1-methylpiperidin-4-yl)sulfamoyl)phenylamino)-1-oxo-3-phenylpropan-2-yl)benzamide (I-33) as a white solid (24% yield). MS (ESI$^+$) m/z 539 [M+H]$^+$. $^1$H NMR (400 MHz, d$_6$-DMSO) δ 10.60 (s, 1H), 8.86 (d, J=7.9 Hz, 1H), 7.88 (dd, J=8.9, 5.5 Hz, 2H), 7.76 (q, J=9.0 Hz, 4H), 7.57 (d, J=7.1 Hz, 1H), 7.39 (d, J=7.2 Hz, 2H), 7.32-7.21 (m, 4H), 7.16 (t, J=7.3 Hz, 1H), 4.81 (m, 1H), 3.17-3.02 (m, 2H), 2.83 (s, 1H), 2.58 (s, 2H), 2.06 (s, 3H), 1.80 (s, 2H), 1.48 (d, J=11.3 Hz, 2H), 1.33 (dd, J=20.4, 10.7 Hz, 2H).

Example 2w: (S)-4-fluoro-N-(1-oxo-3-phenyl-1-(4-(N-(tetrahydro-2H-pyran-4-yl)sulfamoyl)phenylamino)propan-2-yl)benzamide, I-34

Preparation of (S)-4-fluoro-N-(1-oxo-3-phenyl-1-(4-(N-(tetrahydro-2H-pyran-4-yl)sulfamoyl)phenylamino)propan-2-yl)benzamide, I-34

To a mixture of 109 mg tetrahydro-2H-pyran-4-amine (1.08 mmol, 5.0 equiv) and 139 mg N,N-diisopropylethylamine (1.08 mmol, 5.00 equiv) in 10 mL dichloromethane was added 100 mg (S)-4-(2-(4-fluorobenzamido)-3-phenylpropanamido)benzene-1-sulfonyl chloride (0.22 mmol, 1.00 equiv). The mixture was stirred at room temperature for 2 hours and concentrated in vacuo. The compound was purified by reversed phase preparative HPLC on a Gilson GX-281. A concentrated solution of crude product dissolved in DMSO was injected in 700 uL volumes onto a 10 um C18 reversed phase Waters X-SELECT 19 mm diameter×250 mm length column eluting with a gradient of 43-95% acetonitrile in water with 10 mmol/liter ammonium carbonate. Peaks were detected by UV absorbance at 214 nm and 254 nm and fractions collected by 5 mV threshold trigger on the 214 nm channel. Fractions containing product were combined, concentrated and lyophilized to afford 38 mg (S)-4-fluoro-N-(1-oxo-3-phenyl-1-(4-(N-(tetrahydro-2H-pyran-4-yl)sulfamoyl)phenylamino)propan-2-yl)benzamide (I-34) as a white solid (33% yield). MS (ESI$^+$) m/z 526 [M+H]$^+$. $^1$H NMR (400 MHz, d$_6$-DMSO) δ 10.60 (s, 1H), 8.86 (d, J=7.9 Hz, 1H), 7.88 (dd, J=8.9, 5.5 Hz, 2H), 7.82-7.72 (m, 4H), 7.66 (d, J=7.2 Hz, 1H), 7.39 (d, J=7.1 Hz, 2H), 7.34-7.23 (m, 4H), 7.16 (t, J=7.3 Hz, 1H), 4.81 (m, 1H), 3.69 (d, J=11.2 Hz, 2H), 3.23-3.06 (m, 5H), 1.47 (d, J=12.4 Hz, 2H), 1.36-1.23 (m, 2H).

Example 2x: (R)-N-(1-(4-(N-bicyclo[1.1.1]pentan-1-ylsulfamoyl)phenylamino)-1-oxo-3-phenylpropan-2-yl)-4-fluorobenzamide, I-99

Preparation of (R)-N-(1-(4-(N-bicyclo[1.1.1]pentan-1-ylsulfamoyl)phenylamino)-1-oxo-3-phenylpropan-2-yl)-4-fluorobenzamide (I-99)

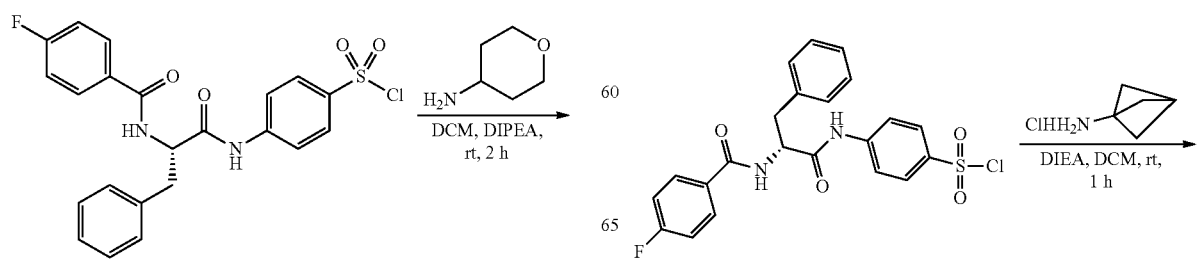

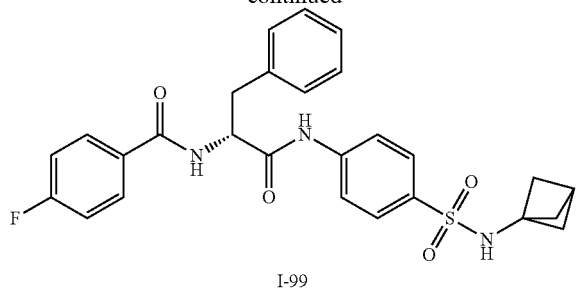

I-99

To a mixture of 126 mg bicyclo[1.1.1]pentan-1-amine hydrochloride (1.05 mmol, 5.0 equiv) and 135.45 mg N,N-diisopropylethylamine (1.05 mmol, 5.00 equiv) in 10 mL dichloromethane was added 96.6 mg (R)-4-(2-(4-fluorobenzamido)-3-phenylpropanamido)benzene-1-sulfonyl chloride (0.21 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (33% ACN up to 55% in 7 min); UV detection at 254/220 nm. The product-containing fractions were combined and evaporated partially in vacuo and lyophilized overnight to afford 33.3 mg (R)-N-(1-(4-(N-bicyclo[1.1.1]pentan-1-ylsulfamoyl)phenylamino)-1-oxo-3-phenylpropan-2-yl)-4-fluorobenzamide (I-99) as a white solid (31% yield). MS (ESI$^+$) m/z 508 [M+H]$^+$; $^1$H NMR (300 MHz, d$_6$-DMSO) δ 10.62 (s, 1H), 8.88 (d, 1H), 8.48 (s, 1H), 7.93-7.88 (m, 2H), 7.83-7.74 (m, 4H), 7.41 (d, 2H), 7.33-7.26 (m, 4H), 7.21-7.16 (m, 1H), 4.86-4.82 (m, 1H), 3.15-3.11 (m, 2H), 2.27 (s, 1H), 1.70 (s, 6H).

Example 3: N-((2S)-1-(4-(N-tert-Butylsulfinamoyl)phenylamino)-1-oxo-3-phenylpropan-2-yl)-4-fluorobenzamide, I-15

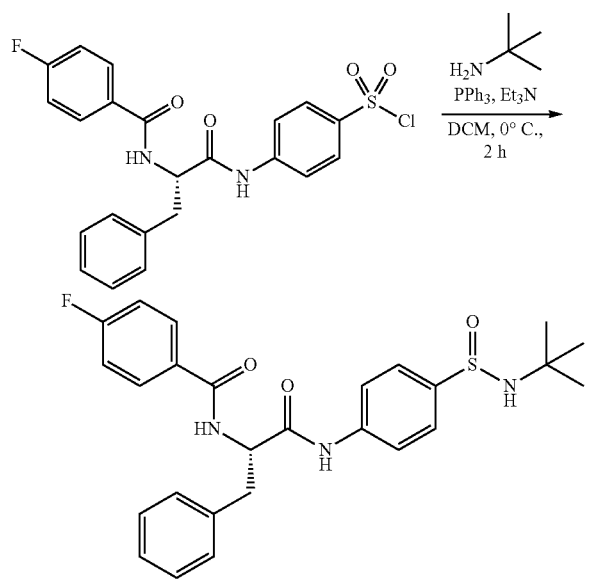

Preparation of N-((2S)-1-(4-(N-tert-butylsulfinamoyl)phenylamino)-1-oxo-3-phenylpropan-2-yl)-4-fluorobenzamide, I-15

To a solution of 200 mg (S)-4-(2-(4-fluorobenzamido)-3-phenylpropanamido)benzene-1-sulfonyl chloride (0.43 mmol, 1.00 eq.) and 434 mg triethylamine (4.30 mmol, 10.0 eq.) in 5.0 mL dichloromethane at 0° C. was added a solution of 112 mg triphenylphosphine (0.43 mmol, 1.00 eq.) and 31.4 mg 2-methylpropan-2-amine (0.43 mmol, 1.00 eq.) in 5.0 mL dichloromethane. After two hours the mixture was concentrated and the residue was purified by preparative scale-HPLC to give 8.0 mg N-((2S)-1-(4-(N-tert-butylsulfinamoyl)phenylamino)-1-oxo-3-phenylpropan-2-yl)-4-fluorobenzamide (I-15) as a white solid (3.8% yield). MS (ESI$^+$) m/z 408.1 [M-73]$^+$; $^1$H NMR (400 MHz, d$_6$-DMSO) δ 10.45 (d, J=3.2 Hz, 1H), 8.82 (d, J=7.8 Hz, 1H), 7.89 (dd, J=8.7, 5.6 Hz, 2H), 7.74 (dd, J=8.8, 3.0 Hz, 2H), 7.54 (d, J=8.7 Hz, 2H), 7.39 (d, J=7.6 Hz, 2H), 7.33-7.21 (m, 4H), 7.16 (t, J=7.3 Hz, 1H), 6.19 (d, J=1.3 Hz, 1H), 4.83 (td, J=9.9, 5.0 Hz, 1H), 3.20-2.98 (m, 2H), 1.27 (s, 9H).

Example 4: N-(4-(N-tert-Butylsulfamoyl)phenyl)-2-(4-fluorobenzoyl)-1,2,3,4-tetrahydroisoquinoline-3-carboxamide, I-22

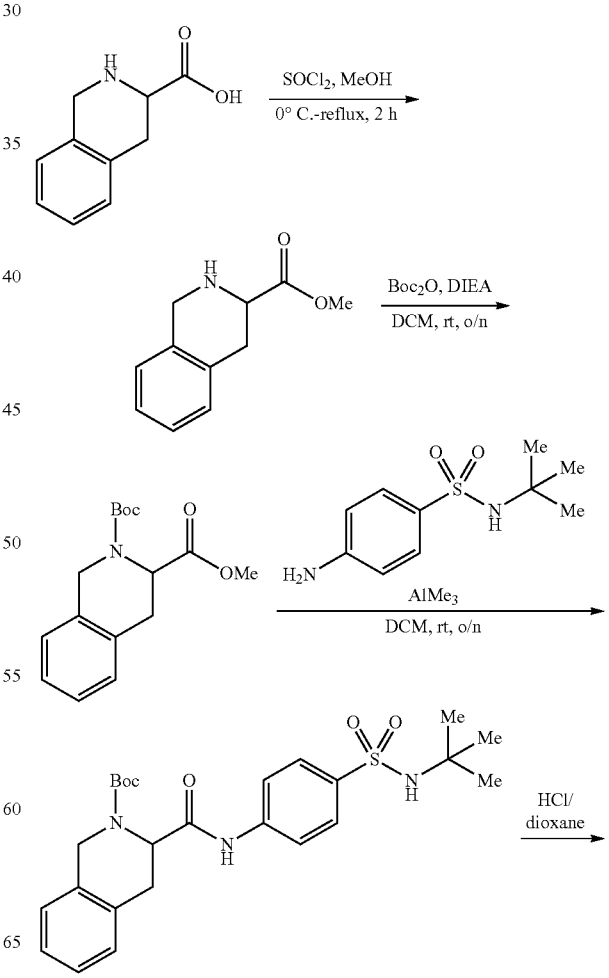

-continued

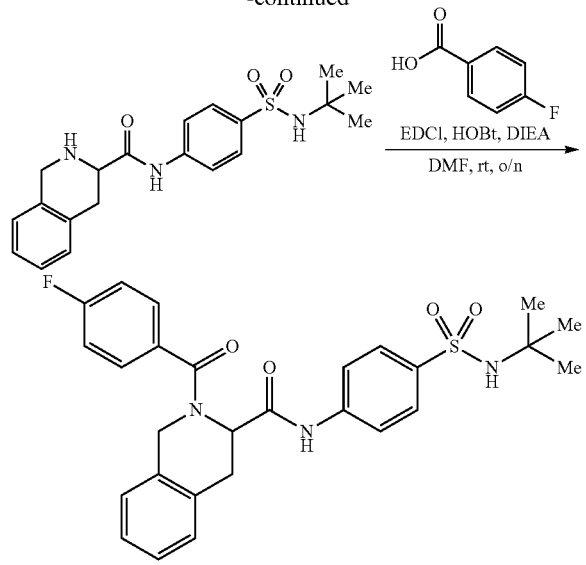

Preparation of methyl 1,2,3,4-tetrahydroisoquinoline-3-carboxylate

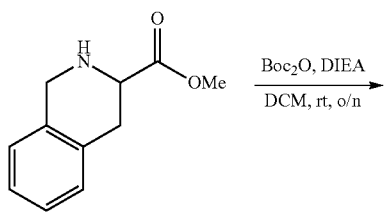

To a solution of 1.77 g 1,2,3,4-tetrahydroisoquinoline-3-carboxylic acid (10.0 mmol, 1.00 eq.) in 50 mL methanol was added 5.95 g thionyl chloride (50.0 mmol, 5.00 eq.) at 0° C. The mixture was refluxed for 2 hours and concentrated to give 1.72 g methyl 1,2,3,4-tetrahydroisoquinoline-3-carboxylate as a light yellow solid (90% yield). MS (ESI$^+$) m/z 192.1 [M+H]$^+$.

Preparation of 2-tert-butyl 3-methyl 3,4-dihydroisoquinoline-2,3(1H)-dicarboxylate

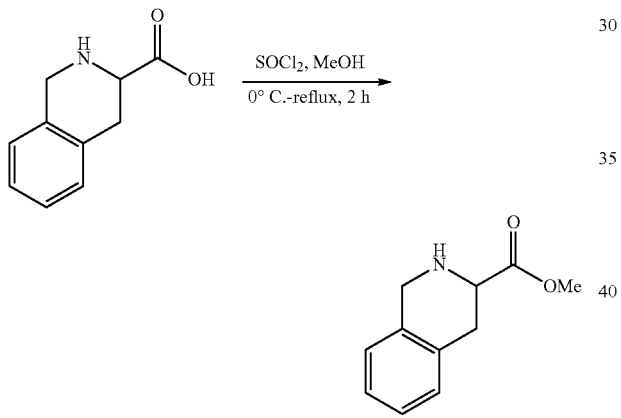

-continued

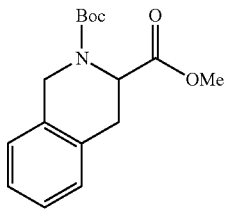

To a mixture of 1.91 g methyl 1,2,3,4-tetrahydroisoquinoline-3-carboxylate (10.0 mmol, 1.00 eq.) and 2.58 g N,N-diisopropylethylamine (20.0 mmol, 2.00 eq.) was added 2.18 g di-tert-butyl dicarbonate (10.0 mmol, 1.00 eq.). The mixture was stirred overnight and concentrated in vacuo. The residue was purified by column chromatography on silica gel (petroleum ether:ethyl acetate (3:1, v:v)) to afford 2.32 g 2-tert-butyl 3-methyl 3,4-dihydroisoquinoline-2,3(1H)-dicarboxylate as a white solid (80% yield). MS (ESI$^+$) m/z 292.1 [M+H]$^+$.

Preparation of tert-butyl 3-(4-(N-tert-butylsulfamoyl)phenylcarbamoyl)-3,4-dihydroisoquinoline-2(1H)-carboxylate

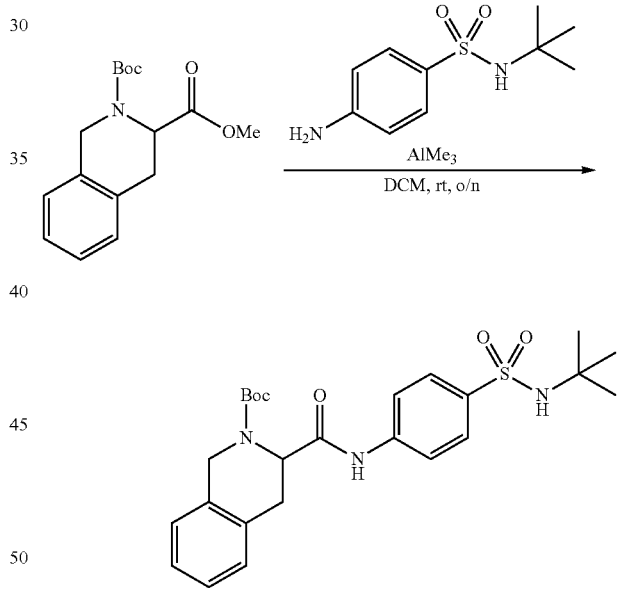

To the mixture of 1.45 g 2-tert-butyl 3-methyl 3,4-dihydroisoquinoline-2,3(1H)-dicarboxylate (5.00 mmol, 1.00 eq.) and 1.14 g 4-amino-N-tert-butylbenzenesulfonamide (5.00 mmol, 1.00 eq.) in 20.0 mL dichloromethane was added 10.0 mL trimethylaluminum (2.0 M. in toluene, 20.0 mmol, 4.00 eq.). The mixture was stirred overnight and poured into 30 mL ice water. The mixture was extracted with 3×50 mL volumes of ethyl acetate. The combined organic layers were concentrated and the residue was purified by column chromatography on silica gel (petroleum ether:ethyl acetate (3:1, v:v)) to give 1.2 g tert-butyl 3-(4-(N-tert-butylsulfamoyl)phenylcarbamoyl)-3,4-dihydroisoquinoline-2(1H)-carboxylate as a light yellow solid (50% yield). MS (ESI$^+$) m/z 488.1 [M+H]$^+$.

Preparation of N-(4-(N-tert-butylsulfamoyl)phenyl)-1,2,3,4-tetrahydroisoquinoline-3-carboxamide

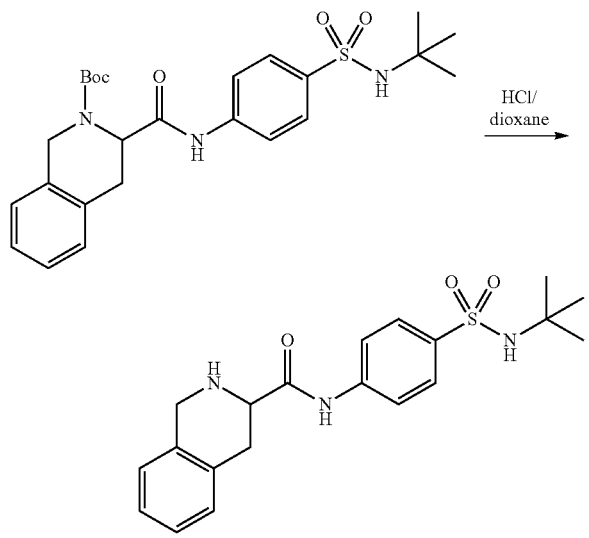

A mixture of 1.22 g tert-butyl 3-(4-(N-tert-butylsulfamoyl)phenylcarbamoyl)-3,4-dihydroisoquinoline-2(1H)-carboxylate (2.50 mmol, 1.00 eq.) in 20 mL hydrochloric acid in dioxane (4.0 M HCl) was stirred at room temperature for 3 hours. The mixture was concentrated in vacuo to give 967 mg N-(4-(N-tert-butylsulfamoyl)phenyl)-1,2,3,4-tetrahydroisoquinoline-3-carboxamide as a white solid (100% yield). MS (ESI$^+$) m/z 388.1 [M+H]$^+$.

Preparation of N-(4-(N-tert-butylsulfamoyl)phenyl)-2-(4-fluorobenzoyl)-1,2,3,4-tetrahydroisoquinoline-3-carboxamide, I-22

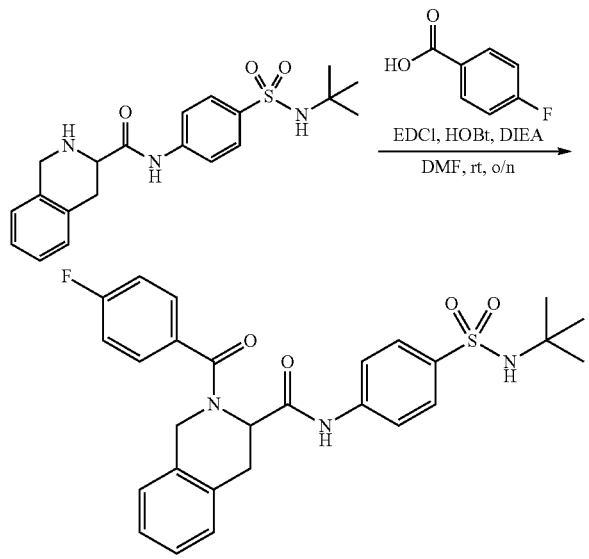

A mixture of 194 mg (S)-2-amino-N-(4-(benzylthio)phenyl)-3-phenylpropanamide (0.50 mmol, 1.00 eq.), 70 mg 4-fluorobenzoic acid (0.50 mmol, 1.00 eq.), 144 mg N-(3-dimethylaminopropyl)-N'-ethylcarbodiimide hydrochloride (0.75 mmol, 1.50 eq.), 81 mg 1-hydroxybenzotriazole (0.60 mmol, 1.2 eq.) and 129 mg N,N-diisopropylethylamine (1.00 mmol, 2.00 eq.) in 10 mL N,N-dimethylformamide was stirred at room temperature overnight. The reaction was diluted with 50 mL ethyl acetate and washed with 3×40 mL volumes of water. The organic phases were concentrated and the residue was purified by preparative scale-HPLC to give 25.0 mg N-(4-(N-tert-butylsulfamoyl)phenyl)-2-(4-fluorobenzoyl)-1,2,3,4-tetrahydroisoquinoline-3-carboxamide (I-22) as a white solid (10% yield). MS (ESI$^+$) m/z 388.1 [M+H]$^+$; $^1$H NMR (400 MHz, CD$_3$OD) δ 7.58-7.81 (m, 5H), 7.03-7.49 (m, 7H), 4.62-4.74 (m, 2H), 3.75-3.42 (m, 1H), 3.20-3.26 (m, 2H), 1.15 (s, 9H).

Example 5: (S)-N-(1-(4-(N-tert-Butylsulfamoyl)phenylamino)-1-oxo-3-phenylpropan-2-yl)-4-fluoro-N-methylbenzamide, I-35

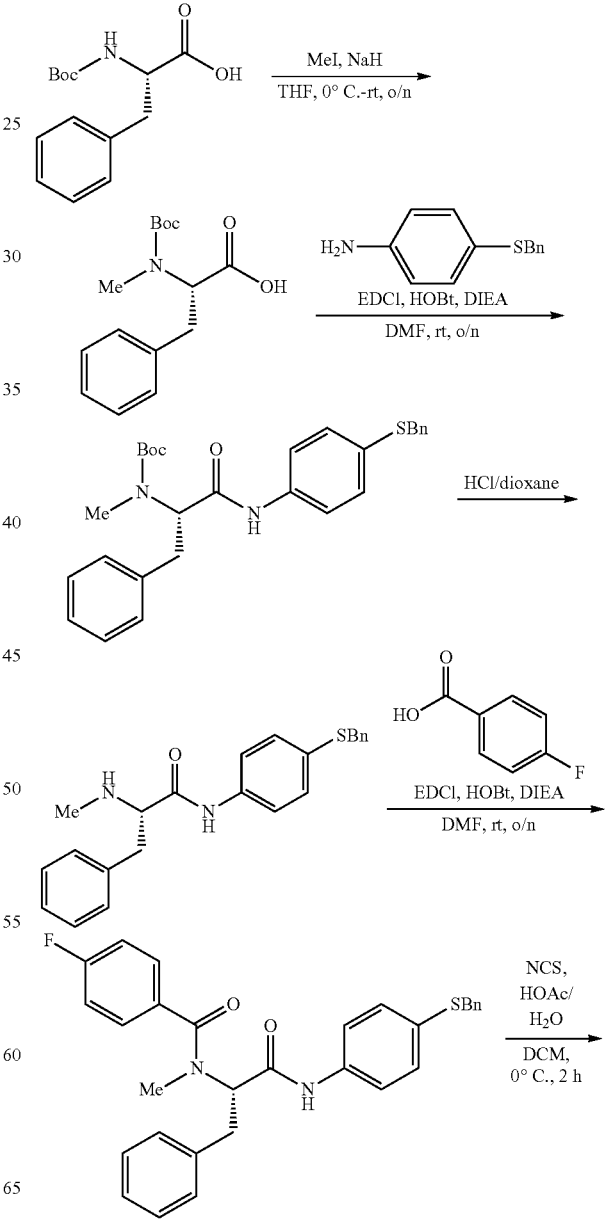

-continued

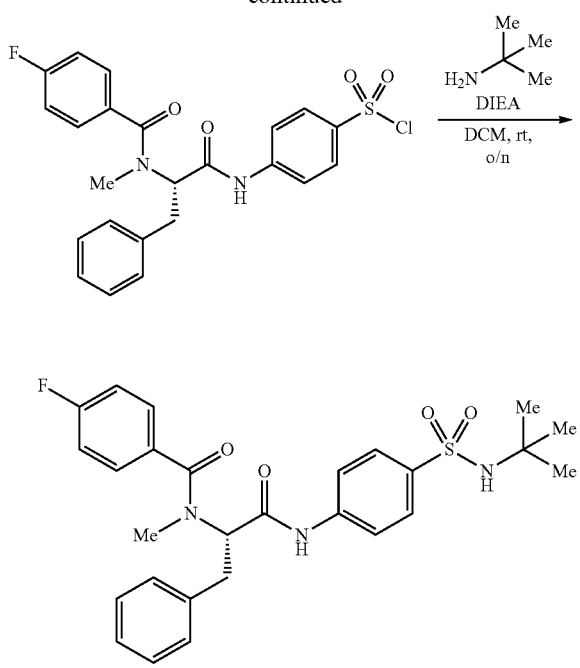

Preparation of (S)-2-(tert-butoxycarbonyl(methyl)amino)-3-phenylpropanoic acid

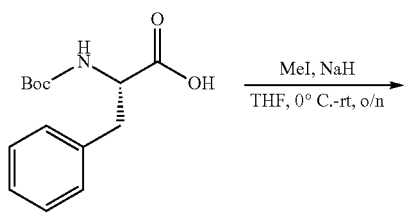

To a solution of 2.65 g (S)-2-(tert-butoxycarbonylamino)-3-phenylpropanoic acid (prepared as in Example 1, 10.0 mmol, 1.00 eq.) in 20 mL tetrahydrofuran was added 0.80 g sodium hydride (60 wt. % dispersion in mineral oil, 20.0 mmol, 2.0 eq.) at 0° C. and the mixture was stirred for 30 minutes. Then 2.84 g iodomethane (20.0 mmol, 2.00 eq.) was added and the reaction was stirred at room temperature overnight. The mixture was poured into 30 mL saturated aqueous ammonium chloride solution and extracted with 3×50 mL volumes of ethyl acetate. The combined organic phases were concentrated and the residue was purified by column chromatography on silica gel (petroleum ether:ethyl acetate (5:1, v:v)) to give 2.23 g (S)-2-(tert-butoxycarbonyl(methyl)amino)-3-phenylpropanoic acid as a light yellow solid (80% yield). MS (ESI$^+$) m/z 280.1 [M+H]$^+$.

Preparation of (S)-tert-butyl 1-(4-(benzylthio)phenylamino)-1-oxo-3-phenylpropan-2-yl(methyl)carbamate

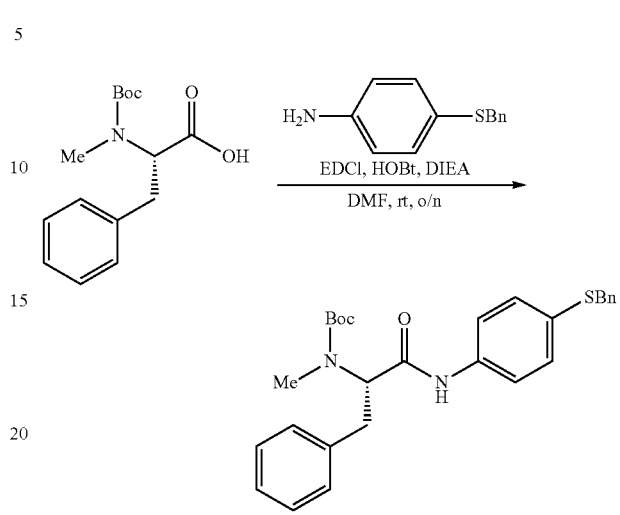

A mixture of 2.79 g (S)-2-(tert-butoxycarbonyl(methyl)amino)-3-phenylpropanoic acid (10.0 mmol, 1.00 eq.), 2.15 g 4-(benzylthio)aniline (10.0 mmol, 1.00 eq.), 2.88 g N-(3-dimethylaminopropyl)-N'-ethylcarbodiimide hydrochloride (15.0 mmol, 1.50 eq.), 1.62 g 1-hydroxybenzotriazole (12.0 mmol, 1.20 eq.) and 2.58 g N,N-diisopropylethylamine (20.0 mmol, 2.00 eq.) in 20 mL N,N-dimethylformamide was stirred at room temperature overnight. The reaction was diluted with 100 mL ethyl acetate and washed with 3×100 mL volumes of water. The organic phases were concentrated and the residue was purified by column chromatography on silica gel (petroleum ether:ethyl acetate (5:1, v:v) to give 3.80 g (S)-tert-butyl 1-(4-(benzylthio)phenylamino)-1-oxo-3-phenylpropan-2-ylcarbamate as a light yellow solid (80% yield). MS (ESI$^+$) m/z 477.1 [M+H]$^+$.

Preparation of (S)-N-(4-(benzylthio)phenyl)-2-(methylamino)-3-phenylpropanamide

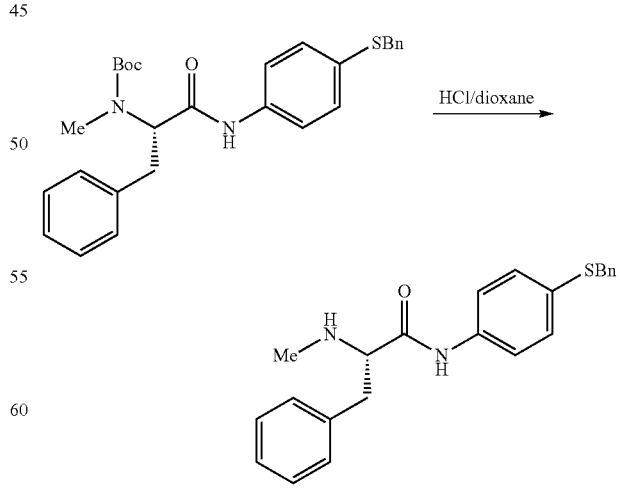

The mixture of 2.38 g (S)-tert-butyl1-(4-(benzylthio)phenylamino)-1-oxo-3-phenylpropan-2-ylcarbamate (5.0 mmol, 1.0 eq.) in 20 mL hydrochloric acid in dioxane (4.0

M HCl) was stirred at room temperature for 3 hours. The mixture was concentrated to give 1.88 g (S)-N-(4-(benzylthio)phenyl)-2-(methylamino)-3-phenylpropanamide as a light yellow solid (100% yield). MS (ESI+) m/z 377.1 [M+H]+.

Preparation of (S)-N-(1-(4-(benzylthio)phenylamino)-1-oxo-3-phenylpropan-2-yl)-4-fluoro-N-methylbenzamide

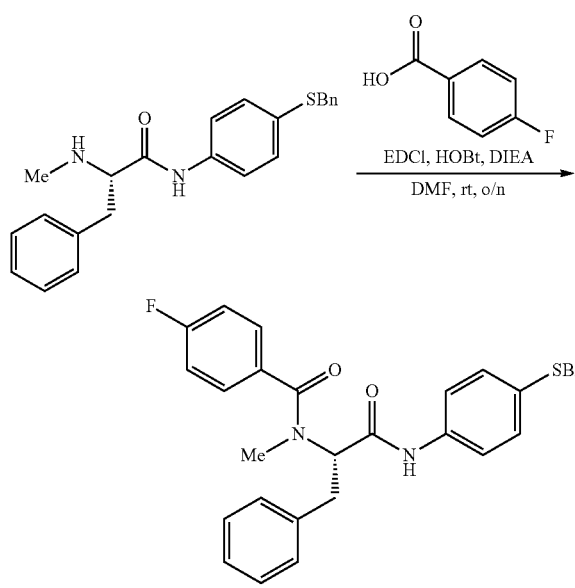

A mixture of 3.76 g (S)-N-(4-(benzylthio)phenyl)-2-(methylamino)-3-phenylpropanamide (10.0 mmol, 1.00 eq.), 1.40 g 4-fluorobenzoic acid (10.0 mmol, 1.00 eq.), 2.88 g N-(3-dimethylaminopropyl)-N'-ethylcarbodiimide hydrochloride (15.0 mmol, 1.50 eq.), 1.62 g 1-hydroxybenzotriazole (12.0 mmol, 1.20 eq.) and 2.58 g N,N-diisopropylethylamine (20.0 mmol, 2.00 eq.) in 30 mL N,N-dimethylformamide was stirred at room temperature overnight. To the mixture was added 100 mL ethyl acetate and washed with 3×100 mL volumes of water. The organic phase was concentrated and the residue was purified by column chromatography on silica gel (petroleum ether:ethyl acetate (5:1, v:v) to give 3.98 g (S)-N-(1-(4-(benzylthio)phenylamino)-1-oxo-3-phenylpropan-2-yl)-4-fluoro-N-methylbenzamide as a light yellow solid (80% yield). MS (ESI+) m/z 499.1 [M+H]+.

Preparation of (S)-4-(2-(4-fluoro-N-methylbenzamido)-3-phenylpropanamido)benzene-1-sulfonyl Chloride

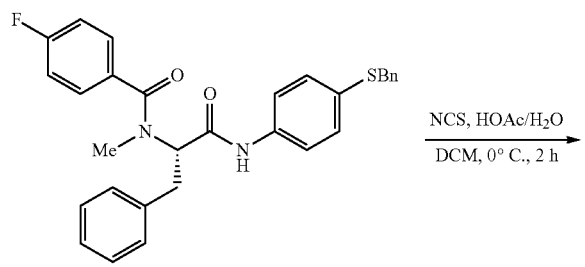

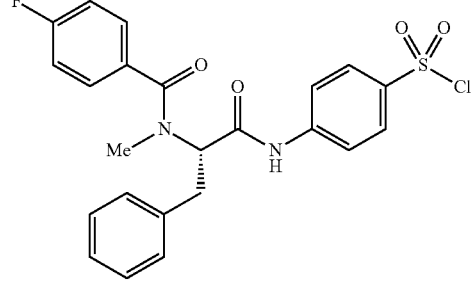

To a solution of 2.49 g (S)-N-(1-(4-(benzylthio)phenylamino)-1-oxo-3-phenylpropan-2-yl)-4-fluoro-N-methylbenzamide (5.00 mmol, 1.00 equiv), 60 mg acetic acid (1.0 mmol, 0.2 equiv) and 18 mg water (1.0 mmol, 0.2 equiv) in 30 mL dichloromethane was added 2.66 g N-chlorosuccinimide (20.0 mmol, 4.00 equiv) at 0° C. The mixture was stirred at room temperature for 1 hour and washed with 3×20 mL volumes of water. The organic phase was concentrated to give 1.65 g (S)-4-(2-(4-fluoro-N-methylbenzamido)-3-phenylpropanamido)benzene-1-sulfonyl chloride as a white solid (70% yield). MS (ESI+) m/z 475.1 [M+H]+.

Preparation of (S)-N-(1-(4-(N-tert-butylsulfamoyl)phenylamino)-1-oxo-3-phenylpropan-2-yl)-4-fluoro-N-methylbenzamide, I-35

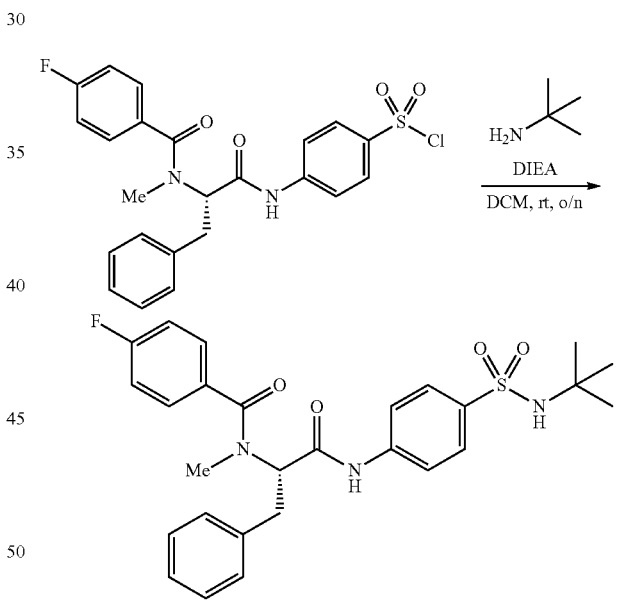

To a mixture of 50 mg 2-methylpropan-2-amine (1.1 mmol, 5.0 eq.) and 142 mg N,N-diisopropylethylamine (1.10 mmol, 5.00 eq.) in 10 mL dichloromethane was added 100 mg (S)-4-(2-(4-fluoro-N-methylbenzamido)-3-phenylpropanamido)benzene-1-sulfonyl chloride (0.21 mmol, 1.00 eq.). The mixture was stirred at room temperature for 1 hour and concentrated. The residue was purified by preparative scale-HPLC to give 25.0 mg (S)-N-(1-(4-(N-tert-butylsulfamoyl)phenylamino)-1-oxo-3-phenylpropan-2-yl)-4-fluoro-N-methylbenzamide (I-35) as a white solid (23% yield). MS (ESI+) m/z 512.1 [M+H]+; $^1$H NMR (400 MHz, d$_6$-DMSO) δ 10.2 (brs, 1H), 7.78 (s, 4H), 7.16-7.34 (m, 10H), 5.16-5.46 (m, 1H), 3.35-3.37 (m, 1H), 3.13-3.17 (m, 1H), 2.93 (s, 3H), 1.12 (s, 9H).

Example 6: 4-fluoro-N-((2S)-1-(4-(neopentylsulfinyl)phenylamino)-1-oxo-3-phenylpropan-2-yl)benzamide (I-4)

Preparation of 4-fluoro-N-((2S)-1-(4-(neopentylsulfinyl)phenylamino)-1-oxo-3-phenylpropan-2-yl)benzamide

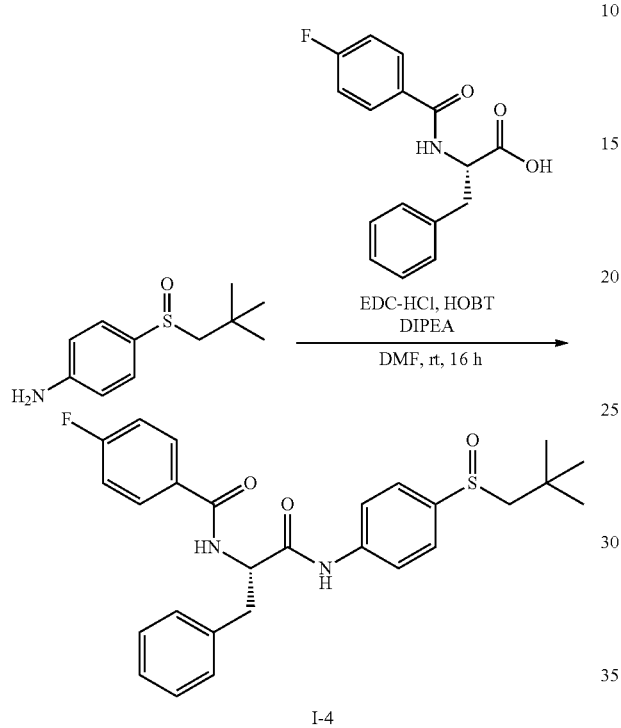

To a solution of 200 mg 4-(neopentylsulfinyl)aniline (0.95 mmol, 1.00 equiv) and 272 mg (S)-2-(4-fluorobenzamido)-3-phenylpropanoic acid (0.95 mmol, 1.00 equiv) dissolved in 5 mL anhydrous N,N-dimethylformamide at room temperature was added 201 mg N-(3-Dimethylaminopropyl)-N'-ethylcarbodiimide hydrochloride (1.05 mmol, 1.10 equiv), 142 mg 1-hydroxybenzotriazole (1.05 mmol, 1.10 equiv), and 245 mg N,N-diisopropylethylamine (1.90 mmol, 2.00 equiv) in succession. Then the reaction mixture was stirred at room temperature for 16 hours and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The compound was purified by reversed phase preparative HPLC on a Gilson GX-281. A concentrated solution of crude product dissolved in DMSO was injected in 500 uL volumes onto a 10 um C18 reversed phase X-Bridge 19 mm diameter×250 mm length column eluting with a gradient of 48-95% acetonitrile in water with 10 mmol/liter ammonium carbonate. Peaks were detected by UV absorbance at 214 nm and 254 nm and fractions collected by 1 mV threshold trigger on the 214 nm channel. Fractions containing product were combined, concentrated and lyophilized to afford 150 mg 4-fluoro-N-((2S)-1-(4-(neopentylsulfinyl)phenylamino)-1-oxo-3-phenylpropan-2-yl)benzamide (I-4) as a white solid (33% yield). MS (ESI$^+$) m/z 481 [M+H]$^+$. $^1$H NMR (400 MHz, d$_6$-DMSO) δ 10.59 (s, 1H), 8.93 (d, J=7.9 Hz, 1H), 7.89 (dd, J=8.8, 5.6 Hz, 2H), 7.80 (d, J=7.5 Hz, 2H), 7.59 (d, J=8.5 Hz, 2H), 7.39 (d, J=7.3 Hz, 2H), 7.31-7.20 (m, 4H), 7.16 (t, J=7.3 Hz, 1H), 4.82 (td, J=9.8, 5.1 Hz, 1H), 3.19-3.02 (m, 2H), 2.71-2.56 (m, 2H), 1.10 (s, 9H).

Example 7: (S)-N-(4-(N-tert-butylsulfamoyl)phenyl)-2-(1-oxo-3,4-dihydroisoquinolin-2(1H)-yl)-3-phenylpropanamide, I-84

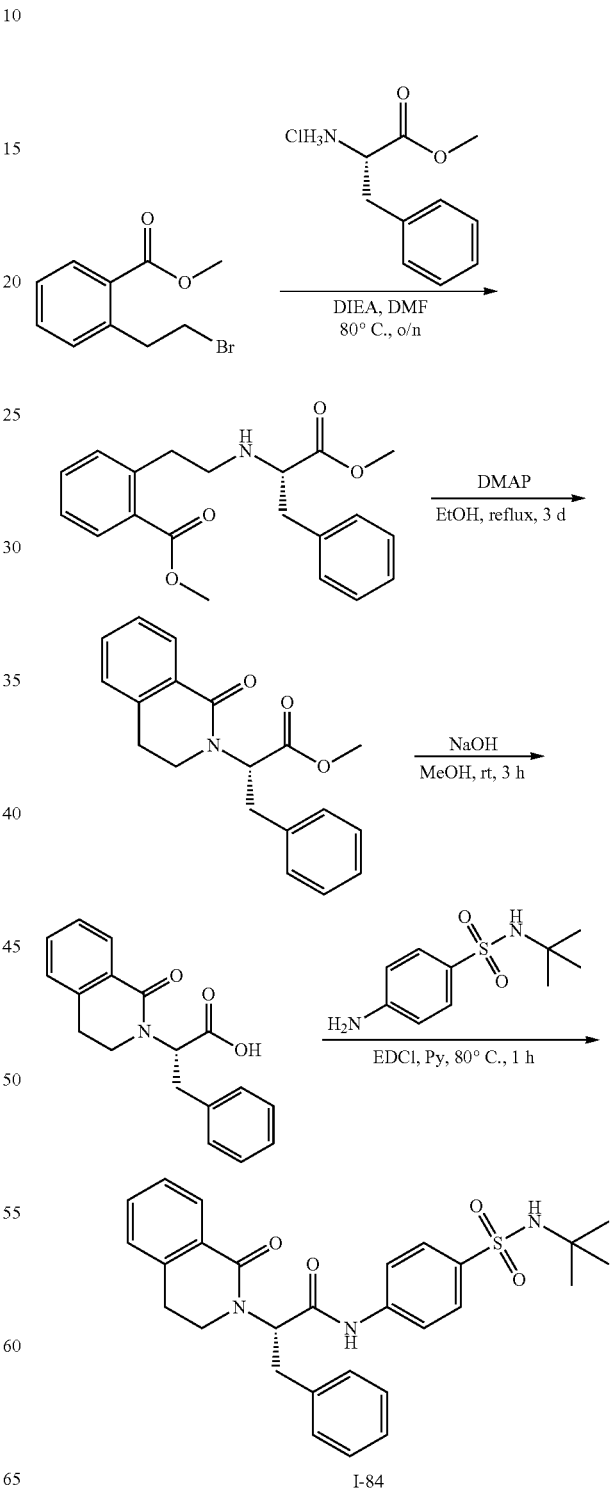

Preparation of (S)-methyl 2-(2-(1-methoxy-1-oxo-3-phenylpropan-2-ylamino)ethyl)benzoate

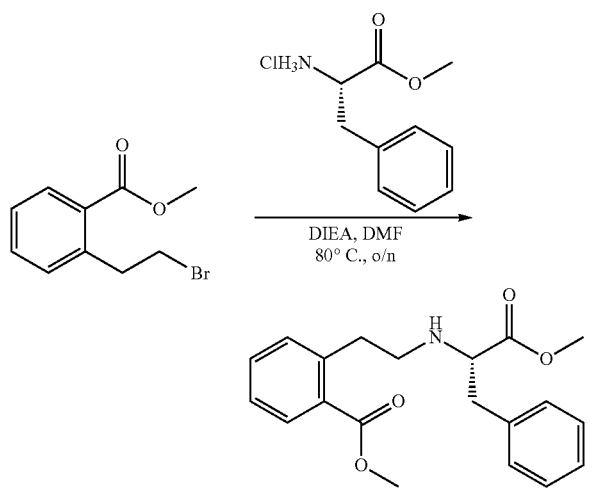

A solution of 600 mg methyl 2-(2-bromoethyl)benzoate (2.5 mmol, 1.0 equiv) and 531 mg (S)-methyl 2-amino-3-phenylpropanoate hydrochloride (2.5 mmol, 1.0 equiv) and 645 mg ethyldiisopropylamine (5.0 mmol, 2.0 equiv) in N,N-dimethylformamide (20 mL) was heated at 80° C. overnight. The reaction was diluted with 50 mL ethyl acetate and washed with 3×40 mL volumes of water. The organic phases were concentrated and the compound was purified by column chromatography (silica gel, petroleum ether:ethyl acetate (15:1, v:v) to afford 250 mg (S)-methyl 2-(2-(1-methoxy-1-oxo-3-phenylpropan-2-ylamino)ethyl)benzoate (29% yield) as colorless oil. MS (ESI⁺) m/z 342 [M+H]⁺.

Preparation of (S)-methyl 2-(1-oxo-3,4-dihydroisoquinolin-2(1H)-yl)-3-phenylpropanoate

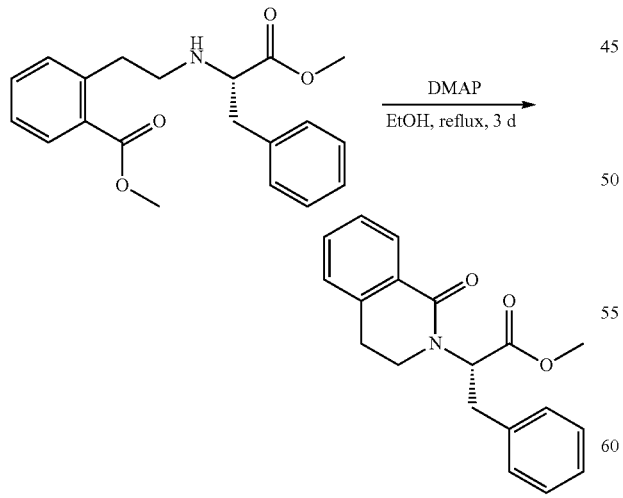

A solution of 250 mg (S)-methyl 2-(2-(1-methoxy-1-oxo-3-phenylpropan-2-ylamino)ethyl)benzoate (0.73 mmol, 1.00 equiv) and 18 mg 4-dimethylaminopyridine (0.15 mmol, 0.2 equiv) in 50 mL ethanol was refluxed for 3 days. The mixture was concentrated and the compound was purified by column chromatography (silica gel, petroleum ether:ethyl acetate (15:1, v:v) to afford 75 mg (S)-methyl 2-(1-oxo-3,4-dihydroisoquinolin-2(1H)-yl)-3-phenylpropanoate as colorless oil (33% yield). MS (ESI⁺) m/z 310 [M+H]⁺.

Preparation of (S)-2-(1-oxo-3,4-dihydroisoquinolin-2(1H)-yl)-3-phenylpropanoic acid

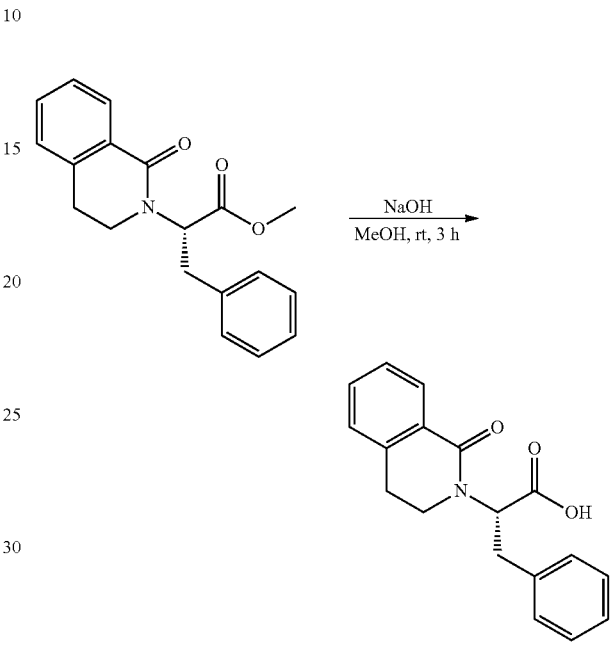

A solution of 75 mg (S)-methyl 2-(1-oxo-3,4-dihydroisoquinolin-2(1H)-yl)-3-phenylpropanoate (0.24 mmol, 1.00 equiv) and 19 mg sodium hydroxide (0.48 mmol, 2.00 equiv) in 10.0 mL methanol was stirred at room temperature for 3 hours. The mixture was concentrated and 10 mL hydrochloric acid (0.1 M) was added. The mixture was extracted with 3×10 mL volumes of ethyl acetate. The combined organic layers were concentrated and the residue was purified by column chromatography on silica gel (petroleum ether:ethyl acetate (1:1, v:v)) to give 50 mg (S)-2-(1-oxo-3,4-dihydroisoquinolin-2(1H)-yl)-3-phenylpropanoic acid as a white solid (70% yield). MS (ESI⁺) m/z 296 [M+H]⁺.

Preparation of (S)-N-(4-(N-tert-butylsulfamoyl)phenyl)-2-(1-oxo-3,4-dihydroisoquinolin-2(1H)-yl)-3-phenylpropanamide, I-84

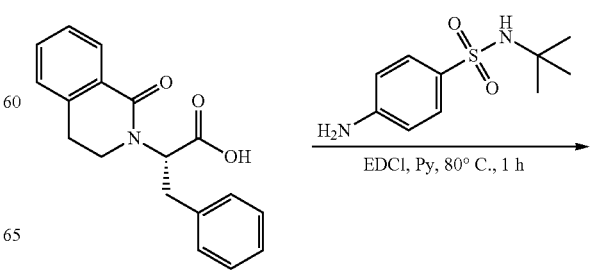

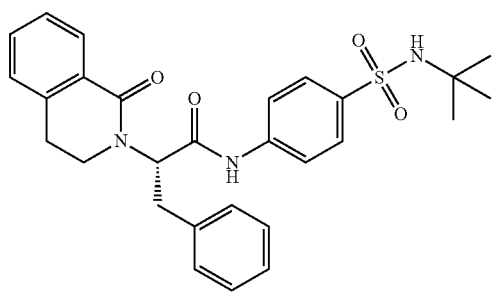

I-84

To a mixture of 31 mg (S)-2-(1-oxo-3,4-dihydroisoquinolin-2(1H)-yl)-3-phenylpropanoic acid (0.105 mmol, 1.0 equiv) and 28.73 mg 4-amino-N-tert-butylbenzenesulfonamide (0.126 mmol, 1.20 equiv) in 3 mL pyridine was added 40 mg EDCI (0.21 mmol, 2.00 equiv). The mixture was stirred at 80° C. for 1 h under nitrogen. The mixture was cooled to r.t, diluted with 10 mL water and extracted with dichloromethane (3×20 mL). The combined organic layers were washed with brine (1×30 mL), dried over anhydrous magnesium sulfate, filtered and the filtrate was concentrated under reduced pressure. The crude product was purified by Prep-HPLC with the following conditions: Column, YMC-Actus Triart C18, 30*250 mm, 5 um; Mobile Phase, water (10% $NH_4HCO_3$) and ACN (25% ACN up to 45% in 7 min); UV detection at 254/220 nm. The product-containing fractions were combined and evaporated partially in vacuo and lyophilized overnight to afford 18.1 mg (S)-N-(4-(N-tert-butylsulfamoyl)phenyl)-2-(1-oxo-3,4-dihydroisoquinolin-2(1H)-yl)-3-phenylpropanamide (I-84) as a white solid (34.07% yield). MS (ESI$^+$) m/z 506 [M+H]$^+$; $^1$H NMR (400 MHz, CD$_3$OD) δ 7.90 (d, 1H), 7.84-7.76 (m, 4H), 7.48-7.44 (m, 1H), 7.37-7.18 (m, 7H), 5.72 (dd, 1H), 3.85-3.78 (m, 1H), 3.74-3.68 (m, 1H), 3.54-3.47 (m, 1H), 3.29-3.24 (m, 1H), 2.97-2.88 (m, 1H), 2.78-2.70 (m, 1H), 1.20 (s, 9H).

Example 8: (S)-N-(1-(4-(N-tert-butylsulfamoyl)phenylamino)-3-(1H-indol-3-yl)-1-oxopropan-2-yl)-4-fluorobenzamide, I-1

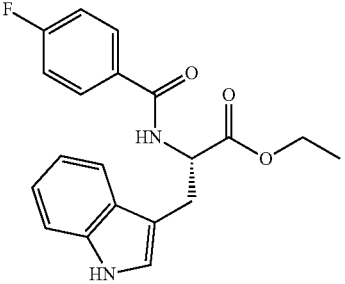

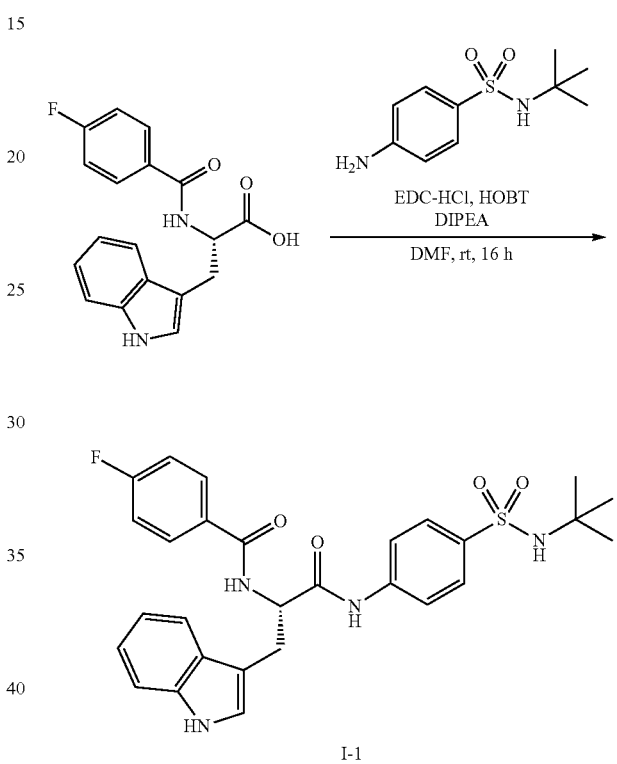

I-1

Preparation of (S)-ethyl 2-(4-fluorobenzamido)-3-(1H-indol-3-yl)propanoate

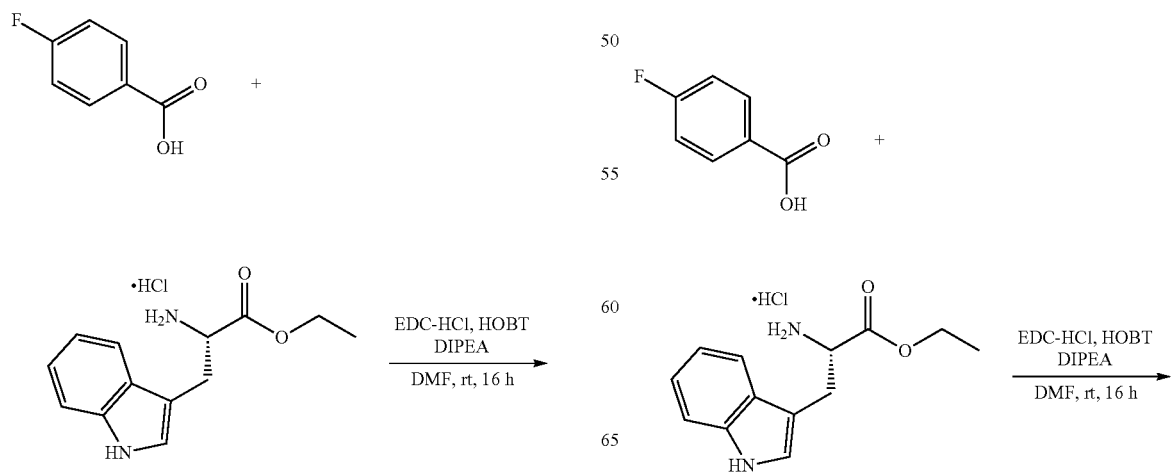

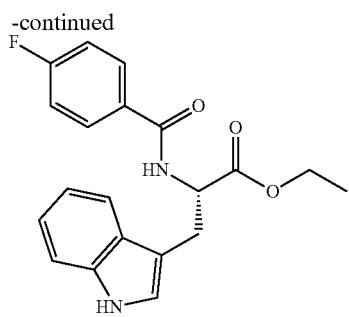

To a solution of 2 g (S)-ethyl 2-amino-3-(1H-indol-3-yl)propanoate hydrochloride (7.5 mmol, 1.00 equiv) and 1.0 g 4-fluorobenzoic acid (7.5 mmol, 1.00 equiv) dissolved in 25 mL anhydrous N,N-dimethylformamide at room temperature was added 1.58 g N-(3-dimethylaminopropyl)-N'-ethylcarbodiimide hydrochloride (8.2 mmol, 1.10 equiv), 1.1 g 1-hydroxybenzotriazole (8.2 mmol, 1.10 equiv), and 1.94 g N,N-diisopropylethylamine (15.0 mmol, 2.00 equiv) in succession. Then the reaction mixture was stirred at room temperature for 16 hours and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. Purification by column chromatography (silica gel, dichloromethane:ethyl acetate (4:1, v:v)) afforded 1.9 g (S)-ethyl 2-(4-fluorobenzamido)-3-(1H-indol-3-yl)propanoate as a white solid (72% yield). MS (ESI+) m/z 355 [M+H]+.

Preparation of (S)-2-(4-fluorobenzamido)-3-(1H-indol-3-yl)propanoic Acid

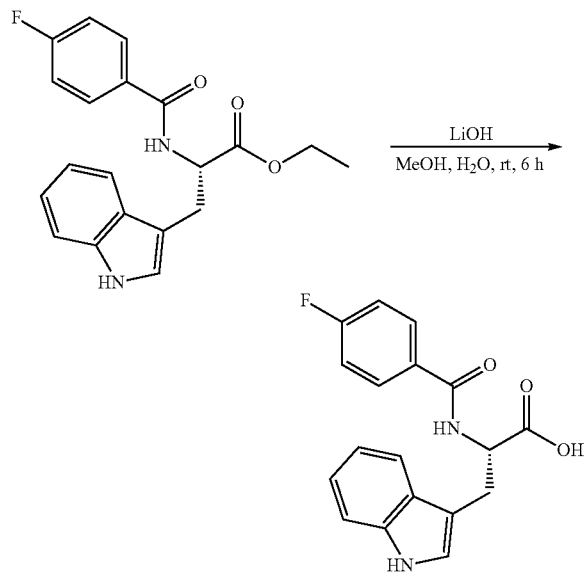

To a solution of 1.9 g (S)-ethyl 2-(4-fluorobenzamido)-3-(1H-indol-3-yl)propanoate (5.4 mmol, 1.00 equiv) in 20 mL (methanol:H$_2$O (5:1, v:v)) was added 258 mg lithium hydroxide (10.8 mmol, 2.00 equiv) and stirred at room temperature for 6 hours. The mixture was concentrated and 100 mL water were added, the pH was adjusted to pH 6 with 6 M HCl. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. Purification by column chromatography (silica gel, dichloromethane:ethyl acetate (2:1, v:v)) afforded 1.5 g (S)-2-(4-fluorobenzamido)-3-(1H-indol-3-yl)propanoic acid as a white solid (86% yield). MS (ESI+) m/z 327[M+H]+.

Preparation of (S)-N-(1-(4-(N-tert-butylsulfamoyl)phenylamino)-3-(1H-indol-3-yl)-1-oxopropan-2-yl)-4-fluorobenzamide, I-1

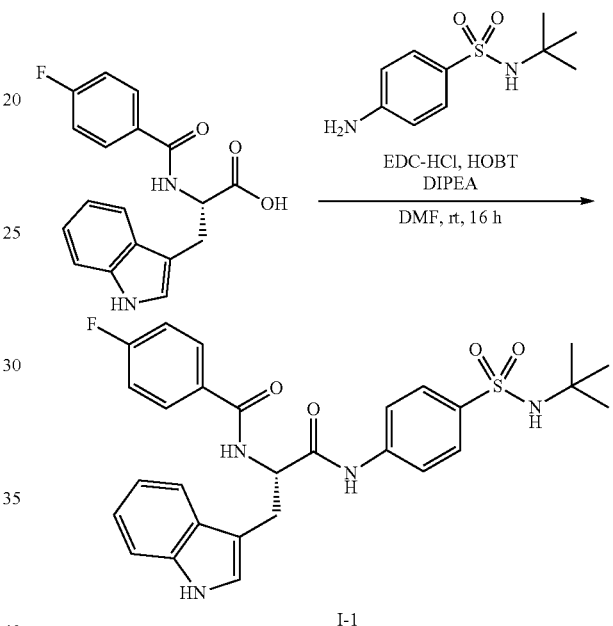

To a solution of 100 mg 4-amino-N-tert-butylbenzenesulfonamide (0.44 mmol, 1.00 equiv) and 143 mg (S)-2-(4-fluorobenzamido)-3-phenylpropanoic acid (0.44 mmol, 1.00 equiv) dissolved in 5 mL anhydrous N,N-dimethylformamide at room temperature was added 93 mg N-(3-dimethylaminopropyl)-N'-ethylcarbodiimide hydrochloride (0.48 mmol, 1.10 equiv), 65 mg 1-hydroxybenzotriazole (0.48 mmol, 1.10 equiv), and 114 mg N,N-diisopropylethylamine (0.88 mmol, 2.00 equiv) in succession. Then the reaction mixture was stirred at room temperature for 16 hours and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The compound was purified by reverse phase preparative HPLC on a Gilson GX-281. A concentrated solution of crude product dissolved in DMSO was injected in 540 uL volumes onto a 10 um C18 OBD reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 8 mV threshold trigger on the 214 nm channel. Fractions containing product were combined, concentrated and lyophilized to afford 30 mg (S)-N-(1-(4-(N-tert-butylsulfamoyl)phenylamino)-3-(1H-indol-3-yl)-1-oxopropan-2-yl)-4-fluorobenzamide (I-1) as a white solid (13% yield). MS (ESI+) m/z 537 [M+H]+. 1H NMR (400 MHz, d6-DMSO) δ 10.83 (s, 1H), 10.69 (s, 1H), 8.89 (d, J=7.6 Hz, 1H), 7.94 (dd, J=8.8, 5.5 Hz, 2H), 7.84-7.66 (m, 5H), 7.42 (s, 1H), 7.36-7.19 (m, 4H), 7.02 (dt, J=28.1, 6.9 Hz, 2H), 4.87 (dd, J=14.0, 8.3 Hz, 1H), 3.25 (m, 2H), 1.08 (s, 9H).

Example 9: N-((2S)-1-(4-(2,2-dimethylpropylsulfonimidoyl)phenylamino)-1-oxo-3-phenylpropan-2-yl)-4-fluorobenzamide, I-3

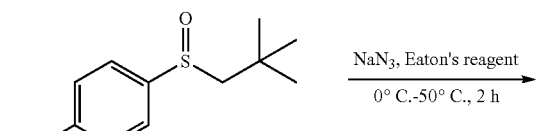

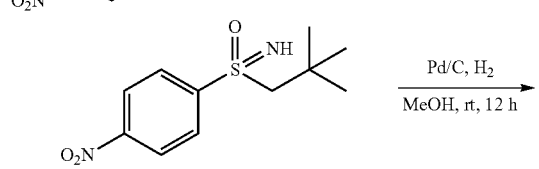

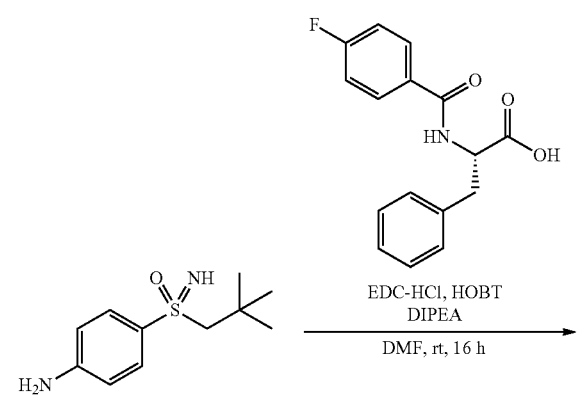

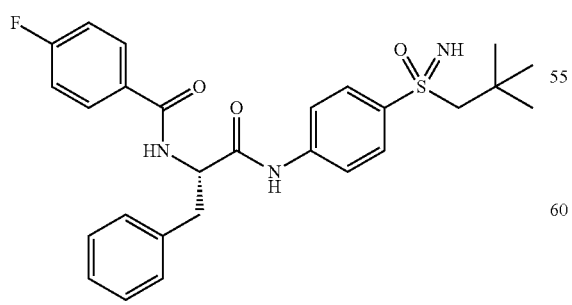

I-3

Preparation of 1-(2,2-dimethylpropylsulfonimidoyl)-4-nitrobenzene

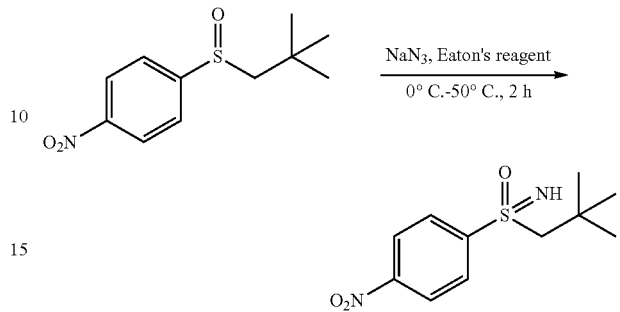

Sodium azide (16 mg, 3.3 mmol, 2.00 equiv) was added all at once to a solution of 400 mg 1-(neopentylsulfinyl)-4-nitrobenzene (1.66 mmol, 1.00 equiv) dissolved in 10 mL of Eatons's reagent. The reaction mixture was stirred at 50° C. for 2 h then it was poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. Purification by column chromatography (silica gel, dichloromethane:ethyl acetate (2:1, v:v)) afforded 260 mg 1-(2,2-dimethylpropylsulfonimidoyl)-4-nitrobenzene as a gray solid (61% yield). MS (ESI+) m/z 257 [M+H]+.

Preparation of 4-(2,2-dimethylpropylsulfonimidoyl)aniline

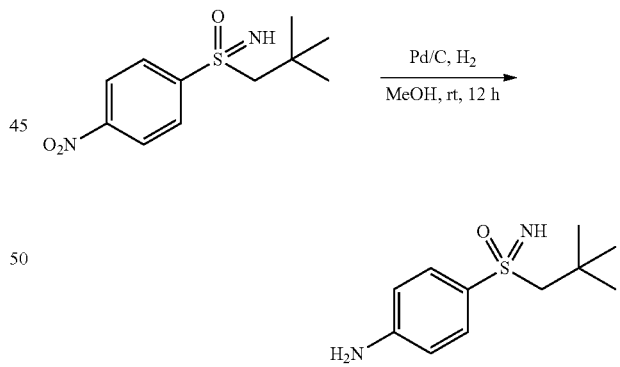

To a solution of 260 mg 1-(2,2-dimethylpropylsulfonimidoyl)-4-nitrobenzene (1.01 mmol, 1.00 equiv) in methanol was added palladium on activated carbon (52 mg wet catalyst, 10 wt. % palladium dry basis). The mixture was placed under hydrogen gas via balloon and stirred at room temperature for 12 hours. The mixture was filtered, and the filtrate concentrated in vacuo. Purification by column chromatography (silica gel, petroleum ether:ethyl acetate (2:1, v:v)) afforded 200 mg 4-(2,2-dimethylpropylsulfonimidoyl) aniline as a white solid (87% yield). MS (ESI+) m/z 227 [M+H]+.

Preparation of N-((2S)-1-(4-(2,2-dimethylpropy-lsulfonimidoyl)phenylamino)-1-oxo-3-phenylpropan-2-yl)-4-fluorobenzamide, I-3

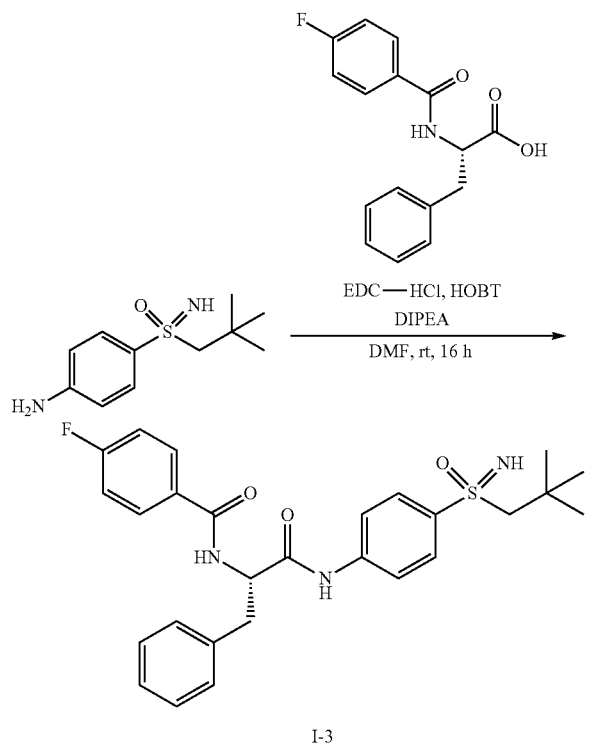

I-3

To a solution of 200 mg 4-(2,2-dimethylpropylsulfonimidoyl)aniline (0.88 mmol, 1.00 equiv) and 253 mg (S)-2-(4-fluorobenzamido)-3-phenylpropanoic acid (0.88 mmol, 1.00 equiv) dissolved in 5 mL anhydrous N,N-dimethylformamide at room temperature was added 187 mg N-(3-dimethylaminopropyl)-N'-ethylcarbodiimide hydrochloride (0.97 mmol, 1.10 equiv), 130 mg 1-hydroxybenzotriazole (0.97 mmol, 1.10 equiv), and 227 mg N,N-diisopropylethylamine (1.76 mmol, 2.00 equiv) in succession. Then the reaction mixture was stirred at room temperature for 16 h and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The compound was purified by reverse phase preparative HPLC on a Gilson GX-281. A concentrated solution of crude product dissolved in DMSO was injected in 500 uL volumes onto a 10 um C18 reversed phase X-Bridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 1 mV threshold trigger on the 214 nm channel. Fractions containing product were combined, concentrated and lyophilized to afford 200 mg N-((2S)-1-(4-(2,2-dimethylpropylsulfonimidoyl)phenylamino)-1-oxo-3-phenylpropan-2-yl)-4-fluorobenzamide (I-3) as a white solid (46% yield). MS (ESI$^+$) m/z 496 [M+H]$^+$. $^1$H NMR (400 MHz, d$_6$-DMSO) δ 8.47 (dd, J=15.4, 6.7 Hz, 1H), 7.84 (dt, J=8.7, 6.1 Hz, 2H), 7.48 (dd, J=14.1, 8.8 Hz, 2H), 7.35-7.17 (m, 6H), 7.14 (dd, J=12.7, 7.0 Hz, 1H), 6.70-6.49 (m, 2H), 6.15 (d, J=5.4 Hz, 2H), 4.60 (dt, J=10.4, 5.3 Hz, 1H), 3.53 (dd, J=14.5, 4.6 Hz, 1H), 3.25 (m, 2H), 2.96 (m, 1H), 0.96 (s, 9H).

Example 10: N-((2S)-1-(4-(1-(tert-butylamino)-2,2,2-trifluoroethyl)phenylamino)-1-oxo-3-phenylpropan-2-yl)-4-fluorobenzamide, I-18

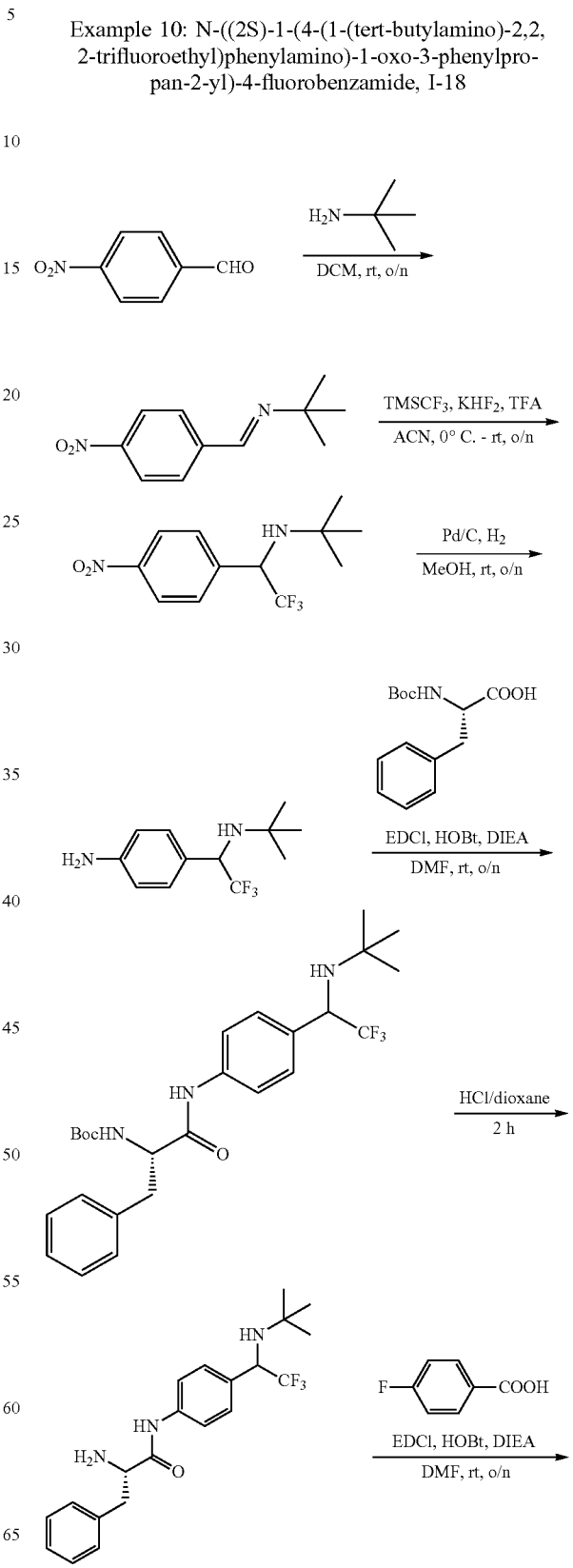

-continued

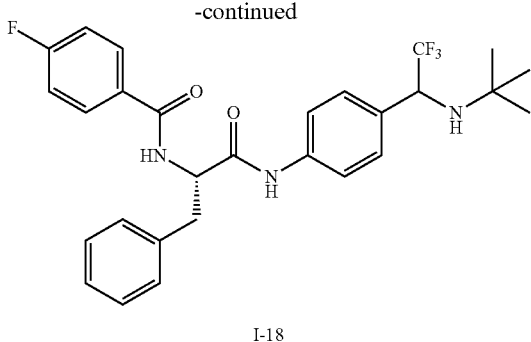

I-18

Preparation of (E)-2-methyl-N-(4-nitrobenzylidene)propan-2-amine

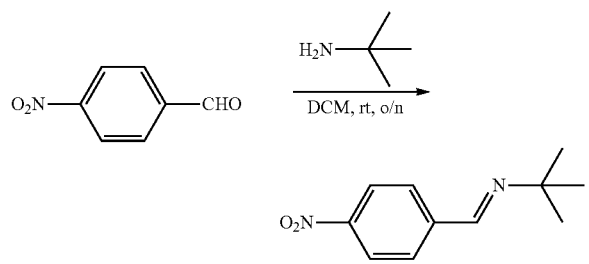

To the solution of 1.51 g 4-nitrobenzaldehyde (10.0 mmol, 1.00 equiv) in 10 mL dichloromethane was added 730 mg 2-methylpropan-2-amine (10.0 mmol, 1.0 equiv). The mixture was stirred at room temperature for overnight and filtered to give 1.85 g (E)-2-methyl-N-(4-nitrobenzylidene)propan-2-amine as a white solid (90% yield). MS (ESI$^+$) m/z 207 [M+H]$^+$.

Preparation of 2-methyl-N-(2,2,2-trifluoro-1-(4-nitrophenyl)ethyl)propan-2-amine

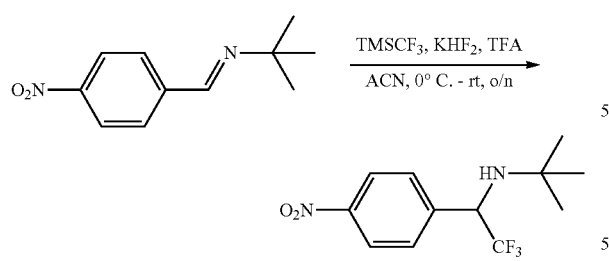

To a mixture of 2.07 g (E)-2-methyl-N-(4-nitrobenzylidene)propan-2-amine (10.0 mmol, 1.00 equiv) and 780 mg potassium bifluoride (10.0 mmol, 1.00 equiv) in 20 mL acetonitrile at 0° C. was added 1.42 g trifluoromethyltrimethylsilane (10.0 mmol, 1.00 equiv). The mixture was stirred at room temperature overnight. The mixture was diluted with 100 mL ethyl acetate and washed with 3×100 mL volumes of water. The organic phase was concentrated and the residue was purified by column chromatography on silica gel (petroleum ether:ethyl acetate (5:1, v:v)) to afford 1.9 g 2-methyl-N-(2,2,2-trifluoro-1-(4-nitrophenyl)ethyl)propan-2-amine as a light yellow solid (70% yield). MS (ESI$^+$) m/z 277 [M+H]$^+$.

Preparation of 4-(1-(tert-butylamino)-2,2,2-trifluoroethyl)aniline

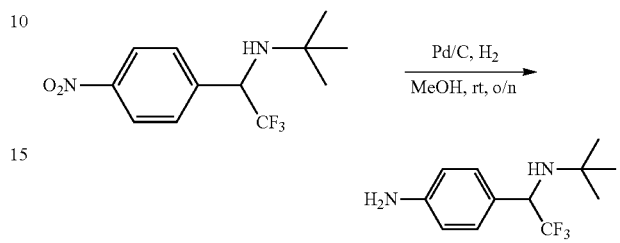

To a solution of 2.76 g 1-(2,2-dimethyl-propylsulfinyl)-4-nitrobenzene (10.0 mmol, 1.00 equiv) in methanol was added palladium on activated carbon (550 mg wet catalyst, 10 wt. % palladium dry basis). The mixture was placed under hydrogen gas via balloon and stirred at room temperature overnight. The mixture was filtered and the filtrate concentrated to afford 2.21 g 4-(1-(tert-butylamino)-2,2,2-trifluoroethyl)aniline as a light yellow solid (90% yield). MS (ESI$^+$) m/z 247 [M+H]$^+$.

Preparation of tert-butyl (2S)-1-(4-(1-(tert-butylamino)-2,2,2-trifluoroethyl)phenylamino)-1-oxo-3-phenylpropan-2-ylcarbamate

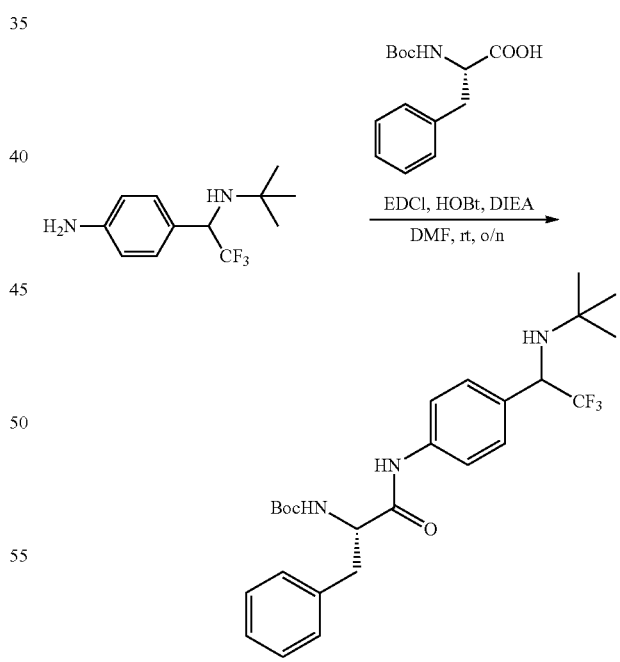

A mixture of 2.65 g (S)-2-(tert-butoxycarbonylamino)-3-phenylpropanoic acid (10.0 mmol, 1.0 equiv), 2.46 g 4-(1-(tert-butylamino)-2,2,2-trifluoroethyl)aniline (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.2 equiv) and 2.58 g N,N-diisopropylethylamine (20.0 mmol, 2.00 equiv) in 20 mL N,N-dimethylformamide was stirred at room temperature overnight. The mixture was diluted with 100 mL ethyl acetate and washed with 3×100 mL volumes of water. The organic phase was concentrated and the residue was purified by column chromatography on silica gel (petroleum ether: ethyl acetate (5:1, v:v)) to yield 3.94 g tert-butyl (2S)-1-(4-(1-(tert-butylamino)-2,2,2-trifluoroethyl)phenylamino)-1-oxo-3-phenylpropan-2-ylcarbamate as a white solid (80% yield). MS (ESI$^+$) m/z 494 [M+H]$^+$.

Preparation of (2S)-2-amino-N-(4-(1-(tert-butylamino)-2,2,2-trifluoroethyl)phenyl)-3-phenylpropanamide

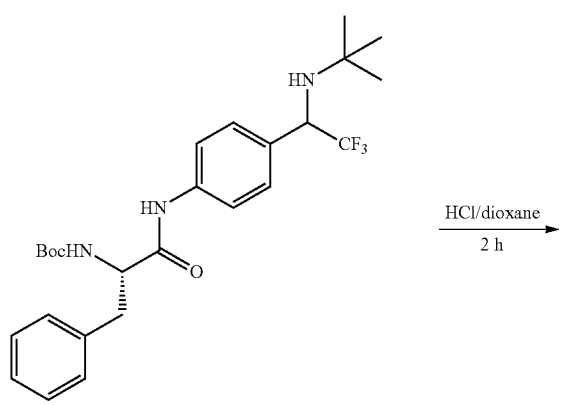

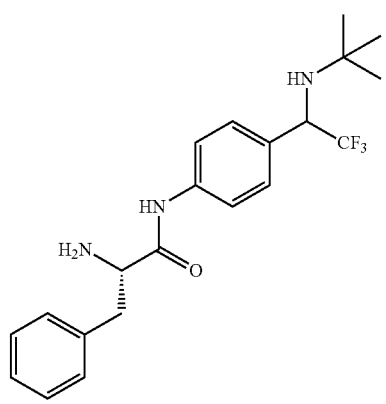

A mixture of 493 mg tert-butyl (2S)-1-(4-(1-(tert-butylamino)-2,2,2-trifluoroethyl)phenylamino)-1-oxo-3-phenylpropan-2-ylcarbamate (1.0 mmol, 1.00 equiv) in 20 mL hydrochloric acid in dioxane (4.0 M HCl) was stirred at room temperature for 2 hours. The mixture was concentrated in vacuo to give 393 mg (2S)-2-amino-N-(4-(1-(tert-butylamino)-2,2,2-trifluoroethyl)phenyl)-3-phenylpropanamide as a white solid (100% yield). MS (ESI$^+$) m/z 394 [M+H]$^+$.

Preparation of N-((2S)-1-(4-(1-(tert-butylamino)-2,2,2-trifluoroethyl)phenylamino)-1-oxo-3-phenylpropan-2-yl)-4-fluorobenzamide, I-18

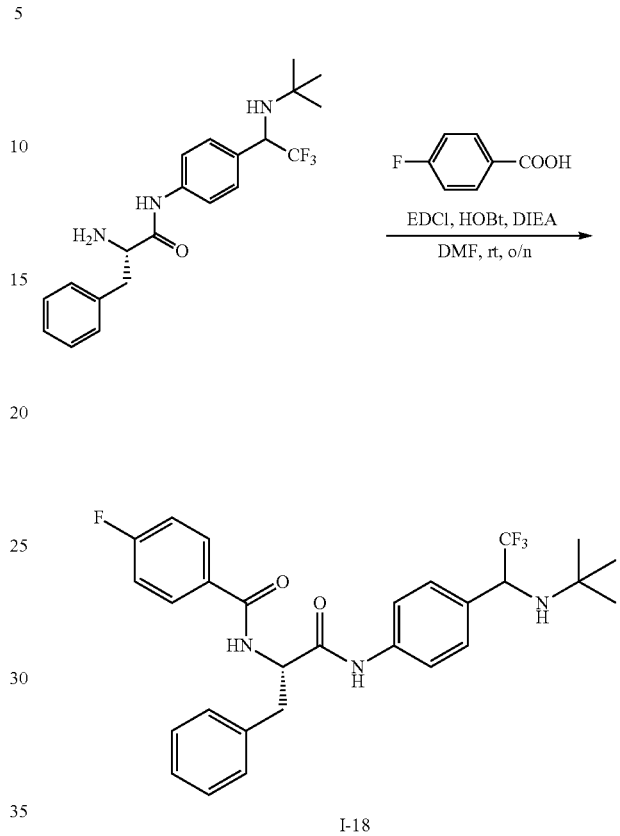

A mixture of 197 mg (2S)-2-amino-N-(4-(1-(tert-butylamino)-2,2,2-trifluoroethyl)phenyl)-3-phenylpropanamide (0.5 mmol, 1.0 equiv), 70 mg 4-fluorobenzoic acid (0.5 mmol, 1.00 equiv), 144 mg N-(3-dimethylaminopropyl)-N'-ethylcarbodiimide hydrochloride (0.75 mmol, 1.50 equiv), 81 mg 1-hydroxybenzotriazole (0.6 mmol, 1.2 equiv) and 129 mg N,N-diisopropylethylamine (1.0 mmol, 2.00 equiv) in 20 mL N,N-dimethylformamide was stirred at room temperature overnight. The mixture was diluted with 100 mL ethyl acetate and washed with 3×100 mL volumes of water. The organic phase was concentrated and the residue was purified by reversed phase preparative HPLC on a Gilson GX-281. A concentrated solution of crude product dissolved in DMSO was injected in 500 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 4 mV threshold trigger on the 214 nm channel. Fractions containing product were combined, concentrated and lyophilized to afford 40.0 mg N-((2S)-1-(4-(1-(tert-butylamino)-2,2,2-trifluoroethyl)phenylamino)-1-oxo-3-phenylpropan-2-yl)-4-fluorobenzamide (I-18) as a white solid (16% yield). MS (ESI$^+$) m/z 516 [M+H]$^+$; $^1$H NMR (400 MHz, d$_6$-DMSO) δ 10.29 (s, 1H), 8.82 (d, J=8.0 Hz, 1H), 7.98-7.72 (m, 2H), 7.59 (d, J=8.5 Hz, 2H), 7.51 (d, J=8.6 Hz, 2H), 7.41 (d, J=7.2 Hz, 2H), 7.32-7.22 (m, 4H), 7.18 (t, J=7.3 Hz, 1H), 4.83 (td, J=10.0, 4.8 Hz, 1H), 4.54-4.30 (m, 1H), 3.22-2.96 (m, 2H), 2.35 (t, J=10.2 Hz, 1H), 0.96 (s, 9H).

Example 11: N-(4-(N-tert-butylsulfamoyl)phenyl)-2-(4-fluorobenzamido)-2,3-dihydro-1H-indene-2-carboxamide, I-19
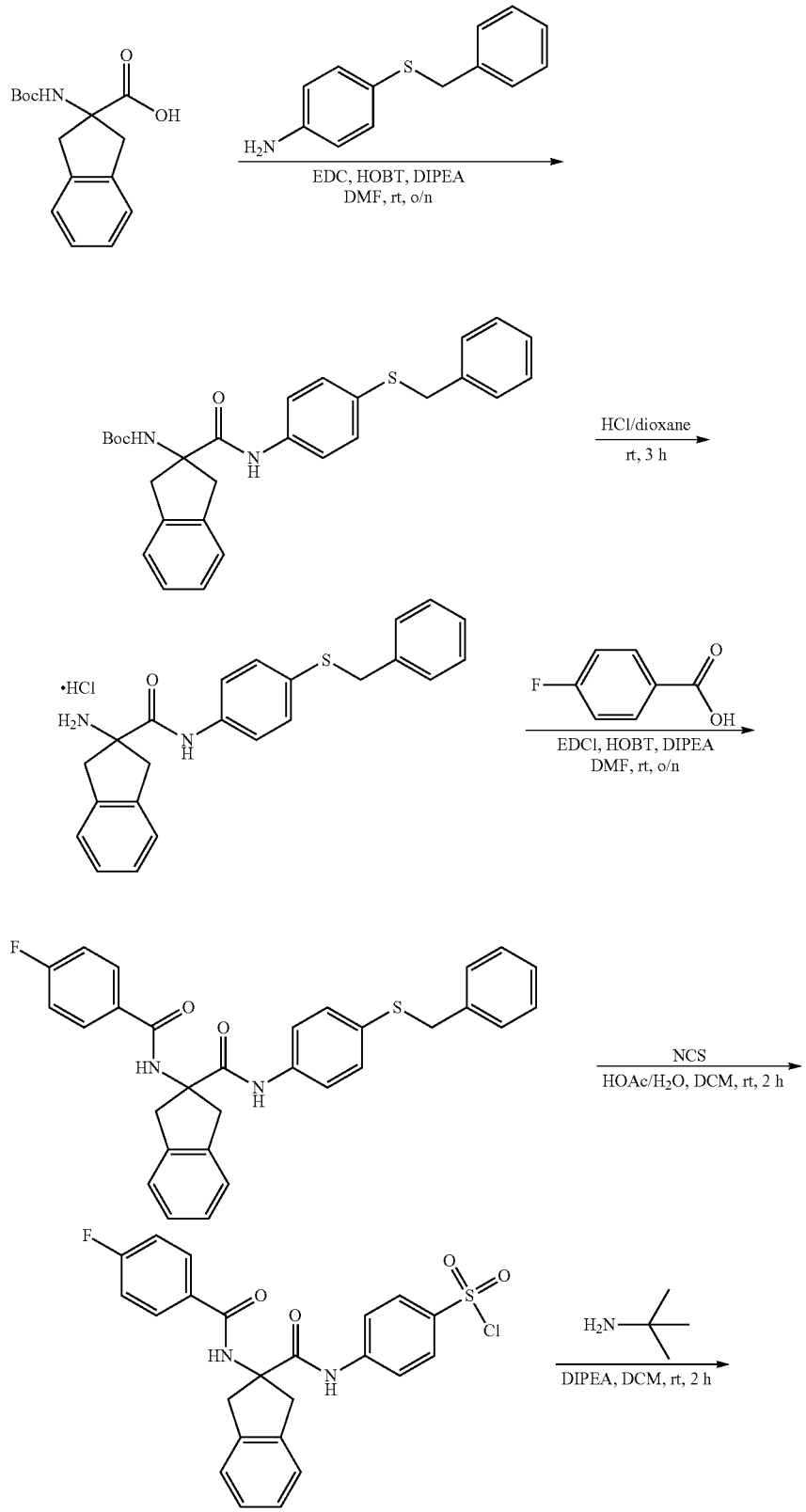

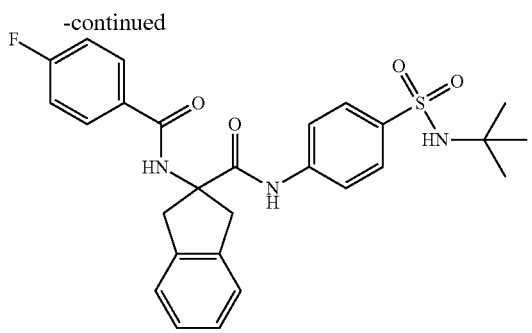

I-19

Preparation of tert-butyl 2-(4-(benzylthio)phenylcarbamoyl)-2,3-dihydro-1H-inden-2-ylcarbamate

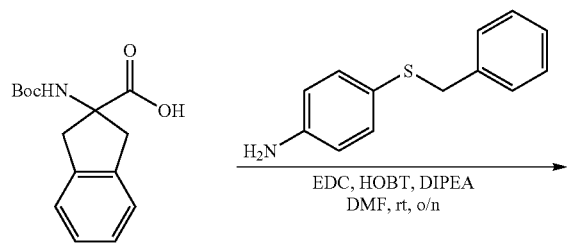

To a solution of 466 mg 4-(benzylthio)aniline (2.20 mmol, 1.00 equiv) and 600 mg 2-(tert-butoxycarbonylamino)-2,3-dihydro-1H-indene-2-carboxylic acid (2.20 mmol, 1.00 equiv) dissolved in 10 mL anhydrous N,N-dimethylformamide at room temperature was added 465 mg N-(3-dimethylaminopropyl)-N'-ethylcarbodiimide hydrochloride (2.42 mmol, 1.10 equiv), 327 mg 1-hydroxybenzotriazole (2.42 mmol, 1.10 equiv), and 567 mg N,N-diisopropylethylamine (4.40 mmol, 2.00 equiv) in succession. Then the reaction mixture was stirred at room temperature for overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (petroleum ether: ethyl acetate (4:1, v:v)) to give 421 mg tert-butyl 2-(4-(benzylthio)phenylcarbamoyl)-2,3-dihydro-1H-inden-2-ylcarbamate as a white solid (40% yield). MS (ESI$^+$) m/z 475 [M+H]$^+$.

Preparation of 2-amino-N-(4-(benzylthio)phenyl)-2,3-dihydro-1H-indene-2-carboxamide, Hydrochloride

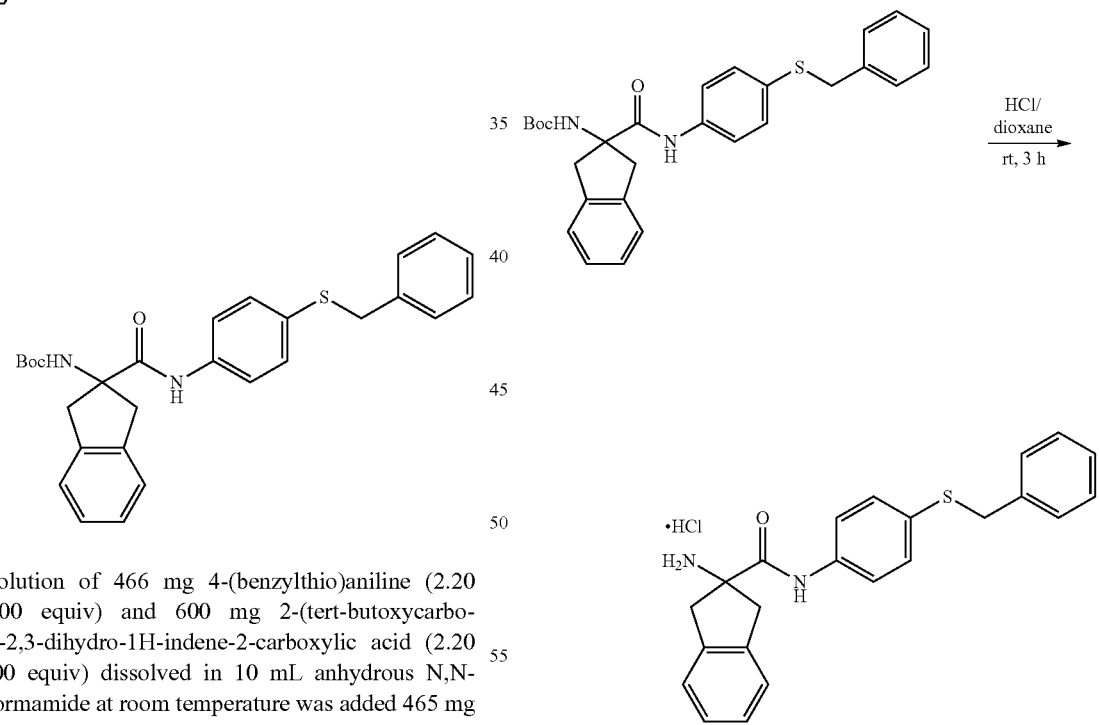

421 mg tert-butyl 2-(4-(benzylthio)phenylcarbamoyl)-2,3-dihydro-1H-inden-2-ylcarbamate (0.87 mmol, 1.00 equiv) was dissolved in 30 mL hydrochloric acid in dioxane (4.0 M) and stirred at room temperature for 3 h. The mixture was concentrated to afford 400 mg 2-amino-N-(4-(benzylthio)phenyl)-2,3-dihydro-1H-indene-2-carboxamide, hydrochloride as a light yellow solid (100% yield). MS (ESI$^+$) m/z 375 [M+H]$^+$.

Preparation of N-(4-(benzylthio)phenyl)-2-(4-fluorobenzamido)-2,3-dihydro-1H-indene-2-carboxamide

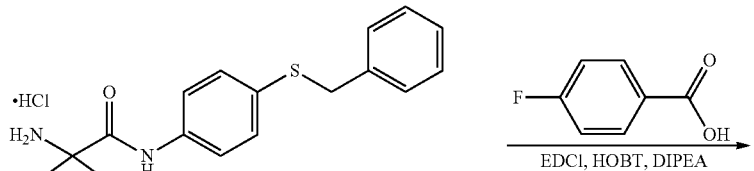

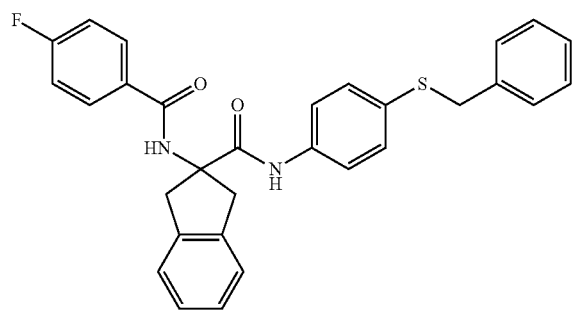

A mixture of 400 mg 2-amino-N-(4-(benzylthio)phenyl)-2,3-dihydro-1H-indene-2-carboxamide, hydrochloride (0.98 mmol, 1.00 equiv), 137 mg 4-fluorobenzoic acid (0.98 mmol, 1.0 equiv), 207 mg N-(3-dimethylaminopropyl)-N'-ethylcarbodiimide hydrochloride (1.1 mmol, 1.1 equiv), 149 mg 1-hydroxybenzotriazole (1.1 mmol, 1.1 equiv) and 253 mg N,N-diisopropylethylamine (1.96 mmol, 2.00 equiv) in 30 mL N,N-dimethylformamide was stirred at room temperature overnight. The reaction was diluted with 100 mL ethyl acetate and washed with 3×100 mL volumes of water. The organic phase was concentrated and the residue was purified by column chromatography on silica gel (petroleum ether:ethyl acetate (3:1, v:v)) to give 380 mg N-(4-(benzylthio)phenyl)-2-(4-fluorobenzamido)-2,3-dihydro-1H-indene-2-carboxamide as a gray solid (78% yield). MS (ESI$^+$) m/z 497 [M+H]$^+$.

Preparation of 4-(2-(4-fluorobenzamido)-2,3-dihydro-1H-indene-2-carboxamido)benzene-1-sulfonyl Chloride

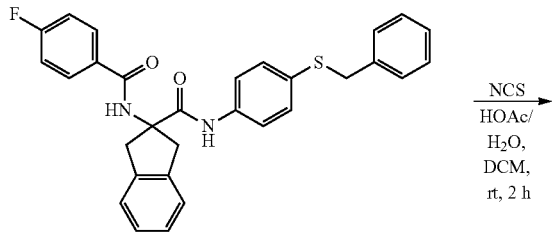

-continued

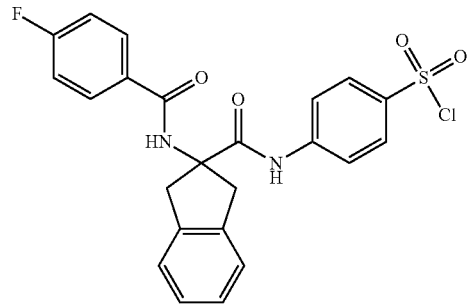

To a solution of 270 mg N-(4-(benzylthio)phenyl)-2-(4-fluorobenzamido)-2,3-dihydro-1H-indene-2-carboxamide (0.54 mmol, 1.00 equiv), 33 mg acetic acid (0.54 mmol, 1 equiv) and 10 mg water (0.54 mmol, 1 equiv) in 30 mL dichloromethane was added 293 mg N-chlorosuccinimide (2.16 mmol, 4.00 equiv) at 0° C. The mixture was stirred at room temperature for 2 h and washed with 3×20 mL volumes of water. The organic phase was concentrated to give 200 mg 4-(2-(4-fluorobenzamido)-2,3-dihydro-1H-indene-2-carboxamido)benzene-1-sulfonyl chloride as a gray solid (78% yield). MS (ESI$^+$) m/z 473[M+H]$^+$.

Preparation of N-(4-(N-tert-butylsulfamoyl)phenyl)-2-(4-fluorobenzamido)-2,3-dihydro-1H-indene-2-carboxamide, I-19

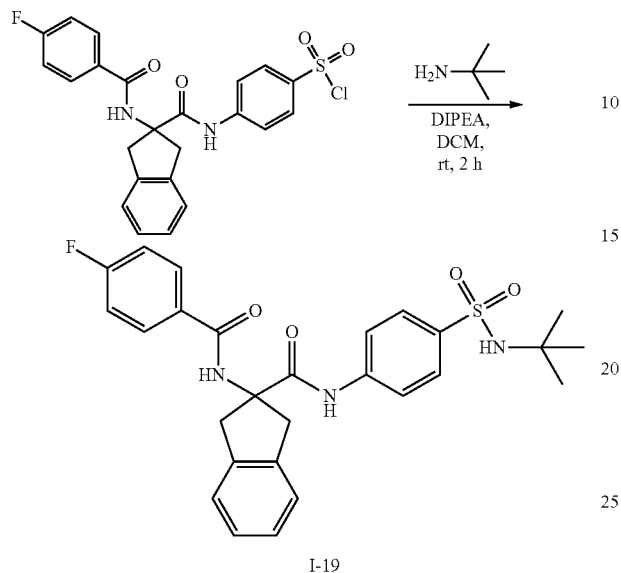

I-19

To a mixture of 155 mg 2-methylpropan-2-amine (2.12 mmol, 5.0 equiv) and 273 mg N,N-diisopropylethylamine (2.12 mmol, 5.00 equiv) in 10 mL dichloromethane was added 200 mg 4-(2-(4-fluorobenzamido)-2,3-dihydro-1H-indene-2-carboxamido)benzene-1-sulfonyl chloride (0.42 mmol, 1.00 equiv). The mixture was stirred at room temperature for 2 h and concentrated in vacuo. The compound was purified by reversed phase preparative HPLC on a Gilson GX-281. A concentrated solution of crude product dissolved in DMSO was injected in 413 uL volumes onto a 10 um C18 reversed phase Waters X-SELECT 19 mm diameter×250 mm length column eluting with a gradient of 58-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 45 mg N-(4-(N-tert-butylsulfamoyl)phenyl)-2-(4-fluorobenzamido)-2,3-dihydro-1H-indene-2-carboxamide (I-19) as a white solid (21% yield). MS (ESI+) m/z 510[M+H]+. 1H NMR (400 MHz, $d_6$-DMSO) δ 10.05 (s, 1H), 8.90 (s, 1H), 8.03 (dd, J=8.9, 5.6 Hz, 2H), 7.75 (dd, J=21.0, 9.0 Hz, 4H), 7.37 (s, 1H), 7.33-7.22 (m, 4H), 7.20-7.15 (m, 2H), 3.75 (d, J=16.8 Hz, 2H), 3.42 (d, J=16.8 Hz, 2H), 1.07 (s, 9H).

Example 12: N-(1-(4-(N-tert-butylsulfamoyl)phenyl)-2-oxo-1,2,3,4-tetrahydroquinolin-3-yl)-4-fluorobenzamide, I-20

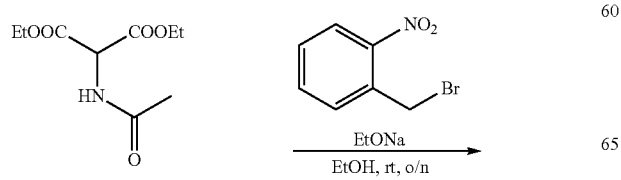

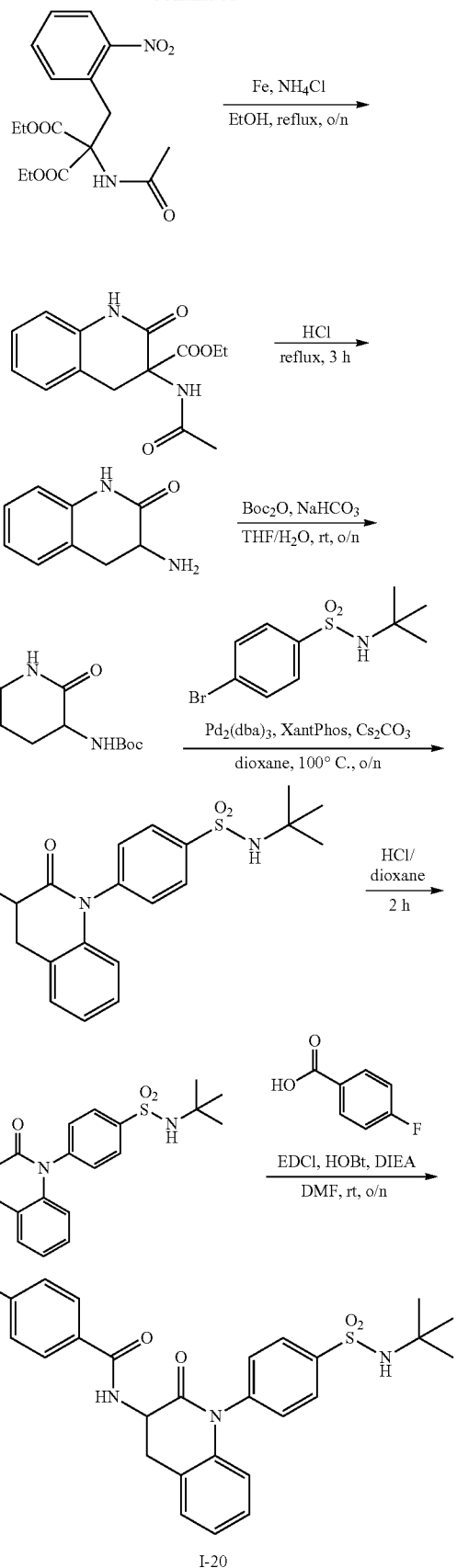

I-20

Preparation of diethyl
2-acetamido-2-(2-nitrobenzyl)malonate

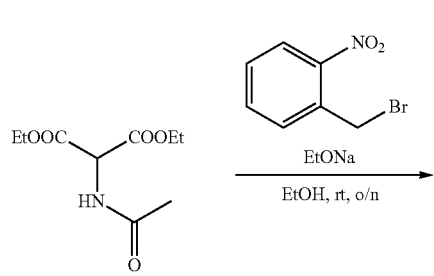

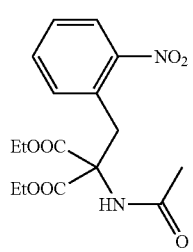

To a solution of 2.17 g diethyl 2-acetamidomalonate (10.0 mmol, 1.0 equiv) in 30 mL ethanol was added 1.06 g sodium ethoxide (20.0 mmol, 2.0 equiv) and the mixture was stirred at room temperature for 0.5 h. 2.14 g 2-nitrobenzyl bromide (10.0 mmol, 1.0 equiv) was added and the mixture was stirred at room temperature overnight. 100 mL water was added to the reaction mixture and filtered. The solid was washed with water and dried under vacuum to give 2.46 g diethyl 2-acetamido-2-(2-nitrobenzyl)malonate as a yellow solid (70% yield). MS (ESI$^+$) m/z 353 [M+H]$^+$.

Preparation of ethyl 3-acetamido-2-oxo-1,2,3,4-tetrahydroquinoline-3-carboxylate

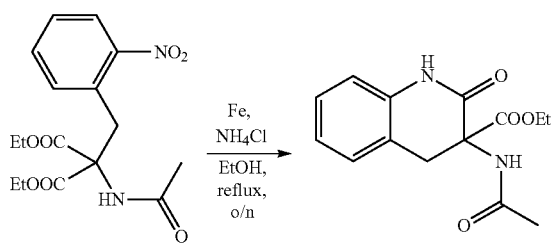 [SMILES: CCOC(=O)C(Cc1ccccc1[N+](=O)[O-])(NC(C)=O)C(=O)OCC ; CCOC(=O)C1(NC(C)=O)Cc2ccccc2NC1=O]

A mixture of 3.52 g diethyl 2-acetamido-2-(2-nitrobenzyl)malonate (10.0 mmol, 1.0 equiv), 2.65 g ammonium chloride (50.0 mmol, 5.0 equiv) and 2.80 g iron powder (50.0 mmol, 5.0 equiv) in 100 mL ethanol was refluxed overnight, then filtered through celite. The solvent was concentrated in vacuo afforded 2.20 g ethyl 3-acetamido-2-oxo-1,2,3,4-tetrahydroquinoline-3-carboxylate as a brown solid (80% yield). MS (ESI$^+$) m/z 277 [M+H]$^+$.

Preparation of
3-amino-3,4-dihydroquinolin-2(1H)-one

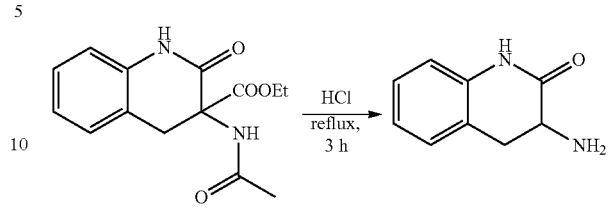

A solution of 2.77 g ethyl 3-acetamido-2-oxo-1,2,3,4-tetrahydroquinoline-3-carboxylate (10.0 mmol, 1.0 equiv) in 50 mL concentrated hydrochloric acid was refluxed for 3 hours. The reaction mixture was diluted with 100 mL water and extracted with 3×100 mL volumes of ethyl acetate. The aqueous phase was basified with saturated sodium bicarbonate solution and extracted with 3×100 mL volumes of ethyl acetate. The combined organic fractions were concentrated in vacuo to give 1.30 g 3-amino-3,4-dihydroquinolin-2(1H)-one as a brown solid (80% yield). MS (ESI$^+$) m/z 163 [M+H]$^+$.

Preparation of tert-butyl
2-oxo-1,2,3,4-tetrahydroquinolin-3-ylcarbamate

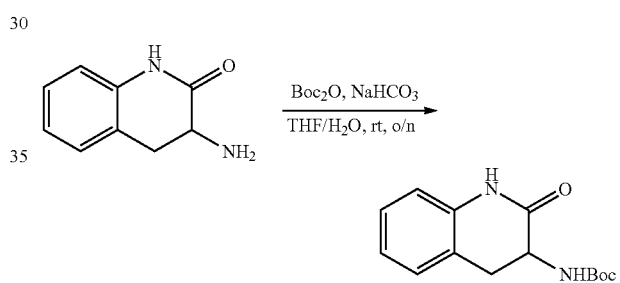

To a solution of 1.62 g 3-amino-3,4-dihydroquinolin-2(1H)-one (10.0 mmol, 1.0 equiv), 1.68 g sodium bicarbonate (20.0 mmol, 2.0 equiv) in 10 mL tetrahydrofuran and 10 mL water was added 2.18 g di-tert-butyl dicarbonate (10.0 mmol, 1.0 equiv) and the mixture was stirred at room temperature overnight. The reaction mixture was extracted with 3×100 mL volumes of ethyl acetate. The combined organic fractions were concentrated in vacuo to give 2.10 g tert-butyl 2-oxo-1,2,3,4-tetrahydroquinolin-3-ylcarbamate as a white solid (80% yield). MS (ESI$^+$) m/z 263 [M+H]$^+$.

Preparation of tert-butyl 1-(4-(N-tert-butylsulfamoyl)phenyl)-2-oxo-1,2,3,4-tetrahydroquinolin-3-ylcarbamate

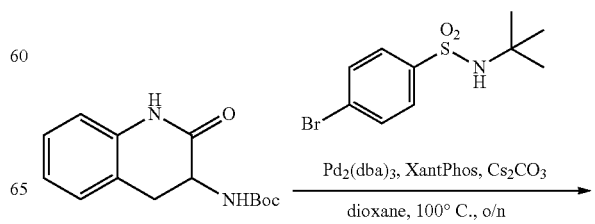

233

-continued

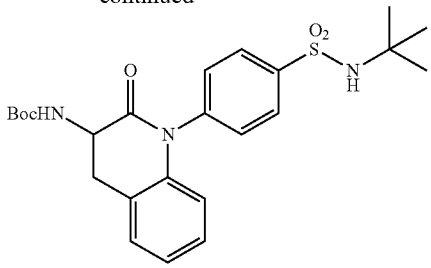

A mixture of 262 mg tert-butyl 2-oxo-1,2,3,4-tetrahydroquinolin-3-ylcarbamate (1.0 mmol, 1.0 equiv), 290 mg 4-bromo-N-tert-butylbenzenesulfonamide (10.0 mmol, 1.00 equiv), 91.5 mg tris(dibenzylideneacetone)dipalladium (0.1 mmol, 0.1 equiv), 115 mg 4,5-bis(diphenylphosphino)-9,9-dimethylxanthene (0.2 mmol, 0.2 equiv) and 276 mg cesium carbonate (2.0 mmol, 2.00 equiv) in 20 mL dioxane was stirred at 100° C. overnight. The mixture was diluted with 100 mL ethyl acetate and washed with 3×100 mL volumes of water. The organic phase was concentrated and the residue was purified by column chromatography on silica gel (petroleum ether:ethyl acetate (3:1, v:v)) to yield 283 mg tert-butyl 1-(4-(N-tert-butylsulfamoyl)phenyl)-2-oxo-1,2,3,4-tetrahydroquinolin-3-ylcarbamate as a white solid (60% yield). MS (ESI$^+$) m/z 474 [M+H]$^+$.

Preparation of 4-(3-amino-2-oxo-3,4-dihydroquinolin-1(2H)-yl)-N-tert-butylbenzenesulfonamide

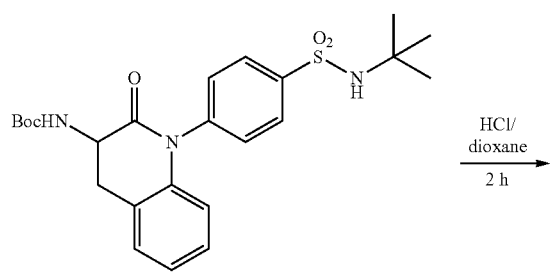

A mixture of 473 mg tert-butyl 1-(4-(N-tert-butylsulfamoyl)phenyl)-2-oxo-1,2,3,4-tetrahydroquinolin-3-ylcarbamate (1.0 mmol, 1.00 equiv) in 20 mL hydrochloric acid in dioxane (4.0 M HCl) was stirred at room temperature for 2 hours. The mixture was concentrated in vacuo to give 373 mg 4-(3-amino-2-oxo-3,4-dihydroquinolin-1(2H)-yl)-N-tert-butylbenzenesulfonamide as a white solid (100% yield). MS (ESI$^+$) m/z 374 [M+H]$^+$.

234

Preparation of N-(1-(4-(N-tert-butylsulfamoyl)phenyl)-2-oxo-1,2,3,4-tetrahydroquinolin-3-yl)-4-fluorobenzamide

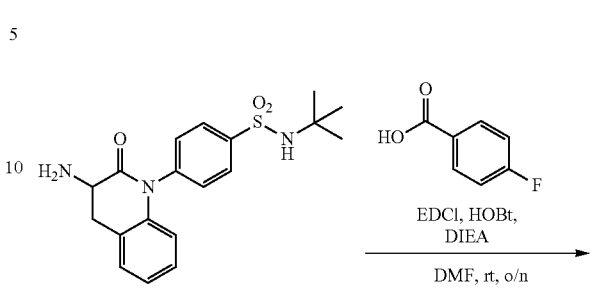

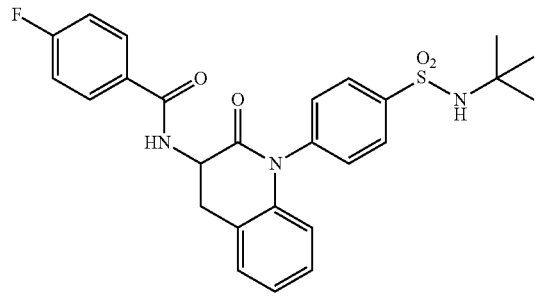

I-20

A mixture of 187 mg 4-(3-amino-2-oxo-3,4-dihydroquinolin-1(2H)-yl)-N-tert-butylbenzenesulfonamide (0.5 mmol, 1.0 equiv), 70 mg 4-fluorobenzoic acid (0.5 mmol, 1.00 equiv), 144 mg N-(3-dimethylaminopropyl)-N'-ethylcarbodiimide hydrochloride (0.75 mmol, 1.50 equiv), 81 mg 1-hydroxybenzotriazole (0.6 mmol, 1.2 equiv) and 129 mg N,N-diisopropylethylamine (1.0 mmol, 2.00 equiv) in 20 mL N,N-dimethylformamide was stirred at room temperature overnight. The mixture was diluted with 100 mL ethyl acetate and washed with 3×100 mL volumes of water. The organic phase was concentrated, and the residue was purified by reverse phase preparative HPLC on a Gilson GX-281. A concentrated solution of crude product dissolved in DMSO was injected in 850 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 30.0 mg N-(1-(4-(N-tert-butylsulfamoyl)phenyl)-2-oxo-1,2,3,4-tetrahydroquinolin-3-yl)-4-fluorobenzamide (I-20) as a white solid (12% yield). MS (ESI$^+$) m/z 496 [M+H]$^+$; $^1$H NMR (400 MHz, d$_6$-DMSO) δ 8.86 (d, J=8.4 Hz, 1H), 7.96 (dt, J=8.9, 2.8 Hz, 4H), 7.64 (s, 1H), 7.50 (d, J=8.4 Hz, 2H), 7.42-7.25 (m, 3H), 7.14 (t, J=7.2 Hz, 1H), 7.05 (t, J=7.0 Hz, 1H), 6.24 (d, J=7.6 Hz, 1H), 5.00 (ddd, J=14.4, 8.2, 6.0 Hz, 1H), 3.35 (dd, J=23.6, 8.9 Hz, 1H), 3.16 (dd, J=15.2, 6.0 Hz, 1H), 1.12 (s, 9H).

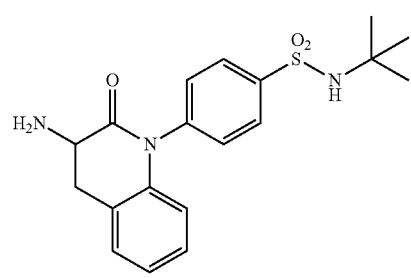

Example 13: N-(2-(4-(N-tert-butylsulfamoyl)phenyl)-3-oxo-2,3,4,5-tetrahydro-1H-benzo[c]azepin-4-yl)-4-fluorobenzamide, I-21
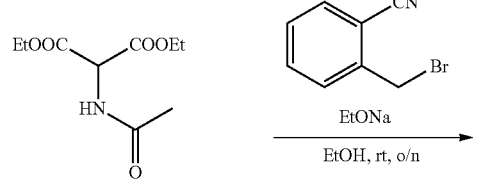
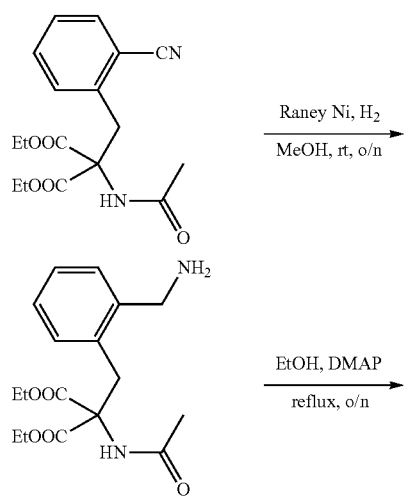
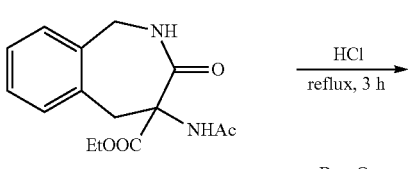
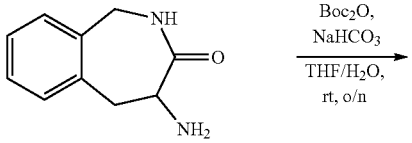
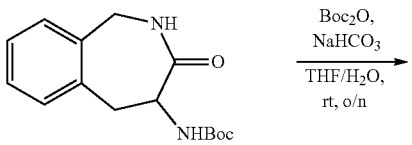
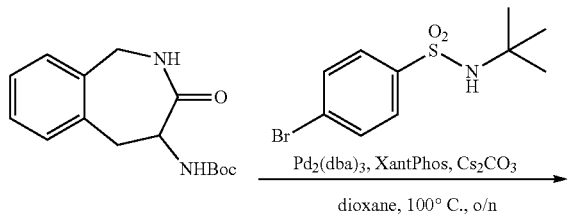
-continued
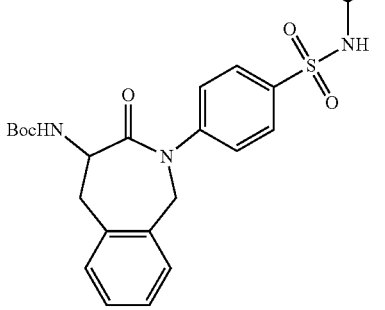
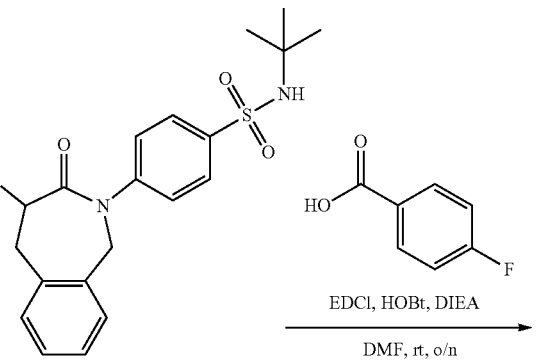
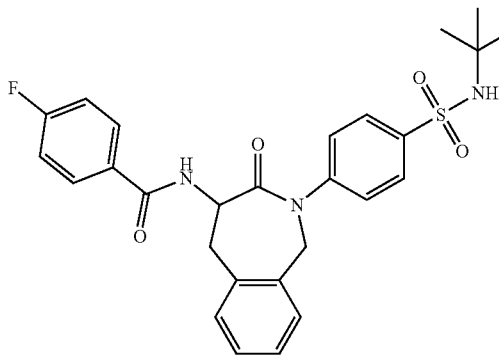
Preparation of diethyl 2-acetamido-2-(2-cyanobenzyl)malonate
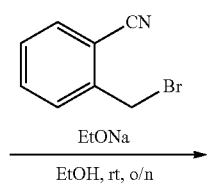
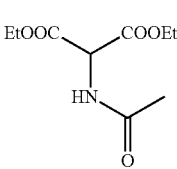

-continued

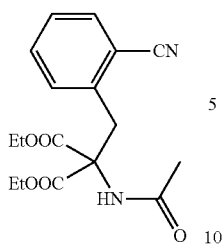

To a solution of 2.17 g diethyl 2-acetamidomalonate (10.0 mmol, 1.0 equiv) in 30 mL ethanol was added 1.06 g sodium ethoxide (20.0 mmol, 2.0 equiv) and the mixture was stirred at room temperature for 0.5 h. A 1.94 g sample of 2-(bromomethyl)benzonitrile (10.0 mmol, 1.0 equiv) was added and the mixture was stirred at room temperature overnight. Then 100 mL water was added to the reaction mixture and the mixture was filtered. The solid was washed with water and dried under vacuum to give 2.32 g diethyl 2-acetamido-2-(2-cyanobenzyl)malonate as a yellow solid (70% yield). MS (ESI$^+$) m/z 333 [M+H]$^+$.

Preparation of diethyl 2-acetamido-2-(2-(aminomethyl)benzyl)malonate

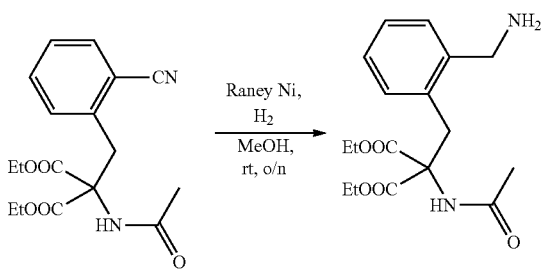 [SMILES: CCOC(=O)C(Cc1ccccc1C#N)(NC(C)=O)C(=O)OCC ; "Raney Ni,H2" ; CCOC(=O)C(Cc1ccccc1CN)(NC(C)=O)C(=O)OCC]

To a solution of 3.32 g diethyl 2-acetamido-2-(2-cyanobenzyl)malonate (10.0 mmol, 1.00 equiv) in methanol was added Raney nickel (550 mg wet catalyst, 10 wt. % palladium dry basis). The mixture was placed under hydrogen gas via balloon and stirred at room temperature overnight. The mixture was filtered and the filtrate concentrated to afford 3.02 g diethyl 2-acetamido-2-(2-(aminomethyl)benzyl)malonate as a light yellow solid (90% yield). MS (ESI$^+$) m/z 337 [M+H]$^+$.

Preparation of ethyl 4-acetamido-3-oxo-2,3,4,5-tetrahydro-1H-benzo[c]azepine-4-carboxylate

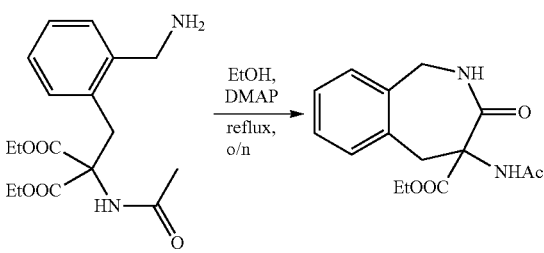

A solution of 3.36 g diethyl 2-acetamido-2-(2-(aminomethyl)benzyl)malonate (10.0 mmol, 1.00 equiv) and 122 mg 4-dimethylaminopyridine (1.0 mmol, 0.1 equiv) in ethanol was refluxed overnight. The mixture was concentrated and the residue was purified by column chromatography on silica gel (petroleum ether:ethyl acetate (3:1, v:v)) to yield 1.74 g ethyl 4-acetamido-3-oxo-2,3,4,5-tetrahydro-1H-benzo[c]azepine-4-carboxylate as a white solid (60% yield). MS (ESI$^+$) m/z 291 [M+H]$^+$.

Preparation of 4-amino-4,5-dihydro-1H-benzo[c]azepin-3(2H)-one

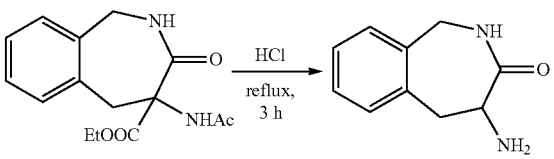 [SMILES: CCOC(=O)C1(NC(C)=O)Cc2ccccc2CNC1=O ; Cl ; NC1Cc2ccccc2CNC1=O]

A solution of 2.91 g diethyl 2-acetamidomalonate (10.0 mmol, 1.0 equiv) in 50 mL concentrated hydrochloric acid was refluxed for 3 h. The reaction mixture was diluted with 100 mL water and extracted with 3×100 mL volumes of ethyl acetate. The aqueous phase was made basic with saturated sodium bicarbonate solution and extracted with 3×100 mL volumes of ethyl acetate. The combined organic fractions were concentrated in vacuo to give 1.40 g 3-amino-3,4-dihydroquinolin-2(1H)-one as a brown solid (80% yield). MS (ESI$^+$) m/z 177 [M+H]$^+$.

Preparation of tert-butyl 3-oxo-2,3,4,5-tetrahydro-1H-benzo[c]azepin-4-ylcarbamate

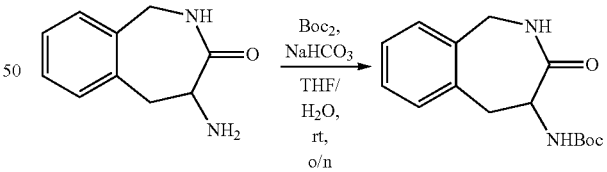

To a solution of 1.76 g of 3-amino-3,4-dihydroquinolin-2(1H)-one (10.0 mmol, 1.0 equiv), 1.68 g sodium bicarbonate (20.0 mmol, 2.0 equiv) in 10 mL tetrahydrofuran and 10 mL water was added 2.18 g di-tert-butyl dicarbonate (10.0 mmol, 1.0 equiv) and the mixture was stirred at room temperature overnight. The reaction mixture was extracted with 3×100 mL volumes of ethyl acetate. The combined organic fractions were concentrated in vacuo to give 2.20 g tert-butyl 3-oxo-2,3,4,5-tetrahydro-1H-benzo[c]azepin-4-ylcarbamate as a white solid (80% yield). MS (ESI$^+$) m/z 277 [M+H]$^+$.

Preparation of tert-butyl 2-(4-(N-tert-butylsulfamoyl)phenyl)-3-oxo-2,3,4,5-tetrahydro-1H-benzo[c]azepin-4-ylcarbamate

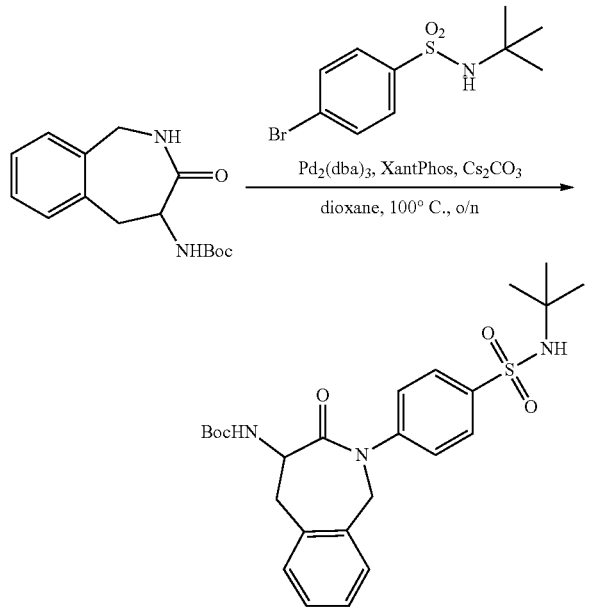

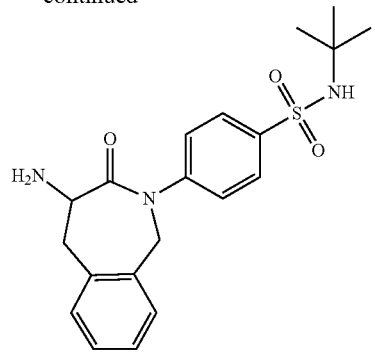

A mixture of 276 mg tert-butyl 2-oxo-1,2,3,4-tetrahydroquinolin-3-ylcarbamate (1.0 mmol, 1.0 equiv), 290 mg 4-bromo-N-tert-butylbenzenesulfonamide (10.0 mmol, 1.00 equiv), 91.5 mg tris(dibenzylideneacetone)dipalladium (0.1 mmol, 0.1 equiv), 115 mg 4,5-bis(diphenylphosphino)-9,9-dimethylxanthene (0.2 mmol, 0.2 equiv) and 276 mg cesium carbonate (2.0 mmol, 2.00 equiv) in 20 mL dioxane was stirred at 100° C. overnight. The mixture was diluted with 100 mL ethyl acetate and washed with 3×100 mL volumes of water. The organic phase was concentrated and the residue was purified by column chromatography on silica gel (petroleum ether:ethyl acetate (3:1, v:v)) to yield 292 mg tert-butyl 2-(4-(N-tert-butylsulfamoyl)phenyl)-3-oxo-2,3,4,5-tetrahydro-1H-benzo[c]azepin-4-ylcarbamate as a white solid (60% yield). MS (ESI$^+$) m/z 488 [M+H]$^+$.

Preparation of 4-(4-amino-3-oxo-4,5-dihydro-1H-benzo[c]azepin-2(3H)-yl)-N-tert-butylbenzenesulfonamide

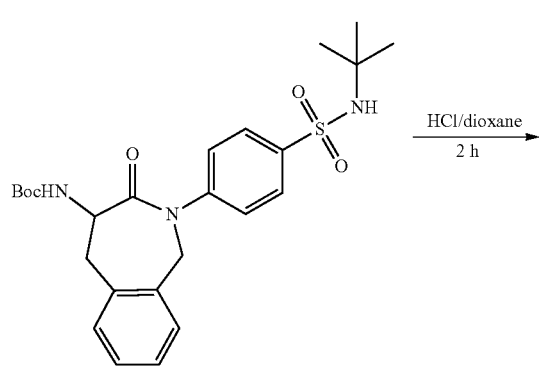

A mixture of 487 mg 2-(4-(N-tert-butylsulfamoyl)phenyl)-3-oxo-2,3,4,5-tetrahydro-1H-benzo[c]azepin-4-ylcarbamate (1.0 mmol, 1.00 equiv) in 20 mL hydrochloric acid in dioxane (4.0 M HCl) was stirred at room temperature for 2 hours. The mixture was concentrated in vacuo to give 387 mg 4-(4-amino-3-oxo-4,5-dihydro-1H-benzo[c]azepin-2(3H)-yl)-N-tert-butylbenzenesulfonamide as a white solid (100% yield). MS (ESI$^+$) m/z 388 [M+H]$^+$.

Preparation of N-(2-(4-(N-tert-butylsulfamoyl)phenyl)-3-oxo-2,3,4,5-tetrahydro-1H-benzo[c]azepin-4-yl)-4-fluorobenzamide

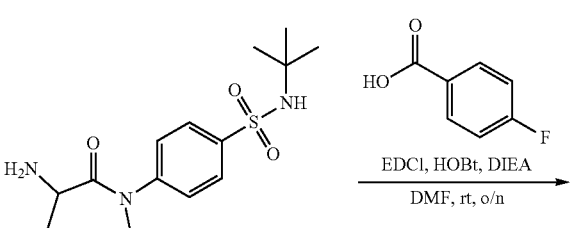

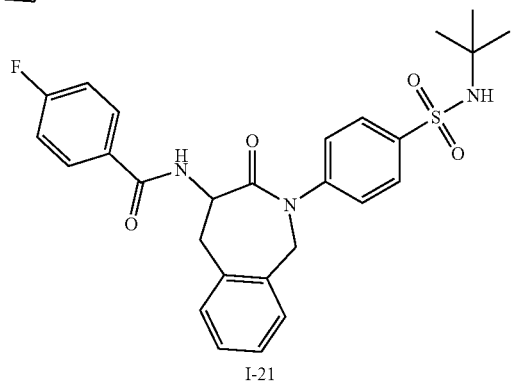

I-21

A mixture of 194 mg 4-(4-amino-3-oxo-4,5-dihydro-1H-benzo[c]azepin-2(3H)-yl)-N-tert-butylbenzenesulfonamide (0.5 mmol, 1.0 equiv), 70 mg 4-fluorobenzoic acid (0.5 mmol, 1.00 equiv), 144 mg N-(3-dimethylaminopropyl)-N'-ethylcarbodiimide hydrochloride (0.75 mmol, 1.50 equiv), 81 mg 1-hydroxybenzotriazole (0.6 mmol, 1.2 equiv) and 129 mg N,N-diisopropylethylamine (1.0 mmol, 2.00 equiv) in 20 mL N,N-dimethylformamide was stirred at room temperature overnight. The mixture was diluted with 100 mL ethyl acetate and washed with 3×100 mL volumes of water. The organic phase was concentrated, and the residue was purified by reverse phase preparative HPLC on a Gilson GX-281. A concentrated solution of crude product dissolved in DMSO was injected in 650 uL volumes onto a 10 um C18 reversed phase XBridge 19 mm diameter×250 mm length column eluting with a gradient of 55-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 25.0 mg N-(2-(4-(N-tert-butylsulfamoyl)phenyl)-3-oxo-2,3,4,5-tetrahydro-1H-benzo[c]azepin-4-yl)-4-fluorobenzamide (I-21) as a white solid (16% yield). MS (ESI$^+$) m/z 510 [M+H]$^+$; $^1$H NMR (400 MHz, d$_6$-DMSO) δ 8.71 (d, J=7.2 Hz, 1H), 8.00 (m, 2H), 7.78 (d, J=8.7 Hz, 2H), 7.52 (s, 1H), 7.44-7.13 (m, 8H), 5.84-5.65 (m, 2H), 4.57 (d, J=17.2 Hz, 1H), 3.46-3.32 (m, 2H), 1.07 (s, 9H).

Example 14: (S)-N-tert-butyl-4-(2-(4-fluorobenzamido)-3-phenylpropanamido)benzamide, I-29

Preparation of (S)-tert-butyl 1-(4-(tert-butylcarbamoyl)phenylamino)-1-oxo-3-phenylpropan-2-ylcarbamate

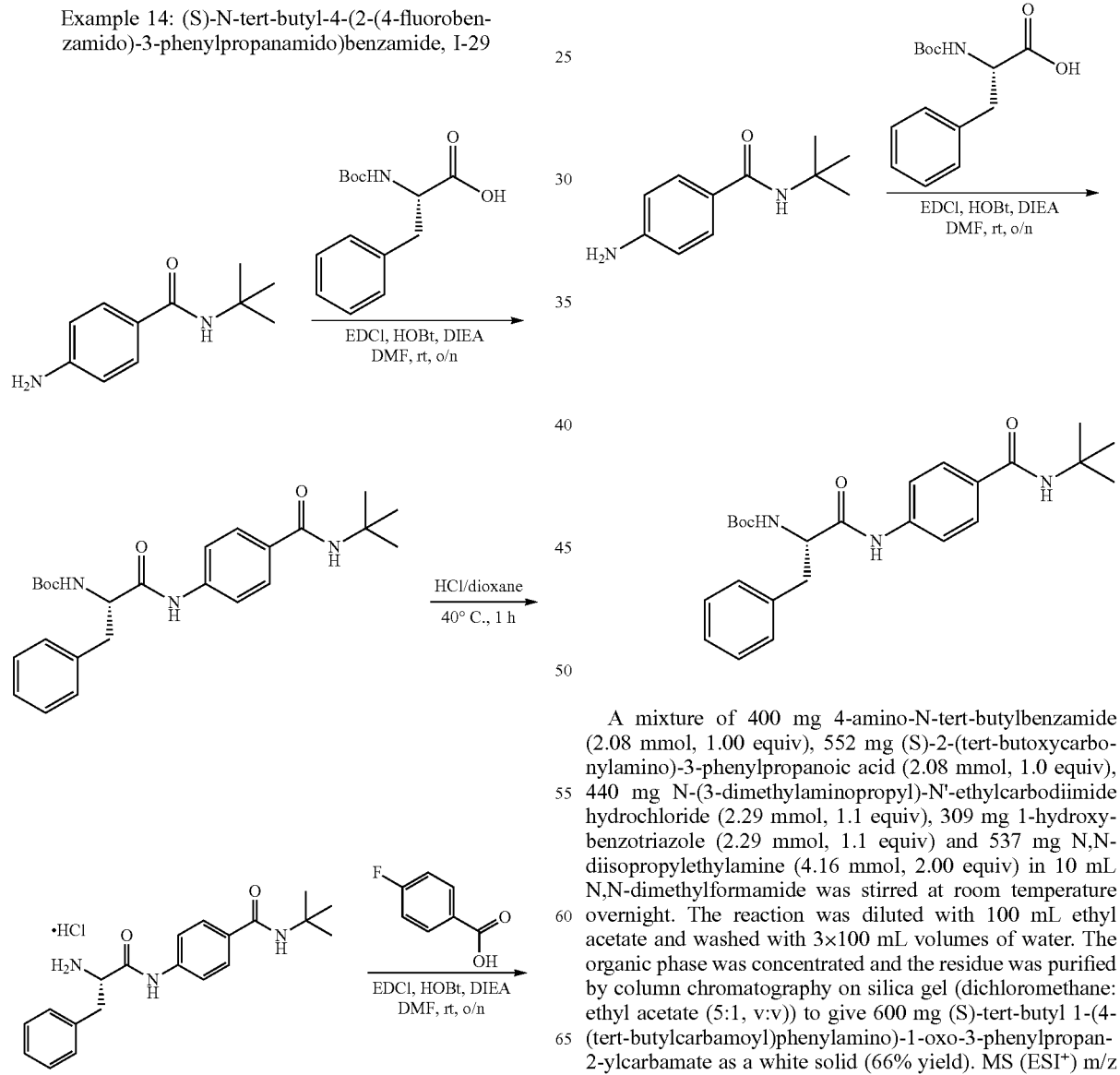

I-29

A mixture of 400 mg 4-amino-N-tert-butylbenzamide (2.08 mmol, 1.00 equiv), 552 mg (S)-2-(tert-butoxycarbonylamino)-3-phenylpropanoic acid (2.08 mmol, 1.0 equiv), 440 mg N-(3-dimethylaminopropyl)-N'-ethylcarbodiimide hydrochloride (2.29 mmol, 1.1 equiv), 309 mg 1-hydroxybenzotriazole (2.29 mmol, 1.1 equiv) and 537 mg N,N-diisopropylethylamine (4.16 mmol, 2.00 equiv) in 10 mL N,N-dimethylformamide was stirred at room temperature overnight. The reaction was diluted with 100 mL ethyl acetate and washed with 3×100 mL volumes of water. The organic phase was concentrated and the residue was purified by column chromatography on silica gel (dichloromethane:ethyl acetate (5:1, v:v)) to give 600 mg (S)-tert-butyl 1-(4-(tert-butylcarbamoyl)phenylamino)-1-oxo-3-phenylpropan-2-ylcarbamate as a white solid (66% yield). MS (ESI$^+$) m/z 440 [M+H]$^+$.

Preparation of (S)-4-(2-amino-3-phenylpropanamido)-N-tert-butylbenzamide, Hydrochloride

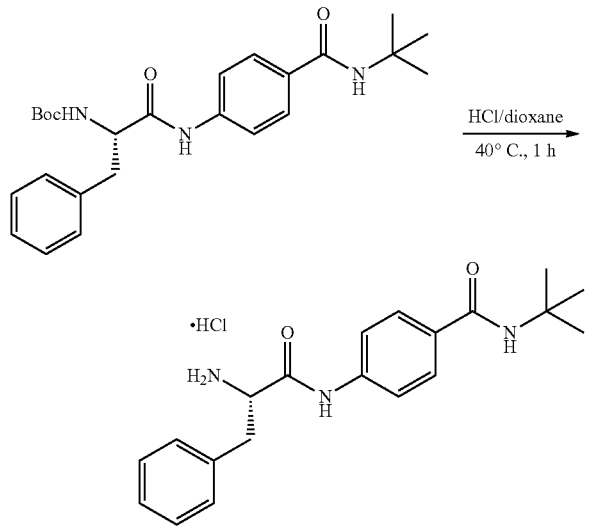

A 600 mg sample of (S)-tert-butyl 1-(4-(tert-butylcarbamoyl)phenylamino)-1-oxo-3-phenylpropan-2-ylcarbamate (1.37 mmol, 1.00 equiv) was dissolved in 30 mL hydrochloric acid in dioxane (4.0 M) and stirred at 40° C. for 1 h. The mixture was concentrated to afford 570 mg (S)-4-(2-amino-3-phenylpropanamido)-N-tert-butylbenzamide, hydrochloride as a light yellow solid (100% yield). MS (ESI$^+$) m/z 340 [M+H]$^+$.

Preparation of (S)-N-tert-butyl-4-(2-(4-fluorobenzamido)-3-phenylpropanamido)benzamide

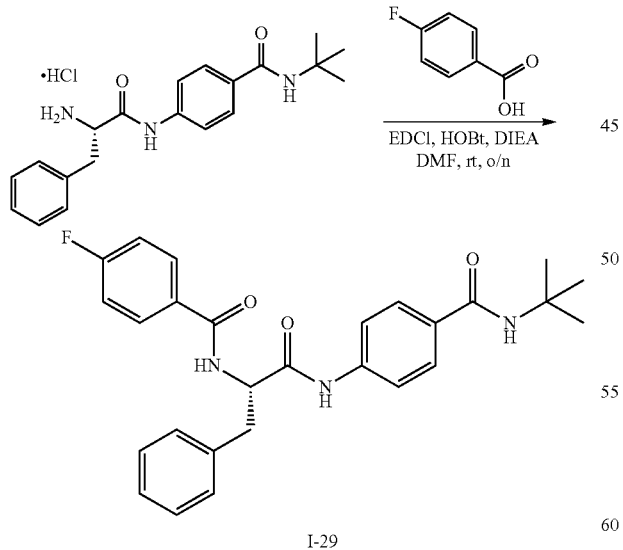

To a solution of 200 mg (S)-4-(2-amino-3-phenylpropanamido)-N-tert-butylbenzamide, hydrochloride (0.53 mmol, 1.00 equiv) and 75 mg 4-fluorobenzoic acid (0.53 mmol, 1.00 equiv) dissolved in 5 mL anhydrous N,N-dimethylformamide at room temperature was added 112 mg N-(3-dimethylaminopropyl)-N'-ethylcarbodiimide hydrochloride (0.58 mmol, 1.10 equiv), 78 mg 1-hydroxybenzotriazole (0.58 mmol, 1.10 equiv), and 137 mg N,N-diisopropylethylamine 1.06 mmol, 2.00 equiv) in succession. Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by reverse phase preparative HPLC on a Gilson GX-281. A concentrated solution of crude product dissolved in DMSO was injected in 540 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 8 mV threshold trigger on the 214 nm channel. Fractions containing product were combined, concentrated and lyophilized to afford 40 mg (S)-N-tert-butyl-4-(2-(4-fluorobenzamido)-3-phenylpropanamido)benzamide (I-29) as a white solid (16% yield). MS (ESI$^+$) m/z 462 [M+H]$^+$. $^1$H NMR (400 MHz, d$_6$-DMSO) δ 10.42 (s, 1H), 8.84 (d, J=8.0 Hz, 1H), 7.91 (dd, J=8.8, 5.5 Hz, 2H), 7.78 (d, J=8.7 Hz, 2H), 7.70-7.53 (m, 3H), 7.41 (d, J=7.3 Hz, 2H), 7.29 (dd, J=14.1, 8.2 Hz, 4H), 7.18 (t, J=7.3 Hz, 1H), 4.84 (m, 1H), 3.22-3.00 (m, 2H), 1.44-1.31 (m, 9H).

Example 15: (S)-N-(1-((4-(N-tert-butylsulfamoyl)phenyl)(methyl)amino)-1-oxo-3-phenylpropan-2-yl)-4-fluorobenzamide, I-36

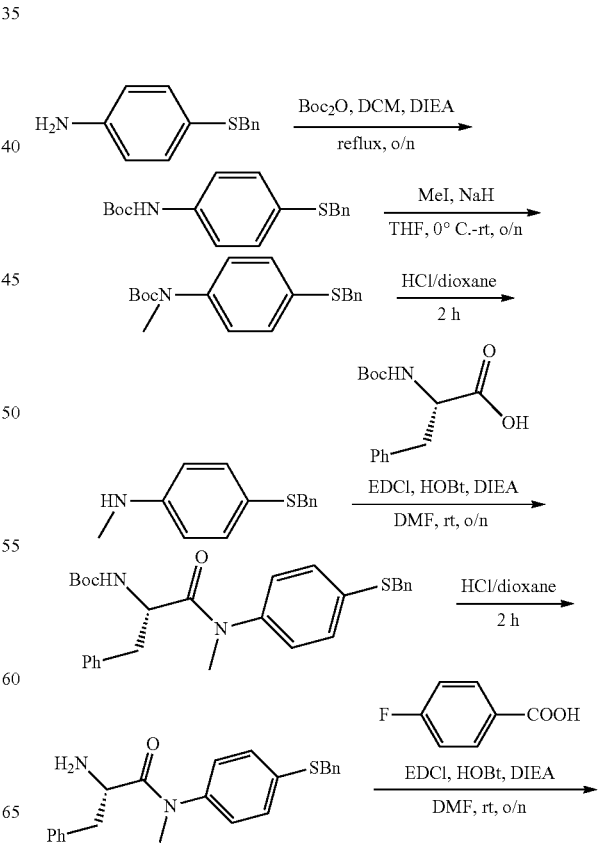

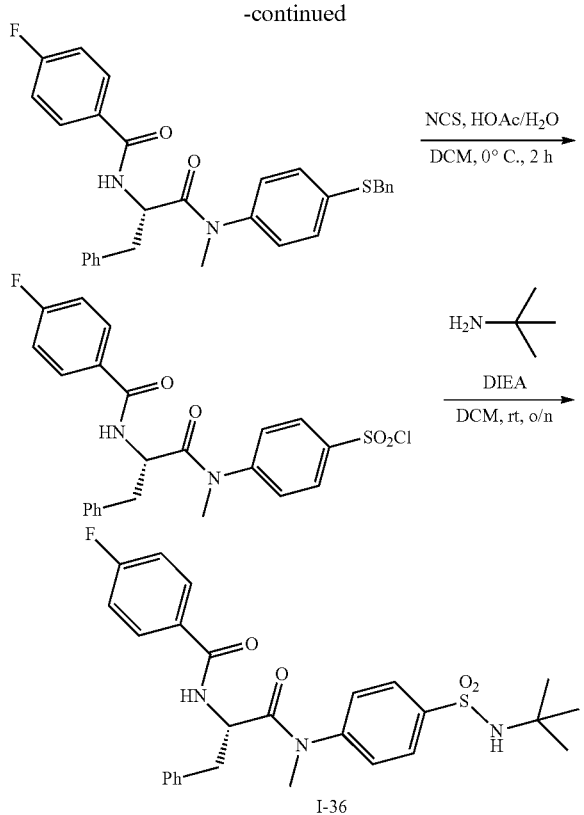

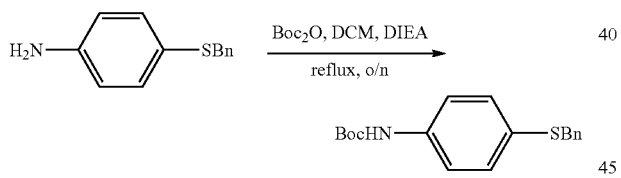

Preparation of tert-butyl 4-(benzylthio)phenylcarbamate

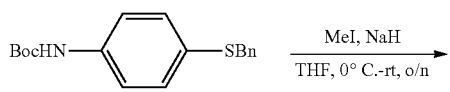

To a solution of 2.15 g 4-(benzylthio)aniline (10.0 mmol, 1.0 equiv), 2.58 g ethyldiisopropylamine (20.0 mmol, 2.0 equiv) in 10 mL dichloromethane was added 2.18 g di-tert-butyl dicarbonate (10.0 mmol, 1.0 equiv) and the mixture was refluxed at room temperature overnight. The mixture was concentrated and the residue was purified by column chromatography on silica gel (petroleum ether:ethyl acetate (3:1, v:v)) to yield 2.83 g tert-butyl 4-(benzylthio)phenyl-carbamate as yellow oil (90% yield). MS (ESI$^+$) m/z 316 [M+H]$^+$.

Preparation of tert-butyl 4-(benzylthio)phenyl(methyl)carbamate

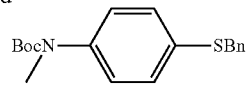

To a solution of 3.15 g tert-butyl 4-(benzylthio)phenyl-carbamate (10.0 mmol, 1.00 equiv) in 20 mL tetrahydrofuran was added 0.80 g sodium hydride (60 wt. % dispersion in mineral oil, 20.0 mmol, 2.0 equiv) at 0° C. and the mixture was stirred for 30 minutes. Then 2.84 g iodomethane (20.0 mmol, 2.00 equiv) was added and the reaction was stirred at room temperature for overnight. The mixture was poured into 30 mL saturated aqueous ammonium chloride solution and extracted with 3×50 mL volumes of ethyl acetate. The combined organic phases were concentrated and the residue was purified by column chromatography on silica gel (petroleum ether:ethyl acetate (5:1, v:v)) to give 2.63 g tert-butyl 4-(benzylthio)phenyl(methyl)carbamate as light yellow oil (80% yield). MS (ESI$^+$) m/z 330 [M+H]$^+$.

Preparation of 4-(benzylthio)-N-methylaniline

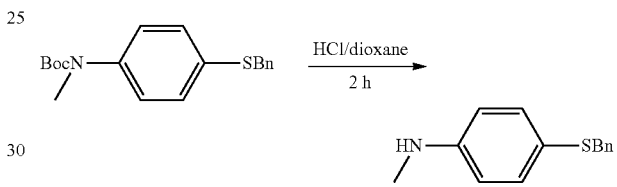

The mixture of 1.65 g tert-butyl 4-(benzylthio)phenyl (methyl)carbamate (5.0 mmol, 1.0 equiv) in 20 mL hydrochloric acid in dioxane (4.0 M HCl) was stirred at room temperature for 2 hours. The mixture was concentrated to give 1.15 g 4-(benzylthio)-N-methylaniline as light yellow oil (100% yield). MS (ESI$^+$) m/z 230 [M+H]$^+$.

Preparation of (S)-tert-butyl 1-((4-(benzylthio)phenyl)(methyl)amino)-1-oxo-3-phenylpropan-2-ylcarbamate

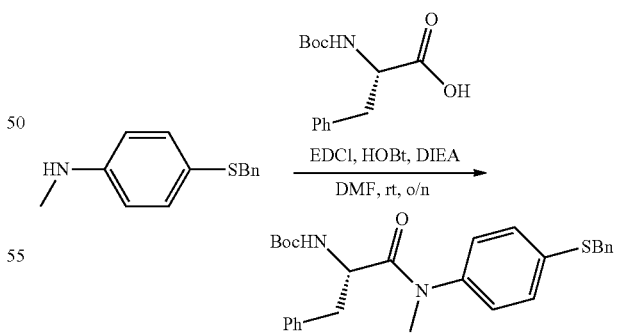

A mixture of 2.65 g (S)-2-(tert-butoxycarbonylamino)-3-phenylpropanoic acid (10.0 mmol, 1.0 equiv), 2.29 g 4-(benzylthio)-N-methylaniline (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.2 equiv) and 2.58 g N,N-diisopropylethylamine (20.0 mmol, 2.00 equiv) in 20 mL N,N-dimethylformamide was stirred at room temperature overnight. The mixture was diluted with 100 mL ethyl acetate and washed with 3×100 mL volumes of water. The organic phase was concentrated and the residue was purified by column chromatography on silica gel (petroleum ether: ethyl acetate (5:1, v:v)) to yield 3.80 g (S)-tert-butyl 1-((4-(benzylthio)phenyl)(methyl)amino)-1-oxo-3-phenylpropan-2-ylcarbamate as a light yellow solid (80% yield). MS (ESI$^+$) m/z 477 [M+H]$^+$.

Preparation of (S)-2-amino-N-(4-(benzylthio)phenyl)-N-methyl-3-phenylpropanamide

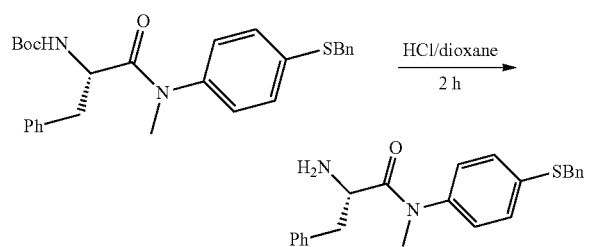

The mixture of 2.38 g (S)-tert-butyl 1-((4-(benzylthio)phenyl)(methyl)amino)-1-oxo-3-phenylpropan-2-ylcarbamate (5.0 mmol, 1.0 equiv) in 20 mL hydrochloric acid in dioxane (4.0 M HCl) was stirred at room temperature for 2 hours. The mixture was concentrated to give 1.88 g (S)-2-amino-N-(4-(benzylthio)phenyl)-N-methyl-3-phenylpropanamide as a light yellow solid (100% yield). MS (ESI$^+$) m/z 377 [M+H]$^+$.

Preparation of (S)-N-(1-((4-(benzylthio)phenyl)(methyl)amino)-1-oxo-3-phenylpropan-2-yl)-4-fluorobenzamide

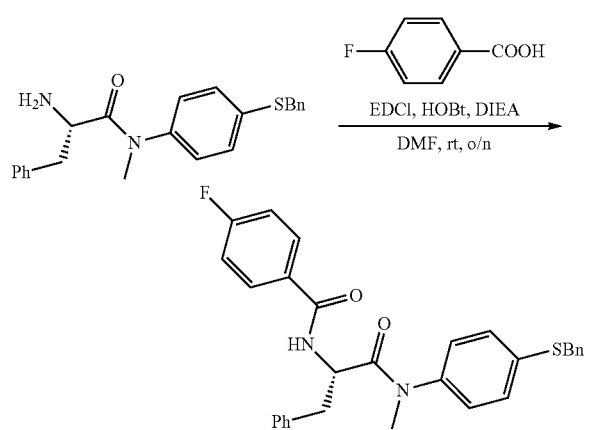

A mixture of 3.76 g (S)-2-amino-N-(4-(benzylthio)phenyl)-N-methyl-3-phenylpropanamide (10.0 mmol, 1.00 equiv), 1.40 g 4-fluorobenzoic acid (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.20 equiv) and 2.58 g N,N-diisopropylethylamine (20.0 mmol, 2.00 equiv) in 30 mL N,N-dimethylformamide was stirred at room temperature overnight. The mixture was diluted with 100 mL ethyl acetate and washed with 3×100 mL volumes of water. The organic phase was concentrated and the residue was purified by column chromatography on silica gel (petroleum ether: ethyl acetate (5:1, v:v) to give 3.98 g (S)-N-(1-((4-(benzylthio)phenyl)(methyl)amino)-1-oxo-3-phenylpropan-2-yl)-4-fluorobenzamide as a light yellow solid (80% yield). MS (ESI$^+$) m/z 499 [M+H]$^+$.

Preparation of (S)-4-(2-(4-fluorobenzamido)-N-methyl-3-phenylpropanamido)benzene-1-sulfonyl Chloride

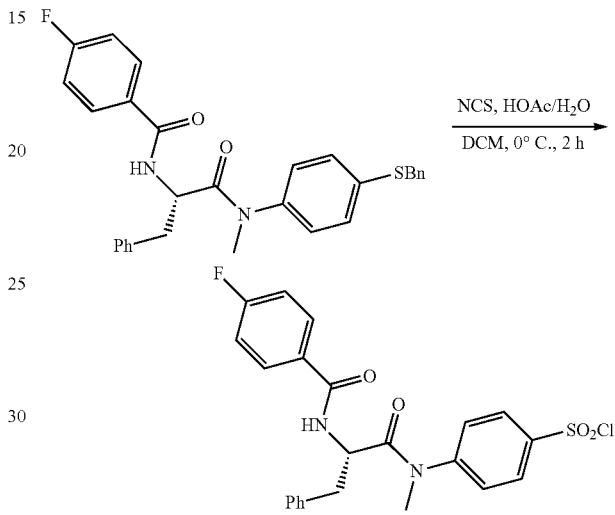

To a solution of 2.49 g (S)-N-(1-((4-(benzylthio)phenyl)(methyl)amino)-1-oxo-3-phenylpropan-2-yl)-4-fluorobenzamide (5.00 mmol, 1.00 equiv), 60 mg acetic acid (1.0 mmol, 0.2 equiv) and 18 mg water (1.0 mmol, 0.2 equiv) in 30 mL dichloromethane was added 2.66 g N-chlorosuccinimide (20.0 mmol, 4.00 equiv) at 0° C. The mixture was stirred at room temperature for 2 hours and washed with 3×20 mL volumes of water. The organic phase was concentrated to give 1.65 g (S)-4-(2-(4-fluorobenzamido)-N-methyl-3-phenylpropanamido)benzene-1-sulfonyl chloride as a white solid (70% yield). MS (ESI$^+$) m/z 475 [M+H]$^+$.

Preparation of (S)-N-(1-((4-(N-tert-butylsulfamoyl)phenyl)(methyl)amino)-1-oxo-3-phenylpropan-2-yl)-4-fluorobenzamide, I-36

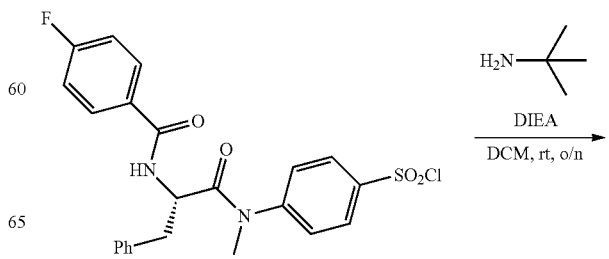

-continued

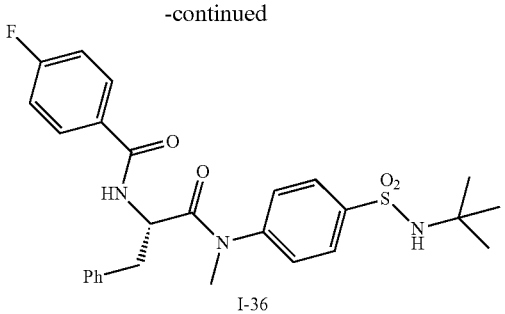

I-36

To a mixture of 80 mg 2-methylpropan-2-amine (1.1 mmol, 5.0 equiv) and 142 mg N,N-diisopropylethylamine (1.10 mmol, 5.00 equiv) in 10 mL dichloromethane was added 100 mg(S)-4-(2-(4-fluorobenzamido)-N-methyl-3-phenylpropanamido)benzene-1-sulfonyl chloride (0.21 mmol, 1.00 equiv). The mixture was stirred at room temperature for 1 hour and concentrated. The compound was purified by reversed phase preparative HPLC on a Gilson GX-281. A concentrated solution of crude product dissolved in DMSO was injected in 900 uL volumes onto a 10 um C18 reversed phase XBridge 19 mm diameter×250 mm length column eluting with a gradient of 45-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 30.0 mg (S)-N-(1-((4-(N-tert-butylsulfamoyl)phenyl)(methyl)amino)-1-oxo-3-phenylpropan-2-yl)-4-fluorobenzamide (I-36) as a white solid (28% yield). MS (ESI$^+$) m/z 512 [M+H]$^+$; $^1$H NMR (400 MHz, d$_6$-DMSO) δ 8.86 (d, J=7.3 Hz, 1H), 7.90 (dd, J=8.6, 5.5 Hz, 4H), 7.76-7.46 (m, 3H), 7.29 (t, J=8.9 Hz, 2H), 7.14 (s, 3H), 6.89 (s, 2H), 4.62 (s, 1H), 3.21 (s, 3H), 2.93 (s, 2H), 1.14 (s, 9H).

Example 16: racemic-N-(Z)-(1-(4-(N-tert-butylsulfamoyl)phenylcarbamoyl)-2-phenylcyclopropyl)-4-fluorobenzamide, I-82

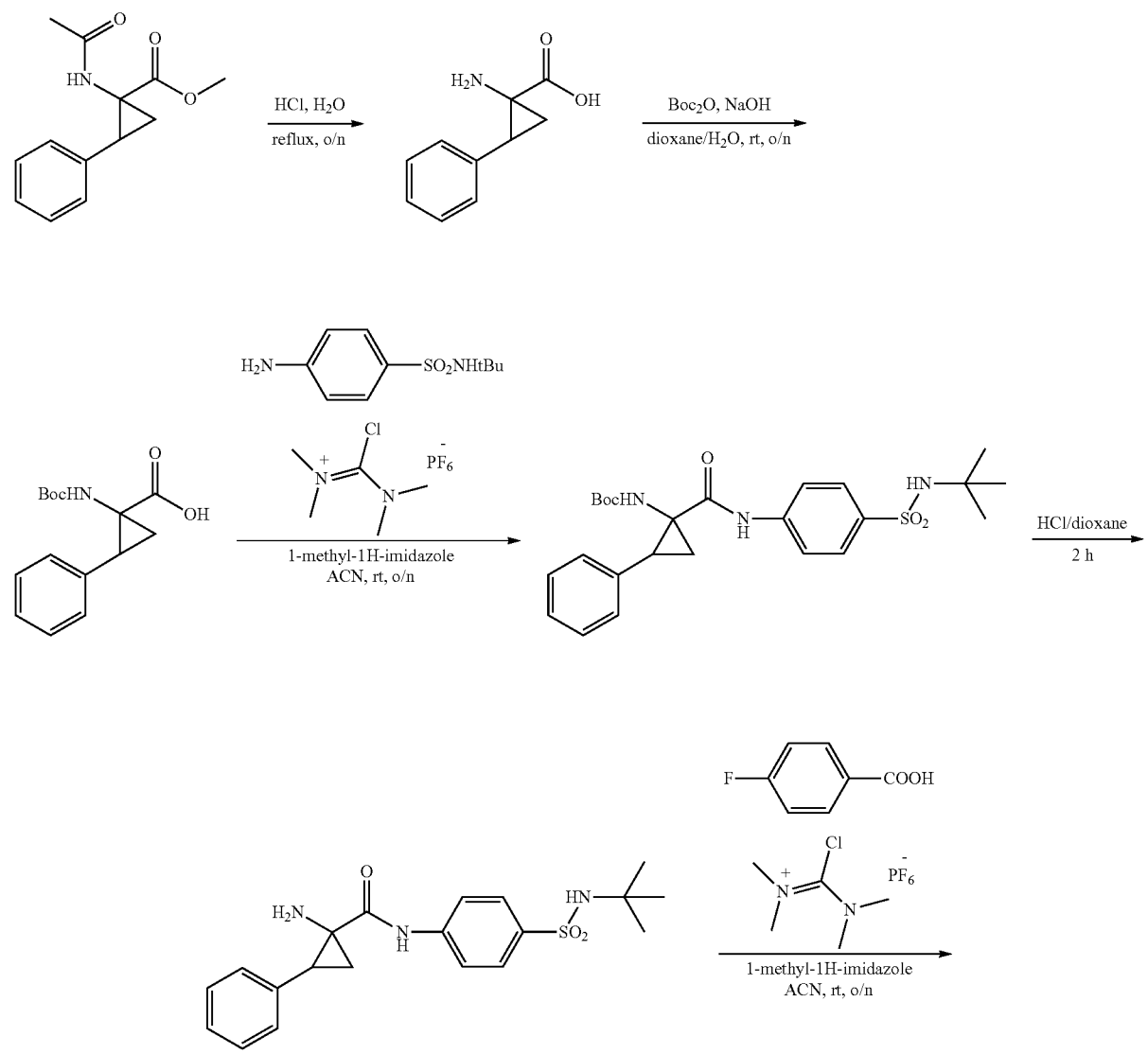

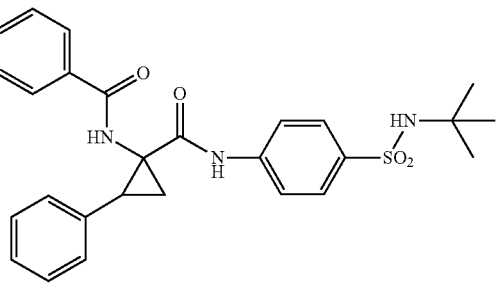

I-82

Preparation of 1-amino-2-phenylcyclopropanecarboxylic Acid

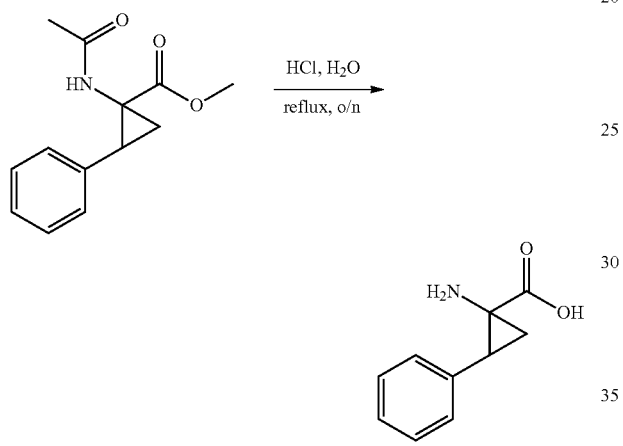

A solution of 2.33 g methyl 1-acetamido-2-phenylcyclopropanecarboxylate (10.0 mmol, 1.0 equiv) in 50 mL concentrated hydrochloric acid was refluxed overnight. The reaction mixture was concentrated in vacuo to give 1.41 g 1-amino-2-phenylcyclopropanecarboxylic acid as a brown solid (80% yield). MS (ESI$^+$) m/z 178 [M+H]$^+$.

Preparation of 1-(tert-butoxycarbonylamino)-2-phenylcyclopropanecarboxylic Acid

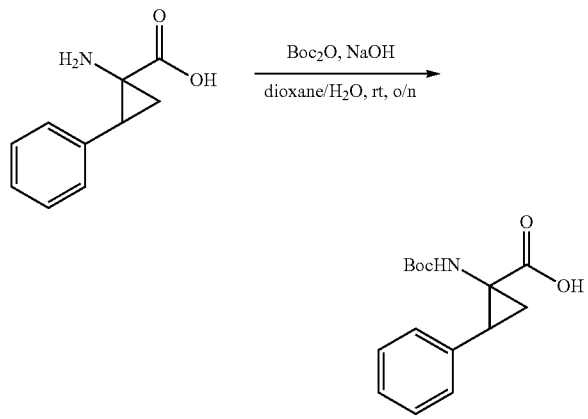

To a solution of 1.77 g 1-amino-2-phenylcyclopropanecarboxylic acid (10.0 mmol, 1.0 equiv), 1.6 g sodium hydroxide (20.0 mmol, 2.0 equiv) in 10 mL dioxane and 10 mL water was added 2.18 g di-tert-butyl dicarbonate (10.0 mmol, 1.0 equiv) and the mixture was stirred at room temperature overnight. The reaction mixture was extracted with 3×100 mL volumes of ethyl acetate. The combined organic fractions were concentrated in vacuo to give 2.21 g tert-butyl1-(tert-butoxycarbonylamino)-2-phenylcyclopropanecarboxylic acid as a white solid (80% yield). MS (ESI$^+$) m/z 278 [M+H]$^+$.

Preparation of tert-butyl 1-(4-(N-tert-butylsulfamoyl)phenylcarbamoyl)-2-phenylcyclopropylcarbamate

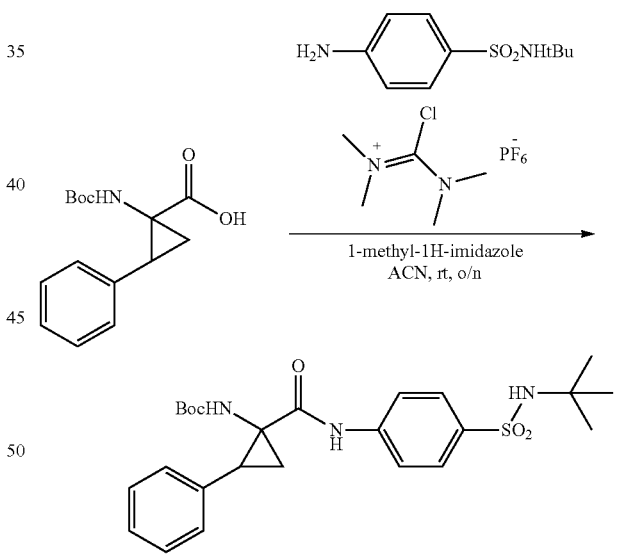

A mixture of 2.77 g tert-butyl1-(tert-butoxycarbonylamino)-2-phenylcyclopropanecarboxylic acid (10.0 mmol, 1.00 equiv), 2.28 g 4-amino-N-tert-butylbenzenesulfonamide (10.0 mmol, 1.00 equiv), 3.08 g N,N,N',N'-tetramethylchloroformamidinium hexafluorophosphate (11.0 mmol, 1.10 equiv) and 2.80 g 1-methyl-1H-imidazole (35.0 mmol, 3.50 equiv) in 10 mL acetonitrile was stirred at room temperature for overnight. To the mixture was added 100 mL ethyl acetate and washed with 3×100 mL volumes of water. The organic phase was concentrated and the residue was purified by column chromatography on silica gel (petroleum ether:ethyl acetate (5:1, v:v) to give 3.90 g tert-butyl 1-(4-(N-tert-butylsulfamoyl)phenylcarbamoyl)-2-phenylcyclopropylcarbamate as a light yellow solid (80% yield). MS (ESI+) m/z 488 [M+H]+.

Preparation of 1-amino-N-(4-(N-tert-butylsulfamoyl)phenyl)-2-phenylcyclopropanecarboxamide

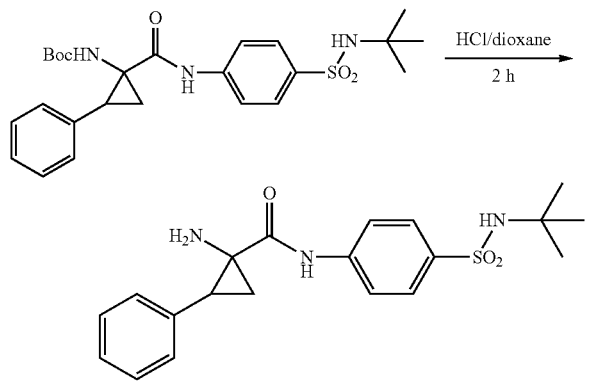

The mixture of 2.44 g tert-butyl 1-(4-(N-tert-butylsulfamoyl)phenylcarbamoyl)-2-phenylcyclopropylcarbamate (5.0 mmol, 1.0 equiv) in 20 mL hydrochloric acid in dioxane (4.0 M HCl) was stirred at room temperature for 2 hours. The mixture was concentrated to give 1.94 g (S)-2-amino-N-(4-(benzylthio)phenyl)-N-methyl-3-phenylpropanamide as a light yellow solid (100% yield). MS (ESI+) m/z 388 [M+H]+.

Preparation of N-(1-(4-(N-tert-butylsulfamoyl)phenylcarbamoyl)-2-phenylcyclopropyl)-4-fluorobenzamide, I-82

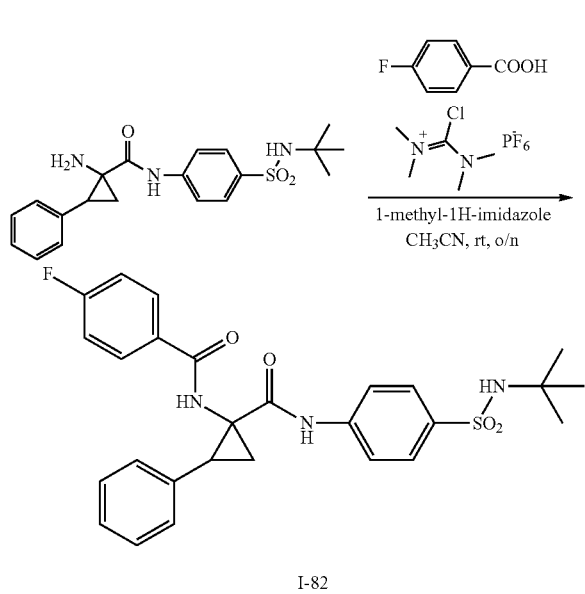

I-82

A mixture of 140 mg 4-fluorobenzoic acid (1.0 mmol, 1.00 equiv), 387 mg (S)-2-amino-N-(4-(benzylthio)phenyl)-N-methyl-3-phenylpropanamide (1.0 mmol, 1.00 equiv), 308 mg N,N,N',N'-tetramethylchloroformamidinium hexafluorophosphate (11.0 mmol, 1.10 equiv) and 280 mg 1-methyl-1H-imidazole (3.50 mmol, 3.50 equiv) in 2 mL acetonitrile was stirred at room temperature overnight. To the mixture was added 100 mL ethyl acetate and washed with 3×100 mL volumes of water. The organic phase was concentrated and the residue was purified by reversed phase preparative HPLC on a Gilson GX-281. A concentrated solution of crude product dissolved in DMSO was injected in 800 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 1 mV threshold trigger on the 214 nm channel. Fractions containing product were combined, concentrated and lyophilized to afford 8.0 mg N-(1-(4-(N-tert-butylsulfamoyl)phenylcarbamoyl)-2-phenylcyclopropyl)-4-fluorobenzamide (I-82) as a white solid (1.5% yield). MS (ESI+) m/z 510 [M+H]+; 1H NMR (400 MHz, DMSO) δ 9.94 (s, 1H), 8.71 (s, 1H), 7.71 (ddd, J=15.3, 14.4, 7.3 Hz, 6H), 7.28-6.97 (m, 8H), 3.23-3.14 (m, 1H), 1.91 (dd, J=7.8, 5.5 Hz, 1H), 1.78 (dd, J=9.6, 5.3 Hz, 1H), 1.05 (s, 9H).

Example 17: racemic-N-((E)-1-(4-(N-tert-butylsulfamoyl)phenylcarbamoyl)-2-phenylcyclopropyl)-4-fluorobenzamide, I-83

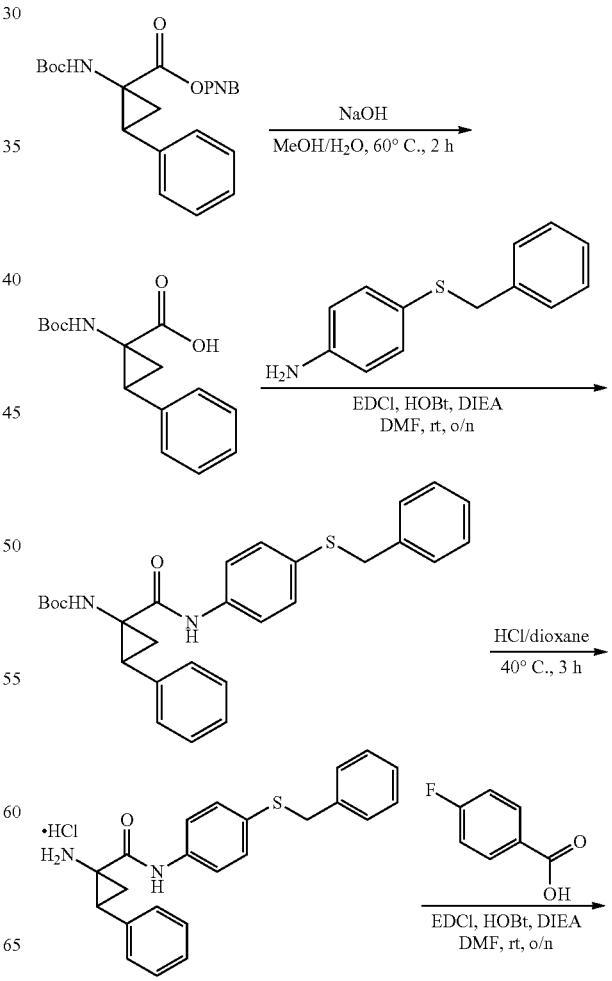

-continued

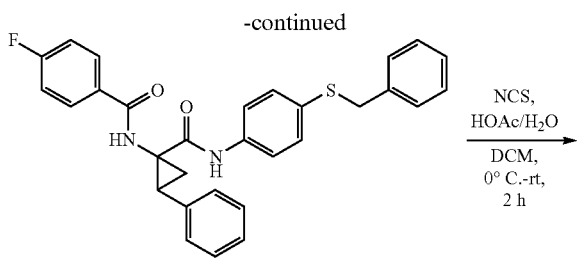

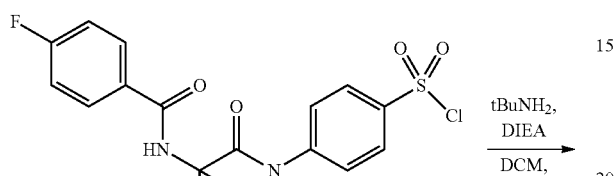

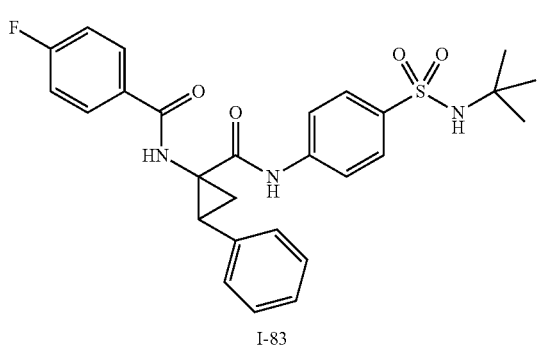

I-83

Preparation of (1S,2R)-1-(tert-butoxycarbonylamino)-2-phenylcyclopropanecarboxylic Acid

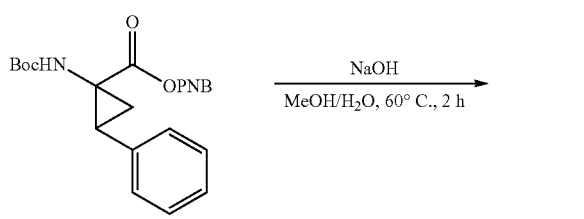

To a solution of 550 mg (1S,2R)-1-(tert-butoxycarbonylamino)-2-phenylcyclopropanecarboxylic 4-nitrobenzoic anhydride (1.29 mmol, 1.00 equiv) in 100 mL (Methanol:H$_2$O (5:1, v:v)) was added 103 mg Sodium hydroxide (2.58 mmol, 2.00 equiv) and stirred at 60° C. for 2 hours. The mixture was concentrated and diluted with 100 mL of water. The pH adjusted to 6 with 3 M HCl and the mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (petroleum ether:ethyl acetate (2:1, v:v)) to give 351 mg (S,2R)-1-(tert-butoxycarbonylamino)-2-phenylcyclopropanecarboxylic acid as a yellow solid (98% yield). MS (ESI$^+$) m/z 278[M+H].

Preparation of tert-butyl (1S,2R)-1-(4-(benzylthio)phenylcarbamoyl)-2-phenylcyclopropylcarbamate

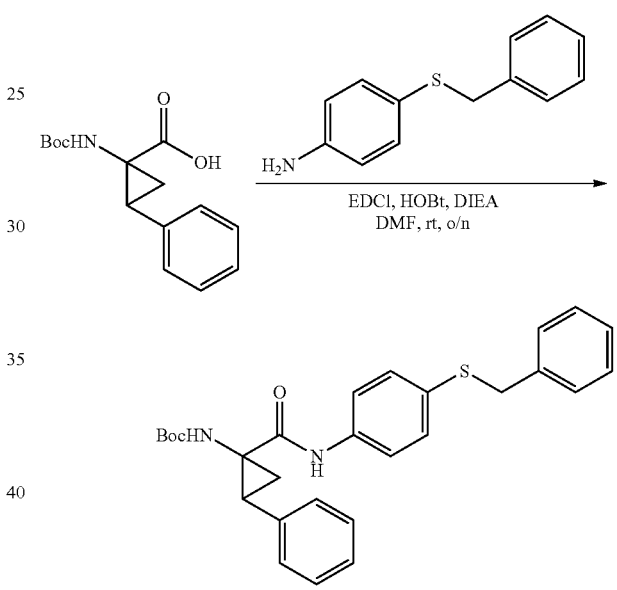

To a solution of 273 mg 4-(benzylthio)aniline (1.27 mmol, 1.00 equiv) and 351 mg (1S,2R)-1-(tert-butoxycarbonylamino)-2-phenylcyclopropanecarboxylic acid (1.27 mmol, 1.00 equiv) dissolved in 10 mL anhydrous N,N-dimethylformamide at room temperature was added 268 mg N-(3-Dimethylaminopropyl)-N'-ethylcarbodiimide hydrochloride (1.39 mmol, 1.10 equiv), 188 mg 1-hydroxybenzotriazole (1.39 mmol, 1.10 equiv), and 328 mg N,N-diisopropylethylamine (2.54 mmol, 2.00 equiv) in succession. Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (petroleum ether:ethyl acetate (5:1, v:v)) to give 570 mg tert-butyl (1S,2R)-1-(4-(benzylthio)phenylcarbamoyl)-2-phenylcyclopropylcarbamate as a light white solid (95% yield). MS (ESI$^+$) m/z 475 [M+H]$^+$.

257

Preparation of (1S,2R)-1-amino-N-(4-(benzylthio)phenyl)-2-phenylcyclopropanecarboxamide, Hydrochloride

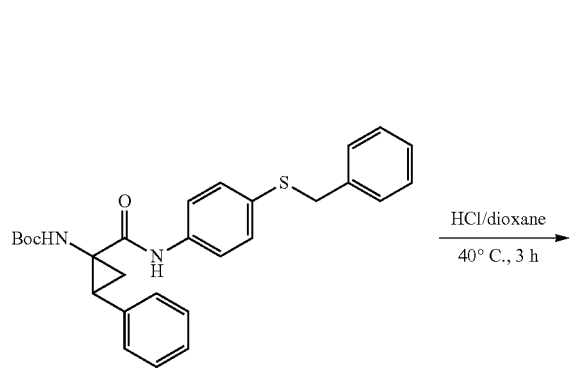

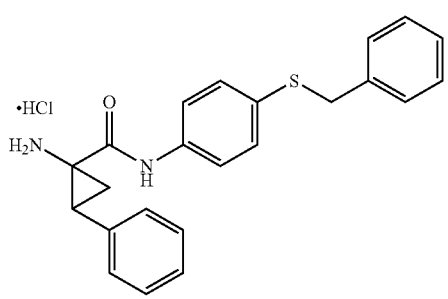

570 mg tert-butyl (1S,2R)-1-(4-(benzylthio)phenylcarbamoyl)-2-phenylcyclopropylcarbamate (1.20 mmol, 1.00 equiv) was dissolved in 30 mL hydrochloric acid in dioxane (4.0 M HCl) and stirred at 40° C. for 3 hours. The mixture was concentrated to afford 520 mg (1S,2R)-1-amino-N-(4-(benzylthio)phenyl)-2-phenylcyclopropanecarboxamide, hydrochloride as a light yellow solid (100% yield). MS (ESI+) m/z 375 [M+H]+.

258

Preparation of N-((1S,2R)-1-(4-(benzylthio)phenylcarbamoyl)-2-phenylcyclopropyl)-4-fluorobenzamide

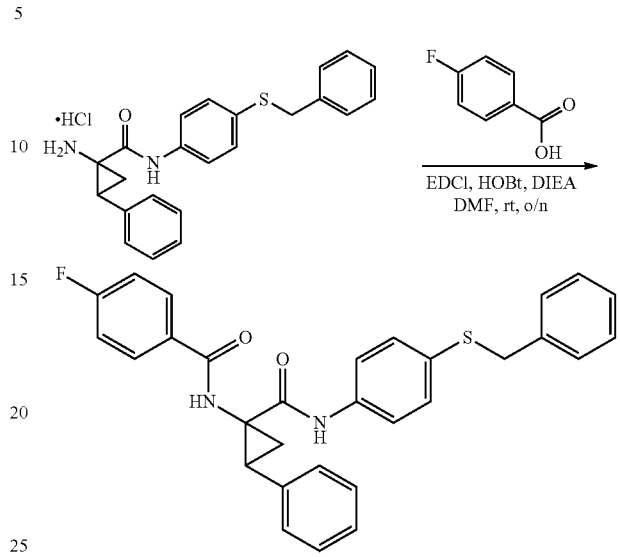

To a solution of 520 mg (1S,2R)-1-amino-N-(4-(benzylthio)phenyl)-2-phenylcyclopropanecarboxamide, hydrochloride (1.27 mmol, 1.00 equiv) and 178 mg 4-fluorobenzoic acid (1.27 mmol, 1.00 equiv) dissolved in 10 mL anhydrous N,N-dimethylformamide at room temperature was added 268 mg N-(3-Dimethylaminopropyl)-N'-ethylcarbodiimide hydrochloride (1.40 mmol, 1.10 equiv), 189 mg 1-hydroxybenzotriazole (1.40 mmol, 1.10 equiv), and 328 mg N,N-diisopropylethylamine (2.54 mmol, 2.00 equiv) in succession. Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (petroleum ether:ethyl acetate (3:1, v:v)) to give 150 mg N-((S,2R)-1-(4-(benzylthio)phenylcarbamoyl)-2-phenylcyclopropyl)-4-fluorobenzamide as a white solid (24% yield). MS (ESI+) m/z 497[M+H]+.

Preparation of 4-((1S,2R)-1-(4-fluorobenzamido)-2-phenylcyclopropanecarboxamido)benzene-1-sulfonyl Chloride

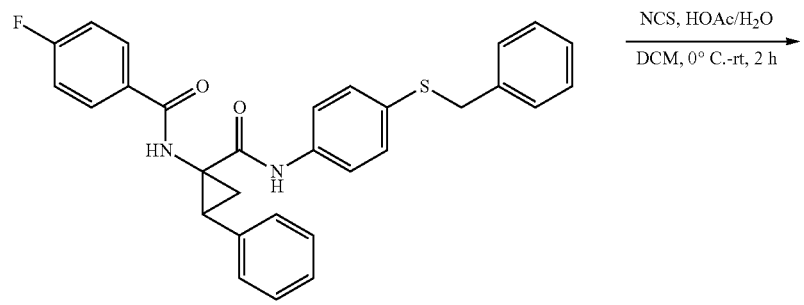

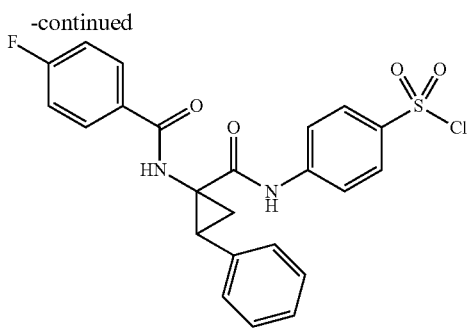

To a solution of 150 mg N-((1S,2R)-1-(4-(benzylthio) phenylcarbamoyl)-2-phenylcyclopropyl)-4-fluorobenzamide (0.30 mmol, 1.00 equiv), 18 mg acetic acid (0.30 mmol, 1 equiv) and 6 mg water (0.30 mmol, 1 equiv) in 30 mL dichloromethane was added 163 mg N-chlorosuccinimide (1.20 mmol, 4.00 equiv) at 0° C. The mixture was stirred at room temperature for 2 hours and washed with 3×20 mL volumes of water. The organic phase was concentrated to give 132 mg 4-((S,2R)-1-(4-fluorobenzamido)-2-phenylcyclopropanecarboxamido)benzene-1-sulfonyl chloride as a gray solid (92% yield). MS (ESI⁺) m/z 473[M+H]⁺.

Preparation of N-((1S,2R)-1-(4-(N-tert-butylsulfamoyl)phenylcarbamoyl)-2-phenylcyclopropyl)-4-fluorobenzamide, I-83

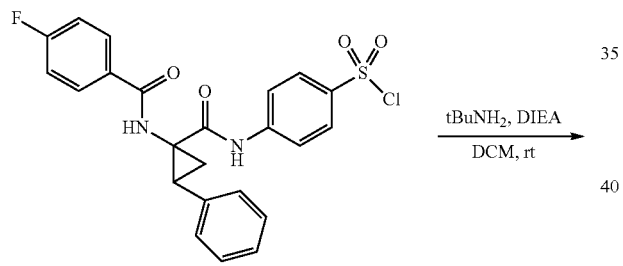

I-83

To a mixture of 102 mg 2-methylpropan-2-amine (1.40 mmol, 5.0 equiv) and 181 mg N,N-diisopropylethylamine (1.40 mmol, 5.00 equiv) in 10 mL dichloromethane was added 132 mg 4-((1S,2R)-1-(4-fluorobenzamido)-2-phenyl-cyclopropanecarboxamido)benzene-1-sulfonyl chloride (0.28 mmol, 1.00 equiv). The mixture was stirred at room temperature for 2 hours and concentrated in vacuo. The residue was purified by reversed phase preparative HPLC on a Gilson GX-281. A concentrated solution of crude product dissolved in DMSO was injected in 500 uL volumes onto a 10 um C18 reversed phase XBridge 19 mm diameter×250 mm length column eluting with a gradient of 55-95% acetonitrile in water with 10 mmol/liter ammonium carbonate. Peaks were detected by UV absorbance at 214 nm and 254 nm and fractions collected by 2 mV threshold trigger on the 214 nm channel. Fractions containing product were combined, concentrated and lyophilized to afford 26 mg N-((1S,2R)-1-(4-(N-tert-butylsulfamoyl)phenylcarbamoyl)-2-phenylcyclopropyl)-4-fluorobenzamide (I-83) as a white solid (18% yield). MS (ESI⁺) m/z 510 [M+H]⁺. ¹H NMR (400 MHz, d₆-DMSO) δ 9.97 (s, 1H), 9.39 (s, 1H), 8.07 (dd, J=8.8, 5.6 Hz, 2H), 7.67-7.59 (m, 2H), 7.52 (t, J=10.7 Hz, 2H), 7.35 (dd, J=16.7, 7.9 Hz, 5H), 7.24 (t, J=7.5 Hz, 2H), 7.14 (t, J=7.3 Hz, 1H), 2.32 (m, 2H), 1.45 (dd, J=9.5, 5.3 Hz, 1H), 1.11-0.94 (m, 9H).

Example 18: N-((2S,3S)-4-(4-(N-tert-butylsulfamoyl)phenylamino)-3-hydroxy-1-phenylbutan-2-yl)-4-fluorobenzamide, I-41

261
-continued

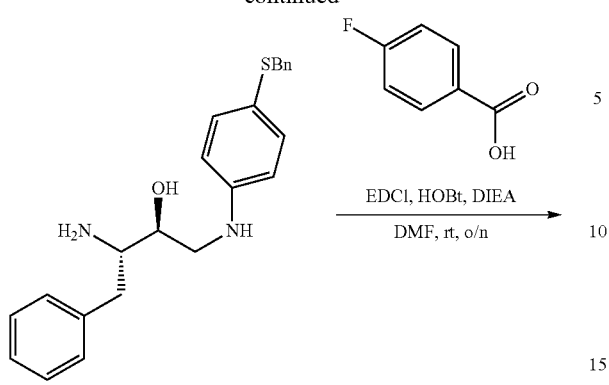

262
-continued

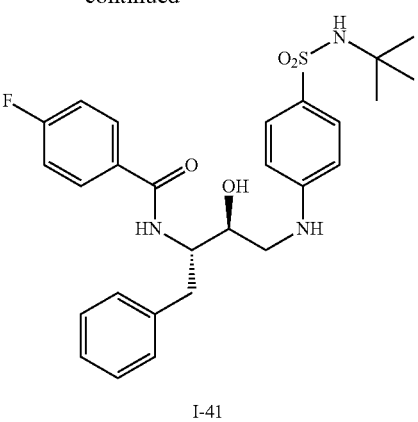

I-41

Preparation of tert-butyl (2R,3S)-4-(4-(benzylthio) phenylamino)-3-hydroxy-1-phenylbutan-2-ylcarbamate

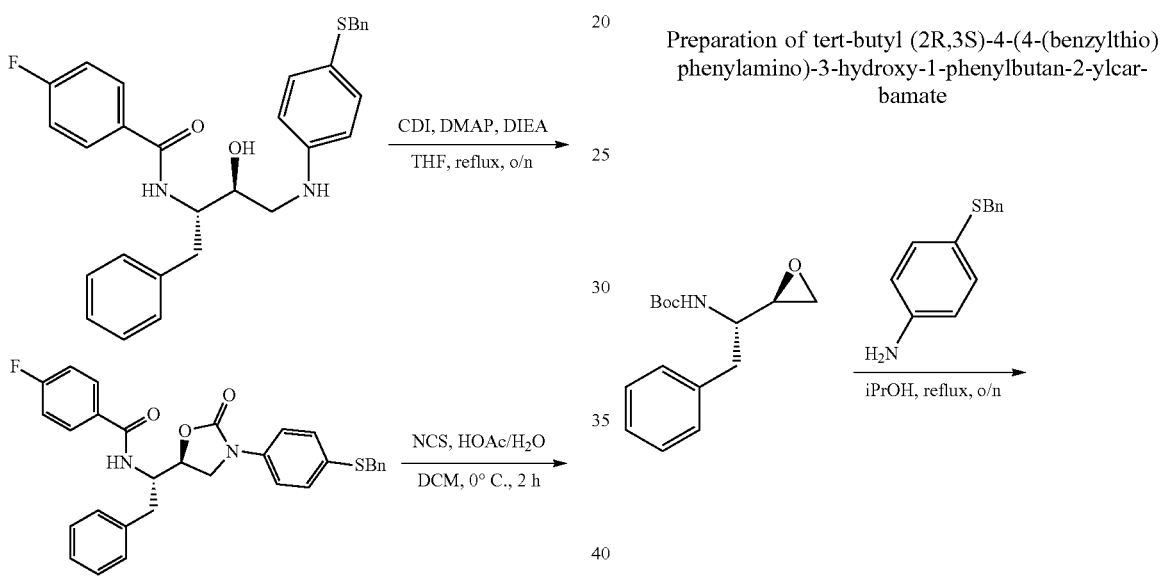

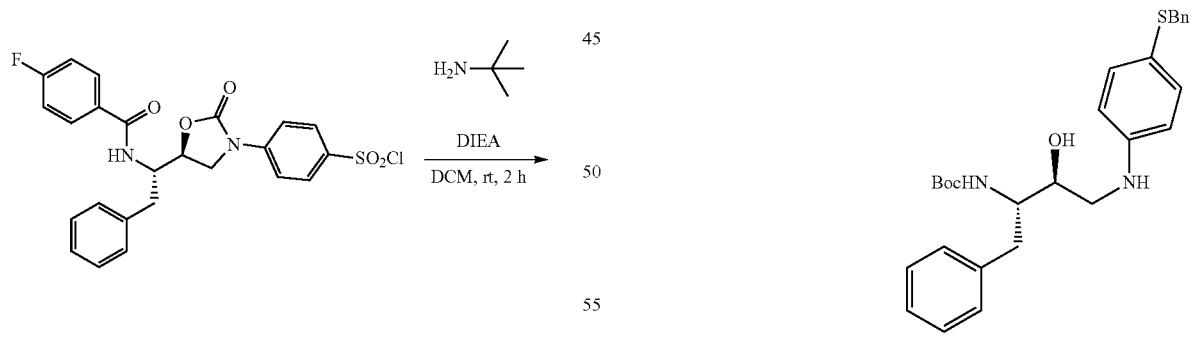

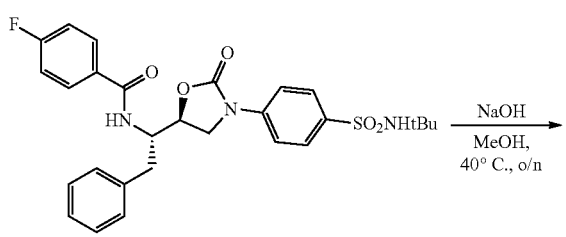

A mixture of 2.63 g tert-butyl (R)-1-((R)-oxiran-2-yl)-2-phenylethylcarbamate (10.0 mmol, 1.00 equiv) and 2.15 g 4-(benzylthio)aniline (10.0 mmol, 1.00 equiv) in 20 mL propan-2-ol was refluxed overnight. The mixture was concentrated and the residue was purified by column chromatography on silica gel (petroleum ether:ethyl acetate (5:1, v:v) to give 3.82 g tert-butyl (2R,3S)-4-(4-(benzylthio) phenylamino)-3-hydroxy-1-phenylbutan-2-ylcarbamate as a white solid (80% yield). MS (ESI$^+$) m/z 479 [M+H]$^+$.

263

Preparation of (2S,3S)-3-amino-1-(4-(benzylthio)phenylamino)-4-phenylbutan-2-ol

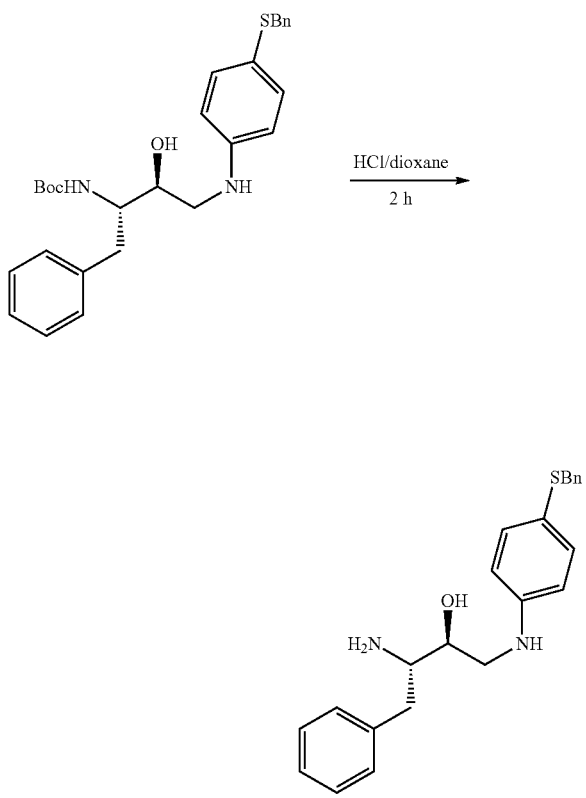

The mixture of 2.39 g tert-butyl (2R,3S)-4-(4-(benzylthio)phenylamino)-3-hydroxy-1-phenylbutan-2-ylcarbamate (5.0 mmol, 1.0 equiv) in 20 mL hydrochloric acid in dioxane (4.0 M HCl) was stirred at room temperature for 2 hours. The mixture was concentrated to give 1.89 g (2S,3S)-3-amino-1-(4-(benzylthio)phenylamino)-4-phenylbutan-2-ol as a white solid (100% yield). MS (ESI$^+$) m/z 379 [M+H]$^+$.

Preparation of N-((2S,3S)-4-(4-(benzylthio)phenylamino)-3-hydroxy-1-phenylbutan-2-yl)-4-fluorobenzamide

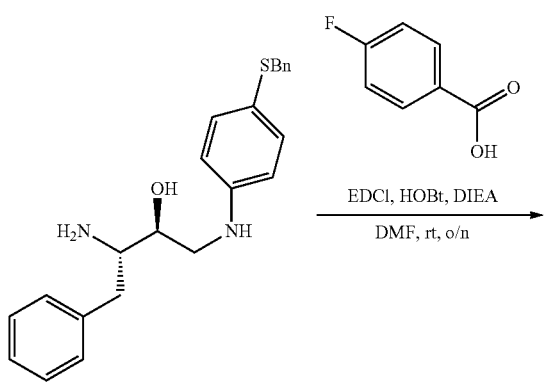

264

-continued

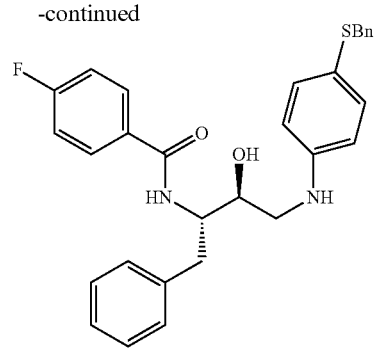

A mixture of 3.78 g (2S,3S)-3-amino-1-(4-(benzylthio)phenylamino)-4-phenylbutan-2-ol (10.0 mmol, 1.00 equiv), 1.40 g 4-fluorobenzoic acid (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.20 equiv) and 2.58 g N,N-diisopropylethylamine (20.0 mmol, 2.00 equiv) in 30 mL N,N-dimethylformamide was stirred at room temperature overnight. The mixture was diluted with 100 mL ethyl acetate and washed with 3×100 mL volumes of water. The organic phase was concentrated and the residue was purified by column chromatography on silica gel (petroleum ether: ethyl acetate (5:1, v:v) to give 4.0 g N-((2S,3S)-4-(4-(benzylthio)phenylamino)-3-hydroxy-1-phenylbutan-2-yl)-4-fluorobenzamide as a light yellow solid (80% yield). MS (ESI$^+$) m/z 501 [M+H]$^+$.

Preparation of N-((S)-1-((S)-3-(4-(benzylthio)phenyl)-2-oxooxazolidin-5-yl)-2-phenylethyl)-4-fluorobenzamide

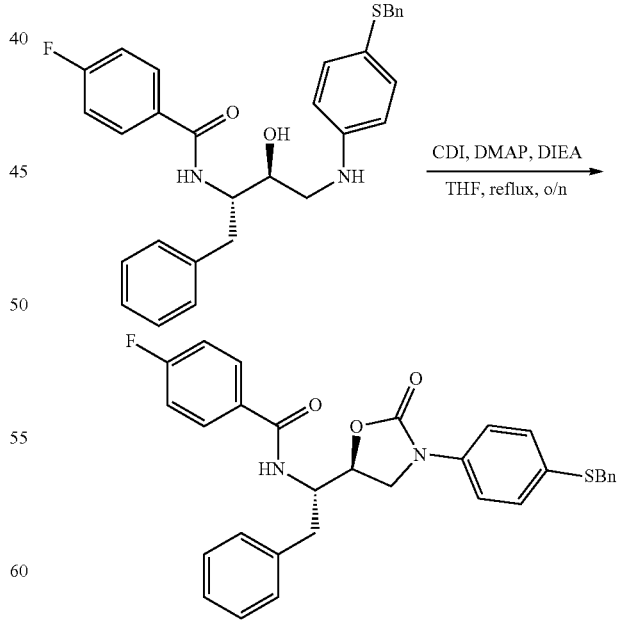

A mixture of 5.0 g N-((2S,3S)-4-(4-(benzylthio)phenylamino)-3-hydroxy-1-phenylbutan-2-yl)-4-fluorobenzamide (10.0 mmol, 1.00 equiv), 3.24 g N,N'-carbonyldiimidazole (20.0 mmol, 2.00 equiv), 244 mg 4-dimethylaminopyridine (2.0 mmol, 0.2 equiv) and 2.58 g N,N-diisopropylethylamine (20.0 mmol, 2.00 equiv) in 30 mL tetrahydrofuran was refluxed overnight. The mixture was concentrated and the residue was purified by column chromatography on silica gel (petroleum ether:ethyl acetate (3:1, v:v) to give 4.2 g N-((S)-1-((S)-3-(4-(benzylthio)phenyl)-2-oxooxazolidin-5-yl)-2-phenylethyl)-4-fluorobenzamide as a light yellow solid (80% yield). MS (ESI+) m/z 527 [M+H]+.

Preparation of 4-((S)-5-((S)-1-(4-fluorobenzamido)-2-phenylethyl)-2-oxooxazolidin-3-yl)benzene-1-sulfonyl Chloride

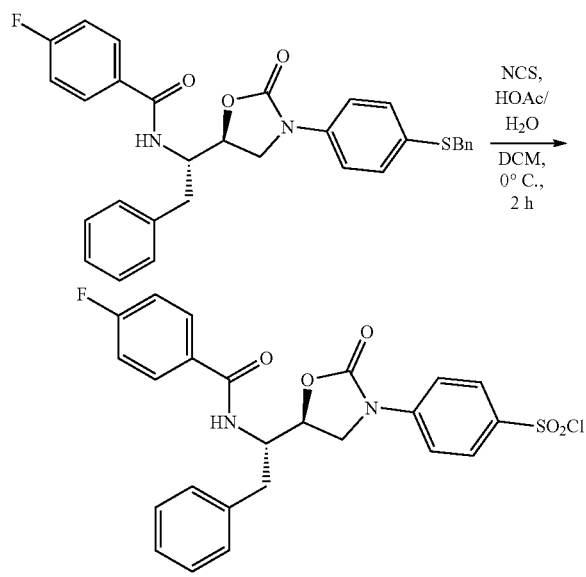

To a solution of 2.63 g N-((S)-1-((S)-3-(4-(benzylthio) phenyl)-2-oxooxazolidin-5-yl)-2-phenylethyl)-4-fluorobenzamide (5.00 mmol, 1.00 equiv), 60 mg acetic acid (1.0 mmol, 0.2 equiv) and 18 mg water (1.0 mmol, 0.2 equiv) in 30 mL dichloromethane was added 2.66 g N-chlorosuccinimide (20.0 mmol, 4.00 equiv) at 0° C. The mixture was stirred at room temperature for 2 hours and washed with 3×20 mL volumes of water. The organic phase was concentrated to give 1.76 g 4-((S)-5-((O)-1-(4-fluorobenzamido)-2-phenylethyl)-2-oxooxazolidin-3-yl)benzene-1-sulfonyl chloride as a white solid (70% yield). MS (ESI+) m/z 503 [M+H]+.

Preparation of N-((S)-1-((S)-3-(4-(N-tert-butylsulfamoyl)phenyl)-2-oxooxazolidin-5-yl)-2-phenylethyl)-4-fluorobenzamide

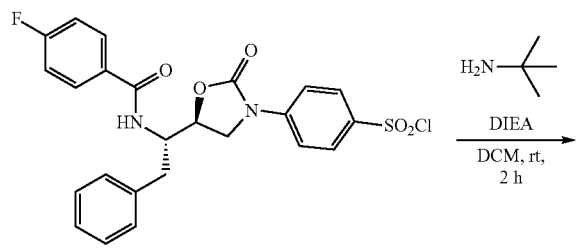

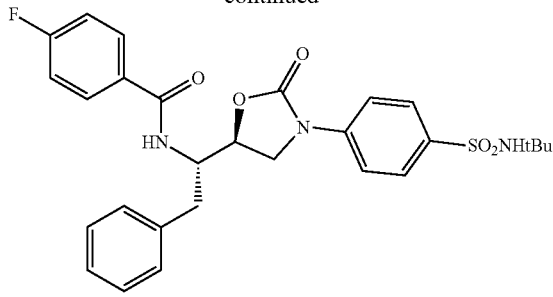

To the mixture of 770 mg 2-methylpropan-2-amine (11 mmol, 5.00 equiv) and 1.42 g N,N-diisopropylethylamine (11 mmol, 5.00 equiv) in 30 mL dichloromethane was added 1.10 g 4-((S)-5-((5)-1-(4-fluorobenzamido)-2-phenylethyl)-2-oxooxazolidin-3-yl)benzene-1-sulfonyl chloride (2.2 mmol, 1.0 equiv). The mixture was stirred at room temperature for 2 hours and concentrated in vacuo. The residue was purified by column chromatography on silica gel (petroleum ether:ethyl acetate (3:1, v:v) to give 830 mg of N-((5)-1-((5)-3-(4-(N-tert-butylsulfamoyl)phenyl)-2-oxooxazolidin-5-yl)-2-phenylethyl)-4-fluorobenzamide as a white solid (70% yield). MS (ESI+) m/z 540 [M+H]+.

Preparation of N-((2S,3S)-4-(4-(N-tert-butylsulfamoyl)phenylamino)-3-hydroxy-1-phenylbutan-2-yl)-4-fluorobenzamide, I-41

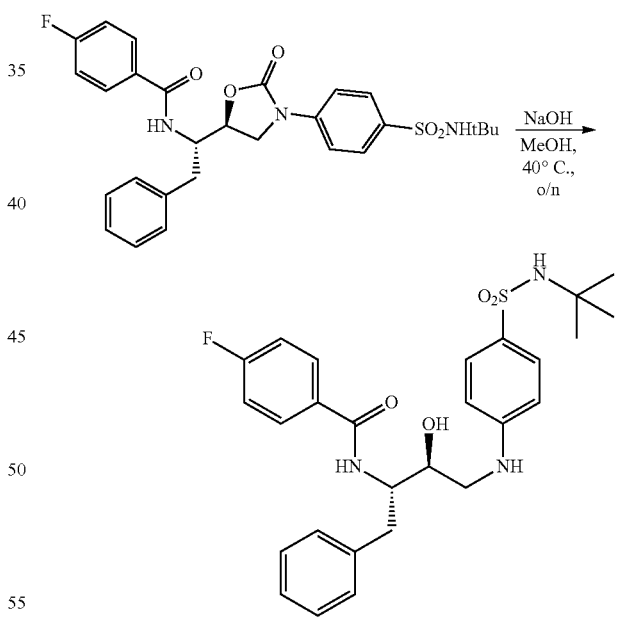

I-41

A mixture of 270 mg N-((S)-1-((S)-3-(4-(N-tert-butylsulfamoyl)phenyl)-2-oxooxazolidin-5-yl)-2-phenylethyl)-4-fluorobenzamide (0.5 mmol, 1.00 equiv) and 40 mg sodium hydroxide (1.0 mmol, 2.00 equiv) in 10 mL methanol was heated at 40° C. overnight. To the mixture was added 20 mL water and washed with 3×20 mL volumes of ethyl acetate. The organic phase was concentrated and the residue was purified by preparative scale-HPLC to give 30.0 mg N-((2S, 3S)-4-(4-(N-tert-butylsulfamoyl)phenylamino)-3-hydroxy- 1-phenylbutan-2-yl)-4-fluorobenzamide (I-41) as a white solid (12% yield). MS (ESI+) m/z 514 [M+H]+; 1H NMR (400 MHz, d6-DMSO) δ 8.31 (d, J=8.9 Hz, 1H), 7.88-7.71 (m, 2H), 7.45 (d, J=8.8 Hz, 2H), 7.33-6.86 (m, 8H), 6.62 (d, J=8.9 Hz, 2H), 6.40 (t, J=5.5 Hz, 1H), 5.33 (s, 1H), 4.23-4.10 (m, 1H), 3.74 (t, J=5.9 Hz, 1H), 3.31-3.20 (m, 1H), 3.14 (dd, J=13.8, 3.0 Hz, 1H), 3.08-2.92 (m, 1H), 2.82 (dd, J=13.8, 10.8 Hz, 1H), 1.04 (s, 9H).
Example 19: N-((2S,3R)-4-(4-(N-tert-butylsulfamoyl)phenylamino)-3-hydroxy-1-phenylbutan-2-yl)-4-fluorobenzamide, I-42
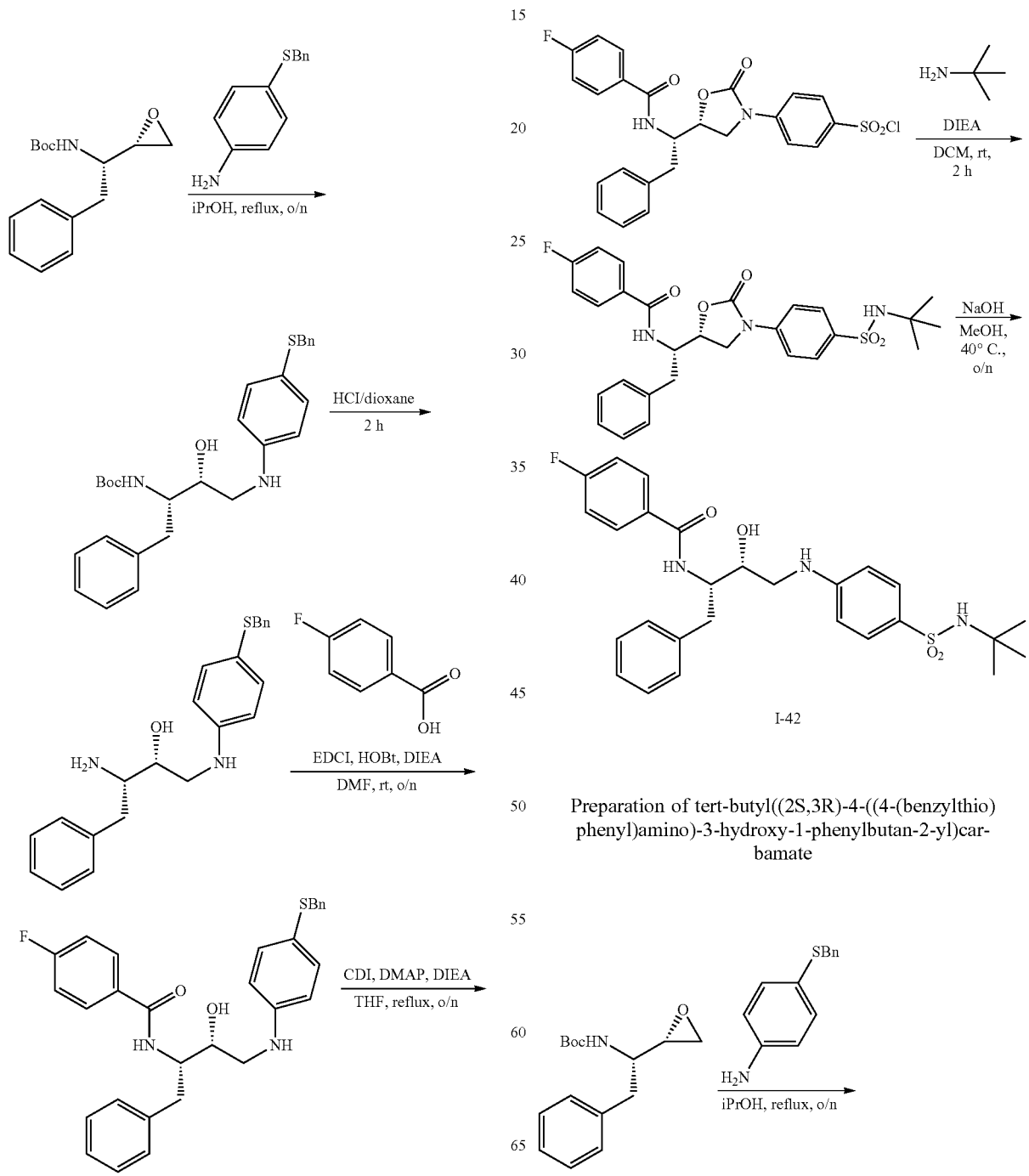
Preparation of tert-butyl((2S,3R)-4-((4-(benzylthio)phenyl)amino)-3-hydroxy-1-phenylbutan-2-yl)carbamate

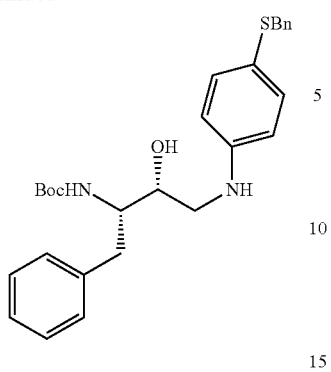

A mixture of 2.63 g tert-butyl ((S)-1-((S)-oxiran-2-yl)-2-phenylethyl)carbamate (10.0 mmol, 1.00 equiv) and 2.15 g 4-(benzylthio)aniline (10.0 mmol, 1.00 equiv) in 20 mL propan-2-ol was refluxed overnight. The mixture was concentrated and the residue was purified by column chromatography on silica gel (petroleum ether:ethyl acetate (5:1, v:v) to give 3.34 g tert-butyl (2S,3R)-4-(4-(benzylthio)phenylamino)-3-hydroxy-1-phenylbutan-2-ylcarbamate as a white solid (70% yield). MS (ESI$^+$) m/z 479 [M+H]$^+$.

Preparation of (2R,3S)-3-amino-1-(4-(benzylthio)phenylamino)-4-phenylbutan-2-ol

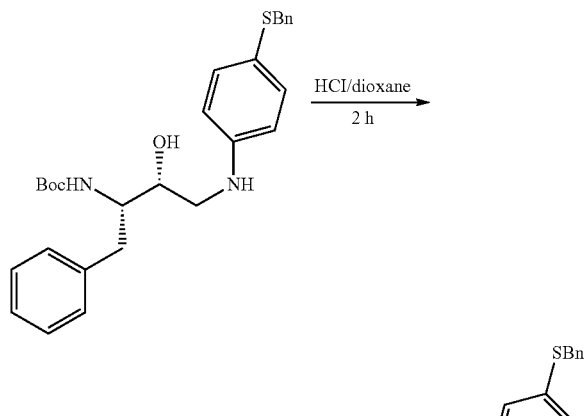

The mixture of 2.39 g tert-butyl (2S,3R)-4-(4-(benzylthio)phenylamino)-3-hydroxy-1-phenylbutan-2-ylcarbamate (5.0 mmol, 1.0 equiv) in 20 mL hydrochloric acid in dioxane (4.0 M HCl) was stirred at room temperature for 2 hours. The mixture was concentrated to give 1.89 g (2R,3S)-3-amino-1-(4-(benzylthio)phenylamino)-4-phenylbutan-2-ol as a white solid (100% yield). MS (ESI$^+$) m/z 379 [M+H]$^+$.

Preparation of N-((2S,3R)-4-(4-(benzylthio)phenylamino)-3-hydroxy-1-phenylbutan-2-yl)-4-fluorobenzamide

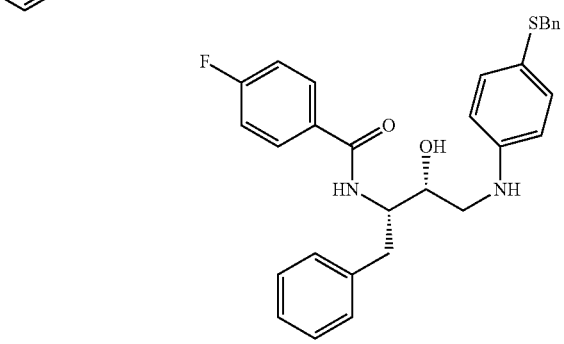

A mixture of 3.78 g (2R,3S)-3-amino-1-(4-(benzylthio)phenylamino)-4-phenylbutan-2-ol (10.0 mmol, 1.00 equiv), 1.40 g 4-fluorobenzoic acid (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.20 equiv) and 2.58 g N,N-diisopropylethylamine (20.0 mmol, 2.00 equiv) in 30 mL N,N-dimethylformamide was stirred at room temperature overnight. The mixture was diluted with 100 mL ethyl acetate and washed with 3×100 mL volumes of water. The organic phase was concentrated and the residue was purified by column chromatography on silica gel (petroleum ether:ethyl acetate (5:1, v:v) to give 4.31 g N-((2S,3R)-4-(4-(benzylthio)phenylamino)-3-hydroxy-1-phenylbutan-2-yl)-4-fluorobenzamide as a light yellow solid (85% yield). MS (ESI$^+$) m/z 501 [M+H]$^+$.

Preparation of N-((S)-1-((R)-3-(4-(benzylthio)phenyl)-2-oxooxazolidin-5-yl)-2-phenylethyl)-4-fluorobenzamide

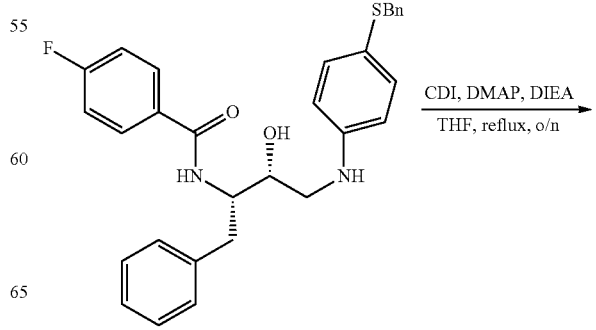

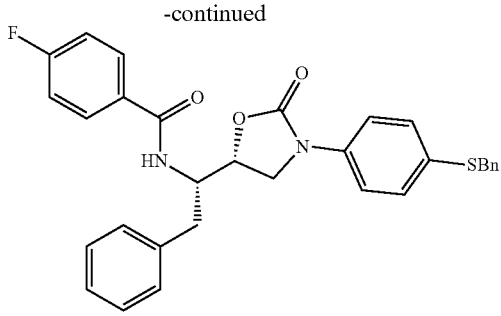

A mixture of 5.0 g N-((2S,3R)-4-(4-(benzylthio)phenylamino)-3-hydroxy-1-phenylbutan-2-yl)-4-fluorobenzamide (10.0 mmol, 1.00 equiv), 3.24 g N,N'-carbonyldiimidazole (20.0 mmol, 2.00 equiv), 244 mg 4-dimethylaminopyridine (2.0 mmol, 0.2 equiv) and 2.58 g N,N-diisopropylethylamine (20.0 mmol, 2.00 equiv) in 30 mL tetrahydrofuran was refluxed overnight. The mixture was concentrated and the residue was purified by column chromatography on silica gel (petroleum ether:ethyl acetate (3:1, v:v) to give 3.9 g N-((S)-1-((R)-3-(4-(benzylthio)phenyl)-2-oxooxazolidin-5-yl)-2-phenylethyl)-4-fluorobenzamide as a light yellow solid (75% yield). MS (ESI$^+$) m/z 527 [M+H]$^+$.

Preparation of 4-((R)-5-((S)-1-(4-fluorobenzamido)-2-phenylethyl)-2-oxooxazolidin-3-yl)benzene-1-sulfonyl Chloride

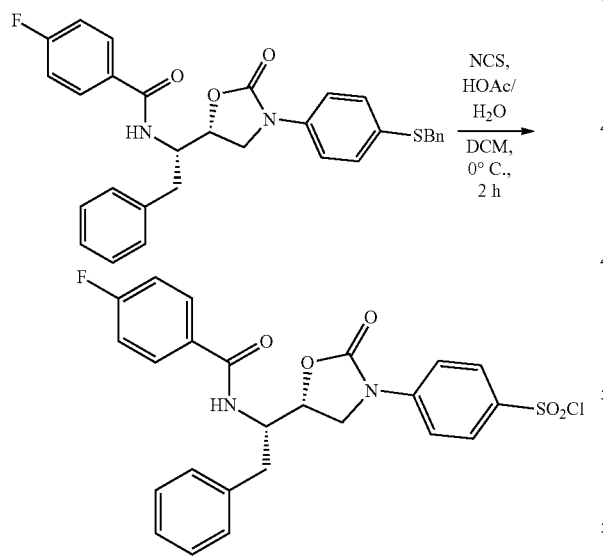

To a solution of 2.63 g N-((S)-1-((R)-3-(4-(benzylthio)phenyl)-2-oxooxazolidin-5-yl)-2-phenylethyl)-4-fluorobenzamide (5.00 mmol, 1.00 equiv), 60 mg acetic acid (1.0 mmol, 0.2 equiv) and 18 mg water (1.0 mmol, 0.2 equiv) in 30 mL dichloromethane was added 2.66 g N-chlorosuccinimide (20.0 mmol, 4.00 equiv) at 0° C. The mixture was stirred at room temperature for 2 hours and washed with 3×20 mL volumes of water. The organic phase was concentrated to give 1.51 g 4-((R)-5-((O)-1-(4-fluorobenzamido)-2-phenylethyl)-2-oxooxazolidin-3-yl)benzene-1-sulfonyl chloride as a white solid (60% yield). MS (ESI$^+$) m/z 503 [M+H]$^+$.

Preparation of N-((S)-1-((R)-3-(4-(N-tert-butylsulfamoyl)phenyl)-2-oxooxazolidin-5-yl)-2-phenylethyl)-4-fluorobenzamide

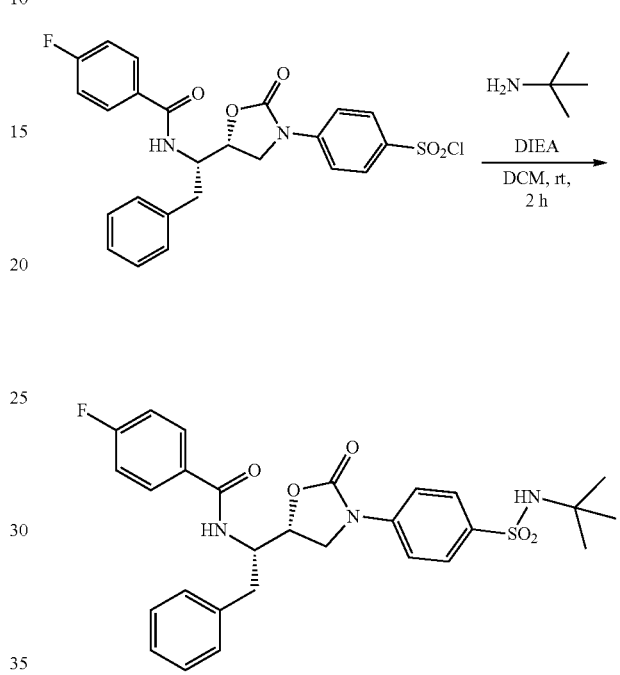

To the mixture of 803 mg 2-methylpropan-2-amine (11 mmol, 5.00 equiv) and 1.42 g N,N-diisopropylethylamine (11 mmol, 5.00 equiv) in 30 mL dichloromethane was added 1.10 g 4-((R)-5-((S)-1-(4-fluorobenzamido)-2-phenylethyl)-2-oxooxazolidin-3-yl)benzene-1-sulfonyl chloride (2.2 mmol, 1.0 equiv). The mixture was stirred at room temperature for 1 hour and concentrated in vacuo. The residue was purified by column chromatography on silica gel (petroleum ether:ethyl acetate (3:1, v:v) to give 949 mg N-((S)-1-((R)-3-(4-(N-tert-butylsulfamoyl)phenyl)-2-oxooxazolidin-5-yl)-2-phenylethyl)-4-fluorobenzamide as a white solid (80% yield). MS (ESI$^+$) m/z 540 [M+H]$^+$.

Preparation of N-((2S,3R)-4-(4-(N-tert-butylsulfamoyl)phenylamino)-3-hydroxy-1-phenylbutan-2-yl)-4-fluorobenzamide, I-42

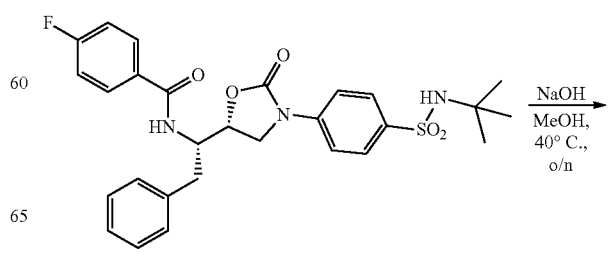

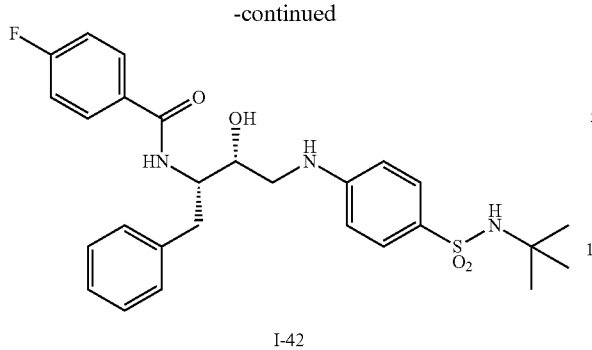

I-42

A mixture of 270 mg N-((S)-1-((R)-3-(4-(N-tert-butylsulfamoyl)phenyl)-2-oxoöxazolidin-5-yl)-2-phenylethyl)-4-fluorobenzamide (0.5 mmol, 1.00 equiv) and 40 mg sodium hydroxide (1.0 mmol, 2.00 equiv) in 10 mL methanol was heated at 40° C. for overnight. To the mixture was added 20 mL water and washed with 3×20 mL volumes of ethyl acetate. The organic phase was concentrated and the residue was purified by reversed phase preparative HPLC on a Gilson GX-281. A concentrated solution of crude product dissolved in DMSO was injected in 875 uL volumes onto a 10 um C18 reversed phase Waters X-SELECT 19 mm diameter×250 mm length column eluting with a gradient of 49-95% acetonitrile in water with 10 mmol/liter ammonium carbonate. Peaks were detected by UV absorbance at 214 nm and 254 nm and fractions collected by 5 mV threshold trigger on the 214 nm channel. Fractions containing product were combined, concentrated and lyophilized to afford 40.0 mg N-((2S,3R)-4-(4-(N-tert-butylsulfamoyl)phenylamino)-3-hydroxy-1-phenylbutan-2-yl)-4-fluorobenzamide (I-42) as a white solid (16% yield). MS (ESI$^+$) m/z 514 [M+H]$^+$; $^1$H NMR (400 MHz, d$_6$-DMSO) δ 8.22 (d, J=8.8 Hz, 1H), 7.96-7.82 (m, 2H), 7.43 (d, J=8.8 Hz, 2H), 7.36-6.88 (m, 8H), 6.60 (d, J=8.9 Hz, 2H), 6.33 (t, J=5.7 Hz, 1H), 5.32 (s, 1H), 4.47-4.15 (m, 1H), 3.98-3.65 (m, 1H), 3.28-3.13 (m, 1H), 3.13-2.83 (m, 3H), 1.04 (s, 9H).

Example 20: (S)-tetrahydro-2H-pyran-4-yl 1-(4-(N-tert-butylsulfamoyl)phenylamino)-1-oxo-3-phenyl-propan-2-ylcarbamate, I-43

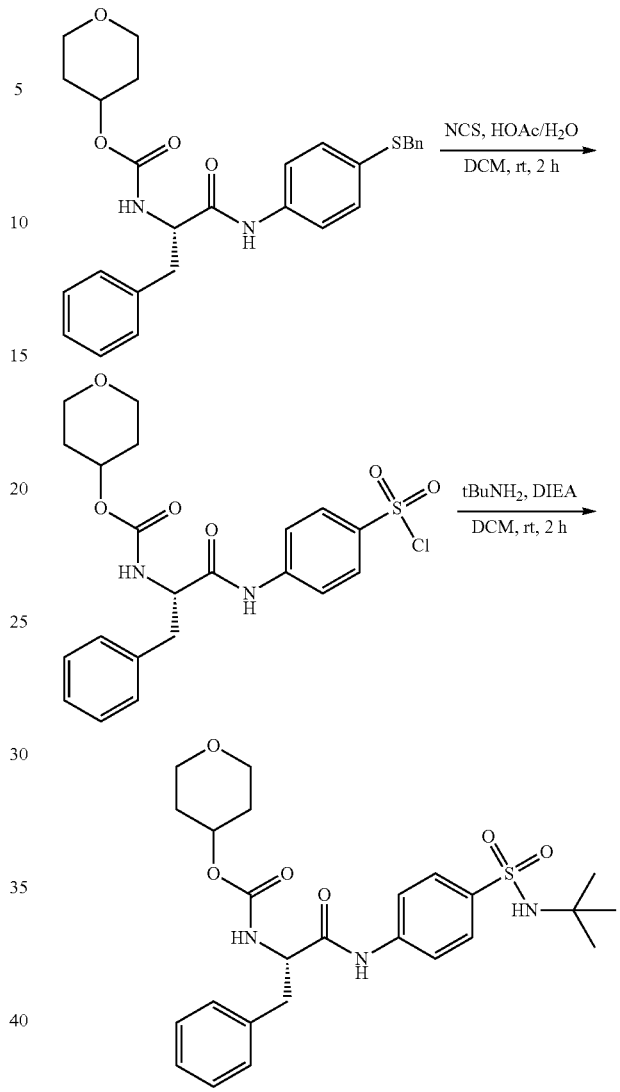

I-43

Preparation of 3-methyl-1-((tetrahydro-2H-pyran-4-yloxy)carbonyl)-1H-imidazol-3-ium iodide

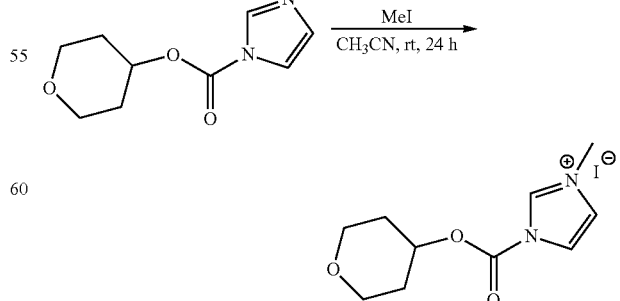

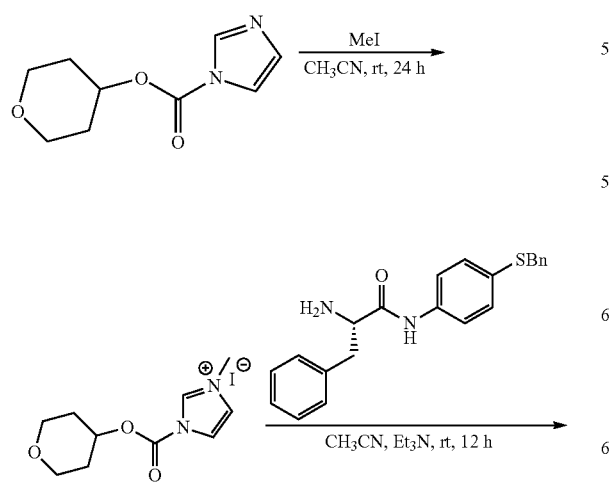

To a solution of 350 mg tetrahydro-2H-pyran-4-yl 1H-imidazole-1-carboxylate (1.79 mmol, 1.00 equiv) in 10 mL of Acetonitrile at room temperature was added 1.27 g Iodomethane (8.95 mmol, 5.00 equiv). Then the reaction mixture was stirred at room temperature for 24 hours. The mixture was concentrated to afford 470 mg 3-methyl-1-((tetrahydro-2H-pyran-4-yloxy)carbonyl)-1H-imidazol-3-ium iodide as a colorless oil (79% yield). MS (ESI⁺) m/z 339[M+H]⁺.

Preparation of (S)-tetrahydro-2H-pyran-4-yl 1-(4-(benzylthio)phenylamino)-1-oxo-3-phenylpropan-2-ylcarbamate

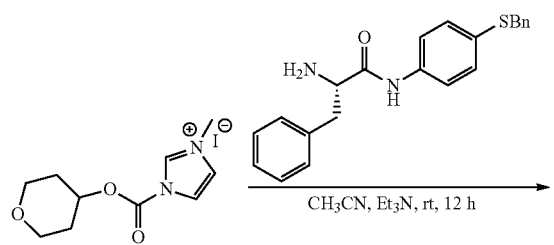

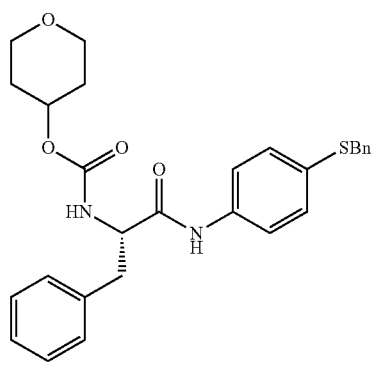

To a solution of 450 mg 3-methyl-1-((tetrahydro-2H-pyran-4-yloxy)carbonyl)-1H-imidazol-3-ium iodide (1.33 mmol, 1.00 equiv) and 269 mg Triethylamine (2.66 mmol, 2.00 equiv) dissolved in 10 mL anhydrous Acetonitrile at room temperature was added 481 mg (S)-2-amino-N-(4-(benzylthio)phenyl)-3-phenylpropanamide (1.33 mmol, 1.0 equiv). Then the reaction mixture was stirred at room temperature for 12 hours and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (petroleum ether: ethyl acetate (2:1, v:v) to give 430 mg (S)-tetrahydro-2H-pyran-4-yl 1-(4-(benzylthio)phenylamino)-1-oxo-3-phenylpropan-2-ylcarbamate as a white solid (66% yield). MS (ESI⁺) m/z 491[M+H]⁺.

Preparation of (S)-tetrahydro-2H-pyran-4-yl 1-(4-(chlorosulfonyl)phenylamino)-1-oxo-3-phenylpropan-2-ylcarbamate

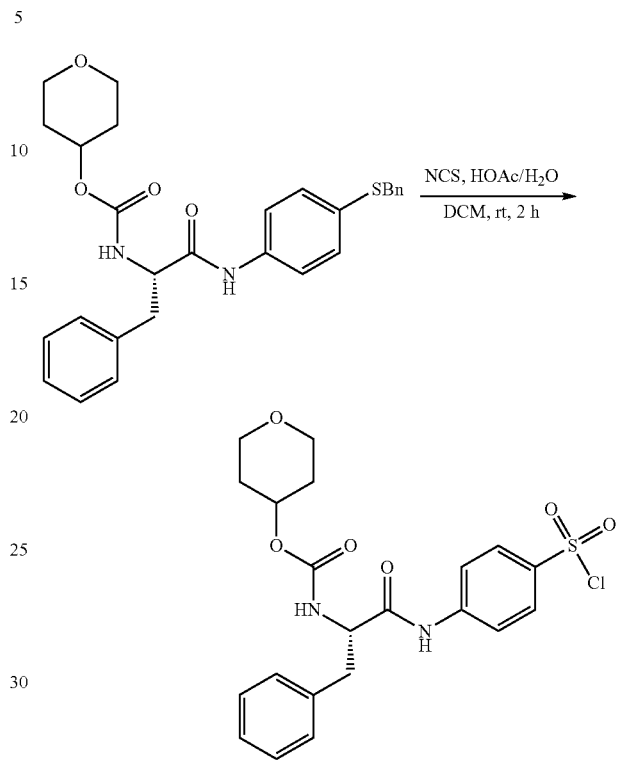

To a solution of 150 mg (S)-tetrahydro-2H-pyran-4-yl 1-(4-(benzylthio)phenylamino)-1-oxo-3-phenylpropan-2-ylcarbamate (0.31 mmol, 1.00 equiv), 18 mg acetic acid (0.31 mmol, 1 equiv) and 6 mg water (0.31 mmol, 1 equiv) in 30 mL dichloromethane was added 168 mg N-chlorosuccinimide (1.24 mmol, 4.00 equiv) at 0° C. The mixture was stirred at room temperature for 2 hours and washed with 3×20 mL volumes of water. The organic phase was concentrated to give 150 mg crude (S)-tetrahydro-2H-pyran-4-yl 1-(4-(chlorosulfonyl)phenylamino)-1-oxo-3-phenylpropan-2-ylcarbamate as a gray solid (100% yield). MS (ESI⁺) m/z 467[M+H]⁺.

Preparation of (S)-tetrahydro-2H-pyran-4-yl 1-(4-(N-tert-butylsulfamoyl)phenylamino)-1-oxo-3-phenylpropan-2-ylcarbamate, I-43

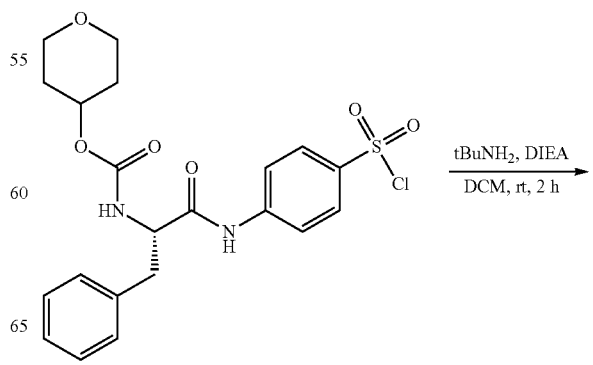

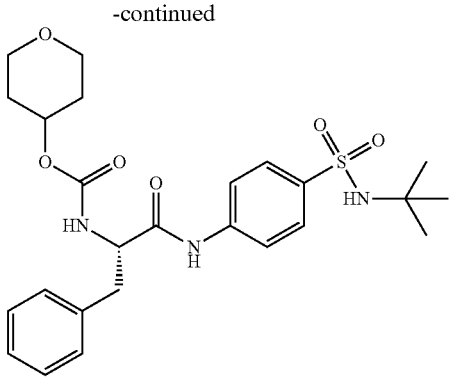

I-43

To a mixture of 117 mg 2-methylpropan-2-amine (1.6 mmol, 5.0 equiv) and 206 mg N,N-diisopropylethylamine (1.6 mmol, 5.00 equiv) in 10 mL dichloromethane was added 150 mg (S)-tetrahydro-2H-pyran-4-yl 1-(4-(chlorosulfonyl)phenylamino)-1-oxo-3-phenylpropan-2-ylcarbamate (0.32 mmol, 1.00 equiv). The mixture was stirred at room temperature for 2 hours and concentrated in vacuo. The residue was purified by reversed phase preparative HPLC on a Gilson GX-281. A concentrated solution of crude product dissolved in DMSO was injected in 400 uL volumes onto a 10 um C18 reversed phase Waters X-SELECT 19 mm diameter×250 mm length column eluting with a gradient of 47-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 60 mg (S)-tetrahydro-2H-pyran-4-yl 1-(4-(N-tert-butylsulfamoyl)phenylamino)-1-oxo-3-phenylpropan-2-ylcarbamate (I-43) as a white solid (37% yield). MS (ESI$^+$) m/z 504 [M+H]$^+$. $^1$H NMR (400 MHz, d$_6$-DMSO) δ 10.46 (s, 1H), 7.77-7.67 (m, 4H), 7.58 (s, 1H), 7.23 (m, 6H), 4.62-4.54 (m, 1H), 4.36 (s, 1H), 3.83-3.68 (m, 2H), 3.47-3.33 (m, 2H), 3.00 (dd, J=13.7, 4.4 Hz, 1H), 2.83 (dd, J=13.6, 10.4 Hz, 1H), 1.74 (dd, J=25.1, 11.7 Hz, 2H), 1.42 (m, 2H), 1.06 (s, 9H).

Example 21: (S)-N-(1-(3-(N-tert-butylsulfamoyl)phenylamino)-1-oxo-3-phenylpropan-2-yl)-4-fluorobenzamide, I-68

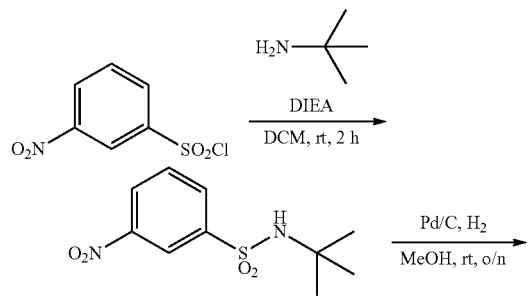

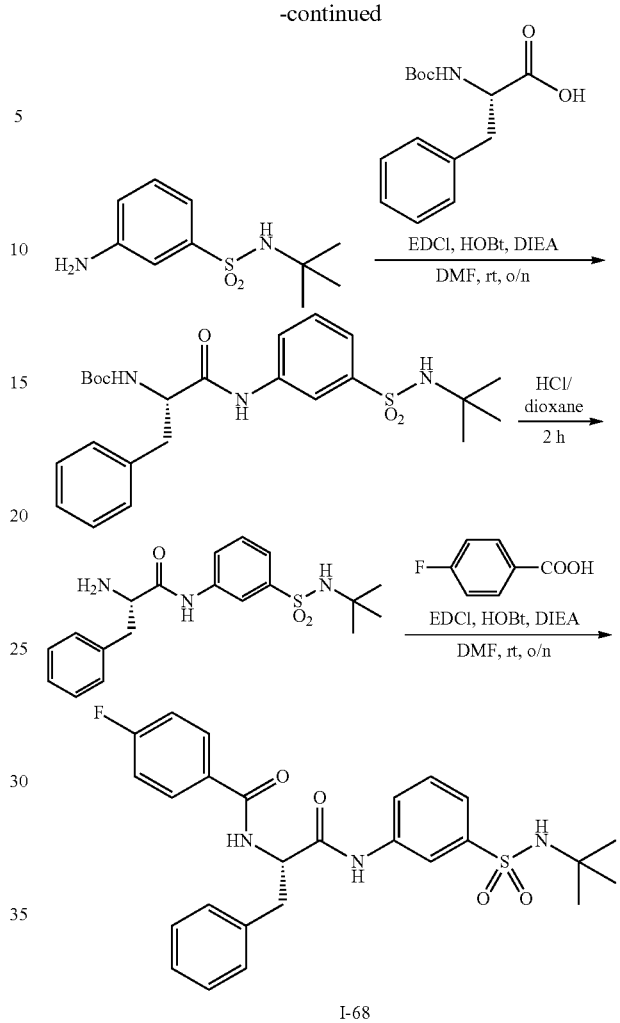

I-68

Preparation of N-tert-butyl-3-nitrobenzenesulfonamide

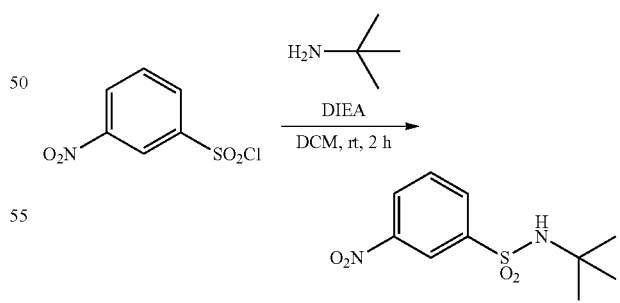

To the mixture of 1.54 g 2-methylpropan-2-amine (20 mmol, 2.00 equiv) and 2.58 g N,N-diisopropylethylamine (20 mmol, 2.00 equiv) in 30 mL dichloromethane was added 2.2 g 3-nitrobenzene-1-sulfonyl chloride (10.0 mmol, 1.0 equiv). The mixture was stirred at room temperature for 2 hours and concentrated in vacuo. The residue was purified by column chromatography on silica gel (petroleum ether:

ethyl acetate (3:1, v:v) to give 1.81 g N-tert-butyl-3-nitrobenzenesulfonamide as a white solid (70% yield). MS (ESI⁺) m/z 259 [M+H]⁺.

Preparation of 3-amino-N-tert-butylbenzenesulfonamide

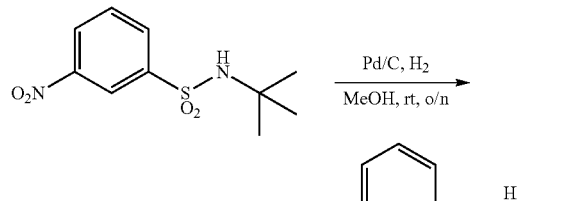

To a solution of 2.58 g N-tert-butyl-3-nitrobenzenesulfonamide (10.0 mmol, 1.00 equiv) in methanol was added palladium on activated carbon (550 mg wet catalyst, 10 wt. % palladium dry basis). The mixture was placed under hydrogen gas via balloon and stirred at room temperature for overnight. The mixture was filtered and the filtrate concentrated to afford 2.05 g 3-amino-N-tert-butylbenzenesulfonamide as a light yellow solid (90% yield). MS (ESI⁺) m/z 229 [M+H]⁺.

Preparation of (S)-tert-butyl 1-(3-(N-tert-butylsulfamoyl)phenylamino)-1-oxo-3-phenylpropan-2-ylcarbamate

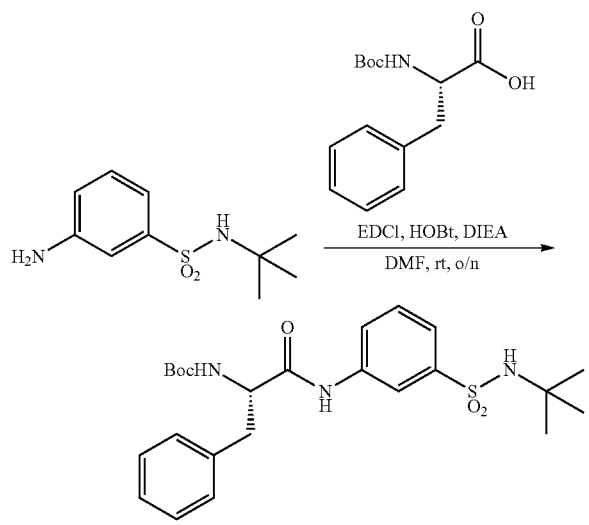

A mixture of 2.65 g (S)-2-(tert-butoxycarbonylamino)-3-phenylpropanoic acid (10.0 mmol, 1.0 equiv), 2.28 g 3-amino-N-tert-butylbenzenesulfonamide (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.2 equiv) and 2.58 g N,N-diisopropylethylamine (20.0 mmol, 2.00 equiv) in 20 mL N,N-dimethylformamide was stirred at room temperature overnight. The mixture was diluted with 100 mL of ethyl acetate and washed with 3×100 mL volumes of water. The organic phase was concentrated and the residue was purified by column chromatography on silica gel (petroleum ether:ethyl acetate (5:1, v:v)) to yield 3.80 g (S)-tert-butyl 1-(3-(N-tert-butylsulfamoyl)phenylamino)-1-oxo-3-phenylpropan-2-ylcarbamate as a light yellow solid (80% yield). MS (ESI⁺) m/z 476 [M+H]⁺.

Preparation of (S)-2-amino-N-(3-(N-tert-butylsulfamoyl)phenyl)-3-phenylpropanamide

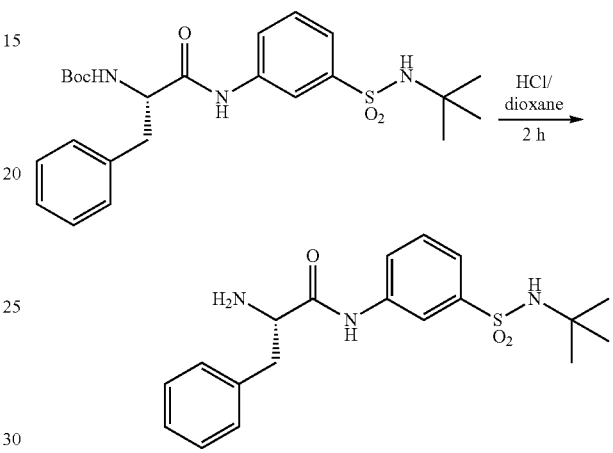

The mixture of 2.38 g (S)-tert-butyl 1-((4-(benzylthio)phenyl)(methyl)amino)-1-oxo-3-phenylpropan-2-ylcarbamate (5.0 mmol, 1.0 equiv) in 20 mL hydrochloric acid in dioxane (4.0 M HCl) was stirred at room temperature for 2 hours. The mixture was concentrated to give 1.88 g (S)-2-amino-N-(3-(N-tert-butylsulfamoyl)phenyl)-3-phenylpropanamide as a white solid (100% yield). MS (ESI⁺) m/z 376 [M+H]⁺.

Preparation of (S)-N-(1-(3-(N-tert-butylsulfamoyl)phenylamino)-1-oxo-3-phenylpropan-2-yl)-4-fluorobenzamide, I-68

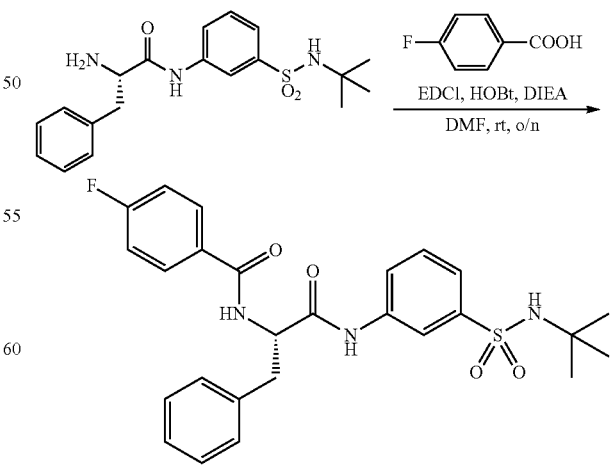

I-68

A mixture of 186 mg (S)-2-amino-N-(3-(N-tert-butylsulfamoyl)phenyl)-3-phenylpropanamide (0.5 mmol, 1.00 equiv), 70 mg 4-fluorobenzoic acid (0.5 mmol, 1.00 equiv), 144 mg N-(3-dimethylaminopropyl)-N'-ethylcarbodiimide hydrochloride (0.75 mmol, 1.50 equiv), 81 mg 1-hydroxybenzotriazole (0.6 mmol, 1.20 equiv) and 129 mg N,N-diisopropylethylamine (1.0 mmol, 2.00 equiv) in 10 mL N,N-dimethylformamide was stirred at room temperature overnight. The mixture was diluted with 20 mL of ethyl acetate and washed with 3×20 mL volumes of water. The organic phase was concentrated and the residue was purified by preparative scale-HPLC The compound was purified by reversed phase preparative HPLC on a Gilson GX-281. A concentrated solution of crude product dissolved in DMSO was injected in 600 uL volumes onto a 10 um C18 reversed phase XBridge 19 mm diameter×250 mm length column eluting with a gradient of 55-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 25.0 mg (S)-N-(1-(3-(N-tert-butylsulfamoyl)phenylamino)-1-oxo-3-phenylpropan-2-yl)-4-fluorobenzamide (I-68) as a white solid (10% yield). MS (ESI$^+$) m/z 498 [M+H]$^+$; $^1$H NMR (400 MHz, d$_6$-DMSO) δ 10.55 (s, 1H), 8.76 (d, J=99.3 Hz, 1H), 8.17 (d, J=1.5 Hz, 1H), 8.00-7.84 (m, 2H), 7.82-7.70 (m, 1H), 7.69-7.34 (m, 5H), 7.34-7.22 (m, 4H), 7.18 (t, J=7.3 Hz, 1H), 4.82 (dd, J=9.7, 4.6 Hz, 1H), 3.14 (ddd, J=23.8, 13.7, 7.6 Hz, 2H), 1.11 (s, 9H).

Example 22: (S)-N-(1-(4-(N-tert-butylsulfamoyl)phenylamino)-3-phenylpropan-2-yl)-4-fluorobenzamide, I-44

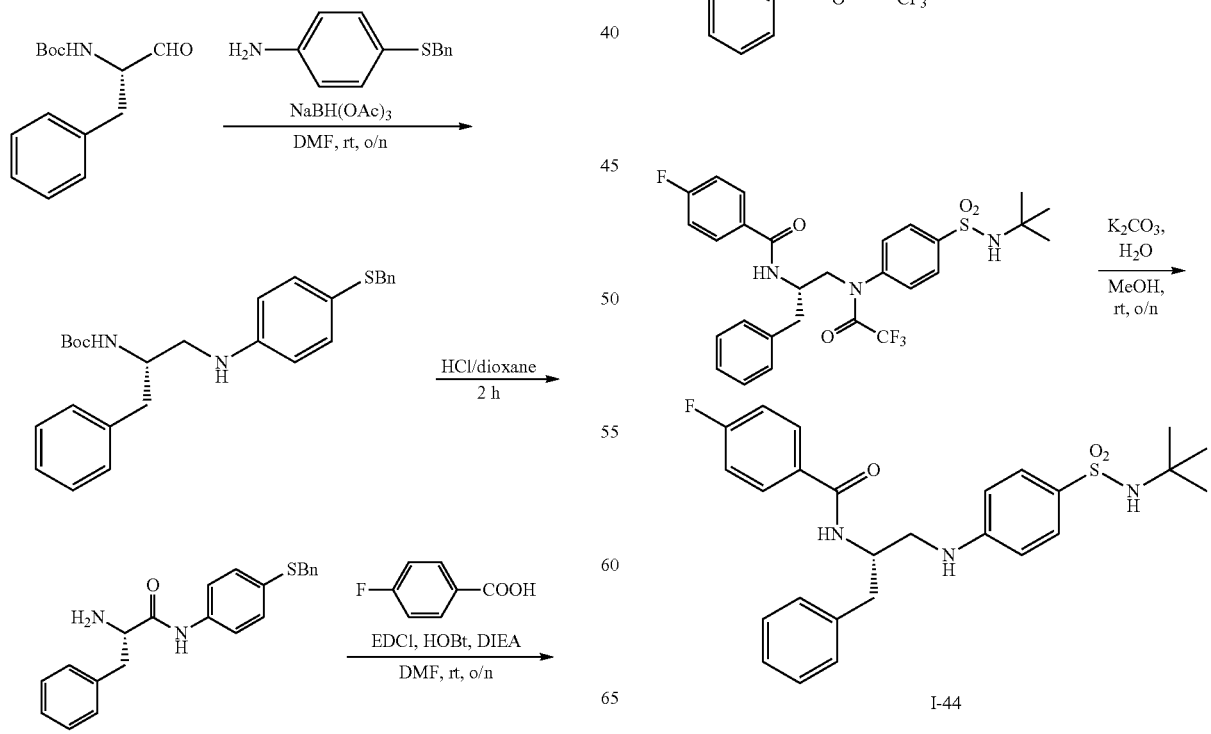

I-44

283

Preparation of (S)-tert-butyl 1-(4-(benzylthio)phenylamino)-3-phenylpropan-2-ylcarbamate

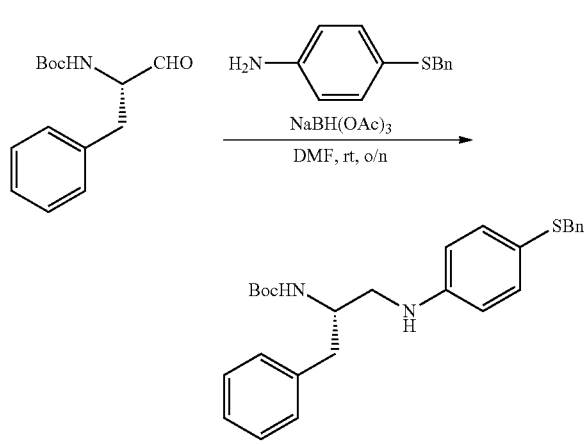

To the mixture of 2.49 g 2-methylpropan-2-amine (10.0 mmol, 1.00 equiv) and 2.15 g 4-(benzylthio)aniline (10.0 mmol, 1.00 equiv) in 30 mL N,N-dimethylformamide was added 4.24 g sodium triacetoborohydride (20.0 mmol, 2.0 equiv). The mixture was stirred at room temperature overnight. The mixture was diluted with 100 mL water and washed with 3×100 mL volumes of ethyl acetate. The organic phase was concentrated and the residue was purified by column chromatography on silica gel (petroleum ether: ethyl acetate (10:1, v:v)) to yield 2.24 g (S)-tert-butyl 1-(4-(benzylthio)phenylamino)-3-phenylpropan-2-ylcarbamate as a light yellow solid (50% yield). MS (ESI+) m/z 449 [M+H]+.

Preparation of (S)-N-(4-(benzylthio)phenyl)-3-phenylpropane-1,2-diamine

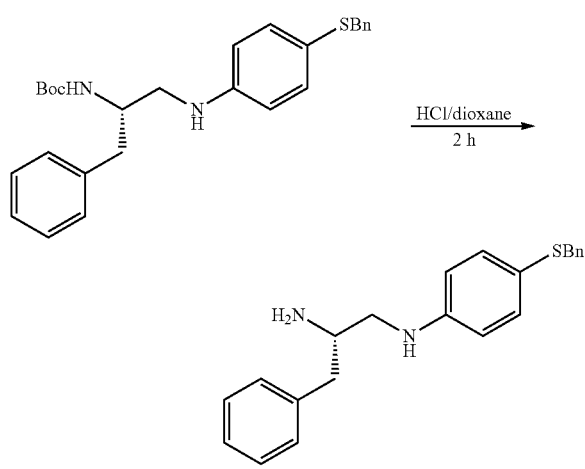

The mixture of 2.24 g (S)-tert-butyl 1-(4-(benzylthio) phenylamino)-3-phenylpropan-2-ylcarbamate (5.0 mmol, 1.0 equiv) in 20 mL hydrochloric acid in dioxane (4.0 M HCl) was stirred at room temperature for 2 hours. The mixture was concentrated to give 1.24 g (S)-N$^1$-(4-(benzylthio)phenyl)-3-phenylpropane-1,2-diamine as a white solid (100% yield). MS (ESI+) m/z 349 [M+H]+.

284

Preparation of (S)-N-(1-(4-(benzylthio)phenylamino)-3-phenylpropan-2-yl)-4-fluorobenzamide

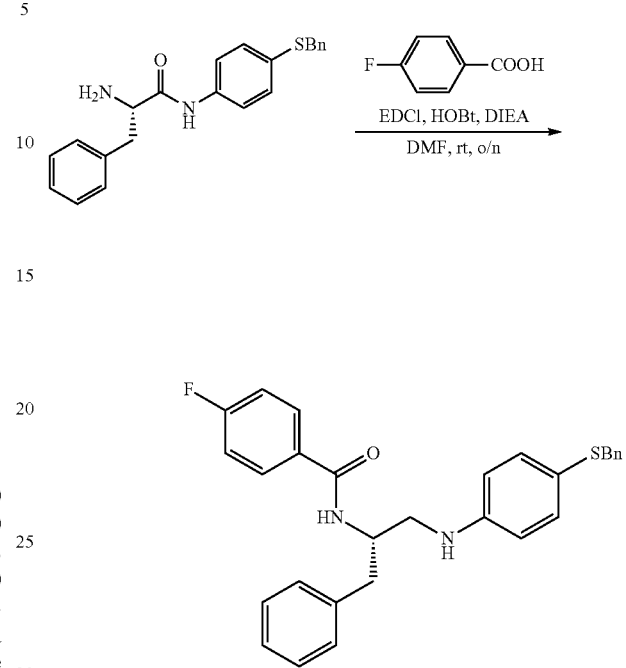

A mixture of 1.74 g (S)-N$^1$-(4-(benzylthio)phenyl)-3-phenylpropane-1,2-diamine (5.0 mmol, 1.00 equiv), 700 mg 4-fluorobenzoic acid (5.0 mmol, 1.00 equiv), 1.44 g N-(3-dimethylaminopropyl)-N'-ethylcarbodiimide hydrochloride (7.5 mmol, 1.50 equiv), 810 mg 1-hydroxybenzotriazole (6.0 mmol, 1.20 equiv) and 1.29 g N,N-diisopropylethylamine (10.0 mmol, 2.00 equiv) in 30 mL N,N-dimethylformamide was stirred at room temperature overnight. The mixture was diluted with 100 mL of ethyl acetate and washed with 3×100 mL volumes of water. The organic phase was concentrated and the residue was purified by column chromatography on silica gel (petroleum ether:ethyl acetate (5:1, v:v)) to give 1.80 g (S)-N-(1-(4-(benzylthio)phenylamino)-3-phenylpropan-2-yl)-4-fluorobenzamide as a white solid (80% yield). MS (ESI+) m/z 471 [M+H]+.

Preparation of (S)-N-(1-(N-(4-(benzylthio)phenyl)-2,2,2-trifluoroacetamido)-3-phenylpropan-2-yl)-4-fluorobenzamide

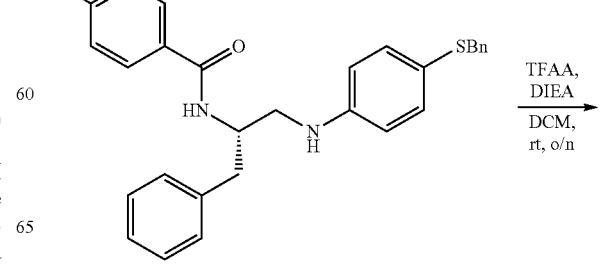

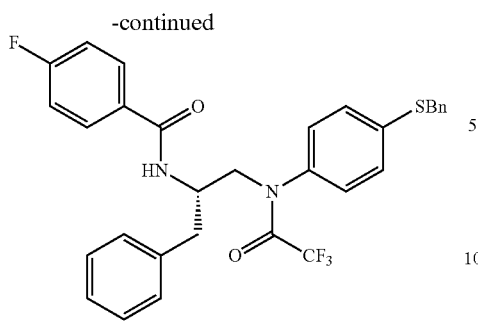

To the mixture of 4.70 g (S)-N-(1-(4-(benzylthio)phenylamino)-3-phenylpropan-2-yl)-4-fluorobenzamide (10.0 mmol, 1.00 equiv) and 2.58 g N,N-diisopropylethylamine (20.0 mmol, 2.00 equiv) in 30 mL dichloromethane was added 4.20 g trifluoroacetic anhydride (20.0 mmol, 2.0 equiv). The mixture was stirred at room temperature for overnight. The mixture was diluted with 100 mL water and washed with 3×100 mL volumes of ethyl acetate. The organic phase was concentrated and the residue was purified by column chromatography on silica gel (petroleum ether: ethyl acetate (10:1, v:v)) to yield 3.96 g (S)-N-(1-(N-(4-(benzylthio)phenyl)-2,2,2-trifluoroacetamido)-3-phenylpropan-2-yl)-4-fluorobenzamide as a light yellow solid (70% yield). MS (ESI+) m/z 567 [M+H]+.

Preparation of (S)-4-(2,2,2-trifluoro-N-(2-(4-fluorobenzamido)-3-phenylpropyl)acetamido)benzene-1-sulfonyl Chloride

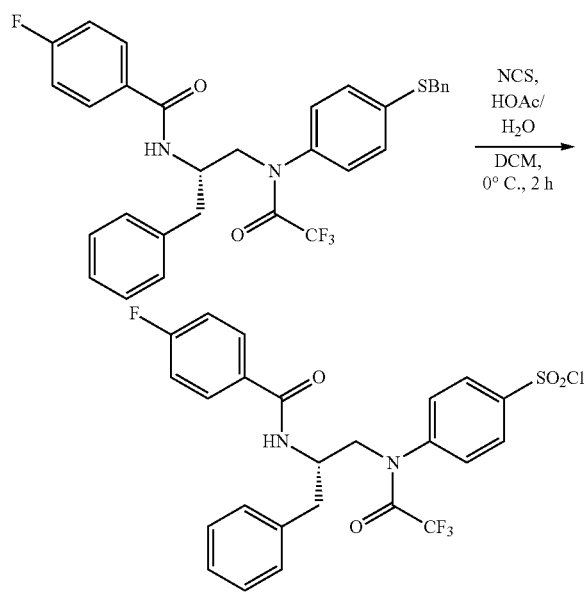

To a solution of 2.83 g N-((S)-1-((R)-3-(4-(benzylthio) phenyl)-2-oxooxazolidin-5-yl)-2-phenylethyl)-4-fluorobenzamide (5.00 mmol, 1.00 equiv), 60 mg acetic acid (1.0 mmol, 0.2 equiv) and 18 mg water (1.0 mmol, 0.2 equiv) in 30 mL dichloromethane was added 2.66 g N-chlorosuccinimide (20.0 mmol, 4.00 equiv) at 0° C. The mixture was stirred at room temperature for 2 hours and washed with 3×20 mL volumes of water. The organic phase was concentrated to give 1.62 g (S)-4-(2,2,2-trifluoro-N-(2-(4-fluorobenzamido)-3-phenylpropyl)acetamido)benzene-1-sulfonyl chloride as a white solid (60% yield). MS (ESI+) m/z 543 [M+H]+.

Preparation of (S)-N-(1-(N-(4-(N-tert-butylsulfamoyl)phenyl)-2,2,2-trifluoroacetamido)-3-phenylpropan-2-yl)-4-fluorobenzamide

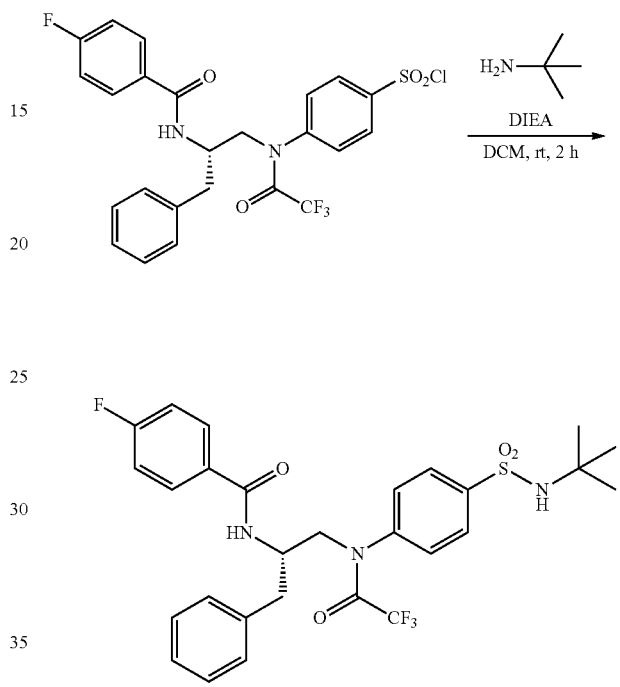

To the mixture of 803 mg 2-methylpropan-2-amine (11.0 mmol, 5.00 equiv) and 1.42 g N,N-diisopropylethylamine (11.0 mmol, 5.00 equiv) in 30 mL dichloromethane was added 1.19 g 4-((S)-5-((R)-1-(4-fluorobenzamido)-2-phenylethyl)-2-oxooxazolidin-3-yl)benzene-1-sulfonyl chloride (2.2 mmol, 1.0 equiv). The mixture was stirred at room temperature for 2 hours and concentrated in vacuo. The residue was purified by column chromatography on silica gel (petroleum ether:ethyl acetate (3:1, v:v) to give 892 mg (S)-N-(1-(N-(4-(N-tert-butylsulfamoyl)phenyl)-2,2,2-trifluoroacetamido)-3-phenylpropan-2-yl)-4-fluorobenzamide as a white solid (70% yield). MS (ESI+) m/z 580 [M+H]+.

Preparation of (S)-N-(1-(4-(N-tert-butylsulfamoyl) phenylamino)-3-phenylpropan-2-yl)-4-fluorobenzamide, I-44

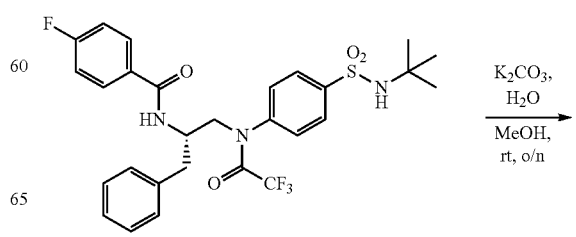

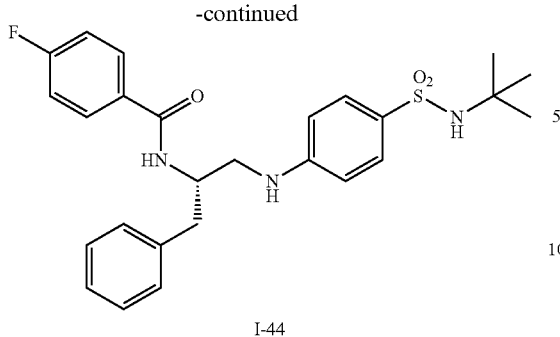

I-44

A mixture of 290 mg (S)-N-(1-(N-(4-(N-tert-butylsulfamoyl)phenyl)-2,2,2 trifluoroacetamido)-3-phenylpropan-2-yl)-4-fluorobenzamide (0.5 mmol, 1.00 equiv) and 138 mg potassium carbonate (1.0 mmol, 2.00 equiv) in 10 mL methanol was stirred at room temperature overnight. The mixture was diluted with 20 mL of water and washed with 3×20 mL volumes of ethyl acetate. The organic phase was concentrated and the residue was purified by reversed phase preparative HPLC on a Gilson GX-281. A concentrated solution of crude product dissolved in DMSO was injected in 675 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 9 mV threshold trigger on the 214 nm channel. Fractions containing product were combined, concentrated and lyophilized to afford 35.0 mg (S)-N-(1-(4-(benzylthio)phenylamino)-3-phenylpropan-2-yl)-4-fluorobenzamide (I-44) as a white solid (14% yield). MS (ESI$^+$) m/z 484 [M+H]$^+$; $^1$H NMR (400 MHz, DMSO) δ 8.36 (d, J=8.3 Hz, 1H), 7.89-7.71 (m, 2H), 7.44 (d, J=8.8 Hz, 2H), 7.32-6.90 (m, 8H), 6.73-6.49 (m, 3H), 4.36-4.23 (m, 1H), 3.30-3.23 (m, 1H), 3.23-3.08 (m, 1H), 2.89 (ddd, J=22.7, 13.7, 7.0 Hz, 2H), 1.02 (s, 9H).

Example 23: (S)-N-(1-(4-(N-tert-butylsulfamoyl)phenoxy)-3-phenylpropan-2-yl)-4-fluorobenzamide, I-45

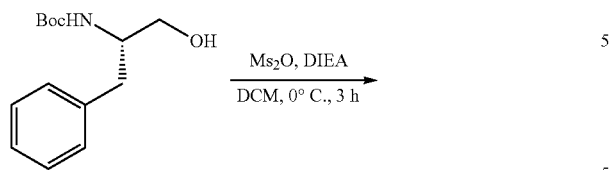

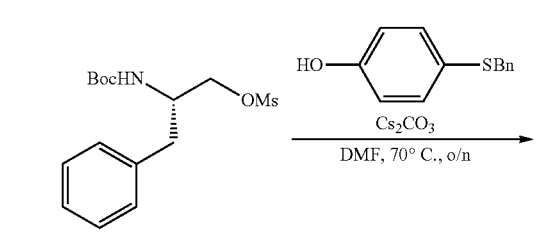

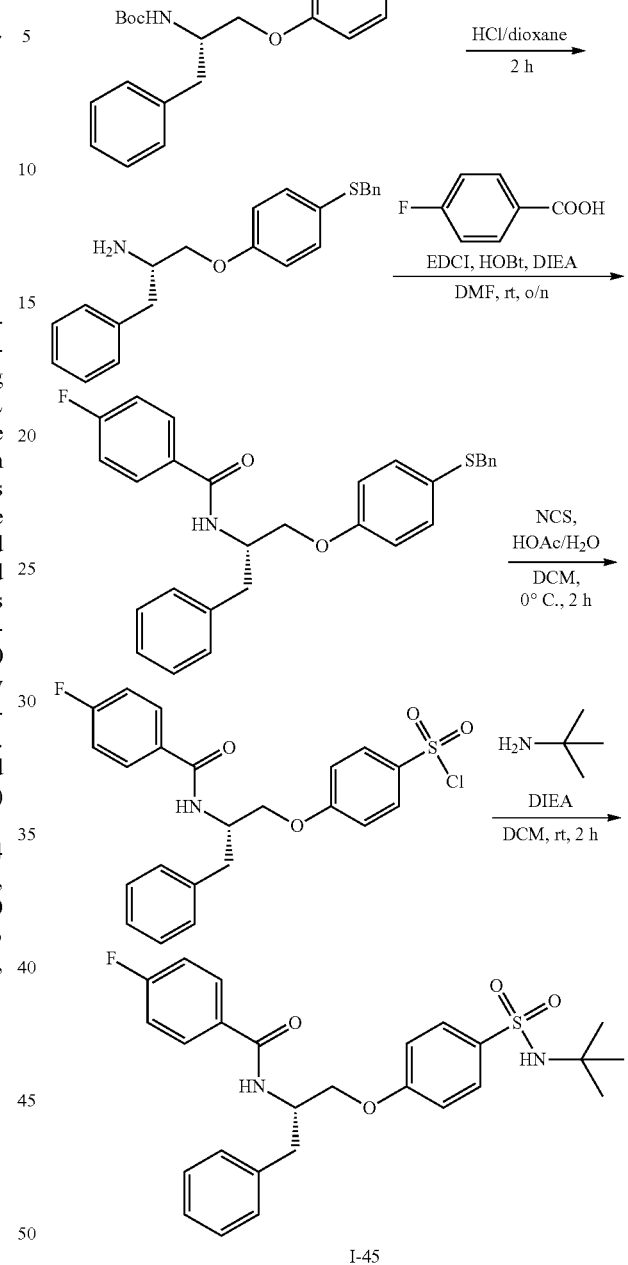

I-45

Preparation of (S)-2-(tert-butoxycarbonylamino)-3-phenylpropyl methanesulfonate

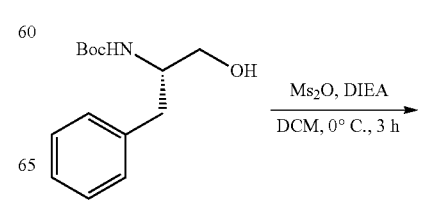

-continued

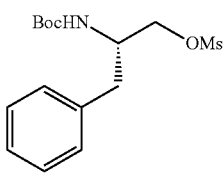

To the mixture of 2.51 g (S)-tert-butyl 1-hydroxy-3-phenylpropan-2-ylcarbamate (10.0 mmol, 1.00 equiv) and 2.58 g N,N-diisopropylethylamine (20.0 mmol, 2.00 equiv) in 30 mL dichloromethane was added 1.74 g methanesulfonic anhydride (10.0 mmol, 1.0 equiv). The mixture was stirred at 0° C. for 3 hours. The mixture was diluted with 100 mL water and washed with 3×100 mL volumes of ethyl acetate. The organic phase was concentrated and the residue was purified by column chromatography on silica gel (petroleum ether:ethyl acetate (10:1, v:v)) to yield 2.30 g (S)-2-(tert-butoxycarbonylamino)-3-phenylpropyl methanesulfonate as a light yellow oil (70% yield). MS (ESI$^+$) m/z 330 [M+H]$^+$.

Preparation of (S)-tert-butyl 1-(4-(benzylthio)phenoxy)-3-phenylpropan-2-ylcarbamate

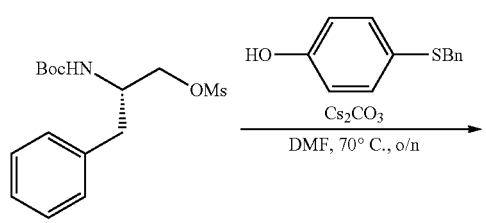

A mixture of 3.29 g (S)-2-(tert-butoxycarbonylamino)-3-phenylpropyl methanesulfonate (10.0 mmol, 1.00 equiv), 2.16 g 4-(benzylthio)phenol (10.0 mmol, 1.00 equiv) and 6.50 g cesium carbonate (20.0 mmol, 2.00 equiv) in 20 mL N,N-dimethylformamide was stirred at 70° C. overnight. The mixture was diluted with 20 mL of water and washed with 3×20 mL volumes of ethyl acetate. The organic phase was concentrated and the residue was purified by column chromatography on silica gel (petroleum ether:ethyl acetate (10:1, v:v)) to give 3.14 g (S)-N-(1-(4-(benzylthio)phenylamino)-3-phenylpropan-2-yl)-4-fluorobenzamide as a white solid (70% yield). MS (ESI$^+$) m/z 450 [M+H]$^+$.

Preparation of (S)-1-(4-(benzylthio)phenoxy)-3-phenylpropan-2-amine

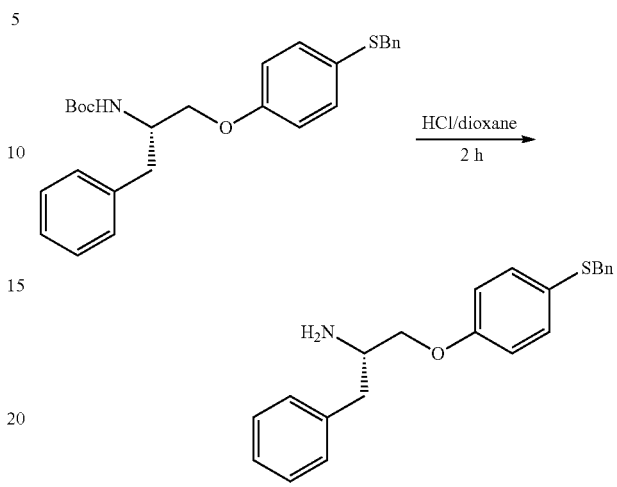

The mixture of 2.25 g (S)-N-(1-(4-(benzylthio)phenylamino)-3-phenylpropan-2-yl)-4-fluorobenzamide (5.0 mmol, 1.0 equiv) in 20 mL hydrochloric acid in dioxane (4.0 M HCl) was stirred at room temperature for 2 hours. The mixture was concentrated to give 1.25 g (S)-1-(4-(benzylthio)phenoxy)-3-phenylpropan-2-amine as a white solid (100% yield). MS (ESI$^+$) m/z 350 [M+H]$^+$.

Preparation of (S)-N-(1-(4-(benzylthio)phenoxy)-3-phenylpropan-2-yl)-4-fluorobenzamide

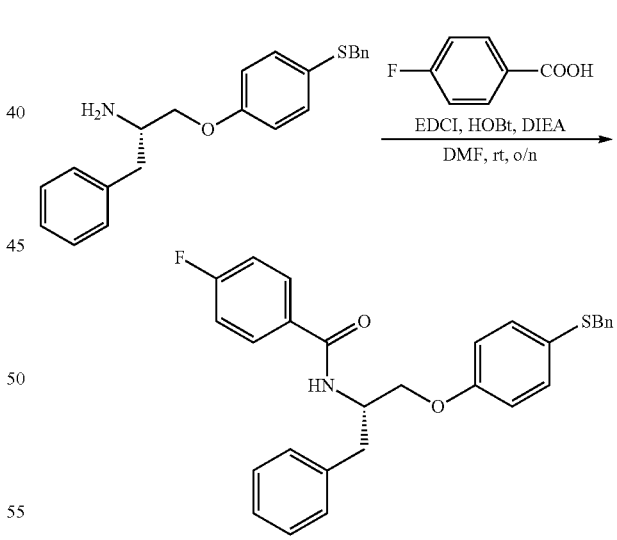

A mixture of 1.75 g (S)-1-(4-(benzylthio)phenoxy)-3-phenylpropan-2-amine (5.0 mmol, 1.00 equiv), 700 mg 4-fluorobenzoic acid (5.0 mmol, 1.00 equiv), 1.44 g N-(3-dimethylaminopropyl)-N'-ethylcarbodiimide hydrochloride (7.5 mmol, 1.50 equiv), 810 mg 1-hydroxybenzotriazole (6.0 mmol, 1.20 equiv) and 1.29 g N,N-diisopropylethylamine (10.0 mmol, 2.00 equiv) in 30 mL N,N-dimethylformamide was stirred at room temperature overnight. The mixture was diluted with 100 mL of ethyl acetate and washed with 3×100 mL volumes of water. The organic phase was concentrated and the residue was purified by column chromatography on silica gel (petroleum ether:ethyl acetate (5:1, v:v)) to give 1.81 g (S)-N-(1-(4-(benzylthio)phenoxy)-3-phenylpropan-2-yl)-4-fluorobenzamide as a white solid (80% yield). MS (ESI$^+$) m/z 472 [M+H]$^+$.

Preparation of (S)-4-(2-(4-fluorobenzamido)-3-phenylpropoxy)benzene-1-sulfonyl Chloride

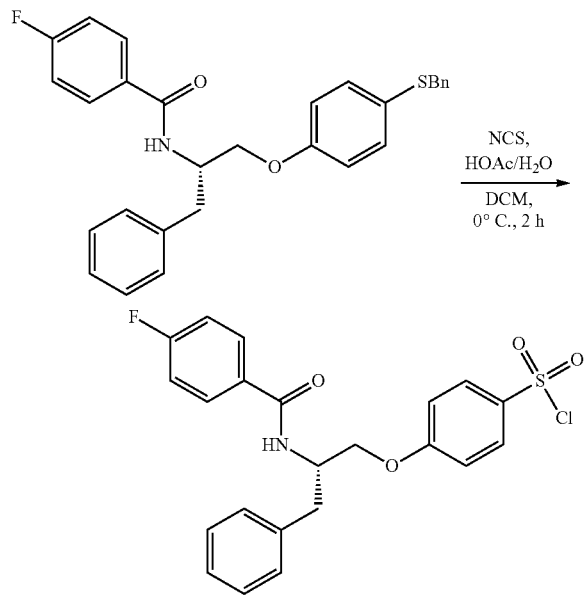

To a solution of 2.35 g N-((S)-1-((R)-3-(4-(benzylthio)phenyl)-2-oxooxazolidin-5-yl)-2-phenylethyl)-4-fluorobenzamide (5.00 mmol, 1.00 equiv), 60 mg acetic acid (1.0 mmol, 0.2 equiv) and 18 mg water (1.0 mmol, 0.2 equiv) in 30 mL dichloromethane was added 2.66 g N-chlorosuccinimide (20.0 mmol, 4.00 equiv) at 0° C. The mixture was stirred at room temperature for 2 hours and washed with 3×20 mL volumes of water. The organic phase was concentrated to give 1.34 g (S)-4-(2-(4-fluorobenzamido)-3-phenylpropoxy)benzene-1-sulfonyl chloride as a white solid (60% yield). MS (ESI$^+$) m/z 448 [M+H]$^+$.

Preparation of (S)-N-(1-(4-(N-tert-butylsulfamoyl)phenoxy)-3-phenylpropan-2-yl)-4-fluorobenzamide, I-45

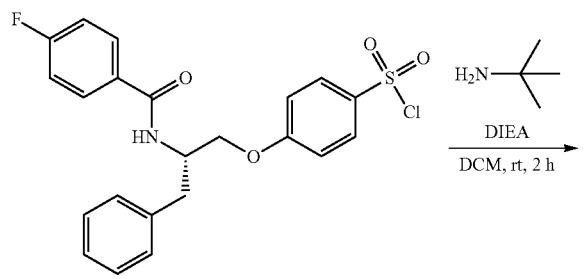

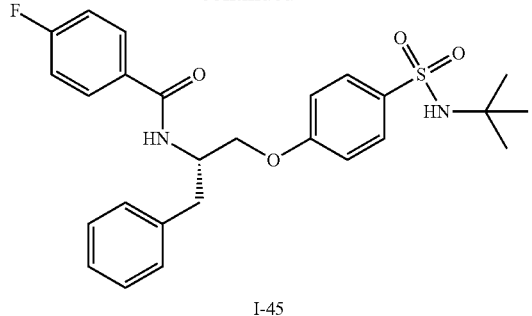

I-45

To the mixture of 730 mg 2-methylpropan-2-amine (10.0 mmol, 5.00 equiv) and 129 mg N,N-diisopropylethylamine (1.0 mmol, 5.00 equiv) in 30 mL dichloromethane was added 89 mg (S)-4-(2-(4-fluorobenzamido)-3-phenylpropoxy)benzene-1-sulfonyl chloride (0.2 mmol, 1.0 equiv). The mixture was stirred at room temperature for 2 hours and concentrated in vacuo. The residue was purified by preparative scale-HPLC. The compound was purified by reversed phase preparative HPLC on a Gilson GX-281. A concentrated solution of crude product dissolved in DMSO was injected in 550 uL volumes onto a 10 um C18 reversed phase Waters X-SELECT 19 mm diameter×250 mm length column eluting with a gradient of 58-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 15.0 mg (S)-N-(1-(4-(N-tert-butylsulfamoyl)phenoxy)-3-phenylpropan-2-yl)-4-fluorobenzamide (I-45) as a white solid (16% yield). MS (ESI$^+$) m/z 485 [M+H]$^+$; $^1$H NMR (400 MHz, d$_6$-DMSO) δ 8.54 (d, J=8.1 Hz, 1H), 7.94-7.78 (m, 2H), 7.72 (d, J=8.9 Hz, 2H), 7.43-7.22 (m, 7H), 7.22-7.13 (m, 1H), 7.10 (d, J=8.9 Hz, 2H), 4.51 (d, J=5.7 Hz, 1H), 4.13 (ddd, J=15.2, 9.9, 5.8 Hz, 2H), 3.00 (ddd, J=22.3, 13.7, 7.1 Hz, 2H), 1.06 (s, 9H).

Example 24: (S)-N-(4-(N-tert-butylsulfamoyl)phenyl)-2-(4-fluorobenzyloxy)-3-phenylpropanamide, I-46

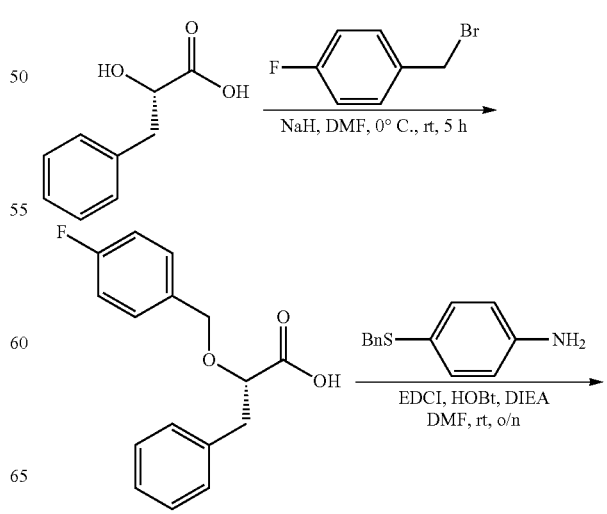

-continued

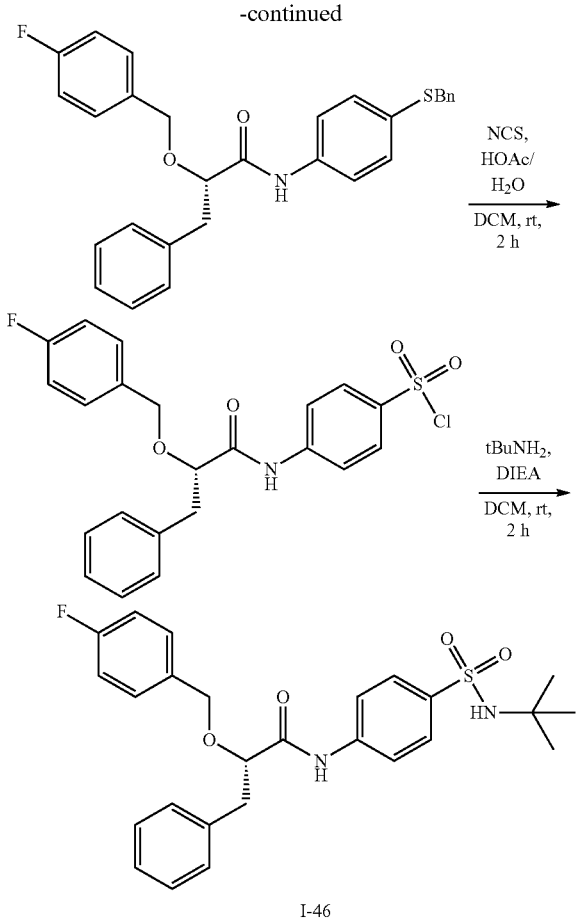

I-46

Preparation of (S)-2-(4-fluorobenzyloxy)-3-phenylpropanoic Acid

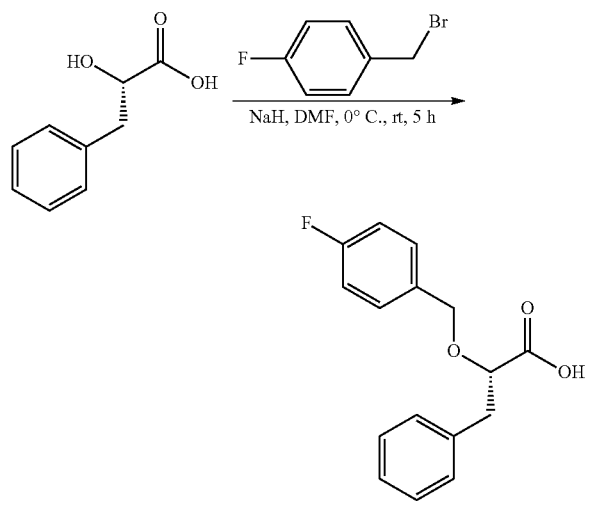

To a solution of 1.0 g (S)-2-hydroxy-3-phenylpropanoic acid (6.0 mmol, 1.00 equiv), and 1.36 g 1-(bromomethyl)-4-fluorobenzene (7.2 mmol, 1.20 equiv) dissolved in 30 mL anhydrous N,N-dimethylformamide at room temperature was added 0.72 g sodium hydride (60 wt. % dispersion in mineral oil; 18.0 mmol, 3.00 equiv) all at once. The reaction was stirred at room temperature for 5 hours. Then poured into 150 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. Purification by column chromatography (silica gel, Dichloromethane:Methanol (10:1, v:v)) afforded 450 mg (S)-2-(4-fluorobenzyloxy)-3-phenylpropanoic acid as a white solid (27% yield). MS (ESI$^+$) m/z 275 [M+H]$^+$.

Preparation of (S)-N-(4-(benzylthio)phenyl)-2-(4-fluorobenzyloxy)-3-phenylpropanamide

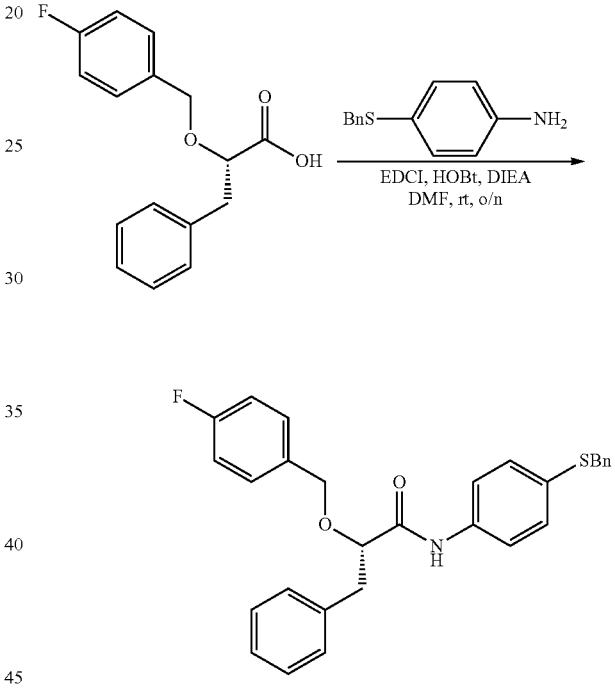

To a solution of 353 mg 4-(benzylthio)aniline (1.64 mmol, 1.00 equiv) and 450 mg (S)-2-(4-fluorobenzyloxy)-3-phenylpropanoic acid (1.64 mmol, 1.00 equiv) dissolved in 10 mL anhydrous N,N-dimethylformamide at room temperature was added 346 mg N-(3-Dimethylaminopropyl)-N'-ethylcarbodiimide hydrochloride (1.80 mmol, 1.10 equiv), 243 mg 1-hydroxybenzotriazole (1.80 mmol, 1.10 equiv), and 3464 mg N,N-diisopropylethylamine (3.60 mmol, 2.00 equiv) in succession. Then the reaction mixture was stirred at room temperature for overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (petroleum ether:ethyl acetate (3:1, v:v)) to afforded 500 mg (S)-N-(4-(benzylthio)phenyl)-2-(4-fluorobenzyloxy)-3-phenylpropanamide as a white solid (65% yield). MS (ESI$^+$) m/z 472 [M+H]$^+$.

Preparation of (S)-4-(2-(4-fluorobenzyloxy)-3-phenylpropanamido)benzene-1-sulfonyl Chloride

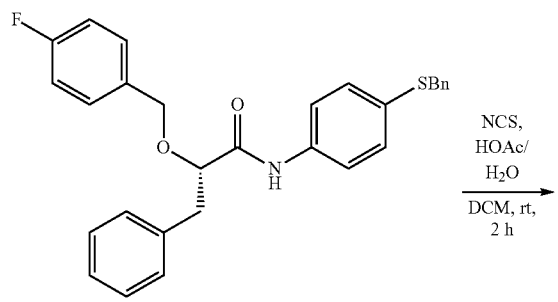

To a solution of 200 mg (S)-N-(4-(benzylthio)phenyl)-2-(4-fluorobenzyloxy)-3-phenylpropanamide (0.42 mmol, 1.00 equiv), 25 mg acetic acid (0.42 mmol, 1 equiv) and 7 mg water (0.42 mmol, 1 equiv) in 30 mL dichloromethane was added 228 mg N-chlorosuccinimide (1.68 mmol, 4.00 equiv) at 0° C. The mixture was stirred at room temperature for 2 hours and washed with 3×20 mL volumes of water. The organic phase was concentrated to give 190 mg crude (S)-4-(2-(4-fluorobenzyloxy)-3-phenylpropanamido)benzene-1-sulfonyl chloride as a gray solid (100% yield). MS (ESI$^+$) m/z 448[M+H]$^+$.

Preparation of (S)-N-(4-(N-tert-butylsulfamoyl)phenyl)-2-(4-fluorobenzyloxy)-3-phenylpropanamide, I-46

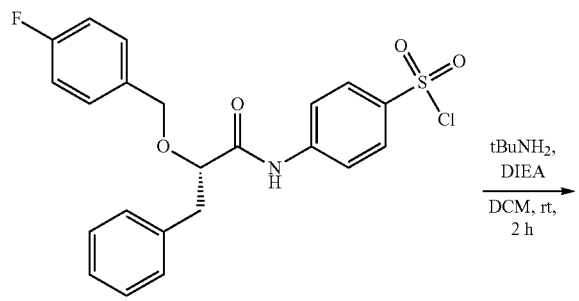

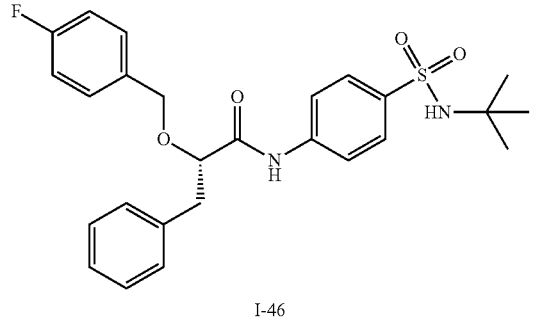

To a mixture of 155 mg 2-methylpropan-2-amine (2.1 mmol, 5.0 equiv) and 271 mg N,N-diisopropylethylamine (2.1 mmol, 5.00 equiv) in 10 mL dichloromethane was added 190 mg (S)-4-(2-(4-fluorobenzyloxy)-3-phenylpropanamido)benzene-1-sulfonyl chloride (0.42 mmol, 1.00 equiv). The mixture was stirred at room temperature for 2 hours and concentrated in vacuo. The residue was purified by reversed phase preparative HPLC on a Gilson GX-281. A concentrated solution of crude product dissolved in DMSO was injected in 500 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 55 mg (S)-N-(4-(N-tert-butylsulfamoyl)phenyl)-2-(4-fluorobenzyloxy)-3-phenylpropanamide (I-46) as a white solid (27% yield). MS (ESI$^+$) m/z 485 [M+H]$^+$. $^1$H NMR (400 MHz, d$_6$-DMSO) δ 10.26 (s, 1H), 7.78 (dd, J=20.8, 8.7 Hz, 4H), 7.42 (s, 1H), 7.33-7.17 (m, 7H), 7.08 (t, J=8.7 Hz, 2H), 4.58 (d, J=11.9 Hz, 1H), 4.39 (d, J=12.0 Hz, 1H), 4.25-4.14 (m, 1H), 3.03 (m, 2H), 1.08 (s, 9H).

Example 25a: 2-benzamido-N-(4-(N-ethylsulfamoyl)phenyl)-1,2,3,4-tetrahydronaphthalene-2-carboxamide, I-47

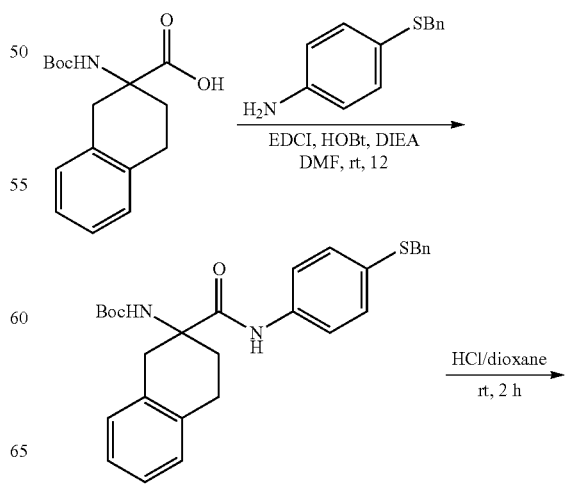

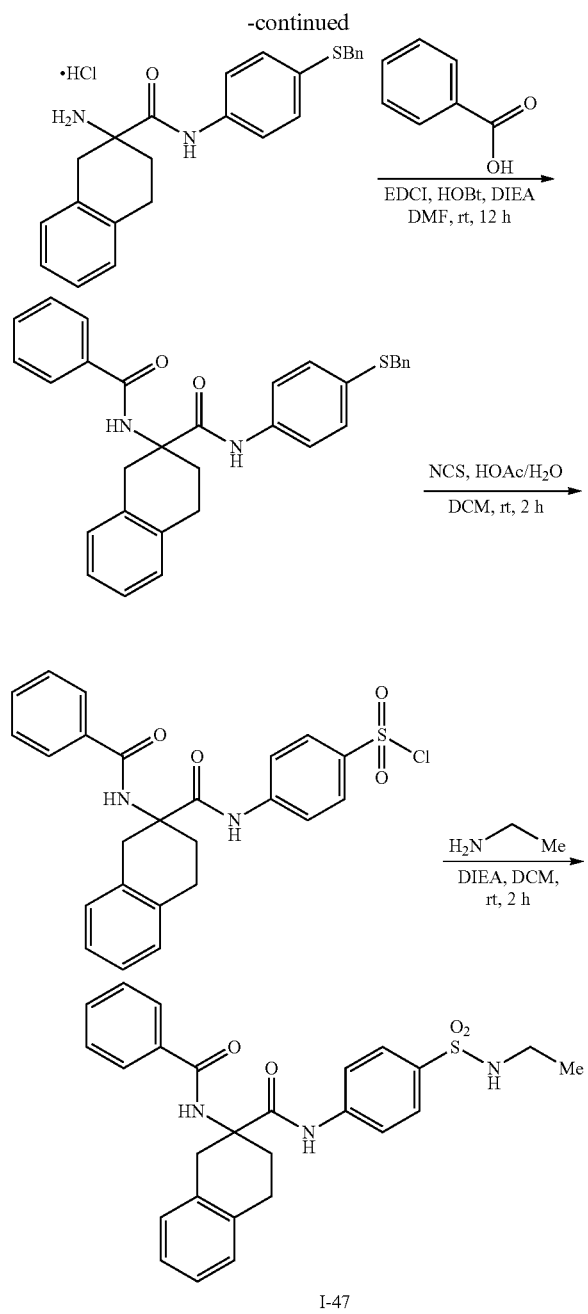

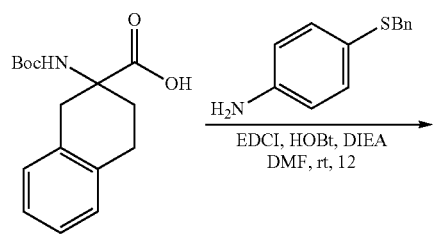

Preparation of tert-butyl 2-(4-(benzylthio)phenylcar-
bamoyl)-1,2,3,4-tetrahydronaphthalen-2-ylcarbamate

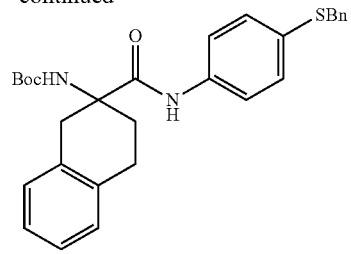

To a solution of 738 mg 4-(benzylthio)aniline (3.4 mmol, 1.00 equiv) and 1.0 g 2-(tert-butoxycarbonylamino)-1,2,3,4-tetrahydronaphthalene-2-carboxylic acid (3.4 mmol, 1.00 equiv) dissolved in 20 mL anhydrous N,N-dimethylformamide at room temperature was added 718 mg N-(3-Dimethylaminopropyl)-N'-ethylcarbodiimide hydrochloride (3.74 mmol, 1.10 equiv), 505 mg 1-hydroxybenzotriazole (3.74 mmol, 1.10 equiv), and 877 mg N,N-diisopropylethylamine (6.8 mmol, 2.00 equiv) in succession. Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (dichloromethane:ethyl acetate (5:1, v:v)) to afforded 1.2 g tert-butyl 2-(4-(benzylthio)phenylcarbamoyl)-1,2,3,4-tetrahydronaphthalen-2-ylcarbamate as a white solid (71% yield). MS (ESI$^+$) m/z 489 [M+H]$^+$.

Preparation of 2-amino-N-(4-(benzylthio)phenyl)-1,2,3,4-tetrahydronaphthalene-2-carboxamide, Hydrochloride

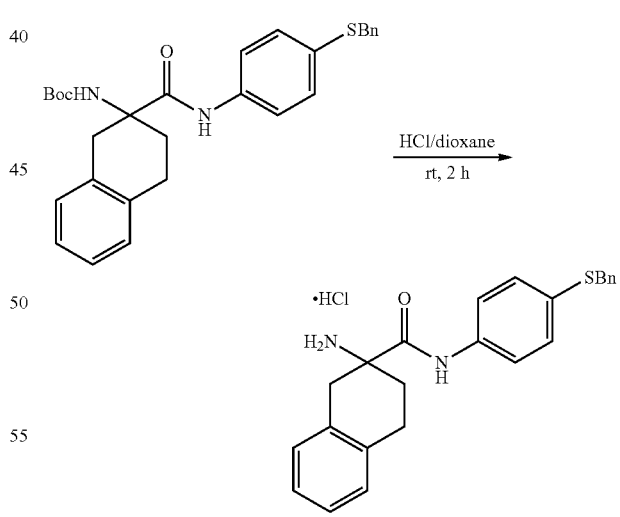

1.2 g tert-butyl 2-(4-(benzylthio)phenylcarbamoyl)-1,2,3,4-tetrahydronaphthalen-2-ylcarbamate (2.45 mmol, 1.00 equiv) was dissolved in 30 mL hydrochloric acid in dioxane (4.0 M HCl) and stirred at room temperature for 2 hours. The mixture was concentrated to afford 1.5 g crude 2-amino-N-(4-(benzylthio)phenyl)-1,2,3,4-tetrahydronaphthalene-2-carboxamide, hydrochloride as a light yellow solid (100% yield). MS (ESI$^+$) m/z 389 [M+H]$^+$.

Preparation of 2-benzamido-N-(4-(benzylthio)phenyl)-1,2,3,4-tetrahydronaphthalene-2-carboxamide

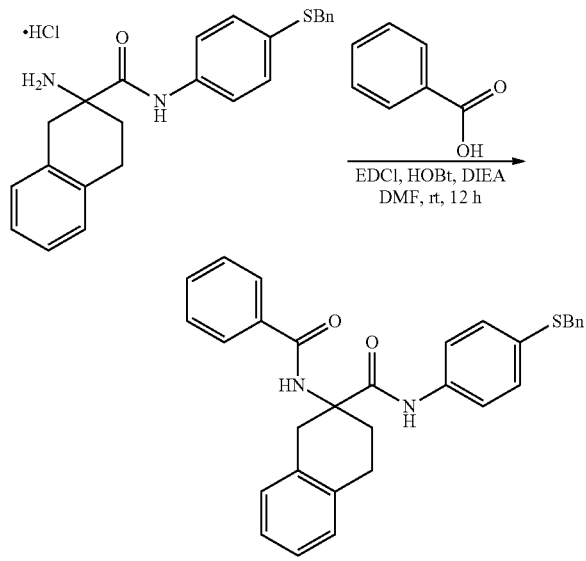

To a solution of 950 mg 2-amino-N-(4-(benzylthio)phenyl)-1,2,3,4-tetrahydronaphthalene-2-carboxamide, hydrochloride (2.24 mmol, 1.00 equiv) and 273 mg benzoic acid (2.24 mmol, 1.00 equiv) dissolved in 10 mL anhydrous N,N-dimethylformamide at room temperature was added 473 mg N-(3-Dimethylaminopropyl)-N'-ethylcarbodiimide hydrochloride (2.46 mmol, 1.10 equiv), 332 mg 1-hydroxybenzotriazole (2.46 mmol, 1.10 equiv), and 578 mg N,N-diisopropylethylamine (4.48 mmol, 2.00 equiv) in succession. Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (dichlormethane:methanol (15:1, v:v)) to give 1.0 g 2-benzamido-N-(4-(benzylthio)phenyl)-1,2,3,4-tetrahydronaphthalene-2-carboxamide as a white solid (90% yield). MS (ESI$^+$) m/z 493[M+H]$^+$.

Preparation of 4-(2-benzamido-1,2,3,4-tetrahydronaphthalene-2-carboxamido)benzene-1-sulfonyl Chloride

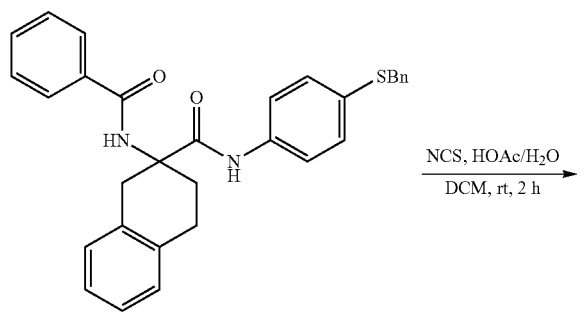

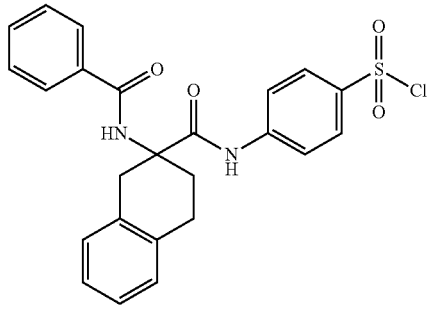

To a solution of 500 mg 2-benzamido-N-(4-(benzylthio)phenyl)-1,2,3,4-tetrahydronaphthalene-2-carboxamide (1.0 mmol, 1.00 equiv), 60 mg acetic acid (1.0 mmol, 1 equiv) and 18 mg water (1.0 mmol, 1 equiv) in 30 mL dichloromethane was added 542 mg N-chlorosuccinimide (4.0 mmol, 4.00 equiv) at 0° C. The mixture was stirred at room temperature for 2 hours and washed with 3×20 mL volumes of water. The organic phase was concentrated to give 400 mg crude 4-(2-benzamido-1,2,3,4-tetrahydronaphthalene-2-carboxamido)benzene-1-sulfonyl chloride as a gray solid (84% yield). MS (ESI$^+$) m/z 469[M+H]$^+$.

Preparation of 2-benzamido-N-(4-(N-ethylsulfamoyl)phenyl)-1,2,3,4-tetrahydronaphthalene-2-carboxamide, I-47

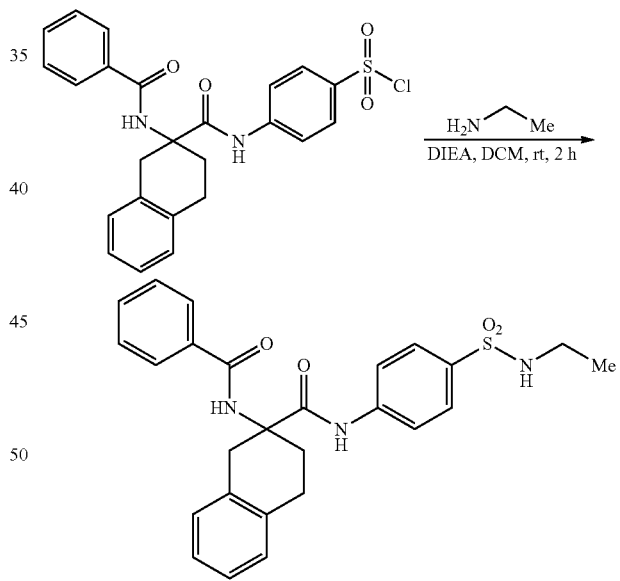

I-47

To a mixture of 95 mg ethanamine (2.1 mmol, 5.0 equiv) and 271 mg N,N-diisopropylethylamine (2.1 mmol, 5.00 equiv) in 10 mL dichloromethane was added 200 mg 4-(2-benzamido-1,2,3,4-tetrahydronaphthalene-2-carboxamido)benzene-1-sulfonyl chloride (0.42 mmol, 1.00 equiv). The mixture was stirred at room temperature for 2 hours and concentrated in vacuo. The residue was purified by reversed phase preparative HPLC on a Gilson GX-281. A concentrated solution of crude product dissolved in DMSO was injected in 500 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 2 mV threshold trigger on the 214 nm channel. Fractions containing product were combined, concentrated and lyophilized to afford 35 mg 2-benzamido-N-(4-(N-ethylsulfamoyl)phenyl)-1,2,3,4-tetrahydronaphthalene-2-carboxamide (I-47) as a white solid (17% yield). MS (ESI+) m/z 478 [M+H]+. 1H NMR (400 MHz, d6-DMSO) δ 9.95 (s, 1H), 8.35 (s, 1H), 7.86-7.75 (m, 4H), 7.66 (d, J=8.9 Hz, 2H), 7.51 (t, J=7.3 Hz, 1H), 7.40 (m, 3H), 7.08 (dd, J=6.4, 3.5 Hz, 4H), 3.48 (d, J=16.9 Hz, 1H), 3.14 (d, J=16.7 Hz, 1H), 2.80 (s, 1H), 2.78-2.63 (m, 3H), 2.57-2.50 (m, 1H), 2.21 (m, 1H), 0.92 (t, J=7.2 Hz, 3H).

Example 25b: 2-benzamido-N-(4-(N-tert-butylsulfamoyl)phenyl)-1,2,3,4-tetrahydronaphthalene-2-carboxamide, I-48

Preparation of 2-benzamido-N-(4-(N-tert-butylsulfamoyl)phenyl)-1,2,3,4-tetrahydronaphthalene-2-carboxamide, I-48

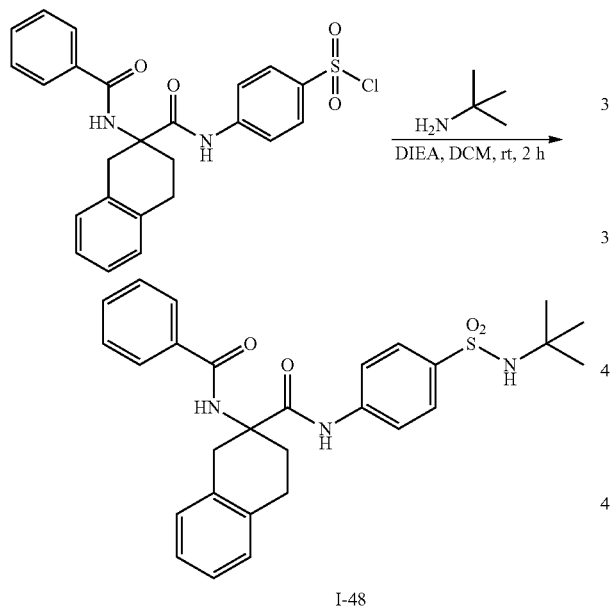

I-48

To a mixture of 156 mg 2-methylpropan-2-amine (2.1 mmol, 5.0 equiv) and 271 mg N,N-diisopropylethylamine (2.1 mmol, 5.00 equiv) in 10 mL dichloromethane was added 200 mg 4-(2-benzamido-1,2,3,4-tetrahydronaphthalene-2-carboxamido)benzene-1-sulfonyl chloride (0.42 mmol, 1.00 equiv). The mixture was stirred at room temperature for 2 hours and concentrated in vacuo. The residue was purified by reversed phase preparative HPLC on a Gilson GX-281. A concentrated solution of crude product dissolved in DMSO was injected in 580 uL volumes onto a 10 um C18 reversed phase Waters X-SELECT 19 mm diameter×250 mm length column eluting with a gradient of 52-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 36 mg 2-benzamido-N-(4-(N-tert-butylsulfamoyl)phenyl)-1,2,3,4-tetrahydronaphthalene-2-carboxamide (I-48) as a white solid (17% yield). MS (ESI+) m/z 506 [M+H]+. 1H NMR (400 MHz, d6-DMSO) δ 9.91 (s, 1H), 8.33 (s, 1H), 7.86-7.81 (m, 2H), 7.72 (dd, J=20.5, 9.0 Hz, 4H), 7.51 (t, J=7.3 Hz, 1H), 7.42 (t, J=7.5 Hz, 2H), 7.35 (s, 1H), 7.08 (dd, J=6.3, 3.5 Hz, 4H), 3.48 (d, J=16.7 Hz, 1H), 3.15 (d, J=16.9 Hz, 1H), 2.83-2.67 (m, 2H), 2.58-2.52 (m, 1H), 2.21 (m, 1H), 1.05 (s, 9H).

Example 26: N-(4-(N-ethylsulfamoyl)phenyl)-2-(4-fluorobenzoyl)-1,2,3,4-tetrahydroisoquinoline-3-carboxamide, I-49

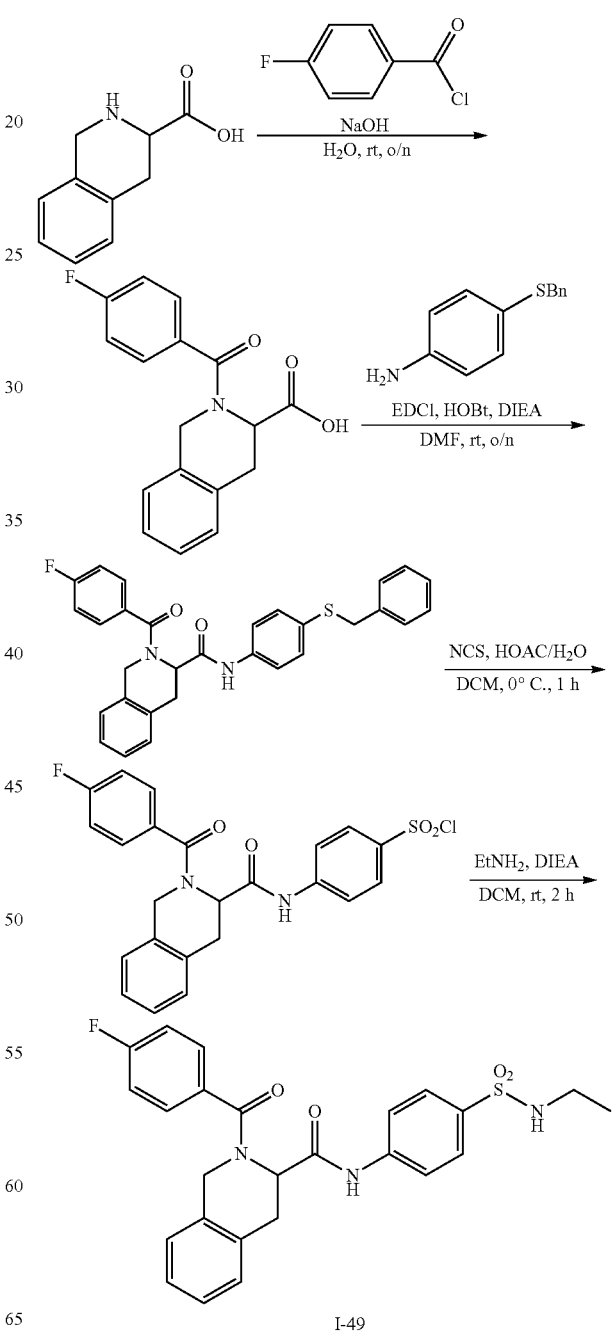

I-49

Preparation of 2-(4-fluorobenzoyl)-1,2,3,4-tetrahydroisoquinoline-3-carboxylic Acid

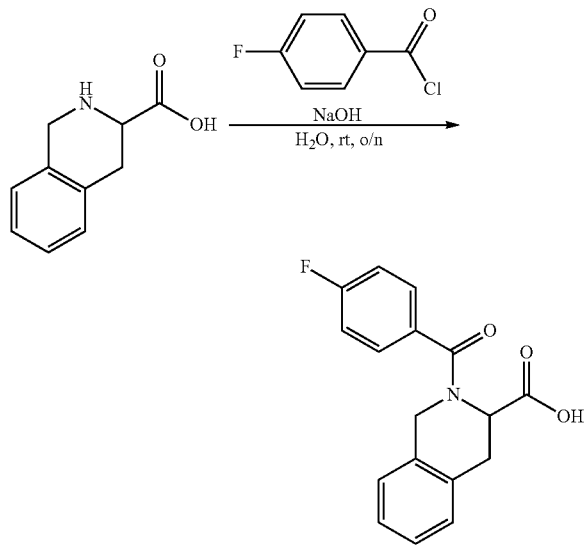

To a solution of 1.77 g 1,2,3,4-tetrahydroisoquinoline-3-carboxylic acid (10.0 mmol, 1.00 equiv) and 800 mg sodium hydroxide (20.0 mmol, 2.00 equiv) in 50 mL water was added 1.57 g 4-fluorobenzoyl chloride (10.0 mmol, 1.00 equiv). The mixture was stirred overnight at room temperature. 2.5 mL concentrated hydrochloric acid was added and filtered to give 2.40 g 2-(4-fluorobenzoyl)-1,2,3,4-tetrahydroisoquinoline-3-carboxylic acid as a white solid (80% yield). MS (ESI$^+$) m/z 300 [M+H]$^+$.

Preparation of N-(4-(benzylthio)phenyl)-2-(4-fluorobenzoyl)-1,2,3,4-tetrahydroisoquinoline-3-carboxamide

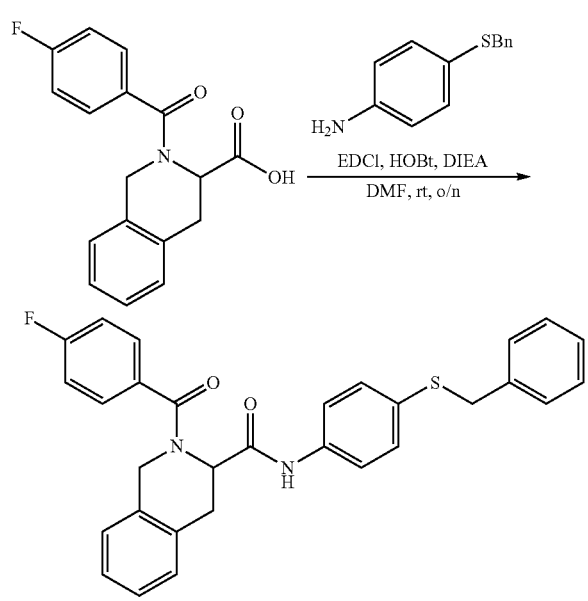

A mixture of 2.99 g 2-(4-fluorobenzoyl)-1,2,3,4-tetrahydroisoquinoline-3-carboxylic acid (10.0 mmol, 1.0 equiv), 2.15 g 4-(benzylthio)aniline (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.2 equiv) and 2.58 g N,N-diisopropylethylamine (20.0 mmol, 2.00 equiv) in 20 mL N,N-dimethylformamide was stirred at room temperature overnight. The mixture was diluted with 100 mL ethyl acetate and washed with 3×100 mL volumes of water. The organic phase was concentrated and the residue was purified by column chromatography on silica gel (petroleum ether: ethyl acetate (5:1, v:v)) to yield 3.96 g N-(4-(benzylthio)phenyl)-2-(4-fluorobenzoyl)-1,2,3,4-tetrahydroisoquinoline-3-carboxamide as a light yellow solid (80% yield). MS (ESI$^+$) m/z 497 [M+H]$^+$.

Preparation of 4-(2-(4-fluorobenzoyl)-1,2,3,4-tetrahydroisoquinoline-3-carboxamido)benzene-1-sulfonyl Chloride

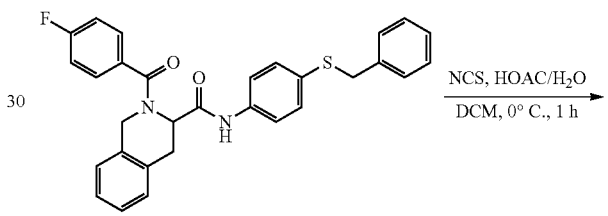

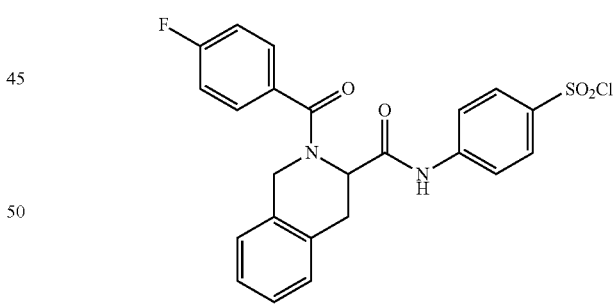

To a solution of 496 mg N-(4-(benzylthio)phenyl)-2-(4-fluorobenzoyl)-1,2,3,4-tetrahydroisoquinoline-3-carboxamide (1.00 mmol, 1.00 equiv), 12 mg acetic acid (1.0 mmol, 0.2 equiv) and 1.5 mg water (1.0 mmol, 0.2 equiv) in 10 mL dichloromethane was added 532 g N-chlorosuccinimide (4.0 mmol, 4.00 equiv) at 0° C. The mixture was stirred at room temperature for 1 hour and washed with 3×20 mL volumes of water. The organic phase was concentrated to give 330 mg 4-(2-(4-fluorobenzoyl)-1,2,3,4-tetrahydroisoquinoline-3-carboxamido)benzene-1-sulfonyl chloride as a white solid (70% yield). MS (ESI$^+$) m/z 473 [M+H]$^+$.

305

Preparation of N-(4-(N-ethylsulfamoyl)phenyl)-2-(4-fluorobenzoyl)-1,2,3,4-tetrahydroisoquinoline-3-carboxamide, I-49

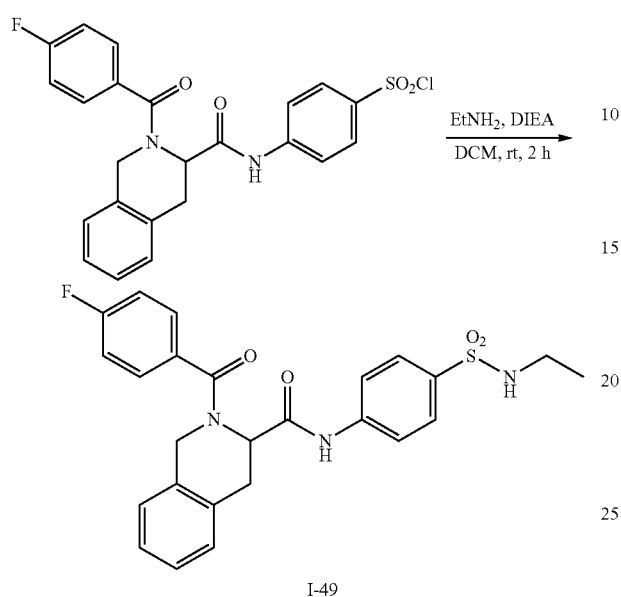

I-49

To the mixture of 50 mg ethanamine (1.10 mmol, 5.00 equiv) and 142 mg N,N-diisopropylethylamine (1.10 mmol, 5.00 equiv) in 10 mL dichloromethane was added 104 mg 4-(2-(4-fluorobenzoyl)-1,2,3,4-tetrahydroisoquinoline-3-carboxamido)benzene-1-sulfonyl chloride (0.22 mmol, 1.0 equiv). The mixture was stirred at room temperature for 2 hours and concentrated in vacuo. The residue was purified by reversed phase preparative HPLC on a Gilson GX-281. A concentrated solution of crude product dissolved in DMSO was injected in 600 uL volumes onto a 10 um C18 reversed phase Waters X-SELECT 19 mm diameter×250 mm length column eluting with a gradient of 44-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 40.0 mg N-(4-(N-ethylsulfamoyl)phenyl)-2-(4-fluorobenzoyl)-1,2,3,4-tetrahydroisoquinoline-3-carboxamide (I-49) as a white solid (38% yield). MS (ESI$^+$) m/z 482 [M+H]$^+$; $^1$H NMR (400 MHz, d$_6$-DMSO) δ 10.55 (s, 1H), 7.77-7.09 (m, 13H), 4.94-4.93 (m, 1H), 4.69-4.60 (m, 2H), 3.16-3.25 (m, 2H), 2.76-2.66 (m, 2H), 0.94 (t, J=7.2 Hz, 3H).

Example 27: N-(4-(N-tert-butylsulfamoyl)phenyl)-2-(4-fluorobenzoyl)-1,2,3,4-tetrahydro-2,6-naphthyridine-3-carboxamide, I-50

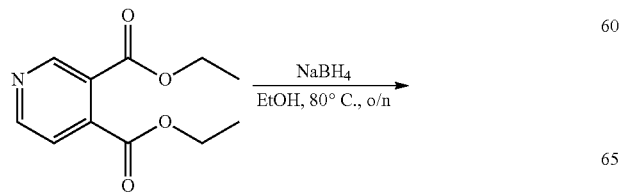

306

-continued

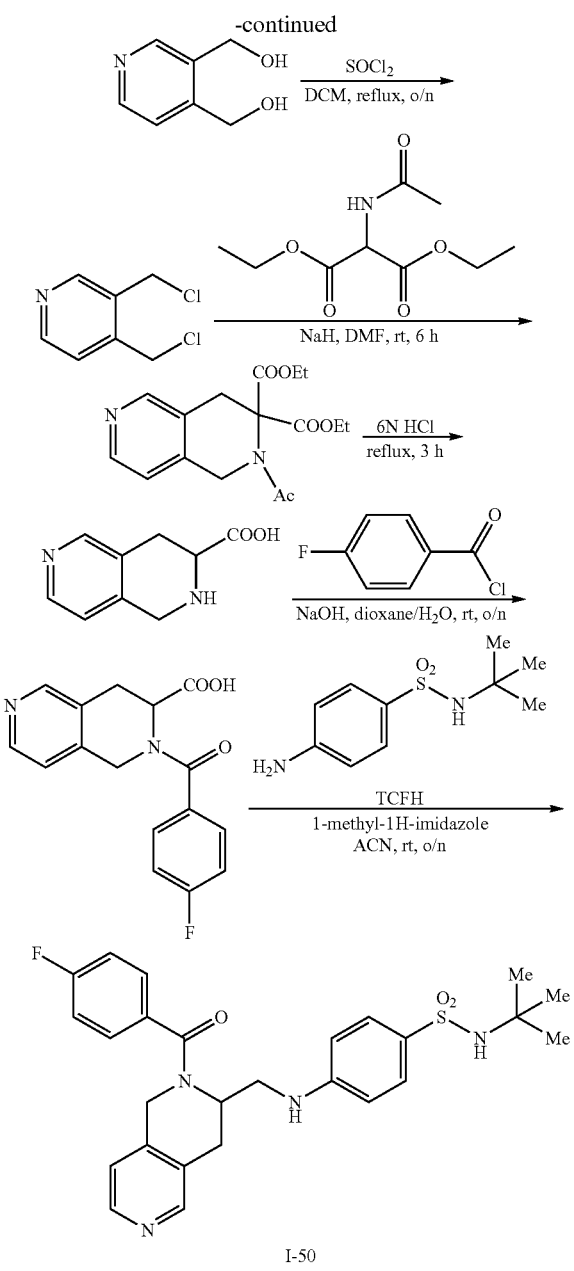

I-50

Preparation of pyridine-3,4-diyldimethanol

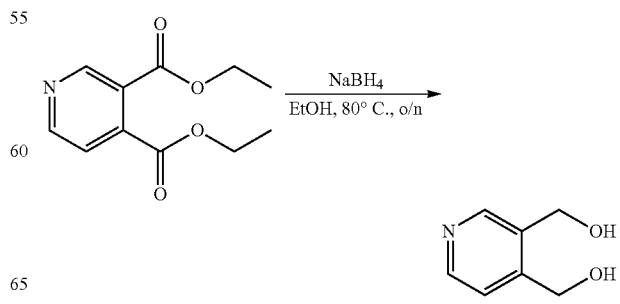

3.4 g Sodium borohydride (89.7 mmol, 4.00 equiv) was added in portions to a solution of 5 g diethyl pyridine-3,4-dicarboxylate (22.4 mmol, 1.00 equiv) in 200 mL ethanol under ice-cooling, and then the resulting mixture was at 80° C. for overnight. After 200 mL ethanol had been added to the hot reaction mixture, insoluble matter was removed by filtration while the diluted mixture was still hot. The filtrate was concentrated in vacuo. The obtained residue was purified by column chromatography on silica gel (chloroform:methanol:triethylamine (15:5:1, v:v:v)) to afforded 3.0 g pyridine-3,4-diyldimethanol as an orange oil (97% yield). MS (ESI$^+$) m/z 140 [M+H]$^+$.

Preparation of 3,4-bis(chloromethyl)pyridine

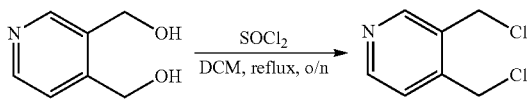

20 mL Thionyl chloride was added to a solution of 3.0 g pyridine-3,4-diyldimethanol (21.5 mmol, 1.00 equiv) in 20 mL dichloromethane under ice-cooling, and then the resulting mixture was stirred at 45° C. overnight. After having been cooled to room temperature, the reaction mixture was concentrated in vacuo to give hydrochloride salt of the title compound as a brown powder. The powder was dissolved in a saturated aqueous solution of sodium hydrogen carbonate, and then the solution was extracted with ethyl acetate. The organic layer was washed with a saturated aqueous solution of sodium chloride, dried over magnesium sulfate, and concentrated in vacuo. The obtained residue was purified by column chromatography on silica gel (ethyl acetate) to afforded 1.8 g 3,4-bis(chloromethyl)pyridine as a dark brown oil (48% yield). MS (ESI$^+$) m/z 176 [M+H]$^+$.

Preparation of diethyl 2-acetyl-1,2-dihydro-2,6-naphthyridine-3,3(4H)-dicarboxylate

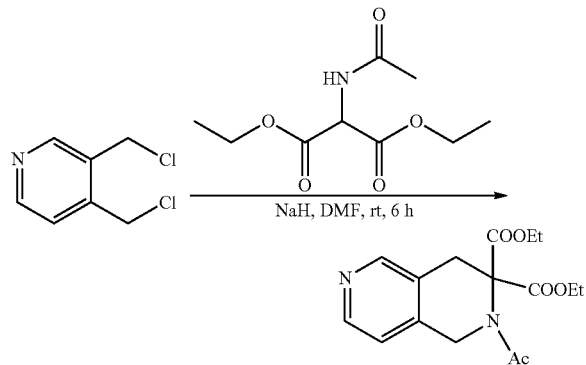

A 3.23 g sample of diethyl acetamidomalonate (10.2 mmol, 1.00 equiv) and 0.41 g sodium hydride (60 wt. % dispersion in mineral oil; 10.2 mmol, 1.00 equiv) were successively added at room temperature to a solution of 1.8 g 3,4-bis(chloromethyl)pyridine (10.2 mmol, 1.00 equiv) in 20 mL dimethylformamide, and then the resulting mixture was stirred at room temperature for 30 min. An additional 0.41 g of sodium hydride (60 wt. % dispersion in mineral oil; 10.2 mmol, 1.00 equiv) was added to the reaction mixture, and then the resulting mixture was stirred at room temperature for 6 h and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (ethyl acetate:methanol (20:1, v:v)) to afford 1.0 g diethyl 2-acetyl-1,2-dihydro-2,6-naphthyridine-3,3(4H)-dicarboxylate as a brown oil (30% yield). MS (ESI$^+$) m/z 321 [M+H]$^+$.

Preparation of 1,2,3,4-tetrahydro-2,6-naphthyridine-3-carboxylic Acid

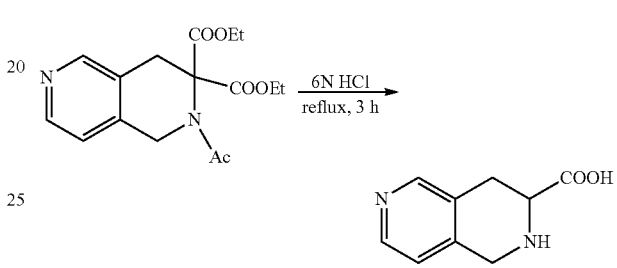

A 20 mL portion of hydrochloric acid (6.0 M HCl) was added to a mixture of diethyl 1.0 g 2-acetyl-1,2-dihydro-2,6-naphthyridine-3,3(4H)-dicarboxylate (3.1 mmol, 1.00 equiv), and then the resulting mixture was refluxed for 3 h. After having been cooled to room temperature, the reaction mixture was concentrated in vacuo. The residue was dissolved in 50 mL of dioxane, and the resulting mixture was concentrated in vacuo to afford 500 mg 1,2,3,4-tetrahydro-2,6-naphthyridine-3-carboxylic acid as a brown powder (90% yield). MS (ESI$^+$) m/z 179 [M+H]$^+$.

Preparation of 2-(4-fluorobenzoyl)-1,2,3,4-tetrahydro-2,6-naphthyridine-3-carboxylic Acid

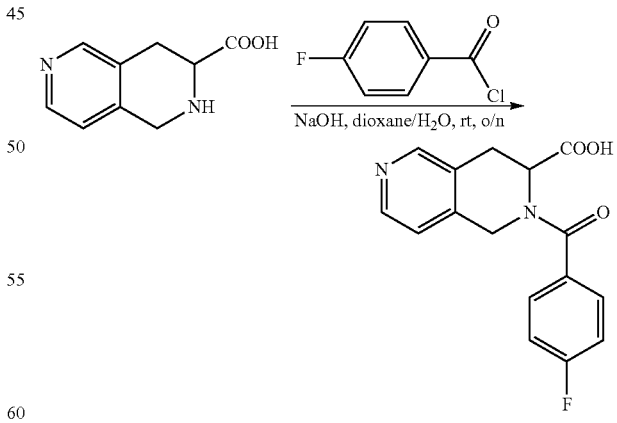

To a solution of 500 mg 1,2,3,4-tetrahydro-2,6-naphthyridine-3-carboxylic acid (2.8 mmol, 1.00 equiv) and 224 mg Sodium hydroxide (5.6 mmol, 2.00 equiv) dissolved in 20 mL (dioxane:H$_2$O (4:1, v:v)) at room temperature was added 487 mg 4-fluorobenzoyl chloride (3.08 mmol, 1.10 equiv). Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (ethyl acetate:methanol (10:1, v:v)) to give 800 mg 2-(4-fluorobenzoyl)-1,2,3,4-tetrahydro-2,6-naphthyridine-3-carboxylic acid as a white solid (95% yield). MS (ESI) m/z 301[M+H]$^+$.

Preparation of N-(4-(N-tert-butylsulfamoyl)phenyl)-2-(4-fluorobenzoyl)-1,2,3,4-tetrahydro-2,6-naphthyridine-3-carboxamide, I-50

[M+H]$^+$. $^1$H NMR (400 MHz, CDCl$_3$) δ 9.16 (s, 1H), 8.57 (s, 1H), 8.45 (d, J=5.0 Hz, 1H), 7.80 (d, J=8.3 Hz, 2H), 7.62 (d, J=8.2 Hz, 2H), 7.55-7.45 (m, 2H), 7.18 (t, J=8.3 Hz, 2H), 6.92 (s, 1H), 5.48 (s, 1H), 4.63 (d, J=26.1 Hz, 2H), 4.45 (d, J=16.6 Hz, 1H), 3.55 (d, J=16.1 Hz, 1H), 3.21 (dd, J=16.5, 6.6 Hz, 1H), 1.21 (s, 9H).

Example 28: (S)-N-(1-(4-(N-ethylsulfamoyl)phenylamino)-1-oxo-3-phenylpropan-2-yl)-4-fluoro-N-methylbenzamide, I-51

Preparation of (S)-N-(1-(4-(N-ethylsulfamoyl)phenylamino)-1-oxo-3-phenylpropan-2-yl)-4-fluoro-N-methylbenzamide, I-51

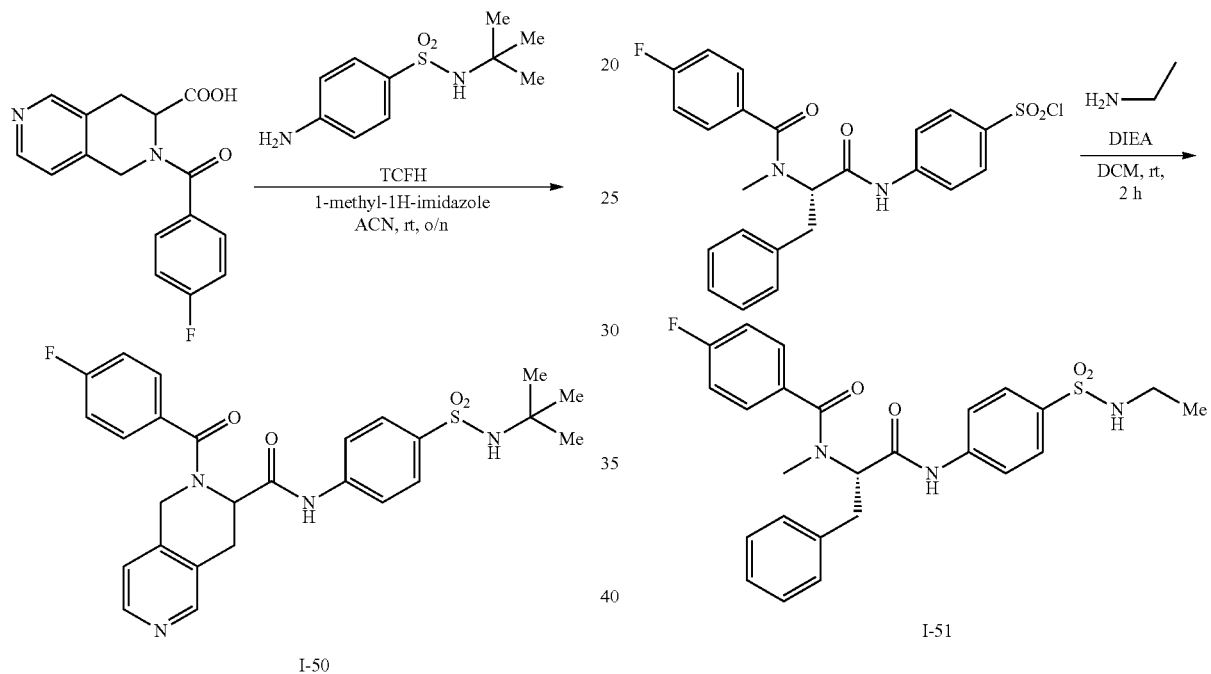

I-50

I-51

A mixture of 200 mg 2-(4-fluorobenzoyl)-1,2,3,4-tetrahydro-2,6-naphthyridine-3-carboxylic acid (0.67 mmol, 1.00 equiv), 152 mg 4-amino-N-tert-butylbenzenesulfonamide (0.67 mmol, 1.00 equiv), 228 mg N,N,N',N'-tetramethylchloroformamidinium hexafluorophosphate (0.80 mmol, 1.20 equiv) and 192 mg 1-methyl-1H-imidazole (2.35 mmol, 3.50 equiv) in 2 mL acetonitrile was stirred at room temperature overnight. The mixture was diluted with 100 mL ethyl acetate and washed with 3×100 mL volumes of water. The organic phase was concentrated and the residue was purified by reversed phase preparative HPLC on a Gilson GX-281. A concentrated solution of crude product dissolved in DMSO was injected in 500 uL volumes onto a 10 um C18 reversed phase Waters X-SELECT 19 mm diameter×250 mm length column eluting with a gradient of 38-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 30 mg N-(4-(N-tert-butylsulfamoyl)phenyl)-2-(4-fluorobenzoyl)-1,2,3,4-tetrahydro-2,6-naphthyridine-3-carboxamide (I-50) as a white solid (8.8% yield). MS (ESI$^+$) m/z 511

To a mixture of 50 mg ethanamine (1.1 mmol, 5.0 equiv) and 142 mg N,N-diisopropylethylamine (1.1 mmol, 5.0 equiv) in 10 mL dichloromethane was added 100 mg (S)-4-(2-(4-fluoro-N-methylbenzamido)-3-phenylpropanamido)benzene-1-sulfonyl chloride (0.21 mmol, 1.00 equiv). The mixture was stirred at room temperature for 2 hours and concentrated. The residue was purified by reversed phase preparative HPLC on a Gilson GX-281. A concentrated solution of crude product dissolved in DMSO was injected in 600 uL volumes onto a 10 um C18 reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 30.0 mg (S)-N-(1-(4-(N-tert-butylsulfamoyl)phenylamino)-1-oxo-3-phenylpropan-2-yl)-4-fluoro-N-methylbenzamide (I-51) as a white solid (29% yield). MS (ESI$^+$) m/z 484 [M+H]$^+$; $^1$H NMR (400 MHz, CD$_3$OD) δ 7.79 (s, 4H), 7.37-7.27 (m, 6H), 7.19-7.09 (m, 3H), 5.57-5.53 (m, 1H), 3.49-3.42 (m, 1H), 3.27-3.16 (m, 2H), 2.98 (s, 2H), 2.88 (q, J=7.2 Hz, 2H), 1.06 (t, J=7.2 Hz, 3H).

Example 29: (S)-N-ethyl-N-(1-(4-(N-ethylsulfamoyl)phenylamino)-1-oxo-3-phenylpropan-2-yl)-4-fluorobenzamide, I-52

Preparation of (S)-2-(tert-butoxycarbonyl(ethyl)amino)-3-phenylpropanoic Acid

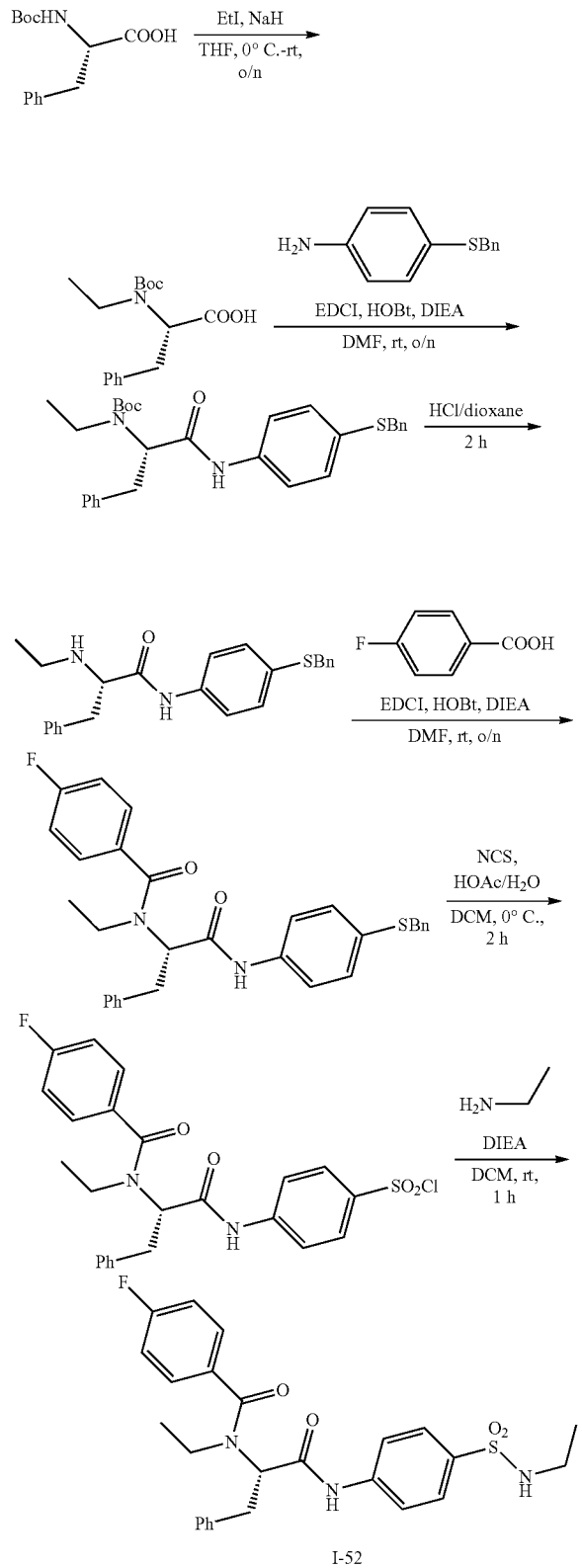

To a solution of 2.65 g (S)-2-(tert-butoxycarbonylamino)-3-phenylpropanoic acid (10.0 mmol, 1.00 equiv) in 20 mL tetrahydrofuran was added 0.80 g sodium hydride (60 wt. % dispersion in mineral oil, 20.0 mmol, 2.0 equiv) at 0° C. and the mixture was stirred for 30 minutes. Then 3.12 g iodoethane (20.0 mmol, 2.00 equiv) was added and the reaction was stirred at room temperature for overnight. The mixture was poured into 30 mL saturated aqueous ammonium chloride solution and extracted with 3×50 mL volumes of ethyl acetate. The combined organic phases were concentrated and the residue was purified by column chromatography on silica gel (petroleum ether:ethyl acetate (5:1, v:v)) to give 2.34 g (S)-2-(tert-butoxycarbonyl(methyl)amino)-3-phenylpropanoic acid as a light yellow solid (80% yield). MS (ESI$^+$) m/z 294 [M+H]$^+$.

Preparation of (S)-tert-butyl 1-(4-(benzylthio)phenylamino)-1-oxo-3-phenylpropan-2-yl(ethyl)carbamate A mixture of 2.94 g (S)-2-(tert-butoxycarbonyl(ethyl)amino)-3-phenylpropanoic acid (10.0 mmol, 1.00 equiv), 2.15 g 4-(benzylthio)aniline (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.20 equiv) and 2.58 g N,N-diisopropylethylamine (20.0 mmol, 2.00 equiv) in 20 mL N,N-dimethylformamide was stirred at room temperature overnight. The reaction was diluted with 100 mL ethyl acetate and washed with 3×100 mL volumes of water. The organic phases were concentrated and the residue was purified by column chromatography on silica gel (petroleum ether:ethyl acetate (5:1, v:v) to give 3.92 g (S)-tert-butyl 1-(4-(benzylthio)phenylamino)-1-oxo-3-phenylpropan-2-yl (ethyl)carbamate as a light yellow solid (80% yield). MS (ESI⁺) m/z 491 [M+H]⁺.

Preparation of (S)-N-(4-(benzylthio)phenyl)-2-(ethylamino)-3-phenylpropanamide

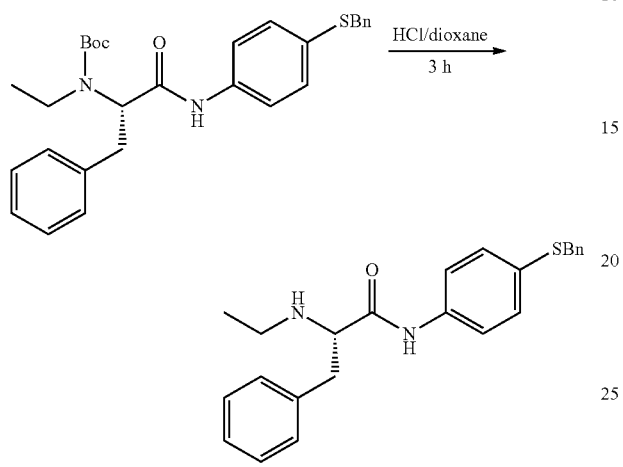

The mixture of 2.45 g (S)-tert-butyl1-(4-(benzylthio)phenylamino)-1-oxo-3-phenylpropan-2-yl(ethyl)carbamate (5.0 mmol, 1.0 equiv) in 20 mL hydrochloric acid in dioxane (4.0 M HCl) was stirred at room temperature for 3 hours. The mixture was concentrated to give 1.95 g (S)-N-(4-(benzylthio)phenyl)-2-(ethylamino)-3-phenylpropanamide as a light yellow solid (100% yield). MS (ESI⁺) m/z 391 [M+H]⁺.

Preparation of (S)-N-(1-(4-(benzylthio)phenylamino)-1-oxo-3-phenylpropan-2-yl)-4-fluoro-N-ethylbenzamide

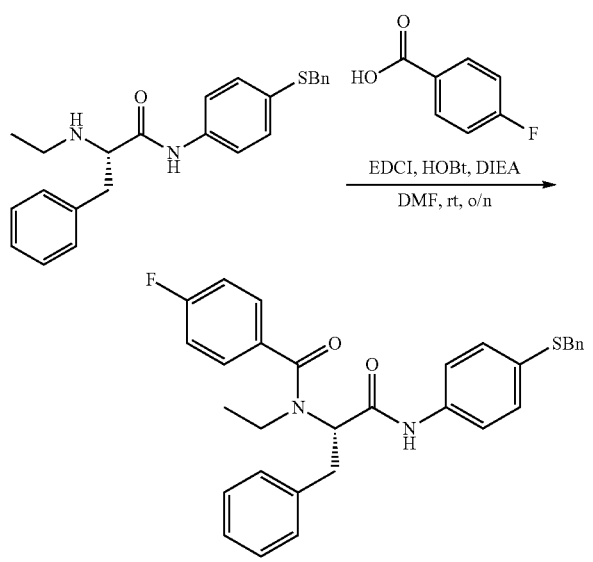

A mixture of 3.91 g (S)-N-(4-(benzylthio)phenyl)-2-(ethylamino)-3-phenylpropanamide (10.0 mmol, 1.00 equiv), 1.40 g 4-fluorobenzoic acid (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.20 equiv) and 2.58 g N,N-diisopropylethylamine (20.0 mmol, 2.00 equiv) in 30 mL N,N-dimethylformamide was stirred at room temperature overnight. To the mixture was added 100 mL ethyl acetate and washed with 3×100 mL volumes of water. The organic phase was concentrated and the residue was purified by column chromatography on silica gel (petroleum ether:ethyl acetate (5:1, v:v) to give 4.10 g (S)-N-(1-(4-(benzylthio)phenylamino)-1-oxo-3-phenylpropan-2-yl)-4-fluoro-N-ethylbenzamide as a light yellow solid (80% yield). MS (ESI⁺) m/z 513 [M+H]⁺.

Preparation of (S)-4-(2-(4-fluoro-N-ethylbenzamido)-3-phenylpropanamido)benzene-1-sulfonyl Chloride

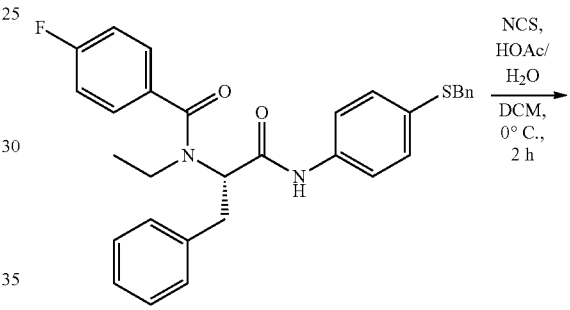

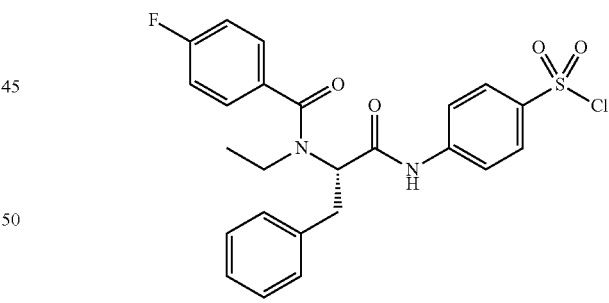

To a solution of 2.56 g (S)-N-(1-(4-(benzylthio)phenylamino)-1-oxo-3-phenylpropan-2-yl)-4-fluoro-N-ethylbenzamide (5.00 mmol, 1.00 equiv), 60 mg acetic acid (1.0 mmol, 0.2 equiv) and 18 mg water (1.0 mmol, 0.2 equiv) in 30 mL dichloromethane was added 2.66 g N-chlorosuccinimide (20.0 mmol, 4.00 equiv) at 0° C. The mixture was stirred at room temperature for 2 hours and washed with 3×20 mL volumes of water. The organic phase was concentrated to give 1.71 g (S)-4-(2-(4-fluoro-N-ethylbenzamido)-3-phenylpropanamido)benzene-1-sulfonyl chloride as a white solid (70% yield). MS (ESI⁺) m/z 489 [M+H]⁺.

315

Preparation of (S)-N-ethyl-N-(1-((4-(N-ethylsulfamoyl)phenyl)amino)-1-oxo-3-phenylpropan-2-yl)-4-fluorobenzamide, I-52

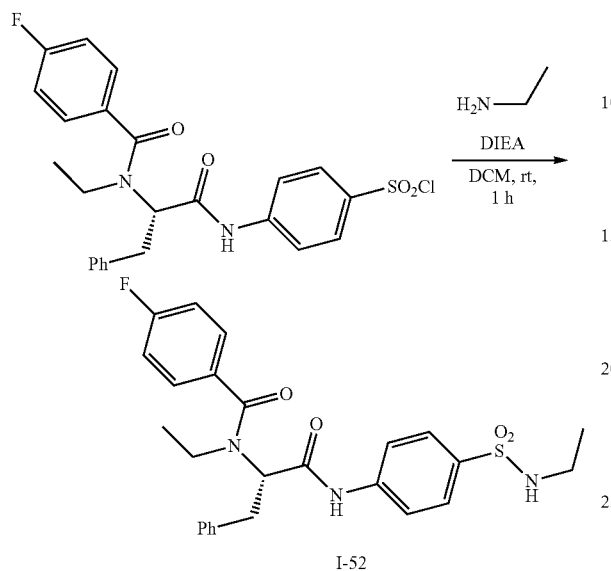

I-52

To a mixture of 50 mg ethylamine (1.1 mmol, 5.0 equiv) and 142 mg N,N-diisopropylethylamine (1.10 mmol, 5.00 equiv) in 10 mL dichloromethane was added 102 mg (S)-4-(2-(4-fluoro-N-ethylbenzamido)-3-phenylpropanamido)benzene-1-sulfonyl chloride (0.21 mmol, 1.00 equiv). The mixture was stirred at room temperature for 1 hour and concentrated. The residue was purified by reversed phase preparative HPLC on a Gilson GX-281. A concentrated solution of crude product dissolved in DMSO was injected in 663 uL volumes onto a 10 um C18 reversed phase Waters X-SELECT 19 mm diameter×250 mm length column eluting with a gradient of 52-95% acetonitrile in water with 10 mmol/liter ammonium carbonate. Peaks were detected by UV absorbance at 214 nm and 254 nm and fractions collected by 8.3 mV threshold trigger on the 214 nm channel. Fractions containing product were combined, concentrated and lyophilized to afford 15.0 mg (S)-N-(1-(4-(N-tert-butylsulfamoyl)phenylamino)-1-oxo-3-phenylpropan-2-yl)-4-fluoro-N-methylbenzamide (I-52) as a white solid (14% yield). MS (ESI+) m/z 498 [M+H]+; 1H NMR (400 MHz, CD3OD) δ 7.80-7.75 (m, 4H), 7.31-7.10 (m, 9H), 5.18-5.07 (m, 1H), 3.50-3.38 (m, 3H), 3.12-3.14 (m, 1H), 2.87 (d, J=7.2 Hz, 2H), 1.06-0.85 (m, 6H).

Example 30: N-(4-(N-tert-butylsulfamoyl)phenyl)-1-(4-fluorobenzoyl)indoline-2-carboxamide, I-53

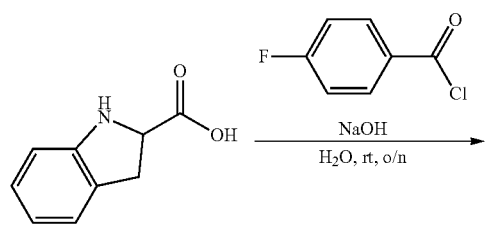

316

-continued

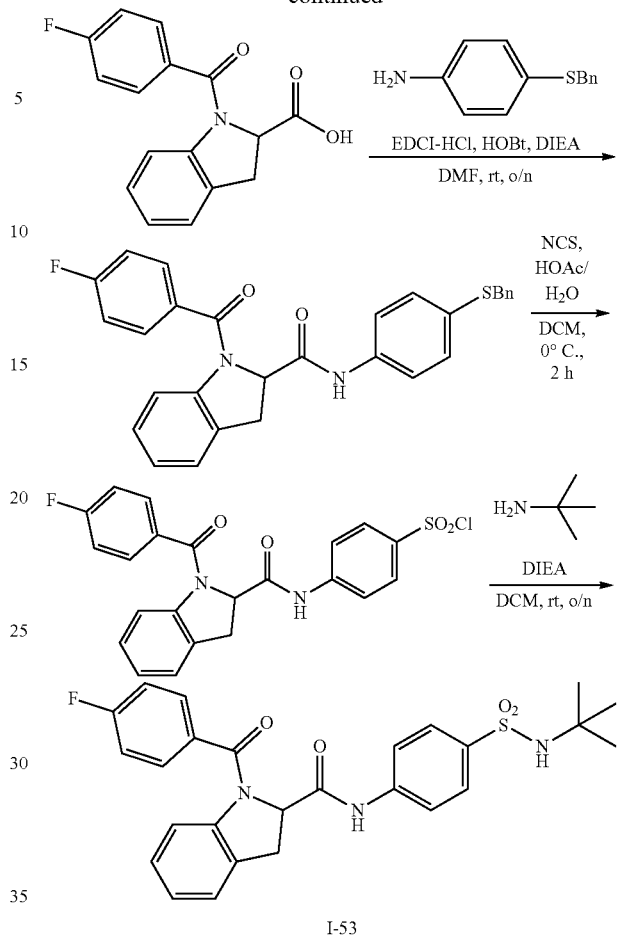

I-53

Preparation of 1-(4-fluorobenzoyl)indoline-2-carboxylic Acid

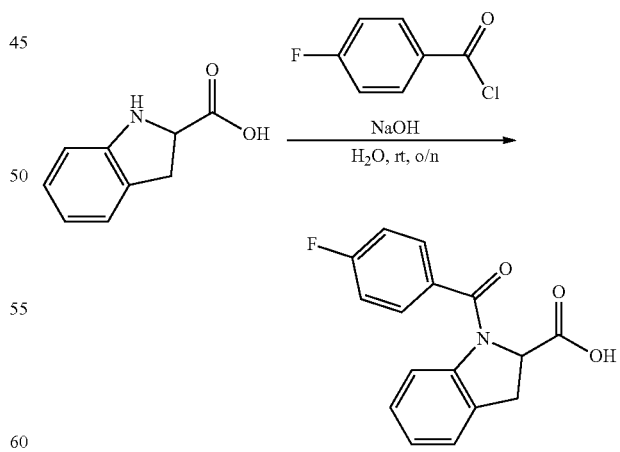

To a solution of 1.63 g indoline-2-carboxylic acid (10.0 mmol, 1.00 equiv) and 800 mg sodium hydroxide (20.0 mmol, 2.00 equiv) in 50 mL water was added 1.57 g 4-fluorobenzoyl chloride (10.0 mmol, 1.00 equiv). The mixture was stirred at room temperature overnight. Then, 2.5 mL concentrated hydrochloric acid was added and the mixture was filtered to give 2.28 g 1-(4-fluorobenzoyl) indoline-2-carboxylic acid as a white solid (80% yield). MS (ESI⁺) m/z 286 [M+H]⁺.

Preparation of N-(4-(benzylthio)phenyl)-1-(4-fluorobenzoyl)indoline-2-carboxamide

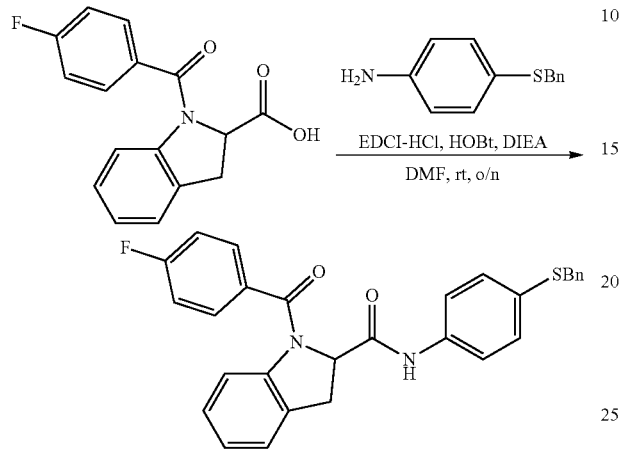

A mixture of 2.85 g 1-(4-fluorobenzoyl)indoline-2-carboxylic acid (10.0 mmol, 1.0 equiv), 2.15 g 4-(benzylthio) aniline (10.0 mmol, 1.00 equiv), 2.88 g N-(3-dimethylaminopropyl)-N'-ethylcarbodiimide hydrochloride (15.0 mmol, 1.50 equiv), 1.62 g 1-hydroxybenzotriazole (12.0 mmol, 1.2 equiv) and 2.58 g N,N-diisopropylethylamine (20.0 mmol, 2.00 equiv) in 20 mL N,N-dimethylformamide was stirred at room temperature overnight. The mixture was diluted with 100 mL ethyl acetate and washed with 3×100 mL volumes of water. The organic phase was concentrated and the residue was purified by column chromatography on silica gel (petroleum ether:ethyl acetate (5:1, v:v)) to yield 3.85 g N-(4-(benzylthio)phenyl)-1-(4-fluorobenzoyl)indoline-2-carboxamide as a light yellow solid (80% yield). MS (ESI⁺) m/z 483 [M+H]⁺.

Preparation of 4-(1-(4-fluorobenzoyl)indoline-2-carboxamido)benzene-1-sulfonyl Chloride

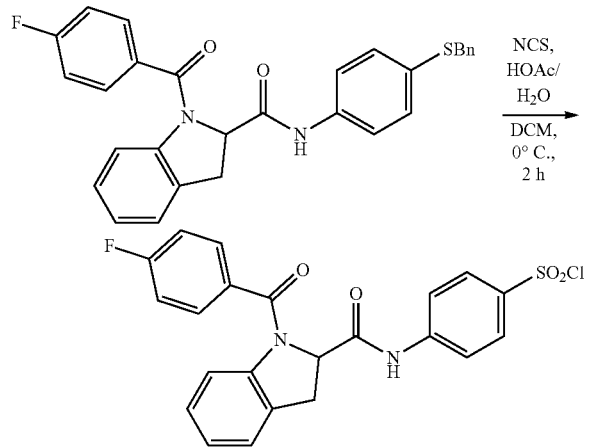

To a solution of 482 mg N-(4-(benzylthio)phenyl)-1-(4-fluorobenzoyl)indoline-2-carboxamide (1.00 mmol, 1.00 equiv), 12 mg acetic acid (1.0 mmol, 0.2 equiv) and 4 mg water (1.0 mmol, 0.2 equiv) in 10 mL dichloromethane was added 532 mg N-chlorosuccinimide (4.0 mmol, 4.00 equiv) at 0° C. The mixture was stirred at room temperature for 2 hours and washed with 3×20 mL volumes of water. The organic phase was concentrated to give 320 mg 4-(1-(4-fluorobenzoyl)indoline-2-carboxamido)benzene-1-sulfonyl chloride as a white solid (70% yield). MS (ESI⁺) m/z 459 [M+H]⁺.

Preparation of N-(4-(N-tert-butylsulfamoyl)phenyl)-1-(4-fluorobenzoyl)indoline-2-carboxamide, I-53

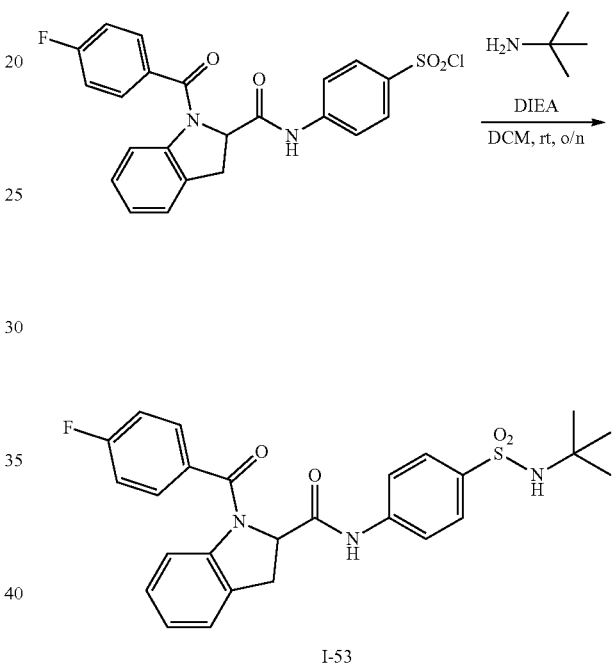

I-53

To the mixture of 183 mg 2-methylpropan-2-amine (2.5 mmol, 5.00 equiv) and 142 mg N,N-diisopropylethylamine (2.5 mmol, 5.00 equiv) in 10 mL dichloromethane was added 323 mg 4-(1-(4-fluorobenzoyl)indoline-2-carboxamido)benzene-1-sulfonyl chloride (0.5 mmol, 1.0 equiv). The mixture was stirred at room temperature for 2 hours and concentrated in vacuo. The residue was purified by reversed phase preparative HPLC on a Gilson GX-281. A concentrated solution of crude product dissolved in DMSO was injected in 800 uL volumes onto a 10 um C18 reversed phase XBridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 1.5 mV threshold trigger on the 214 nm channel. Fractions containing product were combined, concentrated and lyophilized to afford 80.0 mg N-(4-(N-tert-butylsulfamoyl)phenyl)-1-(4-fluorobenzoyl)indoline-2-carboxamide (I-53) as a white solid (32% yield). MS (ESI⁺) m/z 496 [M+H]⁺; ¹H NMR (400 MHz, d₆-DMSO) δ 10.47 (s, 1H), 8.39-7.42 (m, 7H), 7.17 (t, J=49.8 Hz, 6H), 5.13 (s, 1H), 3.63 (dd, J=16.6, 10.8 Hz, 1H), 3.14 (dd, J=16.7, 3.6 Hz, 1H), 1.07 (s, 9H).

Example 31a and Example 31b: N-(4-(N-tert-butylsulfamoyl)phenyl)-7-(4-fluorobenzoyl)-5,6,7,8-tetrahydro-1,7-naphthyridine-6-carboxamide, I-59 and I-60

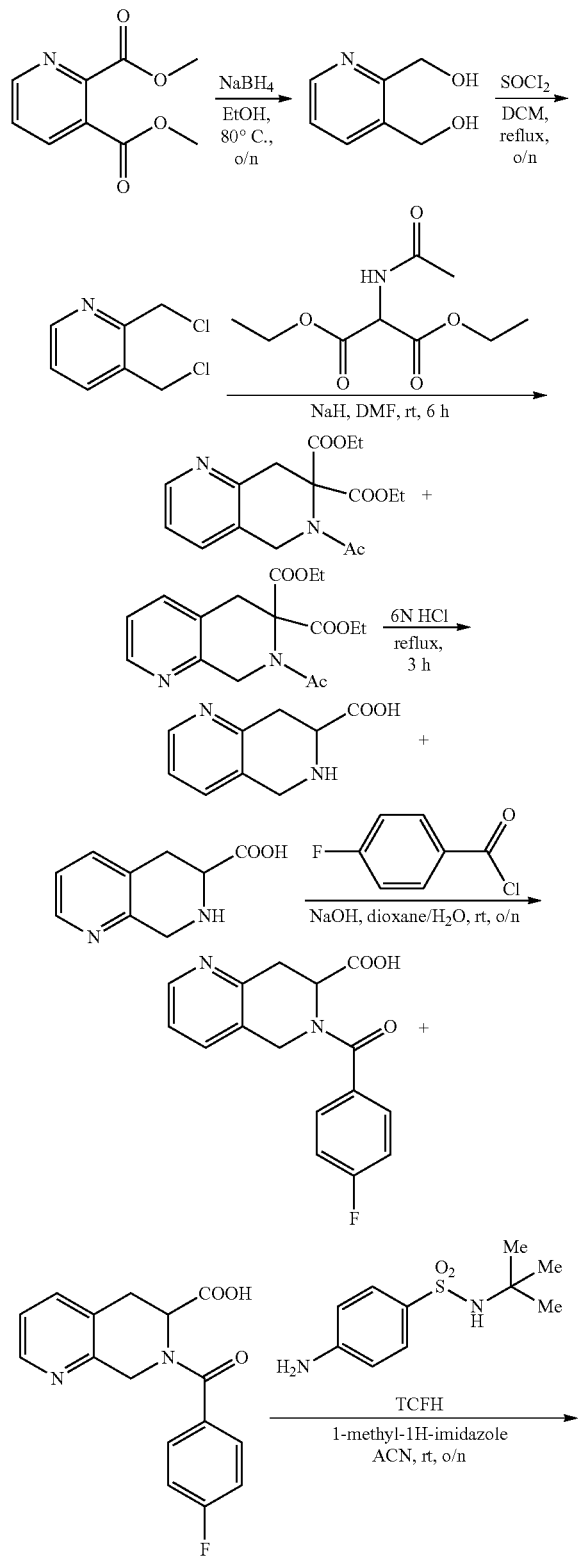

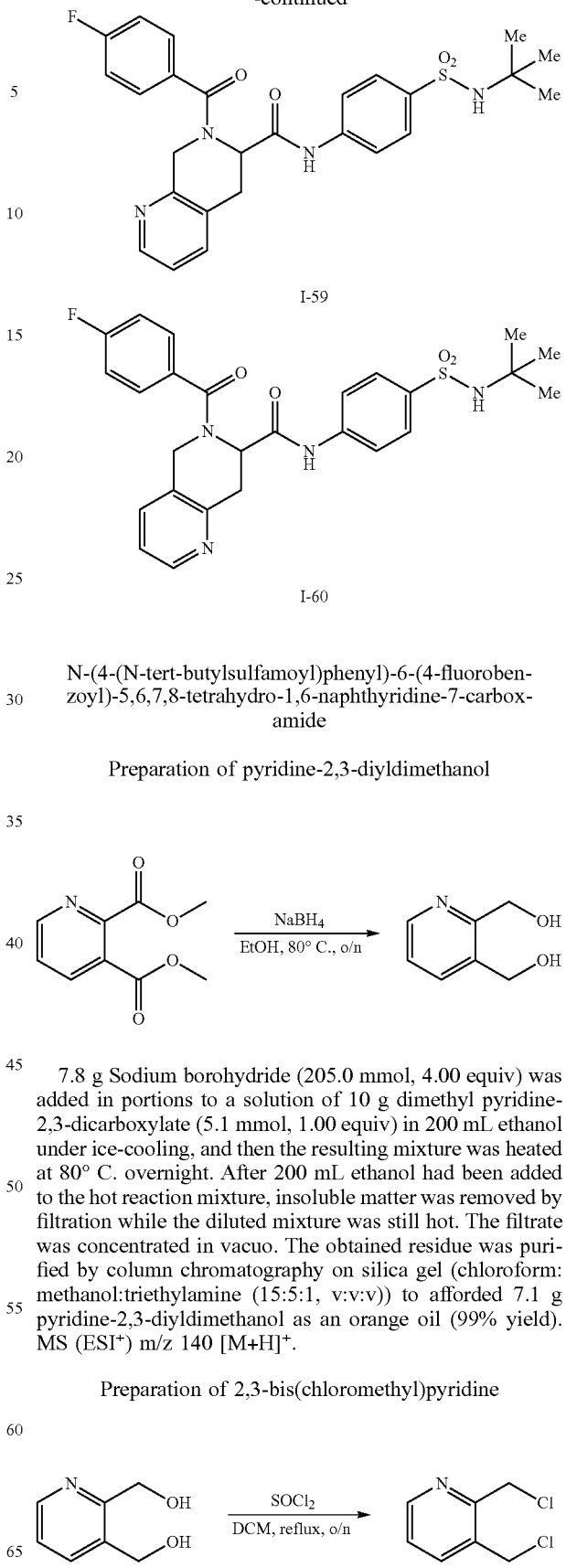

N-(4-(N-tert-butylsulfamoyl)phenyl)-6-(4-fluorobenzoyl)-5,6,7,8-tetrahydro-1,6-naphthyridine-7-carboxamide Preparation of pyridine-2,3-diyldimethanol 7.8 g Sodium borohydride (205.0 mmol, 4.00 equiv) was added in portions to a solution of 10 g dimethyl pyridine-2,3-dicarboxylate (5.1 mmol, 1.00 equiv) in 200 mL ethanol under ice-cooling, and then the resulting mixture was heated at 80° C. overnight. After 200 mL ethanol had been added to the hot reaction mixture, insoluble matter was removed by filtration while the diluted mixture was still hot. The filtrate was concentrated in vacuo. The obtained residue was purified by column chromatography on silica gel (chloroform:methanol:triethylamine (15:5:1, v:v:v)) to afforded 7.1 g pyridine-2,3-diyldimethanol as an orange oil (99% yield). MS (ESI+) m/z 140 [M+H]+.

Preparation of 2,3-bis(chloromethyl)pyridine 50 mL Thionyl chloride was added to a solution of 7.1 g pyridine-2,3-diyldimethanol (51.0 mmol, 1.00 equiv) in 20 mL dichloromethane under ice-cooling, and then the resulting mixture was stirred at 45° C. for overnight. After having been cooled to room temperature, the reaction mixture was concentrated in vacuo to give hydrochloride salt of the title compound as a brown powder. The powder was dissolved in a saturated aqueous solution of sodium hydrogen carbonate, and then the solution was extracted with ethyl acetate. The organic layer was washed with a saturated aqueous solution of sodium chloride, dried over magnesium sulfate, and concentrated in vacuo. The obtained residue was purified by column chromatography on silica gel (ethyl acetate) to afforded 3.6 g 2,3-bis(chloromethyl)pyridine as a dark brown oil (40% yield). MS (ESI$^+$) m/z 176 [M+H]$^+$.

Preparation of diethyl 6-acetyl-5,6-dihydro-1,6-naphthyridine-7,7(8H)-dicarboxylate and diethyl 7-acetyl-7,8-dihydro-1,7-naphthyridine-6,6(5H)-dicarboxylate

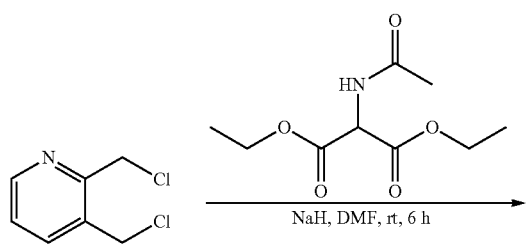

A 6.46 g sample of diethyl acetamidomalonate (20.5 mmol, 1.00 equiv) and 0.82 g sodium hydride (60 wt. % dispersion in mineral oil; 20.5 mmol, 1.00 equiv) were successively added at room temperature to a solution of 3.6 g 2,3-bis(chloromethyl)pyridine (20.5 mmol, 1.00 equiv) in 40 mL dimethylformamide, and then the resulting mixture was stirred at room temperature for 30 min. An additional 0.82 g portion of sodium hydride (60 wt. % dispersion in mineral oil; 20.5 mmol, 1.00 equiv) was then added to the reaction mixture, and the resulting mixture was stirred at room temperature for 6 h and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (ethyl acetate: methanol (20:1, v:v)) to afforded 5.1 g diethyl 6-acetyl-5,6-dihydro-1,6-naphthyridine-7,7(8H)-dicarboxylate and diethyl 7-acetyl-7,8-dihydro-1,7-naphthyridine-6,6(5H)-dicarboxylate as a brown oil (77% yield). MS (ESI$^+$) m/z 321 [M+H]$^+$.

Preparation of 5,6,7,8-tetrahydro-1,6-naphthyridine-7-carboxylic acid and 5,6,7,8-tetrahydro-1,7-naphthyridine-6-carboxylicacid

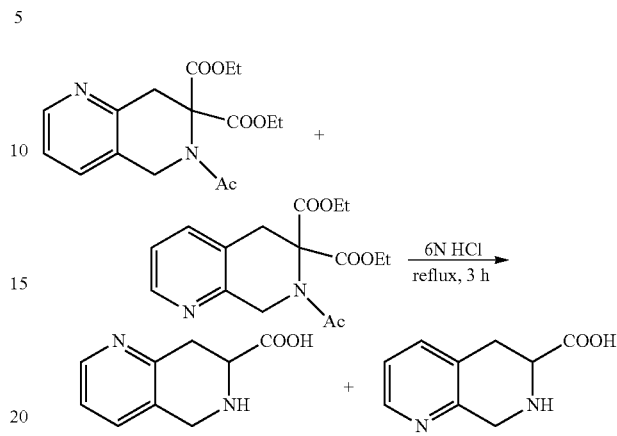

To a mixture of diethyl 5.1 g diethyl 6-acetyl-5,6-dihydro-1,6-naphthyridine-7,7(8H)-dicarboxylate and diethyl 7-acetyl-7,8-dihydro-1,7-naphthyridine-6,6(5H)-dicarboxylate (15.9 mmol, 1.00 equiv), was added 40 mL of hydrochloric acid (6.0 M HCl) and the resulting mixture was refluxed for 3 h. After having been cooled to room temperature, the reaction mixture was concentrated in vacuo. The residue was dissolved in 100 mL of dioxane and the resulting mixture was concentrated in vacuo to afford 2.5 g 5,6,7,8-tetrahydro-1,6-naphthyridine-7-carboxylic acid and 5,6,7,8-tetrahydro-1,7-naphthyridine-6-carboxylic acid as a brown powder (89% yield). MS (ESI$^+$) m/z 179 [M+H]$^+$.

Preparation of 6-(4-fluorobenzoyl)-5,6,7,8-tetrahydro-1,6-naphthyridine-7-carboxylic acid and 6-(4-fluorobenzoyl)-5,6,7,8-tetrahydro-1,6-naphthyridine-7-carboxylic Acid

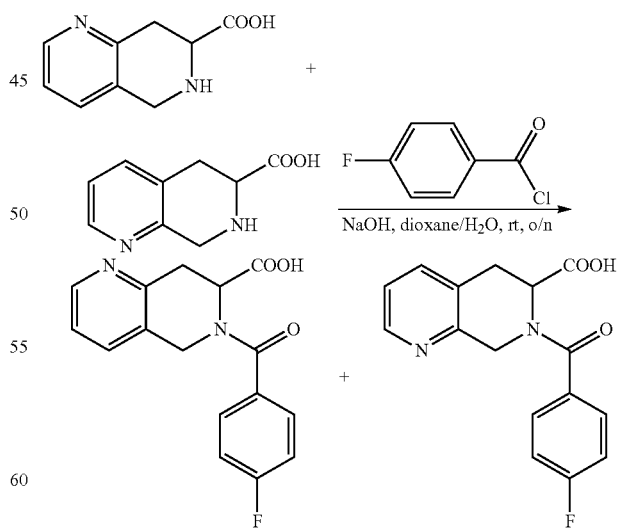

To a solution of 1.0 g 5,6,7,8-tetrahydro-1,6-naphthyridine-7-carboxylic acid and 5,6,7,8-tetrahydro-1,7-naphthyridine-6-carboxylic acid (5.6 mmol, 1.00 equiv) and 448 mg Sodium hydroxide (11.2 mmol, 2.00 equiv) dissolved in 30 mL (dioxane:H₂O (4:1, v:v)) at room temperature was added 974 mg 4-fluorobenzoyl chloride (6.16 mmol, 1.10 equiv). Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (ethyl acetate:methanol (20:1, v:v)) 920 mg 6-(4-fluorobenzoyl)-5,6,7,8-tetrahydro-1,6-naphthyridine-7-carboxylic acid and 6-(4-fluorobenzoyl)-5,6,7,8-tetrahydro-1,6-naphthyridine-7-carboxylic acid as a white solid (55% yield). MS (ESI⁺) m/z 301[M+H]⁺.

Preparation of N-(4-(N-tert-butylsulfamoyl)phenyl)-7-(4-fluorobenzoyl)-5,6,7,8-tetrahydro-1,7-naphthyridine-6-carboxamide and N-(4-(N-tert-butylsulfamoyl)phenyl)-6-(4-fluorobenzoyl)-5,6,7,8-tetrahydro-1,6-naphthyridine-7-carboxamide, I-59 and I-60

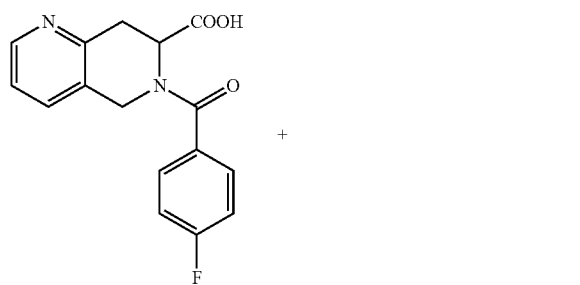

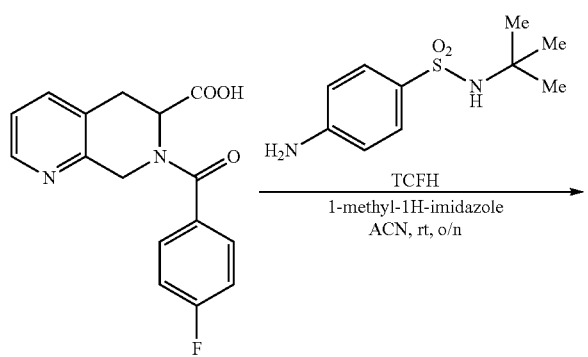

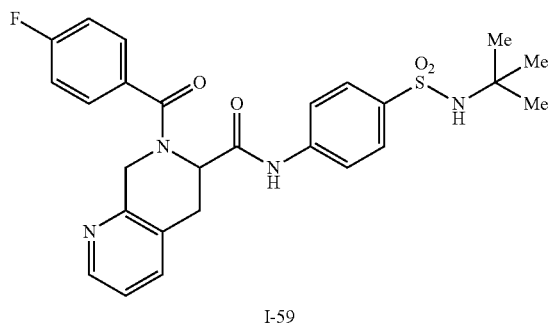

I-59

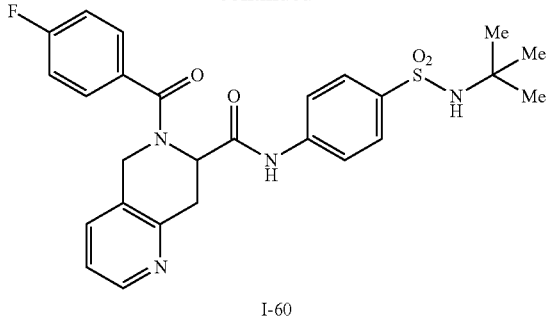

I-60

A mixture of 200 mg 6-(4-fluorobenzoyl)-5,6,7,8-tetrahydro-1,6-naphthyridine-7-carboxylic acid and 6-(4-fluorobenzoyl)-5,6,7,8-tetrahydro-1,6-naphthyridine-7-carboxylic acid (0.67 mmol, 1.00 equiv), 152 mg 4-amino-N-tert-butylbenzenesulfonamide (0.67 mmol, 1.00 equiv), 228 mg N,N,N',N'-tetramethylchloroformamidinium hexafluorophosphate (0.80 mmol, 1.20 equiv) and 192 mg 1-methyl-1H-imidazole (2.35 mmol, 3.50 equiv) in 2 mL acetonitrile was stirred at room temperature for overnight. To the mixture was added 100 mL ethyl acetate and washed with 3×100 mL volumes of water. The organic phase was concentrated and the residue was purified by reversed phase preparative HPLC on a Gilson GX-281. A concentrated solution of crude product dissolved in DMSO was injected in 500 uL volumes onto a 10 um C18 reversed phase Waters X-SELECT 19 mm diameter×250 mm length column eluting with a gradient of 40-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to give 24 mg N-(4-(N-tert-butylsulfamoyl)phenyl)-7-(4-fluorobenzoyl)-5,6,7,8-tetrahydro-1,7-naphthyridine-6-carboxamide (I-59). MS (ESI⁺) m/z 511 [M+H]⁺. ¹H NMR (400 MHz, CDCl₃) δ 9.17 (s, 1H), 8.40 (d, J=3.8 Hz, 1H), 7.80 (d, J=8.8 Hz, 2H), 7.63 (d, J=8.8 Hz, 3H), 7.52 (ddd, J=5.2, 4.3, 2.1 Hz, 2H), 7.23-7.21 (m, 1H), 7.18-7.12 (m, 2H), 5.51 (d, J=9.4 Hz, 1H), 4.89 (d, J=15.5 Hz, 1H), 4.55-4.43 (m, 2H), 3.56 (dd, J=16.6, 3.8 Hz, 1H), 3.18 (dd, J=16.5, 6.9 Hz, 1H), 1.21 (s, 9H). and 30 mg N-(4-(N-tert-butylsulfamoyl)phenyl)-6-(4-fluorobenzoyl)-5,6,7,8-tetrahydro-1,6-naphthyridine-7-carboxamide as a white solid (I-60) (16% yield). MS (ESI⁺) m/z 511 [M+H]⁺. ¹H NMR (400 MHz, CDCl₃) δ 9.27 (s, 1H), 8.52 (d, J=4.1 Hz, 1H), 7.77 (d, J=8.5 Hz, 2H), 7.63 (s, 2H), 7.49 (m, 2H), 7.27 (s, 1H), 7.16 (dd, J=11.8, 5.4 Hz, 3H), 5.51 (d, J=9.0 Hz, 1H), 4.64 (m, 2H), 4.51 (d, J=15.9 Hz, 1H), 3.70 (dd, J=16.9, 4.4 Hz, 1H), 3.39 (dd, J=17.0, 7.1 Hz, 1H), 1.20 (s, 9H).

Example 32: (S)-4-fluoro-N-(1-(4-(N-oxetan-3-ylsulfamoyl)phenylamino)-1-oxo-3-(pyridin-3-yl)propan-2-yl)benzamide, I-66

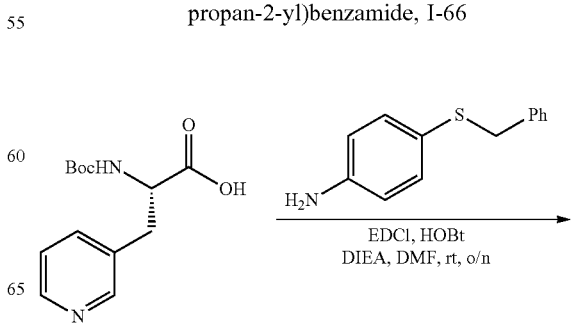

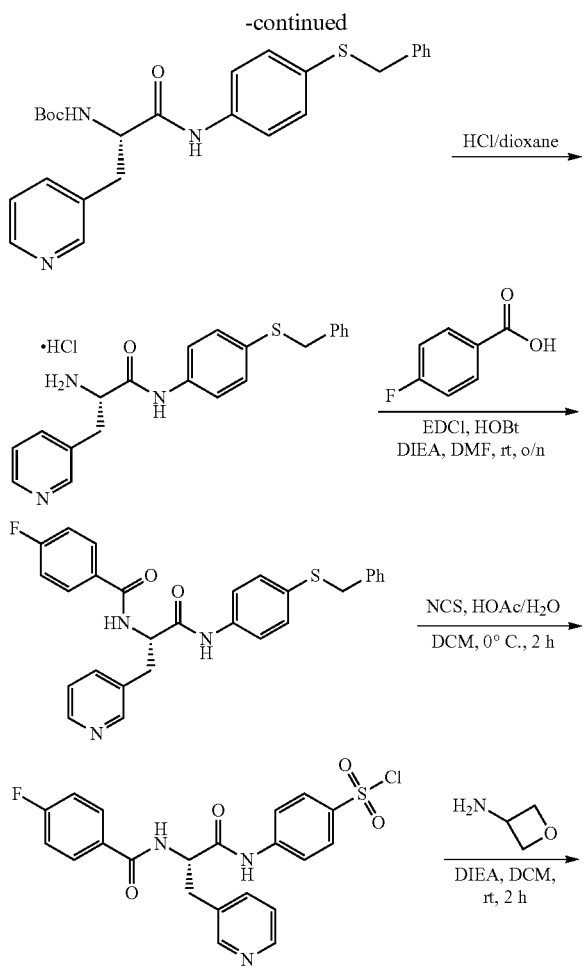

Preparation of (S)-tert-butyl 1-(4-(benzylthio)phenylamino)-1-oxo-3-(pyridin-3-yl)propan-2-ylcarbamate

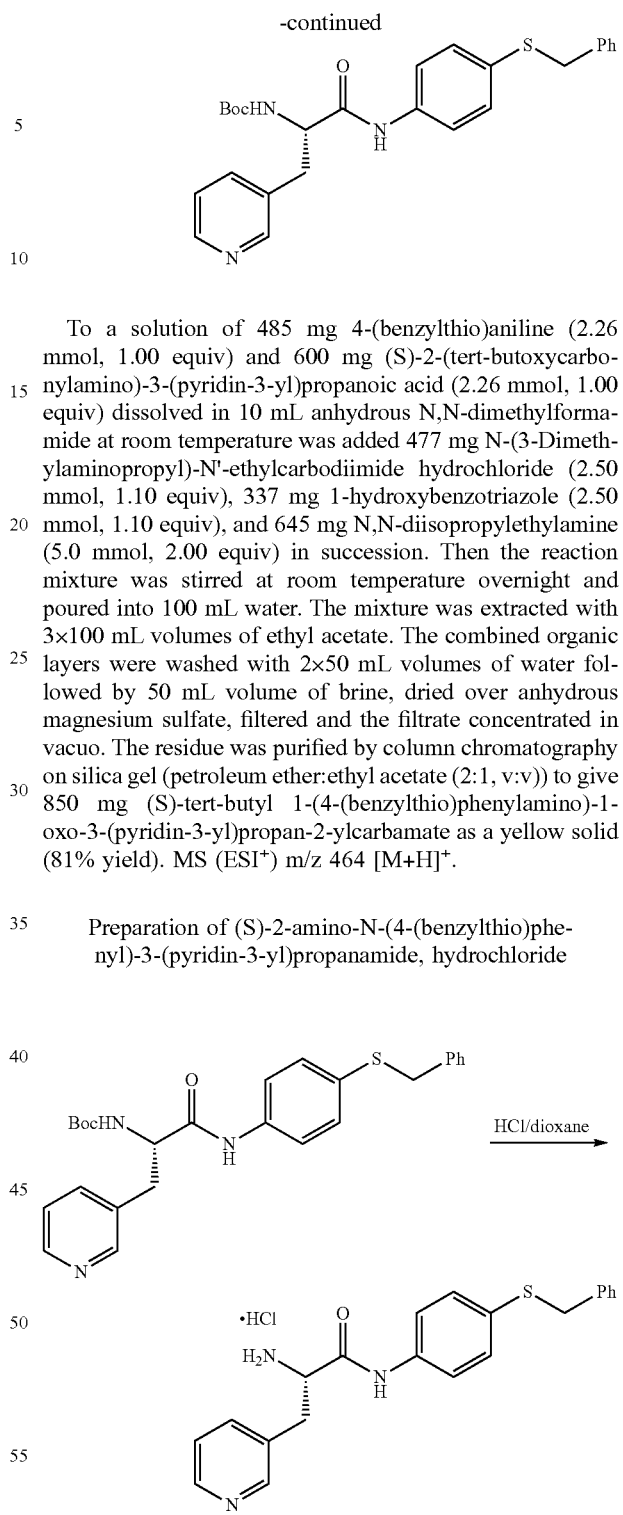

To a solution of 485 mg 4-(benzylthio)aniline (2.26 mmol, 1.00 equiv) and 600 mg (S)-2-(tert-butoxycarbonylamino)-3-(pyridin-3-yl)propanoic acid (2.26 mmol, 1.00 equiv) dissolved in 10 mL anhydrous N,N-dimethylformamide at room temperature was added 477 mg N-(3-Dimethylaminopropyl)-N'-ethylcarbodiimide hydrochloride (2.50 mmol, 1.10 equiv), 337 mg 1-hydroxybenzotriazole (2.50 mmol, 1.10 equiv), and 645 mg N,N-diisopropylethylamine (5.0 mmol, 2.00 equiv) in succession. Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (petroleum ether:ethyl acetate (2:1, v:v)) to give 850 mg (S)-tert-butyl 1-(4-(benzylthio)phenylamino)-1-oxo-3-(pyridin-3-yl)propan-2-ylcarbamate as a yellow solid (81% yield). MS (ESI$^+$) m/z 464 [M+H]$^+$.

Preparation of (S)-2-amino-N-(4-(benzylthio)phenyl)-3-(pyridin-3-yl)propanamide, hydrochloride

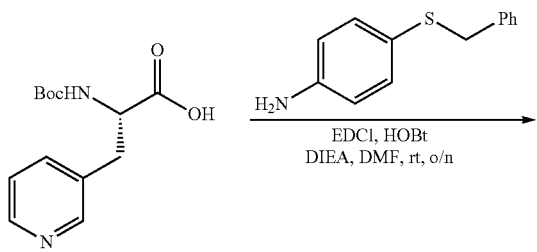

An 850 mg sample (S)-tert-butyl 1-(4-(benzylthio)phenylamino)-1-oxo-3-(pyridin-3-yl)propan-2-ylcarbamate (1.84 mmol, 1.00 equiv) was dissolved in 30 mL hydrochloric acid in dioxane (4.0 M HCl) and stirred at room temperature for 1 hour. The mixture was concentrated to afford 820 mg (S)-2-amino-N-(4-(benzylthio)phenyl)-3-(pyridin-3-yl)propanamide, hydrochloride as a light yellow solid (100% yield). MS (ESI$^+$) m/z 364 [M+H]$^+$.

Preparation of (S)-N-(1-(4-(benzylthio)phenylamino)-1-oxo-3-(pyridin-3-yl)propan-2-yl)-4-fluorobenzamide

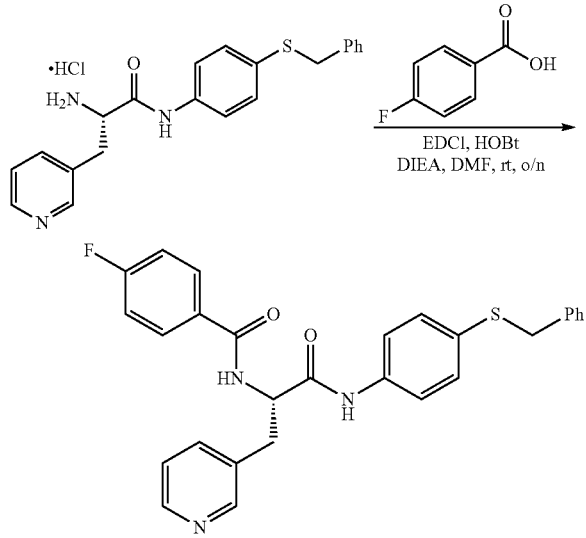

To a solution of 820 mg (S)-2-amino-N-(4-(benzylthio)phenyl)-3-(pyridin-3-yl)propanamide hydrochloride (2.05 mmol, 1.00 equiv) and 288 mg 4-fluorobenzoic acid (2.05 mmol, 1.00 equiv) in 10 mL anhydrous N,N-dimethylformamide at room temperature was added 433 mg N-(3-Dimethylaminopropyl)-N'-ethylcarbodiimide hydrochloride (2.25 mmol, 1.10 equiv), 304 mg 1-hydroxybenzotriazole (2.25 mmol, 1.10 equiv), and 529 mg N,N-diisopropylethylamine (4.1 mmol, 2.00 equiv) in succession. Then the reaction mixture was stirred at room temperature overnight and poured into 100 mL water. The mixture was extracted with 3×100 mL volumes of ethyl acetate. The combined organic layers were washed with 2×50 mL volumes of water followed by 50 mL volume of brine, dried over anhydrous magnesium sulfate, filtered and the filtrate concentrated in vacuo. The residue was purified by column chromatography on silica gel (dichloromethane:ethyl acetate (5:1, v:v)) to give 640 mg (S)-N-(1-(4-(benzylthio)phenylamino)-1-oxo-3-(pyridin-3-yl)propan-2-yl)-4-fluorobenzamide as a gray solid (64% yield). MS (ESI$^+$) m/z 486[M+H]$^+$.

Preparation of (S)-4-(2-(4-fluorobenzamido)-3-(pyridin-3-yl)propanamido)benzene-1-sulfonyl Chloride

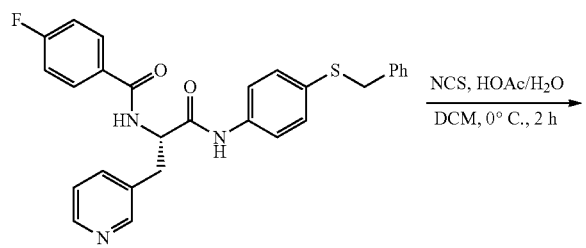

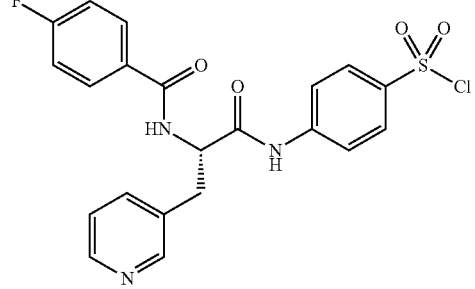

To a solution of 200 mg (S)-N-(1-(4-(benzylthio)phenylamino)-1-oxo-3-(pyridin-3-yl)propan-2-yl)-4-fluorobenzamide (0.41 mmol, 1.00 equiv), 25 mg acetic acid (0.41 mmol, 1 equiv) and 8 mg water (0.41 mmol, 1 equiv) in 30 mL dichloromethane was added 222 mg N-chlorosuccinimide (1.64 mmol, 4.00 equiv) at 0° C. The mixture was stirred at room temperature for 2 hours and washed with 3×20 mL volumes of water. The organic phase was concentrated to give 158 mg (S)-4-(2-(4-fluorobenzamido)-3-(pyridin-3-yl)propanamido)benzene-1-sulfonyl chloride as a white solid (83% yield). MS (ESI$^+$) m/z 462[M+H]$^+$.

Preparation of (S)-4-fluoro-N-(1-(4-(N-oxetan-3-ylsulfamoyl)phenylamino)-1-oxo-3-(pyridin-3-yl)propan-2-yl)benzamide, I-66

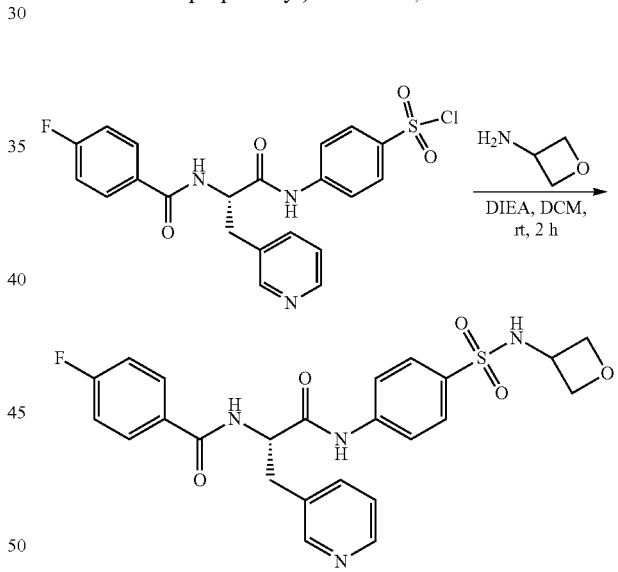

To a mixture of 79 mg oxetan-3-amine (1.08 mmol, 5.0 equiv) and 139 mg N,N-diisopropylethylamine (1.08 mmol, 5.00 equiv) in 10 mL dichloromethane was added 100 mg (S)-4-(2-(4-fluorobenzamido)-3-(pyridin-3-yl)propanamido)benzene-1-sulfonyl chloride (0.22 mmol, 1.00 equiv). The mixture was stirred at room temperature for 2 hours and concentrated in vacuo. The residue was purified by reversed phase preparative HPLC on a Gilson GX-281. A concentrated solution of crude product dissolved in DMSO was injected in 700 uL volumes onto a 10 um C18 reversed phase Waters X-SELECT 19 mm diameter×250 mm length column eluting with a gradient of 45-95% acetonitrile in water with 10 mmol/liter ammonium carbonate. Peaks were detected by UV absorbance at 214 nm and 254 nm and fractions collected by 2 mV threshold trigger on the 214 nm channel. Fractions containing product were combined, concentrated and lyophilized to afford 17 mg (S)-4-fluoro-N-(1-(4-(N-oxetan-3-ylsulfamoyl)phenylamino)-1-oxo-3-(pyridin-3-yl)propan-2-yl)benzamide (I-66) as a white solid (16% yield). MS (ESI$^+$) m/z 499 [M+H]$^+$. $^1$H NMR (400 MHz, d$_6$-DMSO) δ 10.66 (s, 1H), 8.94 (d, J=7.4 Hz, 1H), 8.59 (s, 1H), 8.47-8.36 (m, 2H), 7.93-7.87 (m, 2H), 7.80 (d, J=8.1 Hz, 3H), 7.73 (d, J=8.5 Hz, 2H), 7.31 (t, J=8.7 Hz, 3H), 4.86 (s, 1H), 4.49 (t, J=6.7 Hz, 2H), 4.35 (s, 1H), 4.24 (t, J=6.2 Hz, 2H), 3.15 (dt, J=24.0, 11.8 Hz, 2H).

Example 33: N-((2S)-1-((4-(N-(tert-butyl)-S-methylsulfonimidoyl)phenyl)amino)-1-oxo-3-phenylpropan-2-yl)-4-fluorobenzamide, I-17

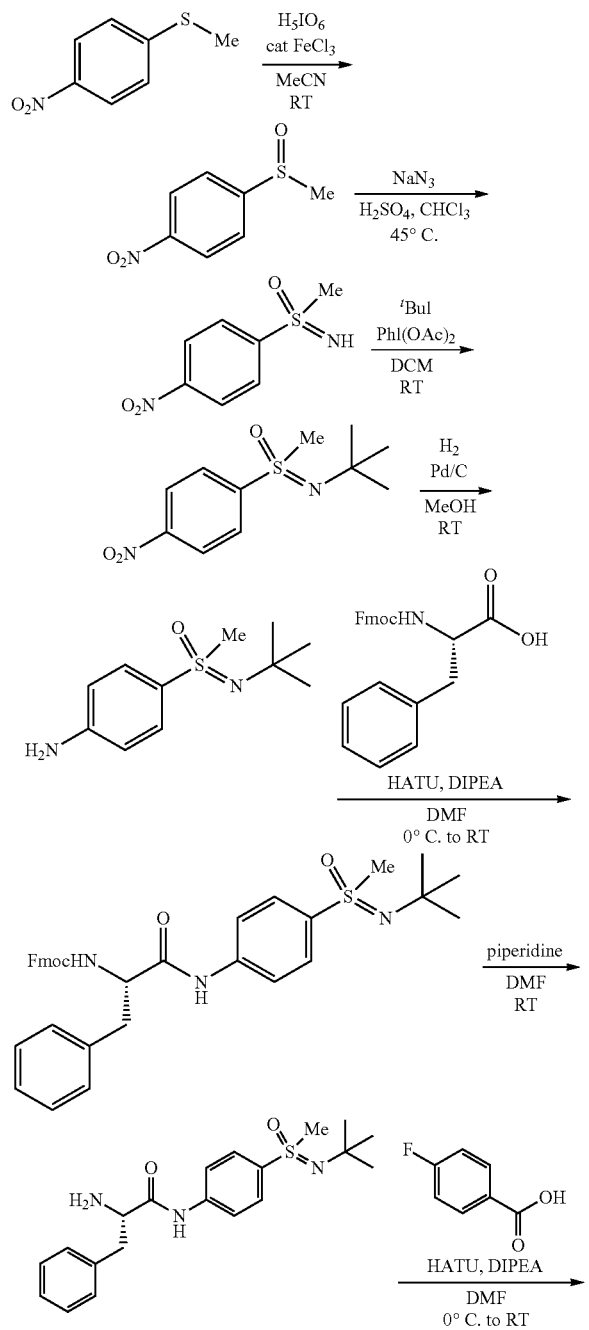

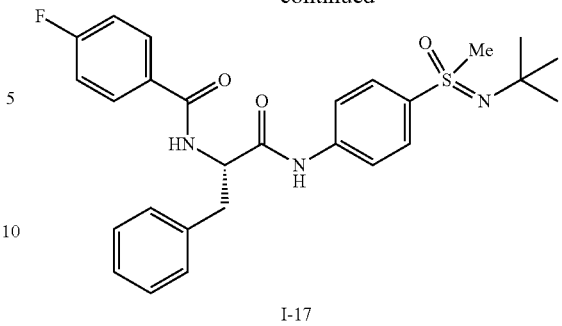

I-17

Preparation of 1-(methylsulfinyl)-4-nitrobenzene

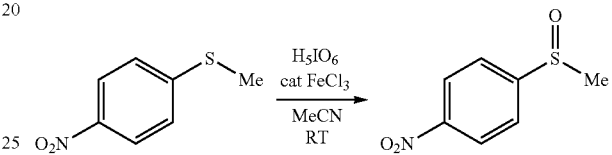

To a solution of 5.13 g methyl(4-nitrophenyl)sulfane (30.3 mmol, 1.00 equiv) and 0.15 g iron(III) chloride (0.91 mmol, 0.030 equiv) dissolved in 32 mL acetonitrile was added 7.60 g periodic acid (33.3 mmol, 1.10 equiv) at room temperature. The mixture was stirred at room temperature for 4 hours then filtered to remove solids, concentrated in vacuo and the concentrate diluted with 100 mL dichloromethane. The organic solution was washed with 100 mL brine, stirred over anhydrous magnesium sulfate, filtered and the filtrate concentrated in vacuo to afford 2.24 g of 1-(methylsulfinyl)-4-nitrobenzene as a yellow solid (12.1 mmol, 39.9% yield). MS (ESI$^+$) m/z 186 [MH]$^+$ Preparation of imino(methyl)(4-nitrophenyl)-λ$^6$-sulfanone

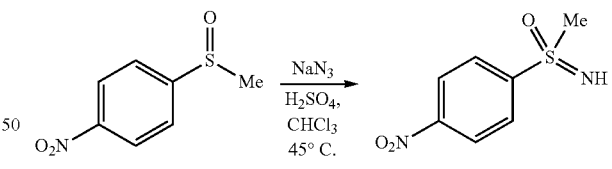

A mixture of 2.00 g 1-(methylsulfinyl)-4-nitrobenzene (10.8 mmol, 1.00 equiv) and 0.79 g sodium azide (12.1 mmol, 1.12 equiv) in 12 mL chloroform was cooled by means of a water-ice bath and then 2.75 mL concentrated sulfuric acid was dropwise over a period of one minute. The reaction was removed from the cold bath, heated to 45° C. and held at this temperature with stirring overnight. After 18 hours the reaction mixture was removed from heat, poured into 50 mL ice water and the organic separation discarded. The aqueous layer was made alkaline by addition of ca. 2.5 g sodium hydroxide and then extracted with 3×30 mL volumes of dichloromethane. The combined organic extracts were stirred over anhydrous magnesium sulfate, filtered and the filtrate concentrated under reduced pressure to afford 1.23 g of imino(methyl)(4-nitrophenyl)-λ⁶-sulfanone as a yellow solid (6.14 mmol, 56.9% yield). MS (ESI⁺) m/z 201 [M]⁺

Preparation of (tert-butylimino)(methyl)(4-nitrophenyl)-λ⁶-sulfanone

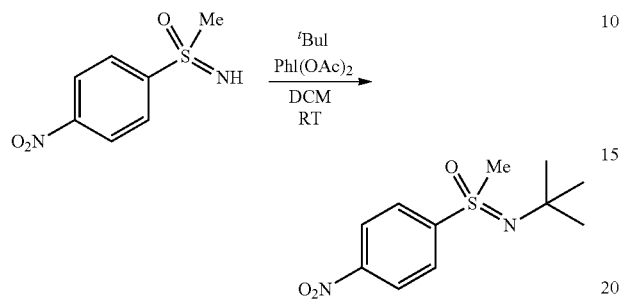

A mixture of 0.938 g imino(methyl)(4-nitrophenyl)-λ⁶-sulfanone (4.69 mmol, 1.00 equiv), 2.8 mL tert-butyl iodide (23 mmol, 5.0 equiv) and 3.02 g (diacetoxyiodo)benzene (9.38 mmol, 2.00 equiv) in 40 mL dichloromethane was stirred at room temperature for 22 hours, after which time LCMS indicated no starting material remained. To the reaction was added 10 g Celite and the mixture was filtered to remove solids. The filtrate was stirred with 100 mL 1N aqueous sodium thiosulfate solution for ten minutes and the organic and aqueous layers separated. The organic layer was washed with 50 mL saturated aqueous sodium bicarbonate solution, stirred over anhydrous magnesium sulfate, filtered and the filtrate concentrated under reduced pressure to afford a red oil. The crude product was adsorbed onto a 25 gram silica gel cartridge (Biotage SNAP Ultra) and eluted with 1:1 hexane:ethyl acetate. Fractions containing product were combined and concentrated under reduced pressure to afford 0.20 g (tert-butylimino)(methyl)(4-nitrophenyl)-λ⁶-sulfanone as a white solid (0.78 mmol, 17% yield). MS (ESI⁺) m/z 257 [M]⁺

Preparation of (4-aminophenyl)(tert-butylimino)(methyl)-λ⁶-sulfanone

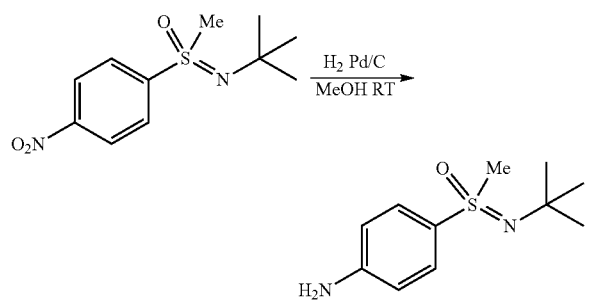

Hydrogen gas was introduced by balloon to a flask charged with a mixture of 0.188 g (tert-butylimino)(methyl)(4-nitrophenyl)-λ⁶-sulfanone (0.733 mmol, 1.00 equiv) and 0.20 g palladium-on-carbon, 10% wt. palladium, wet Degusa type (0.19 mmol, 0.26 equiv) in 10 mL methanol at room temperature. The reaction was stirred overnight under hydrogen at room temperature. After 20 hours LCMS indicated no starting material remained and the hydrogen balloon was removed and reaction headspace purged with nitrogen stream for ten minutes. Two drops of water were added to the reaction mixture, which was filtered through a pad of Celite, rinsing with 30 mL ethyl acetate. The filtrate was stirred over anhydrous magnesium sulfate, filtered and the filtrate concentrated under reduced pressure to afford 0.139 g (4-aminophenyl)(tert-butylimino)(methyl)-λ⁶-sulfanone as a colorless solid (0.614 mmol, 83.8% yield). MS (ESI⁺) m/z 227 [M]⁺

Preparation of (9H-fluoren-9-yl)methyl ((2S)-1-((4-(N-(tert-butyl)-S-methylsulfonimidoyl)phenyl)amino)-1-oxo-3-phenylpropan-2-yl)carbamate

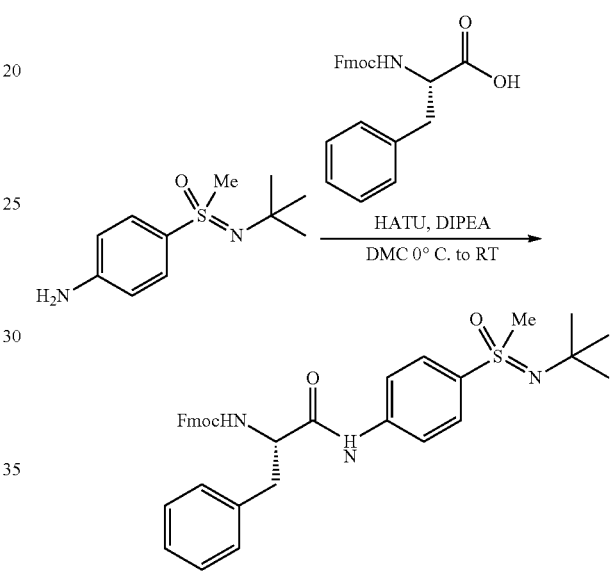

To a solution of 0.152 g (((9H-fluoren-9-yl)methoxy)carbonyl)-L-phenylalanine (0.392 mmol, 1.00 equiv) dissolved in 2 mL N,N-dimethylformamide cooled by a water-ice bath was added 0.209 g 1-[bis(dimethylamino)methylene]-1H-1,2,3-triazolo[4,5-b]pyridinium 3-oxide hexafluorophosphate [HATU] (0.549 mmol, 1.40 equiv) and 0.096 mL N,N-diisopropylethylamine (0.549 mmol, 1.40 equiv). The resulting solution was stirred at 0-5° C. for 20 minutes before a solution of 0.089 g (4-aminophenyl)(tert-butylimino)(methyl)-λ⁶-sulfanone (0.392 mmol, 1.00 equiv) dissolved in 1.5 mL N,N-dimethylformamide was added to the reaction all at once. The cold bath was removed and the reaction left to stir to room temperature. After 2 days LCMS showed starting aniline was consumed and the reaction was partitioned between 50 mL water and 30 mL 10% dichloromethane in diethyl ether. The aqueous separation was extracted again with 2×30 mL volumes 10% dichloromethane in diethyl ether. The combined organic layers were washed with 50 mL brine, stirred over anhydrous magnesium sulfate, filtered and the filtrate concentrated under reduced pressure to afford a yellow foam. The crude product was adsorbed onto a silica gel cartridge (10 g Biotage SNAP Ultra) and eluted with a gradient of 10-100% acetonitrile in dichloromethane. Fractions containing product were combined and concentrated under reduced pressure to afford 0.18 g (9H-fluoren-9-yl)methyl ((2S)-1-((4-(N-(tert-butyl)-S-methylsulfonimidoyl)phenyl)amino)-1-oxo-3-phenylpropan-2-yl)carbamate as a colorless foam (0.30 mmol, 77% yield). MS (ESI⁺) m/z 596 [M]⁺

Preparation of (2S)-2-amino-N-(4-(N-(tert-butyl)-S-methylsulfonimidoyl)phenyl)-3-phenylpropanamide

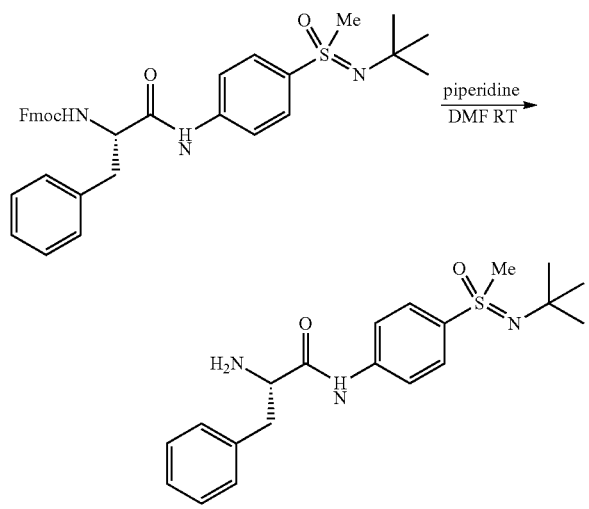

To a solution of 0.18 g (9H-fluoren-9-yl)methyl ((2S)-1-((4-(N-(tert-butyl)-S-methylsulfonimidoyl)phenyl)amino)-1-oxo-3-phenylpropan-2-yl)carbamate (0.302 mmol, 1.00 equiv) dissolved in 2 mL N,N-dimethylformamide dissolved at room temperature was added 0.4 mL neat piperidine all at once. After 30 minutes LCMS showed no starting material remained and the reaction was partitioned between 50 mL water and 30 mL 15% dichloromethane in diethyl ether. The aqueous separation was extracted again with 2×30 mL volumes 15% dichloromethane in diethyl ether. The combined organic layers were washed with 50 mL brine, stirred over anhydrous magnesium sulfate, filtered and the filtrate concentrated under reduced pressure to afford a yellow solid. The crude product was adsorbed onto a silica gel cartridge (10 g Biotage Sfar HC) and eluted with a gradient of 1-5% methanol in dichloromethane with 0.1% volume ammonium hydroxide. Fractions containing product were combined and concentrated under reduced pressure to afford 0.12 g (2S)-2-amino-N-(4-(N-(tert-butyl)-S-methylsulfonimidoyl)phenyl)-3-phenylpropanamide as a colorless foam (0.30 mmol, 100% yield). MS (ESI⁺) m/z 374 [MH]⁺

Preparation of N-((2S)-1-((4-(N-(tert-butyl)-S-methylsulfonimidoyl)phenyl)amino)-1-oxo-3-phenylpropan-2-yl)-4-fluorobenzamide, I-17

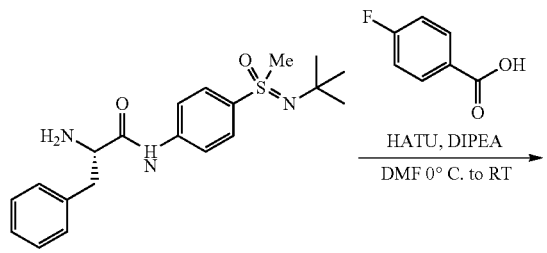

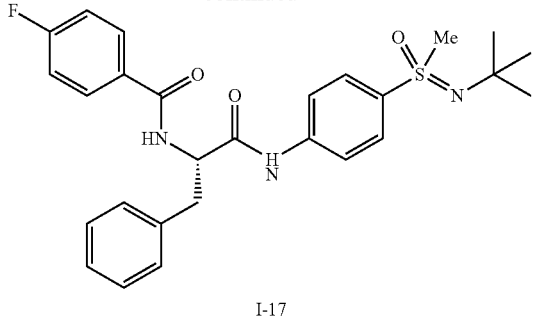

I-17

To a solution of 0.050 g 4-fluorobenzoic acid (0.353 mmol, 1.20 equiv) dissolved in 2 mL N,N-dimethylformamide cooled by a water-ice bath was added 0.168 g 1-[bis(dimethylamino)methylene]-1H-1,2,3-triazolo[4,5-b]pyridinium 3-oxide hexafluorophosphate [HATU] (0.443 mmol, 1.50 equiv) and 0.077 mL N,N-diisopropylethylamine (0.443 mmol, 1.50 equiv). The resulting solution was stirred at 0-5° C. for 20 minutes before a solution of 0.110 g (2S)-2-amino-N-(4-(N-(tert-butyl)-S-methylsulfonimidoyl)phenyl)-3-phenylpropanamide (0.295 mmol, 1.00 equiv) dissolved in 2 mL N,N-dimethylformamide was added to the reaction all at once. The cold bath was removed and the reaction left to stir to room temperature. After 3 hours LCMS showed starting amine was consumed and the reaction was partitioned between 50 mL water and 30 mL 15% dichloromethane in diethyl ether. The aqueous separation was extracted again with 2×30 mL volumes 15% dichloromethane in diethyl ether. The combined organic layers were washed with 50 mL brine, stirred over anhydrous magnesium sulfate, filtered and the filtrate concentrated under reduced pressure to afford a colorless foam. The crude product was adsorbed onto a silica gel cartridge (10 g Biotage Sfar HC) and eluted with a gradient of 10-50% acetonitrile in dichloromethane. Fractions containing product were combined and concentrated under reduced pressure to afford 0.117 g N-((2S)-1-((4-(N-(tert-butyl)-S-methylsulfonimidoyl)phenyl)amino)-1-oxo-3-phenylpropan-2-yl)-4-fluorobenzamide (I-17) as a colorless solid (0.236 mmol, 80% yield). MS (ESI⁺) m/z 496 [MH]⁺. ¹H NMR (400 MHz, CHLOROFORM-d) δ ppm 8.89 (s, 1H), 7.76 (d, J=8.53 Hz, 2H), 7.59-7.71 (m, 1H), 7.47 (d, J=8.53 Hz, 2H), 7.12-7.27 (m, 6H), 6.95-7.07 (m, 3H), 5.05 (q, J=7.45 Hz, 1H), 3.23 (d, J=7.28 Hz, 2H), 2.93 (d, J=0.75 Hz, 3H), 1.11 (d, J=1.51 Hz, 9H).

Example 34: N-(4-(N-tert-butylsulfamoyl)phenyl)-1-(4-fluorobenzoyl)-2,3-dihydro-1H-pyrrolo[3,2-b]pyridine-2-carboxamide, I-54

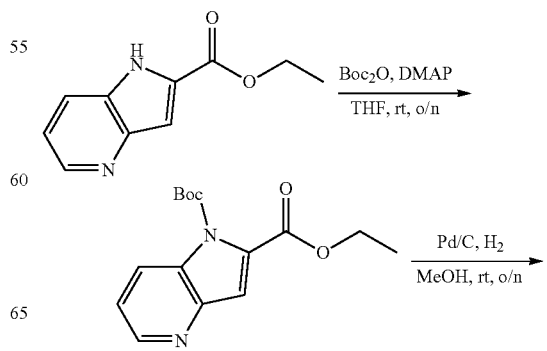

335

-continued

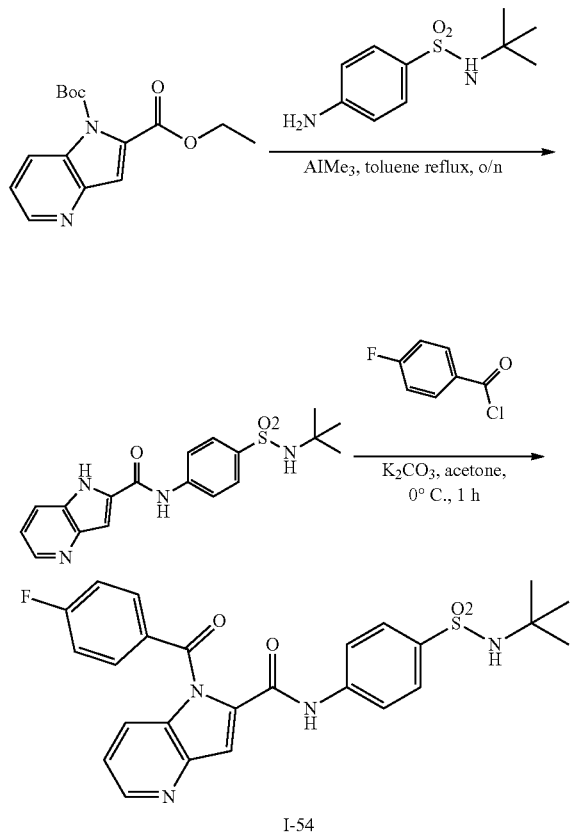

I-54

Preparation of 1-tert-butyl 2-ethyl 1H-pyrrolo[3,2-b]pyridine-1,2-dicarboxylate

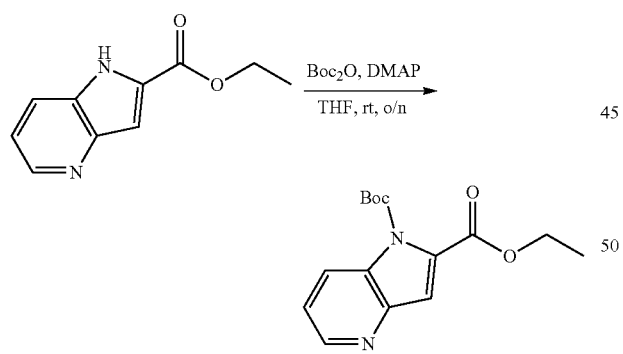

To a solution of 1.0 g ethyl 1H-pyrrolo[3,2-b]pyridine-2-carboxylate (5.3 mmol, 1.0 equiv) and 129 mg 4-dimethylaminopyridine (1.1 mol, 0.2 equiv) in THF (20 mL) was added 1.2 g di-tert-butyl dicarbonate (5.3 mmol, 1.0 equiv). The reaction mixture was stirred at room temperature for 4 h. After the resulting solution was evaporated under reduced pressure and the residue was purified by column chromatography (silica gel, petroleum ether:ethyl acetate (15:1, v:v)) to afford 1.2 g 1-tert-butyl 2-ethyl 1H-pyrrolo[3,2-b]pyridine-1,2-dicarboxylate (80% yield). MS (ESI$^+$) m/z 291 [M+H]$^+$.

336

Preparation of 1-tert-butyl 2-ethyl 2,3-dihydro-1H-pyrrolo[3,2-b]pyridine-1,2-dicarboxylate

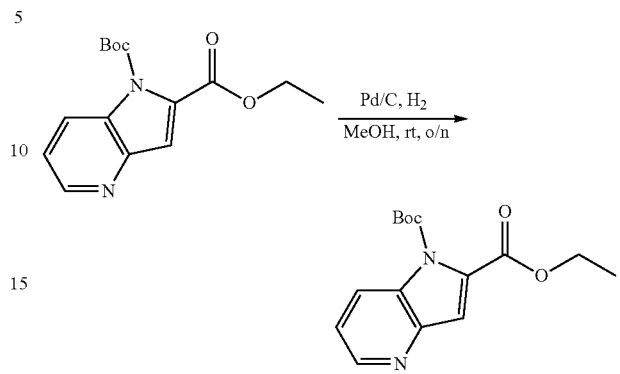

To a solution of 1.2 g 1-tert-butyl 2-ethyl 1H-pyrrolo[3,2-b]pyridine-1,2-dicarboxylate (4.1 mmol, 1.00 equiv) in 50 mL methanol was added palladium on activated carbon (50 mg wet catalyst, 10 wt. % palladium dry basis). The mixture was placed under hydrogen gas via balloon and stirred at room temperature overnight. The mixture was filtered and the filtrate concentrated to afford 1.1 g 1-tert-butyl 2-ethyl 2,3-dihydro-H-pyrrolo[3,2-b]pyridine-1,2-dicarboxylate as a white solid (90% yield). MS (ESI$^+$) m/z 293 [M+H]$^+$.

Preparation of N-(4-(N-tert-butylsulfamoyl)phenyl)-2,3-dihydro-1H-pyrrolo[3,2-b]pyridine-2-carboxamide

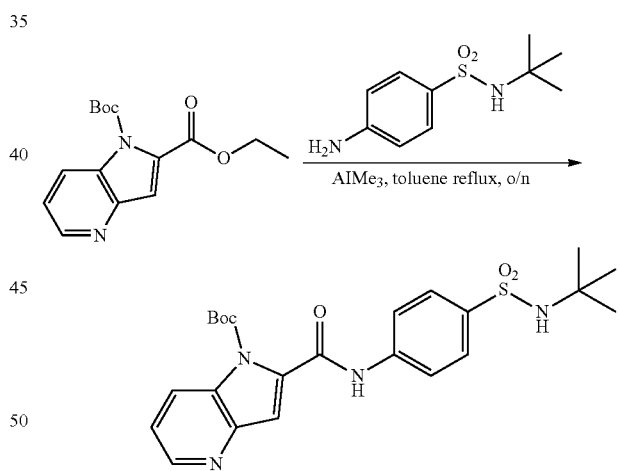

To the mixture of 1.1 g 1-tert-butyl 2-ethyl 2,3-dihydro-1H-pyrrolo[3,2-b]pyridine-1,2-dicarboxylate (3.8 mmol, 1.00 equiv) and 859 mg 4-amino-N-tert-butylbenzenesulfonamide (3.8 mmol, 1.00 equiv) in 20.0 mL toluene was added 7.6 mL trimethylaluminum (2.0 M. in toluene, 15.2 mmol, 4.00 equiv). The mixture was stirred overnight and poured into 30 mL ice water. The mixture was extracted with 3×50 mL volumes of ethyl acetate. The combined organic layers were concentrated and the residue was purified by column chromatography on silica gel (petroleum ether:ethyl acetate (1:1, v:v)) to give 710 mg N-(4-(N-tert-butylsulfamoyl)phenyl)-2,3-dihydro-1H-pyrrolo[3,2-b]pyridine-2-carboxamide as a light yellow solid (50% yield). MS (ESI$^+$) m/z 375 [M+H]$^+$.

337

Preparation of N-(4-(N-tert-butylsulfamoyl)phenyl)-1-(4-fluorobenzoyl)-2,3-dihydro-1H-pyrrolo[3,2-b]pyridine-2-carboxamide, I-54

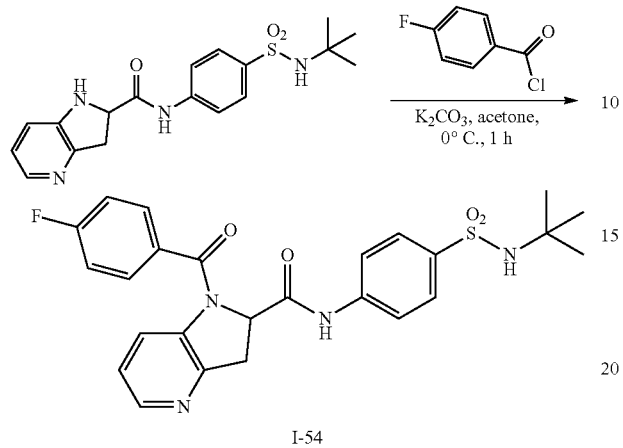

I-54

A mixture of 300 mg N-(4-(N-tert-butylsulfamoyl)phenyl)-2,3-dihydro-1H-pyrrolo[3,2-b]pyridine-2-carboxamide (0.80 mmol, 1.0 equiv), 126 mg 4-fluorobenzoyl chloride (0.80 mmol, 1.0 equiv) and 221 mg potassium carbonate (1.6 mmol, 2.00 equiv) in 10 mL acetone was stirred at 0° C. for 1 hour then poured into 20 mL water. The mixture was extracted with 3×20 mL volumes of ethyl acetate. The combined organic layers were washed with 2×50 mL volumes of water followed by 50 mL volume of brine, dried over anhydrous magnesium sulfate, filtered and the filtrate concentrated in vacuo. The compound was purified by reversed phase preparative HPLC on a Gilson GX-281. A concentrated solution of crude product dissolved in DMSO was injected in 500 uL volumes onto a 10 um C18 reversed phase XBridge 19 mm diameter×250 mm length column eluting with a gradient of 40-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 25 mg N-(4-(N-tert-butylsulfamoyl)phenyl)-1-(4-fluorobenzoyl)-2,3-dihydro-1H-pyrrolo[3,2-b]pyridine-2-carboxamide (I-54) (6.3% yield). MS (ESI+) m/z 497 [M+H]+; 1H NMR (400 MHz, CDCl3) δ 9.62 (s, 1H), 8.18 (dd, J=5.0, 1.2 Hz, 1H), 7.73 (d, J=8.8 Hz, 2H), 7.65-7.46 (m, 4H), 7.16 (t, J=8.6 Hz, 2H), 6.94-6.76 (m, 1H), 6.46 (s, 1H), 5.39 (d, J=8.5 Hz, 1H), 5.01 (s, 1H), 3.81-3.65 (m, 1H), 3.60 (dd, J=17.0, 9.9 Hz, 1H), 1.18 (s, 9H).

Example 35: N-(4-(N-tert-butylsulfamoyl)phenyl)-1-(4-fluorobenzoyl)-2,3-dihydro-1H-pyrrolo[3,2-c]pyridine-2-carboxamide, I-55

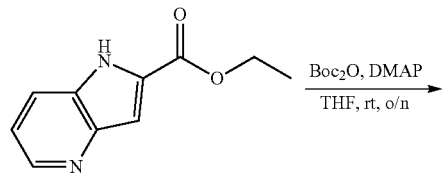

338

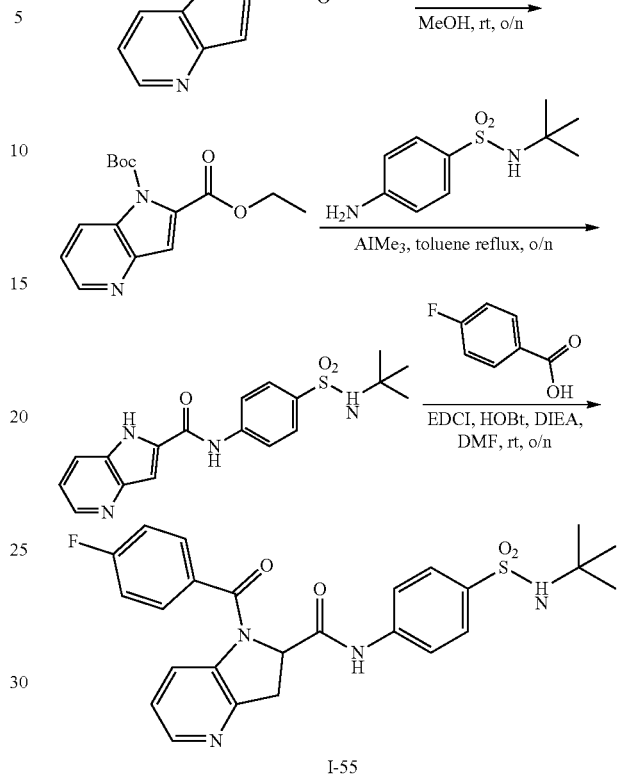

I-55

Preparation of 1-tert-butyl 2-ethyl 1H-pyrrolo[3,2-c]pyridine-1,2-dicarboxylate

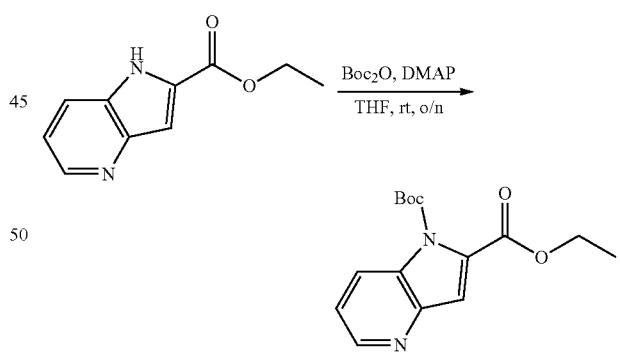

To a solution of 1.0 g ethyl 1H-pyrrolo[3,2-c]pyridine-2-carboxylate (5.3 mmol, 1.0 equiv) and 129 mg 4-dimethylaminopyridine (1.1 mol, 0.2 equiv) in THF (20 mL) was added 1.2 g di-tert-butyl dicarbonate (5.3 mmol, 1.0 equiv). The reaction mixture was stirred at room temperature for 4 h. After the resulting solution was evaporated under reduced pressure, the residue was purified by column chromatography (silica gel, petroleum ether:ethyl acetate (10:1, v:v)) afforded 1.0 g 1-tert-butyl 2-ethyl 1H-pyrrolo[3,2-c]pyridine-1,2-dicarboxylate (66% yield). MS (ESI+) m/z 291 [M+H]+.

339
Preparation of 1-tert-butyl 2-ethyl 2,3-dihydro-1H-pyrrolo[3,2-c]pyridine-1,2-dicarboxylate

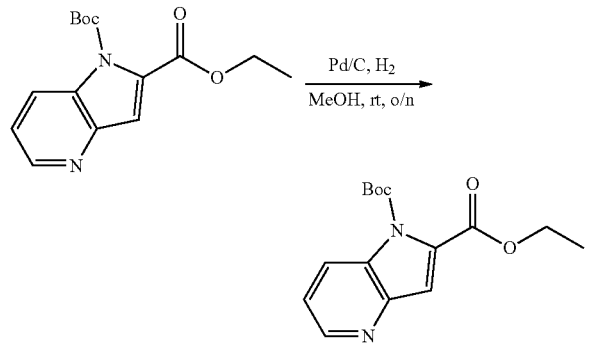

To a solution of 1.0 g 1-tert-butyl 2-ethyl 1H-pyrrolo[3,2-c]pyridine-1,2-dicarboxylate (3.4 mmol, 1.00 equiv) in 50 mL methanol was added palladium on activated carbon (50 mg wet catalyst, 10 wt. % palladium dry basis). The mixture was placed under hydrogen gas via balloon and stirred at room temperature overnight. The mixture was filtered and the filtrate concentrated to afford 906 mg 1-tert-butyl 2-ethyl 2,3-dihydro-H-pyrrolo[3,2-c]pyridine-1,2-dicarboxylate as a white solid (90% yield). MS (ESI$^+$) m/z 293 [M+H]$^+$.

Preparation of N-(4-(N-tert-butylsulfamoyl)phenyl)-2,3-dihydro-1H-pyrrolo[3,2-c]pyridine-2-carboxamide

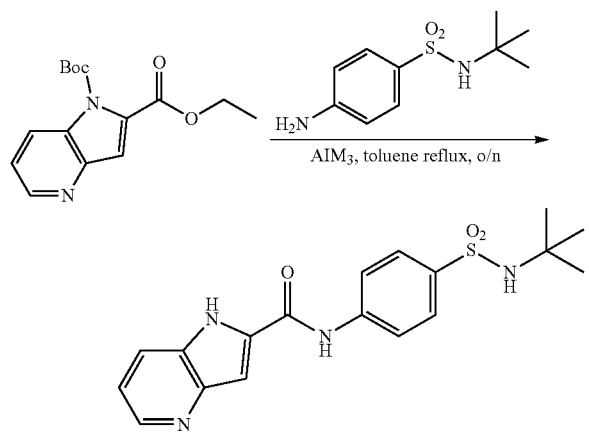

To the mixture of 906 mg 1-tert-butyl 2-ethyl 2,3-dihydro-H-pyrrolo[3,2-c]pyridine-1,2-dicarboxylate (3.1 mmol, 1.00 equiv) and 707 mg 4-amino-N-tert-butylbenzenesulfonamide (3.1 mmol, 1.00 equiv) in 20.0 mL toluene was added 6.2 mL trimethylaluminum (2.0 M. in toluene, 12.4 mmol, 4.00 equiv). The mixture was stirred overnight and poured into 30 mL ice water. The mixture was extracted with 3×50 mL volumes of ethyl acetate. The combined organic layers were concentrated and the residue was purified by column chromatography on silica gel (petroleum ether:ethyl acetate (1:1, v:v)) to give 638 mg N-(4-(N-tert-butylsulfamoyl)phenyl)-2,3-dihydro-1H-pyrrolo[3,2-c]pyridine-2-carboxamide as a light yellow solid (55% yield). MS (ESI$^+$) m/z 375 [M+H]$^+$.

340
Preparation of N-(4-(N-tert-butylsulfamoyl)phenyl)-1-(4-fluorobenzoyl)-2,3-dihydro-1H-pyrrolo[3,2-c]pyridine-2-carboxamide, I-55

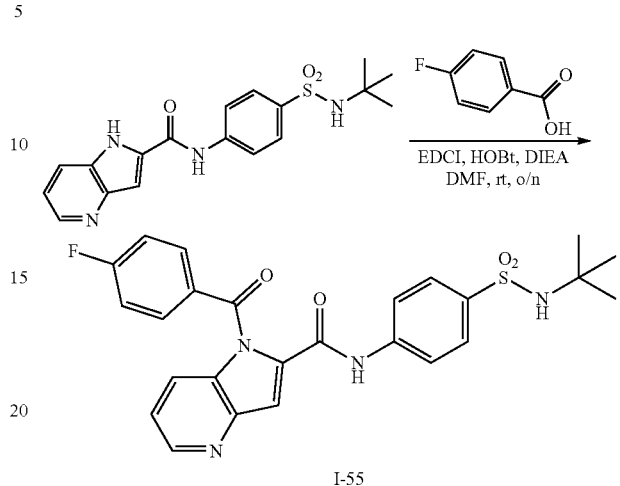

I-55

A mixture of 300 mg N-(4-(N-tert-butylsulfamoyl)phenyl)-2,3-dihydro-1H-pyrrolo[3,2-c]pyridine-2-carboxamide (0.80 mmol, 1.00 equiv), 112 mg 4-fluorobenzoic acid (0.80 mmol, 1.00 equiv), 230 mg N-(3-dimethylaminopropyl)-N'-ethylcarbodiimide hydrochloride (1.2 mmol, 1.50 equiv), 130 mg 1-hydroxybenzotriazole (0.96 mmol, 1.2 equiv) and 206 mg N,N-diisopropylethylamine (1.6 mmol, 2.00 equiv) in 10 mL N,N-dimethylformamide was stirred at room temperature overnight. The reaction was diluted with 50 mL ethyl acetate and washed with 3×40 mL volumes of water. The organic phases were concentrated and the compound was purified by reversed phase preparative HPLC on a Gilson GX-281. A concentrated solution of crude product dissolved in DMSO was injected in 800 uL volumes onto a 10 um C18 reversed phase XBridge 19 mm diameter×250 mm length column eluting with a gradient of 55-95% acetonitrile in water with 10 mmol/liter ammonium carbonate. Peaks were detected by UV absorbance at 214 nm and 254 nm and fractions collected by 7 mV threshold trigger on the 214 nm channel. Fractions containing product were combined, concentrated and lyophilized to afford 30.0 mg N-(4-(N-tert-butylsulfamoyl)phenyl)-1-(4-fluorobenzoyl)-2,3-dihydro-1H-pyrrolo[3,2-c]pyridine-2-carboxamide (I-55) as a white solid (7.6% yield). MS (ESI$^+$) m/z 497 [M+H]$^+$; $^1$H NMR (400 MHz, d$_6$-DMSO) δ 10.50 (s, 1H), 8.36 (s, 1H), 8.23 (s, 1H), 7.69 (t, J=12.3 Hz, 2H), 7.61 (dd, J=8.6, 5.5 Hz, 4H), 7.33 (d, J=4.54 Hz, 3H), 5.20 (dd, J=10.8, 3.8 Hz, 1H), 3.64 (dd, J=16.7, 11.0 Hz, 1H), 3.20 (dd, J=16.8, 3.7 Hz, 1H), 1.05 (s, 9H).

Example 36: N-(4-(N-tert-butylsulfamoyl)phenyl)-1-(4-fluorobenzoyl)-2,3-dihydro-1H-pyrrolo[2,3-c]pyridine-2-carboxamide, I-56

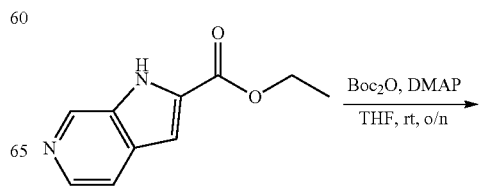

341

-continued

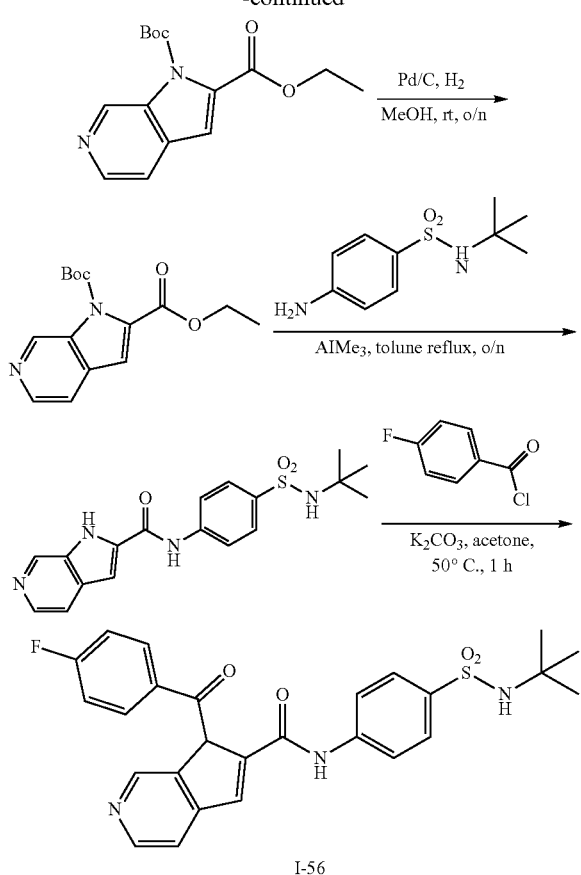

I-56

Preparation of 1-tert-butyl 2-ethyl 1H-pyrrolo[2,3-c]pyridine-1,2-dicarboxylate

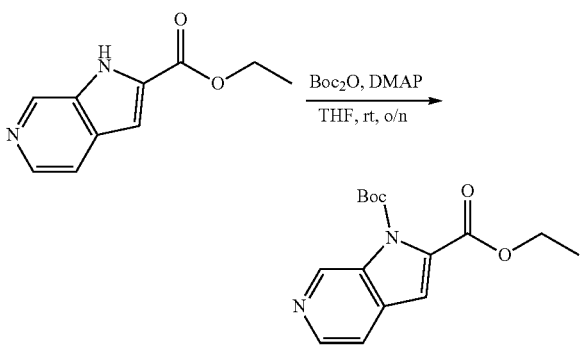

To a solution of 2.0 g ethyl H-pyrrolo[2,3-c]pyridine-2-carboxylate (10.5 mmol, 1.0 equiv) and 129 mg 4-dimethylaminopyridine (1.05 mol, 0.1 equiv) in THF (20 mL) was added 2.4 g di-tert-butyl dicarbonate (10.5 mmol, 1.0 equiv). The reaction mixture was stirred at room temperature 4 h. The resulting solution was evaporated under reduced pressure and the residue was purified by column chromatography (silica gel, petroleum ether:ethyl acetate (15:1, v:v)) to afford 2.4 g 1-tert-butyl 2-ethyl 1H-pyrrolo[2,3-c]pyridine-1,2-dicarboxylate (80% yield). MS (ESI⁺) m/z 291 [M+H]⁺.

342

Preparation of 1-tert-butyl 2-ethyl 2,3-dihydro-1H-pyrrolo[2,3-c]pyridine-1,2-dicarboxylate

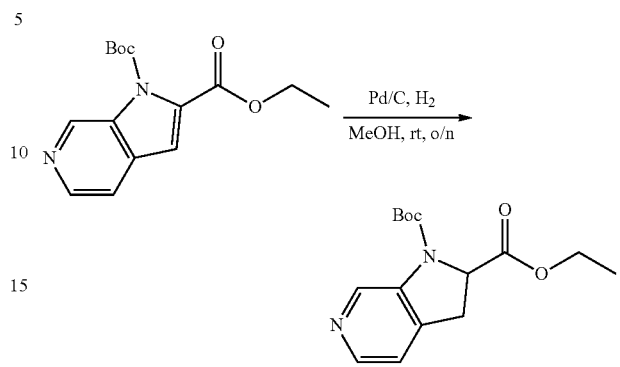

To a solution of 2.4 g 1-tert-butyl 2-ethyl-1H-pyrrolo[2,3-c]pyridine-1,2-dicarboxylate (8.2 mmol, 1.00 equiv) in 50 mL methanol was added palladium on activated carbon (150 mg wet catalyst, 10 wt. % palladium dry basis). The mixture was placed under hydrogen gas via balloon and stirred at room temperature overnight. The mixture was filtered and the filtrate concentrated to afford 2.2 g 1-tert-butyl 2-ethyl 2,3-dihydro-1H-pyrrolo[2,3-c]pyridine-1,2-dicarboxylate as a white solid (90% yield). MS (ESI⁺) m/z 293 [M+H]⁺.

Preparation of N-(4-(N-tert-butylsulfamoyl)phenyl)-2,3-dihydro-1H-pyrrolo[2,3-c]pyridine-2-carboxamide

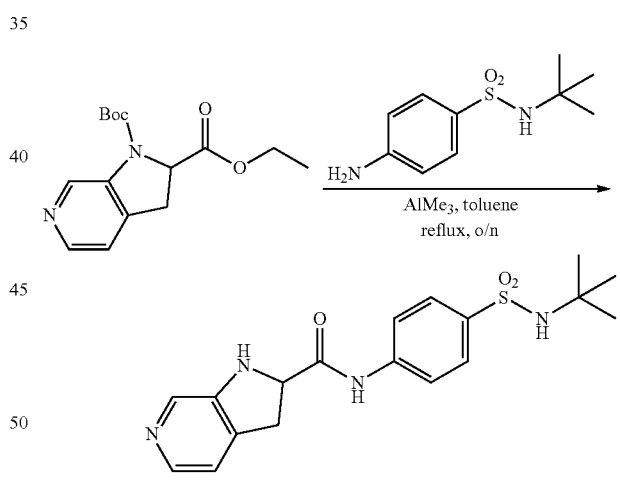

To the mixture of 0.6 g 1-tert-butyl 2-ethyl 2,3-dihydro-H-pyrrolo[2,3-c]pyridine-1,2-dicarboxylate (2.04 mmol, 1.00 equiv) and 934 mg 4-amino-N-tert-butylbenzenesulfonamide (4.08 mmol, 1.00 equiv) in 20.0 mL toluene was added 16 mL trimethylaluminum (2.0 M. in toluene, 8.16 mmol, 4.00 equiv). The mixture was stirred overnight and poured into 30 mL ice water. The mixture was extracted with 3×50 mL volumes of ethyl acetate. The combined organic layers were concentrated and the residue was purified by column chromatography on silica gel (petroleum ether:ethyl acetate (1:1, v:v)) to give 300 mg N-(4-(N-tert-butylsulfamoyl)phenyl)-2,3-dihydro-1H-pyrrolo[2,3-c]pyridine-2-carboxamide as a light yellow solid (39% yield). MS (ESI⁺) m/z 375 [M+H]⁺.

343

Preparation of N-(4-(N-tert-butylsulfamoyl)phenyl)-1-(4-fluorobenzoyl)-2,3-dihydro-1H-pyrrolo[2,3-c]pyridine-2-carboxamide, I-56

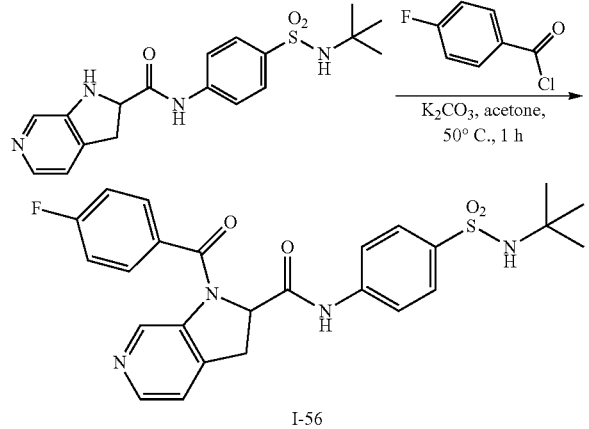

I-56

A mixture of 300 mg N-(4-(N-tert-butylsulfamoyl)phenyl)-2,3-dihydro-1H-pyrrolo[2,3-c]pyridine-2-carboxamide (0.80 mmol, 1.0 equiv), 126 mg 4-fluorobenzoyl chloride (0.80 mmol, 1.0 equiv) and 221 mg potassium carbonate (1.6 mmol, 2.00 equiv) in 10 mL acetone was stirred at 50° C. for 1 hour then poured into 20 mL water. The mixture was extracted with 3×20 mL volumes of ethyl acetate. The combined organic layers were washed with 2×50 mL volumes of water followed by 50 mL volume of brine, dried over anhydrous magnesium sulfate, filtered and the filtrate concentrated in vacuo. The compound was purified by reversed phase preparative HPLC on a Gilson GX-281. A concentrated solution of crude product dissolved in DMSO was injected in 500 uL volumes onto a 10 um C18 reversed phase XBridge 19 mm diameter×250 mm length column eluting with a gradient of 40-95% acetonitrile in water with 10 mmol/liter ammonium carbonate. Peaks were detected by UV absorbance at 214 nm and 254 nm and fractions collected by 5 mV threshold trigger on the 214 nm channel. Fractions containing product were combined, concentrated and lyophilized to afford 27 mg N-(4-(N-tert-butylsulfamoyl)phenyl)-1-(4-fluorobenzoyl)-2,3-dihydro-H-pyrrolo[2,3-c]pyridine-2-carboxamide (I-56) (6.8% yield). MS (ESI$^+$) m/z 497 [M+H]$^+$; $^1$H NMR (400 MHz, d$_6$-DMSO) δ 10.37 (s, 1H), 8.25 (s, 1H), 7.72-7.40 (m, 6H), 7.37-7.12 (m, 5H), 5.16 (s, 1H), 3.69 (dd, J=17.5, 10.9 Hz, 1H), 3.23 (dd, J=17.5, 3.4 Hz, 1H), 1.07 (s, 9H).

Example 37: N-(4-(N-tert-butylsulfamoyl)phenyl)-1-(4-fluorobenzoyl)-2,3-dihydro-1H-pyrrolo[2,3-b]pyridine-2-carboxamide, I-57

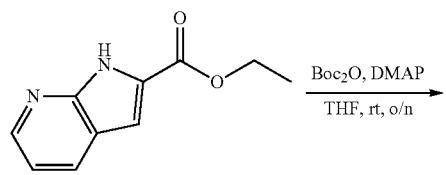

344

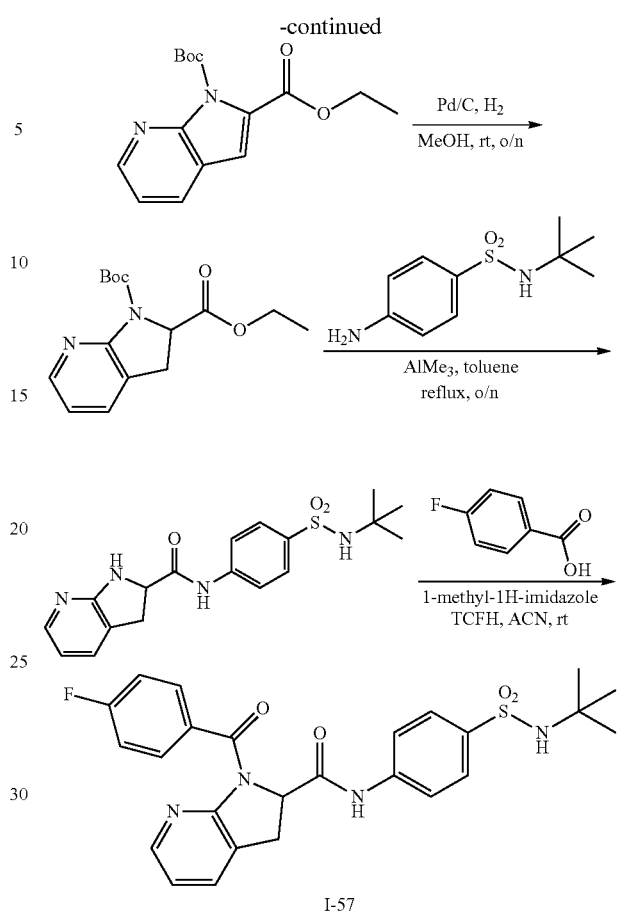

I-57

Preparation of 1-tert-butyl 2-ethyl 1H-pyrrolo[2,3-b]pyridine-1,2-dicarboxylate

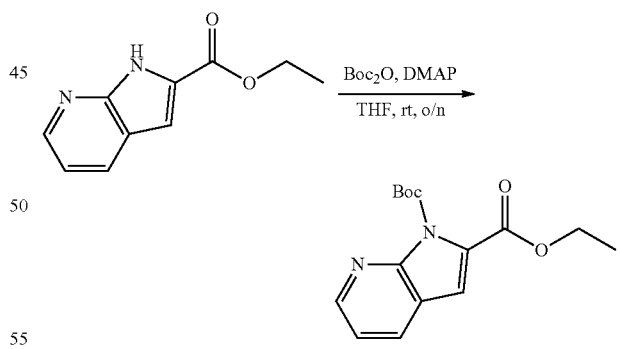

To a solution of 1.0 g ethyl 1H-pyrrolo[2,3-b]pyridine-2-carboxylate (5.3 mmol, 1.0 equiv) and 129 mg 4-dimethylaminopyridine (1.1 mol, 0.2 equiv) in THF (20 mL) was added 1.2 g di-tert-butyl dicarbonate (5.3 mmol, 1.0 equiv). The reaction mixture was stirred at room temperature for 4 h. After the resulting solution was evaporated under reduced pressure, the residue was purified by column chromatography (silica gel, petroleum ether:ethyl acetate (10:1, v:v)) to afford 1.1 g 1-tert-butyl 2-ethyl 1H-pyrrolo[2,3-b]pyridine-1,2-dicarboxylate (71% yield). MS (ESI$^+$) m/z 291 [M+H]$^+$.

Preparation of 1-tert-butyl 2-ethyl 2,3-dihydro-1H-pyrrolo[2,3-b]pyridine-1,2-dicarboxylate

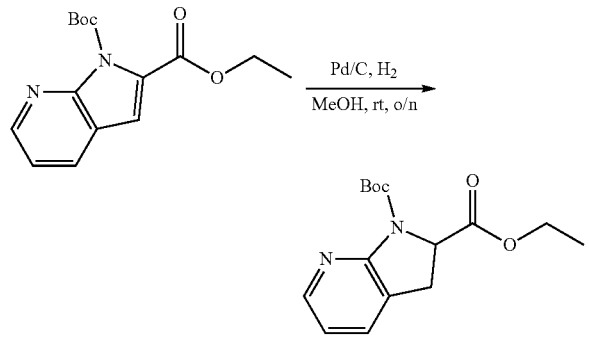

To a solution of 1.1 g 1-tert-butyl 2-ethyl 1H-pyrrolo[2,3-b]pyridine-1,2-dicarboxylate (3.8 mmol, 1.00 equiv) in 50 mL methanol was added palladium on activated carbon (50 mg wet catalyst, 10 wt. % palladium dry basis). The mixture was placed under hydrogen gas via balloon and stirred at room temperature overnight. The mixture was filtered and the filtrate concentrated to afford 1.0 g 1-tert-butyl 2-ethyl 2,3-dihydro-H-pyrrolo[2,3-b]pyridine-1,2-dicarboxylate as a white solid (90% yield). MS (ESI+) m/z 293 [M+H]+.

Preparation of N-(4-(N-tert-butylsulfamoyl)phenyl)-2,3-dihydro-1H-pyrrolo[2,3-b]pyridine-2-carboxamide

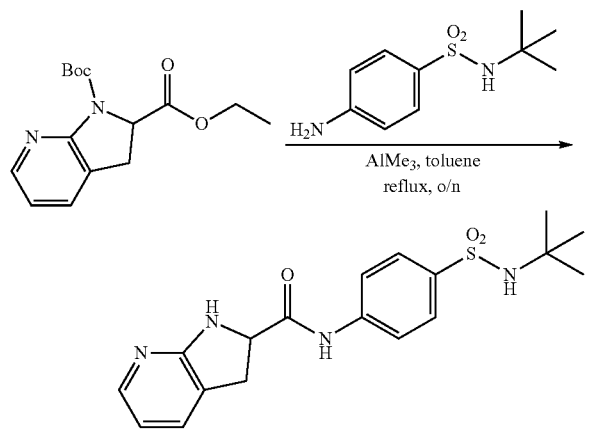

To the mixture of 1.0 g 1-tert-butyl 2-ethyl 2,3-dihydro-H-pyrrolo[2,3-b]pyridine-1,2-dicarboxylate (3.4 mmol, 1.00 equiv) and 780 mg 4-amino-N-tert-butylbenzenesulfonamide (3.4 mmol, 1.00 equiv) in 20.0 mL toluene was added 6.8 mL trimethylaluminum (2.0 M. in toluene, 13.6 mmol, 4.00 equiv). The mixture was stirred overnight and poured into 30 mL ice water. The mixture was extracted with 3×50 mL volumes of ethyl acetate. The combined organic layers were concentrated and the residue was purified by column chromatography on silica gel (petroleum ether:ethyl acetate (1:1, v:v)) to give 738 mg N-(4-(N-tert-butylsulfamoyl)phenyl)-2,3-dihydro-1H-pyrrolo[2,3-b]pyridine-2-carboxamide as a light yellow solid (58% yield). MS (ESI+) m/z 375 [M+H]+.

Preparation of N-(4-(N-tert-butylsulfamoyl)phenyl)-1-(4-fluorobenzoyl)-2,3-dihydro-1H-pyrrolo[2,3-b]pyridine-2-carboxamide, I-57

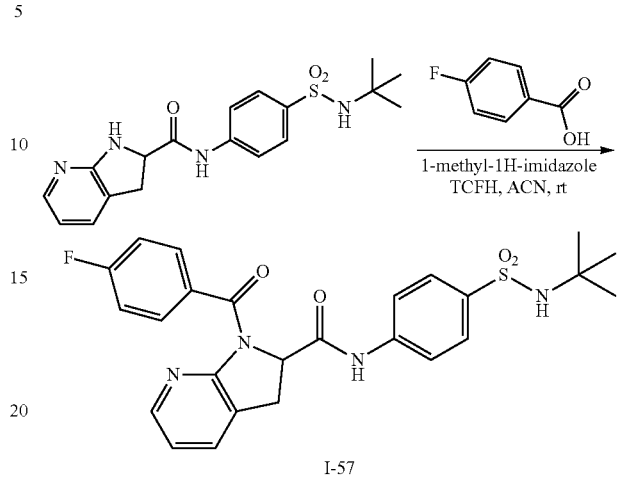

I-57

A mixture of 300 mg N-(4-(N-tert-butylsulfamoyl)phenyl)-2,3-dihydro-1H-pyrrolo[2,3-b]pyridine-2-carboxamide (0.80 mmol, 1.00 equiv), 112 mg 4-fluorobenzoic acid (0.80 mmol, 1.00 equiv), 246 mg N,N,N',N'-tetramethylchloroformamidinium hexafluorophosphate (0.88 mmol, 1.10 equiv) and 230 mg 1-methyl-1H-imidazole (2.8 mmol, 3.50 equiv) in 5 mL acetonitrile was stirred at room temperature overnight. The reaction was diluted with 50 mL ethyl acetate and washed with 3×40 mL volumes of water. The organic phases were concentrated and the compound was purified by reversed phase preparative HPLC on a Gilson GX-281. A concentrated solution of crude product dissolved in DMSO was injected in 540 uL volumes onto a 10 um C18 OBD reversed phase Waters X-SELECT 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 3 mV threshold trigger on the 214 nm channel. Fractions containing product were combined, concentrated and lyophilized to afford 30.0 mg N-(4-(N-tert-butylsulfamoyl)phenyl)-1-(4-fluorobenzoyl)-2,3-dihydro-1H-pyrrolo[2,3-b]pyridine-2-carboxamide (I-57) as a white solid (7.6% yield). MS (ESI+) m/z 497 [M+H]+; $^1$H NMR (400 MHz, $d_6$-DMSO) δ 10.74 (s, 1H), 7.84-7.72 (m, 5H), 7.67-7.50 (m, 3H), 7.42 (s, 1H), 7.24 (t, J=8.9 Hz, 2H), 6.93 (dd, J=7.3, 5.1 Hz, 1H), 5.22 (dd, J=10.5, 4.0 Hz, 1H), 3.59 (dd, J=16.9, 10.6 Hz, 1H), 3.13 (dd, J=17.0, 3.9 Hz, 1H), 1.08 (d, J=3.6 Hz, 9H).

Example 38: (S)-N-(1-(5-(N-tert-butylsulfamoyl)pyridin-2-ylamino)-1-oxo-3-phenylpropan-2-yl)-4-fluorobenzamide, I-61

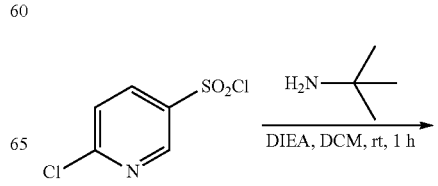

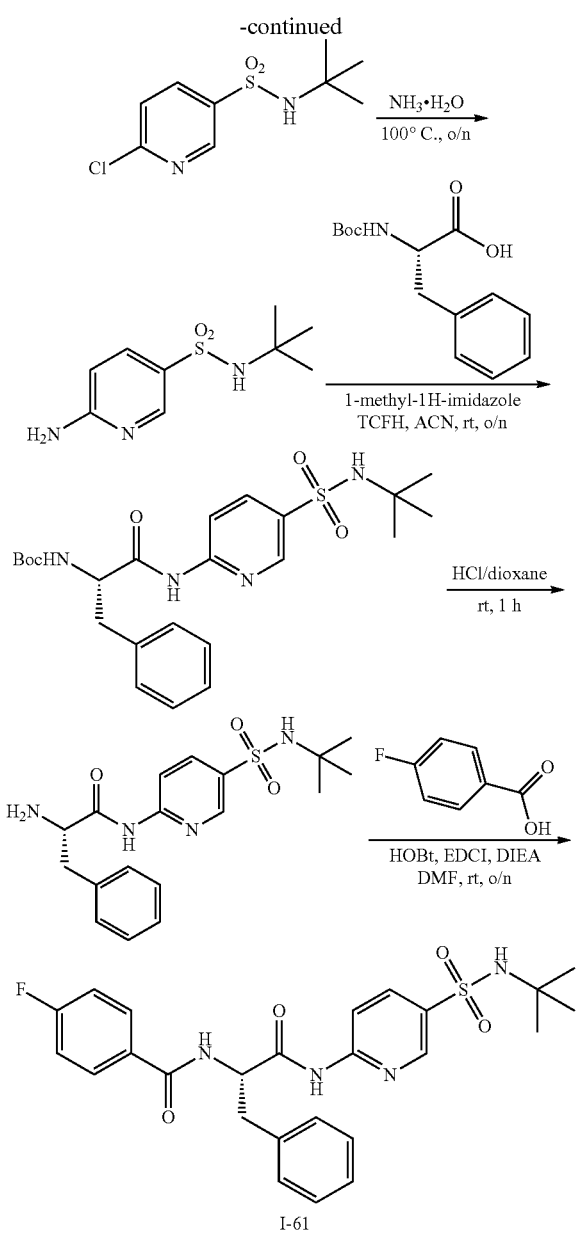

Preparation of
N-tert-butyl-6-chloropyridine-3-sulfonamide

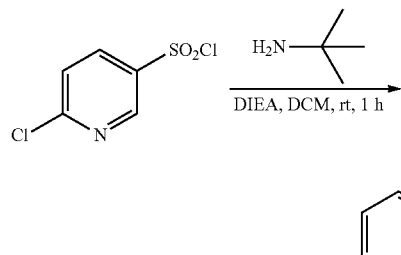

To the mixture of 344 mg 2-methylpropan-2-amine (4.72 mmol, 2.00 equiv) and 609 mg N,N-diisopropylethylamine (4.72 mmol, 2.00 equiv) in 30 mL dichloromethane was added 500 mg 6-chloropyridine-3-sulfonyl chloride (2.36 mmol, 1.0 equiv). The mixture was stirred at room temperature for 1 hour and concentrated in vacuo. The residue was purified by column chromatography (silica gel, dichloromethane:ethyl acetate (4:1, v:v)) to afford 500 mg N-tert-butyl-6-chloropyridine-3-sulfonamide as a white solid (85% yield). MS (ESI+) m/z 249 [M+H]+.

Preparation of
6-amino-N-tert-butylpyridine-3-sulfonamide

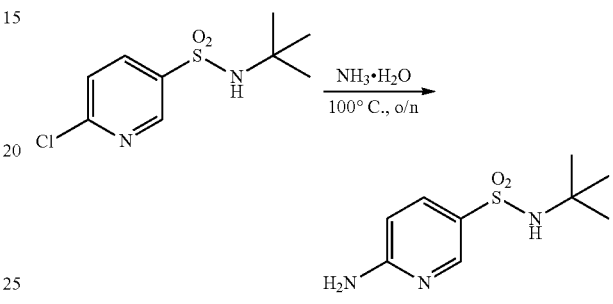

A solution of 500 mg N-tert-butyl-6-chloropyridine-3-sulfonamide (2.0 mmol, 1.00 equiv) in 30 mL ammonium hydroxide in water was stirred at 100° C. overnight. The mixture was concentrated and the residue was purified by column chromatography (silica gel, dichloromethane:ethyl acetate (2:1, v:v)) to afford 300 mg 6-amino-N-tert-butylpyridine-3-sulfonamide as a white solid (66% yield). MS (ESI+) m/z 230 [M+H]+.

Preparation of (S)-tert-butyl 1-(5-(N-tert-butylsulfamoyl)pyridin-2-ylamino)-1-oxo-3-phenylpropan-2-ylcarbamate

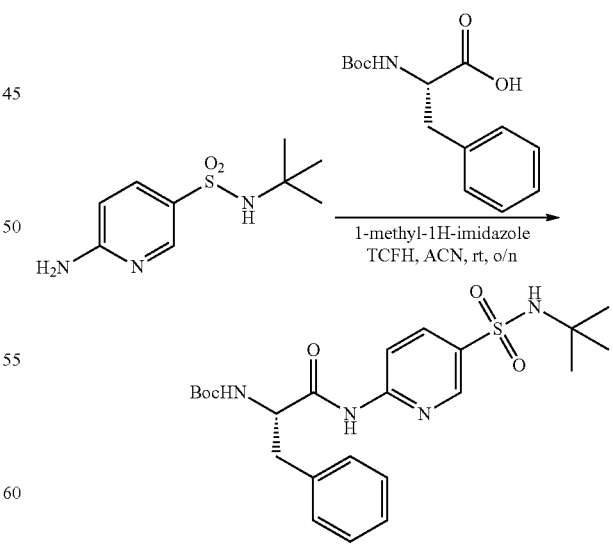

A mixture of 300 mg 6-amino-N-tert-butylpyridine-3-sulfonamide (1.3 mmol, 1.00 equiv), 347 mg (S)-2-(tert-butoxycarbonylamino)-3-phenylpropanoic acid (1.3 mmol, 1.00 equiv), 400 mg N,N,N',N'-tetramethylchloroformamidinium hexafluorophosphate (1.43 mmol, 1.10 equiv) and 373 mg 1-methyl-1H-imidazole (4.55 mmol, 3.50 equiv) in 5 mL acetonitrile was stirred at room temperature overnight. To the mixture was added 20 mL ethyl acetate and washed with 3×20 mL volumes of water. The organic phase was concentrated and the residue was purified by column chromatography on silica gel (petroleum ether:ethyl acetate (5:1, v:v) to give 200 mg (S)-tert-butyl 1-(5-(N-tert-butylsulfamoyl)pyridin-2-ylamino)-1-oxo-3-phenylpropan-2-ylcarbamate as a white solid (32% yield). MS (ESI+) m/z 477 [M+H]+.

Preparation of (S)-2-amino-N-(5-(N-tert-butylsulfamoyl)pyridin-2-yl)-3-phenylpropanamide

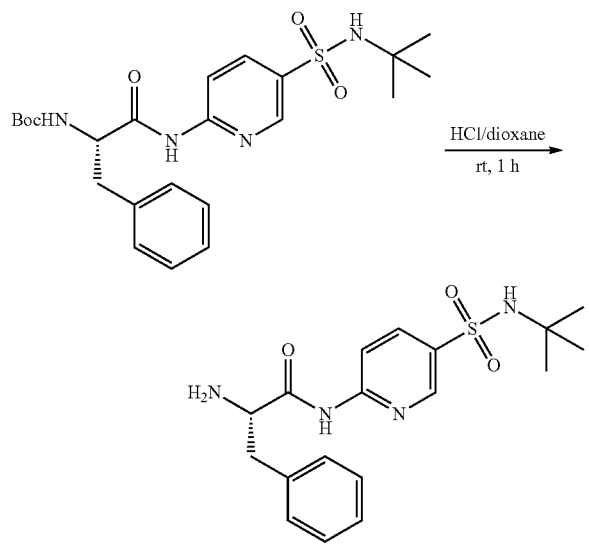

The mixture of 200 mg (S)-tert-butyl 1-(5-(N-tert-butylsulfamoyl)pyridin-2-ylamino)-1-oxo-3-phenylpropan-2-ylcarbamate (0.42 mmol, 1.0 equiv) in 20 mL hydrochloric acid in dioxane (4.0 M HCl) was stirred at room temperature for 1 hour. The mixture was concentrated to give 158 mg (S)-2-amino-N-(4-(benzylthio)phenyl)-N-methyl-3-phenylpropanamide as a light yellow solid (100% yield). MS (ESI+) m/z 377 [M+H]+.

Preparation of (S)-N-(1-(5-(N-tert-butylsulfamoyl)pyridin-2-ylamino)-1-oxo-3-phenylpropan-2-yl)-4-fluorobenzamide, I-61

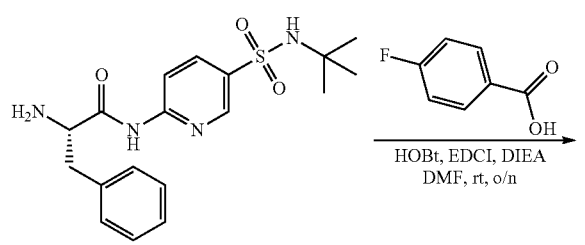

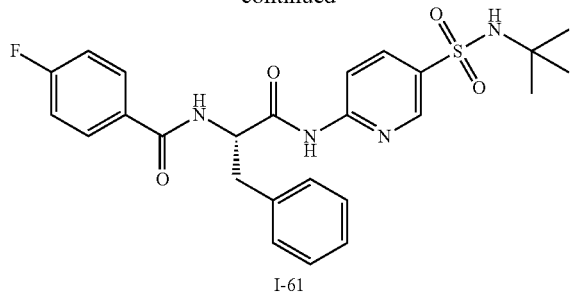

I-61

A mixture of 158 mg (S)-2-amino-N-(4-(benzylthio)phenyl)-N-methyl-3-phenylpropanamide (0.42 mmol, 1.0 equiv), 59 mg 4-fluorobenzoic acid (0.42 mmol, 1.00 equiv), 121 mg N-(3-dimethylaminopropyl)-N'-ethylcarbodiimide hydrochloride (0.63 mmol, 1.50 equiv), 68 mg 1-hydroxybenzotriazole (0.5 mmol, 1.2 equiv) and 108 mg N,N-diisopropylethylamine (0.84 mmol, 2.00 equiv) in 20 mL N,N-dimethylformamide was stirred at room temperature overnight. The mixture was diluted with 50 mL ethyl acetate and washed with 3×50 mL volumes of water. The organic phase was concentrated and the compound was purified by reversed phase preparative HPLC on a Gilson GX-281. A concentrated solution of crude product dissolved in DMSO was injected in 500 uL volumes onto a 10 um C18 reversed phase X-Bridge 19 mm diameter×250 mm length column eluting with a gradient of 52-95% acetonitrile in water with 10 mmol/liter ammonium carbonate. Peaks were detected by UV absorbance at 214 nm and 254 nm and fractions collected by 1.5 mV threshold trigger on the 214 nm channel. Fractions containing product were combined, concentrated and lyophilized to afford 30.0 mg (S)-N-(1-(5-(N-tert-butylsulfamoyl)pyridin-2-ylamino)-1-oxo-3-phenylpropan-2-yl)-4-fluorobenzamide (I-61) as a white solid (14% yield). MS (ESI+) m/z 499 [M+H]+; $^1$H NMR (400 MHz, d$_6$-DMSO) δ 11.31 (s, 1H), 8.81 (d, J=7.9 Hz, 1H), 8.74-8.62 (m, 1H), 8.18 (dt, J=8.9, 5.7 Hz, 2H), 7.91-7.75 (m, 2H), 7.63 (s, 1H), 7.46 (d, J=7.2 Hz, 2H), 7.30-7.20 (m, 4H), 7.16 (t, J=7.3 Hz, 1H), 5.00-4.85 (m, 1H), 3.17 (dd, J=13.6, 3.9 Hz, 1H), 3.10-2.94 (m, 1H), 1.10 (s, 9H).

Example 46: (S)-N-(1-(6-(N-tert-butylsulfamoyl)pyridin-3-ylamino)-1-oxo-3-phenylpropan-2-yl)-4-fluorobenzamide, I-62

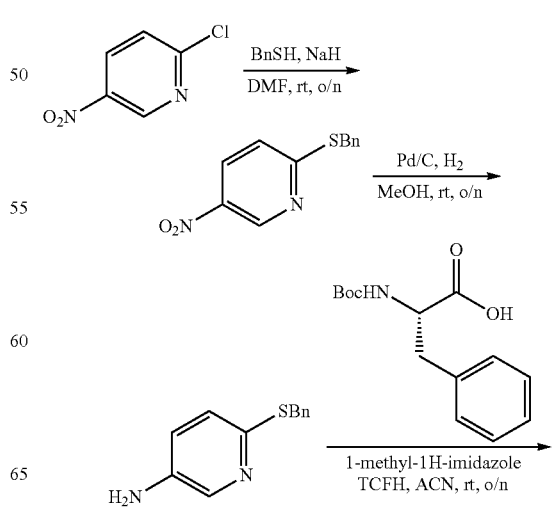

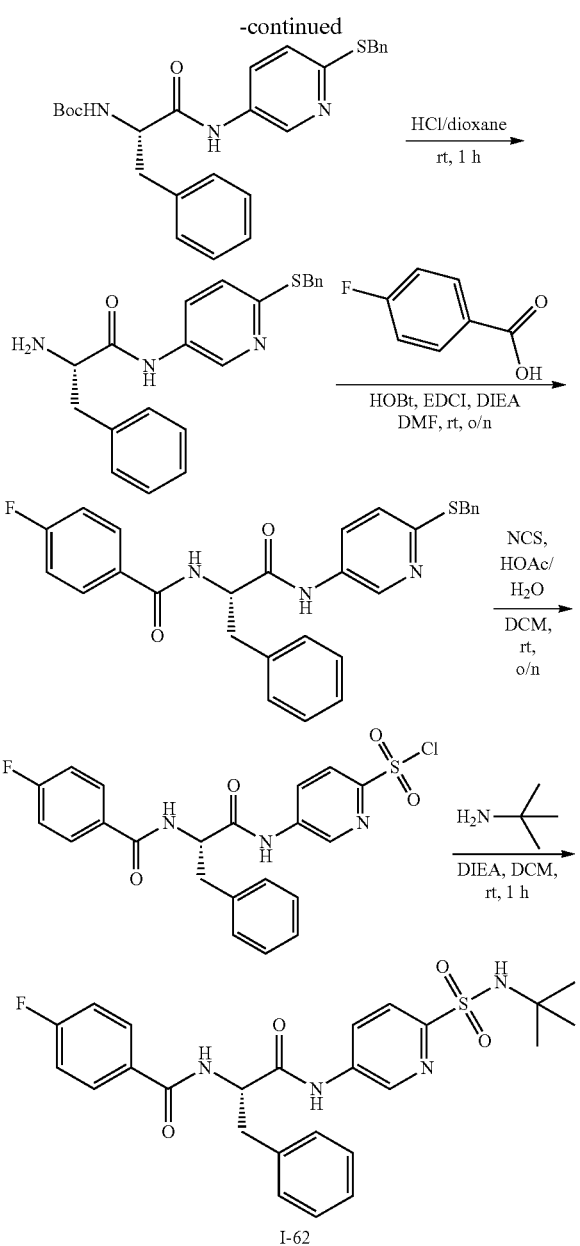

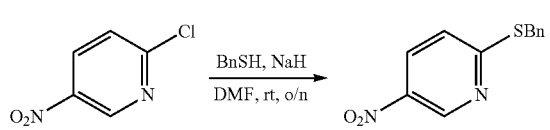

Preparation of 2-(benzylthio)-5-nitropyridine

To a solution of 1.57 g phenylmethanethiol (12.7 mmol, 1.00 equiv) in 10 mL N,N-dimethylformamide was added 1.0 g sodium hydride (60 wt. % dispersion in mineral oil, 25.4 mmol, 2.0 equiv) at room temperature and the mixture was stirred for 30 minutes. Then 2.0 g 2-chloro-5-nitropyridine (12.7 mmol, 1.00 equiv) was added and the reaction was stirred at room temperature overnight. The mixture was poured into 30 mL saturated aqueous ammonium chloride solution and extracted with 3×50 mL volumes of ethyl acetate. The combined organic phases were concentrated and the residue was purified by column chromatography on silica gel (petroleum ether:ethyl acetate (10:1, v:v)) to give 2.0 g 2-(benzylthio)-5-nitropyridine as a yellow solid (64% yield). MS (ESI$^+$) m/z 247 [M+H]$^+$.

Preparation of 6-(benzylthio)pyridin-3-amine

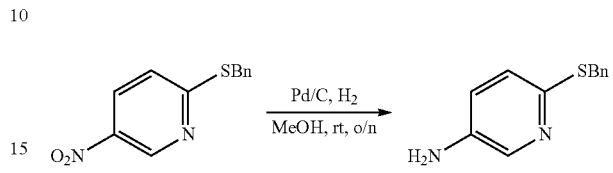

To a solution of 300 mg 2-(benzylthio)-5-nitropyridine (1.2 mmol, 1.00 equiv) in 50 mL methanol was added palladium on activated carbon (50 mg wet catalyst, 10 wt. % palladium dry basis). The mixture was placed under hydrogen gas via balloon and stirred at room temperature overnight. The mixture was filtered and the filtrate concentrated to afford 250 mg 6-(benzylthio)pyridin-3-amine as a white solid (96% yield). MS (ESI$^+$) m/z 217 [M+H]$^+$.

Preparation of (S)-tert-butyl 1-(6-(benzylthio)pyridin-3-ylamino)-1-oxo-3-phenylpropan-2-ylcarbamate

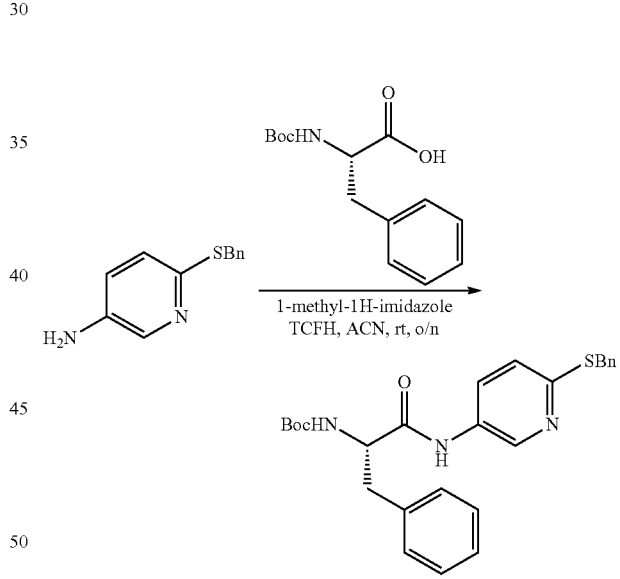

A mixture of 250 mg 6-(benzylthio)pyridin-3-amine (1.2 mmol, 1.00 equiv), 318 mg (S)-2-(tert-butoxycarbonylamino)-3-phenylpropanoic acid (1.2 mmol, 1.00 equiv), 370 mg N,N,N',N'-tetramethylchloroformamidinium hexafluorophosphate (1.32 mmol, 1.10 equiv) and 344 mg 1-methyl-1H-imidazole (4.55 mmol, 3.50 equiv) in 5 mL acetonitrile was stirred at room temperature overnight. To the mixture was added 20 mL ethyl acetate and washed with 3×20 mL volumes of water. The organic phase was concentrated and the residue was purified by column chromatography on silica gel (petroleum ether:ethyl acetate (5:1, v:v) to give 300 mg (S)-tert-butyl 1-(6-(benzylthio)pyridin-3-ylamino)-1-oxo-3-phenylpropan-2-ylcarbamate as a white solid (54% yield). MS (ESI$^+$) m/z 464 [M+H]$^+$.

Preparation of (S)-2-amino-N-(6-(benzylthio)pyridin-3-yl)-3-phenylpropanamide

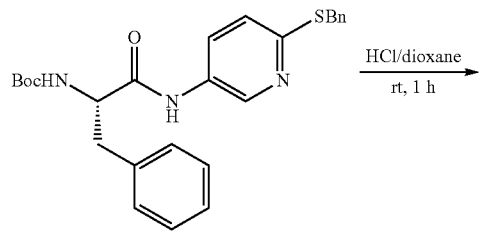

The mixture of 300 mg (S)-tert-butyl 1-(6-(benzylthio)pyridin-3-ylamino)-1-oxo-3-phenylpropan-2-ylcarbamate (0.65 mmol, 1.0 equiv) in 20 mL hydrochloric acid in dioxane (4.0 M HCl) was stirred at room temperature for 1 hours. The mixture was concentrated to give 236 mg (S)-2-amino-N-(6-(benzylthio)pyridin-3-yl)-3-phenylpropanamide as a light yellow solid (100% yield). MS (ESI$^+$) m/z 364 [M+H]$^+$.

Preparation of (S)-N-(1-(6-(benzylthio)pyridin-3-ylamino)-1-oxo-3-phenylpropan-2-yl)-4-fluorobenzamide

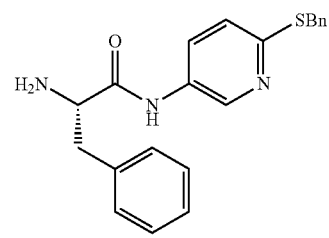

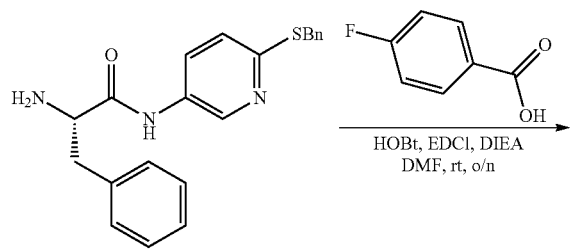

A mixture of 236 mg (S)-2-amino-N-(6-(benzylthio)pyridin-3-yl)-3-phenylpropanamide (0.65 mmol, 1.0 equiv), 91 mg 4-fluorobenzoic acid (0.65 mmol, 1.00 equiv), 187 mg N-(3-dimethylaminopropyl)-N'-ethylcarbodiimide hydrochloride (0.98 mmol, 1.50 equiv), 105 mg 1-hydroxybenzotriazole (0.78 mmol, 1.2 equiv) and 168 mg N,N-diisopropylethylamine (1.3 mmol, 2.00 equiv) in 20 mL N,N-dimethylformamide was stirred at room temperature overnight. The mixture was diluted with 50 mL ethyl acetate and washed with 3×50 mL volumes of water. The organic phase was concentrated and the residue was purified by column chromatography on silica gel (petroleum ether:ethyl acetate (5:1, v:v) to give 250 mg (S)-N-(1-(6-(benzylthio)pyridin-3-ylamino)-1-oxo-3-phenylpropan-2-yl)-4-fluorobenzamide as a white solid (79% yield). MS (ESI$^+$) m/z 486 [M+H]$^+$.

Preparation of (S)-5-(2-(4-fluorobenzamido)-3-phenylpropanamido)pyridine-2-sulfonyl Chloride

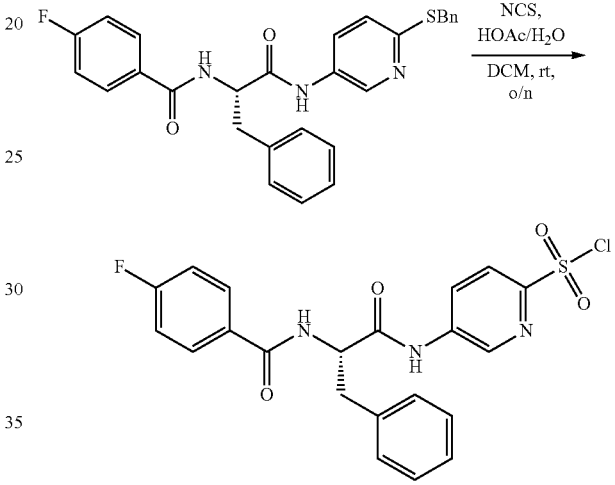

To a solution of 250 mg (S)-N-(1-(6-(benzylthio)pyridin-3-ylamino)-1-oxo-3-phenylpropan-2-yl)-4-fluorobenzamide (0.51 mmol, 1.00 equiv), 6.2 mg acetic acid (0.1 mmol, 0.2 equiv) and 1.8 mg water (0.1 mmol, 0.2 equiv) in 10 mL dichloromethane was added 266 mg N-chlorosuccinimide (2.0 mmol, 4.00 equiv) at 0° C. The mixture was stirred at room temperature overnight and washed with 3×20 mL volumes of water. The organic phase was concentrated to give 141 mg (S)-5-(2-(4-fluorobenzamido)-3-phenylpropanamido)pyridine-2-sulfonyl chloride as a white solid (60% yield). MS (ESI$^+$) m/z 462 [M+H]$^+$.

Preparation of (S)-N-(1-(6-(N-tert-butylsulfamoyl)pyridin-3-ylamino)-1-oxo-3-phenylpropan-2-yl)-4-fluorobenzamide, I-62

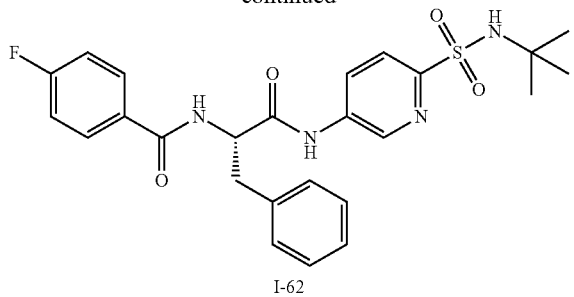

I-62

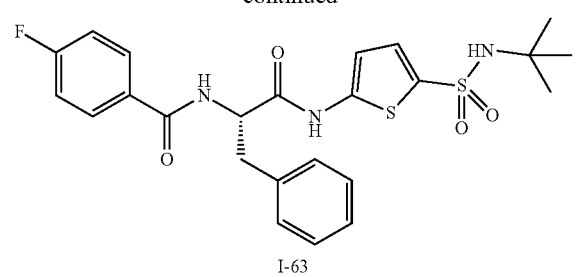

I-63

To the mixture of 45 mg 2-methylpropan-2-amine (0.62 mmol, 2.00 equiv) and 80 mg N,N-diisopropylethylamine (0.62 mmol, 2.00 equiv) in 30 mL dichloromethane was added 141 mg 6-(S)-5-(2-(4-fluorobenzamido)-3-phenylpropanamido)pyridine-2-sulfonyl chloride (0.31 mmol, 1.0 equiv). The mixture was stirred at room temperature for 1 hour and concentrated in vacuo. The compound was purified by reversed phase preparative HPLC on a Gilson GX-281. A concentrated solution of crude product dissolved in DMSO was injected in 500 uL volumes onto a 10 um C18 reversed phase X-Bridge 19 mm diameter×250 mm length column eluting with a gradient of 48-95% acetonitrile in water with 10 mmol/liter ammonium carbonate. Peaks were detected by UV absorbance at 214 nm and 254 nm and fractions collected by 1 mV threshold trigger on the 214 nm channel. Fractions containing product were combined, concentrated and lyophilized to afford 30 mg N-tert-butyl-6-chloropyridine-3-sulfonamide (I-62) as a white solid (20% yield). MS (ESI$^+$) m/z 499 [M+H]$^+$; $^1$H NMR (400 MHz, d$_6$-DMSO) δ 10.81 (s, 1H), 8.93 (d, J=7.8 Hz, 1H), 8.86 (d, J=2.3 Hz, 1H), 8.27 (dd, J=8.6, 2.5 Hz, 1H), 8.01-7.81 (m, 3H), 7.60 (s, 1H), 7.40 (d, J=7.2 Hz, 2H), 7.35-7.22 (m, 4H), 7.18 (t, J=7.3 Hz, 1H), 4.84 (ddd, J=10.0, 7.8, 5.0 Hz, 1H), 3.15 (ddd, J=23.8, 13.7, 7.6 Hz, 2H), 1.08 (s, 9H).

Example 40: (S)-N-(1-(5-(N-tert-butylsulfamoyl)thiophen-2-ylamino)-1-oxo-3-phenylpropan-2-yl)-4-fluorobenzamide, I-63

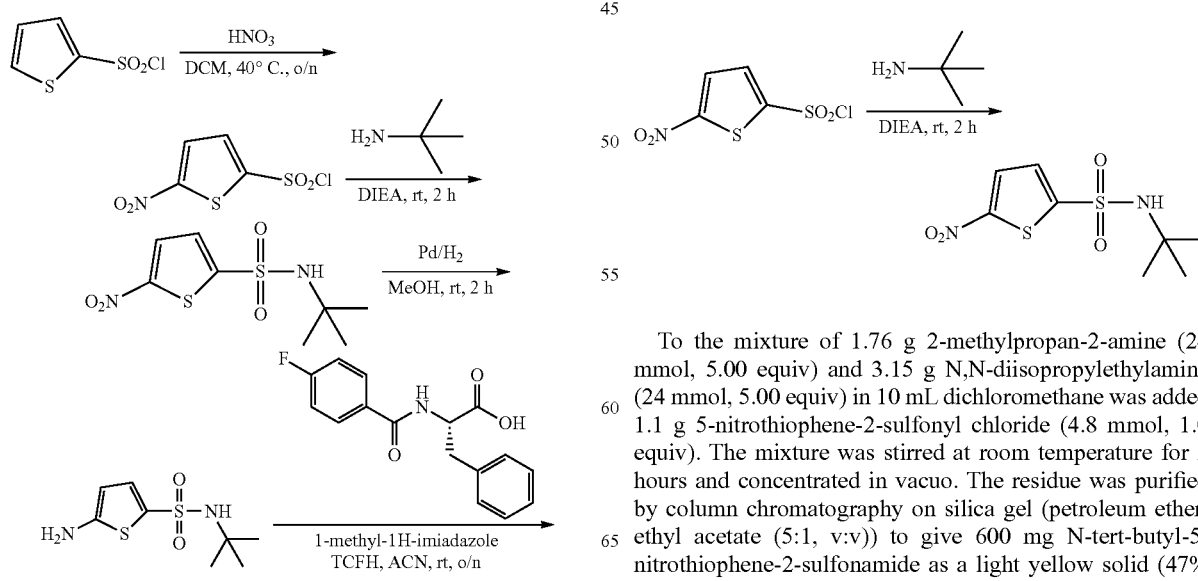

Preparation of 5-nitrothiophene-2-sulfonyl Chloride

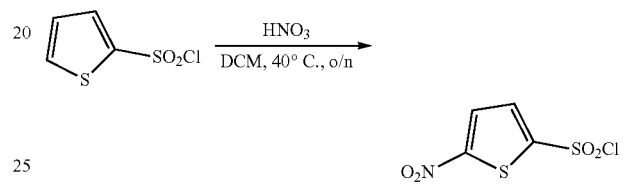

A solution of 3 g thiophene-2-sulfonyl chloride (16.5 mmol, 1.00 equiv) in 5 mL of dichloromethane slowly while stirring to 20 mL of conc. Nitric acid is added dropwise. The reaction mixture is stirred for 12 hours at 40° C. and then placed on ice. The mixture was extracted with 3×100 mL volumes of ethyl acetate. The combined organic layers were concentrated and the residue was purified by column chromatography on silica gel (petroleum ether:ethyl acetate (10:1, v:v)) to give 1.1 g 5-nitrothiophene-2-sulfonyl chloride as a light yellow solid (30% yield). MS (ESI$^+$) m/z 228 [M+H]$^+$.

Preparation of N-tert-butyl-5-nitrothiophene-2-sulfonamide

To the mixture of 1.76 g 2-methylpropan-2-amine (24 mmol, 5.00 equiv) and 3.15 g N,N-diisopropylethylamine (24 mmol, 5.00 equiv) in 10 mL dichloromethane was added 1.1 g 5-nitrothiophene-2-sulfonyl chloride (4.8 mmol, 1.0 equiv). The mixture was stirred at room temperature for 2 hours and concentrated in vacuo. The residue was purified by column chromatography on silica gel (petroleum ether:ethyl acetate (5:1, v:v)) to give 600 mg N-tert-butyl-5-nitrothiophene-2-sulfonamide as a light yellow solid (47% yield). MS (ESI$^+$) m/z 265 [M+H]$^+$.

Preparation of 5-amino-N-tert-butylthiophene-2-sulfonamide

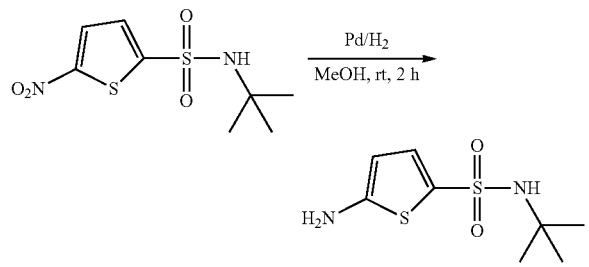

To a solution of 600 mg N-tert-butyl-5-nitrothiophene-2-sulfonamide (2.27 mmol, 1.00 equiv) in 20 mL methanol was added palladium on activated carbon (100 mg wet catalyst, 10 wt. % palladium dry basis). The mixture was placed under hydrogen gas via balloon and stirred at room temperature overnight. The mixture was filtered and the filtrate concentrated to afford 420 mg 5-amino-N-tert-butyl-thiophene-2-sulfonamide as a yellow solid (79% yield). MS (ESI$^+$) m/z 235 [M+H]$^+$.

Preparation of (S)-N-(1-(5-(N-tert-butylsulfamoyl)thiophen-2-ylamino)-1-oxo-3-phenylpropan-2-yl)-4-fluorobenzamide, I-63

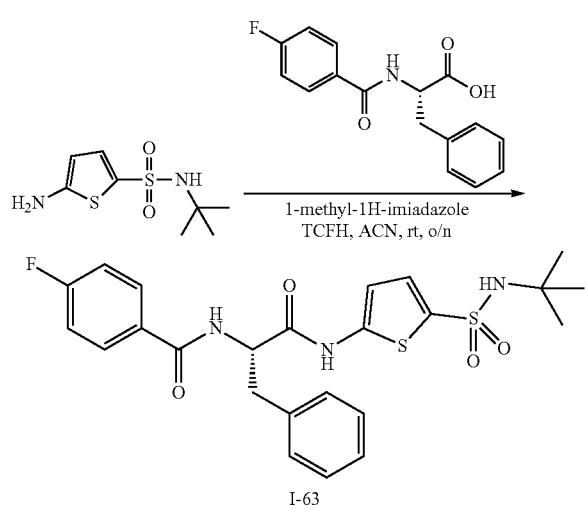

A mixture of 307 mg (S)-2-(4-fluorobenzamido)-3-phenylpropanoic acid (1.07 mmol, 1.00 equiv), 250 mg 5-amino-N-tert-butylthiophene-2-sulfonamide (1.07 mmol, 1.00 equiv), 330 mg N,N,N',N'-tetramethylchloroformamidinium hexafluorophosphate (1.18 mmol, 1.10 equiv) and 307 mg 1-methyl-1H-imidazole (3.75 mmol, 3.50 equiv) in 3 mL acetonitrile was stirred at room temperature overnight. The reaction was diluted with 50 mL ethyl acetate and washed with 3×50 mL volumes of water. The organic phases were concentrated and the compound was purified by reversed phase preparative HPLC on a Gilson GX-281. A concentrated solution of crude product dissolved in DMSO was injected in 400 uL volumes onto a 10 um C18 OBD reversed phase Waters X-SELECT 19 mm diameter×250 mm length column eluting with a gradient of 45-95% acetonitrile in water with 10 mmol/liter ammonium carbonate. Peaks were detected by UV absorbance at 214 nm and 254 nm and fractions collected by 2 mV threshold trigger on the 214 nm channel. Fractions containing product were combined, concentrated and lyophilized to afford 20 mg (S)-N-(1-(5-(N-tert-butylsulfamoyl)thiophen-2-ylamino)-1-oxo-3-phenylpropan-2-yl)-4-fluorobenzamide (I-63) as a white solid (5% yield). MS (ESI$^+$) m/z 504 [M+H]$^+$; $^1$H NMR (400 MHz, d$_6$-DMSO) δ 11.86 (s, 1H), 8.94 (d, J=7.8 Hz, 1H), 7.89 (dd, J=8.8, 5.5 Hz, 2H), 7.49 (s, 1H), 7.38-7.20 (m, 7H), 7.16 (t, J=7.3 Hz, 1H), 6.66 (d, J=4.1 Hz, 1H), 4.89-4.73 (m, 1H), 3.20-2.97 (m, 2H), 1.11 (s, 9H).

Example 41: (S)-N-(4-(N-tert-butylsulfamoyl)phenyl)-2-(1-oxoisoindolin-2-yl)-3-phenylpropanamide, I-69

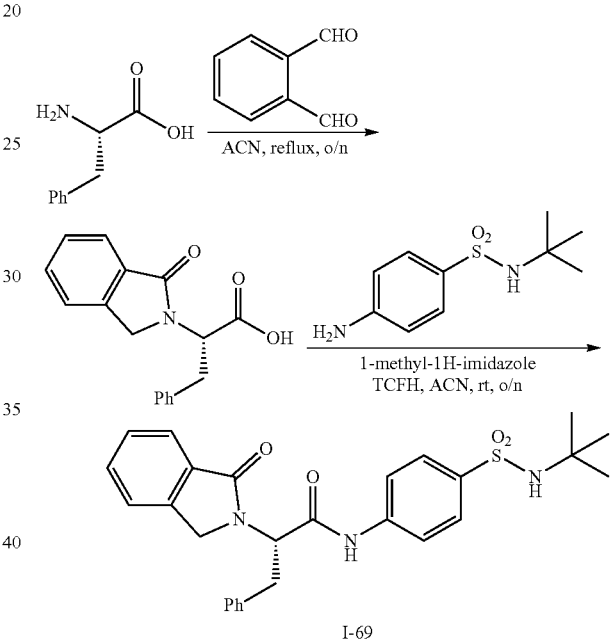

Preparation of (S)-2-(1-oxoisoindolin-2-yl)-3-phenylpropanoic Acid

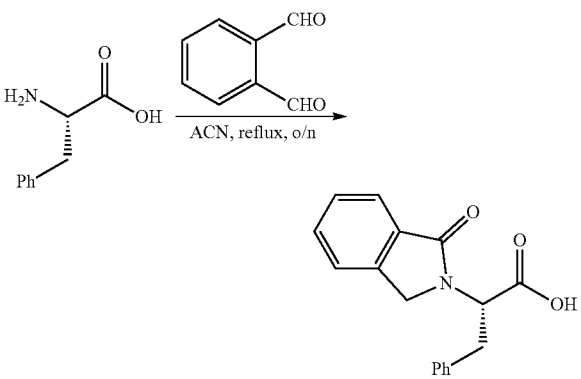

A mixture of 1.0 g (S)-2-amino-3-phenylpropanoic acid (6.1 mmol, 1.0 equiv) and 812 mg phthalaldehyde (6.1 mmol, 1.00 equiv) in 20 mL acetonitrile was refluxed overnight. The solid was filtered to give 300 mg (S)-2-(1-oxoisoindolin-2-yl)-3-phenylpropanoic acid as a white solid (18% yield). MS (ESI+) m/z 282 [M+H]+.

Preparation of (S)-N-(4-(N-tert-butylsulfamoyl)phenyl)-2-(1-oxoisoindolin-2-yl)-3-phenylpropanamide, I-69

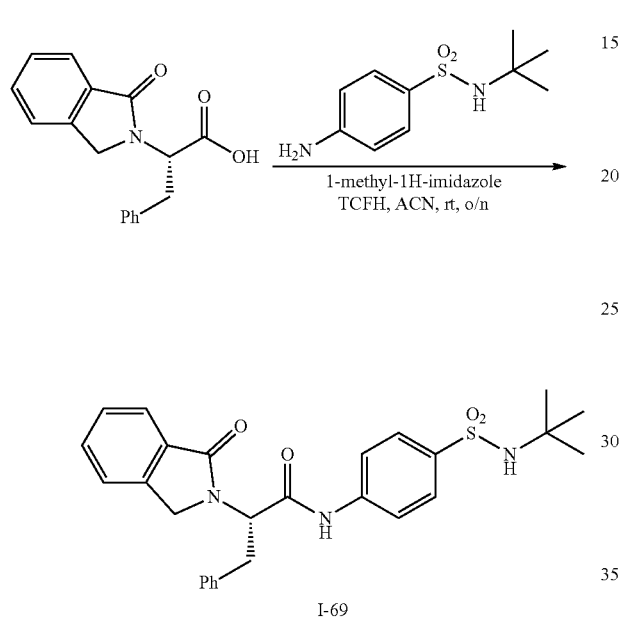

I-69

A mixture of 300 mg (S)-2-(1-oxoisoindolin-2-yl)-3-phenylpropanoic acid (1.1 mmol, 1.00 equiv), 251 mg 4-amino-N-tert-butylbenzenesulfonamide (1.1 mmol, 1.00 equiv), 339 mg N,N,N′,N′-tetramethylchloroformamidinium hexafluorophosphate (1.21 mmol, 1.10 equiv) and 316 mg 1-methyl-1H-imidazole (3.85 mmol, 3.50 equiv) in 5 mL acetonitrile was stirred at room temperature overnight. To the mixture was added 20 mL ethyl acetate and the solution washed with 3×20 mL volumes of water. The organic phase was concentrated and the compound was purified by reversed phase preparative HPLC on a Gilson GX-281. A concentrated solution of crude product dissolved in DMSO was injected in 800 uL volumes onto a 10 um C18 reversed phase X-Bridge 19 mm diameter×250 mm length column eluting with a gradient of 50-95% acetonitrile in water with 10 mmol/liter ammonium carbonate. Peaks were detected by UV absorbance at 214 nm and 254 nm and fractions collected by 1.5 mV threshold trigger on the 214 nm channel. Fractions containing product were combined, concentrated and lyophilized to afford 30 mg (S)-N-(4-(N-tert-butylsulfamoyl)phenyl)-2-(1-oxoisoindolin-2-yl)-3-phenylpropanamide (I-69) as a white solid (5.6% yield). MS (ESI+) m/z 492 [M+H]+; 1H NMR (400 MHz, d6-DMSO) δ 10.71 (s, 1H), 7.75 (s, 4H), 7.64 (d, J=7.5 Hz, 1H), 7.58 (t, J=5.9 Hz, 2H), 7.52-7.19 (m, 6H), 7.15 (t, J=7.3 Hz, 1H), 5.40 (dd, J=10.4, 5.5 Hz, 1H), 4.80 (d, J=17.7 Hz, 1H), 4.57 (d, J=17.7 Hz, 1H), 3.39 (dt, J=14.0, 7.0 Hz, 1H), 3.24 (dd, J=14.5, 10.5 Hz, 1H), 1.07 (s, 9H).

Example 42: (S)-4-fluoro-N-methyl-N-(1-(4-(N-oxetan-3-ylsulfamoyl)phenylamino)-1-oxo-3-phenylpropan-2-yl)benzamide, I-70

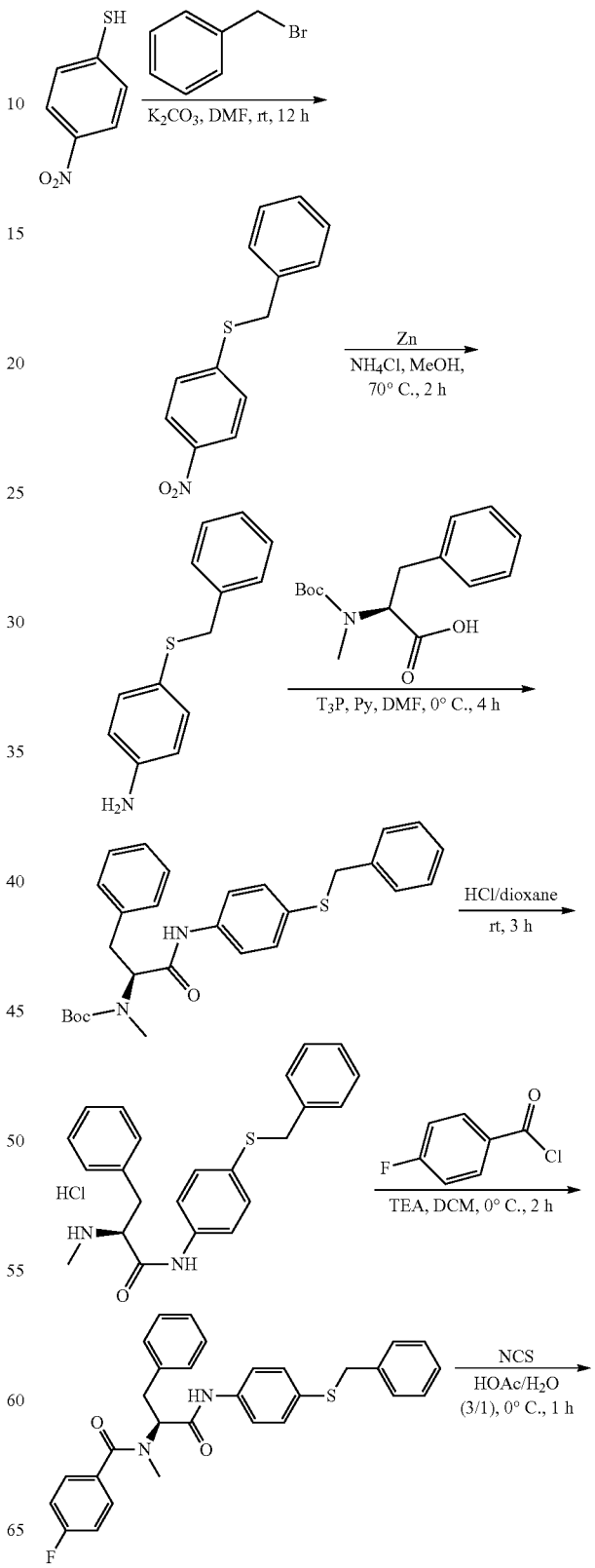

-continued

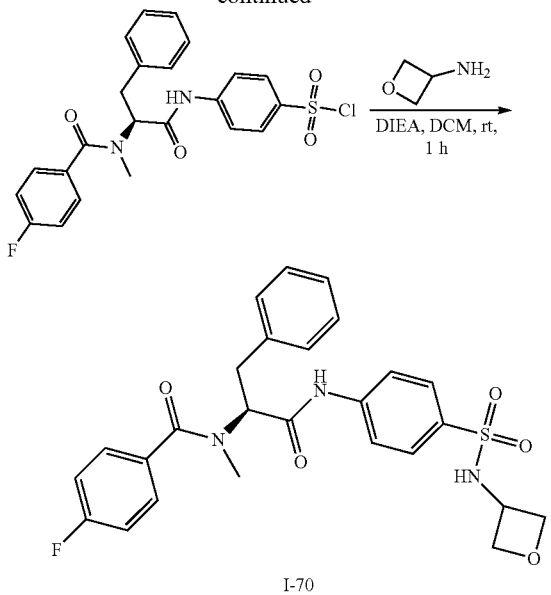

I-70

Preparation of benzyl(4-nitrophenyl)sulfane

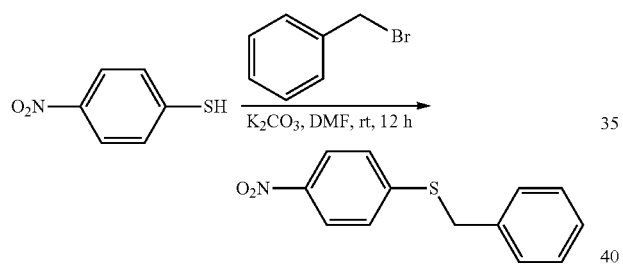

Benzyl bromide (19.84 g, 116.00 mmol) was added dropwise to a solution of 15 g of 4-nitrobenzenethiol (96.67 mmol) and 26.72 g of potassium carbonate (193.34 mmol) in 500 mL anhydrous N,N-dimethylformamide at room temperature and stirred for 12 h at room temperature. The reaction was diluted with 500 mL water and extracted with ethyl acetate (3×500 mL). The combined organic layers were washed with brine (3×200 mL), dried over anhydrous magnesium sulfate, filtered, and concentrated in vacuo. Purification by column chromatography (silica gel, petroleum ether:ethyl acetate (10:1)) afforded 18 g of benzyl(4-nitrophenyl)sulfane as a yellow solid (76% yield). MS (ESI$^+$) m/z 246 [M+H]$^+$.

Preparation of 4-(benzylthio)benzenamine

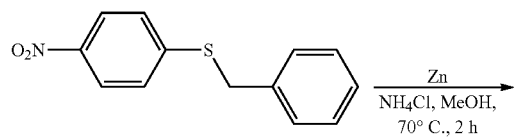

-continued

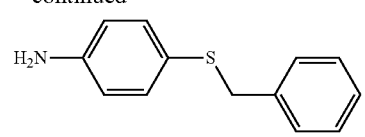

Zinc (19.19 g, 293.52 mmol, 4.00 equiv) was added portionwise to a solution of 18 g of benzyl(4-nitrophenyl)sulfane (73.38 mmol, 1.00 equiv) and 19.63 g ammonium chloride (366.90 mmol, 5.00 equiv) in 300 mL methanol at room temperature. The reaction was stirred for 2 h at 70° C. under a nitrogen atmosphere. The mixture was cooled to room temperature, filtered, and concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and concentrated in vacuo. Purification by column chromatography (silica gel, petroleum ether:ethyl acetate (5:1)) afforded 10 g of 4-(benzylthio)benzenamine as an orange oil (63.4% yield). MS (ESI$^+$) m/z 216 [M+H]$^+$.

Preparation of (S)-tert-butyl 1-(4-(benzylthio)phenylamino)-1-oxo-3-phenylpropan-2-yl-(methyl)carbamate

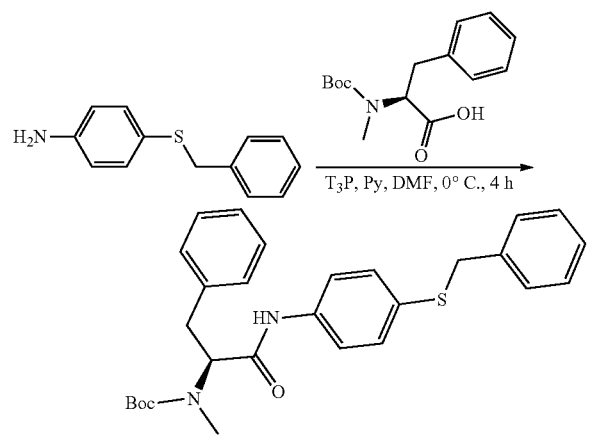

A solution of 27.73 g propanephosphonic acid cyclic anhydride in ethyl acetate (50%, 53.75 mmol) was added dropwise to a solution of 3 g of (2S)-2-[(tert-butoxycarbonyl)(methyl)amino]-3-phenylpropanoic acid (10.75 mmol), 2.54 g 4-(benzylthio)benzenamine (11.83 mmol) and 8.49 g pyridine (107.51 mmol) in 40 mL of N,N-dimethylformamide at 0° C. The reaction was stirred for 4 h at 0° C. Then it was diluted with 100 mL water and extracted with ethyl acetate (3×200 mL). The combined organic layers were washed with brine (3×100 mL), dried over anhydrous magnesium sulfate, filtered and concentrated in vacuo. Purification by column chromatography (silica gel, petroleum ether: ethyl acetate (2:1)) provided 4 g (S)-tert-butyl 1-(4-(benzylthio)phenylamino)-1-oxo-3-phenylpropan-2-yl (methyl)carbamate as a yellow solid (78.2% yield). MS (ESI$^+$) m/z 477 [M+H]$^+$.

Preparation of (S)-N-(4-(benzylthio)phenyl)-2-(methylamino)-3-phenylpropanamide Hydrochloride

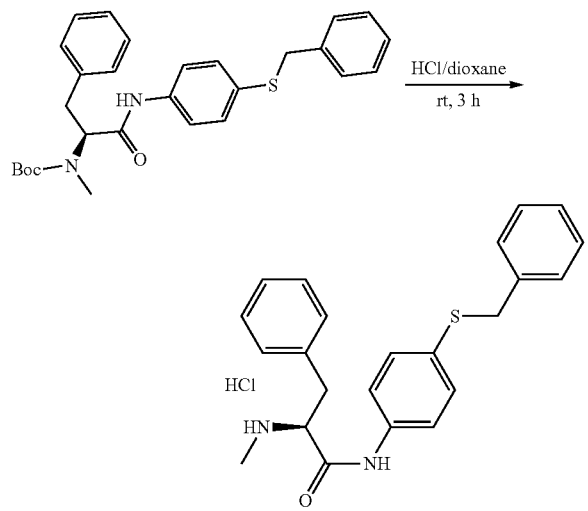

A mixture of 2 g (S)-tert-butyl 1-(4-(benzylthio)phenylamino)-1-oxo-3-phenylpropan-2-yl(methyl)carbamate (4.20 mmol) in 20 mL of hydrochloric acid in 1,4-dioxane (4.0 M) was stirred at room temperature for 3 h. The mixture was concentrated to afford 1.73 g (S)-N-(4-(benzylthio)phenyl)-2-(methylamino)-3-phenylpropanamide hydrochloride as a light yellow solid (100% yield). MS (ESI+) m/z 377 [M+H]+.

Preparation of (S)-N-(1-(4-(benzylthio)phenylamino)-1-oxo-3-phenylpropan-2-yl)-4-fluoro-N-methylbenzamide

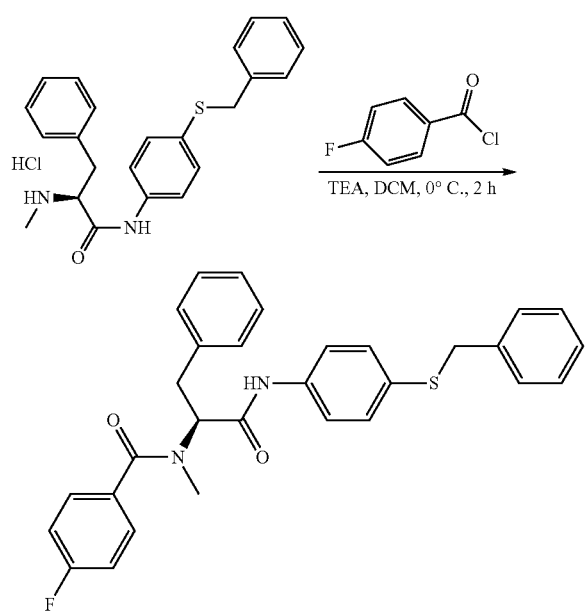

4-Fluorobenzoyl chloride (568.8 mg, 3.60 mmol) was added dropwise to a solution of 1.236 g (S)-N-(4-(benzylthio)phenyl)-2-(methylamino)-3-phenylpropanamide hydrochloride (3.00 mmol) and 1.818 g triethylamine (18.00 mmol) in 20 mL dichloromethane at 0° C. The reaction was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and concentrated in vacuo. Purification by column chromatography (silica gel, petroleum ether:ethyl acetate (1:1)) afforded 1.1 g of (S)-N-(1-(4-(benzylthio)phenylamino)-1-oxo-3-phenylpropan-2-yl)-4-fluoro-N-methylbenzamide as a yellow solid (73.6% yield). MS (ESI+) m/z 499 [M+H]+.

Preparation of (S)-4-(2-(4-fluoro-N-methylbenzamido)-3-phenylpropanamido)benzene-1-sulfonyl Chloride

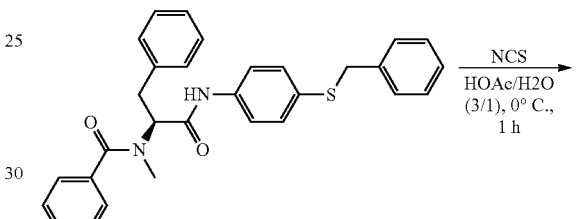

N-chlorosuccinimide (1.18 g, 8.84 mmol) was added to a solution of 1.1 g of (S)-N-(1-(4-(benzylthio)phenylamino)-1-oxo-3-phenylpropan-2-yl)-4-fluoro-N-methylbenzamide (2.21 mmol) in 6 mL acetic acid and 2 mL water at 0° C. The reaction was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and concentrated to give 0.66 g of (S)-4-(2-(4-fluoro-N-methylbenzamido)-3-phenylpropanamido)benzene-1-sulfonyl chloride as a white solid (63% yield). MS (ESI+) m/z 475 and 477 [M+H]+.

Preparation of (S)-4-fluoro-N-methyl-N-(1-(4-(N-oxetan-3-ylsulfamoyl)phenylamino)-1-oxo-3-phenylpropan-2-yl)benzamide, I-70

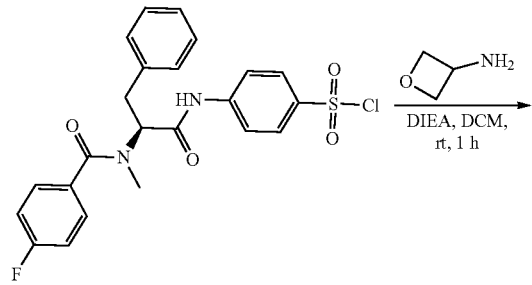

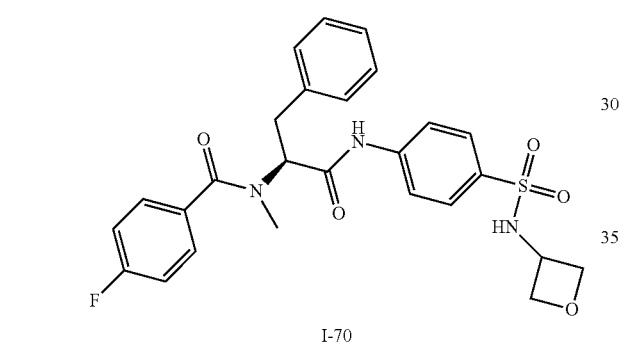

I-70

(S)-4-(2-(4-fluoro-N-methylbenzamido)-3-phenylpropanamido)benzene-1-sulfonyl chloride (100 mg, 0.21 mmol) was added to a mixture of 76.65 mg of oxetan-3-amine (1.05 mmol) and 135.45 mg N,N-diisopropylethylamine (1.05 mmol) in 10 mL dichloromethane. The reaction was stirred at room temperature for 1 h. Then it was diluted with 10 mL water and extracted with dichloromethane (3×20 mL). The combined organic layers were washed with brine (1×30 mL), dried over anhydrous magnesium sulfate, filtered and concentrated under reduced pressure. The crude product was purified by Prep-HPLC under the following conditions: Column, YMC-Actus Triart C18, 30*250 mm, 5 um; Mobile Phase, water (10% $NH_4HCO_3$+0.1% $NH_3$—$H_2O$) and ACN (35% ACN up to 65% in 7 min); UV detection at 254/220 nm. The product-containing fractions were combined and evaporated partially in vacuo and lyophilized overnight to afford 47.4 mg of (S)-4-fluoro-N-methyl-N-(1-(4-(N-oxetan-3-ylsulfamoyl)phenylamino)-1-oxo-3-phenylpropan-2-yl)benzamide (I-70) as a white solid (44.2% yield). MS (ESI$^+$) m/z 512 [M+H]$^+$; 1H NMR (400 MHz, d6-DMSO) δ 10.50 (br s, 1H), 8.45 (s, 1H), 7.88-7.82 (m, 2H), 7.79-7.73 (m, 2H), 7.42-6.81 (m, 9H), 5.45-4.62 (m, 1H), 4.51 (t, 2H), 4.38-4.33 (m, 1H), 4.26 (t, 2H), 3.31-3.14 (m, 2H), 2.89 (s, 3H).

Example 43: (S)-4-fluoro-N-methyl-N-(1-(4-(N-(1-methylpiperidin-4-yl)sulfamoyl)phenylamino)-1-oxo-3-phenylpropan-2-yl)benzamide, I-71

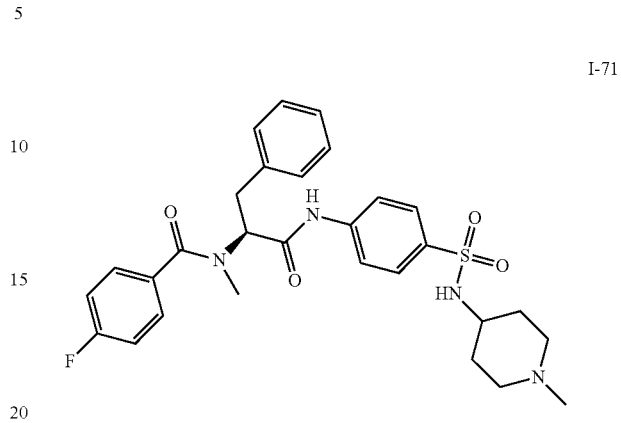

I-71

Using the same procedure as example 42, the title compound (I-71) was obtained as a white solid (22.2% yield). MS (ESI$^+$) m/z 553 [M+H]$^+$; $^1$H NMR (400 MHz, d$_6$-DMSO) δ 10.38 (br s, 1H), 7.88-7.77 (m, 4H), 7.66-7.58 (m, 1H), 7.42-6.83 (m, 9H), 5.46-4.63 (m, 1H), 3.44-3.35 (m, 1H), 3.25-3.02 (m, 2H), 2.87 (s, 3H), 2.66-2.58 (m, 2H), 2.09 (s, 3H), 1.87-1.78 (m, 2H), 1.58-1.49 (m, 2H), 1.48-1.32 (m, 2H).

Example 44: (S)-N-(1-(4-(N-bicyclo[1.1.1]pentan-1-ylsulfamoyl)phenylamino)-1-oxo-3-phenylpropan-2-yl)-4-fluoro-N-methylbenzamide, I-72

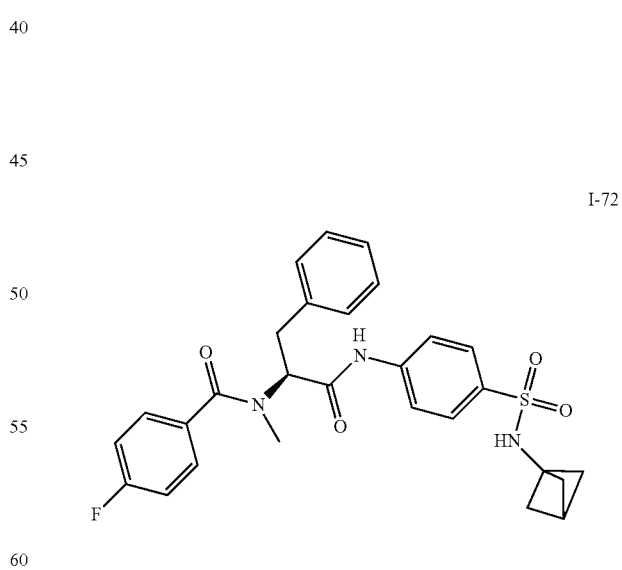

I-72

Using the same procedure as example 42, the title compound (I-72) was obtained as a white solid (52.8% yield). MS (ESI$^+$) m/z 522 [M+H]$^+$; $^1$H NMR (300 MHz, d$_6$-DMSO) δ 10.36 (br s, 1H), 8.48 (s, 1H), 7.85-7.75 (m, 4H), 7.66-7.58 (m, 1H), 7.43-6.83 (m, 9H), 5.47-4.63 (m, 1H), 3.44-3.35 (m, 1H), 3.25-2.84 (m, 4H), 2.27 (s, 1H), 1.71 (s, 6H).

Example 45: (S)-N-(1-(4-(N-bicyclo[1.1.1]pentan-1-ylsulfamoyl)phenylamino)-1-oxo-3-phenylpropan-2-yl)-5-fluoropicolinamide, I-73

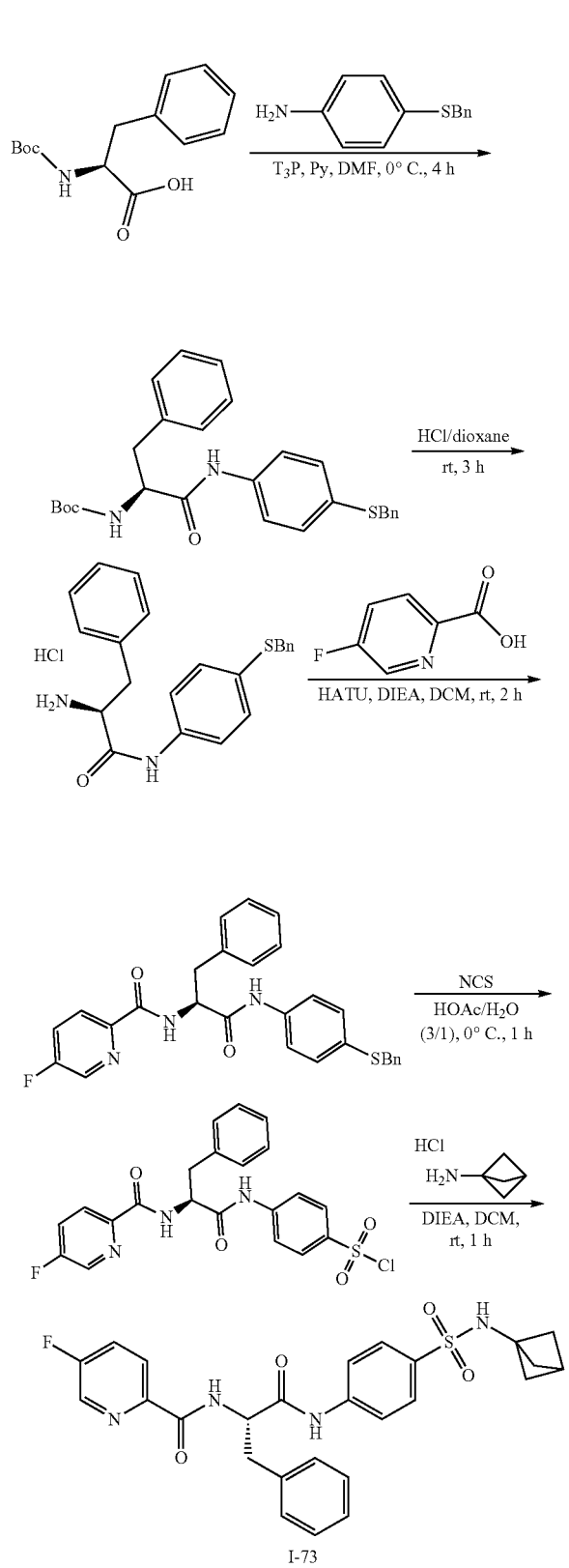

Preparation of (S)-tert-butyl 1-(4-(benzylthio)phenylamino)-1-oxo-3-phenylpropan-2-ylcarbamate

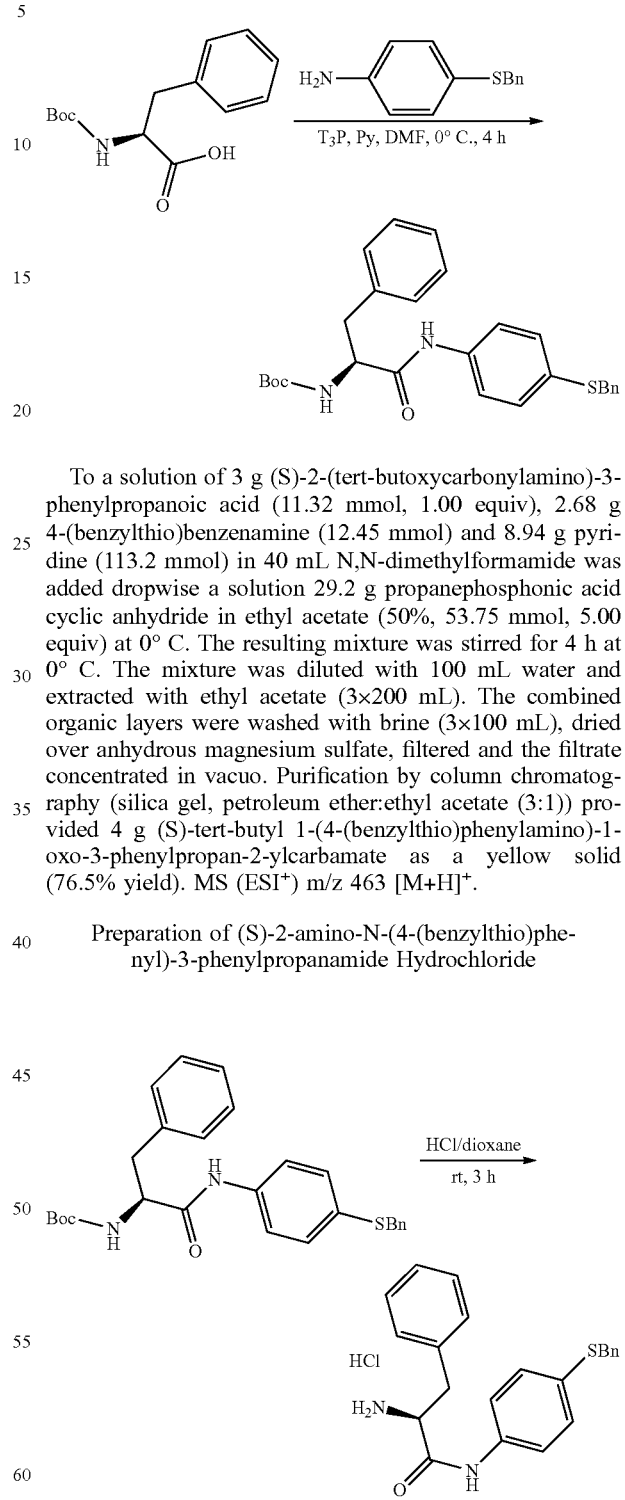

To a solution of 3 g (S)-2-(tert-butoxycarbonylamino)-3-phenylpropanoic acid (11.32 mmol, 1.00 equiv), 2.68 g 4-(benzylthio)benzenamine (12.45 mmol) and 8.94 g pyridine (113.2 mmol) in 40 mL N,N-dimethylformamide was added dropwise a solution 29.2 g propanephosphonic acid cyclic anhydride in ethyl acetate (50%, 53.75 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (3:1)) provided 4 g (S)-tert-butyl 1-(4-(benzylthio)phenylamino)-1-oxo-3-phenylpropan-2-ylcarbamate as a yellow solid (76.5% yield). MS (ESI+) m/z 463 [M+H]+.

Preparation of (S)-2-amino-N-(4-(benzylthio)phenyl)-3-phenylpropanamide Hydrochloride A mixture of 4 g (S)-tert-butyl 1-(4-(benzylthio)phenylamino)-1-oxo-3-phenylpropan-2-ylcarbamate (8.66 mmol) in 40 mL hydrochloric acid in 1,4-dioxane (4.0 M) was stirred at room temperature for 3 h. The mixture was concentrated to afford 1.73 g (S)-2-amino-N-(4-(benzylthio)

phenyl)-3-phenylpropanamide hydrochloride as a light yellow solid (100% yield). MS (ESI+) m/z 363 [M+H]+.

Preparation of (S)-N-(1-(4-(benzylthio)phenylamino)-1-oxo-3-phenylpropan-2-yl)-5-fluoropicolinamide

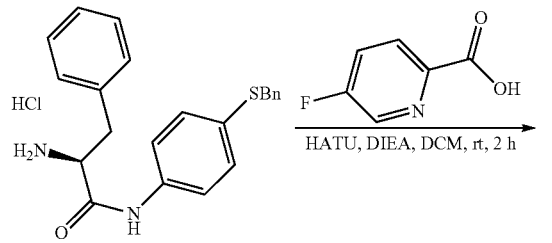

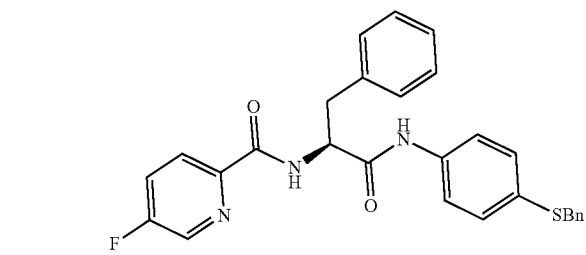

To a solution of 1.2 g (S)-N-(4-(benzylthio)phenyl)-2-(methylamino)-3-phenylpropanamide hydrochloride (3.00 mmol) in 20 mL dichloromethane was added and 1.935 g N,N-diisopropylethylamine (15.00 mmol, 5.00 equiv), 0.635 g 5-fluoropicolinic acid (4.50 mmol) and 1.368 g HATU (3.60 mmol) at room temperature. The resulting mixture was stirred for 2 h at room temperature. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1 g (S)-N-(1-(4-(benzylthio)phenylamino)-1-oxo-3-phenylpropan-2-yl)-5-fluoropicolinamide as a yellow solid (68.7% yield). MS (ESI+) m/z 486 [M+H]+.

Preparation of (S)-4-(2-(5-fluoropicolinamido)-3-phenylpropanamido)benzene-1-sulfonylchloride

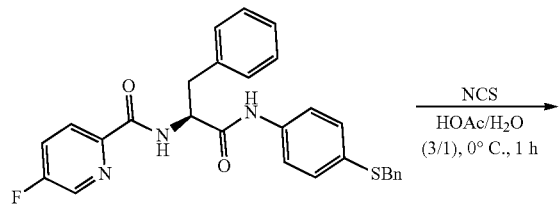

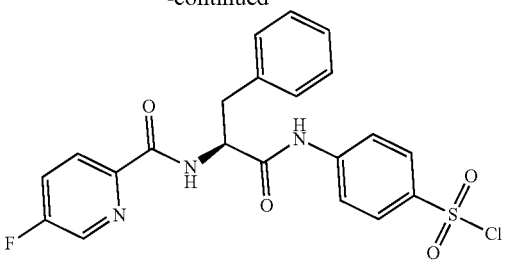

To a solution of 0.5 g (S)-N-(1-(4-(benzylthio)phenylamino)-1-oxo-3-phenylpropan-2-yl)-5-fluoropicolinamide (1.03 mmol) in 6 mL acetic acid and 2 mL water was added 0.55 g N-chlorosuccinimide (4.12 mmol) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.285 g (S)-4-(2-(5-fluoropicolinamido)-3-phenylpropanamido)benzene-1-sulfonyl chloride as a white solid (60% yield). MS (ESI+) m/z 462 and 464 [M+H]+.

Preparation of (S)-N-(1-(4-(N-bicyclo[1.1.1]pentan-1-ylsulfamoyl)phenylamino)-1-oxo-3-phenylpropan-2-yl)-5-fluoropicolinamide, I-73

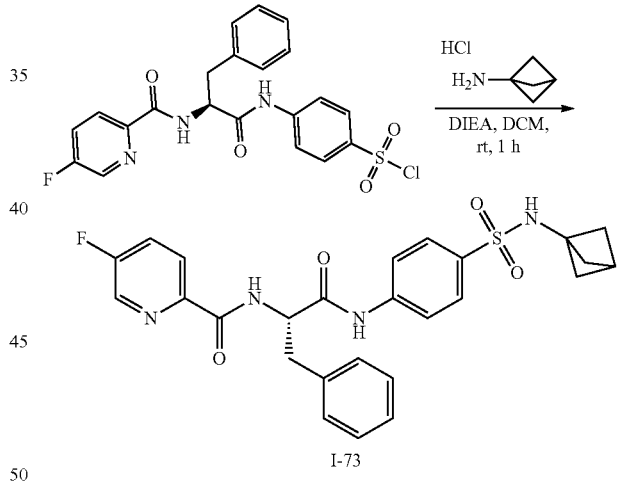

I-73

To a mixture of 110.4 mg bicyclo[1.1.1]pentan-1-amine hydrochloride (0.92 mmol, 5.0 equiv) and 118.68 mg N,N-diisopropylethylamine (0.92 mmol) in 10 mL dichloromethane was added 85 mg (S)-4-(2-(5-fluoropicolinamido)-3-phenylpropanamido)benzene-1-sulfonyl chloride (0.184 mmol). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, SunFire Prep C18 OBD Column, 19*150 mm, 10 um; Mobile Phase, water (0.1% FA) and ACN (38% ACN up to 58% in 10 min); UV detection at 254/220 nm. The product-containing fractions were combined and evaporated partially in vacuo and lyophilized overnight to afford 38.7 mg (S)-N-(1-(4-(N-bicyclo[1.1.1]pentan-1-ylsulfamoyl)phenylamino)-1-oxo-3-phenylpropan-2-yl)-5-fluoropicolinamide (I-73) as a white solid (41.7% yield). MS (ESI+) m/z 509 [M+H]+; 1H NMR (400 MHz, d6-DMSO) δ 10.62 (s, 1H), 8.75 (d, 1H), 8.69 (s, 1H), 8.48 (s, 1H), 8.09-8.05 (m, 1H), 7.90-7.88 (m, 1H), 7.80-7.75 (m, 4H), 7.32-7.16 (m, 5H), 4.95 (dd, 1H), 3.22 (d, 2H), 2.27 (s, 1H), 1.71 (s, 6H).

Example 46: (S)-N-(1-(4-(N-cyclopentylsulfamoyl)phenylamino)-1-oxo-3-phenylpropan-2-yl)-5-fluoropicolinamide, I-74

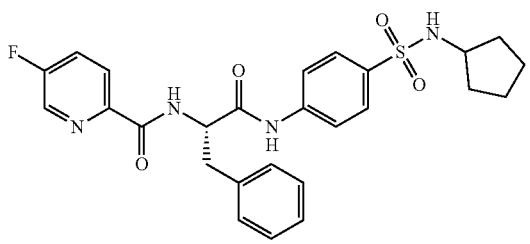

I-74

Using the same procedure as example 45, the title compound (I-74) was obtained as a white solid (50.9% yield). MS (ESI+) m/z 497 [M+H]+; 1H NMR (300 MHz, d6-DMSO) δ 10.59 (s, 1H), 8.74-8.68 (m, 2H), 8.08-8.04 (m, 1H), 7.93-7.87 (m, 1H), 7.81-7.72 (m, 4H), 7.50 (d, 1H), 7.32-7.14 (m, 5H), 4.94 (dd, 1H), 3.40-3.36 (m, 1H), 3.29-3.20 (m, 2H), 1.67-1.21 (m, 8H).

Example 47: (S)-N-(1-(4-(N-cyclobutylsulfamoyl)phenylamino)-1-oxo-3-phenylpropan-2-yl)-5-fluoropicolinamide, I-75

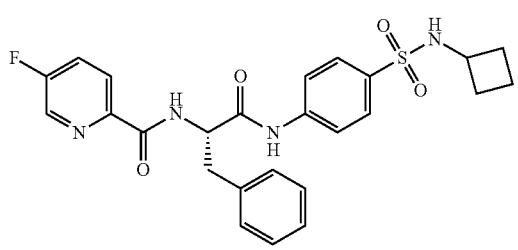

I-75

Using the same procedure as example 45, the title compound (I-75) was obtained as a white solid (48.2% yield). MS (ESI+) m/z 522 [M+H]+; 1H NMR (400 MHz, d6-DMSO) δ 10.61 (s, 1H), 8.75 (d, 1H), 8.69 (s, 1H), 8.08-8.05 (m, 1H), 7.93-7.74 (m, 6H), 7.30-7.16 (m, 5H), 4.94 (dd, 1H), 3.69-3.56 (m, 1H), 3.30-3.17 (m, 2H), 1.94-1.85 (m, 2H), 1.79-1.68 (m, 2H), 1.56-1.42 (m, 2H).

Example 48: (S)-N-(1-(4-(N-bicyclo[1.1.1]pentan-1-ylsulfamoyl)phenylamino)-1-oxo-3-phenylpropan-2-yl)picolinamide, I-76

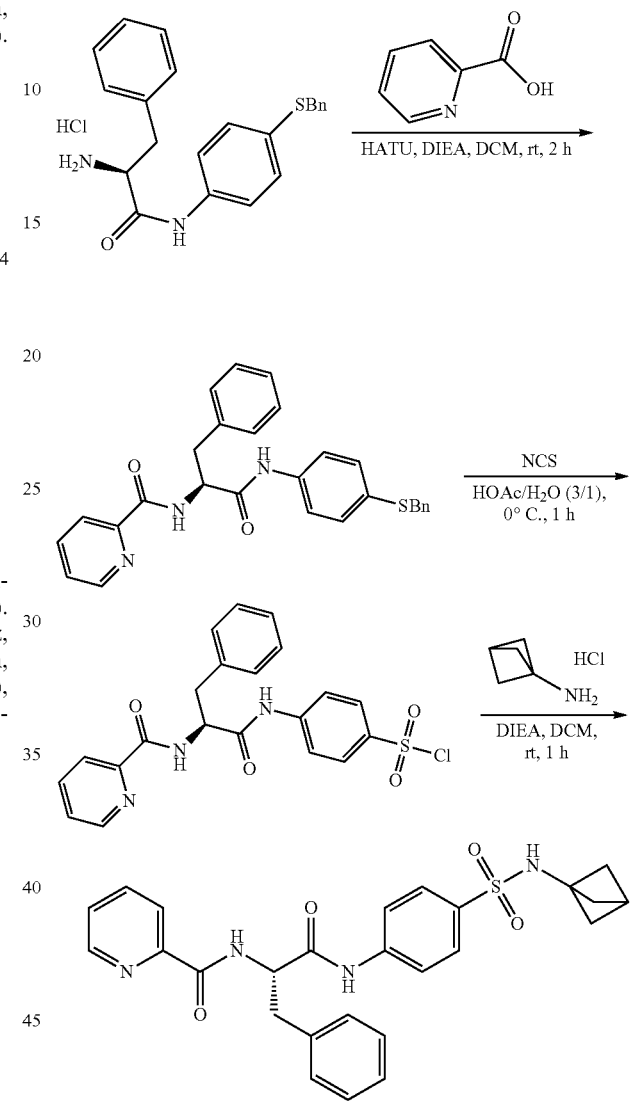

I-76

Preparation of (S)-N-(1-(4-(benzylthio)phenylamino)-1-oxo-3-phenylpropan-2-yl) picolinamide

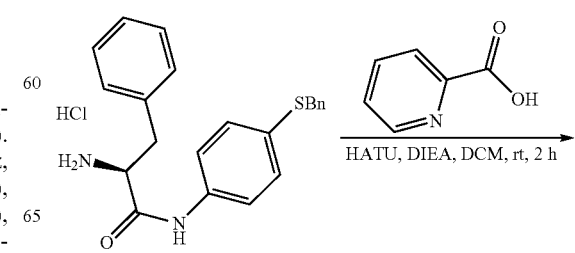

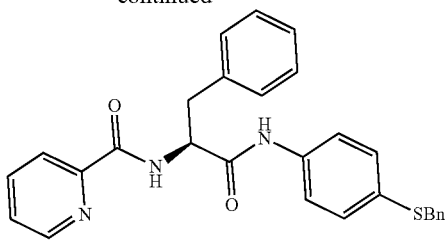

To a solution of 1.2 g (S)-N-(4-(benzylthio)phenyl)-2-(methylamino)-3-phenylpropanamide hydrochloride (3.00 mmol) in 20 mL dichloromethane was added and 1.935 g N,N-diisopropylethylamine (15.00 mmol), 0.554 g picolinic acid (4.50 mmol) and 1.368 g HATU (3.60 mmol) at room temperature. The resulting mixture was stirred for 2 h at room temperature. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 0.96 g (S)-N-(1-(4-(benzylthio)phenylamino)-1-oxo-3-phenylpropan-2-yl)picolinamide as a yellow solid (68.4% yield). MS (ESI$^+$) m/z 468 [M+H]$^+$.

Preparation of (S)-4-(3-phenyl-2-(picolinamido)propanamido)benzene-1-sulfonyl Chloride

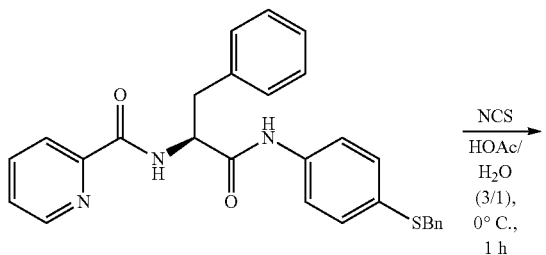

To a solution of 0.48 g (S)-N-(1-(4-(benzylthio)phenylamino)-1-oxo-3-phenylpropan-2-yl)-5-fluoropicolinamide (1.03 mmol) in 6 mL acetic acid and 2 mL water was added 0.55 g N-chlorosuccinimide (4.12 mmol) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.25 g (S)-4-(3-phenyl-2-(picolinamido)propanamido)benzene-1-sulfonyl chloride as a white solid (52.6% yield). MS (ESI$^+$) m/z 444 and 446 [M+H]$^+$.

Preparation of (S)-N-(1-(4-(N-bicyclo[1.1.1]pentan-1-ylsulfamoyl)phenylamino)-1-oxo-3-phenylpropan-2-yl)picolinamide, I-76

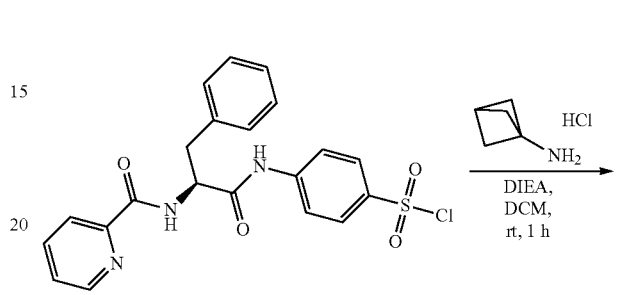

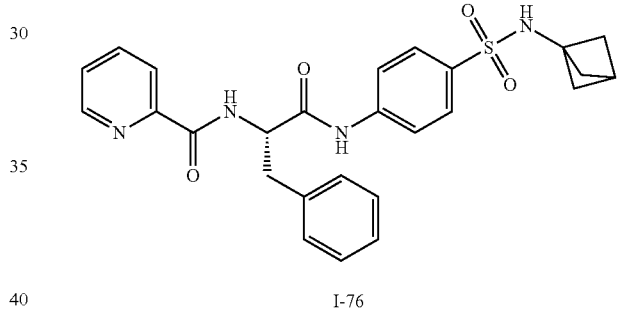

I-76

To a mixture of 108 mg of bicyclo[1.1.1]pentan-1-amine hydrochloride (0.90 mmol) and 116.1 mg N,N-diisopropylethylamine (0.90 mmol) in 10 mL dichloromethane was added 80 mg (S)-4-(2-(5-fluoropicolinamido)-3-phenylpropanamido)benzene-1-sulfonyl chloride (0.18 mmol). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, SunFire Prep C18 OBD Column, 19*150 mm, 10 um; Mobile Phase, water (0.1% FA) and ACN (35% ACN up to 55% in 10 min); UV detection at 254/220 nm. The product-containing fractions were combined and evaporated partially in vacuo and lyophilized overnight to afford 34.4 mg (S)-N-(1-(4-(N-bicyclo[1.1.1]pentan-1-ylsulfamoyl)phenylamino)-1-oxo-3-phenylpropan-2-yl)picolinamide (I-76) as a white solid (39% yield). MS (ESI$^+$) m/z 491 [M+H]$^+$; $^1$H NMR (400 MHz, d$_6$-DMSO) δ 10.64 (s, 1H), 8.81 (d, 1H), 8.68 (d, 1H), 8.49 (s, 1H), 8.03-7.97 (m, 2H), 7.81-7.72 (m, 4H), 7.63 (dd, 1H), 7.30-7.16 (m, 5H), 4.97 (dd, 1H), 3.25-3.21 (m, 2H), 2.27 (s, 1H), 1.70 (s, 6H).

Example 49: (S)-N-(1-(4-(N-cyclopentylsulfamoyl)phenylamino)-1-oxo-3-phenylpropan-2-yl)picolinamide, I-77

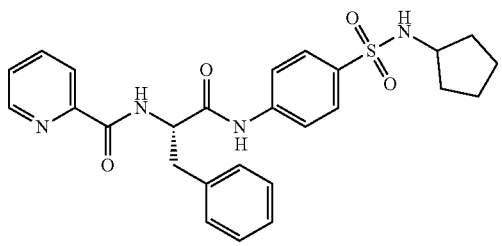

I-77

Using the same procedure for example 48, the title compound (I-77) was obtained as a white solid (44.3% yield). MS (ESI⁺) m/z 493 [M+H]⁺; ¹H NMR (300 MHz, $d_6$-DMSO) δ 10.61 (s, 1H), 8.81-8.67 (m, 2H), 8.03-7.95 (m, 2H), 7.81-7.72 (m, 4H), 7.68-7.46 (m, 2H), 7.38-7.16 (m, 5H), 4.97 (d, 1H), 3.41-3.34 (m, 1H), 3.30-3.16 (m, 2H), 1.74-1.22 (m, 8H).

Example 50: (S)-N-(1-(4-(N-cyclobutylsulfamoyl)phenylamino)-1-oxo-3-phenylpropan-2-yl) picolinamide, I-78

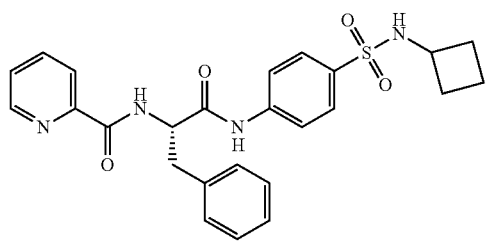

I-78

Using the same procedure for example 48, the title compound (I-78) was obtained as a white solid (33.2% yield). MS (ESI⁺) m/z 479 [M+H]⁺; ¹H NMR (400 MHz, $d_6$-DMSO) δ 10.61 (s, 1H), 8.80 (d, 1H), 6.69-6.67 (m, 1H), 8.03-7.97 (m, 2H), 7.84 (d, 1H), 7.78-7.82 (m, 4H), 7.65-7.61 (m, 1H), 7.33-7.17 (m, 5H), 4.96 (dd, 1H), 3.68-3.54 (m, 1H), 3.30-3.18 (m, 2H), 1.96-1.87 (m, 2H), 1.80-1.68 (m, 2H), 1.56-1.41 (m, 2H).

Example 51: (S)-N-(1-(4-(N-bicyclo[1.1.1]pentan-1-ylsulfamoyl)phenylamino)-1-oxo-3-phenylpropan-2-yl)nicotinamide, I-79

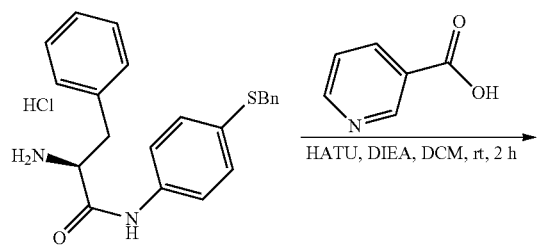

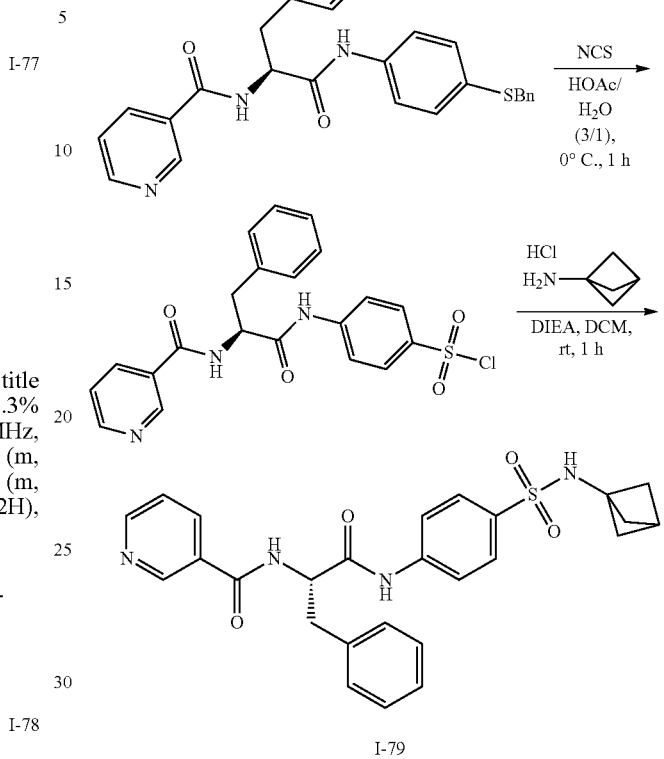

I-79

Preparation of (S)-N-(1-(4-(benzylthio)phenylamino)-1-oxo-3-phenylpropan-2-yl) nicotinamide

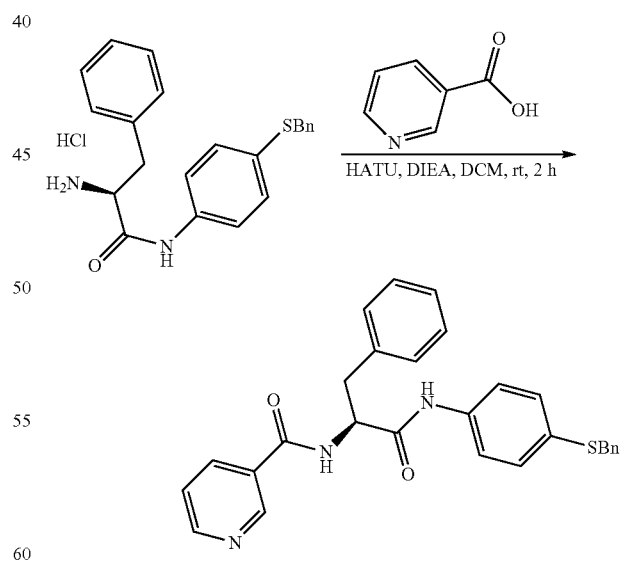

To a solution of 1.2 g (S)-N-(4-(benzylthio)phenyl)-2-(methylamino)-3-phenylpropanamide hydrochloride (3.00 mmol) in 20 mL dichloromethane was added and 1.935 g N,N-diisopropylethylamine (15.00 mmol), 0.554 g nicotinic acid (4.50 mmol) and 1.368 g HATU (3.60 mmol) at room temperature. The resulting mixture was stirred for 2 h at room temperature. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 0.94 g (S)-N-(1-(4-(benzylthio)phenylamino)-1-oxo-3-phenylpropan-2-yl)nicotinamide as a yellow solid (66.95% yield). MS (ESI$^+$) m/z 468 [M+H]$^+$.

Preparation of (S)-4-(2-(nicotinamido)-3-phenylpropanamido)benzene-1-sulfonyl Chloride

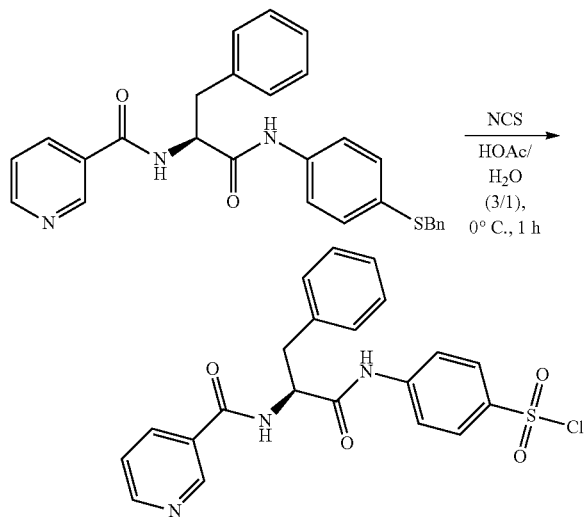

To a solution of 0.48 g (S)-N-(1-(4-(benzylthio)phenylamino)-1-oxo-3-phenylpropan-2-yl)nicotinamide (1.03 mmol) in 6 mL acetic acid and 2 mL water was added 0.55 g N-chlorosuccinimide (4.12 mmol) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.24 g (S)-4-(2-(nicotinamido)-3-phenylpropanamido)benzene-1-sulfonyl chloride as a white solid (52.48% yield). MS (ESI$^+$) m/z 444 and 446 [M+H]$^+$.

Preparation of (S)-N-(1-(4-(N-bicyclo[1.1.1]pentan-1-ylsulfamoyl)phenylamino)-1-oxo-3-phenylpropan-2-yl)nicotinamide, I-79

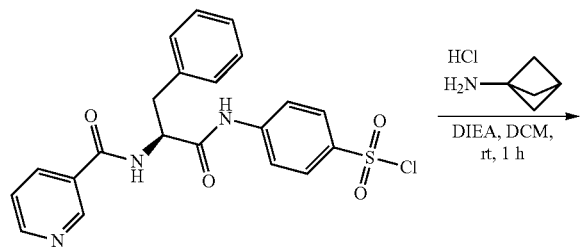

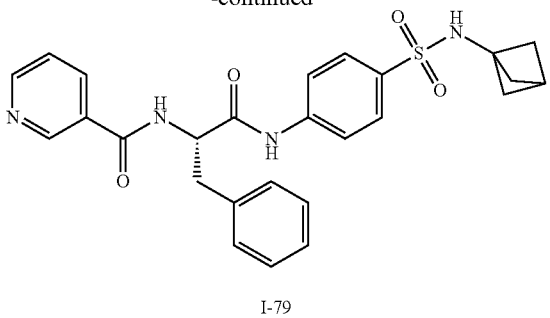

I-79

To a mixture of 108 mg of bicyclo[1.1.1]pentan-1-amine hydrochloride (0.90 mmol) and 116.1 mg N,N-diisopropylethylamine (0.90 mmol) in 10 mL dichloromethane was added 80 mg (S)-4-(2-(nicotinamido)-3-phenylpropanamido)benzene-1-sulfonyl chloride (0.18 mmol). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, SunFire Prep C18 OBD Column, 19*150 mm, 10 um; Mobile Phase, water (0.1% FA) and ACN (37% ACN up to 56% in 10 min); UV detection at 254/220 nm. The product-containing fractions were combined and evaporated partially in vacuo and lyophilized overnight to afford 43.8 mg (S)-N-(1-(4-(N-bicyclo[1.1.1]pentan-1-ylsulfamoyl)phenylamino)-1-oxo-3-phenylpropan-2-yl)nicotinamide (I-79) as a white solid (49.7% yield). MS (ESI$^+$) m/z 491 [M+H]$^+$; $^1$H NMR (400 MHz, d$_6$-DMSO) δ 10.65 (s, 1H), 9.11 (d, 1H), 8.97 (s, 1H), 8.71 (dd, 1H), 8.48 (s, 1H), 8.18-8.15 (m, 1H), 7.78 (dd, 4H), 7.51 (dd, 1H), 7.42 (d, 2H), 7.30 (t, 2H), 7.22-7.18 (m, 1H), 4.92-4.86 (m, 1H), 3.23-3.08 (m, 2H), 2.27 (s, 1H), 1.71 (s, 6H).

Example 52: (S)-N-(1-(4-(N-cyclopentylsulfamoyl)phenylamino)-1-oxo-3-phenylpropan-2-yl)nicotinamide, I-80

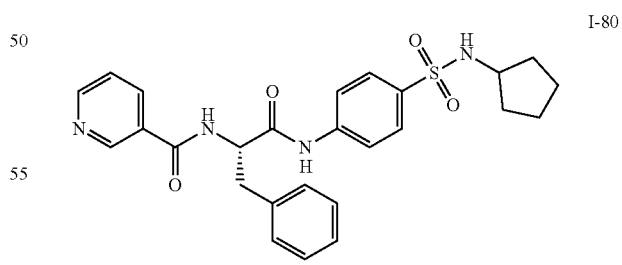

I-80

Using the same procedure for example 51, the title compound (I-80) was obtained as a white solid (40.31% yield). MS (ESI$^+$) m/z 493 [M+H]$^+$; $^1$H NMR (400 MHz, d$_6$-DMSO) δ 10.64 (s, 1H), 9.09 (d, 1H), 8.97 (s, 1H), 8.71 (dd, 1H), 8.18-8.15 (m, 1H), 7.78 (dd, 4H), 7.58-7.41 (m, 4H), 7.30 (t, 2H), 7.22-7.19 (m, 1H), 4.94-4.87 (m, 1H), 3.43-3.36 (m, 1H), 3.25-3.10 (m, 2H), 1.64-1.25 (m, 8H).

Example 53: (S)-N-(1-(4-(N-cyclobutylsulfamoyl)phenylamino)-1-oxo-3-phenylpropan-2-yl)nicotinamide, I-81

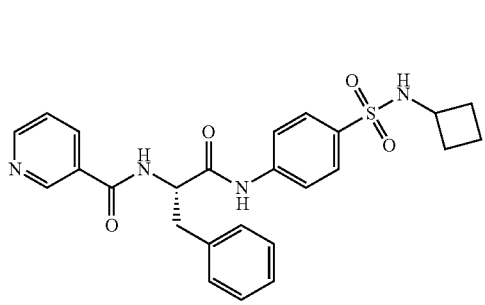

Using the same procedure for example 51, the title compound (I-81) was obtained as a white solid (59.3% yield). MS (ESI+) m/z 479 [M+H]+; ¹H NMR (400 MHz, d₆-DMSO) δ 10.64 (s, 1H), 9.10 (d, 1H), 8.97 (s, 1H), 8.71 (dd, 1H), 8.18-8.15 (m, 1H), 7.85-7.73 (m, 5H), 7.52-7.41 (m, 3H), 7.30 (t, 2H), 7.21-7.18 (m, 1H), 4.94-4.87 (m, 1H), 3.65-3.58 (m, 1H), 3.23-3.10 (m, 2H), 1.98-1.85 (m, 2H), 1.81-1.68 (m, 2H), 1.58-1.41 (m, 2H).

Example 54: (S)-N-(1-(4-(N-tert-butylsulfamoyl)phenylamino)-1-oxo-3-phenylpropan-2-yl)-5-fluoropicolinamide, I-85

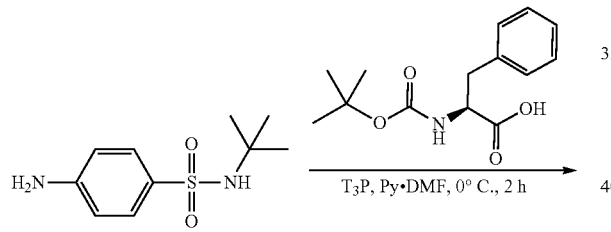

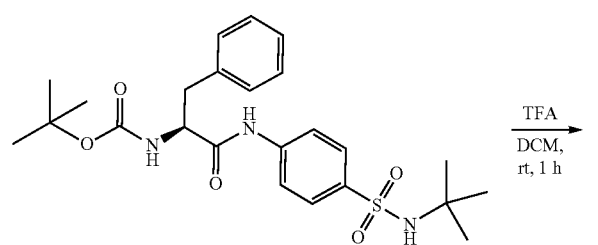

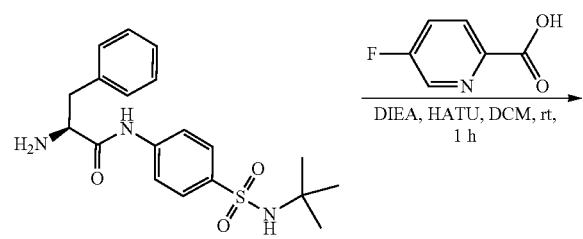

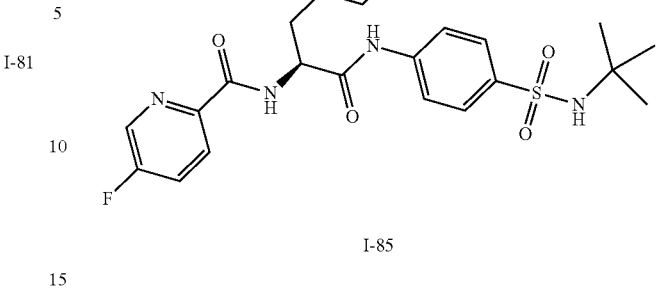

Preparation of (S)-tert-butyl 1-(4-(N-tert-butylsulfamoyl)phenylamino)-1-oxo-3-phenylpropan-2-ylcarbamate

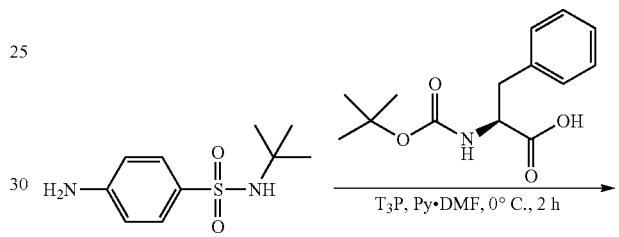

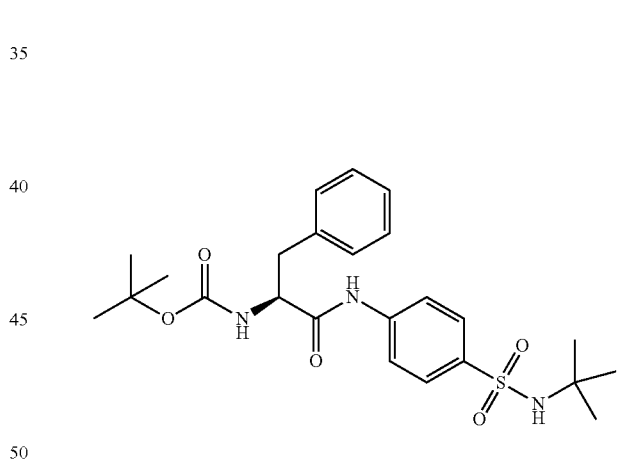

To a mixture of 1 g 4-amino-N-tert-butylbenzenesulfonamide (4.39 mmol, 1.0 equiv) and 1.16 g (S)-2-(tert-butoxycarbonylamino)-3-phenylpropanoic acid (4.39 mmol, 1.0 equiv) in 20 mL N,N-dimethylformamide was added 693 mg pyridine (8.77 mmol, 2.0 equiv) and 3.37 mL a solution of T₃P in ethyl acetate (50%, 6.58 mmol, 1.5 equiv) at 0° C. The mixture was stirred at r.t for 2 h. The mixture was diluted with 30 mL water and extracted with ethyl acetate (3×50 mL). The combined organic layers were washed with brine (2×50 mL), dried over anhydrous magnesium sulfate, filtered and the filtrate concentrated under reduced pressure. Purification by column chromatography (silica gel, petroleum ether:ethyl acetate (2:1)) afforded 1.63 g (S)-tert-butyl 1-(4-(N-tert-butylsulfamoyl)phenylamino)-1-oxo-3-phenylpropan-2-ylcarbamate as an off-white solid (78% yield). MS (ESI+) m/z 474 [M−H]+.

381
Preparation of (S)-2-amino-N-(4-(N-tert-butylsulfamoyl)phenyl)-3-phenylpropanamide

382
Preparation of (S)-N-(1-(4-(N-tert-butylsulfamoyl)phenylamino)-1-oxo-3-phenylpropan-2-yl)-5-fluoropicolinamide (I-85)

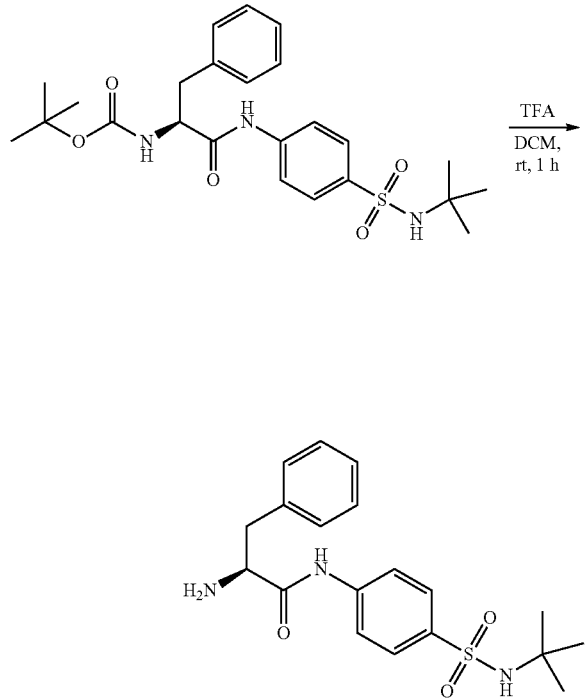

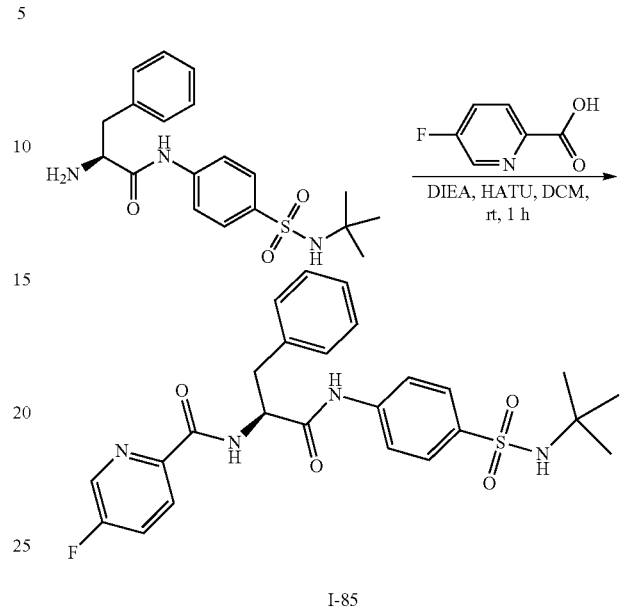

I-85

To a mixture of 1.63 g (S)-tert-butyl 1-(4-(N-tert-butylsulfamoyl)phenylamino)-1-oxo-3-phenylpropan-2-ylcarbamate (3.43 mmol, 1.0 equiv) in 20 mL dichloromethane was added 5 mL 2,2,2-trifluoroacetic acid. The mixture was stirred at r.t for 1 h. The mixture was concentrated under reduced pressure. The residue was diluted with 10 mL water. The pH value of the solution was adjusted to 8 with saturated aqueous sodium bicarbonate and extracted with ethyl acetate (3×50 mL). The combined organic layers were washed with brine (2×50 mL), dried over anhydrous magnesium sulfate, filtered and the filtrate concentrated under reduced pressure to afforded 1 g (S)-2-amino-N-(4-(N-tert-butylsulfamoyl)phenyl)-3-phenylpropanamide as a yellow solid (78% yield). MS (ESI$^+$) m/z 376 [M+H]$^+$.

To a solution of 150 mg (S)-2-amino-N-(4-(N-tert-butylsulfamoyl)phenyl)-3-phenylpropanamide (0.4 mmol, 1.00 equiv) and 56.4 mg 5-fluoropicolinic acid (0.4 mmol, 1.0 equiv) in 10 mL dichloromethane was added 154.8 mg DIEA (1.2 mmol, 3.0 equiv) and 167.2 mg HATU (0.44 mmol, 1.1 equiv). The mixture was stirred at r.t for 1 h. The mixture was diluted with 20 mL water and extracted with dichloromethane (3×30 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$) and ACN (36% ACN up to 66% in 7 min); UV detection at 254/220 nm. The product-containing fractions were combined and evaporated partially in vacuo and lyophilized overnight to afford 77.8 mg (S)-N-(1-(4-(N-tert-butylsulfamoyl)phenylamino)-1-oxo-3-phenylpropan-2-yl)-5-fluoropicolinamide as a white solid.

Using this general procedure for the preparation of I-85 and substituting the appropriate acid in the last step, the following compounds were prepared.

TABLE 2

Compounds prepared according to Example 54.

| Compound | Name | Yield | MS | 1HNMR |
|---|---|---|---|---|
| I-85 | (S)-N-(1-(4-(N-tert-butylsulfamoyl)phenylamino)-1-oxo-3-phenylpropan-2-yl)-5-fluoropicolinamide | 39% | MS (ESI$^+$, m/z): Calcd for C25H27FN4O4S: 498; found 499 [M + H]$^+$; | $^1$H NMR (400 MHz, d$_6$-DMSO) δ 10.60 (s, 1H), 8.75 (d, 1H), 8.69 (d, 1H), 8.07 (dd, 1H), 7.92 (dd, 1H), 7.82-7.73 (m, 4H), 7.42 (s, 1H), 7.32-7.15 (m, 5H), 4.94 (t, 1H), 3.21 (d, 2H), 1.09 (s, 9H). |

TABLE 2-continued

Compounds prepared according to Example 54.

| Compound | Name | Yield | MS | 1HNMR |
|---|---|---|---|---|
| I-86 | (S)-N-(1-(4-(N-tert-butylsulfamoyl)phenylamino)-1-oxo-3-phenylpropan-2-yl)oxetane-3-carboxamide | 40% | MS (ESI$^+$, m/z): Calcd for C23H29N3O5S: 459; found 460 [M + H]$^+$; | $^1$H NMR (300 MHz, d$_6$-DMSO) δ 10.51 (s, 1H), 8.39 (d, 1H), 7.82-7.73 (m, 4H), 7.39 (s, 1H), 7.32-7.15 (m, 5H), 4.74 (t, 1H), 4.66-4.51 (m, 3H), 4.33 (t, 1H), 3.77 (t, 1H),3.14-3.02 (m, 1H), 2.91-2.82 (m, 1H), 1.08 (s, 9H). |
| I-87 | (S)-N-(1-(4-(N-tert-butylsulfamoyl)phenylamino)-1-oxo-3-phenylpropan-2-yl)nicotinamide | 46% | MS (ESI$^+$, m/z): Calcd for C25H28N4O4S: 480; found 481 [M + H]$^+$; | $^1$H NMR (400 MHz, d$_6$-DMSO) δ 10.60 (s, 1H), 9.07 (d, 1H), 8.96 (s, 1H), 8.70 (dd, 1H), 8.17-8.14 (m, 1H), 7.82-7.73 (m, 4H), 7.50 (dd, 1H), 7.46-7.41 (m, 3H), 7.29 (t, 2H), 7.19 (t, 1H), 4.87 (t, 1H), 3.25-3.08 (m, 2H), 1.08 (s, 9H). |
| I-88 | (S)-N-(1-(4-(N-tert-butylsulfamoyl)phenylamino)-1-oxo-3-phenylpropan-2-yl)-3-fluorobenzamide | 47% | MS (ESI$^+$, mz): Calcd for C26H28FN3O4S: 497; found 498 [M + H]$^+$; | $^1$H NMR (400 MHz, d$_6$-DMSO) δ 10.59 (s, 1H), 8.93 (d, 1H), 7.84-7.77 (m, 4H), 7.72-7.62 (m, 2H), 7.52 (dd, 1H), 7.45-7.37 (m, 4H), 7.29 (t, 2H), 7.19 (t, 1H), 4.88 (t, 1H), 3.22-3.10 (m, 2H), 1.08 (s, 9H). |

Example 55: (S)-4-fluoro-N-methyl-N-(1-(4-(N-oxetan-3-ylsulfamoyl)phenylamino)-1-oxo-3-(pyridin-3-yl)propan-2-yl)benzamide, I-89

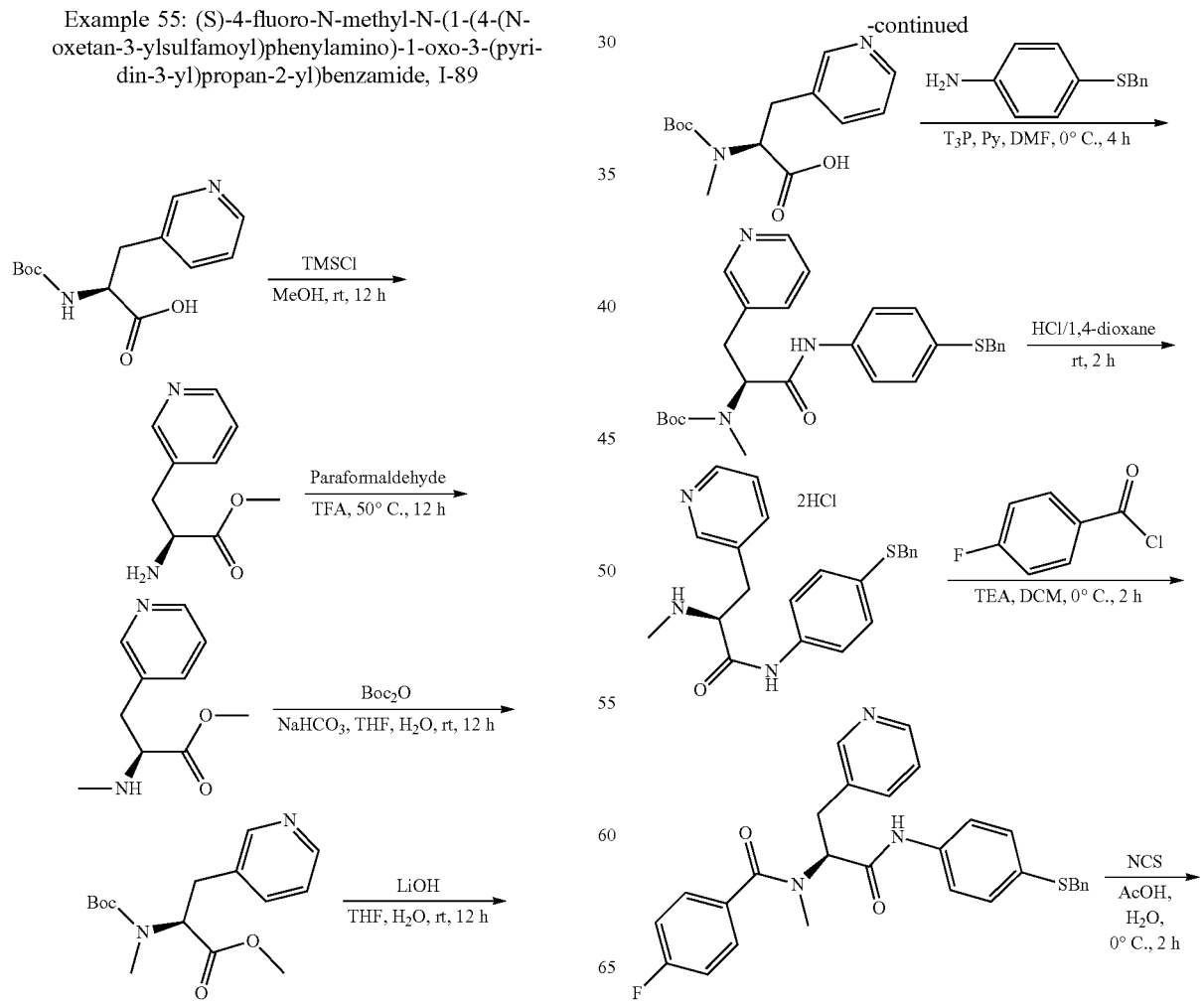

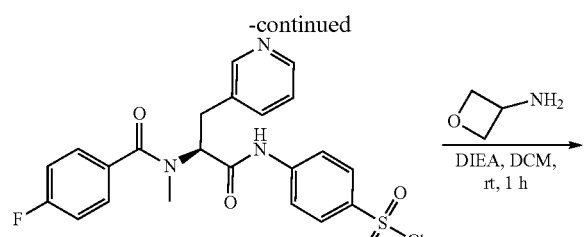

I-89

Preparation of (S)-methyl 2-amino-3-(pyridin-3-yl)propanoate

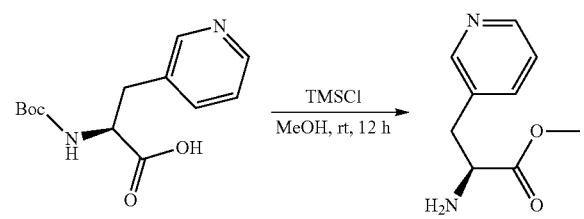 [SMILES: "TMSCl" ; CC(C)(C)OC(=O)N[C@@H](Cc1cccnc1)C(=O)O ; COC(=O)[C@@H](N)Cc1cccnc1]

To a solution of 5 g (S)-2-(tert-butoxycarbonylamino)-3-(pyridin-3-yl)propanoic acid (18.80 mmol, 1.00 equiv) in 80 mL methanol was added dropwise 10.15 g chlorotrimethylsilane (94.00 mmol, 5.00 equiv) at 0° C. The resulting mixture was stirred for 12 h at room temperature. The mixture was concentrated in vacuo. The residue was diluted with 50 mL water, then adjusted to pH 9 with sodium bicarbonate (aq.). The mixture was extracted with ethyl acetate (3×200 mL). The combined organic layers were washed with brine (1×100 mL), dried over anhydrous magnesium sulfate, filtered and the filtrate concentrated to give 2.57 g (S)-methyl 2-amino-3-(pyridin-3-yl)propanoate as a yellow oil (76% yield). MS (ESI$^+$) m/z 181 [M+H]$^+$.

Preparation of (S)-methyl 2-(methylamino)-3-(pyridin-3-yl)propanoate

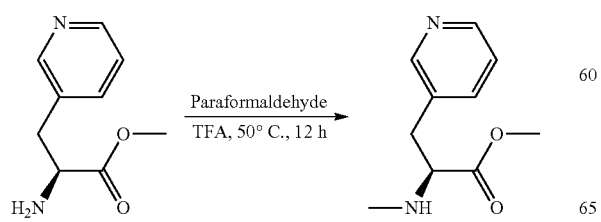

To a solution of 2.57 g (S)-methyl 2-amino-3-(pyridin-3-yl)propanoate (14.28 mmol, 1.00 equiv) in 30 mL 2,2,2-trifluoroacetic acid was added 1.29 g paraformaldehyde (42.84 mmol, 3.00 equiv) at room temperature. The resulting mixture was stirred for 12 h at 50° C. under nitrogen atmosphere. The mixture was cooled to room temperature and concentrated to give 5.4 g crude (S)-methyl 2-(methylamino)-3-(pyridin-3-yl)propanoate as an orange oil. MS (ESI$^+$) m/z 195 [M+H]$^+$.

Preparation of (S)-methyl 2-(tert-butoxycarbonyl(methyl)amino)-3-(pyridin-3-yl)propanoate

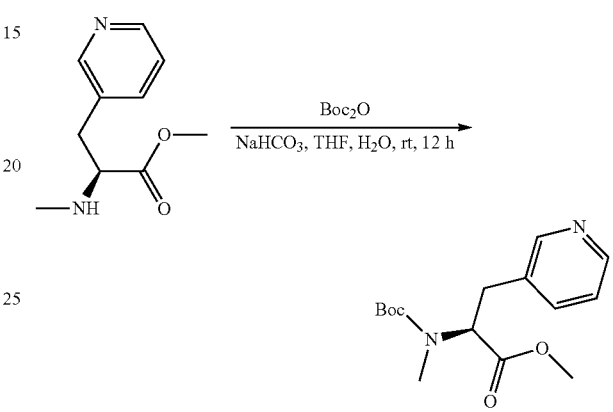

To a solution of 5.4 g crude (S)-methyl 2-(methylamino)-3-(pyridin-3-yl)propanoate (14.28 mmol, 1.00 equiv) in 120 mL tetrahydrofuran and 40 mL water was added 12 g sodium bicarbonate (142.80 mmol, 10.00 equiv) and 9.34 g di-tert-butyl dicarbonate (42.84 mmol, 3.00 equiv) at room temperature. The resulting mixture was stirred for 12 h at room temperature. The mixture was diluted with 100 mL water and extracted with ethyl acetate (3×200 mL). The combined organic layers were washed with brine (1×100 mL), dried over anhydrous magnesium sulfate, filtered and the filtrate concentrated in vacuo. Purification by column chromatography (silica gel, dichloromethane:methanol (40:1)) provided 3 g (S)-methyl 2-(tert-butoxycarbonyl(methyl)amino)-3-(pyridin-3-yl)propanoate as a yellow solid (71% yield). MS (ESI$^+$) m/z 295 [M+H]$^+$.

Preparation of (S)-2-(tert-butoxycarbonyl(methyl)amino)-3-(pyridin-3-yl)propanoic Acid

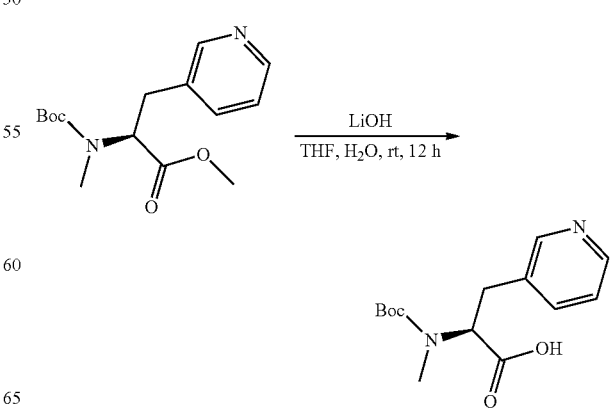

To a solution of 3 g (S)-methyl 2-(tert-butoxycarbonyl (methyl)amino)-3-(pyridin-3-yl)propanoate (10.17 mmol, 1.00 equiv) in 40 mL tetrahydrofuran and 10 mL water was added 0.73 g lithium hydroxide (30.51 mmol, 3.00 equiv) at room temperature. The resulting mixture was stirred for 12 h at room temperature. The mixture was concentrated in vacuo. The residue was diluted with 50 mL water, then adjusted to pH 3 with 1 N hydrogen chloride (aq.). The mixture was extracted with ethyl acetate (3×100 mL). The combined organic layers were washed with brine (1×100 mL), dried over anhydrous magnesium sulfate, filtered and the filtrate concentrated to give 2 g (S)-2-(tert-butoxycarbonyl(methyl)amino)-3-(pyridin-3-yl)propanoic acid as a yellow oil (70% yield). MS (ESI⁺) m/z 281 [M+H]⁺.

Preparation of (S)-tert-butyl 1-(4-(benzylthio)phenylamino)-1-oxo-3-(pyridin-3-yl)propan-2-yl (methyl)carbamate

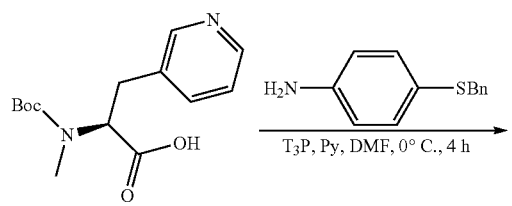

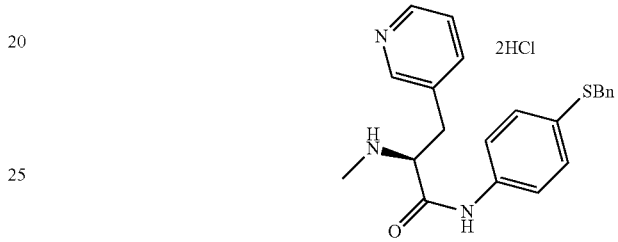

To a solution of 2 g (S)-2-(tert-butoxycarbonyl(methyl) amino)-3-(pyridin-3-yl)propanoic acid (7.14 mmol, 1.00 equiv), 1.69 g 4-(benzylthio)benzenamine (7.85 mmol, 1.10 equiv) and 5.64 g pyridine (71.40 mmol, 10.00 equiv) in 40 mL N,N-dimethylformamide was added dropwise a solution 18.42 g propanephosphonic acid cyclic anhydride in ethyl acetate (50%, 35.70 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, dichloromethane:methanol (20:1)) provided 2.2 g (S)-tert-butyl 1-(4-(benzylthio)phenylamino)-1-oxo-3-(pyridin-3-yl)propan-2-yl (methyl)carbamate as a yellow solid (65% yield). MS (ESI⁺) m/z 478 [M+H]⁺.

Preparation of (S)-N-(4-(benzylthio)phenyl)-2-(methylamino)-3-(pyridin-3-yl)propanamide Dihydrochloride

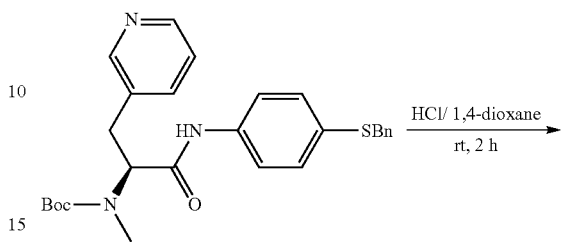

A mixture of 2.2 g (S)-tert-butyl 1-(4-(benzylthio)phenylamino)-1-oxo-3-(pyridin-3-yl)propan-2-yl(methyl)carbamate (4.61 mmol, 1.00 equiv) in 20 mL hydrochloric acid in 1,4-dioxane (4.0 M) was stirred at room temperature for 2 h. The mixture was concentrated to afford 2.07 g (S)-N-(4-(benzylthio)phenyl)-2-(methylamino)-3-(pyridin-3-yl) propanamide dihydrochloride as a light yellow solid (100% yield). MS (ESI⁺) m/z 378 [M+H]⁺.

Preparation of (S)-N-(1-(4-(benzylthio)phenylamino)-1-oxo-3-(pyridin-3-yl)propan-2-yl)-4-fluoro-N-methylbenzamide

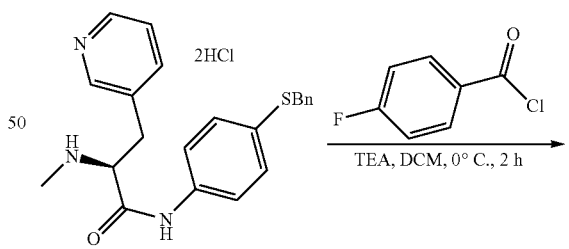

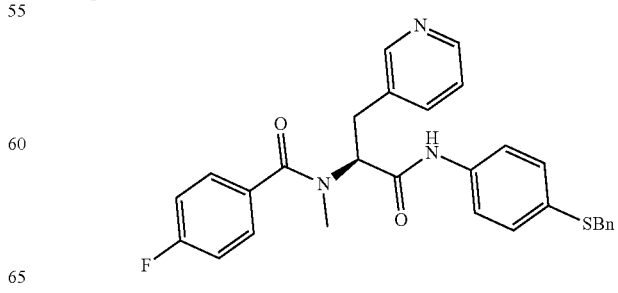

To a solution of 2.07 g (S)-N-(4-(benzylthio)phenyl)-2-(methylamino)-3-(pyridin-3-yl)propanamide dihydrochloride (4.61 mmol, 1.00 equiv) and 2.79 g triethylamine (27.66 mmol, 6.00 equiv) in 20 mL dichloromethane was added dropwise 874 mg 4-fluorobenzoyl chloride (5.53 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, dichloromethane:methanol (15:1)) afforded 1.45 g (S)-N-(1-(4-(benzylthio)phenylamino)-1-oxo-3-(pyridin-3-yl)propan-2-yl)-4-fluoro-N-methylbenzamide as a yellow solid (63% yield). MS (ESI+) m/z 500 [M+H]+.

Preparation of (S)-4-(2-(4-fluoro-N-methylbenzamido)-3-(pyridin-3-yl)propanamido)benzene-1-sulfonyl Chloride

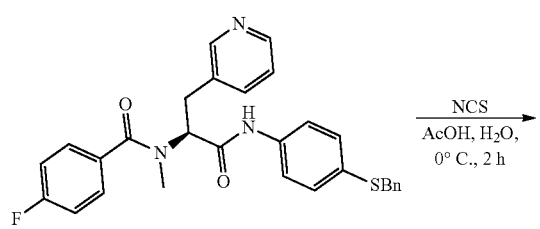

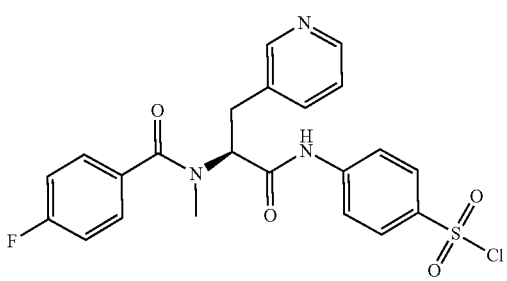

To a solution of 1.45 g (S)-N-(1-(4-(benzylthio)phenylamino)-1-oxo-3-(pyridin-3-yl)propan-2-yl)-4-fluoro-N-methylbenzamide (2.90 mmol, 1.00 equiv) in 12 mL acetic acid and 4 mL water was added 1.55 g N-chlorosuccinimide (11.6 mmol, 4.00 equiv) at 0° C. The resulting mixture was stirred at 0° C. for 2 h. The mixture was diluted with 30 mL water and extracted with dichloromethane (3×50 mL). The combined organic layers were washed with brine (1×50 mL), dried over anhydrous magnesium sulfate, filtered and the filtrate concentrated to give 0.66 g (S)-4-(2-(4-fluoro-N-methylbenzamido)-3-(pyridin-3-yl)propanamido)benzene-1-sulfonyl chloride as a white solid (48% yield). MS (ESI+) m/z 476 [M+H]+.

Preparation of (S)-4-fluoro-N-methyl-N-(1-(4-(N-oxetan-3-ylsulfamoyl)phenylamino)-1-oxo-3-(pyridin-3-yl)propan-2-yl)benzamide (I-89)

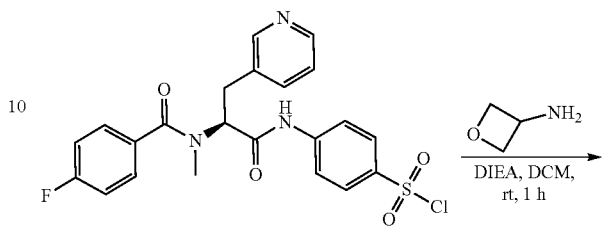

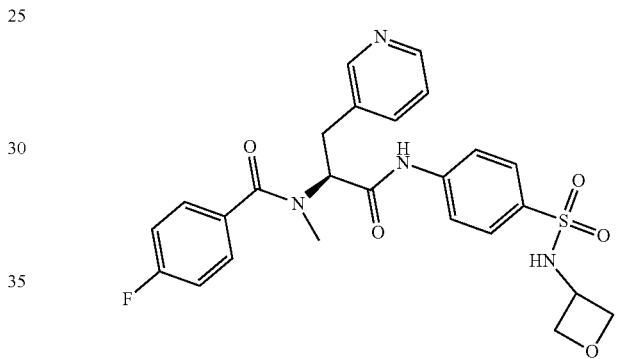

I-89

To a mixture of 229.95 mg oxetan-3-amine (3.15 mmol, 5.0 equiv) and 406.35 mg N,N-diisopropylethylamine (3.15 mmol, 5.00 equiv) in 10 mL dichloromethane was added 300 mg (S)-4-(2-(4-fluoro-N-methylbenzamido)-3-(pyridin-3-yl)propanamido)benzene-1-sulfonyl chloride (0.63 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$·H$_2$O) and ACN (15% ACN up to 35% in 7 min); UV detection at 254/220 nm. The product-containing fractions were combined and evaporated partially in vacuo and lyophilized overnight to afford 88.7 mg (S)-4-fluoro-N-methyl-N-(1-(4-(N-oxetan-3-ylsulfamoyl)phenylamino)-1-oxo-3-(pyridin-3-yl)propan-2-yl)benzamide as a white solid.

Using this general procedure for the preparation of I-89 and substituting the appropriate amine in the last step, the following compounds were prepared.

TABLE 3

Compounds prepared according to Example 55.

| Compound | Chemical Name | Yield | MS | 1H NMR |
|---|---|---|---|---|
| I-89 | (S)-4-fluoro-N-methyl-N-(1-(4-(N-oxetan-3-ylsulfamoyl)phenylamino)-1-oxo-3-(pyridin-3-yl)propan-2-yl)benzamide | 28% | MS (ESI$^+$, m/z): Calcd for C25H25FN4O5S: 512; found 513 [M + H]$^+$; | $^1$H NMR (400 MHz, d$_6$-DMSO) δ 10.50 (br s, 1H), 8.62-8.30 (m, 3H), 7.88-7.74 (m, 5H), 7.50-6.89 (m, 5H), 5.54-4.60 (m, 1H), 4.51 (t, 2H), 4.39-4.34 (m, 1H), 4.25 (t, 2H), 3.44-3.15 (m, 2H), 2.94 (s, 3H) |
| I-90 | (S)-N-(1-(4-(N-ethylsulfamoyl)phenylamino)-1-oxo-3-(pyridin-3-yl)propan-2-yl)-4-fluoro-N-methylbenzamide | 36% | MS (ESI$^+$, m/z): Calcd for C24H25FN4O4S: 484; found 485 [M + H]$^+$ | $^1$H NMR (400 MHz, d$_6$-DMSO) δ 10.50 (br s, 1H), 8.62-8.30 (m, 2H), 7.88-7.74 (m, 5H), 7.52-6.89 (m, 6H), 5.54-4.60 (m, 1H), 3.44-3.15 (m, 2H), 2.94 (s, 3H), 2.77 (q, 2H), 097 (t, 3H). |
| I-91 | (S)-N-(1-(4-(N-tert-butylsulfamoyl)phenylamino)-1-oxo-3-(pyridin-3-yl)propan-2-yl)-4-fluoro-N-methylbenzamide | 32% | MS (ESI$^+$, m/z): Calcd for C26H29FN4O4S: 512; found 513 [M + H]$^+$ | $^1$H NMR (400 MHz, d$_6$-DMSO) δ 10.48 (br s, 1H), 8.64-8.30 (m, 2H), 7.92-7.71 (m, 5H), 7.52-6.88 (m, 6H), 5.54-4.60 (m, 1H), 3.31-3.15 (m, 2H), 2.94 (s, 3H), 1.10 (s, 9H). |
| I-92 | (S)-N-(1-(4-(N-bicyclo[1.1.1]pentan-1-ylsulfamoyl)phenylamino)-1-oxo-3-(pyridin-3-yl)propan-2-yl)-4-fluoro-N-methylbenzamide | 38% | MS (ESI$^+$, m/z): Calcd for C27H27FN4O4S: 522; found 523 [M + H]$^+$; | $^1$H NMR (300 MHz, d$_6$-DMSO) δ 10.50 (br s, 1H), 8.64-8.30 (m, 3H), 7.92-7.71 (m, 5H), 7.42-6.88 (m, 5H), 5.54-4.60 (m, 1H), 3.31-3.15 (m, 2H), 2.94 (s, 3H), 2.27 (s, 1H), 1.71 (s, 6H). |

Example 56: (S)-N-(1-(4-(N-tert-butylsulfamoyl)-2-methylphenylamino)-1-oxo-3-phenylpropan-2-yl)-4-fluorobenzamide, I-93

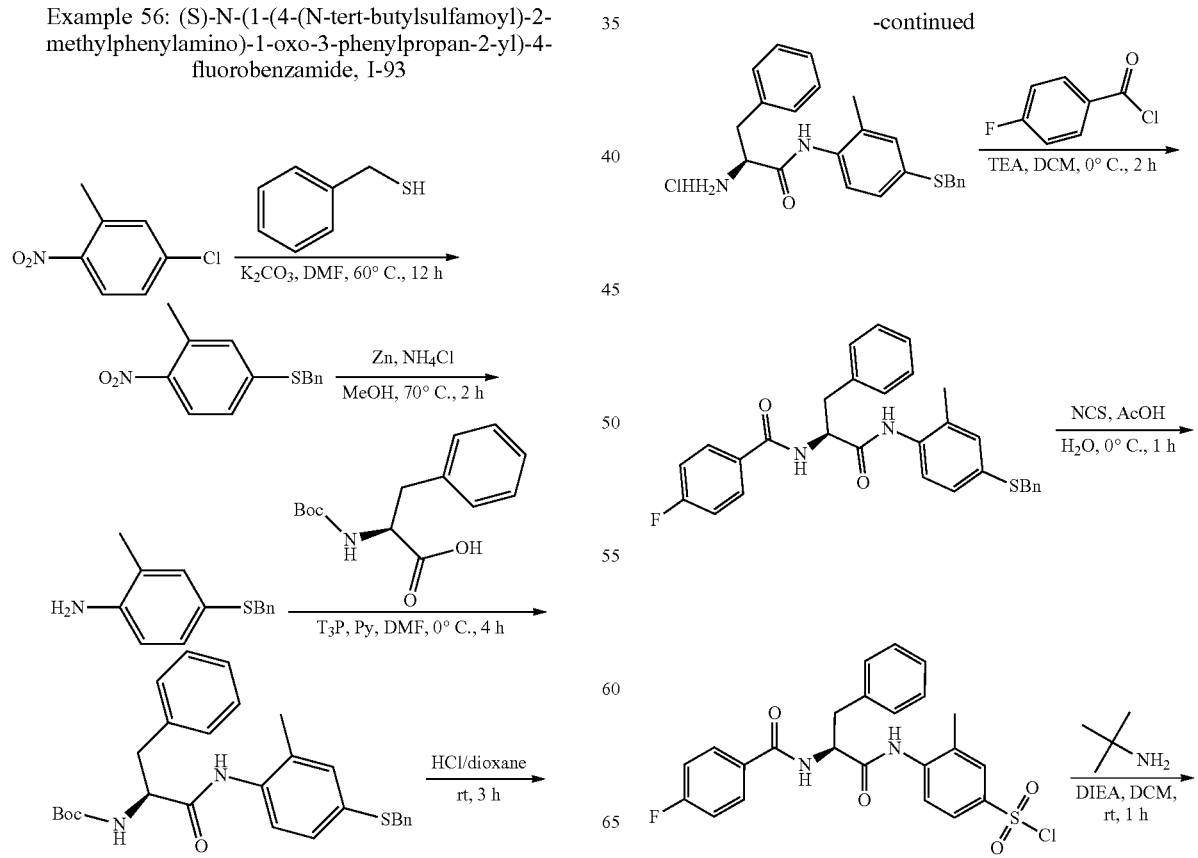

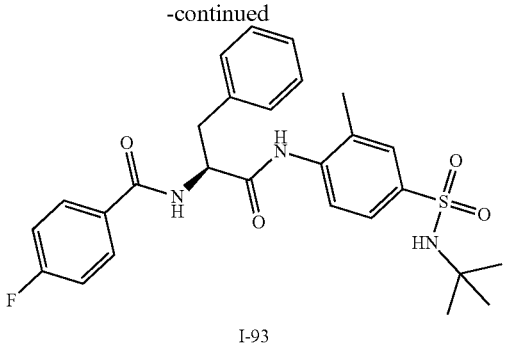

I-93

Preparation of benzyl(3-methyl-4-nitrophenyl)sulfane

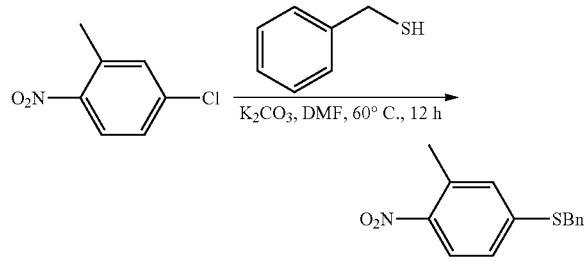

To a solution 8.6 g 4-chloro-2-methyl-1-nitrobenzene (50 mmol, 1.00 equiv) and 13.8 g potassium carbonate (100 mmol, 2.00 equiv) in 300 mL anhydrous N,N-dimethylformamide was added dropwise 7.44 g of phenylmethanethiol (60 mmol, 1.20 equiv) at room temperature. The resulting mixture was stirred for 12 h at 60° C. The mixture was cooled to room temperature, diluted with 500 mL water and extracted with ethyl acetate (3×500 mL). The combined organic layers were washed with brine (3×200 mL), dried over anhydrous magnesium sulfate, filtered and the filtrate was concentrated in vacuo. Purification by column chromatography (silica gel, petroleum ether:ethyl acetate (8:1)) afforded 8.8 g benzyl(3-methyl-4-nitrophenyl)sulfane as a yellow solid (68% yield). MS (ESI+) m/z 260 [M+H]+.

Preparation of 4-(benzylthio)-2-methylbenzenamine

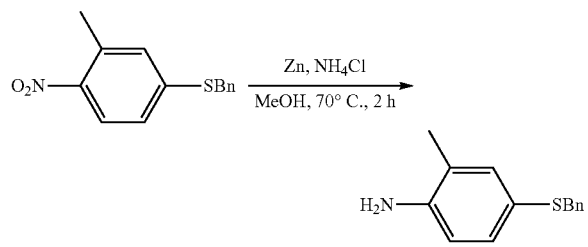

To a solution of 8.8 g benzyl(3-methyl-4-nitrophenyl)sulfane (33.85 mmol, 1.00 equiv) in 200 mL methanol was added 9.05 g ammonium chloride (169.25 mmol, 5.00 equiv) and 8.6 g zinc (135.4 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (5:1)) afforded 4.75 g 4-(benzylthio)-2-methylbenzenamine as an orange oil (61% yield). MS (ESI+) m/z 230 [M+H]+.

Preparation of (S)-tert-butyl 1-(4-(benzylthio)-2-methylphenylamino)-1-oxo-3-phenylpropan-2-ylcarbamate

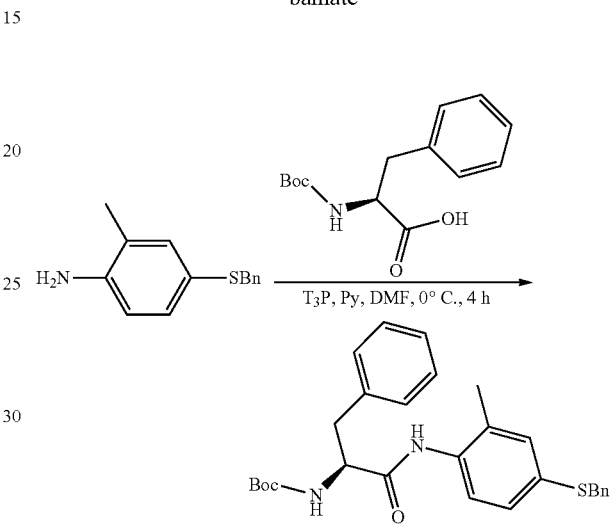

To a solution of 2.3 g 4-(benzylthio)-2-methylbenzenamine (10 mmol, 1.00 equiv), 2.65 g (S)-2-(tert-butoxycarbonylamino)-3-phenylpropanoic acid (10 mmol, 1.00 equiv) and 7.9 g pyridine (100 mmol, 10.00 equiv) in 30 mL N,N-dimethylformamide was added dropwise a solution 25.8 g propanephosphonic acid cyclic anhydride in ethyl acetate (50%, 50 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (2:1)) provided 3 g (S)-tert-butyl 1-(4-(benzylthio)-2-methylphenylamino)-1-oxo-3-phenylpropan-2-ylcarbamate as a yellow solid (63% yield). MS (ESI+) m/z 421 [M-56+H]+.

Preparation of (S)-2-amino-N-(4-(benzylthio)-2-methylphenyl)-3-phenylpropanamide Hydrochloride

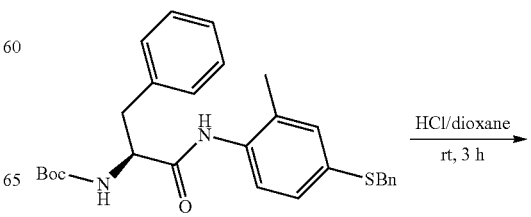

395

-continued

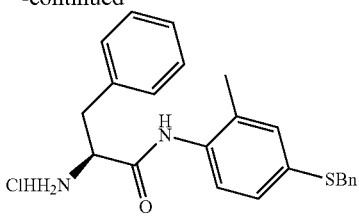

A mixture of 3 g (S)-tert-butyl 1-(4-(benzylthio)-2-methylphenylamino)-1-oxo-3-phenylpropan-2-ylcarbamate (6.3 mmol, 1.00 equiv) in 30 mL hydrochloric acid in 1,4-dioxane (4.0 M) was stirred at room temperature for 3 h. The mixture was concentrated to afford 2.6 g (S)-2-amino-N-(4-(benzylthio)-2-methylphenyl)-3-phenylpropanamide hydrochloride as a light yellow solid (100% yield). MS (ESI$^+$) m/z 377 [M+H]$^+$.

Preparation of (S)-N-(1-(4-(benzylthio)-2-methylphenylamino)-1-oxo-3-phenylpropan-2-yl)-4-fluorobenzamide

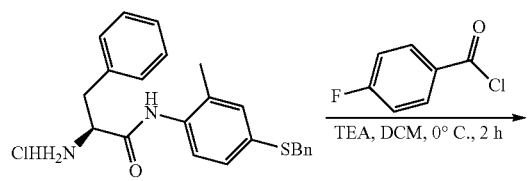

To a solution of 1.3 g (S)-2-amino-N-(4-(benzylthio)-2-methylphenyl)-3-phenylpropanamide hydrochloride (3.15 mmol, 1.00 equiv) and 1.91 g triethylamine (18.9 mmol, 6.00 equiv) in 20 mL dichloromethane was added dropwise 597.2 mg 4-fluorobenzoyl chloride (3.78 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1.11 g (S)-N-(1-(4-(benzylthio)-2-methylphenylamino)-1-oxo-3-phenylpropan-2-yl)-4-fluorobenzamide as a yellow solid (71% yield). MS (ESI$^+$) m/z 499 [M+H]$^+$.

396

Preparation of (S)-4-(2-(4-fluorobenzamido)-3-phenylpropanamido)-3-methylbenzene-1-sulfonyl Chloride

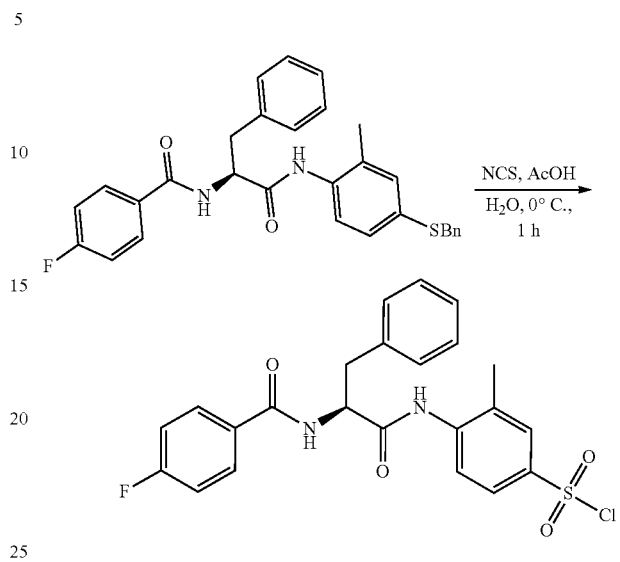

To a solution of 1.11 g (S)-N-(1-(4-(benzylthio)phenylamino)-1-oxo-3-phenylpropan-2-yl)-4-fluoro-N-methylbenzamide (2.23 mmol, 1.00 equiv) in 9 mL acetic acid and 3 mL water was added 1.19 g N-chlorosuccinimide (8.92 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.65 g (S)-4-(2-(4-fluorobenzamido)-3-phenylpropanamido)-3-methylbenzene-1-sulfonyl chloride as a white solid (61% yield). MS (ESI$^+$) m/z 475 and 477 [M+H]$^+$.

Preparation of (S)-N-(1-(4-(N-tert-butylsulfamoyl)-2-methylphenylamino)-1-oxo-3-phenylpropan-2-yl)-4-fluorobenzamide (I-93)

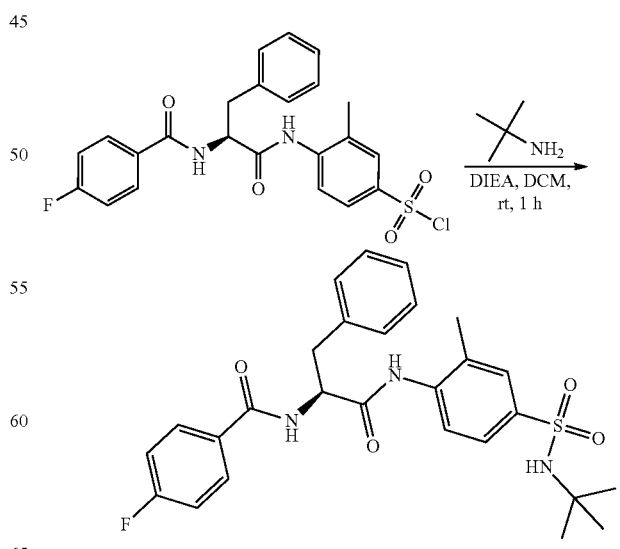

I-93

To a mixture of 76.65 mg 2-methylpropan-2-amine (1.05 mmol, 5.0 equiv) and 135.45 mg N,N-diisopropylethylamine (1.05 mmol, 5.00 equiv) in 10 mL dichloromethane was added 100 mg (S)-4-(2-(4-fluorobenzamido)-3-phenylpropanamido)-3-methylbenzene-1-sulfonyl chloride (0.21 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (35% ACN up to 65% in 7 min); UV detection at 254/220 nm. The product-containing fractions were combined and evaporated partially in vacuo and lyophilized overnight to afford 54.2 mg (S)-N-(1-(4-(N-tert-butylsulfamoyl)-2-methylphenylamino)-1-oxo-3-phenyl-propan-2-yl)-4-fluorobenzamide (I-93) as a white solid (51% yield). MS (ESI$^+$, m/z) 512 [M+H]$^+$; $^1$H NMR (400 MHz, CD$_3$OD) δ 7.90-7.85 (m, 2H), 7.72-7.64 (m, 3H), 7.41-7.15 (m, 7H), 5.00 (t, 1H), 3.29-3.18 (m, 2H), 2.17 (s, 3H), 1.17 (s, 9H).

Example 57: (S)-3-fluoro-N-(1-(4-(N-oxetan-3-ylsulfamoyl)phenylamino)-1-oxo-3-phenylpropan-2-yl)benzamide, I-94

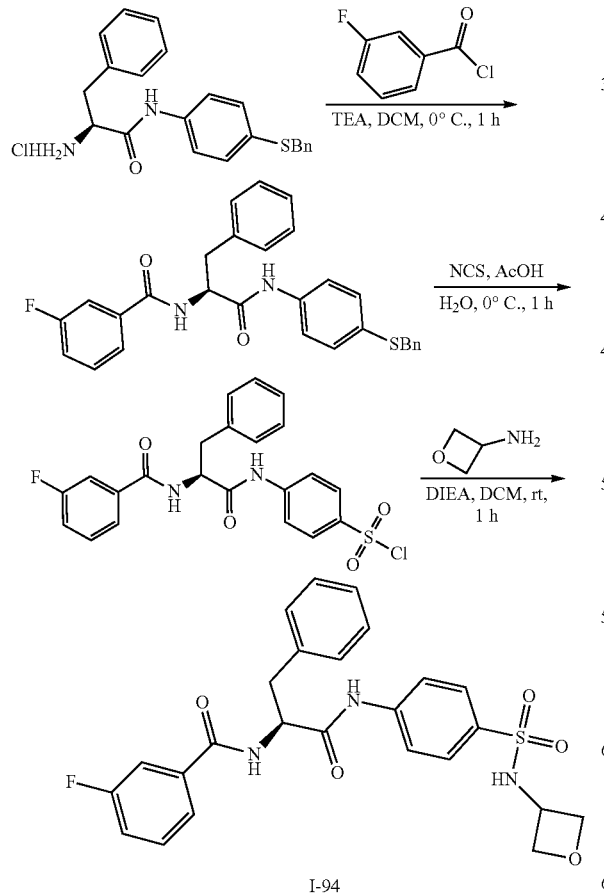

I-94

Preparation of (S)-N-(1-(4-(benzylthio)phenylamino)-1-oxo-3-phenylpropan-2-yl)-3-fluorobenzamide

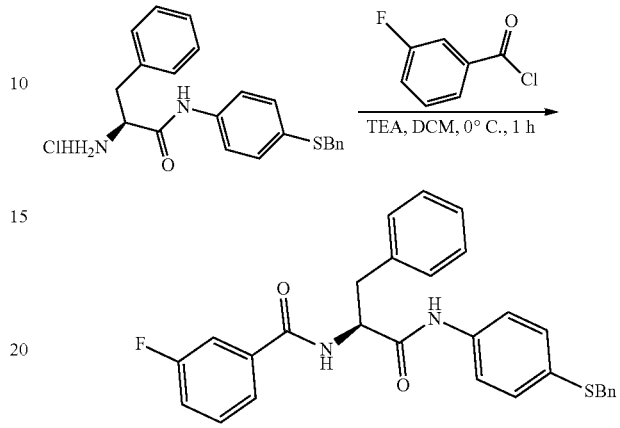

To a solution of 1.25 g (S)-2-amino-N-(4-(benzylthio)phenyl)-3-phenylpropanamide hydrochloride (3.15 mmol, 1.00 equiv) and 1.91 g triethylamine (18.9 mmol, 6.00 equiv) in 20 mL dichloromethane was added dropwise 597.2 mg 3-fluorobenzoyl chloride (3.78 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1 g (S)-N-(1-(4-(benzylthio)phenylamino)-1-oxo-3-phenylpropan-2-yl)-3-fluorobenzamide as a yellow solid (66% yield). MS (ESI$^+$) m/z 485 [M+H]$^+$.

Preparation of (S)-4-(2-(3-fluorobenzamido)-3-phenylpropanamido)benzene-1-sulfonyl Chloride

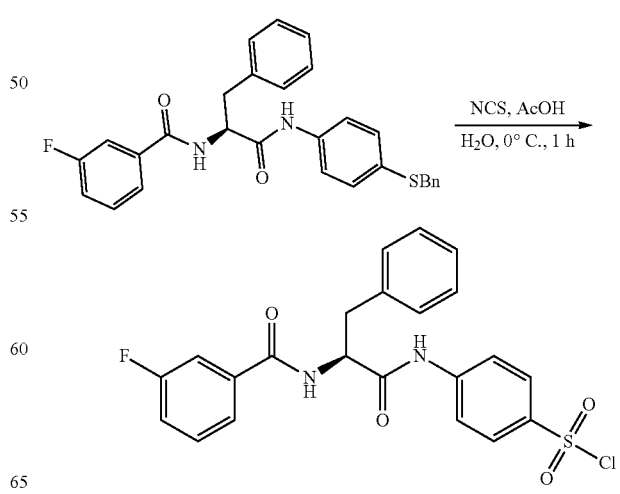

To a solution of 1 g (S)-N-(1-(4-(benzylthio)phenylamino)-1-oxo-3-phenylpropan-2-yl)-3-fluorobenzamide (2.06 mmol, 1.00 equiv) in 9 mL acetic acid and 3 mL water was added 1.1 g N-chlorosuccinimide (8.24 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.55 g (S)-4-(2-(3-fluorobenzamido)-3-phenylpropanamido)benzene-1-sulfonyl chloride as a white solid (58% yield). MS (ESI+) m/z 461 and 463 [M+H]+.

Preparation of (S)-3-fluoro-N-(1-(4-(N-oxetan-3-ylsulfamoyl)phenylamino)-1-oxo-3-phenylpropan-2-yl)benzamide

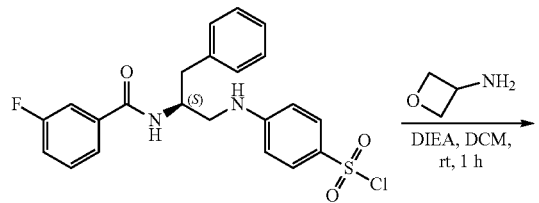

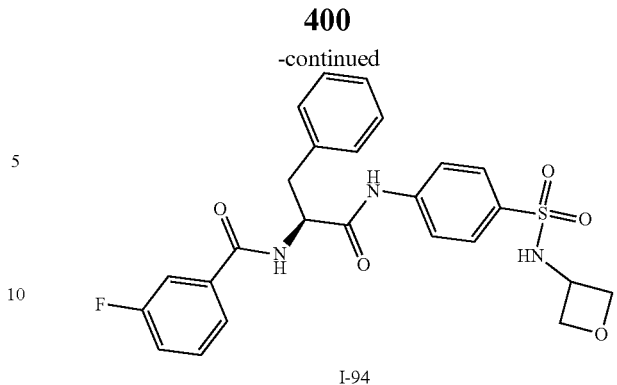

I-94

To a mixture of 80.3 mg oxetan-3-amine (1.1 mmol, 5.0 equiv) and 141.9 mg N,N-diisopropylethylamine (1.1 mmol, 5.00 equiv) in 10 mL dichloromethane was added 100 mg (S)-4-(2-(3-fluorobenzamido)-3-phenylpropanamido)benzene-1-sulfonyl chloride (0.22 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% $NH_4HCO_3$+0.1% $NH_3$—$H_2O$) and ACN (35% ACN up to 65% in 7 min); UV detection at 254/220 nm. The product-containing fractions were combined and evaporated partially in vacuo and lyophilized overnight to afford 49.8 mg (S)-3-fluoro-N-(1-(4-(N-oxetan-3-ylsulfamoyl)phenylamino)-1-oxo-3-phenylpropan-2-yl)benzamide (I-94) as a white solid.

Using this general procedure for the preparation of I-94 and substituting the appropriate amine in the last step, the following compounds were prepared.

TABLE 4

Compounds prepared according to Example 57.

| Compound | Chemical Name | Yield | MS | 1HNMR |
|---|---|---|---|---|
| I-94 | (S)-3-fluoro-N-(1-(4-(N-oxetan-3-ylsulfamoyl)phenylamino)-1-oxo-3-phenylpropan-2-yl)benzamide | 46% | MS (ESI+, m/z): Calcd for C25H24FN3O5S: 497; found 498 [M + H]+; | 1H NMR (400 MHz, CD3OD) δ 7.80-7.69 (m, 4H), 7.60 (d, 1H), 7.55-7.43 (m, 2H), 7.36-7.15 (m, 6H), 4.92 (t, 1H), 4.61 (t, 2H), 4.50-4.43 (m, 1H), 4.34 (t, 2H), 3.29-3.12 (m, 2H). |
| I-95 | (S)-N-(1-(4-(N-bicyclo[1.1.1]pentan-1-ylsulfamoyl)phenylamino)-1-oxo-3-phenylpropan-2-yl)-3-fluorobenzamide | 48% | MS (ESI+, m/z): Calcd for C27H26FN3O4S: 507; found 508 [M + H]+ | 1H NMR (400 MHz, CD3OD) δ 7.80-7.69 (m, 4H), 7.60 (d, 1H), 7.55-7.43 (m, 2H), 7.36-7.15 (m, 6H), 4.93 (t, 1H), 3.29-3.12 (m, 2H), 2.27 (s, 1H), 1.78 (s, 6H). |

Example 58: (S)-N-(1-(4-(N-tert-butylsulfamoyl)-3-methylphenylamino)-1-oxo-3-phenylpropan-2-yl)-4-fluorobenzamide, I-96

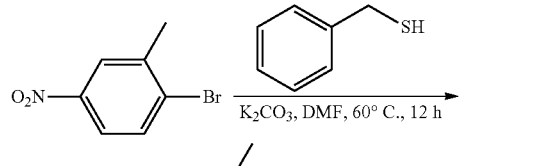

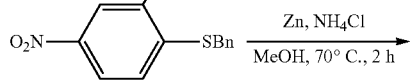

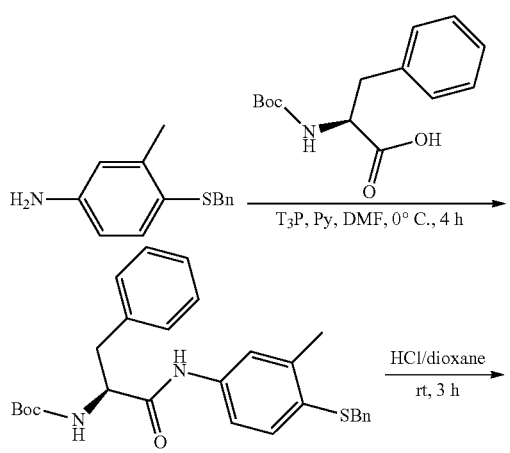

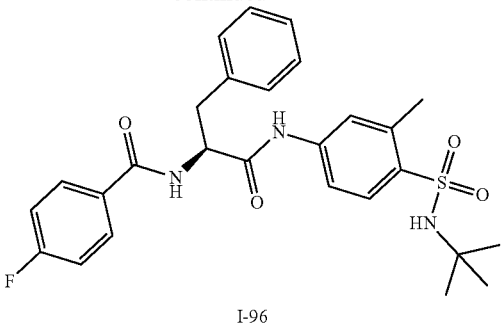

I-96

Preparation of benzyl(2-methyl-4-nitrophenyl)sulfane

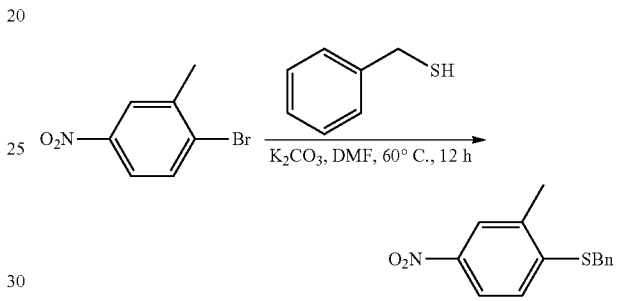

To a solution of 10.8 g 1-bromo-2-methyl-4-nitrobenzene (50 mmol, 1.00 equiv) and 13.8 g potassium carbonate (100 mmol, 2.00 equiv) in 300 mL anhydrous N,N-dimethylformamide was added dropwise 7.44 g of phenylmethanethiol (60 mmol, 1.20 equiv) at room temperature. The resulting mixture was stirred for 12 h at 60° C. The mixture was cooled to room temperature, diluted with 500 mL water and extracted with ethyl acetate (3×500 mL). The combined organic layers were washed with brine (3×200 mL), dried over anhydrous magnesium sulfate, filtered and the filtrate was concentrated in vacuo. Purification by column chromatography (silica gel, petroleum ether:ethyl acetate (8:1)) afforded 8.6 g benzyl(2-methyl-4-nitrophenyl)sulfane as a yellow solid (66% yield). MS (ESI⁺) m/z 260 [M+H]⁺.

Preparation of 4-(benzylthio)-3-methylbenzenamine

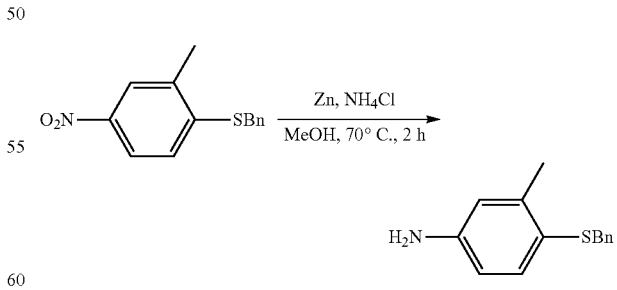

To a solution of 8.6 g benzyl(3-methyl-4-nitrophenyl)sulfane (33.08 mmol, 1.00 equiv) in 200 mL methanol was added 8.85 g ammonium chloride (165.4 mmol, 5.00 equiv) and 8.4 g zinc (132.32 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (5:1)) afforded 4.56 g 4-(benzylthio)-3-methylbenzenamine as an orange oil (60% yield). MS (ESI$^+$) m/z 230 [M+H]$^+$.

Preparation of (S)-tert-butyl 1-(4-(benzylthio)-3-methylphenylamino)-1-oxo-3-phenylpropan-2-ylcarbamate

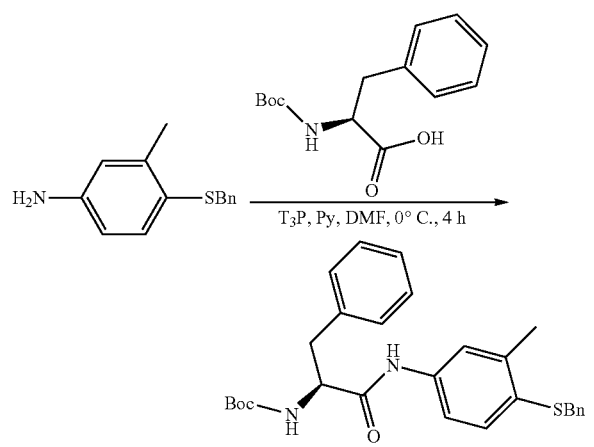

To a solution of 2.3 g 4-(benzylthio)-3-methylbenzenamine (10 mmol, 1.00 equiv), 2.65 g (S)-2-(tert-butoxycarbonylamino)-3-phenylpropanoic acid (10 mmol, 1.00 equiv) and 7.9 g pyridine (100 mmol, 10.00 equiv) in 30 mL N,N-dimethylformamide was added dropwise a solution 25.8 g propanephosphonic acid cyclic anhydride in ethyl acetate (50%, 50 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (2:1)) provided 3 g (S)-tert-butyl 1-(4-(benzylthio)-3-methylphenylamino)-1-oxo-3-phenylpropan-2-ylcarbamate as a yellow solid (63% yield). MS (ESI$^+$) m/z 421 [M-56+H]$^+$.

Preparation of (S)-2-amino-N-(4-(benzylthio)-3-methylphenyl)-3-phenylpropanamide Hydrochloride

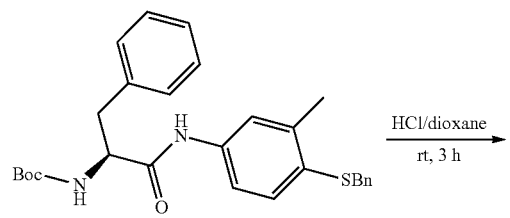

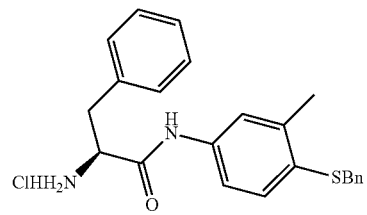

A mixture of 3 g (S)-tert-butyl 1-(4-(benzylthio)-3-methylphenylamino)-1-oxo-3-phenylpropan-2-ylcarbamate (6.3 mmol, 1.00 equiv) in 30 mL hydrochloric acid in 1,4-dioxane (4.0 M) was stirred at room temperature for 3 h. The mixture was concentrated to afford 2.6 g (S)-2-amino-N-(4-(benzylthio)-3-methylphenyl)-3-phenylpropanamide hydrochloride as a light yellow solid (100% yield). MS (ESI$^+$) m/z 377 [M+H]$^+$.

Preparation of (S)-N-(1-(4-(benzylthio)-3-methylphenylamino)-1-oxo-3-phenylpropan-2-yl)-4-fluorobenzamide

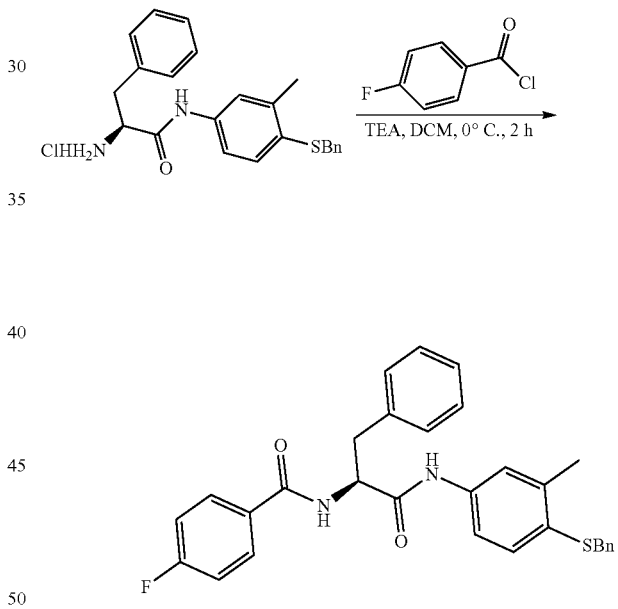

To a solution of 1.3 g (S)-2-amino-N-(4-(benzylthio)-3-methylphenyl)-3-phenylpropanamide hydrochloride (3.15 mmol, 1.00 equiv) and 1.91 g triethylamine (18.9 mmol, 6.00 equiv) in 20 mL dichloromethane was added dropwise 597.2 mg 4-fluorobenzoyl chloride (3.78 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1.08 g (S)-N-(1-(4-(benzylthio)-3-methylphenylamino)-1-oxo-3-phenylpropan-2-yl)-4-fluorobenzamide as a yellow solid (69% yield). MS (ESI$^+$) m/z 499 [M+H]$^+$.

Preparation of (S)-4-(2-(4-fluorobenzamido)-3-phenylpropanamido)-2-methylbenzene-1-sulfonyl Chloride

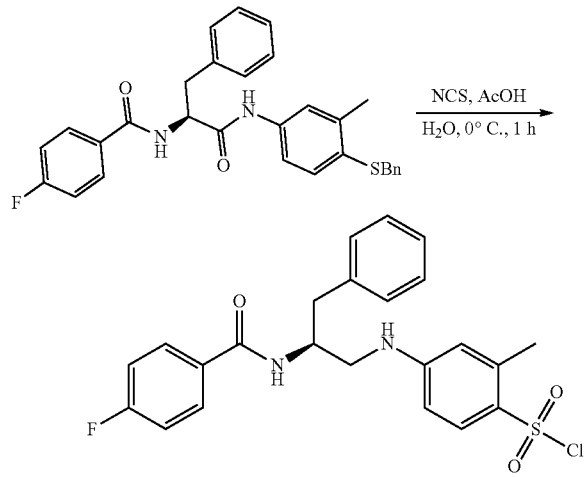

To a solution of 1.08 g (S)-N-(1-(4-(benzylthio)-3-methylphenylamino)-1-oxo-3-phenylpropan-2-yl)-4-fluorobenzamide (2.16 mmol, 1.00 equiv) in 9 mL acetic acid and 3 mL water was added 1.15 g N-chlorosuccinimide (8.64 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.6 g (S)-4-(2-(4-fluorobenzamido)-3-phenylpropanamido)-2-methylbenzene-1-sulfonyl chloride as a white solid (58% yield). MS (ESI+) m/z 475 and 477 [M+H]+.

Preparation of (S)-N-(1-(4-(N-tert-butylsulfamoyl)-3-methylphenylamino)-1-oxo-3-phenylpropan-2-yl)-4-fluorobenzamide (I-96)

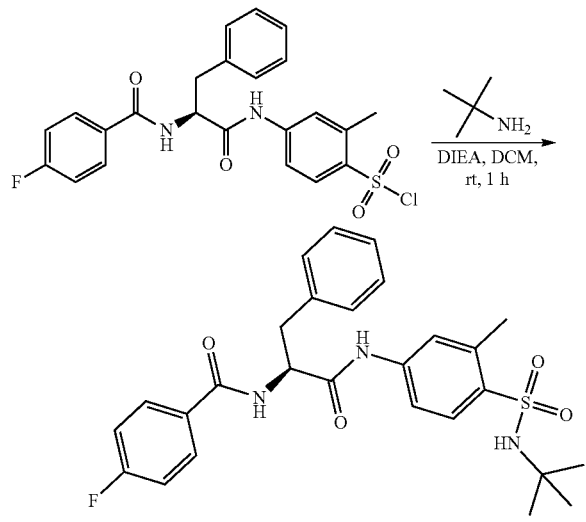

To a mixture of 76.65 mg 2-methylpropan-2-amine (1.05 mmol, 5.0 equiv) and 135.45 mg N,N-diisopropylethylamine (1.05 mmol, 5.00 equiv) in 10 mL dichloromethane was added 100 mg (S)-4-(2-(4-fluorobenzamido)-3-phenylpropanamido)-2-methylbenzene-1-sulfonyl chloride (0.21 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (35% ACN up to 65% in 7 min); UV detection at 254/220 nm. The product-containing fractions were combined and evaporated partially in vacuo and lyophilized overnight to afford 60.2 mg (S)-N-(1-(4-(N-tert-butylsulfamoyl)-3-methylphenylamino)-1-oxo-3-phenylpropan-2-yl)-4-fluorobenzamide (I-96) as a white solid (56% yield). MS (ESI+, m/z) 512 [M+H]+; $^1$H NMR (400 MHz, d$_6$-DMSO) δ 10.50 (s, 1H), 8.85 (d, 1H), 7.95-7.80 (m, 3H), 7.66-7.60 (m, 2H), 7.46-7.19 (m, 8H), 4.86-4.80 (m, 1H), 3.24-3.18 (m, 2H), 2.56 (s, 3H), 1.09 (s, 9H).

Example 59: (S)-N-(1-(4-(N-bicyclo[1.1.1]pentan-1-ylsulfamoyl)-2-methylphenylamino)-1-oxo-3-phenylpropan-2-yl)-5-fluoropicolinamide, I-97

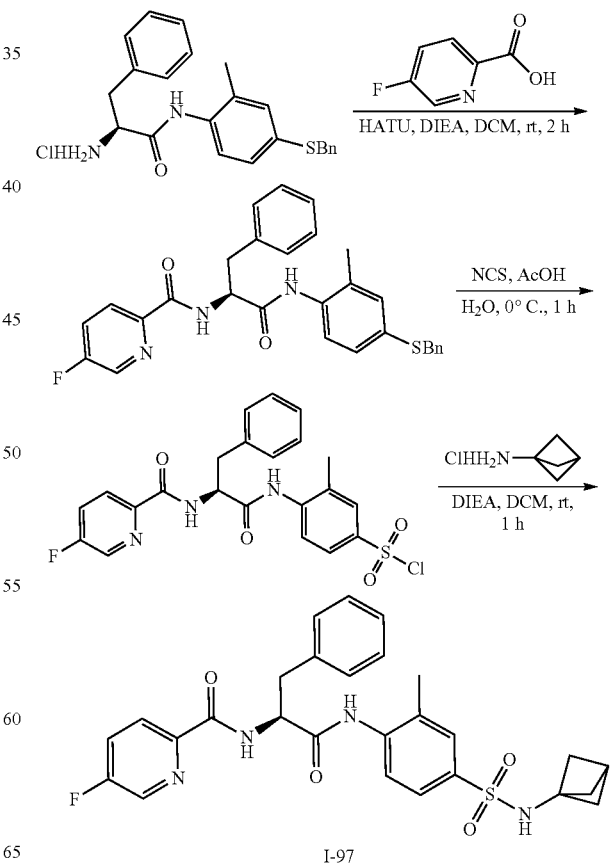

Preparation of (S)-N-(1-(4-(benzylthio)-2-methylphenylamino)-1-oxo-3-phenylpropan-2-yl)-5-fluoropicolinamide

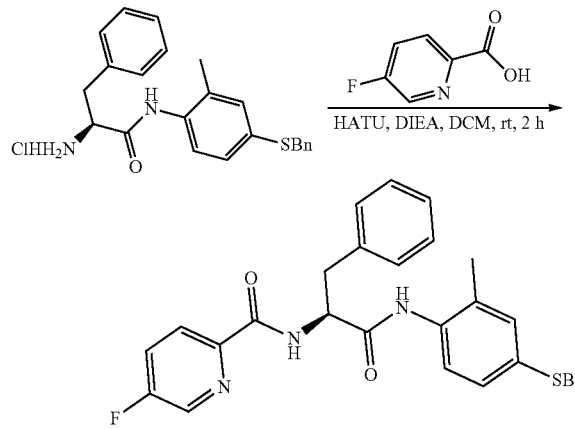

To a solution of 1.3 g (S)-2-amino-N-(4-(benzylthio)-2-methylphenyl)-3-phenylpropanamide hydrochloride (3.15 mmol, 1.00 equiv) and 2.44 g DIEA (18.9 mmol, 6.00 equiv) in 20 mL dichloromethane was added 533 mg 5-fluoropicolinic acid (3.78 mmol, 1.20 equiv) and 1.44 g HATU (3.78 mmol, 1.20 equiv) at r.t. The resulting mixture was stirred for 2 h at r.t. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1.07 g (S)-N-(1-(4-(benzylthio)-2-methylphenylamino)-1-oxo-3-phenylpropan-2-yl)-5-fluoropicolinamide as a yellow solid (68% yield). MS (ESI$^+$) m/z 500 [M+H]$^+$.

Preparation of (S)-4-(2-(5-fluoropicolinamido)-3-phenylpropanamido)-3-ethylbenzene-1-sulfonyl Chloride

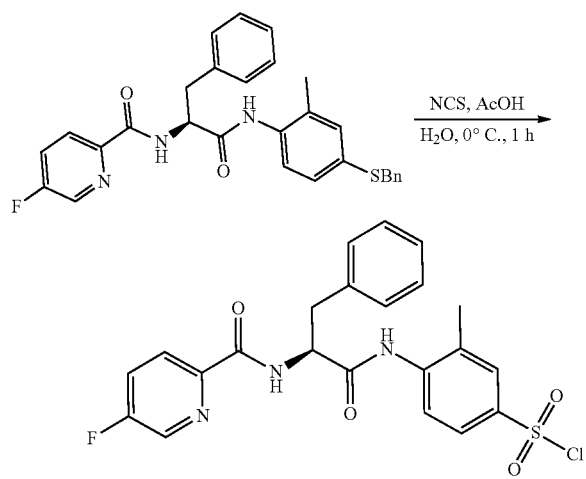

To a solution of 1.07 g (S)-N-(1-(4-(benzylthio)-2-methylphenylamino)-1-oxo-3-phenylpropan-2-yl)-5-fluoropicolinamide (2.14 mmol, 1.00 equiv) in 9 mL acetic acid and 3 mL water was added 1.14 g N-chlorosuccinimide (8.56 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.57 g (S)-4-(2-(5-fluoropicolinamido)-3-phenylpropanamido)-3-methylbenzene-1-sulfonyl chloride as a white solid (56% yield). MS (ESI$^+$) m/z 476 and 478 [M+H]$^+$.

Preparation of (S)-N-(1-(4-(N-bicyclo[1.1.1]pentan-1-ylsulfamoyl)-2-methylphenylamino)-1-oxo-3-phenylpropan-2-yl)-5-fluoropicolinamide

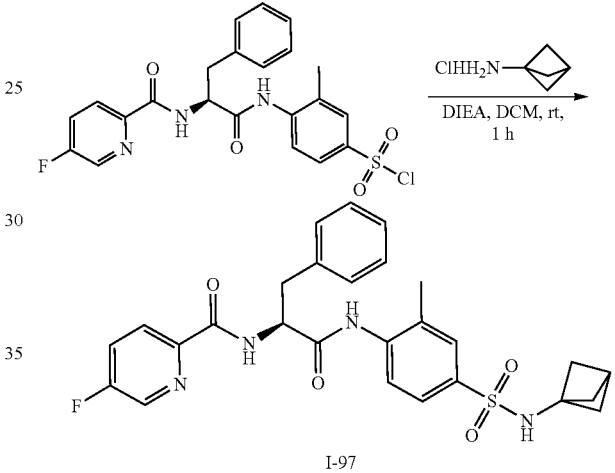

I-97

To a mixture of 126 mg bicyclo[1.1.1]pentan-1-amine hydrochloride (1.05 mmol, 5.0 equiv) and 135.45 mg N,N-diisopropylethylamine (1.05 mmol, 5.00 equiv) in 10 mL dichloromethane was added 100 mg (S)-4-(2-(5-fluoropicolinamido)-3-phenylpropanamido)-3-methylbenzene-1-sulfonyl chloride (0.21 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+ 0.1% NH$_3$—H$_2$O) and ACN (35% ACN up to 65% in 7 min); UV detection at 254/220 nm. The product-containing fractions were combined and evaporated partially in vacuo and lyophilized overnight to afford 19.3 mg (S)-N-(1-(4-(N-bicyclo[1.1.1]pentan-1-ylsulfamoyl)-2-methylphenylamino)-1-oxo-3-phenylpropan-2-yl)-5-fluoropicolinamide (I-97) as a white solid (18% yield). MS (ESI$^+$, m/z) 523 [M+H]$^+$; $^1$H NMR (400 MHz, CD$_3$OD) δ 8.56 (s, 1H), 8.17 (dd, 1H), 7.78 (t, 1H), 7.76-7.65 (m, 3H), 7.41-7.20 (m, 5H), 5.07 (t, 1H), 3.29-3.25 (m, 2H), 2.29 (s, 1H), 2.18 (s, 3H), 1.84 (s, 6H).

Example 60: (S)-N-(1-(4-(N-bicyclo[1.1.1]pentan-1-ylsulfamoyl)-3-methylphenylamino)-1-oxo-3-phenylpropan-2-yl)-5-fluoropicolinamide, I-98

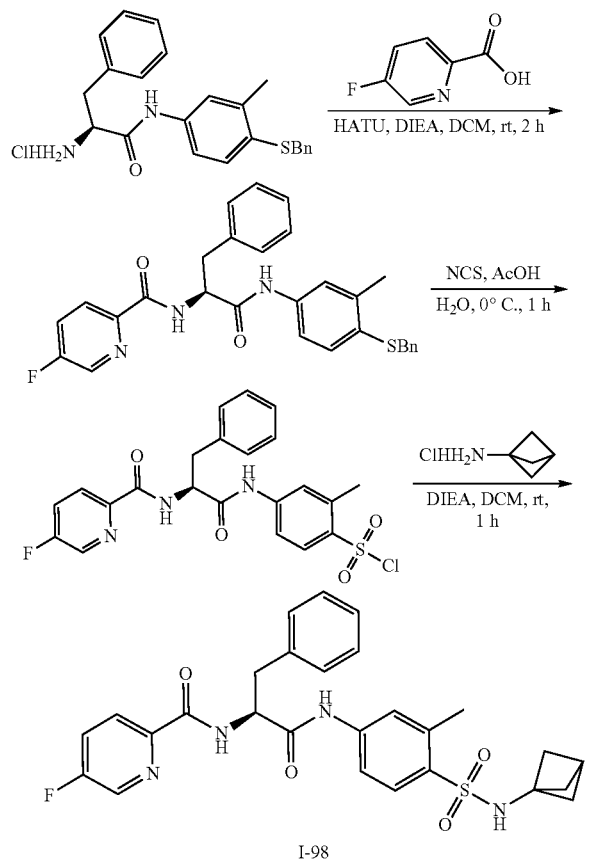

Preparation of (S)-N-(1-(4-(benzylthio)-3-methylphenylamino)-1-oxo-3-phenylpropan-2-yl)-5-fluoropicolinamide

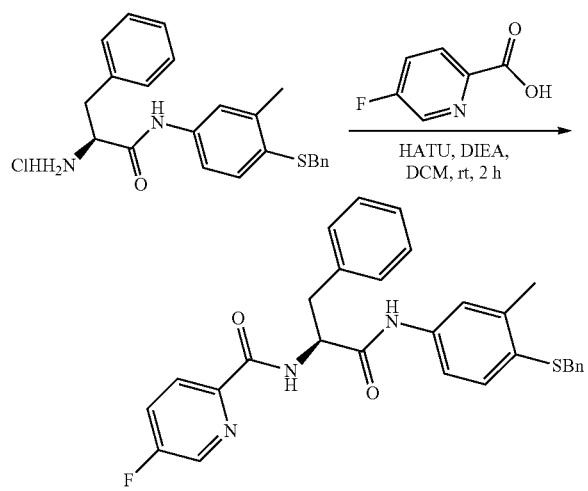

To a solution of 1.3 g (S)-2-amino-N-(4-(benzylthio)-3-methylphenyl)-3-phenylpropanamide hydrochloride (3.15 mmol, 1.00 equiv) and 2.44 g DIEA (18.9 mmol, 6.00 equiv) in 20 mL dichloromethane was added 533 mg 5-fluoropicolinic acid (3.78 mmol, 1.20 equiv) and 1.44 g HATU (3.78 mmol, 1.20 equiv) at r.t. The resulting mixture was stirred for 2 h at r.t. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1.05 g (S)-N-(1-(4-(benzylthio)-3-methylphenylamino)-1-oxo-3-phenylpropan-2-yl)-5-fluoropicolinamide as a yellow solid (67% yield). MS (ESI$^+$) m/z 500 [M+H]$^+$.

Preparation of (S)-4-(2-(5-fluoropicolinamido)-3-phenylpropanamido)-2-methylbenzene-1-sulfonyl Chloride

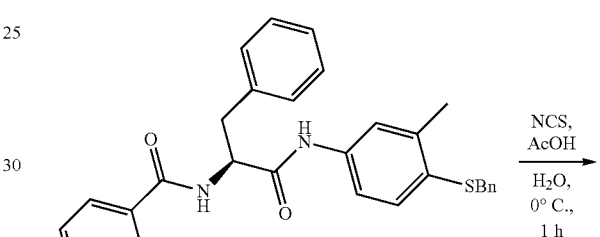

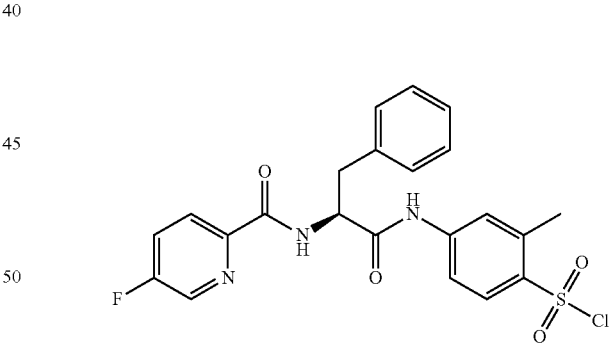

To a solution of 1.05 g (S)-N-(1-(4-(benzylthio)-3-methylphenylamino)-1-oxo-3-phenylpropan-2-yl)-5-fluoropicolinamide (2.1 mmol, 1.00 equiv) in 9 mL acetic acid and 3 mL water was added 1.12 g N-chlorosuccinimide (8.4 mmol, 4.0 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.55 g (S)-4-(2-(5-fluoropicolinamido)-3-phenylpropanamido)-2-methylbenzene-1-sulfonyl chloride as a white solid (55% yield). MS (ESI$^+$) m/z 476 and 478 [M+H]$^+$.

Preparation of (S)-N-(1-(4-(N-bicyclo[1.1.1]pentan-1-ylsulfamoyl)-3-methylphenylamino)-1-oxo-3-phenylpropan-2-yl)-5-fluoropicolinamide

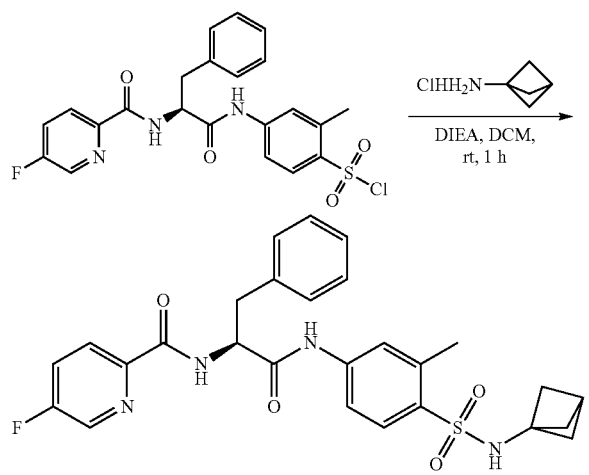

I-98

To a mixture of 126 mg bicyclo[1.1.1]pentan-1-amine hydrochloride (1.05 mmol, 5.0 equiv) and 135.45 mg N,N-diisopropylethylamine (1.05 mmol, 5.00 equiv) in 10 mL dichloromethane was added 100 mg (S)-4-(2-(5-fluoropicolinamido)-3-phenylpropanamido)-2-methylbenzene-1-sulfonyl chloride (0.21 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% $NH_4HCO_3$+ 0.1% $NH_3$—$H_2O$) and ACN (35% ACN up to 65% in 7 min); UV detection at 254/220 nm. The product-containing fractions were combined and evaporated partially in vacuo and lyophilized overnight to afford 33.6 mg (S)-N-(1-(4-(N-bicyclo[1.1.1]pentan-1-ylsulfamoyl)-3-methylphenylamino)-1-oxo-3-phenylpropan-2-yl)-5-fluoropicolinamide (I-98) as a white solid (31% yield). MS (ESI$^+$, m/z) 523 [M+H]$^+$; $^1$H NMR (400 MHz, $d_6$-DMSO) δ 10.54 (s, 1H), 8.76 (d, 1H), 8.69 (d, 1H), 8.50 (s, 1H), 8.08-8.05 (m, 1H), 7.96-7.88 (m, 1H), 7.84-7.78 (m, 1H), 7.65-7.60 (m, 2H), 7.32-7.16 (m, 5H), 4.96-4.91 (m, 1H), 3.29-3.25 (m, 2H), 2.51 (s, 3H), 2.25 (s, 1H), 1.68 (s, 6H).

Example 61: (S)-N-(1-(4-(N-bicyclo[1.1.1]pentan-1-ylsulfamoyl)-3-cyanophenylamino)-1-oxo-3-phenylpropan-2-yl)-4-fluorobenzamide, I-166

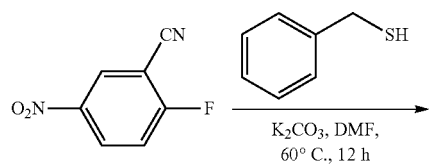

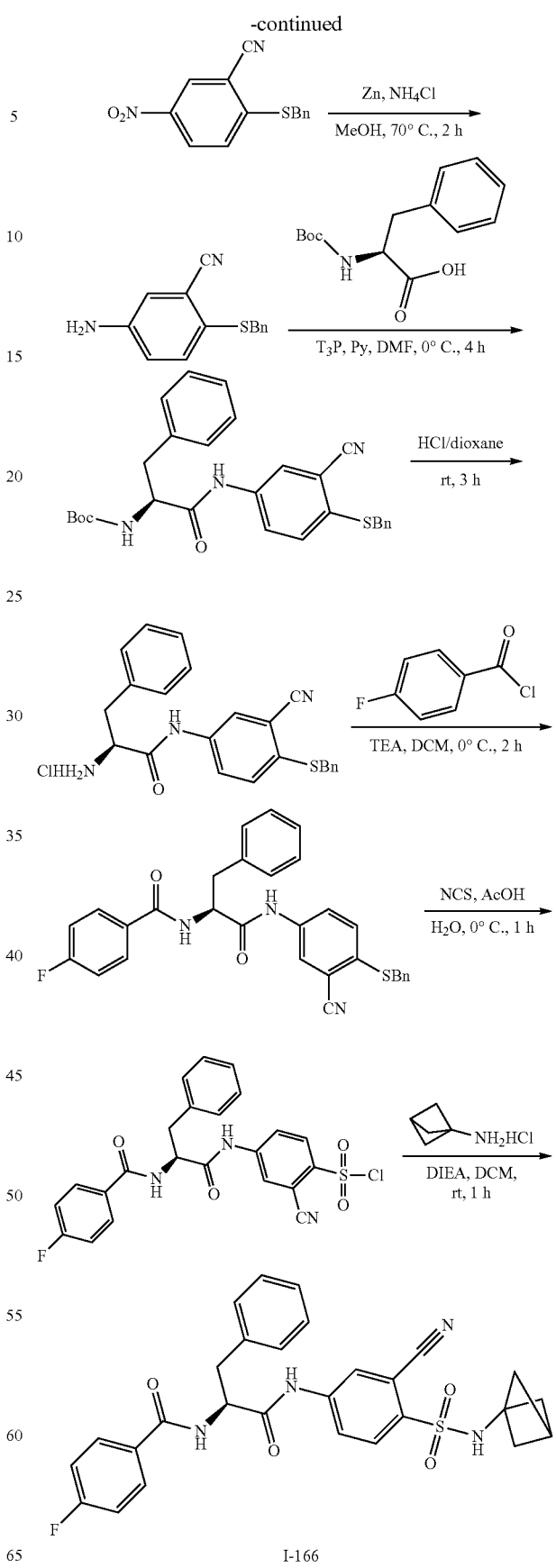

I-166

Preparation of 2-(benzylthio)-5-nitrobenzonitrile

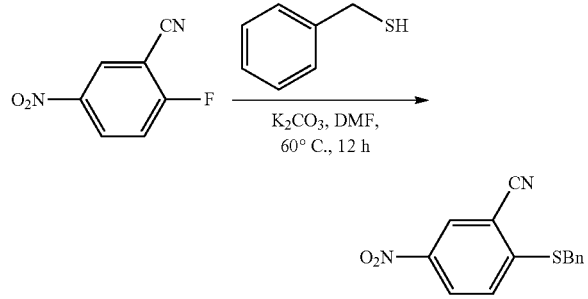

To a solution of 8.3 g 2-fluoro-5-nitrobenzonitrile (50 mmol, 1.00 equiv) and 13.8 g potassium carbonate (100 mmol, 2.00 equiv) in 300 mL anhydrous N,N-dimethylformamide was added dropwise 7.44 g of phenylmethanethiol (60 mmol, 1.20 equiv) at room temperature. The resulting mixture was stirred for 12 h at 60° C. The mixture was cooled to room temperature, diluted with 500 mL water and extracted with ethyl acetate (3×500 mL). The combined organic layers were washed with brine (3×200 mL), dried over anhydrous magnesium sulfate, filtered and the filtrate was concentrated in vacuo. Purification by column chromatography (silica gel, petroleum ether:ethyl acetate (5:1)) afforded 8.1 g 2-(benzylthio)-5-nitrobenzonitrile as a yellow solid (60% yield). MS (ESI$^+$) m/z 271 [M+H]$^+$.

Preparation of 5-amino-2-(benzylthio)benzonitrile

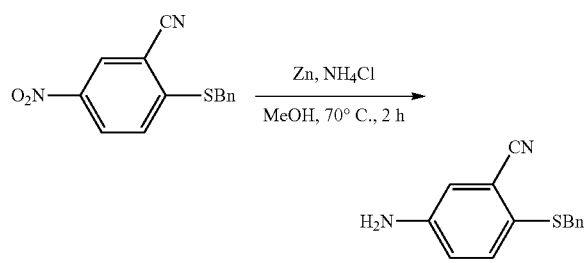

To a solution of 8.1 g 2-(benzylthio)-5-nitrobenzonitrile (30 mmol, 1.00 equiv) in 200 mL methanol was added 8.03 g ammonium chloride (150 mmol, 5.00 equiv) and 7.62 g zinc (120 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (2:1)) afforded 4.2 g 5-amino-2-(benzylthio)benzonitrile as an orange oil (58% yield). MS (ESI$^+$) m/z 241 [M+H]$^+$.

Preparation of (S)-tert-butyl 1-(4-(benzylthio)-3-cyanophenylamino)-1-oxo-3-phenylpropan-2-ylcarbamate

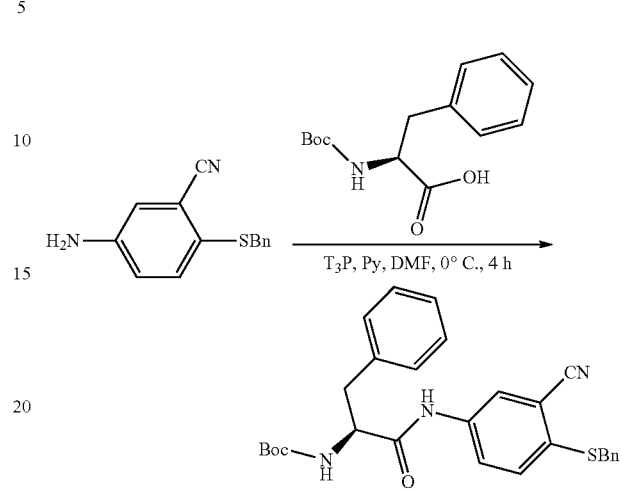

To a solution of 1.9 g (S)-2-(tert-butoxycarbonylamino)-3-phenylpropanoic acid (7.14 mmol, 1.00 equiv), 1.88 g 4-(benzylthio)-3-chlorobenzenamine (7.85 mmol, 1.10 equiv) and 5.64 g pyridine (71.40 mmol, 10.00 equiv) in 40 mL N,N-dimethylformamide was added dropwise a solution 18.42 g propanephosphonic acid cyclic anhydride in ethyl acetate (50%, 35.70 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (3:1)) provided 2.2 g (S)-tert-butyl 1-(4-(benzylthio)-3-cyanophenylamino)-1-oxo-3-phenylpropan-2-ylcarbamate as a yellow solid (63% yield). MS (ESI$^+$) m/z 488 [M+H]$^+$.

Preparation of (S)-2-amino-N-(4-(benzylthio)-3-cyanophenyl)-3-phenylpropanamide Hydrochloride

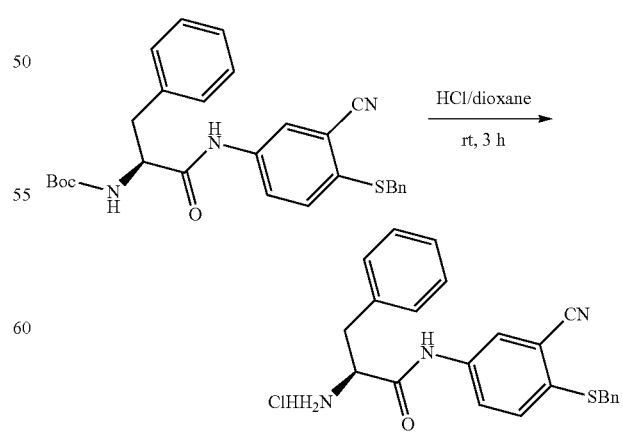

A mixture of 2.2 g (S)-tert-butyl 1-(4-(benzylthio)-3-cyanophenylamino)-1-oxo-3-phenylpropan-2-ylcarbamate (4.5 mmol, 1.00 equiv) in 20 mL hydrochloric acid in 1,4-dioxane (4.0 M) was stirred at room temperature for 2 h. The mixture was concentrated to afford 1.92 g (S)-2-amino-N-(4-(benzylthio)-3-cyanophenyl)-3-phenylpropanamide hydrochloride as a light yellow solid (100% yield). MS (ESI+) m/z 388 [M+H]+.

Preparation of (S)-N-(1-(4-(benzylthio)-3-cyanophenylamino)-1-oxo-3-phenylpropan-2-yl)-4-fluorobenzamide

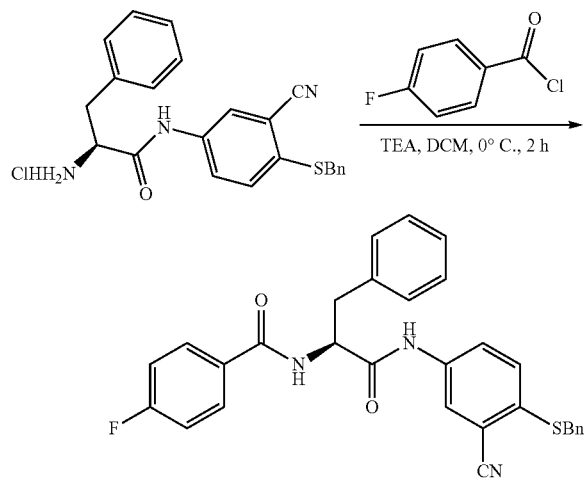

To a solution of 1.92 g (S)-2-amino-N-(4-(benzylthio)-3-cyanophenyl)-3-phenylpropanamide hydrochloride (4.5 mmol, 1.00 equiv) and 2.72 g triethylamine (27 mmol, 6.00 equiv) in 20 mL dichloromethane was added dropwise 854 mg 4-fluorobenzoyl chloride (5.4 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1.46 g (S)-N-(1-(4-(benzylthio)-3-cyanophenylamino)-1-oxo-3-phenylpropan-2-yl)-4-fluorobenzamide as a yellow solid (64% yield). MS (ESI+) m/z 510 [M+H]+.

Preparation of (S)-2-cyano-4-(2-(4-fluorobenzamido)-3-phenylpropanamido)benzene-1-sulfonyl Chloride

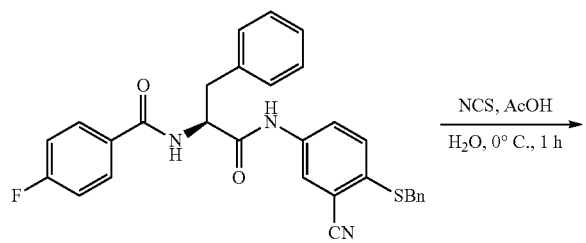

-continued

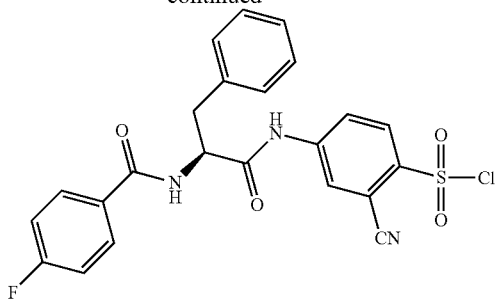

To a solution of 1.46 g (S)-N-(1-(4-(benzylthio)-3-cyanophenylamino)-1-oxo-3-phenylpropan-2-yl)-4-fluorobenzamide (2.87 mmol, 1.00 equiv) in 12 mL acetic acid and 4 mL water was added 1.53 g N-chlorosuccinimide (11.48 mmol, 4.00 equiv) at 0° C. The resulting mixture was stirred at 0° C. for 2 h. The mixture was diluted with 30 mL water and extracted with dichloromethane (3×50 mL). The combined organic layers were washed with brine (1×50 mL), dried over anhydrous magnesium sulfate, filtered and the filtrate concentrated to give 0.57 g (S)-2-cyano-4-(2-(4-fluorobenzamido)-3-phenylpropanamido)benzene-1-sulfonyl chloride as a white solid (41% yield). MS (ESI+) m/z 486 [M+H]+.

Preparation of (S)-N-(1-(4-(N-bicyclo[1.1.1]pentan-1-ylsulfamoyl)-3-cyanophenylamino)-1-oxo-3-phenylpropan-2-yl)-4-fluorobenzamide (I-166)

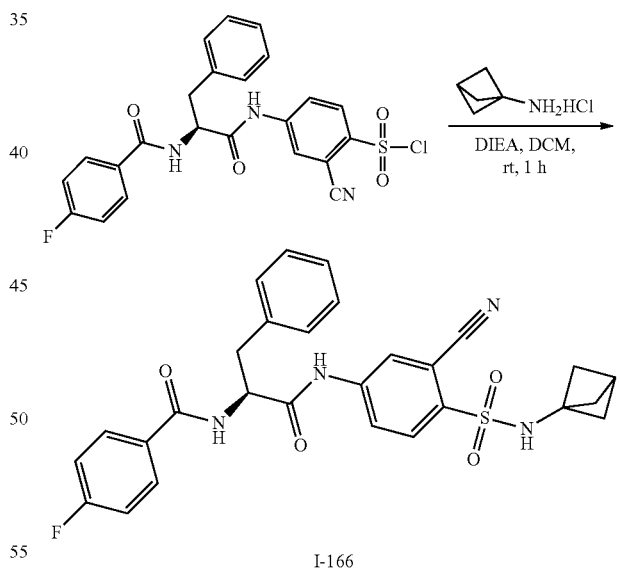

I-166

To a mixture of 123.6 mg bicyclo[1.1.1]pentan-1-amine hydrochloride (1.03 mmol, 5.0 equiv) and 132.87 mg N,N-diisopropylethylamine (1.03 mmol, 5.00 equiv) in 10 mL dichloromethane was added 100 mg (S)-2-cyano-4-(2-(4-fluorobenzamido)-3-phenylpropanamido)benzene-1-sulfonyl chloride (0.206 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% $NH_4HCO_3$+ 0.1% $NH_3·H_2$) and ACN (28% ACN up to 42% in 7 min); UV detection at 254/220 nm. The product-containing fractions were combined and evaporated partially in vacuo and lyophilized overnight to afford 48.6 mg (S)-N-(1-(4-(N-bicyclo[1.1.1]pentan-1-ylsulfamoyl)-3-cyanophenylamino)-1-oxo-3-phenylpropan-2-yl)-4-fluorobenzamide (I-166) as a white solid.

Using this general procedure for the preparation of I-166 and substituting the appropriate amine in the last step, the following compounds were prepared.

TABLE 5

Compounds prepare according to Example 61.

| Compound | Chemical Name | yield | MS | 1HNMR |
|---|---|---|---|---|
| I-166 | (S)-N-(1-(4-(N-bicyclo[1.1.1]pentan-1-ylsulfamoyl)-3-cyanophenylamino)-1-oxo-3-phenylpropan-2-yl)-4-fluorobenzamide | 44% | MS (ESI+, m/z): Calcd for C28H25FN4O4S: 532; found 533 [M + H]+; | $^1$H NMR (300 MHz, CD$_3$OD) δ 8.19 (s, 1H), 8.00 (d, 1H), 7.90-7.82 (m, 3H), 7.34-7.14 (m, 7H), 4.93-4.89 (m, 1H), 3.31-3.15 (m, 2H), 2.30 (s, 1H), 1.83 (s, 6H). |
| I-167 | (S)-N-(1-(4-(N-tert-butylsulfamoyl)-3-cyanophenylamino)-1-oxo-3-phenylpropan-2-yl)-4-fluorobenzamide | 41% | MS (ESI+, m/z): Calcd for C27H27FN4O4S: 522; found 523 [M + H]+ | $^1$H NMR (300 MHz, d$_6$-DMSO) δ 10.87 (s, 1H), 8.92 (d, 1H), 8.24 (s, 1H), 8.03-7.85 (m, 5H), 7.40 (t, 2H), 7.35-7.24 (m, 4H), 7.19-7.14 (m, 1H), 4.86-4.77 (m, 1H), 3.22-3.03 (m, 2H), 1.13 (s, 9H). |

Example 62: N-(4-(N-ethylsulfamoyl)phenyl)-2-(4-fluorobenzamido)-2,3-dihydro-1H-indene-2-carboxamide

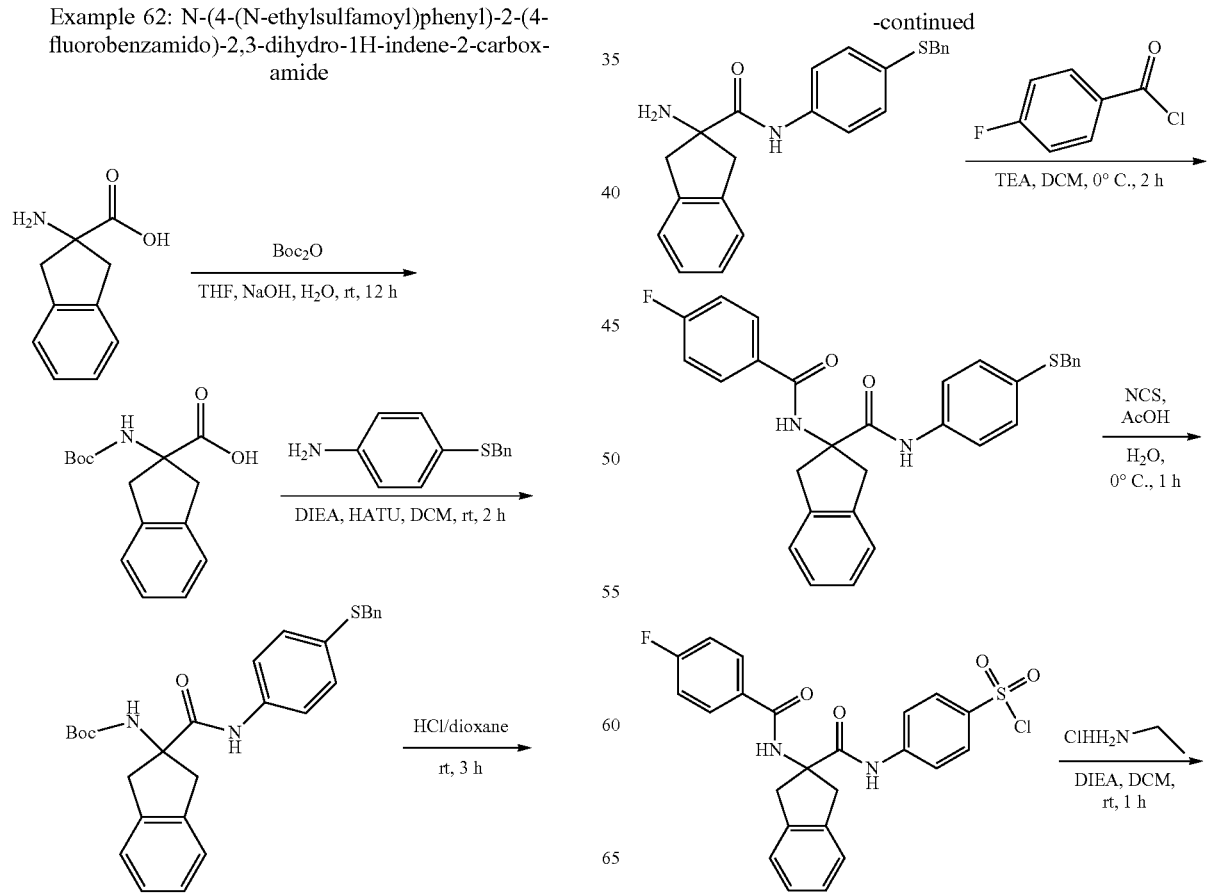

419

-continued

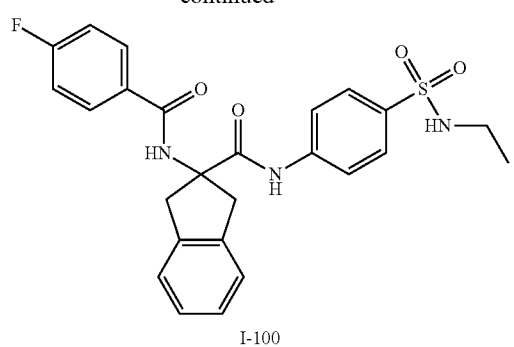

I-100

Preparation of 2-(tert-butoxycarbonylamino)-2,3-dihydro-1H-indene-2-carboxylic Acid

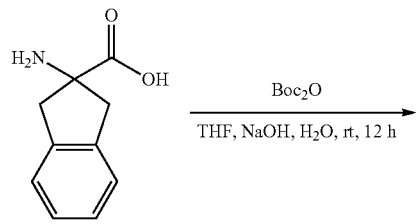

To a solution of 3.54 g 2-amino-2,3-dihydro-1H-indene-2-carboxylic acid (20 mmol, 1.00 equiv) and 1.6 g sodium hydroxide (40 mmol, 2.00 equiv) in 50 mL tetrahydrofuran and 10 mL water was added 8.72 g di-tert-butyl dicarbonate (40 mmol, 2.00 equiv) at room temperature. The resulting mixture was stirred for 12 h at r.t. The mixture was concentrated in vacuo and diluted with 100 mL water. The pH value of the solution was adjusted to 3 with 1N hydrochloric acid. The mixture was extracted with ethyl acetate (3×200 mL). The combined organic layers were washed with brine (1×200 mL), dried over anhydrous magnesium sulfate, filtered and the filtrate was concentrated in vacuo. Purification by column chromatography (silica gel, petroleum ether:ethyl acetate (1:1)) afforded 5.3 g 2-(tert-butoxycarbonylamino)-2,3-dihydro-1H-indene-2-carboxylic acid as a white solid (48% yield). MS (ESI$^+$) m/z 276 [M−H]$^-$.

420

Preparation of tert-butyl 2-(4-(benzylthio)phenylcarbamoyl)-2,3-dihydro-1H-inden-2-ylcarbamate

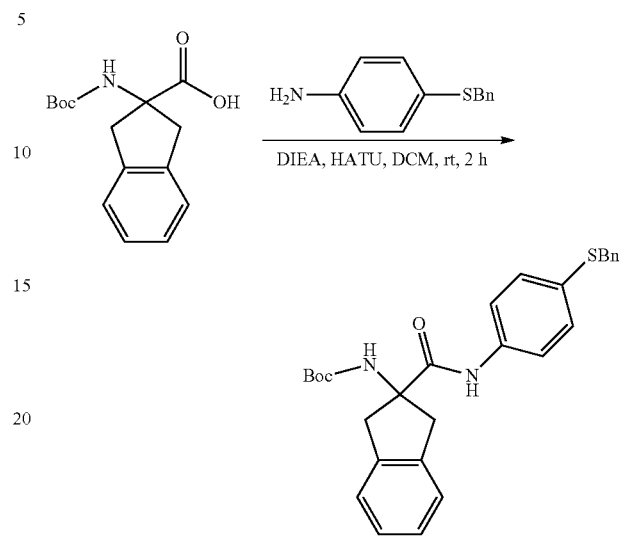

To a solution of 2.15 g 4-(benzylthio)benzenamine (10 mmol, 1.00 equiv) and 2.77 g 2-(tert-butoxycarbonylamino)-2,3-dihydro-1H-indene-2-carboxylic acid (10 mmol, 1.00 equiv) in 50 mL dichloromethane was added 3.87 g DIEA (30 mmol, 3.00 equiv) and 4.56 g HATU (12 mmol, 1.20 equiv) at r.t. The resulting mixture was stirred for 2 h at r.t. The mixture was diluted with 50 mL water and extracted with dichloromethane (3×100 mL). The combined organic layers were washed with brine (1×100 mL), dried over anhydrous magnesium sulfate, filtered and the filtrate concentrated in vacuo. Purification by column chromatography (silica gel, petroleum ether:ethyl acetate (4:1)) provided 2.9 g tert-butyl 2-(4-(benzylthio)phenylcarbamoyl)-2,3-dihydro-1H-inden-2-ylcarbamate as a yellow solid (61% yield). MS (ESI$^+$) m/z 475 [M+H]$^+$.

Preparation of 2-amino-N-(4-(benzylthio)phenyl)-2,3-dihydro-1H-indene-2-carboxamide Hydrochloride

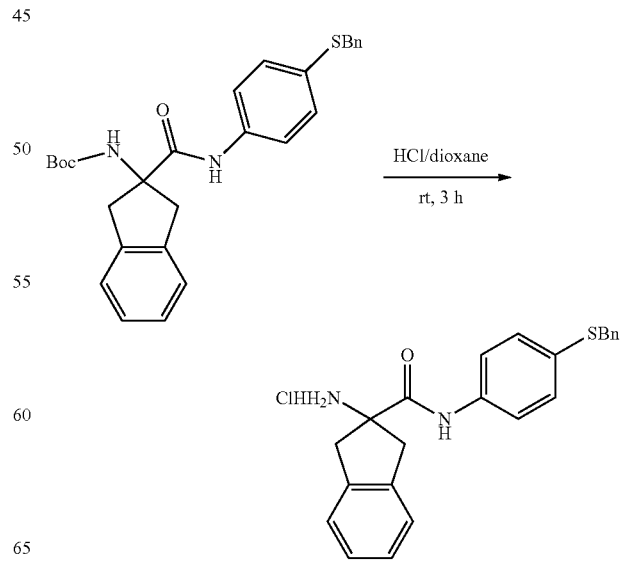

A mixture of 2.9 g tert-butyl 2-(4-(benzylthio)phenylcarbamoyl)-2,3-dihydro-1H-inden-2-ylcarbamate (6.1 mmol, 1.00 equiv) in 30 mL hydrochloric acid in 1,4-dioxane (4.0 M) was stirred at room temperature for 3 h. The mixture was concentrated to afford 2.5 g 2-amino-N-(4-(benzylthio)phenyl)-2,3-dihydro-1H-indene-2-carboxamide hydrochloride as a light yellow solid (100% yield). MS (ESI$^+$) m/z 375 [M+H]$^+$.

Preparation of N-(4-(benzylthio)phenyl)-2-(4-fluorobenzamido)-2,3-dihydro-1H-indene-2-carboxamide

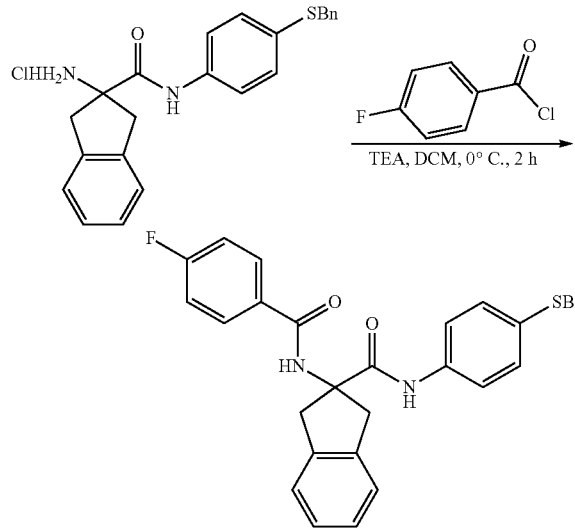

To a solution of 1.29 g 2-amino-N-(4-(benzylthio)phenyl)-2,3-dihydro-1H-indene-2-carboxamide hydrochloride (3.15 mmol, 1.00 equiv) and 1.91 g triethylamine (18.9 mmol, 6.00 equiv) in 20 mL dichloromethane was added dropwise 597.2 mg 4-fluorobenzoyl chloride (3.78 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (2:1)) afforded 1.03 g N-(4-(benzylthio)phenyl)-2-(4-fluorobenzamido)-2,3-dihydro-1H-indene-2-carboxamide as a yellow solid (66% yield). MS (ESI$^+$) m/z 497 [M+H]$^+$.

Preparation of 4-(2-(4-fluorobenzamido)-2,3-dihydro-1H-indene-2-carboxamido)benzene-1-sulfonyl Chloride

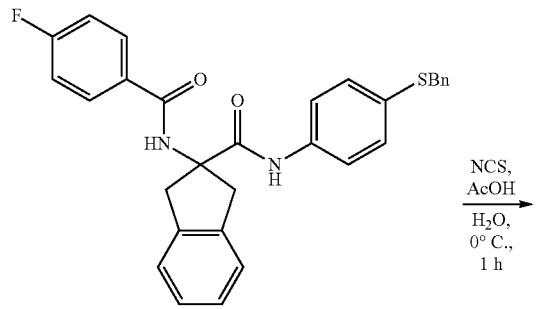

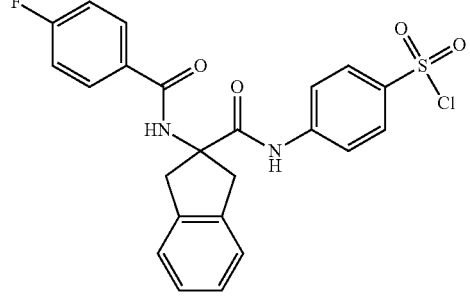

To a solution of 1.03 g N-(4-(benzylthio)phenyl)-2-(4-fluorobenzamido)-2,3-dihydro-1H-indene-2-carboxamide (2.07 mmol, 1.00 equiv) in 9 mL acetic acid and 3 mL water was added 1.1 g N-chlorosuccinimide (8.28 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.64 g 4-(2-(4-fluorobenzamido)-2,3-dihydro-1H-indene-2-carboxamido)benzene-1-sulfonyl chloride as a white solid (65% yield). MS (ESI$^+$) m/z 473 and 475 [M+H]$^+$.

Preparation of N-(4-(N-ethylsulfamoyl)phenyl)-2-(4-fluorobenzamido)-2,3-dihydro-1H-indene-2-carboxamide (I-100)

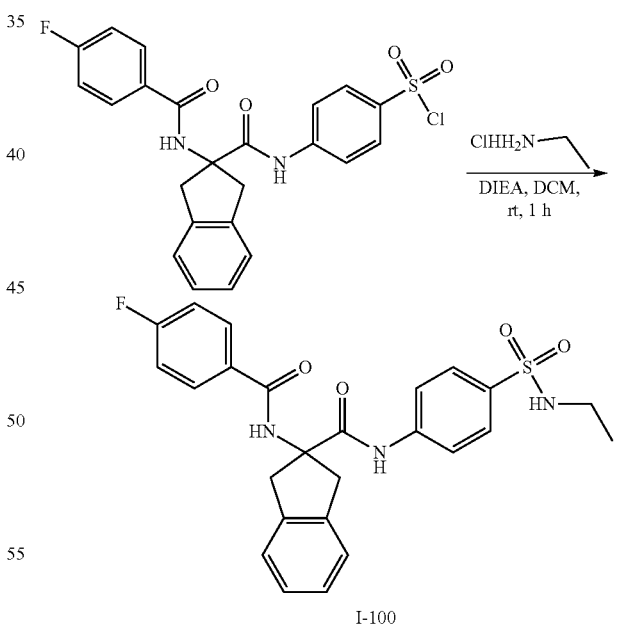

I-100

To a mixture of 85.05 mg ethanamine hydrochloride (1.05 mmol, 5.0 equiv) and 135.45 mg N,N-diisopropylethylamine (1.05 mmol, 5.00 equiv) in 10 mL dichloromethane was added 100 mg 4-(2-(4-fluorobenzamido)-2,3-dihydro-1H-indene-2-carboxamido)benzene-1-sulfonyl chloride (0.21 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (31% ACN up to 52% in 7 min); UV detection at 254/220 nm. The product-containing fractions were combined and evaporated partially in vacuo and lyophilized overnight to afford 43 mg N-(4-(N-ethylsulfamoyl)phenyl)-2-(4-fluorobenzamido)-2,3-dihydro-1H-indene-2-carboxamide (I-100) as a white solid.

Using this general procedure for the preparation of I-100 and substituting the appropriate amine in the last step, the following compounds were prepared.

TABLE 6

Compounds prepared according to Example 62.

| Compound | Chemical Name | yield | MS | 1HNMR |
|---|---|---|---|---|
| I-100 | N-(4-(N-ethylsulfamoyl)phenyl)-2-(4-fluorobenzamido)-2,3-dihydro-1H-indene-2-carboxamide | 42% | MS (ESI$^+$, m/z): Calcd for C25H24FN3O4S: 481; found 482 [M + H]$^+$; | $^1$H NMR (300 MHz, d$_6$-DMSO) δ 10.08 (s, 1H), 8.91 (s, 1H), 8.06-8.01 (m, 2H), 7.81 (d, 2H), 7.69 (d, 2H), 7.39 (t, 1H), 7.33-7.16 (m, 6H), 3.76 (d, 2H), 3.43 (d, 2H), 2.78-2.69 (m, 2H), 0.95 (t, 3H). |
| I-101 | 2-(4-fluorobenzamido)-N-(4-(N-oxetan-3-ylsulfamoyl)phenyl)-2,3-dihydro-1H-indene-2-carboxamide | 41% | MS (ESI$^+$, m/z): Calcd for C26H24FN3O5S: 509; found 510 [M + H]$^+$ | $^1$H NMR (300 MHz, d$_6$-DMSO) δ 10.14 (s, 1H), 8.96 (s, 1H), 8.39 (s, 1H), 8.03 (dd, 2H), 7.81 (d, 2H), 7.69 (d, 2H), 7.33-7.16 (m, 6H), 4.50 (t, 2H), 4.35-4.22 (m, 3H), 3.80 (d, 2H), 3.46 (d, 2H). |
| I-102 | N-(4-(N-bicyclo[1.1.1]pentan-1-ylsulfamoyl)phenyl)-2-(4-fluorobenzamido)-2,3-dihydro-1H-indene-2-carboxamide | 43% | MS (ESI$^+$, m/z): Calcd for C28H26FN3O4S: 519; found 520 [M + H]$^+$; | $^1$H NMR (300 MHz, d$_6$-DMSO) δ 10.11 (s, 1H), 8.94 (s, 1H), 8.44 (s, 1H), 8.03 (dd, 2H), 7.81 (d, 2H), 7.71 (d, 2H), 7.32-7.17 (m, 6H), 3.75 (d, 2H), 3.42 (d, 2H), 3.25 (s, 1H), 1.70 (s, 6H). |
| I-103 | N-(4-(N-cyclopropylsulfamoyl)phenyl)-2-(4-fluorobenzamido)-2,3-dihydro-1H-indene-2-carboxamide | 45% | MS (ESI$^+$, m/z): Calcd for C26H24FN3O4S: 493; found 494 [M + H]$^+$; | $^1$H NMR (300 MHz, d$_6$-DMSO) δ 10.10 (s, 1H), 8.92 (s, 1H), 8.04 (dd, 2H), 7.83 (d, 2H), 7.76-7.70 (m, 3H), 7.33-7.16 (m, 6H), 3.75 (d, 2H), 3.43 (d, 2H), 2.13-2.00 (m, 1H), 0.48-0.37 (m, 4H). |

Example 63: (S)-N-(1-(6-(N-bicyclo[1.1.1]pentan-1-ylsulfamoyl)pyridin-3-ylamino)-1-oxo-3-phenylpropan-2-yl)-4-fluorobenzamide, I-104

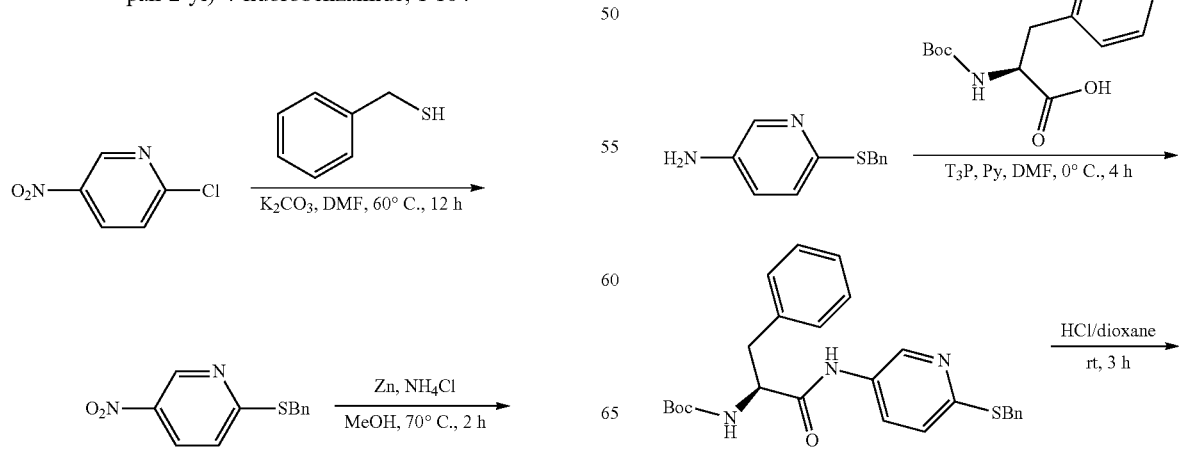

425

-continued

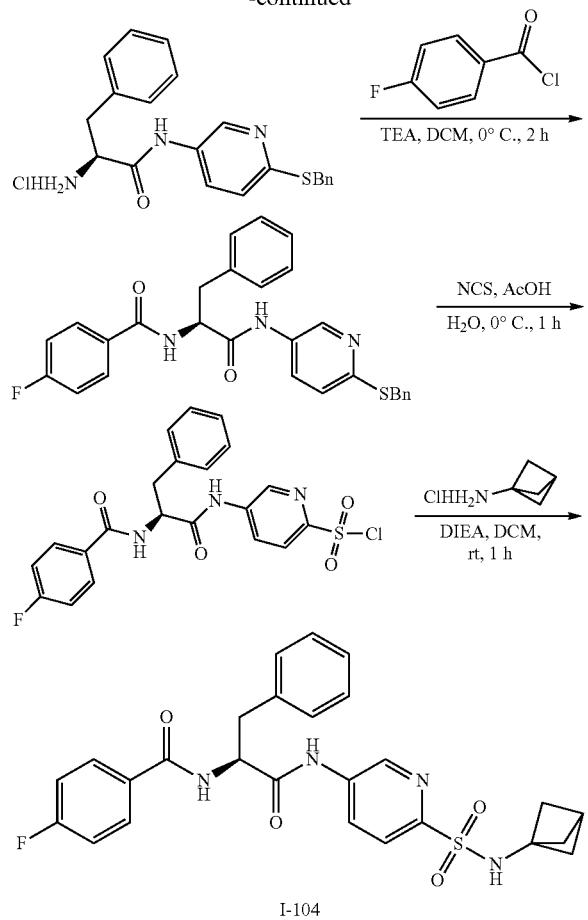

I-104

Preparation of 2-(benzylthio)-5-nitropyridine

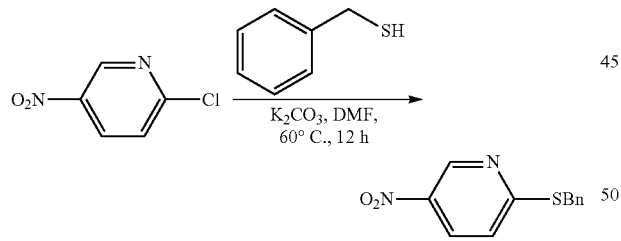

To a solution of 7.9 g 2-chloro-5-nitropyridine (50 mmol, 1.00 equiv) and 13.8 g potassium carbonate (100 mmol, 2.00 equiv) in 300 mL anhydrous N,N-dimethylformamide was added dropwise 7.44 g of phenylmethanethiol (60 mmol, 1.20 equiv) at room temperature. The resulting mixture was stirred for 12 h at 60° C. The mixture was cooled to room temperature, diluted with 500 mL water and extracted with ethyl acetate (3×500 mL). The combined organic layers were washed with brine (3×200 mL), dried over anhydrous magnesium sulfate, filtered and the filtrate was concentrated in vacuo. Purification by column chromatography (silica gel, petroleum ether:ethyl acetate (5:1)) afforded 8.33 g 2-(benzylthio)-5-nitropyridine as a yellow solid (68% yield). MS (ESI$^+$) m/z 247 [M+H]$^+$.

426

Preparation of 6-(benzylthio)pyridin-3-amine

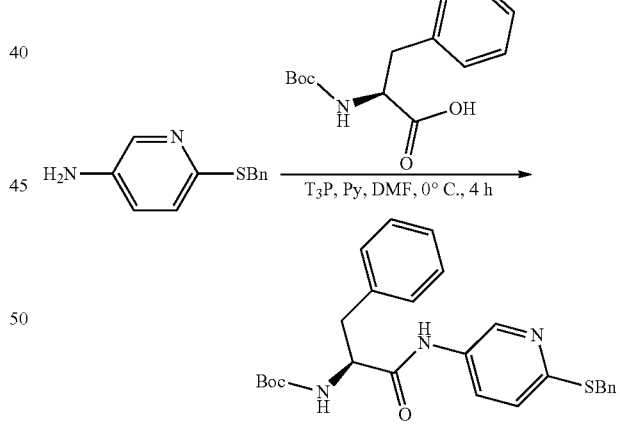

To a solution of 8.33 g 2-(benzylthio)-5-nitropyridine (33.85 mmol, 1.00 equiv) in 200 mL methanol was added 9.05 g ammonium chloride (169.25 mmol, 5.00 equiv) and 8.6 g zinc (135.4 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (2:1)) afforded 3.73 g 6-(benzylthio)pyridin-3-amine as an orange oil (51% yield). MS (ESI$^+$) m/z 217 [M+H]$^+$.

Preparation of (S)-tert-butyl 1-(6-(benzylthio)pyridin-3-ylamino)-1-oxo-3-phenylpropan-2-ylcarbamate To a solution of 2.16 g 6-(benzylthio)pyridin-3-amine (10 mmol, 1.00 equiv), 2.65 g (S)-2-(tert-butoxycarbonylamino)-3-phenylpropanoic acid (10 mmol, 1.00 equiv) and 7.9 g pyridine (100 mmol, 10.00 equiv) in 30 mL N,N-dimethylformamide was added dropwise a solution 25.8 g propanephosphonic acid cyclic anhydride in ethyl acetate (50%, 50 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (1:1)) provided 2.92 g (S)-tert-butyl 1-(6-(benzylthio)pyridin-3-ylamino)-1-oxo-3-phenylpropan-2-ylcarbamate as a yellow solid (63% yield). MS (ESI+) m/z 464 [M+H]+.

Preparation of (S)-2-amino-N-(6-(benzylthio)pyridin-3-yl)-3-phenylpropanamide Hydrochloride

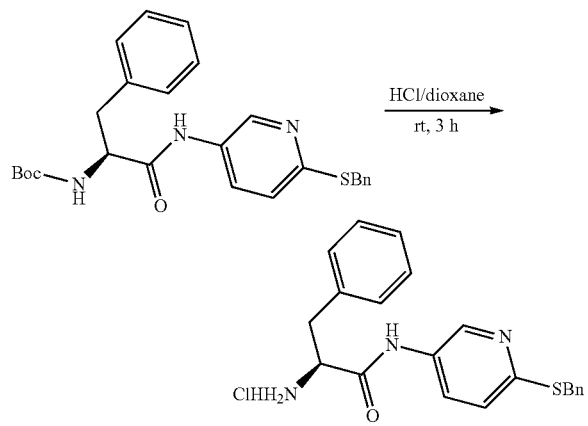

A mixture of 2.92 g (S)-tert-butyl 1-(6-(benzylthio)pyridin-3-ylamino)-1-oxo-3-phenylpropan-2-ylcarbamate (6.3 mmol, 1.00 equiv) in 30 mL hydrochloric acid in 1,4-dioxane (4.0 M) was stirred at room temperature for 3 h. The mixture was concentrated to afford 2.52 g (S)-2-amino-N-(6-(benzylthio)pyridin-3-yl)-3-phenylpropanamide hydrochloride as a light yellow solid (100% yield). MS (ESI+) m/z 364 [M+H]+.

Preparation of (S)-N-(1-(6-(benzylthio)pyridin-3-ylamino)-1-oxo-3-phenylpropan-2-yl)-4-fluorobenzamide

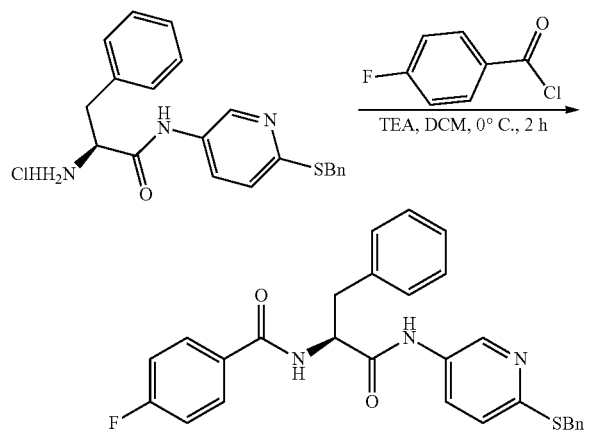

To a solution of 1.26 g (S)-2-amino-N-(6-(benzylthio)pyridin-3-yl)-3-phenylpropanamide hydrochloride (3.15 mmol, 1.00 equiv) and 1.91 g triethylamine (18.9 mmol, 6.00 equiv) in 20 mL dichloromethane was added dropwise 597.2 mg 4-fluorobenzoyl chloride (3.78 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1.08 g (S)-N-(1-(6-(benzylthio)pyridin-3-ylamino)-1-oxo-3-phenylpropan-2-yl)-4-fluorobenzamide as a yellow solid (71% yield). MS (ESI+) m/z 486 [M+H]+.

Preparation of (S)-5-(2-(4-fluorobenzamido)-3-phenylpropanamido)pyridine-2-sulfonyl Chloride

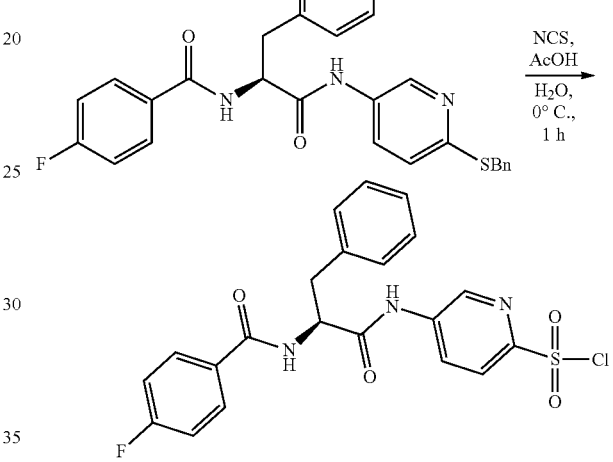

To a solution of 1.08 g (S)-N-(1-(6-(benzylthio)pyridin-3-ylamino)-1-oxo-3-phenylpropan-2-yl)-4-fluorobenzamide (2.23 mmol, 1.00 equiv) in 9 mL acetic acid and 3 mL water was added 1.19 g N-chlorosuccinimide (8.92 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.67 g (S)-5-(2-(4-fluorobenzamido)-3-phenylpropanamido)pyridine-2-sulfonyl chloride as a white solid (65% yield). MS (ESI+) m/z 462 and 464 [M+H]+.

Preparation of (S)-N-(1-(6-(N-bicyclo[1.1.1]pentan-1-ylsulfamoyl)pyridin-3-ylamino)-1-oxo-3-phenylpropan-2-yl)-4-fluorobenzamide (I-104)

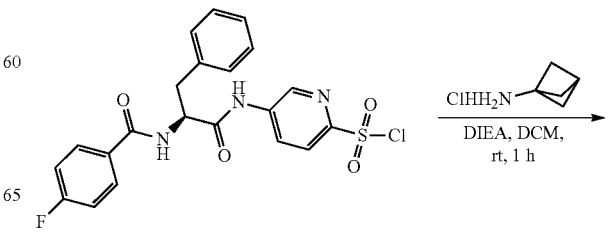

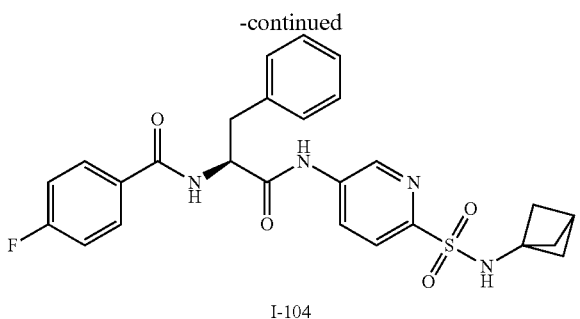

I-104

To a mixture of 132 mg bicyclo[1.1.1]pentan-1-amine hydrochloride (1.1 mmol, 5.0 equiv) and 141.9 mg N,N-diisopropylethylamine (1.1 mmol, 5.00 equiv) in 10 mL dichloromethane was added 100 mg (S)-5-(2-(4-fluorobenzamido)-3-phenylpropanamido)pyridine-2-sulfonyl chloride (0.22 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (28% ACN up to 55% in 7 min); UV detection at 254/220 nm. The product-containing fractions were combined and evaporated partially in vacuo and lyophilized overnight to afford 42.9 mg (S)-N-(1-(6-(N-bicyclo[1.1.1]pentan-1-ylsulfamoyl)pyridin-3-ylamino)-1-oxo-3-phenylpropan-2-yl)-4-fluorobenzamide (I-104) as a white solid.

Using this general procedure for the preparation of I-104 and substituting the appropriate amine in the last step, the following compounds were prepared.

TABLE 7

Compounds prepared according to Example 63.

| Compound | Chemical Name | Yield | MS | 1H NMR |
| --- | --- | --- | --- | --- |
| I-104 | (S)-N-(1-(6-(N-bicyclo[1.1.1]pentan-1-ylsulfamoyl)pyridin-3-ylamino)-1-oxo-3-phenylpropan-2-yl)-4-fluorobenzamide | 38% | MS (ESI$^+$, m/z): Calcd for C26H25FN4O4S: 508; found 509 [M + H]$^+$; | $^1$H NMR (400 MHz, d$_6$-DMSO) δ 10.83 (s, 1H), 8.93 (d, 1H), 8.88 (s, 1H), 8.73 (br s, 1H), 8.30 (d, 1H), 7.96-7.90 (m, 3H), 7.41-7.17 (m, 7H), 4.88-4.82 (m, 1H), 3.22-3.09 (m, 2H), 2.25 (s, 1H), 1.69 (s, 6H). |
| I-105 | (S)-N-(1-(6-(N-ethylsulfamoyl)pyridin-3-ylamino)-1-oxo-3-phenylpropan-2-yl)-4-fluorobenzamide | 36% | MS (ESI$^+$, m/z): Calcd for C23H23FN4O4S: 470; found 471 [M + H]$^+$ | $^1$H NMR (300 MHz, d$_6$-DMSO) δ 10.82 (s, 1H), 8.92 (d, 1H), 8.86 (s, 1H), 8.28 (dd, 1H), 7.93-7.89 (m, 3H), 7.69 (t, 1H), 7.41-7.12 (m, 7H), 4.91-4.84 (m, 1H), 3.24-3.08 (m, 2H), 2.94 (q, 2H), 0.98 (t, 3H). |
| I-106 | (S)-4-fluoro-N-(1-(6-(N-oxetan-3-ylsulfamoyl)pyridin-3-ylamino)-1-oxo-3-phenylpropan-2-yl)benzamide | 39% | MS (ESI$^+$, mz): Calcd for C24H23FN4O5S: 498; found 499 [M + H]$^+$; | $^1$H NMR (400 MHz, d$_6$-DMSO) δ 8.94 (d, 1H), 8.84 (s, 1H), 8.30 (dd, 1H), 7.93-7.90 (m, 3H), 7.40 (d, 2H), 7.33-7.27 (m, 4H), 7.19 (t, 1H), 4.87-4.82 (m, 1H), 4.58-4.50 (m, 3H), 4.34 (t, 2H), 3.21-3.08 (m, 2H). |
| I-107 | (S)-4-fluoro-N-(1-oxo-3-phenyl-1-(6-(N-(tetrahydro-2H-pyran-4-yl)sulfamoyl)pyridin-3-ylamino)propan-2-yl)benzamide | 38% | MS (ESI$^+$, m/z): Calcd for C26H27FN4O5S: 526; found 527 [M + H]$^+$; | $^1$H NMR (300 MHz, CD$_3$OD) δ 8.78 (s, 1H), 8.27 (d, 1H), 7.94 (dd, 1H), 7.88-7.85 (m, 2H), 7.35-7.16 (m, 7H), 4.96-4.90 (m, 1H), 3.91-3.83 (m, 2H), 3.52-3.35 (m, 3H), 3.28-3.15 (m, 2H), 1.78-1.70 (m, 2H), 1.62-1.45 (m, 2H). |
| I-108 | (S)-4-fluoro-N-(1-(6-(N-(2-methoxyethyl)sulfamoyl)pyridin-3-ylamino)-1-oxo-3-phenylpropan-2-yl)benzamide | 35% | MS (ESI$^+$, m/z): Calcd for C24H25FN4O5S: 500; found 501 [M + H]$^+$; | $^1$H NMR (400 MHz, CD$_3$OD) δ 8.77 (s, 1H), 8.26 (dd, 1H), 7.93 (d, 1H), 7.89-7.85 (m, 2H), 7.35-7.18 (m, 7H), 4.96-4.90 (m, 1H), 3.42-3.39 (m, 2H), 3.33-3.15 (m, 7H). |
| I-109 | (S)-N-(1-(6-(N-(2-(dimethylamino)ethyl)sulfamoyl)pyridin-3-ylamino)-1-oxo-3-phenylpropan-2-yl)-4-fluorobenzamide formate | 32% | MS (ESI$^+$, m/z): Calcd for C25H28FN5O4S: 513; found 514 [M + H]$^+$; | $^1$H NMR (300 MHz, CD$_3$OD) δ 8.81 (s, 1H), 8.52 (s, 0.8 H, HCOOH), 8.25 (dd, 1H), 7.95 (d, 1H), 7.90-7.84 (m, 2H), 7.35-7.15 (m, 7H), 4.96-4.90 (m, 1H), 3.30-3.20 (m, 4H), 2.73 (t, 2H), 2.47 (s, 6H). |
| I-110 | (S)-4-fluoro-N-(1-(6-(N-(2-hydroxyethyl) | 33% | MS (ESI$^+$, m/z): Calcd for C23H23FN4O5S: | $^1$H NMR (300 MHz, CD$_3$OD) δ 8.78 (s, 1H), 8.26 (dd, 1H), 7.94 (d, 1H), |

TABLE 7-continued

Compounds prepared according to Example 63.

| Compound | Chemical Name | Yield | MS | 1H NMR |
|---|---|---|---|---|
| | sulfamoyl)pyridin-3-ylamino)-1-oxo-3-phenylpropan-2-yl)benzamide | | 486; found 487 [M + H]⁺; | 7.88-7.82 (m, 2H), 7.35-7.14 (m, 7H), 4.96-4.90 (m, 1H), 3.56 (t, 2H), 3.32-3.18 (m, 2H), 3.13 (t, 2H). |
| I-111 | (S)-4-fluoro-N-(1-(6-(N-(2-morpholinoethyl)sulfamoyl)pyridin-3-ylamino)-1-oxo-3-phenylpropan-2-yl)benzamide | 35% | MS (ESI⁺, m/z): Calcd for C27H30FN5O5S: 555; found 556 [M + H]⁺; | ¹H NMR (400 MHz, CD₃OD) δ 8.78 (s, 1H), 8.25 (dd, 1H), 7.95 (d, 1H), 7.88-7.84 (m, 2H), 7.35-7.16 (m, 7H), 4.96-4.90 (m, 1H), 3.70-3.65 (m, 4H), 3.32-3.18 (m, 2H), 3.15 (t, 2H), 2.53-2.45 (m, 6H). |
| I-112 | (S)-4-fluoro-N-(1-(6-(N-(3-morpholinopropyl)sulfamoyl)pyridin-3-ylamino)-1-oxo-3-phenylpropan-2-yl)benzamide | 34% | MS (ESI⁺, m/z): Calcd for C28H32FN5O5S: 569; found 570 [M + H]⁺; | ¹H NMR (300 MHz, CD₃OD) δ 8.80 (s, 1H), 8.25 (dd, 1H), 7.94 (d, 1H), 7.89-7.84 (m, 2H), 7.35-7.17 (m, 7H), 4.96-4.90 (m, 1H), 3.72-3.68 (m, 4H), 3.32-3.18 (m, 2H), 3.08 (t, 2H), 2.58-2.42 (m, 6H), 1.76-1.63 (m, 2H). |
| I-113 | (S)-4-fluoro-N-(1-(6-(N-(1-methoxy-2-methylpropan-2-yl)sulfamoyl)pyridin-3-ylamino)-1-oxo-3-phenylpropan-2-yl)benzamide | 37% | MS (ESI⁺, m/z): Calcd for C26H29FN4O5S: 528; found 529 [M + H]⁺; | ¹H NMR (300 MHz, CD₃OD) δ 8.75 (s, 1H), 8.24 (dd, 1H), 7.95 (d, 1H), 7.88-7.84 (m, 2H), 7.35-7.16 (m, 7H), 4.96-4.90 (m, 1H), 3.32-3.16 (m, 7H), 1.17 (s, 6H). |
| I-114 | (S)-N-(1-(6-(N-(2-tert-butoxyethyl)sulfamoyl)pyridin-3-ylamino)-1-oxo-3-phenylpropan-2-yl)-4-fluorobenzamide | 38% | MS (ESI⁺, m/z): Calcd for C27H31FN4O5S: 542; found 543 [M + H]⁺; | ¹H NMR (300 MHz, CD₃OD) δ 8.77 (s, 1H), 8.26 (dd, 1H), 7.94 (d, 1H), 7.89-7.84 (m, 2H), 7.35-7.16 (m, 7H), 4.96-4.90 (m, 1H), 3.40 (t, 2H), 3.32-3.18 (m, 2H), 3.16 (t, 2H), 1.12 (s, 9H). |
| I-115 | (S)-4-fluoro-N-(1-(6-(N-(3-methyloxetan-3-yl)sulfamoyl)pyridin-3-ylamino)-1-oxo-3-phenylpropan-2-yl)benzamide | 35% | MS (ESI⁺, m/z): Calcd for C25H25FN4O5S: 512; found 513 [M + H]⁺; | ¹H NMR (300 MHz, CD₃OD) δ 8.77 (s, 1H), 8.25 (dd, 1H), 7.94 (d, 1H), 7.88-7.82 (m, 2H), 7.35-7.15 (m, 7H), 4.96-4.90 (m, 1H), 4.78 (d, 2H), 4.25 (d, 2H), 3.32-3.18 (m, 2H), 1.54 (s, 3H). |
| I-116 | (S)-4-fluoro-N-(1-(6-(N-(1-hydroxy-2-methylpropan-2-yl)sulfamoyl)pyridin-3-ylamino)-1-oxo-3-phenylpropan-2-yl)benzamide | 36% | MS (ESI⁺, m/z): Calcd for C25H27FN4O5S: 514; found 515 [M + H]⁺; | ¹H NMR (400 MHz, CD₃OD) δ 8.78 (s, 1H), 8.26 (dd, 1H), 7.98 (d, 1H), 7.89-7.84 (m, 2H), 7.35-7.17 (m, 7H), 4.96-4.90 (m, 1H), 3.42 (s, 2H), 3.32-3.18 (m, 2H), 1.15 (s, 6H). |
| I-176 | (S)-N-(1-(6-(N-(2-cyanopropan-2-yl)sulfamoyl)pyridin-3-ylamino)-1-oxo-3-phenylpropan-2-yl)-4-fluorobenzamide | 38% | MS (ESI⁺, m/z): Calcd for C25H24FN5O4S: 509; found 510 [M + H]⁺; | ¹H NMR (400 MHz, CD₃OD) δ 8.83 (s, 1H), 8.29 (dd, 1H), 8.01 (dd, 1H), 7.88-7.85 (m, 2H), 7.35-7.17 (m, 7H), 4.97-4.93 (m, 1H), 3.31-3.15 (m, 2H), 1.64 (s, 6H). |
| I-177 | (S)-4-fluoro-N-(1-(6-(N-(2-methylbut-3-yn-2-yl)sulfamoyl)pyridin-3-ylamino)-1-oxo-3-phenylpropan-2-yl)benzamide | 39% | MS (ESI⁺, m/z): Calcd for C26H25FN4O4S: 508; found 509 [M + H]⁺ | ¹H NMR (300 MHz, CD₃OD) δ 8.76 (s, 1H), 8.24 (dd, 1H), 7.98 (d, 1H), 7.89-7.84 (m, 2H), 7.36-7.17 (m, 7H), 4.96-4.91 (m, 1H), 3.31-3.15 (m, 2H), 2.34 (s, 1H), 1.54 (s, 6H). |
| I-178 | 4-fluoro-N-((S)-1-oxo-3-phenyl-1-(6-(N-((S)-tetrahydrofuran-3-yl)sulfamoyl)pyridin- | 36% | MS (ESI⁺, m/z): Calcd for C25H25FN4O5S: 512; found 513 [M + H]⁺; | ¹H NMR (300 MHz, CD₃OD) δ 8.77 (s, 1H), 8.26 (dd, 1H), 7.93 (d, 1H), 7.87-7.82 (m, 2H), 7.34-7.15 (m, 7H), 4.94-4.89 |

TABLE 7-continued

Compounds prepared according to Example 63.

| Compound | Chemical Name | Yield | MS | 1H NMR |
|---|---|---|---|---|
| | 3-ylamino)propan-2-yl)benzamide | | | (m, 1H), 4.08-4.00 (m, 1H), 3.88-3.68 (m, 3H), 3.50 (dd, 1H), 3.31-3.15 (m, 2H), 2.16-2.00 (m, 1H), 1.83-1.70 (m, 1H). |
| I-179 | 4-fluoro-N-((S)-1-oxo-3-phenyl-1-(6-(N-((R)-tetrahydrofuran-3-yl)sulfamoyl)pyridin-3-ylamino)propan-2-yl)benzamide | 41% | MS (ESI$^+$, m/z): Calcd for C25H25FN4O5S: 512; found 513 [M + H]$^+$; | $^1$H NMR (300 MHz, CD$_3$OD) δ 8.77 (s, 1H), 8.25 (dd, 1H), 7.93 (d, 1H), 7.87-7.82 (m, 2H), 7.34-7.15 (m, 7H), 4.94-4.89 (m, 1H), 4.10-4.01 (m, 1H), 3.87-3.69 (m, 3H), 3.51 (dd, 1H), 3.31-3.13 (m, 2H), 2.16-2.00 (m, 1H), 1.82-1.71 (m, 1H). |

Example 64: (S)-N-(1-(5-(N-ethylsulfamoyl)pyridin-2-ylamino)-1-oxo-3-phenylpropan-2-yl)-4-fluorobenzamide, I-117

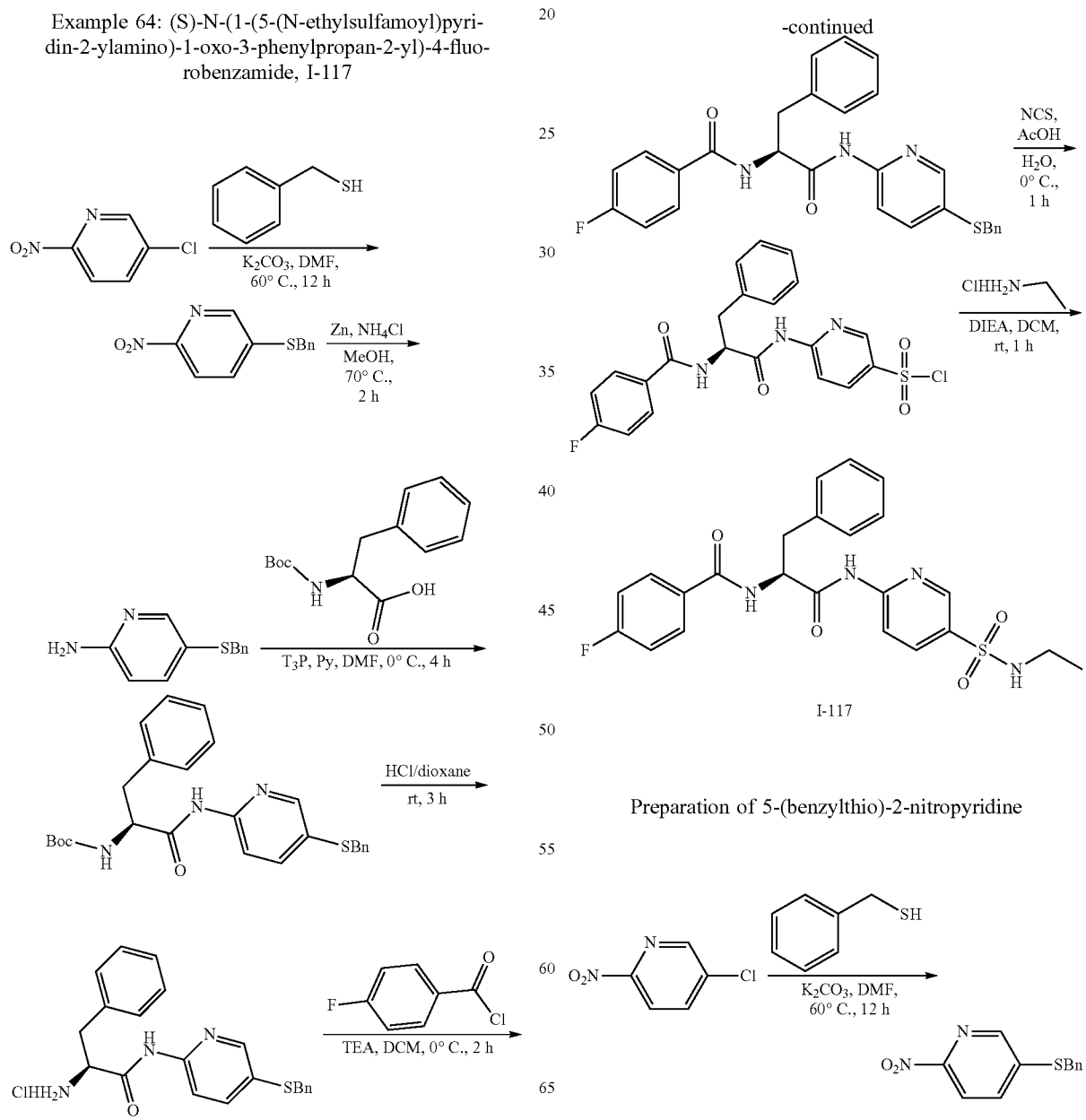

Preparation of 5-(benzylthio)-2-nitropyridine

To a solution of 7.9 g 5-chloro-2-nitropyridine (50 mmol, 1.00 equiv) and 13.8 g potassium carbonate (100 mmol, 2.00 equiv) in 300 mL anhydrous N,N-dimethylformamide was added dropwise 7.44 g of phenylmethanethiol (60 mmol, 1.20 equiv) at room temperature. The resulting mixture was stirred for 12 h at 60° C. The mixture was cooled to room temperature, diluted with 500 mL water and extracted with ethyl acetate (3×500 mL). The combined organic layers were washed with brine (3×200 mL), dried over anhydrous magnesium sulfate, filtered and the filtrate was concentrated in vacuo. Purification by column chromatography (silica gel, petroleum ether:ethyl acetate (5:1)) afforded 8 g 5-(benzylthio)-2-nitropyridine as a yellow solid (65% yield). MS (ESI$^+$) m/z 247 [M+H]$^+$.

Preparation of 5-(benzylthio)pyridin-2-amine

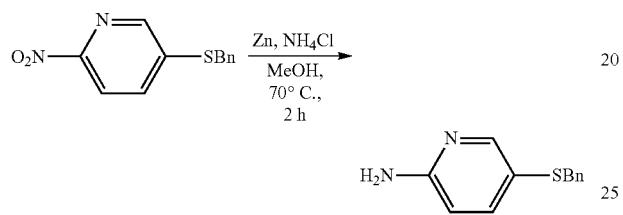

To a solution of 8 g 5-(benzylthio)-2-nitropyridine (32.52 mmol, 1.00 equiv) in 200 mL methanol was added 8.7 g ammonium chloride (162.6 mmol, 5.00 equiv) and 8.26 g zinc (130.08 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (2:1)) afforded 3.52 g 5-(benzylthio)pyridin-2-amine as an orange oil (50% yield). MS (ESI$^+$) m/z 217 [M+H]$^+$.

Preparation of (S)-tert-butyl 1-(5-(benzylthio)pyridin-2-ylamino)-1-oxo-3-phenylpropan-2-ylcarbamate

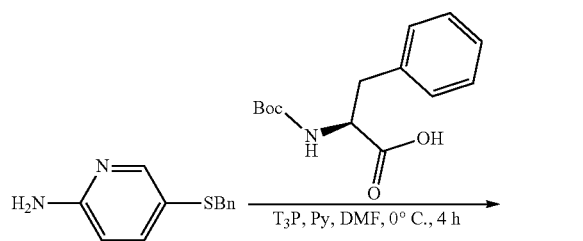

To a solution of 2.16 g 5-(benzylthio)pyridin-2-amine (10 mmol, 1.00 equiv), 2.65 g (S)-2-(tert-butoxycarbonylamino)-3-phenylpropanoic acid (10 mmol, 1.00 equiv) and 7.9 g pyridine (100 mmol, 10.00 equiv) in 30 mL N,N-dimethylformamide was added dropwise a solution 25.8 g propanephosphonic acid cyclic anhydride in ethyl acetate (50%, 50 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (1:1)) provided 2.83 g (S)-tert-butyl 1-(5-(benzylthio)pyridin-2-ylamino)-1-oxo-3-phenylpropan-2-ylcarbamate as a yellow solid (61% yield). MS (ESI$^+$) m/z 464 [M+H]$^+$.

Preparation of (S)-2-amino-N-(5-(benzylthio)pyridin-2-yl)-3-phenylpropanamide Hydrochloride

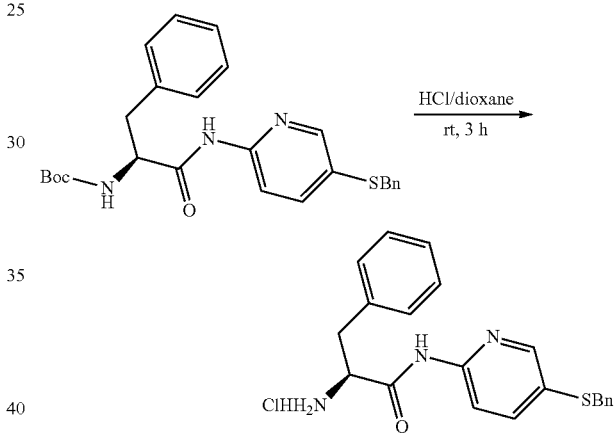

A mixture of 2.83 g (S)-tert-butyl 1-(5-(benzylthio)pyridin-2-ylamino)-1-oxo-3-phenylpropan-2-ylcarbamate (6.11 mmol, 1.00 equiv) in 30 mL hydrochloric acid in 1,4-dioxane (4.0 M) was stirred at room temperature for 3 h. The mixture was concentrated to afford 2.45 g (S)-2-amino-N-(5-(benzylthio)pyridin-2-yl)-3-phenylpropanamide hydrochloride as a light yellow solid (100% yield). MS (ESI$^+$) m/z 364 [M+H]$^+$.

Preparation of (S)-N-(1-(5-(benzylthio)pyridin-2-ylamino)-1-oxo-3-phenylpropan-2-yl)-4-fluorobenzamide

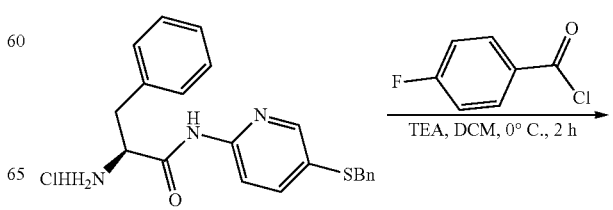

-continued

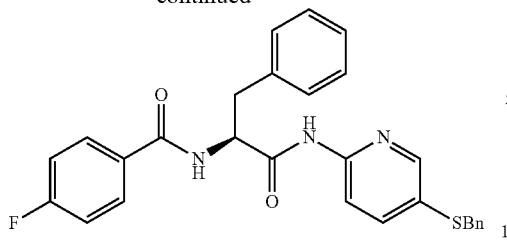

To a solution of 1.26 g (S)-2-amino-N-(5-(benzylthio)pyridin-2-yl)-3-phenylpropanamide hydrochloride (3.15 mmol, 1.00 equiv) and 1.91 g triethylamine (18.9 mmol, 6.00 equiv) in 20 mL dichloromethane was added dropwise 597.2 mg 4-fluorobenzoyl chloride (3.78 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1 g (S)-N-(1-(5-(benzylthio)pyridin-2-ylamino)-1-oxo-3-phenylpropan-2-yl)-4-fluorobenzamide as a yellow solid (66% yield). MS (ESI$^+$) m/z 486 [M+H]$^+$.

Preparation of (S)-6-(2-(4-fluorobenzamido)-3-phenylpropanamido)pyridine-3-sulfonyl Chloride

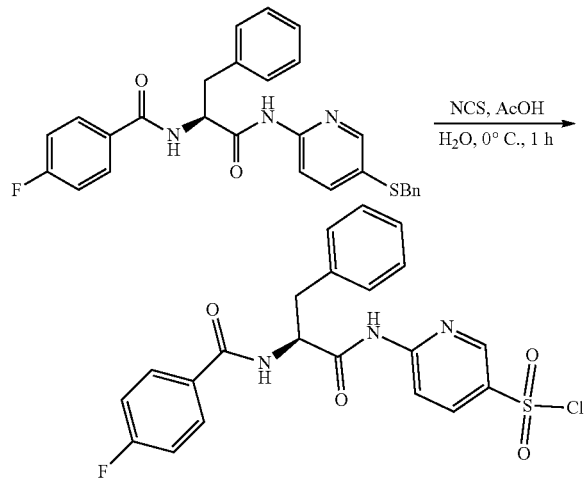

To a solution of 1 g (S)-N-(1-(5-(benzylthio)pyridin-2-ylamino)-1-oxo-3-phenylpropan-2-yl)-4-fluorobenzamide (2.06 mmol, 1.00 equiv) in 9 mL acetic acid and 3 mL water was added 1.1 g N-chlorosuccinimide (8.24 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.62 g (S)-6-(2-(4-fluorobenzamido)-3-phenylpropanamido)pyridine-3-sulfonyl chloride as a white solid (65% yield). MS (ESI$^+$) m/z 462 and 464 [M+H]$^+$.

Preparation of (S)-N-(1-(5-(N-ethylsulfamoyl)pyridin-2-ylamino)-1-oxo-3-phenylpropan-2-yl)-4-fluorobenzamide (I-117)

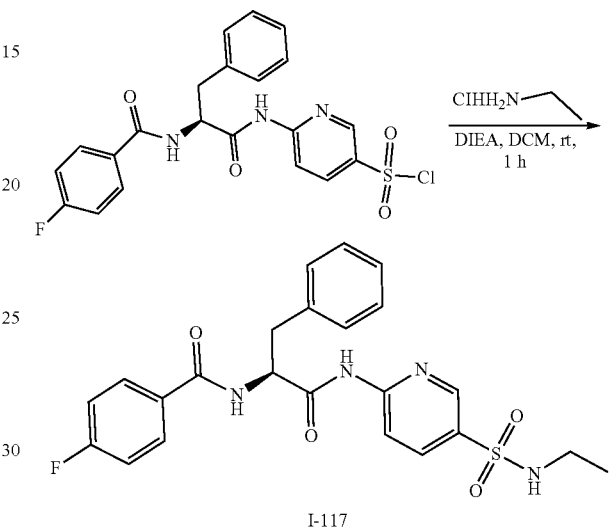

I-117

To a mixture of 89.1 mg ethanamine hydrochloride (1.1 mmol, 5.0 equiv) and 141.9 mg N,N-diisopropylethylamine (1.1 mmol, 5.00 equiv) in 10 mL dichloromethane was added 100 mg (S)-6-(2-(4-fluorobenzamido)-3-phenylpropanamido)pyridine-3-sulfonyl chloride (0.22 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (35% ACN up to 58% in 7 min); UV detection at 254/220 nm. The product-containing fractions were combined and evaporated partially in vacuo and lyophilized overnight to afford 47.5 mg (S)-N-(1-(5-(N-ethylsulfamoyl)pyridin-2-ylamino)-1-oxo-3-phenylpropan-2-yl)-4-fluorobenzamide (I-117) as a white solid.

Using this general procedure for the preparation of I-117 and substituting the appropriate amine in the last step, the following compounds were prepared.

TABLE 8

Compounds prepared according to Example 64.

| Compound | Chemical Name | Yield | MS | 1HNMR |
|---|---|---|---|---|
| I-117 | (S)-N-(1-(5-(N-ethylsulfamoyl)pyridin-2-ylamino)-1-oxo-3-phenylpropan-2-yl)-4-fluorobenzamide | 46% | MS (ESI$^+$, m/z): Calcd for C23H23FN4O4S: 470; found 471 [M + H]$^+$; | $^1$H NMR (300 MHz, d$_6$-DMSO) δ 11.37 (s, 1H), 8.83 (d, 1H), 8.71 (s, 1H), 8.27 (d, 1H), 8.18 (d, 1H), 7.90-7.83 (m, 2H), 7.67 (t, 1H), 7.50-7.43 (m, 2H), 7.33-7.16 |

TABLE 8-continued

Compounds prepared according to Example 64.

| Compound | Chemical Name | Yield | MS | 1HNMR |
|---|---|---|---|---|
| | | | | (m, 5H), 5.00-4.93 (m, 1H), 3.23-3.03 (m, 2H), 2.85 (q, 2H), 1.00 (t, 3H). |
| I-118 | (S)-N-(1-(5-(N-bicyclo[1.1.1]pentan-1-ylsulfamoyl)pyridin-2-ylamino)-1-oxo-3-phenylpropan-2-yl)-4-fluorobenzamide | 41% | MS (ESI+, m/z): Calcd for C26H25FN4O4S: 508; found 509 [M + H]+ | $^1$H NMR (400 MHz, d$_6$-DMSO) δ 11.38 (s, 1H), 8.85 (d, 1H), 8.72 (s, 1H), 8.28 (d, 1H), 8.18 (d, 1H), 7.90-7.83 (m, 2H), 7.54-7.46 (m, 2H), 7.35-7.16 (m, 5H), 5.00-4.93 (m, 1H), 3.23-3.03 (m, 2H), 2.31 (s, 1H), 1.75 (s, 6H). |
| I-119 | (S)-4-fluoro-N-(1-(5-(N-oxetan-3-ylsulfamoyl)pyridin-2-ylamino)-1-oxo-3-phenylpropan-2-yl)benzamide | 43% | MS (ESI+, m/z): Calcd for C24H23FN4O5S: 498; found 499 [M + H]+; | $^1$H NMR (300 MHz, d$_6$-DMSO) δ 11.32 (br s, 1H), 8.85 (d, 1H), 8.72-8.34 (m, 2H), 8.30-8.24 (m, 1H), 8.22-8.15 (m, 1H), 7.94-7.85 (m, 2H), 7.50-7.43 (m, 2H), 7.33-7.16 (m, 5H), 5.00-4.93 (m, 1H), 4.58-4.40 (m, 3H), 4.29 (t, 2H), 3.30-3.09 (m, 2H). |
| I-120 | (S)-4-fluoro-N-(1-(5-(N-(2-methoxyethyl)sulfamoyl)pyridin-2-ylamino)-1-oxo-3-phenylpropan-2-yl)benzamide | 45% | MS (ESI+, m/z): Calcd for C24H25FN4O5S: 500; found 501 [M + H]+; | $^1$H NMR (300 MHz, CD$_3$OD) δ 8.70 (s, 1H), 8.29 (d, 1H), 8.15 (dd, 1H), 7.90-7.80 (m, 2H), 7.44-7.14 (m, 7H), 5.07-5.02 (m, 1H), 3.38 (t, 2H), 3.23 (s, 3H), 3.20-3.00 (m, 4H). |
| I-121 | (S)-4-fluoro-N-(1-(5-(N-(2-hydroxyethyl)sulfamoyl)pyridin-2-ylamino)-1-oxo-3-phenylpropan-2-yl)benzamide | 44% | MS (ESI+, m/z): Calcd for C23H23FN4O5S: 486; found 487 [M + H]+; | $^1$H NMR (400 MHz, CD$_3$OD) δ 8.72 (s, 1H), 8.32 (d, 1H), 8.18 (dd, 1H), 7.85-7.82 (m, 2H), 7.37-7.17 (m, 7H), 5.07-5.03 (m, 1H), 3.57 (t, 2H), 3.38-3.33 (m, 1H), 3.22-3.15 (m, 1H), 3.02 (t, 2H). |
| I-122 | (S)-4-fluoro-N-(1-(5-(N-(2-morpholinoethyl)sulfamoyl)pyridin-2-ylamino)-1-oxo-3-phenylpropan-2-yl)benzamide | 43% | MS (ESI+, m/z): Calcd for C27H30FN5O5S: 555; found 556 [M + H]+; | $^1$H NMR (300 MHz, CD$_3$OD) δ 8.72 (s, 1H), 8.31 (d, 1H), 8.17 (dd, 1H), 7.86-7.79 (m, 2H), 7.44-7.13 (m, 7H), 5.06-5.01 (m, 1H), 3.66-3.58 (m, 4H), 3.40-3.33 (m, 1H), 3.22-3.10 (m, 1H), 3.07 (t, 2H), 2.50-2.41 (m, 6H). |
| I-123 | (S)-4-fluoro-N-(1-(5-(N-(3-morpholinopropyl)sulfamoyl)pyridin-2-ylamino)-1-oxo-3-phenylpropan-2-yl)benzamide | 46% | MS (ESI+, m/z): Calcd for C28H32FN5O5S: 569; found 570 [M + H]+; | $^1$H NMR (400 MHz, CD$_3$OD) (5δ 8.71 (s, 1H), 8.32 (d, 1H), 8.16 (dd, 1H), 7.84-7.80 (m, 2H), 7.36-7.15 (m, 7H), 5.06-5.03 (m, 1H), 3.76-3.70 (m, 4H), 3.38-3.33 (m, 1H), 3.22-3.14 (m, 1H), 2.98 (t, 2H), 2.62-2.50 (m, 6H), 1.76-1.69 (m, 2H). |

Example 65: (S)-N-(1-(5-(N-ethylsulfamoyl)naphthalen-1-ylamino)-1-oxo-3-phenylpropan-2-yl)cyclohexanecarboxamide, I-124

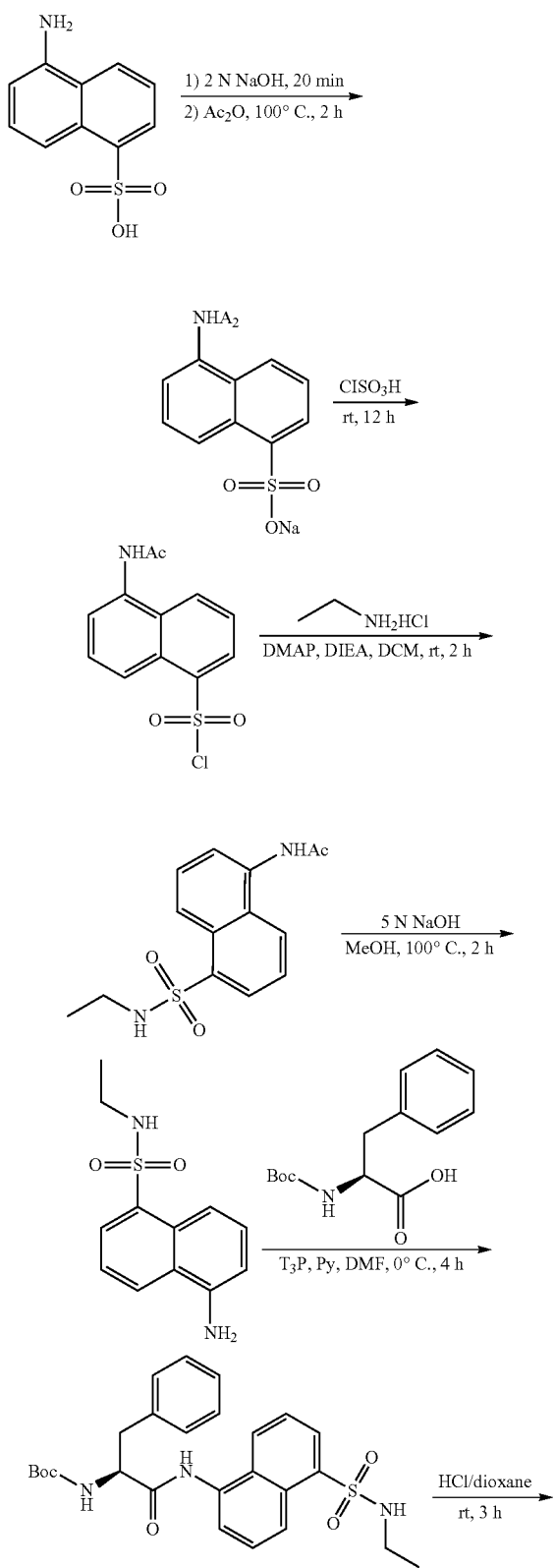

-continued

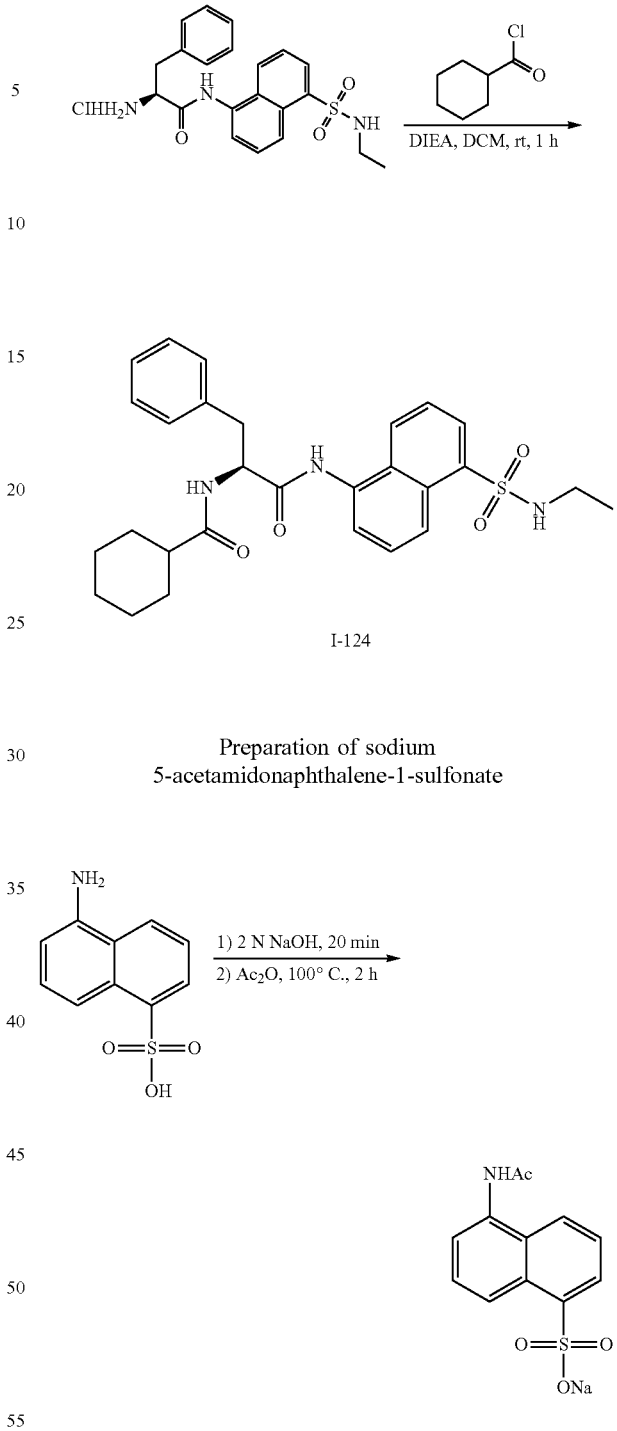

Preparation of sodium 5-acetamidonaphthalene-1-sulfonate

To a solution of 6.66 g 5-aminonaphthalene-1-sulfonic acid (30 mmol, 1.00 equiv) in 20 mL water was added dropwise 30 mL of a 2 N sodium hydroxide solution (60 mmol, 2.00 equiv) at 0° C. After 20 min, was concentrated in vacuo. To the residue was added 60 mL acetic anhydride. The mixture was stirred for 2 h at 100° C. The mixture was cooled to room temperature and poured onto ethanol. The crude product was precipitated out. The solid was filtered, dried under vacuum to afforded 4.23 g sodium 5-acetamidonaphthalene-1-sulfonate as an off-white solid (50% yield). MS (ESI+) m/z 266 [M+H]+.

Preparation of 5-acetamidonaphthalene-1-sulfonyl Chloride

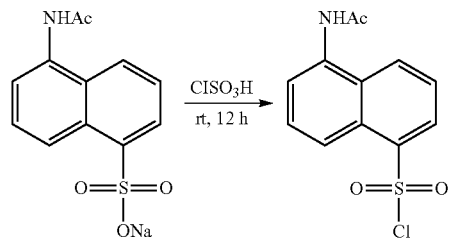

A solution of 4.23 g sodium 5-acetamidonaphthalene-1-sulfonate (14.74 mmol, 1.00 equiv) in 25 mL sulfurochloridic acid was stirred for 12 h at r.t. The mixture was poured onto ice water. The crude product was precipitated out. The solid was filtered, dried under vacuum to afforded 2.96 g 5-acetamidonaphthalene-1-sulfonyl chloride as a white solid (71% yield). MS (ESI$^+$) m/z 284 and 286 [M+H]$^+$.

Preparation of N-(5-(N-ethylsulfamoyl)naphthalen-1-yl)acetamide

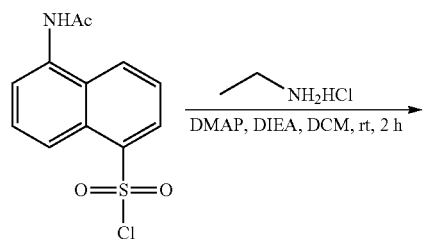

To a solution of 0.81 g ethanamine hydrochloride (10 mmol, 1.00 equiv), 3.87 g DIEA (30 mmol, 3.00 equiv) and 122 mg DMAP (1 mmol, 0.10 equiv) in 50 mL dichloromethane was added 2.83 g 5-acetamidonaphthalene-1-sulfonyl chloride (10 mmol, 1.00 equiv) at 0° C. The resulting mixture was stirred for 2 h at r.t. The mixture was diluted with 100 mL water and extracted with dichloromethane (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (3:1)) provided 2.4 g N-(5-(N-ethylsulfamoyl)naphthalen-1-yl)acetamide as a yellow solid (82% yield). MS (ESI$^+$) m/z 293 [M+H]$^+$.

Preparation of 5-amino-N-ethylnaphthalene-1-sulfonamide

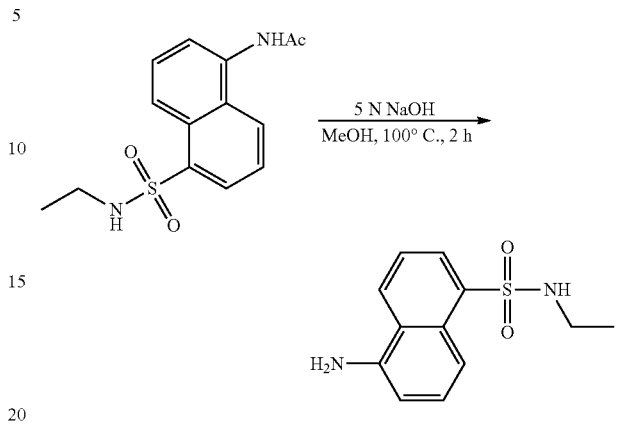

To a solution of 2.4 g N-(5-(N-ethylsulfamoyl)naphthalen-1-yl)acetamide (8.22 mmol, 1.00 equiv) in 30 mL methanol was added 13.2 mL of a 5 N sodium hydroxide solution. The mixture was stirred for 2 h at 100° C. The mixture was cooled to r.t, concentrated in vacuo and diluted with 50 mL water. The pH value of the solution was adjusted to 8 with 2N hydrochloric acid. The crude product was precipitated out. The solid was filtered, dried under vacuum to afford 1.19 g 5-amino-N-ethylnaphthalene-1-sulfonamide as a light yellow solid (58% yield). MS (ESI$^+$) m/z 251 [M+H]$^+$.

Preparation of (S)-tert-butyl 1-(5-(N-ethylsulfamoyl)naphthalen-1-ylamino)-1-oxo-3-phenylpropan-2-ylcarbamate

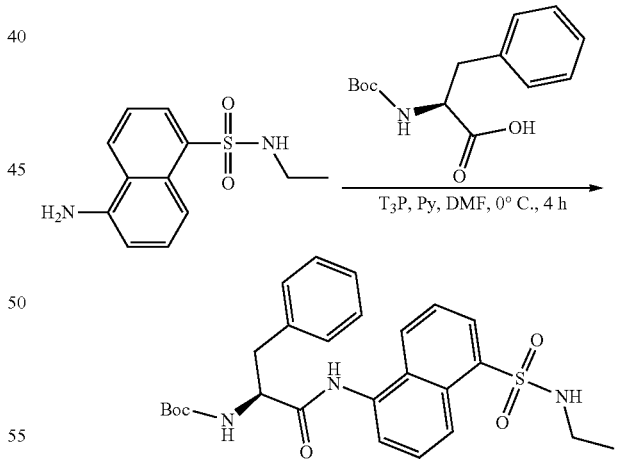

To a solution of 1.19 g 5-amino-N-ethylnaphthalene-1-sulfonamide (4.76 mmol, 1.00 equiv), 1.26 g (S)-2-(tert-butoxycarbonylamino)-3-phenylpropanoic acid (4.76 mmol, 1.00 equiv) and 3.76 g pyridine (47.6 mmol, 10.00 equiv) in 20 mL N,N-dimethylformamide was added dropwise a solution 12.28 g propanephosphonic acid cyclic anhydride in ethyl acetate (50%, 23.8 mmol, 5.00 equiv) at 0° C. The resulting mixture was stirred for 4 h at 0° C. The mixture was diluted with 50 mL water and extracted with ethyl acetate (3×100 mL). The combined organic layers were washed with brine (3×50 mL), dried over anhydrous magnesium sulfate, filtered and the filtrate concentrated in vacuo. Purification by column chromatography (silica gel, petroleum ether:ethyl acetate (1:1)) provided 1.44 g (S)-tert-butyl 1-(5-(N-ethylsulfamoyl)naphthalen-1-ylamino)-1-oxo-3-phenylpropan-2-ylcarbamate as a yellow solid (61% yield). MS (ESI⁺) m/z 442 [M-56+H]⁺.

Preparation of (S)-2-amino-N-(5-(N-ethylsulfamoyl)naphthalen-1-yl)-3-phenylpropanamide Hydrochloride

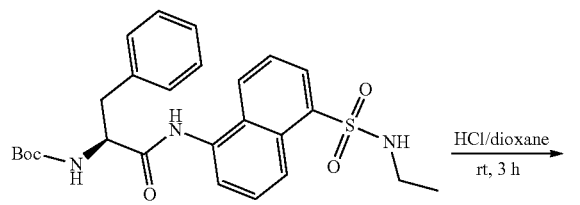

A mixture of 1.44 g (S)-tert-butyl 1-(5-(N-ethylsulfamoyl)naphthalen-1-ylamino)-1-oxo-3-phenylpropan-2-ylcarbamate (2.9 mmol, 1.00 equiv) in 30 mL hydrochloric acid in 1,4-dioxane (4.0 M) was stirred at room temperature for 3 h. The mixture was concentrated to afford 1.26 g (S)-2-amino-N-(5-(N-ethylsulfamoyl)naphthalen-1-yl)-3-phenylpropanamide hydrochloride as a light yellow solid (100% yield). MS (ESI⁺) m/z 398 [M+H]⁺.

Preparation of (S)-N-(1-(5-(N-ethylsulfamoyl)naphthalen-1-ylamino)-1-oxo-3-phenylpropan-2-yl)cyclohexanecarboxamide (I-124)

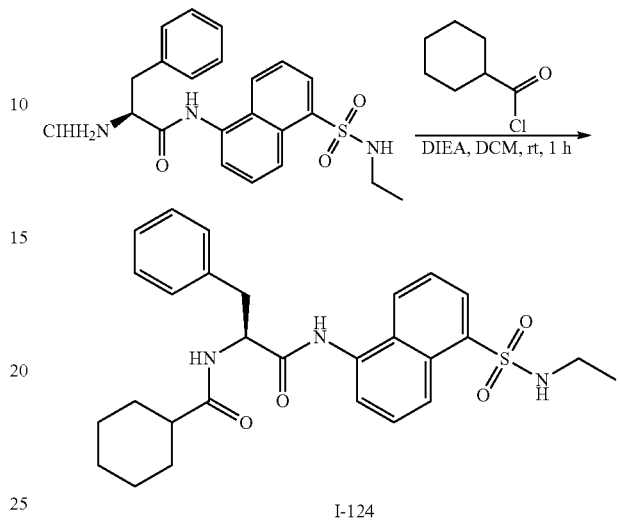

I-124

To a mixture of 200 mg (S)-2-amino-N-(5-(N-ethylsulfamoyl)naphthalen-1-yl)-3-phenylpropanamide hydrochloride (0.46 mmol, 1.0 equiv) and 296.7 mg N,N-diisopropylethylamine (2.3 mmol, 5.00 equiv) in 10 mL dichloromethane was added 67.16 mg cyclohexanecarbonyl chloride (0.46 mmol, 1.00 equiv) at 0° C. The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH₄HCO₃+0.1% NH₃—H₂O) and ACN (28% ACN up to 48% in 7 min); UV detection at 254/220 nm. The product-containing fractions were combined and evaporated partially in vacuo and lyophilized overnight to afford 92.2 mg (S)-N-(1-(5-(N-ethylsulfamoyl)naphthalen-1-ylamino)-1-oxo-3-phenylpropan-2-yl)cyclohexanecarboxamide (I-124) as a white solid.

Using this general procedure for the preparation of I-124 and substituting the appropriate acid chloride in the last step, the following compounds were prepared.

TABLE 9

Compounds prepared according to Example 65

| Compound | Chemical Name | Yield | MS | 1HNMR |
|---|---|---|---|---|
| I-124 | (S)-N-(1-(5-(N-ethylsulfamoyl)naphthalen-1-ylamino)-1-oxo-3-phenylpropan-2-yl)cyclohexanecarboxamide | 40% | MS (ESI⁺, m/z): Calcd for C28H33N3O4S: 507; found 508 [M + H]⁺; | ¹H NMR (400 MHz, CD₃OD) δ 8.62 (d, 1H), 8.22 (d, 1H), 7.84 (d, 1H), 7.66 (t, 1H), 7.55-7.50 (m, 2H), 7.38-7.32 (m, 5H), 4.95-4.89 (m, 1H), 3.28-3.13 (m, 2H), 2.87 (q, 2H), 2.37-2.30 (m, 1H), 1.92-1.70 (m, 5H), 1.56-1.22 (m, 5H), 0.98 (t, 3H). |

TABLE 9-continued

Compounds prepared according to Example 65

| Compound | Chemical Name | Yield | MS | 1HNMR |
|---|---|---|---|---|
| I-125 | (S)-N-(1-(5-(N-ethylsulfamoyl)naphthalen-1-ylamino)-1-oxo-3-phenylpropan-2-yl)-4-fluorobenzamide | 38% | MS (ESI+, m/z): Calcd for C28H26FN3O4S: 519; found 520 [M + H]+ | $^1$H NMR (300 MHz, CD$_3$OD) δ 8.62 (d, 1H), 8.22 (d, 1H), 7.96-7.86 (m, 3H), 7.66 (t, 1H), 7.58-7.50 (m, 2H), 7.48-7.30 (m, 5H), 7.26-7.16 (m, 2H), 5.13-5.07 (m, 1H), 3.41-3.34 (m, 1H), 3.32-3.28 (m, 1H), 2.86 (q, 2H), 0.98 (t, 3H). |

Example 66: (S)-N-(1-(1-(N-ethylsulfamoyl)-1,2,3,4-tetrahydroquinolin-5-ylamino)-1-oxo-3-phenylpropan-2-yl)cyclohexanecarboxamide, I-126

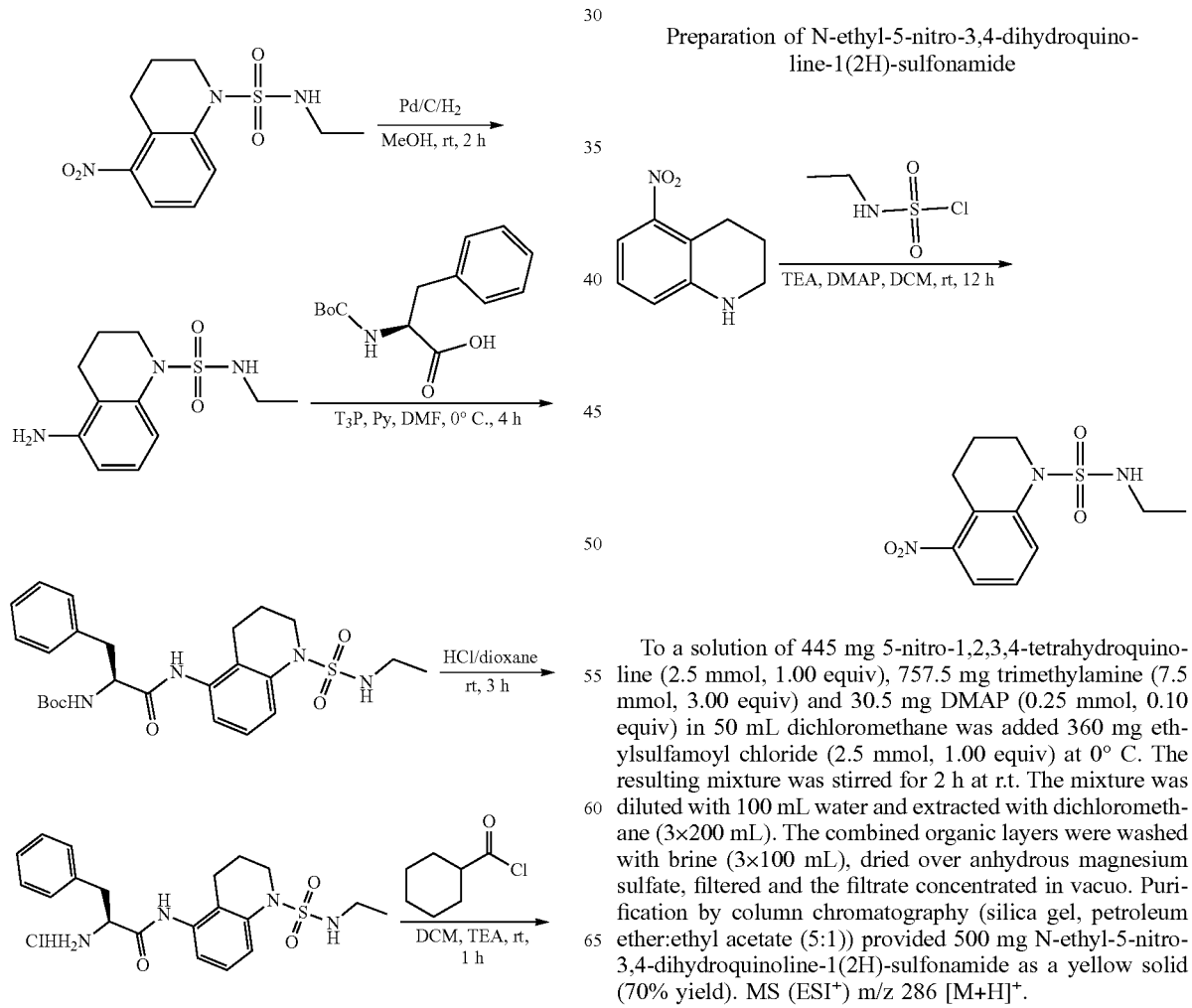

I-126

Preparation of N-ethyl-5-nitro-3,4-dihydroquinoline-1(2H)-sulfonamide

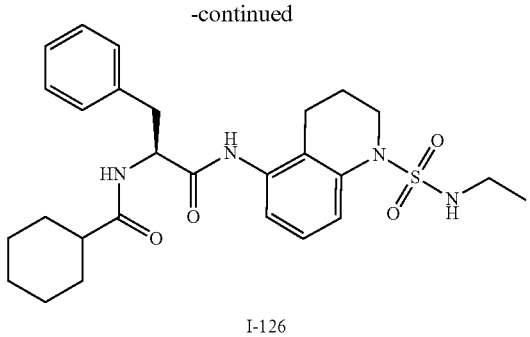

To a solution of 445 mg 5-nitro-1,2,3,4-tetrahydroquinoline (2.5 mmol, 1.00 equiv), 757.5 mg trimethylamine (7.5 mmol, 3.00 equiv) and 30.5 mg DMAP (0.25 mmol, 0.10 equiv) in 50 mL dichloromethane was added 360 mg ethylsulfamoyl chloride (2.5 mmol, 1.00 equiv) at 0° C. The resulting mixture was stirred for 2 h at r.t. The mixture was diluted with 100 mL water and extracted with dichloromethane (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (5:1)) provided 500 mg N-ethyl-5-nitro-3,4-dihydroquinoline-1(2H)-sulfonamide as a yellow solid (70% yield). MS (ESI+) m/z 286 [M+H]+.

Preparation of 5-amino-N-ethyl-3,4-dihydroquinoline-1(2H)-sulfonamide

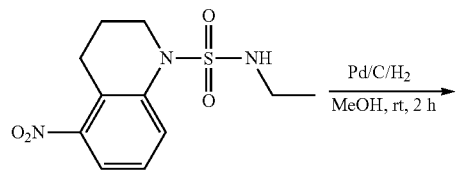

To a solution of 500 mg N-ethyl-5-nitro-3,4-dihydroquinoline-1(2H)-sulfonamide (1.75 mmol, 1.00 equiv) in 10 mL methanol was added 200 mg palladium on carbon. To the above hydrogen (g) was introduced in. The resulting mixture was stirred at r.t for 2 h. The solid was filtered out. The filtrate was concentrated under vacuum to afford 360 mg 5-amino-N-ethyl-3,4-dihydroquinoline-1(2H)-sulfonamide as a white solid (81% yield). MS (ESI$^+$) m/z 256 [M+H]$^+$.

Preparation of (S)-tert-butyl 1-(1-(N-ethylsulfamoyl)-1,2,3,4-tetrahydroquinolin-5-ylamino)-1-oxo-3-phenylpropan-2-ylcarbamate

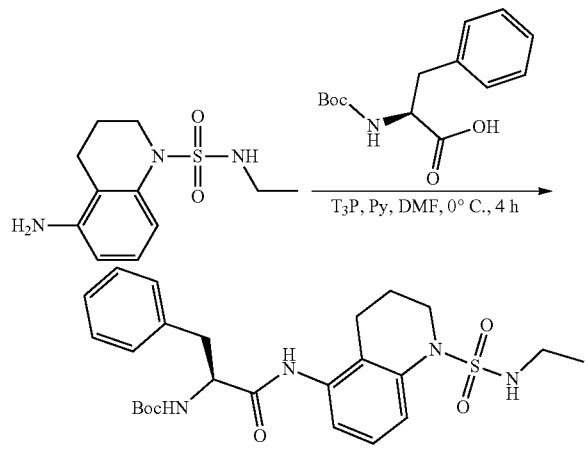

To a solution of 360 mg 5-amino-N-ethyl-3,4-dihydroquinoline-1(2H)-sulfonamide (1.41 mmol, 1.00 equiv), 374 mg (S)-2-(tert-butoxycarbonylamino)-3-phenylpropanoic acid (1.41 mmol, 1.00 equiv) and 1.11 g pyridine (14.1 mmol, 10.00 equiv) in 5 mL N,N-dimethylformamide was added dropwise a solution 3.64 g propanephosphonic acid cyclic anhydride in ethyl acetate (50%, 7.05 mmol, 5.00 equiv) at 0° C. The resulting mixture was stirred for 4 h at 0° C. The mixture was diluted with 20 mL water and extracted with ethyl acetate (3×50 mL). The combined organic layers were washed with brine (3×20 mL), dried over anhydrous magnesium sulfate, filtered and the filtrate concentrated in vacuo. Purification by column chromatography (silica gel, petroleum ether:ethyl acetate (1:1)) provided 380 mg (S)-tert-butyl 1-(1-(N-ethylsulfamoyl)-1,2,3,4-tetrahydroquinolin-5-ylamino)-1-oxo-3-phenylpropan-2-ylcarbamate as a yellow oil (54% yield). MS (ESI$^+$) m/z 525 [M+Na]$^+$.

Preparation of (S)-2-amino-N-(1-(N-ethylsulfamoyl)-1,2,3,4-tetrahydroquinolin-5-yl)-3-phenylpropanamide Hydrochloride

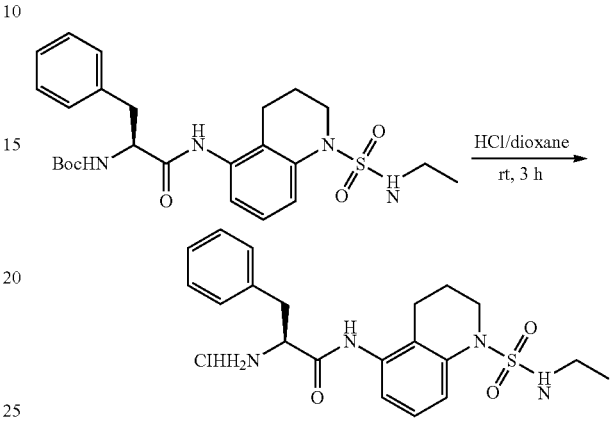

A mixture of 380 mg (S)-tert-butyl 1-(1-(N-ethylsulfamoyl)-1,2,3,4-tetrahydroquinolin-5-ylamino)-1-oxo-3-phenylpropan-2-ylcarbamate (0.76 mmol, 1.00 equiv) in 6 mL hydrochloric acid in 1,4-dioxane (4.0 M) was stirred at room temperature for 3 h. The mixture was concentrated to afford 333 mg (S)-2-amino-N-(1-(N-ethylsulfamoyl)-1,2,3,4-tetrahydroquinolin-5-yl)-3-phenylpropanamide hydrochloride as a white solid (100% yield). MS (ESI$^+$) m/z 403 [M+H]$^+$.

Preparation of (S)-N-(1-(1-(N-ethylsulfamoyl)-1,2,3,4-tetrahydroquinolin-5-ylamino)-1-oxo-3-phenylpropan-2-yl)cyclohexanecarboxamide (I-126)

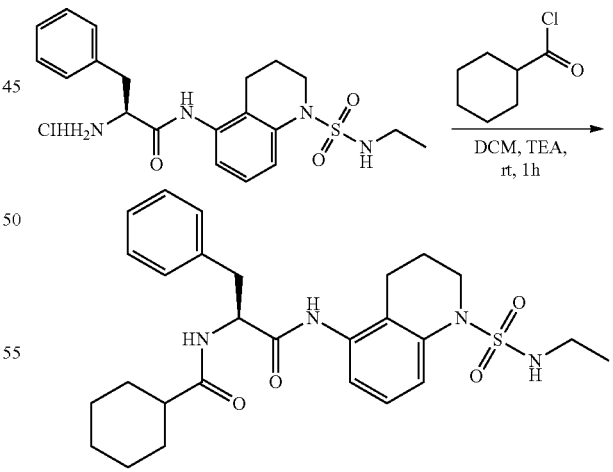

I-126

To a mixture of 150 mg (S)-2-amino-N-(1-(N-ethylsulfamoyl)-1,2,3,4-tetrahydroquinolin-5-yl)-3-phenylpropanamide hydrochloride (0.34 mmol, 1.0 equiv) and 171.7 mg trimethylamine (1.7 mmol, 5.00 equiv) in 10 mL dichloromethane was added 49.64 mg cyclohexanecarbonyl chloride (0.34 mmol, 1.00 equiv) at 0° C. The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+ 0.1% NH$_3$—H$_2$O) and ACN (32% ACN up to 48% in 7 min); UV detection at 254/220 nm. The product-containing fractions were combined and evaporated partially in vacuo and lyophilized overnight to afford 36.1 mg (S)-N-(1-(1-(N-ethylsulfamoyl)-1,2,3,4-tetrahydroquinolin-5-ylamino)-1-oxo-3-phenylpropan-2-yl)cyclohexanecarboxamide (I-126) as a white solid (21% yield). MS (ESI$^+$) m/z 513 [M+H]$^+$; $^1$H NMR (400 MHz, CD$_3$OD) δ 7.49 (d, 1H), 7.33-7.25 (m, 5H), 7.13 (t, 1H), 6.99 (d, 1H), 4.78 (t, 1H), 3.68-3.65 (m, 2H), 3.24-3.15 (m, 1H), 3.09-3.01 (m, 1H), 2.94 (q, 2H), 2.57-2.20 (m, 3H), 2.00-1.90 (m, 2H), 1.85-1.66 (m, 5H), 1.52-1.18 (m, 5H), 1.08 (t, 3H).

Example 67: (S)-N-(1-(5-(N,N-dimethylsulfamoyl)naphthalen-1-ylamino)-1-oxo-3-phenylpropan-2-yl)cyclohexanecarboxamide, I-127

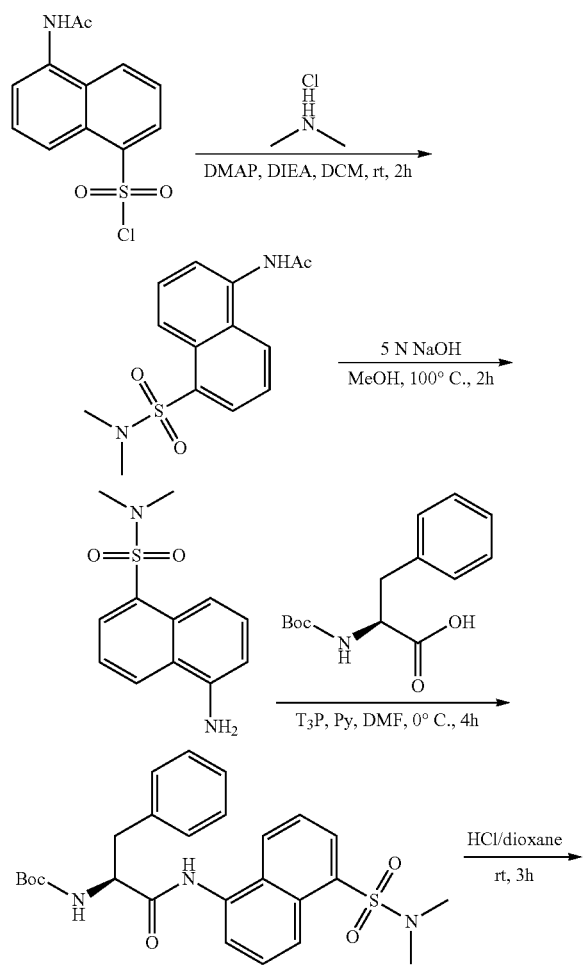

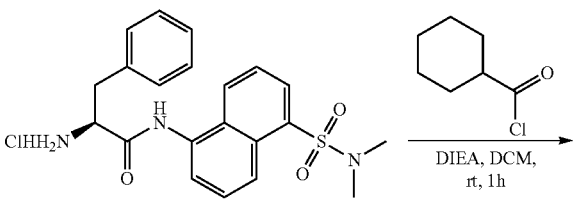

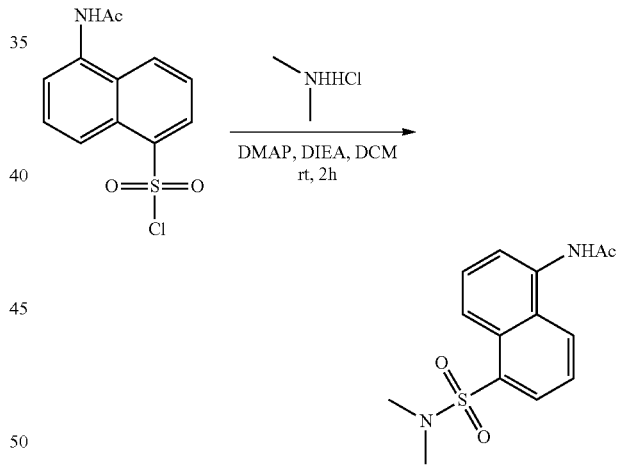

I-127

Preparation of N-(5-(N,N-dimethylsulfamoyl)naphthalen-1-yl)acetamide

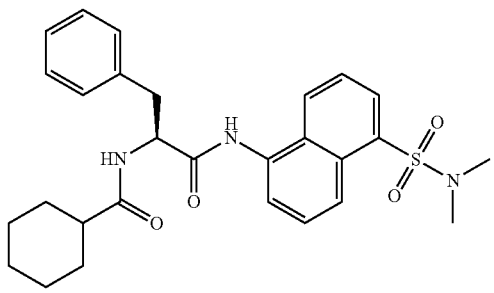

To a solution of 0.81 g dimethylamine hydrochloride (10 mmol, 1.00 equiv), 3.87 g DIEA (30 mmol, 3.00 equiv) and 122 mg DMAP (1 mmol, 0.10 equiv) in 50 mL dichloromethane was added 2.83 g 5-acetamidonaphthalene-1-sulfonyl chloride (10 mmol, 1.00 equiv) at 0° C. The resulting mixture was stirred for 2 h at r.t. The mixture was diluted with 100 mL water and extracted with dichloromethane (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (3:1)) provided 2.41 g N-(5-(N,N-dimethylsulfamoyl)naphthalen-1-yl)acetamide as a yellow solid (82% yield). MS (ESI$^+$) m/z 293 [M+H]$^+$.

Preparation of 5-amino-N,N-dimethylnaphthalene-1-sulfonamide

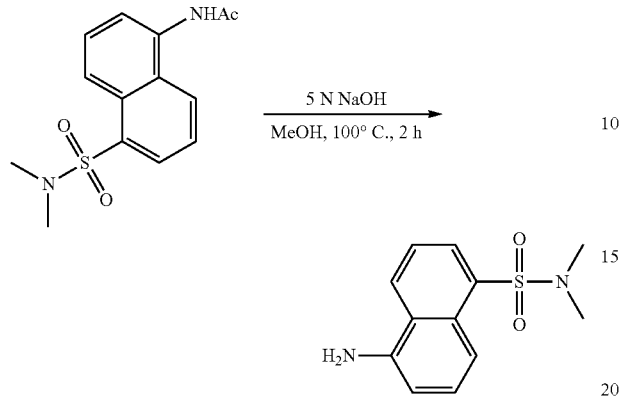

To a solution of 2.41 g N-(5-(N,N-dimethylsulfamoyl)naphthalen-1-yl)acetamide (8.22 mmol, 1.00 equiv) in 30 mL methanol was added 13.2 mL of a 5 N sodium hydroxide solution. The mixture was stirred for 2 h at 100° C. The mixture was cooled to r.t, concentrated in vacuo and diluted with 50 mL water. The pH value of the solution was adjusted to 8 with 2N hydrochloric acid. The crude product was precipitated out. The solid was filtered, dried under vacuum to afford 1.19 g 5-amino-N,N-dimethylnaphthalene-1-sulfonamide as a light yellow solid (58% yield). MS (ESI$^+$) m/z 251 [M+H]$^+$.

Preparation of (S)-tert-butyl 1-(5-(N,N-dimethylsulfamoyl)naphthalen-1-ylamino)-1-oxo-3-phenylpropan-2-ylcarbamate

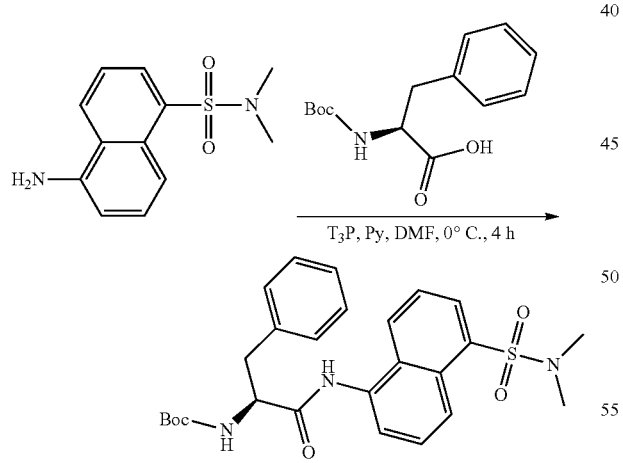

To a solution of 1.19 g 5-amino-N,N-dimethylnaphthalene-1-sulfonamide (4.76 mmol, 1.00 equiv), 1.26 g (S)-2-(tert-butoxycarbonylamino)-3-phenylpropanoic acid (4.76 mmol, 1.00 equiv) and 3.76 g pyridine (47.6 mmol, 10.00 equiv) in 20 mL N,N-dimethylformamide was added dropwise a solution 12.28 g propanephosphonic acid cyclic anhydride in ethyl acetate (50%, 23.8 mmol, 5.00 equiv) at 0° C. The resulting mixture was stirred for 4 h at 0° C. The mixture was diluted with 50 mL water and extracted with ethyl acetate (3×100 mL). The combined organic layers were washed with brine (3×50 mL), dried over anhydrous magnesium sulfate, filtered and the filtrate concentrated in vacuo. Purification by column chromatography (silica gel, petroleum ether:ethyl acetate (1:1)) provided 1.44 g (S)-tert-butyl 1-(5-(N,N-dimethylsulfamoyl)naphthalen-1-ylamino)-1-oxo-3-phenylpropan-2-ylcarbamate as a yellow solid (61% yield). MS (ESI$^+$) m/z 442 [M-56+H]$^+$.

Preparation of (S)-2-amino-N-(5-(N,N-dimethylsulfamoyl)naphthalen-1-yl)-3-phenylpropanamide Hydrochloride

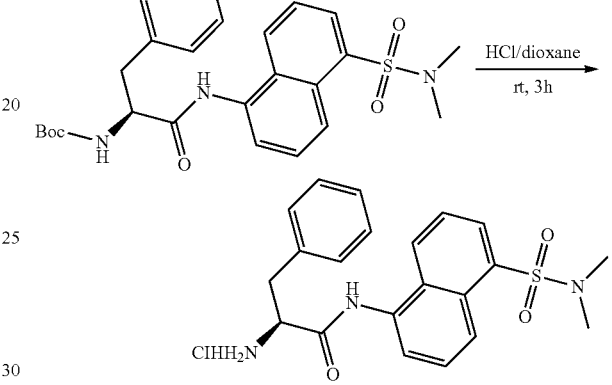

A mixture of 1.44 g (S)-tert-butyl 1-(5-(N,N-dimethylsulfamoyl)naphthalen-1-ylamino)-1-oxo-3-phenylpropan-2-ylcarbamate (2.9 mmol, 1.00 equiv) in 30 mL hydrochloric acid in 1,4-dioxane (4.0 M) was stirred at room temperature for 3 h. The mixture was concentrated to afford 1.26 g (S)-2-amino-N-(5-(N,N-dimethylsulfamoyl)naphthalen-1-yl)-3-phenylpropanamide hydrochloride as a light yellow solid (100% yield). MS (ESI$^+$) m/z 398 [M+H]$^+$.

Preparation of (S)-N-(1-(5-(N,N-dimethylsulfamoyl)naphthalen-1-ylamino)-1-oxo-3-phenylpropan-2-yl)cyclohexanecarboxamide

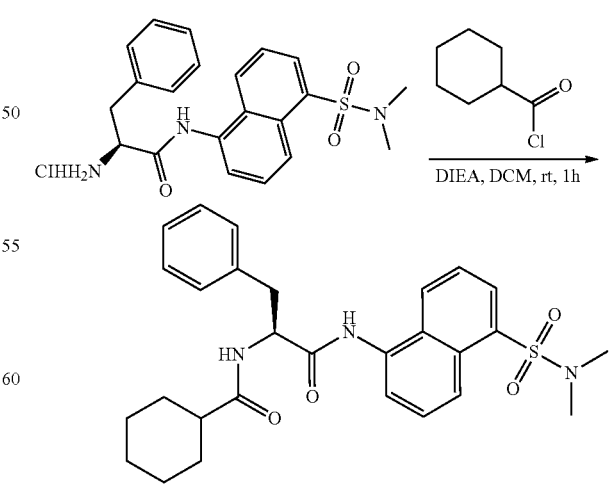

I-127

To a mixture of 150 mg (S)-2-amino-N-(5-(N,N-dimethylsulfamoyl)naphthalen-1-yl)-3-phenylpropanamide hydrochloride (0.35 mmol, 1.0 equiv) and 225.8 mg N,N-diisopropylethylamine (1.75 mmol, 5.00 equiv) in 10 mL dichloromethane was added 51.1 mg cyclohexanecarbonyl chloride (0.35 mmol, 1.00 equiv) at 0° C. The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+ 0.1% NH$_3$—H$_2$O) and ACN (29% ACN up to 45% in 7 min); UV detection at 254/220 nm. The product-containing fractions were combined and evaporated partially in vacuo and lyophilized overnight to afford 62.9 mg (S)-N-(1-(5-(N,N-dimethylsulfamoyl)naphthalen-1-ylamino)-1-oxo-3-phenylpropan-2-yl)cyclohexanecarboxamide (I-127) as a white solid.

Using this general procedure for the preparation of I-127 and substituting the appropriate acid chloride in the last step, the following two compounds were prepared.

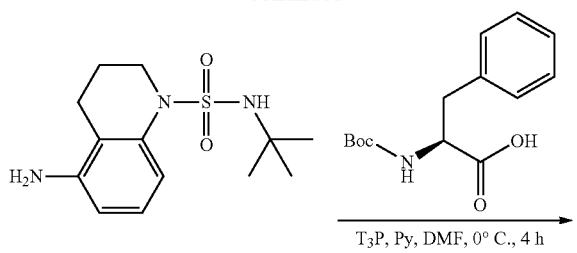

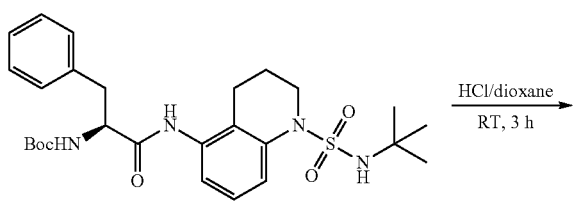

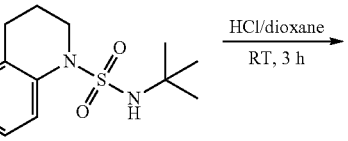

TABLE 10

Compounds prepared according to Example 67.

| Compound | Chemical Name | Yield | MS | 1HNMR |
|---|---|---|---|---|
| I-127 | (S)-N-(1-(5-(N,N-dimethylsulfamoyl)naphthalen-1-ylamino)-1-oxo-3-phenylpropan-2-yl)cyclohexanecarboxamide | 35% | MS (ESI$^+$, m/z): Calcd for C28H33N3O4S: 507; found 508 [M + H]$^+$; | $^1$H NMR (300 MHz, CD$_3$OD) δ 8.69 (d, 1H), 8.18 (dd, 1H), 7.88 (d, 1H), 7.70-7.48 (m, 3H), 7.44-7.28 (m, 5H), 4.95-4.89 (m, 1H), 3.28-3.13 (m, 2H), 2.80 (s, 6H), 2.37-2.30 (m, 1H), 1.90-1.70 (m, 5H), 1.5 6-1.22 (m, 5H). |
| I-128 | (S)-N-(1-(5-(N,N-dimethylsulfamoyl)naphthalen-1-ylamino)-1-oxo-3-phenylpropan-2-yl)-4-fluorobenzamide | 38% | MS (ESI$^+$, m/z): Calcd for C28H26FN3O4S: 519; found 520 [M + H]$^+$ | $^1$H NMR (300 MHz, CD3OD) δ 8.68 (d, 1H), 8.17 (dd, 1H), 7.95-7.90 (m, 3H), 7.70-7.30 (m, 8H), 7.28-7.18 (m, 2H), 5.11-5.06 (m, 1H), 3.41-3.34 (m, 2H), 2.79 (s, 6H). |

Example 68: (S)-N-(1-(1-(N-tert-butylsulfamoyl)-1,2,3,4-tetrahydroquinolin-5-ylamino)-1-oxo-3-phenylpropan-2-yl)cyclohexanecarboxamide, I-129

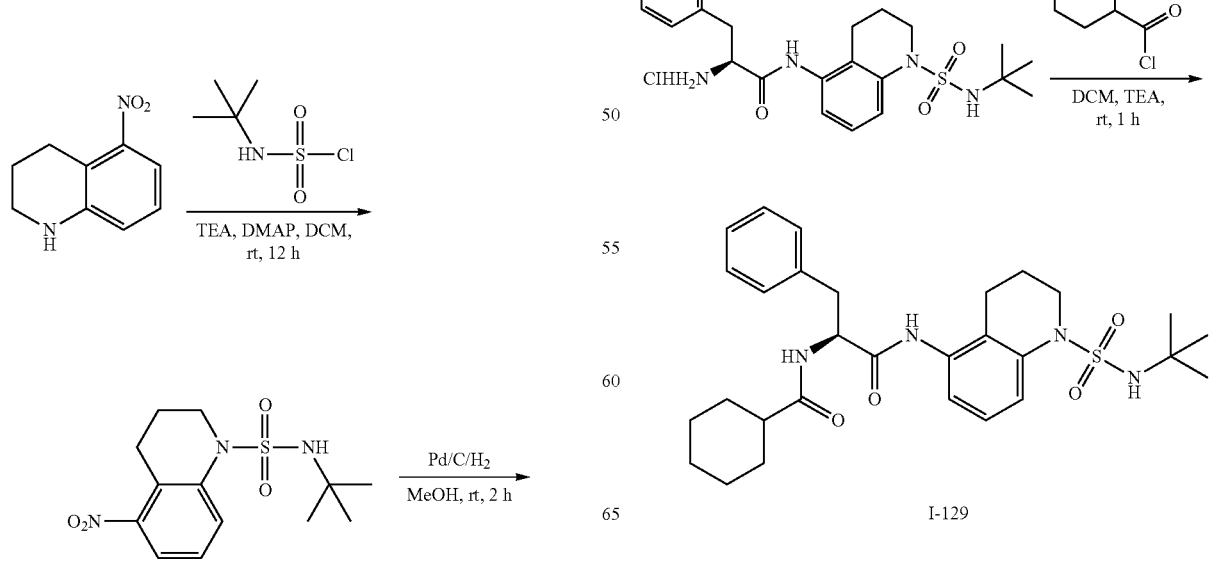

Preparation of N-tert-butyl-5-nitro-3,4-dihydroquinoline-1(2H)-sulfonamide

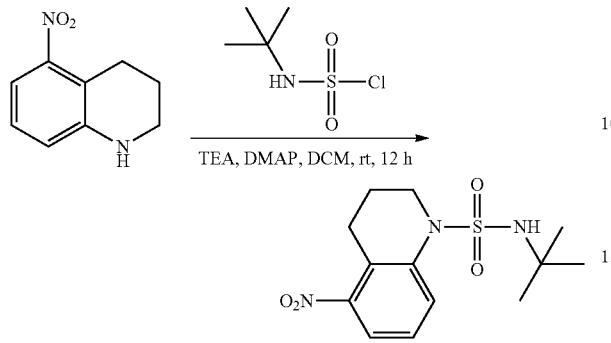

To a solution of 445 mg 5-nitro-1,2,3,4-tetrahydroquinoline (2.5 mmol, 1.00 equiv), 757.5 mg trimethylamine (7.5 mmol, 3.00 equiv) and 30.5 mg DMAP (0.25 mmol, 0.10 equiv) in 50 mL dichloromethane was added 427.5 mg tert-butylsulfamoyl chloride (2.5 mmol, 1.00 equiv) at 0° C. The resulting mixture was stirred for 2 h at r.t. The mixture was diluted with 100 mL water and extracted with dichloromethane (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (5:1)) provided 550 mg N-tert-butyl-5-nitro-3,4-dihydroquinoline-1(2H)-sulfonamide as a yellow solid (70% yield). MS (ESI$^+$) m/z 314 [M+H]$^+$.

Preparation of 5-amino-N-tert-butyl-3,4-dihydroquinoline-1(2H)-sulfonamide

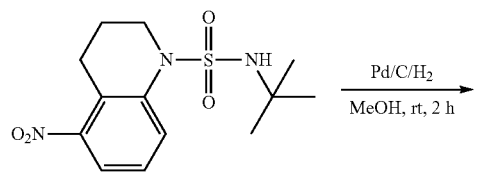

To a solution of 550 mg N-tert-butyl-5-nitro-3,4-dihydroquinoline-1(2H)-sulfonamide (1.75 mmol, 1.00 equiv) in 10 mL methanol was added 200 mg palladium on carbon. To the above hydrogen (g) was introduced in. The resulting mixture was stirred at r.t for 2 h. The solid was filtered out. The filtrate was concentrated under vacuum to afford 400 mg 5-amino-N-tert-butyl-3,4-dihydroquinoline-1(2H)-sulfonamide as a white solid (81% yield). MS (ESI$^+$) m/z 284 [M+H]$^+$.

Preparation of (S)-tert-butyl 1-(1-(N-tert-butylsulfamoyl)-1,2,3,4-tetrahydroquinolin-5-ylamino)-1-oxo-3-phenylpropan-2-ylcarbamate

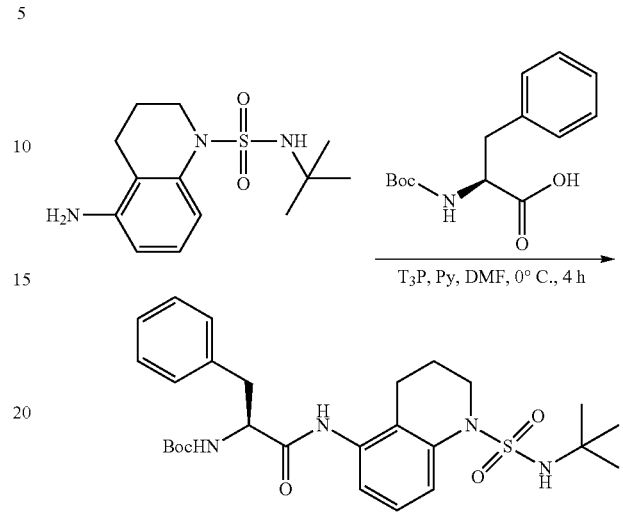

To a solution of 400 mg 5-amino-N-tert-butyl-3,4-dihydroquinoline-1(2H)-sulfonamide (1.41 mmol, 1.00 equiv), 374 mg (S)-2-(tert-butoxycarbonylamino)-3-phenylpropanoic acid (1.41 mmol, 1.00 equiv) and 1.11 g pyridine (14.1 mmol, 10.00 equiv) in 5 mL N,N-dimethylformamide was added dropwise a solution 3.64 g propanephosphonic acid cyclic anhydride in ethyl acetate (50%, 7.05 mmol, 5.00 equiv) at 0° C. The resulting mixture was stirred for 4 h at 0° C. The mixture was diluted with 20 mL water and extracted with ethyl acetate (3×50 mL). The combined organic layers were washed with brine (3×20 mL), dried over anhydrous magnesium sulfate, filtered and the filtrate concentrated in vacuo. Purification by column chromatography (silica gel, petroleum ether:ethyl acetate (1:1)) provided 371 mg (S)-tert-butyl 1-(1-(N-tert-butylsulfamoyl)-1,2,3,4-tetrahydroquinolin-5-ylamino)-1-oxo-3-phenylpropan-2-ylcarbamate as a yellow oil (50% yield). MS (ESI$^+$) m/z 553 [M+Na]$^+$.

Preparation of (S)-2-amino-N-(1-(N-tert-butylsulfamoyl)-1,2,3,4-tetrahydroquinolin-5-yl)-3-phenylpropanamide Hydrochloride

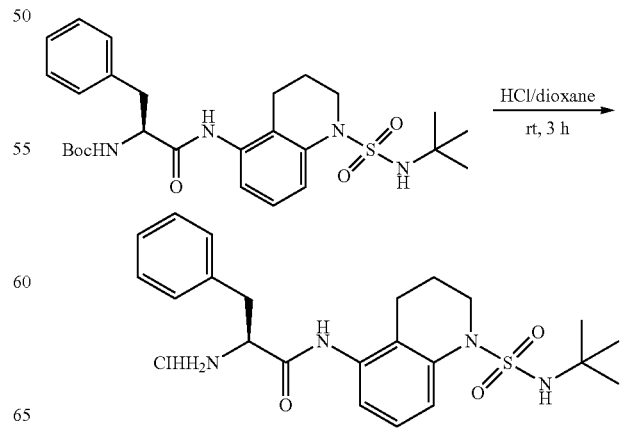

A mixture of 371 mg (S)-tert-butyl 1-(1-(N-tert-butylsulfamoyl)-1,2,3,4-tetrahydroquinolin-5-ylamino)-1-oxo-3-phenylpropan-2-ylcarbamate (0.7 mmol, 1.00 equiv) in 6 mL hydrochloric acid in 1,4-dioxane (4.0 M) was stirred at room temperature for 3 h. The mixture was concentrated to afford 328 mg (S)-2-amino-N-(1-(N-tert-butylsulfamoyl)-1,2,3,4-tetrahydroquinolin-5-yl)-3-phenylpropanamide hydrochloride as a white solid (100% yield). MS (ESI+) m/z 431 [M+H]+.

Preparation of (S)-N-(1-(1-(N-tert-butylsulfamoyl)-1,2,3,4-tetrahydroquinolin-5-ylamino)-1-oxo-3-phenylpropan-2-yl)cyclohexanecarboxamide (I-129)

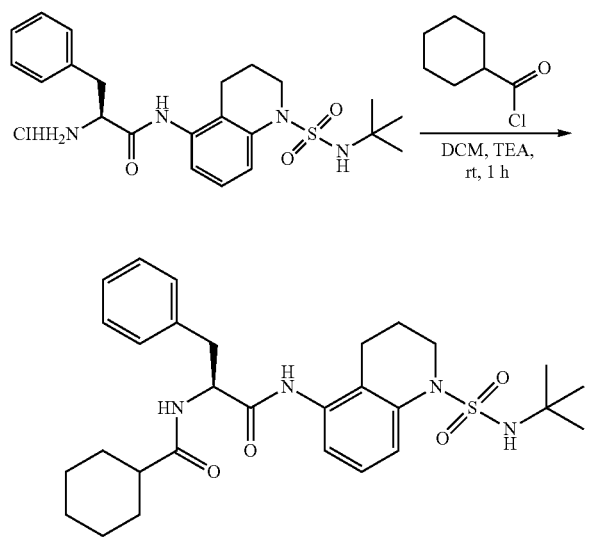

I-129

To a mixture of 150 mg (S)-2-amino-N-(1-(N-tert-butylsulfamoyl)-1,2,3,4-tetrahydroquinolin-5-yl)-3-phenylpropanamide hydrochloride (0.32 mmol, 1.0 equiv) and 161.6 mg trimethylamine (1.6 mmol, 5.00 equiv) in 10 mL dichloromethane was added 46.72 mg cyclohexanecarbonyl chloride (0.32 mmol, 1.00 equiv) at 0° C. The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+ 0.1% NH$_3$—H$_2$O) and ACN (34% ACN up to 49% in 7 min); UV detection at 254/220 nm. The product-containing fractions were combined and evaporated partially in vacuo and lyophilized overnight to afford 53.6 mg (S)-N-(1-(1-(N-tert-butylsulfamoyl)-1,2,3,4-tetrahydroquinolin-5-ylamino)-1-oxo-3-phenylpropan-2-yl)cyclohexanecarboxamide (I-129) as a white solid (31% yield). MS (ESI+) m/z 541 [M+H]+; $^1$H NMR (300 MHz, CD$_3$OD) δ 7.56 (d, 1H), 7.46-7.20 (m, 5H), 7.12 (t, 1H), 6.97 (d, 1H), 4.78 (t, 1H), 3.72-3.65 (m, 2H), 3.24-3.13 (m, 1H), 3.09-3.01 (m, 1H), 2.55-2.18 (m, 3H), 2.00-1.90 (m, 2H), 1.85-1.66 (m, 5H), 1.58-1.18 (m, 14H).

Example 69: (S)-N-(1-(5-(N-oxetan-3-ylsulfamoyl)naphthalen-1-ylamino)-1-oxo-3-phenylpropan-2-yl)cyclohexanecarboxamide, I-130

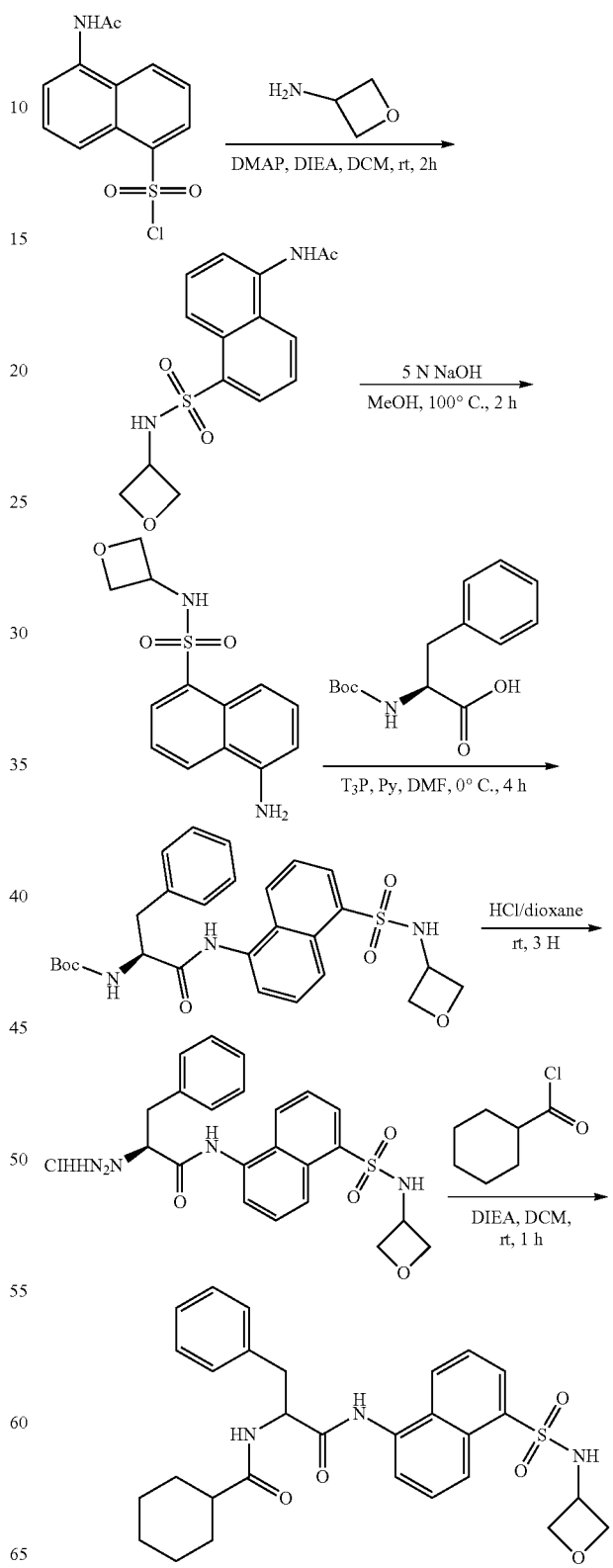

461

Preparation of N-(5-(N-oxetan-3-ylsulfamoyl)naphthalen-1-yl)acetamide

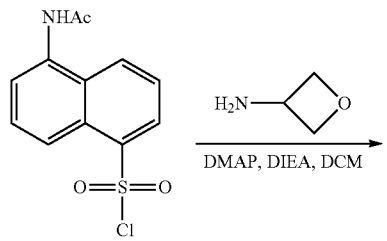

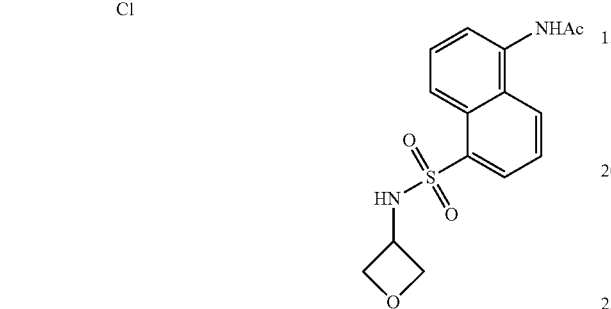

To a solution of 0.73 g oxetan-3-amine (10 mmol, 1.00 equiv), 3.87 g DIEA (30 mmol, 3.00 equiv) and 122 mg DMAP (1 mmol, 0.10 equiv) in 50 mL dichloromethane was added 2.83 g 5-acetamidonaphthalene-1-sulfonyl chloride (10 mmol, 1.00 equiv) at 0° C. The resulting mixture was stirred for 2 h at r.t. The mixture was diluted with 100 mL water and extracted with dichloromethane (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (3:1)) provided 2.63 g N-(5-(N-oxetan-3-ylsulfamoyl)naphthalen-1-yl)acetamide as a yellow solid (82% yield). MS (ESI⁺) m/z 321 [M+H]⁺.

Preparation of 5-amino-N-(oxetan-3-yl)naphthalene-1-sulfonamide

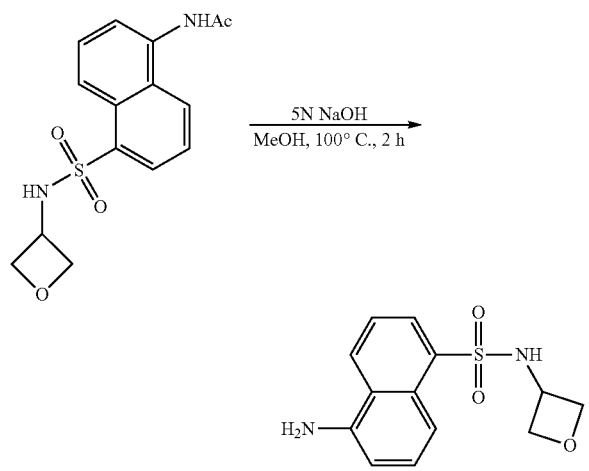

462

To a solution of 2.63 g N-(5-(N-oxetan-3-ylsulfamoyl)naphthalen-1-yl)acetamide (8.22 mmol, 1.00 equiv) in 30 mL methanol was added 13.2 mL of a 5 N sodium hydroxide solution. The mixture was stirred for 2 h at 100° C. The mixture was cooled to r.t, concentrated in vacuo and diluted with 50 mL water. The pH value of the solution was adjusted to 8 with 2N hydrochloric acid. The crude product was precipitated out. The solid was filtered, dried under vacuum to afford 1.32 g 5-amino-N-(oxetan-3-yl)naphthalene-1-sulfonamide as a light yellow solid (58% yield). MS (ESI⁺) m/z 279 [M+H]⁺.

Preparation of (S)-tert-butyl 1-(5-(N-oxetan-3-ylsulfamoyl)naphthalen-1-ylamino)-1-oxo-3-phenylpropan-2-ylcarbamate

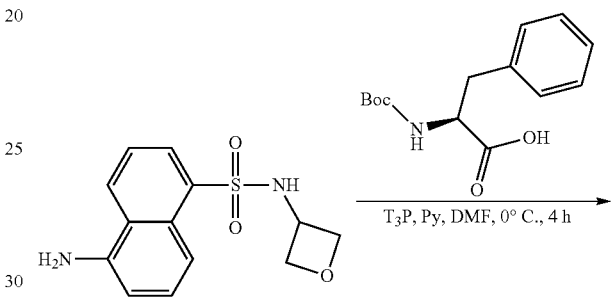

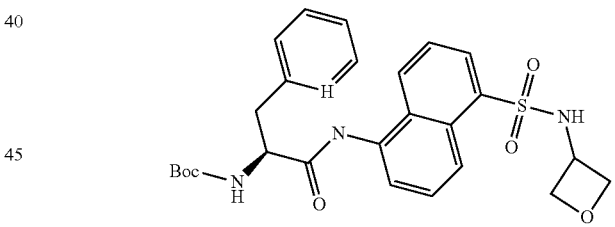

To a solution of 1.32 g 5-amino-N-(oxetan-3-yl)naphthalene-1-sulfonamide (4.76 mmol, 1.00 equiv), 1.26 g (S)-2-(tert-butoxycarbonylamino)-3-phenylpropanoic acid (4.76 mmol, 1.00 equiv) and 3.76 g pyridine (47.6 mmol, 10.00 equiv) in 20 mL N,N-dimethylformamide was added dropwise a solution 12.28 g propanephosphonic acid cyclic anhydride in ethyl acetate (50%, 23.8 mmol, 5.00 equiv) at 0° C. The resulting mixture was stirred for 4 h at 0° C. The mixture was diluted with 50 mL water and extracted with ethyl acetate (3×100 mL). The combined organic layers were washed with brine (3×50 mL), dried over anhydrous magnesium sulfate, filtered and the filtrate concentrated in vacuo. Purification by column chromatography (silica gel, petroleum ether:ethyl acetate (1:1)) provided 1.52 g (S)-tert-butyl 1-(5-(N-oxetan-3-ylsulfamoyl)naphthalen-1-ylamino)-1-oxo-3-phenylpropan-2-ylcarbamate as a yellow solid (61% yield). MS (ESI⁺) m/z 470 [M-56+H]⁺.

463

Preparation of (S)-2-amino-N-(5-(N-oxetan-3-ylsulfamoyl)naphthalen-1-yl)-3-phenylpropanamide Hydrochloride

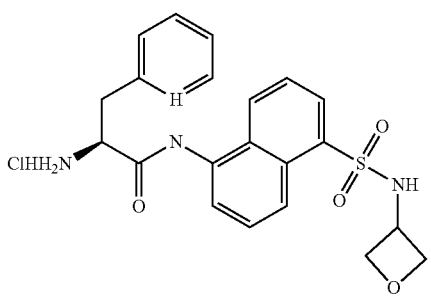

A mixture of 1.52 g (S)-tert-butyl 1-(5-(N-oxetan-3-ylsulfamoyl)naphthalen-1-ylamino)-1-oxo-3-phenylpropan-2-ylcarbamate (2.9 mmol, 1.00 equiv) in 30 mL hydrochloric acid in 1,4-dioxane (4.0 M) was stirred at room temperature for 3 h. The mixture was concentrated to afford 1.34 g (S)-2-amino-N-(5-(N-oxetan-3-ylsulfamoyl)naphthalen-1-yl)-3-phenylpropanamide hydrochloride as a light yellow solid (100% yield). MS (ESI+) m/z 426 [M+H]+.

464

Preparation of (S)-N-(1-(5-(N-oxetan-3-ylsulfamoyl)naphthalen-1-ylamino)-1-oxo-3-phenylpropan-2-yl)cyclohexanecarboxamide (I-130)

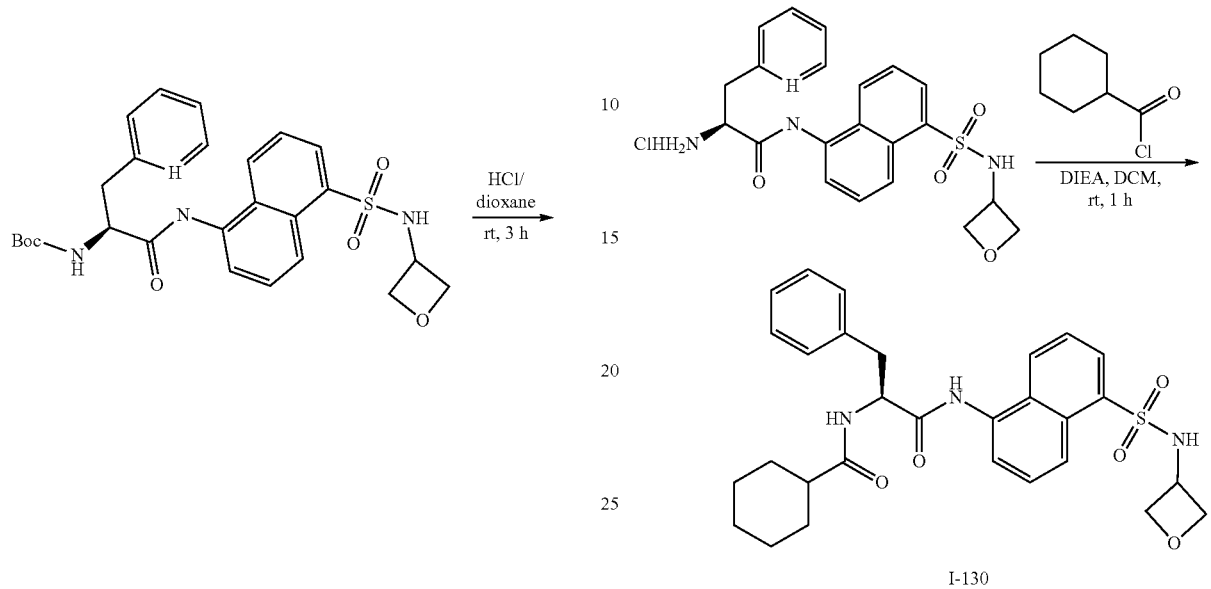

I-130

To a mixture of 150 mg (S)-2-amino-N-(5-(N-oxetan-3-ylsulfamoyl)naphthalen-1-yl)-3-phenylpropanamide hydrochloride (0.32 mmol, 1.0 equiv) and 206.4 mg N,N-diisopropylethylamine (1.6 mmol, 5.00 equiv) in 10 mL dichloromethane was added 46.8 mg cyclohexanecarbonyl chloride (0.32 mmol, 1.00 equiv) at 0° C. The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+ 0.1% NH$_3$—H$_2$O) and ACN (30% ACN up to 46% in 7 min); UV detection at 254/220 nm. The product-containing fractions were combined and evaporated partially in vacuo and lyophilized overnight to afford 44.3 mg (S)-N-(1-(5-(N-oxetan-3-ylsulfamoyl)naphthalen-1-ylamino)-1-oxo-3-phenylpropan-2-yl)cyclohexanecarboxamide (I-130) as a white solid.

Using this general procedure for the preparation of I-130 and substituting the appropriate acid chloride in the last step, the following compounds were prepared.

TABLE 11

Compounds prepared according to Example 69.

| Compound | Chemical Name | Yield | MS | 1HNMR |
|---|---|---|---|---|
| I-130 | (S)-N-(1-(5-(N-oxetan-3-ylsulfamoyl)naphthalen-1-ylamino)-1-oxo-3-phenylpropan-2-yl)cyclohexanecarboxamide | 26% | MS (ESI+, m/z): Calcd for C29H33N3O5S: 535; found 536 [M + H]+; | 1H NMR (400 MHz, CD$_3$OD) δ 8.63 (d, 1H), 8.21 (dd, 1H), 7.86 (d, 1H), 7.69 (dd, 1H), 7.55-7.51 (m, 2H), 7.39-7.32 (m, 5H), 4.90-4.86 (m, 1H), 4.55-4.40 (m, 3H), 4.30-4.27 (m, 2H), 3.28-3.13 (m, 2H), 2.47-2.28 (m, 1H), 1.90-1.70 (m, 5H), 1.56-1.22 (m, 5H). |

TABLE 11-continued

Compounds prepared according to Example 69.

| Compound | Chemical Name | Yield | MS | 1HNMR |
|---|---|---|---|---|
| I-131 | (S)-4-fluoro-N-(1-(5-(N-oxetan-3-ylsulfamoyl)naphthalen-1-ylamino)-1-oxo-3-phenylpropan-2-yl)benzamide | 28% | MS (ESI+, m/z): Calcd for C29H26FN3O5S: 547; found 548 [M + H]+ | $^1$H NMR (300 MHz, CD3OD) δ 8.63 (d, 1H), 8.20 (dd, 1H), 7.96-7.88 (m, 3H), 7.68 (dd, 1H), 7.58-7.51 (m, 2H), 7.50-7.32 (m, 5H), 7.21 (t, 2H), 5.13-5.06 (m, 1H), 4.52-4.38 (m, 3H), 4.32-4.24 (m, 2H), 3.41-3.34 (m, 1H), 3.28-3.20 (m, 1H). |

Example 70. Preparation of (S)-4-fluoro-N-(1-(4-(N-(2-methoxyethyl)sulfamoyl)phenylamino)-1-oxo-3-phenylpropan-2-yl)benzamide, I-132

Using the general N-sulfonylation procedure described in Example 2a and substituting the appropriate amine in the last step, I-132 and the following compounds were prepared.

TABLE 12

Preparation of compounds according to Example 2a.

| Compound | Chemical Name | Yield | MS | 1HNMR |
|---|---|---|---|---|
| I-132 | (S)-4-fluoro-N-(1-(4-(N-(2-methoxyethyl)sulfamoyl)phenylamino)-1-oxo-3-phenylpropan-2-yl)benzamide | 48% | MS (ESI+, m/z): Calcd for C25H26FN3O5S: 499; found 500 [M + H]+; | $^1$H NMR (300 MHz, CD$_3$OD) δ 7.86-7.70 (m, 6H), 7.34-7.14 (m, 7H), 4.95-4.90 (m, 1H), 3.35 (t, 2H), 3.27 (s, 3H), 3.24-3.15 (m, 2H), 3.01 (t, 2H). |
| I-133 | (S)-N-(1-(4-(N-(2-(dimethylamino)ethyl)sulfamoyl)phenylamino)-1-oxo-3-phenylpropan-2-yl)-4-fluorobenzamide | 50% | MS (ESI+, m/z): Calcd for C26H29FN4O4S: 512; found 513 [M + H]+ | $^1$H NMR (400 MHz, CD$_3$OD) δ 7.87-7.74 (m, 6H), 7.36-7.17 (m, 7H), 4.96-4.90 (m, 1H), 3.32-3.14 (m, 2H), 2.97 (t, 2H), 2.42 (t, 2H), 2.22 (s, 6H). |
| I-134 | (S)-4-fluoro-N-(1-(4-(N-(1-methoxy-2-methylpropan-2-yl)sulfamoyl)phenylamino)-1-oxo-3-phenylpropan-2-yl)benzamide | 49% | MS (ESI+, m/z): Calcd for C27H30FN3O5S: 527; found 528 [M + H]+; | $^1$H NMR (400 MHz, CD$_3$OD) δ 7.88-7.81 (m, 4H), 7.73-7.69 (m, 2H), 7.36-7.17 (m, 7H), 4.95-4.90 (m, 1H), 3.32-3.25 (m, 1H), 3.23-3.18 (m, 6H), 1.20 (s, 6H). |
| I-135 | (S)-N-(1-(4-(N-(2-tert-butoxyethyl)sulfamoyl)phenylamino)-1-oxo-3-phenylpropan-2-yl)-4-fluorobenzamide | 46% | MS (ESI+, m/z): Calcd for C28H32FN3O5S: 541; found 542 [M + H]+; | $^1$H NMR (400 MHz, CD$_3$OD) δ 7.87-7.73 (m, 6H), 7.36-7.17 (m, 7H), 4.95-4.90 (m, 1H), 3.37 (t, 2H), 3.32-3.15 (m, 2H), 2.99 (t, 2H), 1.13 (s, 9H). |
| I-136 | (S)-4-fluoro-N-(1-(4-(N-(3-methyloxetan-3-yl)sulfamoyl)phenylamino)-1-oxo-3-phenylpropan-2-yl)benzamide | 45% | MS (ESI+, m/z): Calcd for C26H26FN3O5S: 511; found 512 [M + H]+; | $^1$H NMR (400 MHz, CD$_3$OD) δ 7.87-7.72 (m, 6H), 7.34-7.15 (m, 7H), 4.95-4.90 (m, 1H), 4.68 (d, 2H), 4.22 (d, 2H), 3.32-3.15 (m, 2H), 1.54 (s, 3H). |
| I-137 | (S)-4-fluoro-N-(1-(4-(N-(1-hydroxy-2-methylpropan-2-yl)sulfamoyl)phenylamino)-1-oxo-3-phenylpropan-2-yl)benzamide | 42% | MS (ESI+, m/z): Calcd for C26H28FN3O5S: 513; found 514 [M + H]+; | $^1$H NMR (300 MHz, d$_6$-DMSO) δ 10.59 (s, 1H), 8.87 (d, 1H), 7.90 (dd, 2H), 7.84-7.75 (m, 4H), 7.40 (d, 2H), 7.32-7.15 (m, 5H), 4.84-4.81 (m, 1H), 4.74-4.70 (m, 1H), 3.18-3.10 (m, 4H), 1.00 (s, 6H). |
| I-138 | (S)-4-fluoro-N-(1-(4-(N-(2-hydroxyethyl)sulfamoyl)phenylamino)-1-oxo-3-phenylpropan-2-yl)benzamide | 43% | MS (ESI+, m/z): Calcd for C24H24FN3O5S: 485; found 486 [M + H]+; | $^1$H NMR (400 MHz, CD$_3$OD) δ 7.76-7.61 (m, 6H), 7.24-7.06 (m, 7H), 4.85-4.80 (m, 1H), 3.44-3.38 (m, 2H), 3.24-3.03 (m, 2H), 2.96 (t, 2H). |

467

Example 71: (S)-N-(1-(4-(N-ethylsulfamoyl)phenylamino)-1-oxo-3-(pyridin-2-yl)propan-2-yl)-4-fluorobenzamide, 1-139

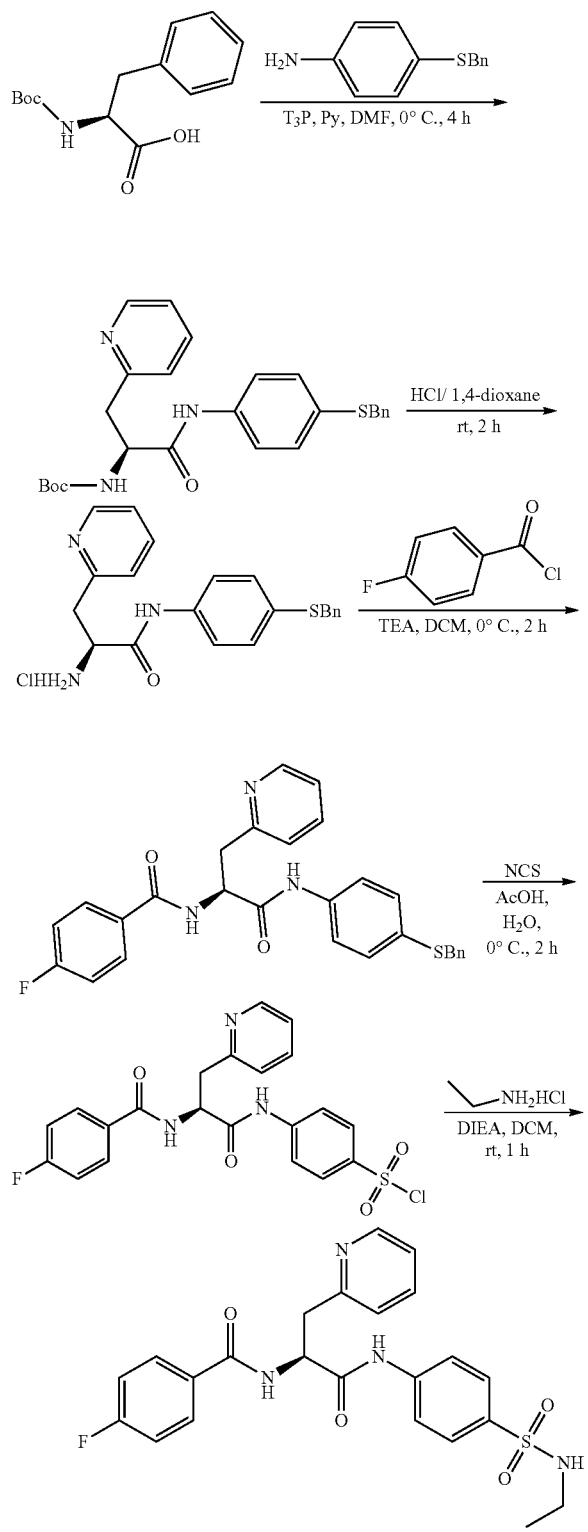

468

Preparation of (S)-tert-butyl 1-(4-(benzylthio)phenylamino)-1-oxo-3-(pyridin-2-yl)propan-2-ylcarbamate

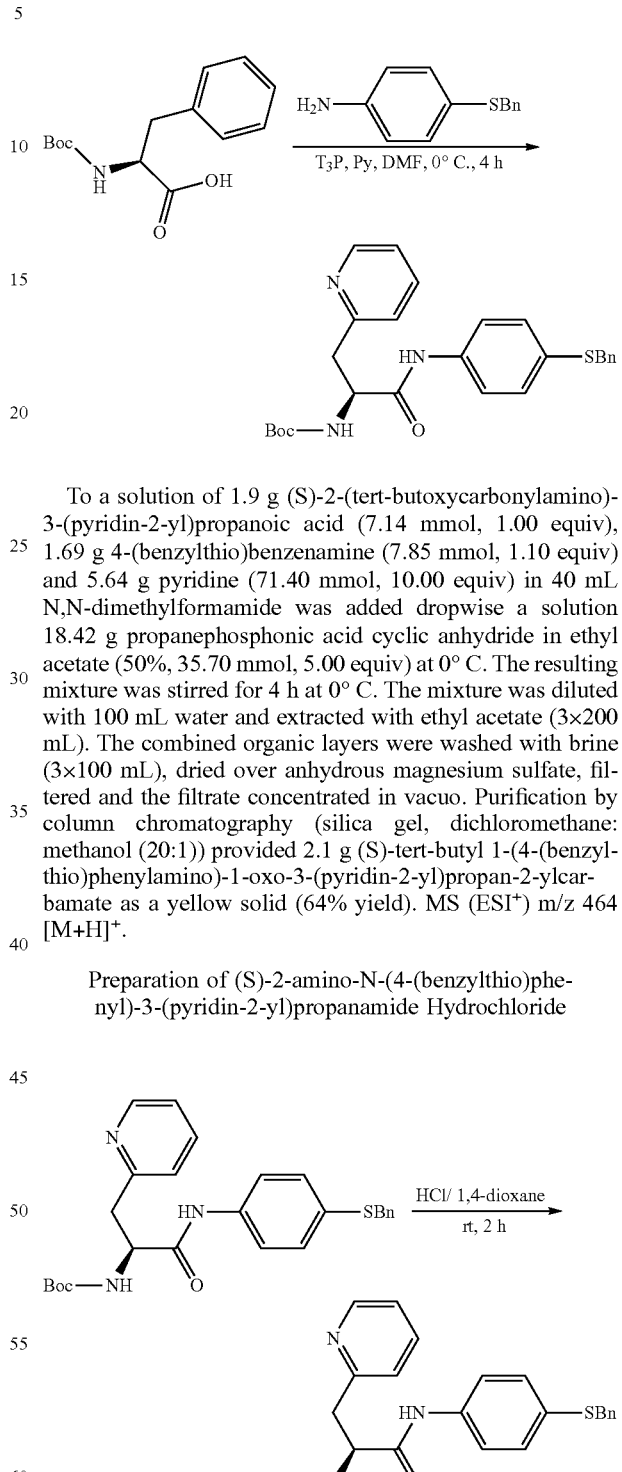

To a solution of 1.9 g (S)-2-(tert-butoxycarbonylamino)-3-(pyridin-2-yl)propanoic acid (7.14 mmol, 1.00 equiv), 1.69 g 4-(benzylthio)benzenamine (7.85 mmol, 1.10 equiv) and 5.64 g pyridine (71.40 mmol, 10.00 equiv) in 40 mL N,N-dimethylformamide was added dropwise a solution 18.42 g propanephosphonic acid cyclic anhydride in ethyl acetate (50%, 35.70 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, dichloromethane:methanol (20:1)) provided 2.1 g (S)-tert-butyl 1-(4-(benzylthio)phenylamino)-1-oxo-3-(pyridin-2-yl)propan-2-ylcarbamate as a yellow solid (64% yield). MS (ESI$^+$) m/z 464 [M+H]$^+$.

Preparation of (S)-2-amino-N-(4-(benzylthio)phenyl)-3-(pyridin-2-yl)propanamide Hydrochloride A mixture of 2.1 g (S)-tert-butyl 1-(4-(benzylthio)phenylamino)-1-oxo-3-(pyridin-2-yl)propan-2-ylcarbamate (4.61 mmol, 1.00 equiv) in 20 mL hydrochloric acid in 1,4-dioxane (4.0 M) was stirred at room temperature for 2 h. The mixture was concentrated to afford 1.85 g (S)-2-amino- N-(4-(benzylthio)phenyl)-3-(pyridin-2-yl)propanamide hydrochloride as a light yellow solid (100% yield). MS (ESI⁺) m/z 364 [M+H]⁺.

Preparation of (S)-N-(1-(4-(benzylthio)phenylamino)-1-oxo-3-(pyridin-2-yl)propan-2-yl)-4-fluorobenzamide

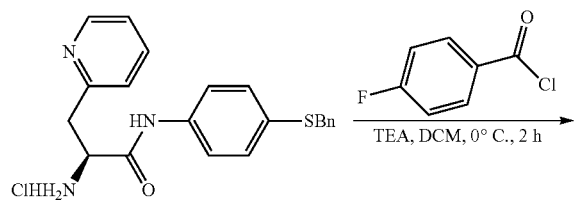

To a solution of 1.85 g (S)-2-amino-N-(4-(benzylthio)phenyl)-3-(pyridin-2-yl)propanamide hydrochloride (4.61 mmol, 1.00 equiv) and 2.79 g triethylamine (27.66 mmol, 6.00 equiv) in 20 mL dichloromethane was added dropwise 874 mg 4-fluorobenzoyl chloride (5.53 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, dichloromethane:methanol (15:1)) afforded 1.4 g (S)-N-(1-(4-(benzylthio)phenylamino)-1-oxo-3-(pyridin-2-yl)propan-2-yl)-4-fluorobenzamide as a yellow solid (63% yield). MS (ESI⁺) m/z 486 [M+H]⁺.

Preparation of (S)-4-(2-(4-fluorobenzamido)-3-(pyridin-2-yl)propanamido)benzene-1-sulfonyl Chloride

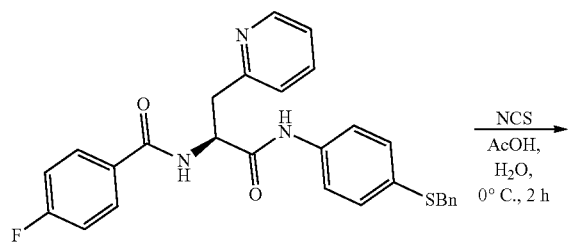

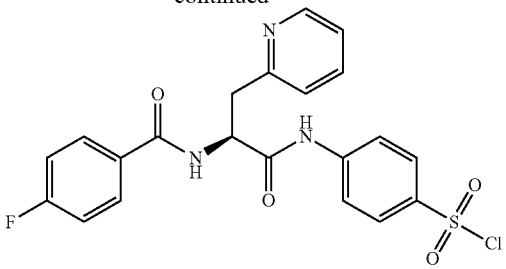

To a solution of 1.4 g (S)-N-(1-(4-(benzylthio)phenylamino)-1-oxo-3-(pyridin-2-yl)propan-2-yl)-4-fluorobenzamide (2.90 mmol, 1.00 equiv) in 12 mL acetic acid and 4 mL water was added 1.55 g N-chlorosuccinimide (11.6 mmol, 4.00 equiv) at 0° C. The resulting mixture was stirred at 0° C. for 2 h. The mixture was diluted with 30 mL water and extracted with dichloromethane (3×50 mL). The combined organic layers were washed with brine (1×50 mL), dried over anhydrous magnesium sulfate, filtered and the filtrate concentrated to give 0.6 g (S)-4-(2-(4-fluorobenzamido)-3-(pyridin-2-yl)propanamido)benzene-1-sulfonyl chloride as a white solid (45% yield). MS (ESI⁺) m/z 462 [M+H]⁺.

Preparation of (S)-N-(1-(4-(N-ethylsulfamoyl)phenylamino)-1-oxo-3-(pyridin-2-yl)propan-2-yl)-4-fluorobenzamide (I-139)

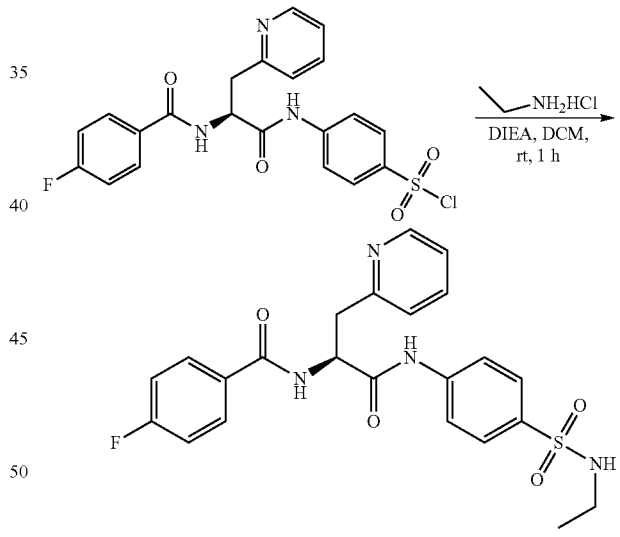

I-139

To a mixture of 89.1 mg ethanamine hydrochloride (1.1 mmol, 5.0 equiv) and 141.9 mg N,N-diisopropylethylamine (1.1 mmol, 5.00 equiv) in 10 mL dichloromethane was added 100 mg (S)-4-(2-(4-fluorobenzamido)-3-(pyridin-2-yl)propanamido)benzene-1-sulfonyl chloride (0.22 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH₄HCO₃+0.1% NH₃·H₂O) and ACN (22% ACN up to 38% in 7 min); UV detection at 254/220 nm. The product-containing fractions were combined and evaporated partially in vacuo and lyophilized overnight to afford 37.3 mg (S)-N-(1-(4-(N-ethylsulfamoyl)phenylamino)-1-oxo-3-(pyridin-2-yl)propan-2-yl)-4-fluorobenzamide (I-139) as a white solid.

Using this general procedure for the preparation of I-139 and substituting the appropriate amine in the last step, the following compounds were prepared.

TABLE 13

Compounds prepared according to Example 71.

| Compound | Chemical Name | yield | MS | 1HNMR |
|---|---|---|---|---|
| I-139 | (S)-N-(1-(4-(N-ethylsulfamoyl)phenylamino)-1-oxo-3-(pyridin-2-yl)propan-2-yl)-4-fluorobenzamide | 36% | MS (ESI⁺, m/z): Calcd for C23H23FN4O4S: 470; found 471 [M + H]⁺; | ¹H NMR (300 MHz, CD₃OD) δ 8.54 (dd, 1H), 7.91-7.74 (m, 7H), 7.42 (d, 1H), 7.32-7.28 (m, 1H), 7.23-7.17 (m, 2H), 5.13-5.08 (m, 1H), 3.48-3.34 (m, 2H), 2.89 (q, 2H), 1.07 (t, 3H). |
| I-140 | (S)-4-fluoro-N-(1-(4-(N-oxetan-3-ylsulfamoyl)phenylamino)-1-oxo-3-(pyridin-2-yl)propan-2-yl)benzamide | 38% | MS (ESI⁺, m/z): Calcd for C24H23FN4O5S: 498; found 499 [M + H]⁺ | ¹H NMR (300 MHz, CD₃OD) δ 8.52 (d, 1H), 7.89-7.72 (m, 7H), 7.39 (d, 1H), 7.30-7.26 (m, 1H), 7.21-7.15 (m, 2H), 5.10-5.05 (m, 1H), 4.61 (t, 2H), 4.51-4.42 (m, 1H), 4.34 (t, 2H), 3.48-3.34 (m, 2H). |
| I-141 | (S)-N-(1-(4-(N-bicyclo[1.1.1]pentan-1-ylsulfamoyl)phenylamino)-1-oxo-3-(pyridin-2-yl)propan-2-yl)-4-fluorobenzamide | 32% | MS (ESI⁺, m/z): Calcd for C26H25FN4O4S: 508; found 509 [M + H]⁺; | ¹H NMR (400 MHz, CD₃OD) δ 8.54 (dd, 1H), 7.91-7.75 (m, 7H), 7.42 (d, 1H), 7.30-7.29 (m, 1H), 7.23-7.18 (m, 2H), 5.12-5.09 (m, 1H), 3.50-3.34 (m, 2H), 2.29 (s, 1H), 1.81 (s, 6H). |
| I-142 | (S)-N-(1-(4-(N-cyclobutylsulfamoyl)phenylamino)-1-oxo-3-(pyridin-2-yl)propan-2-yl)-4-fluorobenzamide | 37% | MS (ESI⁺, m/z): Calcd for C25H25FN4O4S: 496; found 497 [M + H]⁺; | ¹H NMR (400 MHz, CD₃OD) δ 8.54 (d, 1H), 7.90-7.75 (m, 7H), 7.42 (d, 1H), 7.32-7.28 (m, 1H), 7.23-7.18 (m, 2H), 5.12-5.08 (m, 1H), 3.75-3.71 (m, 1H), 3.49-3.34 (m, 2H), 2.04-1.99 (m, 2H), 1.83-1.77 (m, 2H), 1.62-1.55 (m, 2H). |

Example 72: (S)-N-(1-(4-(N-ethylsulfamoyl)-2-methoxyphenylamino)-1-oxo-3-phenylpropan-2-yl)-4-fluorobenzamide, I-143

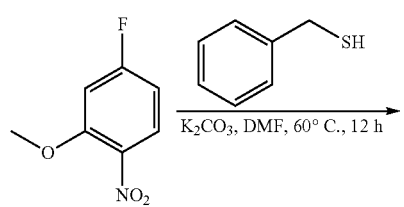

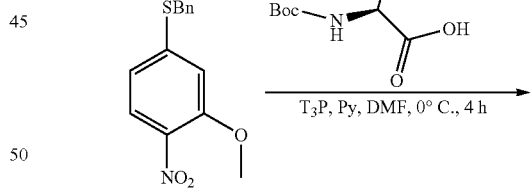

-continued

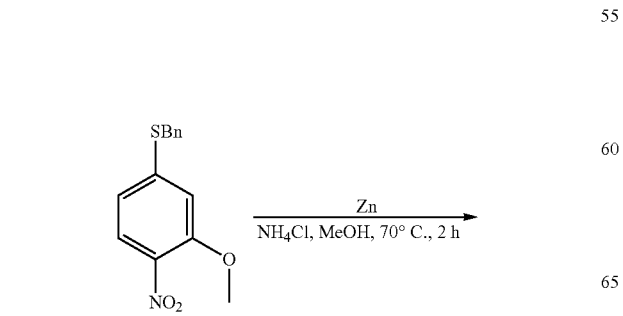

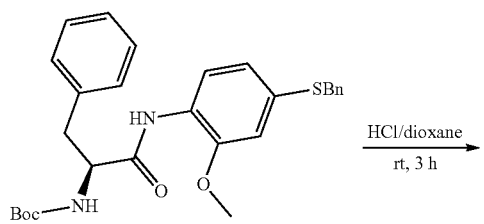

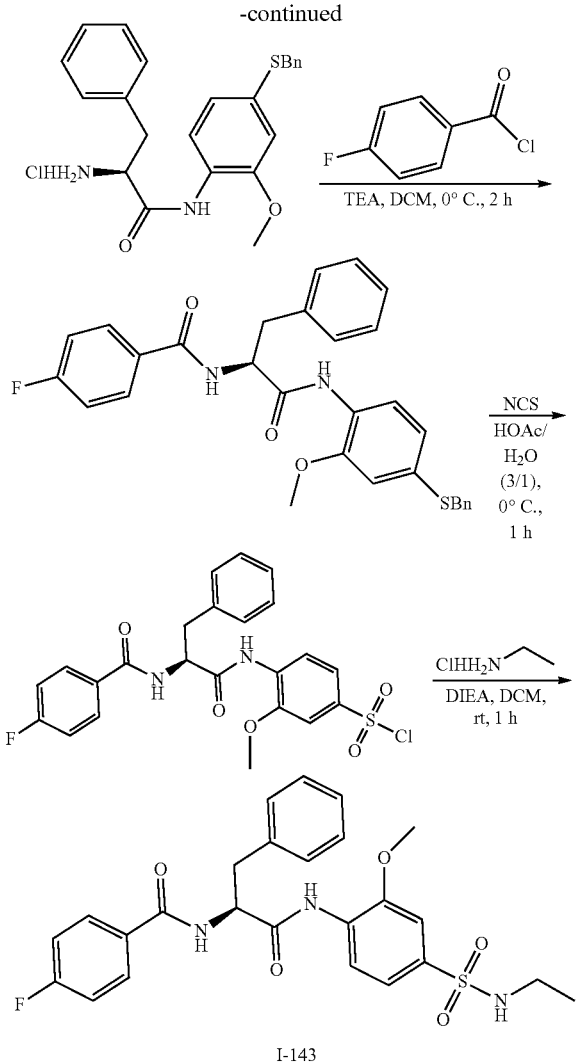

I-143

Preparation of benzyl(3-methoxy-4-nitrophenyl)sulfane

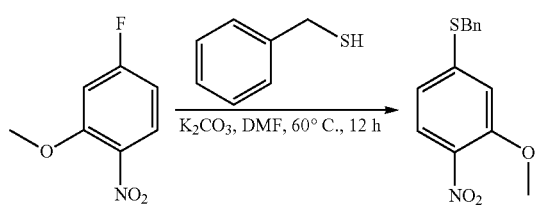

To a solution of 17.1 g 4-fluoro-2-methoxy-1-nitrobenzene (100 mmol, 1.00 equiv) and 27.6 g potassium carbonate (200 mmol, 2.00 equiv) in 500 mL anhydrous N,N-dimethylformamide was added dropwise 14.88 g phenylmethanethiol (120 mmol, 1.20 equiv) at room temperature. The resulting mixture was stirred for 12 h at 60° C. The mixture was cooled to r.t, diluted with 500 mL water. The solids were collected by filtration to afforded 17.6 g benzyl(3-methoxy-4-nitrophenyl)sulfane as a yellow solid (64% yield). MS (ESI$^+$) m/z 276 [M+H]$^+$.

Preparation of 4-(benzylthio)-2-methoxybenzenamine

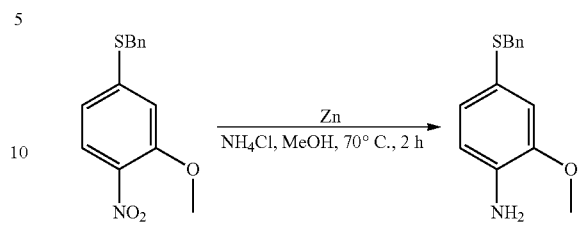

To a solution of 17.6 g benzyl(3-methoxy-4-nitrophenyl)sulfane (64 mmol, 1.00 equiv) in 300 mL methanol was added 17.12 g ammonium chloride (320 mmol, 5.00 equiv) and 16.26 g zinc (256 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (5:1)) afforded 8 g 4-(benzylthio)-2-methoxybenzenamine as an orange oil (51% yield). MS (ESI$^+$) m/z 246 [M+H]$^+$.

Preparation of (S)-tert-butyl 1-(4-(benzylthio)-2-methoxyphenylamino)-1-oxo-3-phenylpropan-2-ylcarbamate

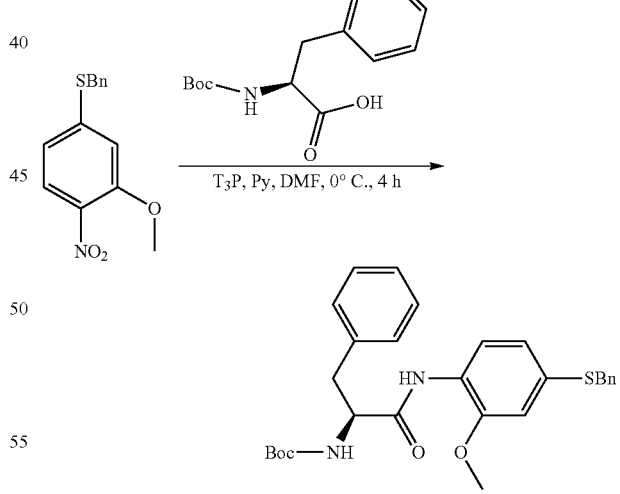

To a solution of 2.85 g (S)-2-(tert-butoxycarbonylamino)-3-phenylpropanoic acid (10.75 mmol, 1.00 equiv), 2.9 g 4-(benzylthio)-2-methoxybenzenamine (11.83 mmol, 1.10 equiv) and 8.49 g pyridine (107.51 mmol, 10.00 equiv) in 40 mL N,N-dimethylformamide was added dropwise a solution 27.73 g propanephosphonic acid cyclic anhydride in ethyl acetate (50%, 53.75 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (2:1)) provided 3 g (S)-tert-butyl 1-(4-(benzylthio)-2-methoxyphenylamino)-1-oxo-3-phenylpropan-2-ylcarbamate as a yellow solid (57% yield). MS (ESI⁺) m/z 493 [M+H]⁺.

Preparation of (S)-2-amino-N-(4-(benzylthio)-2-methoxyphenyl)-3-phenylpropanamide Hydrochloride

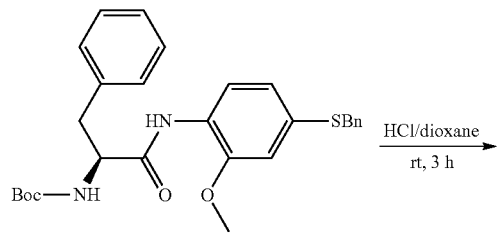

A mixture of 3 g (S)-tert-butyl 1-(4-(benzylthio)-2-methoxyphenylamino)-1-oxo-3-phenylpropan-2-ylcarbamate (6.1 mmol, 1.00 equiv) in 20 mL hydrochloric acid in 1,4-dioxane (4.0 M) was stirred at room temperature for 3 h. The mixture was concentrated to afford 2.62 g (S)-2-amino-N-(4-(benzylthio)-2-methoxyphenyl)-3-phenylpropanamide hydrochloride as a light yellow solid (100% yield). MS (ESI⁺) m/z 393 [M+H]⁺.

Preparation of (S)-N-(1-(4-(benzylthio)-2-methoxyphenylamino)-1-oxo-3-phenylpropan-2-yl)-4-fluorobenzamide

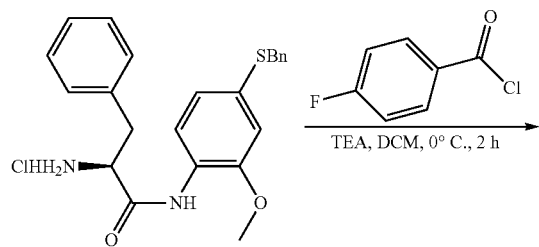

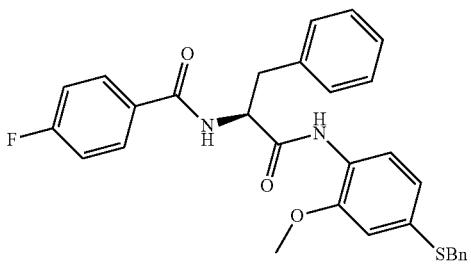

To a solution of 1.29 g (S)-2-amino-N-(4-(benzylthio)-2-methoxyphenyl)-3-phenylpropanamide hydrochloride (3.00 mmol, 1.00 equiv) and 1.818 g triethylamine (18.00 mmol, 6.00 equiv) in 20 mL dichloromethane was added dropwise 568.8 mg 4-fluorobenzoyl chloride (3.60 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1 g (S)-N-(1-(4-(benzylthio)-2-methoxyphenylamino)-1-oxo-3-phenylpropan-2-yl)-4-fluorobenzamide as a yellow solid (65% yield). MS (ESI⁺) m/z 515 [M+H]⁺.

Preparation of (S)-4-(2-(4-fluorobenzamido)-3-phenylpropanamido)-3-methoxybenzene-1-sulfonyl Chloride

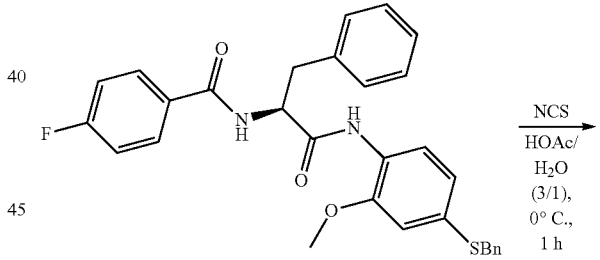

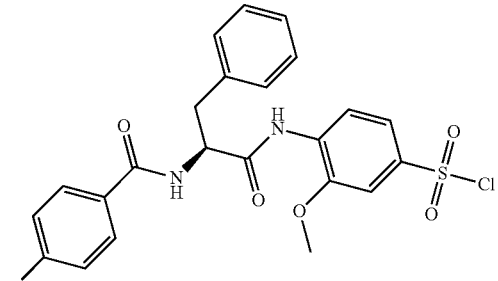

To a solution of 1 g (S)-N-(1-(4-(benzylthio)-2-methoxyphenylamino)-1-oxo-3-phenylpropan-2-yl)-4-fluorobenzamide (1.94 mmol, 1.00 equiv) in 6 mL acetic acid and 2 mL water was added 1.04 g N-chlorosuccinimide (7.76 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.58 g (S)-4-(2-(4-fluorobenzamido)-3-phenylpropanamido)-3-methoxybenzene-1-sulfonyl chloride as a white solid (61% yield). MS (ESI+) m/z 491 and 493 [M+H]+.

Preparation of (S)-N-(1-(4-(N-ethylsulfamoyl)-2-methoxyphenylamino)-1-oxo-3-phenylpropan-2-yl)-4-fluorobenzamide (I-143)

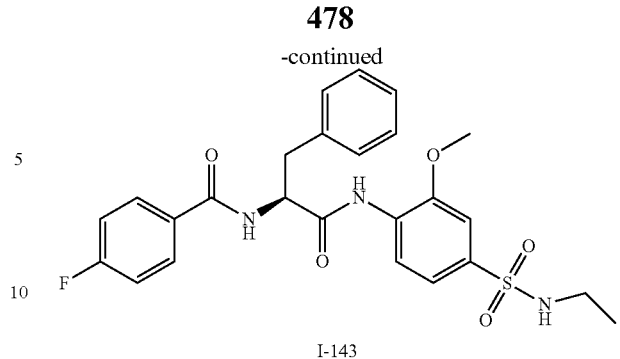

I-143

To a mixture of 85.05 mg ethanamine hydrochloride (1.05 mmol, 5.0 equiv) and 135.45 mg N,N-diisopropylethylamine (1.05 mmol, 5.00 equiv) in 10 mL dichloromethane was added 103 mg (S)-4-(2-(4-fluorobenzamido)-3-phenylpropanamido)-3-methoxybenzene-1-sulfonyl chloride (0.21 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH4HCO3+0.1% NH3—H2O) and ACN (32% ACN up to 64% in 7 min); UV detection at 254/220 nm. The product-containing fractions were combined and evaporated partially in vacuo and lyophilized overnight to afford 42.1 mg (S)-N-(1-(4-(N-ethylsulfamoyl)-2-methoxyphenylamino)-1-oxo-3-phenylpropan-2-yl)-4-fluorobenzamide (I-143) as a white solid.

Using this general procedure for the preparation of I-143 and substituting the appropriate amine in the last step, the following compounds were prepared.

TABLE 14

Compounds prepared according to Example 72.

| Compound | Chemical Name | yield | MS | 1HNMR |
|---|---|---|---|---|
| I-232 | (S)-N-(1-(4-(N-ethylsulfamoyl)-2-methoxyphenylamino)-1-oxo-3-phenylpropan-2-yl)-4-fluorobenzamide | 40% | MS (ESI+, m/z): Calcd for C25H26FN3O5S: 499; found 500 [M + H]+; | 1H NMR (300 MHz, CD3OD) δ 8.34 (d, 1H), 7.85-7.78 (m, 2H), 7.44-7.15 (m, 9H), 5.06-5.00 (m, 1H), 3.89 (s, 3H), 3.39-3.34 (m, 1H), 3.20-3.12 (m, 1H), 2.87 (q, 2H), 1.05 (t, 3H). |
| I-144 | (S)-4-fluoro-N-(1-(2-methoxy-4-(N-oxetan-3-ylsulfamoyl)phenylamino)-1-oxo-3-phenylpropan-2-yl)benzamide | 38% | MS (ESI+, m/z): Calcd for C26H26FN3O6S: 527; found 528 [M + H]+ | 1H NMR (300 MHz, CD3OD) δ 8.36 (d, 1H), 7.86-7.79 (m, 2H), 7.43-7.15 (m, 9H), 5.06-5.01 (m, 1H), 4.63 (t, 2H), 4.53-4.44 (m, 1H), 4.35 (t, 2H), 3.90 (s, 3H), 3.40-3.34 (m, 1H), 3.21-3.13 (m, 1H). |
| I-145 | (S)-N-(1-(4-(N-bicyclo[1.1.1]pentan-1-ylsulfamoyl)-2-methoxyphenylamino)-1-oxo-3-phenylpropan-2-yl)-4-fluorobenzamide | 36% | MS (ESI+, m/z): Calcd for C28H28FN3O5S: 537; found 538 [M + H]+; | 1H NMR (300 MHz, CD3OD) δ 8.37 (d, 1H), 7.86-7.82 (m, 2H), 7.47-7.17 (m, 9H), 5.08-5.02 (m, 1H), 3.90 (s, 3H), 3.40-3.34 (m, 1H), 3.22-3.13 (m, 1H), 2.30 (s, 1H), 1.82 (s, 6H). |

Example 73: (S)-N-(1-(4-(N-ethylsulfamoyl)-3-methoxyphenylamino)-1-oxo-3-phenylpropan-2-yl)-4-fluorobenzamide, I-146

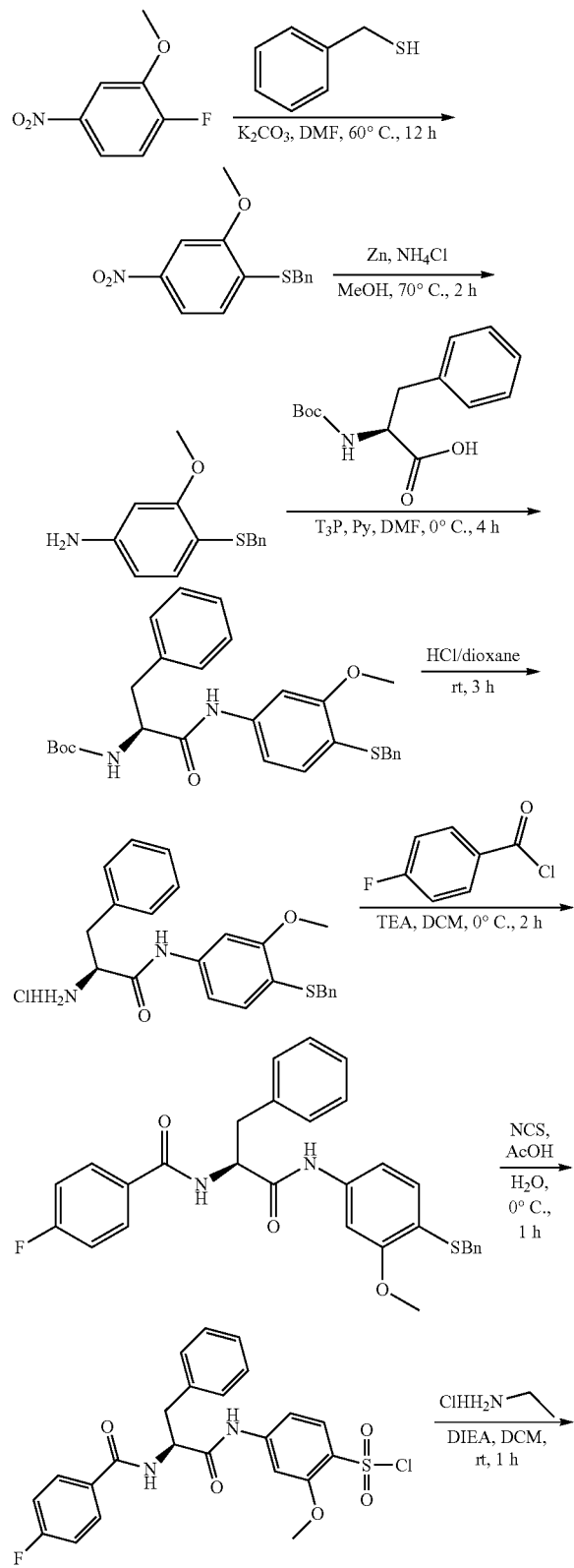

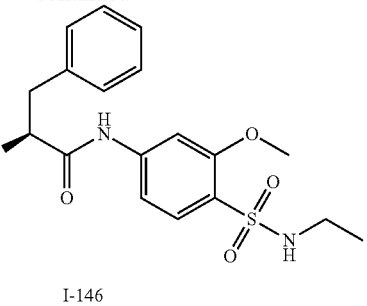

I-146

Preparation of benzyl(2-methoxy-4-nitrophenyl)sulfane

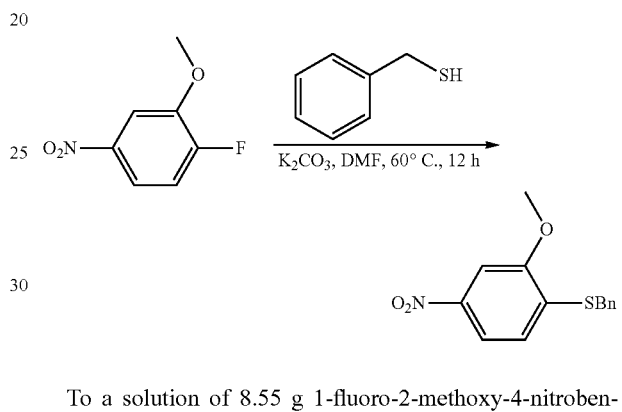

To a solution of 8.55 g 1-fluoro-2-methoxy-4-nitrobenzene (50 mmol, 1.00 equiv) and 13.8 g potassium carbonate (100 mmol, 2.00 equiv) in 300 mL anhydrous N,N-dimethylformamide was added dropwise 7.44 g of phenylmethanethiol (60 mmol, 1.20 equiv) at room temperature. The resulting mixture was stirred for 12 h at 60° C. The mixture was cooled to room temperature, diluted with 500 mL water and extracted with ethyl acetate (3×500 mL). The combined organic layers were washed with brine (3×200 mL), dried over anhydrous magnesium sulfate, filtered and the filtrate was concentrated in vacuo. Purification by column chromatography (silica gel, petroleum ether:ethyl acetate (5:1)) afforded 8.4 g benzyl(2-methoxy-4-nitrophenyl)sulfane as a yellow solid (61% yield). MS (ESI+) m/z 276 [M+H]+.

Preparation of 4-(benzylthio)-3-methoxybenzenamine

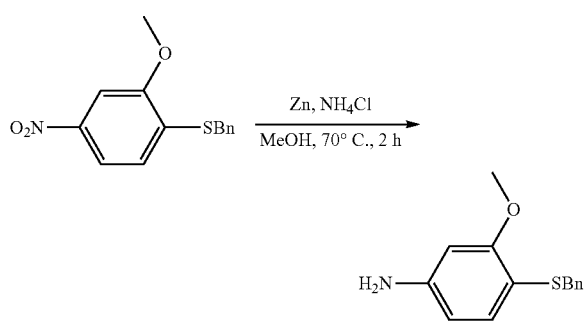

481

To a solution of 8.4 g benzyl(2-methoxy-4-nitrophenyl)sulfane (30.55 mmol, 1.00 equiv) in 200 mL methanol was added 8.17 g ammonium chloride (152.75 mmol, 5.00 equiv) and 7.76 g zinc (122.2 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (2:1)) afforded 4.5 g 4-(benzylthio)-3-methoxybenzenamine as an orange oil (60% yield). MS (ESI$^+$) m/z 246 [M+H]$^+$.

Preparation of (S)-tert-butyl 1-(4-(benzylthio)-3-methoxyphenylamino)-1-oxo-3-phenylpropan-2-ylcarbamate

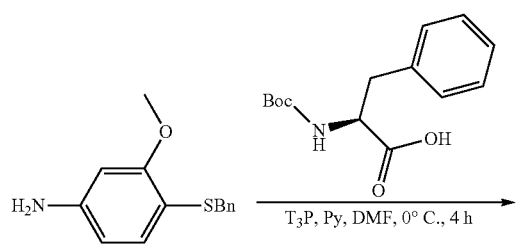

To a solution of 2.46 g 4-(benzylthio)-3-methoxybenzenamine (10 mmol, 1.00 equiv), 2.65 g (S)-2-(tert-butoxycarbonylamino)-3-phenylpropanoic acid (10 mmol, 1.00 equiv) and 7.9 g pyridine (100 mmol, 10.00 equiv) in 30 mL N,N-dimethylformamide was added dropwise a solution 25.8 g propanephosphonic acid cyclic anhydride in ethyl acetate (50%, 50 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (1:1)) provided 3.1 g (S)-tert-butyl 1-(4-(benzylthio)-3-methoxyphenylamino)-1-oxo-3-phenylpropan-2-ylcarbamate as a yellow solid (63% yield). MS (ESI$^+$) m/z 437 [M-56+H]$^+$.

482

Preparation of (S)-2-amino-N-(4-(benzylthio)-3-methoxyphenyl)-3-phenylpropanamide Hydrochloride

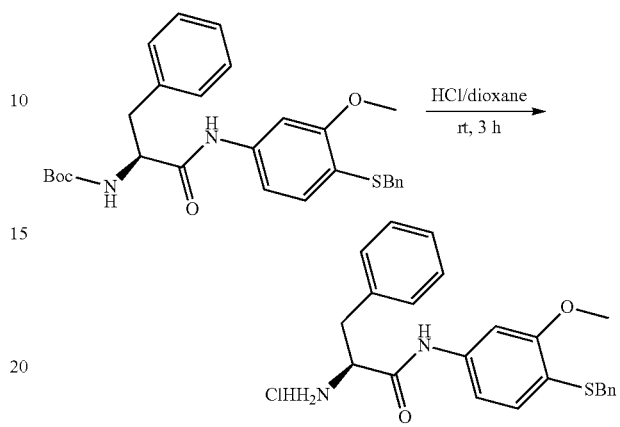

A mixture of 3.1 g (S)-tert-butyl 1-(4-(benzylthio)-3-methoxyphenylamino)-1-oxo-3-phenylpropan-2-ylcarbamate (6.3 mmol, 1.00 equiv) in 30 mL hydrochloric acid in 1,4-dioxane (4.0 M) was stirred at room temperature for 3 h. The mixture was concentrated to afford 2.7 g (S)-2-amino-N-(4-(benzylthio)-3-methoxyphenyl)-3-phenylpropanamide hydrochloride as a light yellow solid (100% yield). MS (ESI$^+$) m/z 393 [M+H]$^+$.

Preparation of (S)-N-(1-(4-(benzylthio)-3-methoxyphenylamino)-1-oxo-3-phenylpropan-2-yl)-4-fluorobenzamide

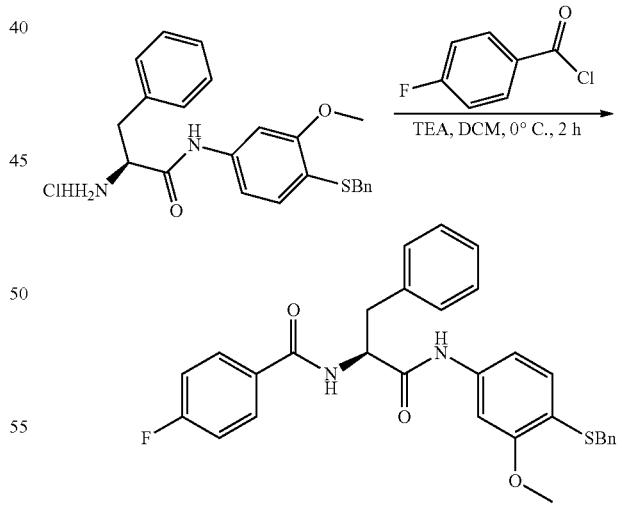

To a solution of 1.35 g (S)-2-amino-N-(4-(benzylthio)-3-methoxyphenyl)-3-phenylpropanamide hydrochloride (3.15 mmol, 1.00 equiv) and 1.91 g triethylamine (18.9 mmol, 6.00 equiv) in 20 mL dichloromethane was added dropwise 597.2 mg 4-fluorobenzoyl chloride (3.78 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1.06 g (S)-N-(1-(4-(benzylthio)-3-methoxyphenylamino)-1-oxo-3-phenylpropan-2-yl)-4-fluorobenzamide as a yellow solid (65% yield). MS (ESI$^+$) m/z 515 [M+H]$^+$.

Preparation of (S)-4-(2-(4-fluorobenzamido)-3-phenylpropanamido)-2-methoxybenzene-1-sulfonyl Chloride

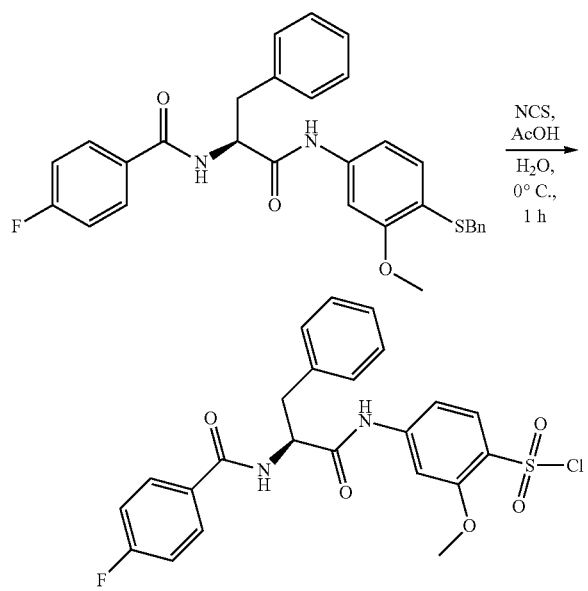

To a solution of 1.06 g (S)-N-(1-(4-(benzylthio)-3-methoxyphenylamino)-1-oxo-3-phenylpropan-2-yl)-4-fluorobenzamide (2.06 mmol, 1.00 equiv) in 9 mL acetic acid and 3 mL water was added 1.1 g N-chlorosuccinimide (8.24 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.7 g (S)-4-(2-(4-fluorobenzamido)-3-phenylpropanamido)-2-methoxybenzene-1-sulfonyl chloride as a white solid (69% yield). MS (ESI$^+$) m/z 491 and 493 [M+H]$^+$.

Preparation of (S)-N-(1-(4-(N-ethylsulfamoyl)-3-methoxyphenylamino)-1-oxo-3-phenylpropan-2-yl)-4-fluorobenzamide (I-146)

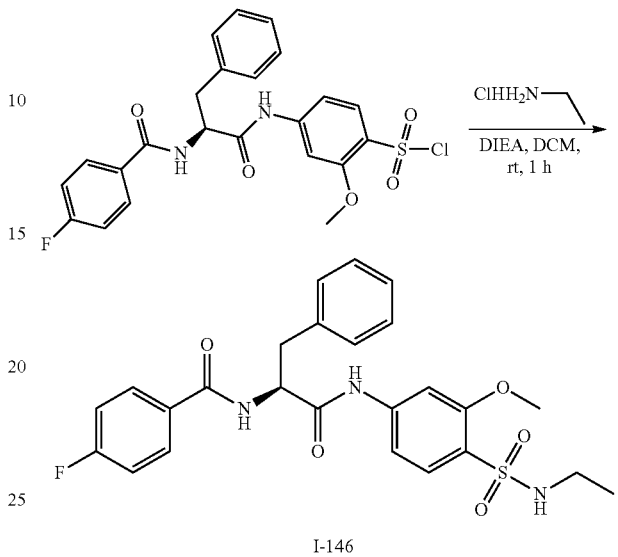

To a mixture of 82.62 mg ethanamine hydrochloride (1.02 mmol, 5.0 equiv) and 131.58 mg N,N-diisopropyl ethyl amine (1.02 mmol, 5.00 equiv) in 10 mL dichloromethane was added 100 mg (S)-6-(2-(4-fluorobenzamido)-3-phenylpropanamido)pyridine-3-sulfonyl chloride (0.204 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (34% ACN up to 56% in 7 min); UV detection at 254/220 nm. The product-containing fractions were combined and evaporated partially in vacuo and lyophilized overnight to afford 41.2 mg (S)-N-(1-(4-(N-ethylsulfamoyl)-3-methoxyphenylamino)-1-oxo-3-phenylpropan-2-yl)-4-fluorobenzamide (I-146) as a white solid.

Using this general procedure for the preparation of I-146 and substituting the appropriate amine in the last step, the following compounds were prepared.

TABLE 15

Compounds prepared according to Example 73.

| Compound | Chemical Name | yield | MS | 1HNMR |
|---|---|---|---|---|
| I-146 | (S)-N-(1-(4-(N-ethylsulfamoyl)-3-methoxyphenylamino)-1-oxo-3-phenylpropan-2-yl)-4-fluorobenzamide | 40% | MS (ESI$^+$, m/z): Calcd for C25H26FN3O5S: 499; found 500 [M + H]$^+$; | $^1$H NMR (300 MHz, CD$_3$OD) δ 7.87-7.83 (m, 2H), 7.73 (d, 1H), 7.60 (s, 1H), 7.36-7.12 (m, 8H), 4.98-4.90 (m, 1H), 3.94 (s, 3H), 3.30-3.13 (m, 2H), 2.87 (q, 2H), 1.05 (t, 3H). |

TABLE 15-continued

Compounds prepared according to Example 73.

| Compound | Chemical Name | yield | MS | 1HNMR |
|---|---|---|---|---|
| I-147 | (S)-4-fluoro-N-(1-(3-methoxy-4-(N-oxetan-3-ylsulfamoyl)phenylamino)-1-oxo-3-phenylpropan-2-yl)benzamide | 41% | MS (ESI⁺, m/z): Calcd for C26H26FN3O6S: 527; found 528 [M + H]⁺ | ¹H NMR (300 MHz, CD₃OD) δ 7.87-7.82 (m, 2H), 7.72 (d, 1H), 7.60 (s, 1H), 7.35-7.10 (m, 8H), 4.94-4.88 (m, 1H), 4.62-4.57 (m, 2H), 4.55-4.44 (m, 3H), 3.96 (s, 3H), 3.30-3.13 (m, 2H). |
| I-148 | (S)-N-(1-(4-(N-bicyclo[1.1.1]pentan-1-ylsulfamoyl)-3-methoxyphenylamino)-1-oxo-3-phenylpropan-2-yl)-4-fluorobenzamide | 43% | MS (ESI⁺, m/z): Calcd for C28H28FN3O5S: 537; found 538 [M + H]⁺; | ¹H NMR (300 MHz, CD₃OD) δ 7.88-7.83 (m, 2H), 7.73 (d, 1H), 7.60 (s, 1H), 7.35-7.12 (m, 8H), 4.94-4.88 (m, 1H), 3.94 (s, 3H), 3.30-3.13 (m, 2H), 2.24 (s, 1H), 1.72 (s, 6H). |
| I-149 | (S)-4-fluoro-N-(1-(3-methoxy-4-(N-(1-methoxy-2-methylpropan-2-yl)sulfamoyl)phenylamino)-1-oxo-3-phenylpropan-2-yl)benzamide | 44% | MS (ESI⁺, m/z): Calcd for C28H32FN3O6S: 557; found 558 [M + H]⁺; | ¹H NMR (400 MHz, CD₃OD) δ 7.76-7.73 (m, 2H), 7.61 (d, 1H), 7.48 (s, 1H), 7.24-7.01 (m, 8H), 4.83-4.79 (m, 1H), 3.84 (s, 3H), 3.24-3.15 (m, 1H), 3.10 (s, 3H), 3.09-3.04 (m, 1H), 3.02 (s, 2H), 1.00 (s, 6H). |
| I-150 | (S)-4-fluoro-N-(1-(3-methoxy-4-(N-(tetrahydro-2H-pyran-4-yl)sulfamoyl)phenylamino)-1-oxo-3-phenylpropan-2-yl)benzamide | 41% | MS (ESI⁺, m/z): Calcd for C28H30FN3O6S: 555; found 556 [M + H]⁺; | ¹H NMR (400 MHz, CD₃OD) δ 7.87-7.84 (m, 2H), 7.76 (d, 1H), 7.61 (s, 1H), 7.36-7.13 (m, 8H), 4.98-4.90 (m, 1H), 3.96 (s, 3H), 3.85-3.82 (m, 2H), 3.40-3.34 (m, 2H), 3.30-3.15 (m, 3H), 1.62-1.51 (m, 4H). |
| I-151 | (S)-4-fluoro-N-(1-(3-methoxy-4-(N-(2-methoxyethyl)sulfamoyl)phenylamino)-1-oxo-3-phenylpropan-2-yl)benzamide | 43% | MS (ESI⁺, m/z): Calcd for C26H28FN3O6S: 529; found 530 [M + H]⁺; | ¹H NMR (400 MHz, CD₃OD) δ 7.76-7.73 (m, 2H), 7.61 (d, 1H), 7.49 (s, 1H), 7.24-7.01 (m, 8H), 4.84-4.80 (m, 1H), 3.83 (s, 3H), 3.30-3.03 (m, 7H), 2.90 (t, 2H). |
| I-152 | (S)-4-fluoro-N-(1-(4-(N-(2-hydroxyethyl)sulfamoyl)-3-methoxyphenylamino)-1-oxo-3-phenylpropan-2-yl)benzamide | 45% | MS (ESI⁺, m/z): Calcd for C25H26FN3O6S: 515; found 516 [M + H]⁺; | ¹H NMR (400 MHz, CD₃OD) δ 7.88-7.85 (m, 2H), 7.74 (d, 1H), 7.63 (s, 1H), 7.36-7.14 (m, 8H), 4.95-4.90 (m, 1H), 3.96 (s, 3H), 3.54 (t, 2H), 3.30-3.15 (m, 2H), 2.93 (t, 2H). |
| I-153 | (S)-4-fluoro-N-(1-(3-methoxy-4-(N-(2-methyl-1-morpholinopropan-2-yl)sulfamoyl)phenylamino)-1-oxo-3-phenylpropan-2-yl)benzamide | 41% | MS (ESI⁺, m z): Calcd for C31H37FN4O6S: 612; found 613 [M + H]⁺; | ¹H NMR (300 MHz, CD₃OD) δ 7.87-7.83 (m, 2H), 7.73 (d, 1H), 7.61 (s, 1H), 7.35-7.12 (m, 8H), 4.95-4.90 (m, 1H), 3.99 (s, 3H), 3.73-3.67 (m, 4H), 3.30-3.15 (m, 2H), 2.62-2.55 (m, 4H), 2.33 (s, 2H), 1.08 (s, 6H). |
| I-154 | (S)-4-fluoro-N-(1-(3-methoxy-4-(N-(2-methyl-4-morpholinobutan-2-yl)sulfamoyl)phenylamino)-1-oxo-3-phenylpropan-2-yl)benzamide | 42% | MS (ESI⁺, m/z): Calcd for C32H39FN4O6S: 626; found 627 [M + H]⁺; | ¹H NMR (300 MHz, CD₃OD) δ 7.89-7.84 (m, 2H), 7.76 (d, 1H), 7.62 (s, 1H), 7.37-7.13 (m, 8H), 4.95-4.90 (m, 1H), 3.96 (s, 3H), 3.80-3.75 (m, 4H), 3.30-3.15 (m, 2H), 2.72-2.62 (m, 4H), 1.75 (t, 2H), 1.14 (s, 6H). |
| I-180 | (S)-N-(1-(4-(N-(2-cyanopropan-2-yl)sulfamoyl)-3-methoxyphenylamino)-1-oxo-3-phenylpropan-2-yl)-4-fluorobenzamide | 42% | MS (ESI⁺, m z): Calcd for C27H27FN4O5S: 538; found 539 [M + H]⁺; | ¹H NMR (300 MHz, CD₃OD) δ 7.87-7.76 (m, 3H), 7.63 (s, 1H), 7.34-7.15 (m, 8H), 4.95-4.90 (m, 1H), 3.96 (s, 3H), 3.30-3.13 (m, 2H), 1.58 (s, 6H). |
| I-181 | (S)-4-fluoro-N-(1-(3-methoxy-4-(N-(2-methylbut-3-yn-2-yl)sulfamoyl)phenylamino)-1-oxo-3-phenylpropan-2-yl)benzamide | 39% | MS (ESI⁺, m/z): Calcd for C28H28FN3O5S: 537; found 538 [M + H]⁺ | ¹H NMR (300 MHz, CD₃OD) δ 7.86-7.81 (m, 2H), 7.71 (d, 1H), 7.55 (s, 1H), 7.34-7.08 (m, 8H), 4.94-4.89 (m, 1H), 3.93 (s, 3H), 3.30-3.13 (m, 2H), 2.28 (s, 1H), 1.47 (s, 6H). |
| I-182 | 4-fluoro-N-((S)-1-(3-methoxy-4-(N-((S)-tetrahydrofuran-3-yl)sulfamoyl)phenylamino)-1-oxo-3-phenylpropan-2-yl)benzamide | 41% | MS (ESI⁺, m/z): Calcd for C27H28FN3O6S: 541; found 542 [M + H]⁺; | ¹H NMR (300 MHz, CD₃OD) δ 7.86-7.82 (m, 2H), 7.73 (d, 1H), 7.59 (s, 1H), 7.35-7.12 (m, 8H), 4.94-4.90 (m, 1H), 3.93 (s, 3H), 3.88-3.78 (m, 2H), 3.75-3.62 (m, 2H), 3.48 (dd, 1H), 3.31-3.13 (m, 2H), 2.06-1.92 (m, 1H), 1.85-1.70 (m, 1H). |

TABLE 15-continued

Compounds prepared according to Example 73.

| Compound | Chemical Name | yield | MS | 1HNMR |
|---|---|---|---|---|
| I-183 | 4-fluoro-N-((S)-1-(3-methoxy-4-(N-((R)-tetrahydrofuran-3-yl)sulfamoyl)phenylamino)-1-oxo-3-phenylpropan-2-yl)benzamide | 43% | MS (ESI+, m/z): Calcd for C27H28FN3O6S: 541; found 542 [M + H]+; | $^1$H NMR (300 MHz, CD$_3$OD) δ 7.87- 7.83 (m, 2H), 7.75 (d, 1H), 7.62 (s, 1H), 7.35-7.11 (m, 8H), 4.95-4.90 (m, 1H), 3.95 (s, 3H), 3.88- 3.78 (m, 2H), 3.75-3.62 (m, 2H), 3.49 (dd, 1H), 3.31-3.13 (m, 2H), 2.06-1.92 (m, 1H), 1.85-1.70 (m, 1H). |

Example 74: (S)-N-(1-(4-(N-ethylsulfamoyl)-3-fluorophenylamino)-1-oxo-3-phenylpropan-2-yl)-4-fluorobenzamide, I-155

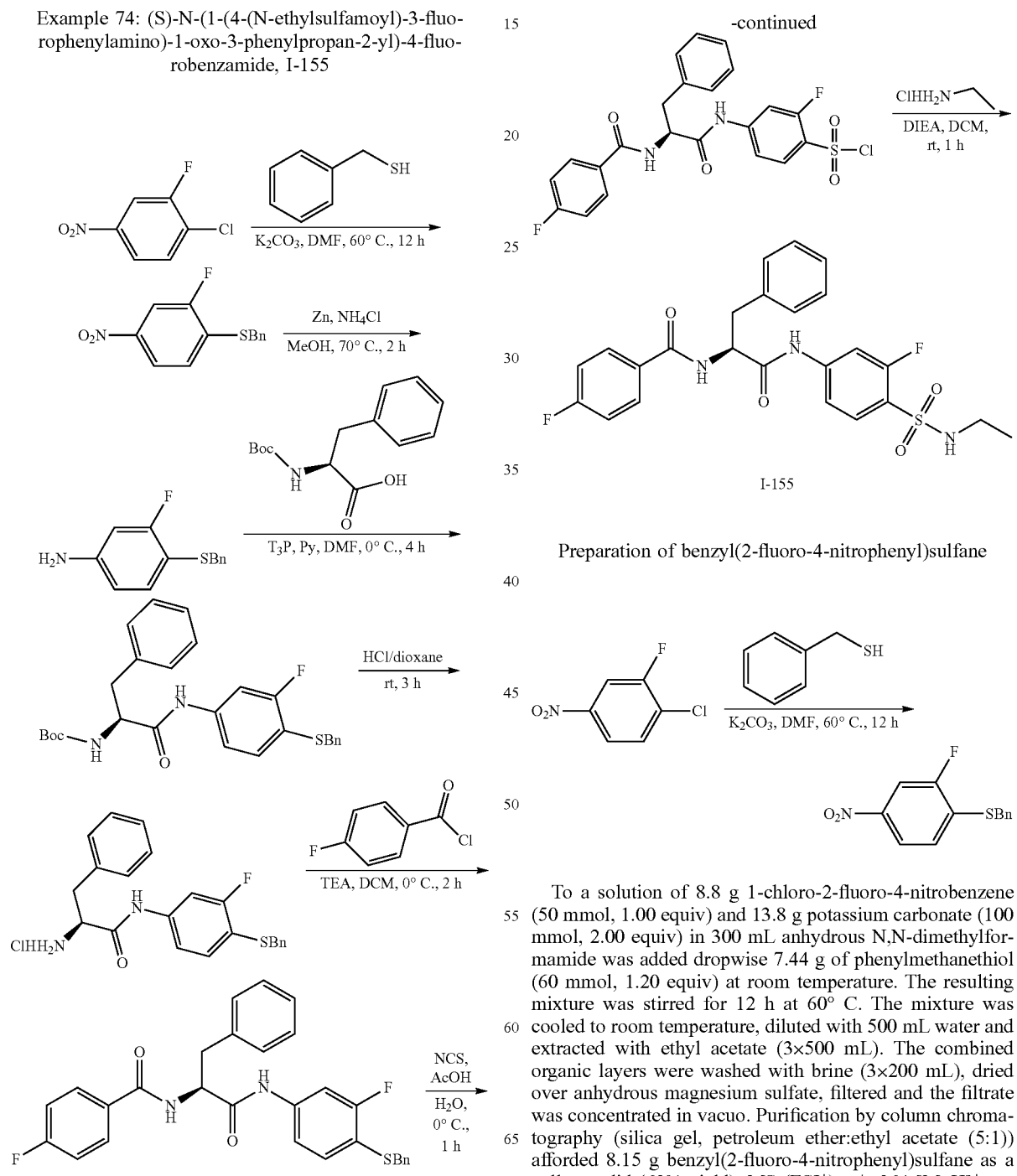

Preparation of benzyl(2-fluoro-4-nitrophenyl)sulfane

To a solution of 8.8 g 1-chloro-2-fluoro-4-nitrobenzene (50 mmol, 1.00 equiv) and 13.8 g potassium carbonate (100 mmol, 2.00 equiv) in 300 mL anhydrous N,N-dimethylformamide was added dropwise 7.44 g of phenylmethanethiol (60 mmol, 1.20 equiv) at room temperature. The resulting mixture was stirred for 12 h at 60° C. The mixture was cooled to room temperature, diluted with 500 mL water and extracted with ethyl acetate (3×500 mL). The combined organic layers were washed with brine (3×200 mL), dried over anhydrous magnesium sulfate, filtered and the filtrate was concentrated in vacuo. Purification by column chromatography (silica gel, petroleum ether:ethyl acetate (5:1)) afforded 8.15 g benzyl(2-fluoro-4-nitrophenyl)sulfane as a yellow solid (62% yield). MS (ESI+) m/z 264 [M+H]+.

Preparation of 4-(benzylthio)-3-fluorobenzenamine

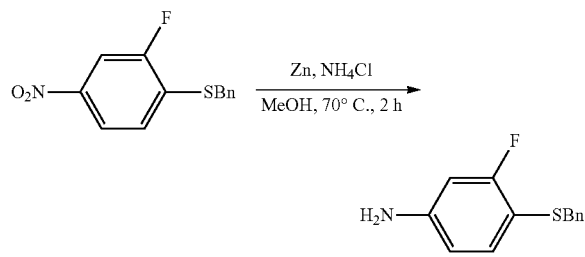

To a solution of 8.15 g benzyl(2-fluoro-4-nitrophenyl)sulfane (31 mmol, 1.00 equiv) in 200 mL methanol was added 8.19 g ammonium chloride (153 mmol, 5.00 equiv) and 7.87 g zinc (124 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (2:1)) afforded 4.19 g 4-(benzylthio)-3-fluorobenzenamine as an orange oil (58% yield). MS (ESI$^+$) m/z 234 [M+H]$^+$.

Preparation of (S)-tert-butyl 1-(4-(benzylthio)-3-fluorophenylamino)-1-oxo-3-phenylpropan-2-ylcarbamate

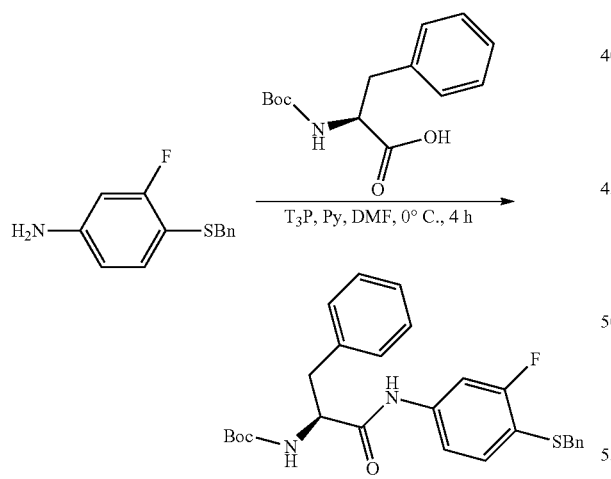

To a solution of 2.34 g 4-(benzylthio)-3-fluorobenzenamine (10 mmol, 1.00 equiv), 2.65 g (S)-2-(tert-butoxycarbonylamino)-3-phenylpropanoic acid (10 mmol, 1.00 equiv) and 7.9 g pyridine (100 mmol, 10.00 equiv) in 30 mL N,N-dimethylformamide was added dropwise a solution 25.8 g propanephosphonic acid cyclic anhydride in ethyl acetate (50%, 50 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (1:1)) provided 3.17 g (S)-tert-butyl 1-(4-(benzylthio)-3-fluorophenylamino)-1-oxo-3-phenylpropan-2-ylcarbamate as a yellow solid (66% yield). MS (ESI$^+$) m/z 425 [M-56+H]$^+$.

Preparation of (S)-2-amino-N-(4-(benzylthio)-3-fluorophenyl)-3-phenylpropanamide Hydrochloride

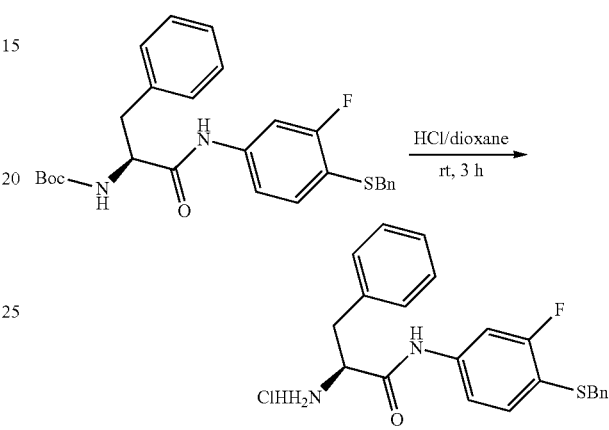

A mixture of 3.17 g (S)-tert-butyl 1-(4-(benzylthio)-3-fluorophenylamino)-1-oxo-3-phenylpropan-2-ylcarbamate (6.6 mmol, 1.00 equiv) in 30 mL hydrochloric acid in 1,4-dioxane (4.0 M) was stirred at room temperature for 3 h. The mixture was concentrated to afford 2.75 g (S)-2-amino-N-(4-(benzylthio)-3-fluorophenyl)-3-phenylpropanamide hydrochloride as a light yellow solid (100% yield). MS (ESI$^+$) m/z 381 [M+H]$^+$.

Preparation of (S)-N-(1-(4-(benzylthio)-3-fluorophenylamino)-1-oxo-3-phenylpropan-2-yl)-4-fluorobenzamide

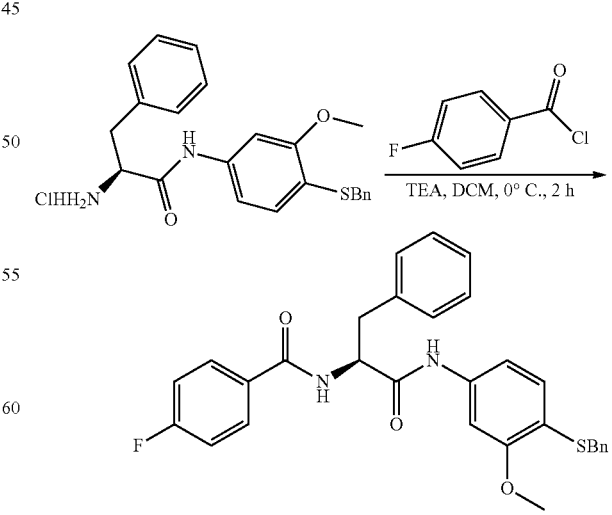

To a solution of 1.31 g (S)-2-amino-N-(4-(benzylthio)-3-fluorophenyl)-3-phenylpropanamide hydrochloride (3.15 mmol, 1.00 equiv) and 1.91 g triethylamine (18.9 mmol, 6.00 equiv) in 20 mL dichloromethane was added dropwise 597.2 mg 4-fluorobenzoyl chloride (3.78 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 0.98 g (S)-N-(1-(4-(benzylthio)-3-fluorophenylamino)-1-oxo-3-phenylpropan-2-yl)-4-fluorobenzamide as a yellow solid (62% yield). MS (ESI+) m/z 503 [M+H]+.

Preparation of (S)-2-fluoro-4-(2-(4-fluorobenzamido)-3-phenylpropanamido)benzene-1-sulfonyl Chloride

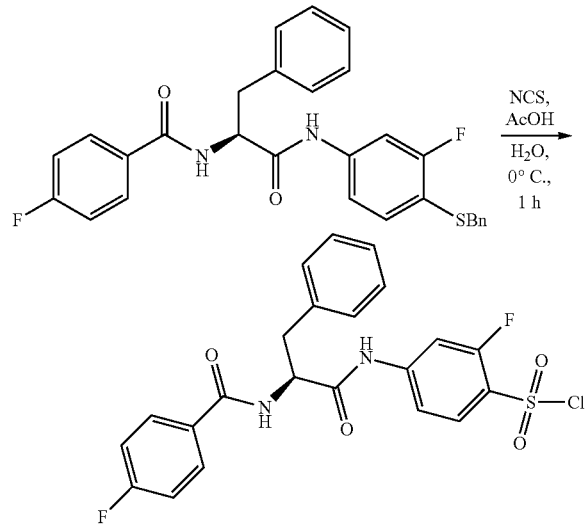

To a solution of 0.98 g (S)-N-(1-(4-(benzylthio)-3-fluorophenylamino)-1-oxo-3-phenylpropan-2-yl)-4-fluorobenzamide (1.95 mmol, 1.00 equiv) in 9 mL acetic acid and 3 mL water was added 1.04 g N-chlorosuccinimide (7.8 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.6 g (S)-2-fluoro-4-(2-(4-fluorobenzamido)-3-phenylpropanamido)benzene-1-sulfonyl chloride as a white solid (64% yield). MS (ESI+) m/z 479 and 481 [M+H]+.

Preparation of (S)-N-(1-(4-(N-ethylsulfamoyl)-3-fluorophenylamino)-1-oxo-3-phenylpropan-2-yl)-4-fluorobenzamide (I-155)

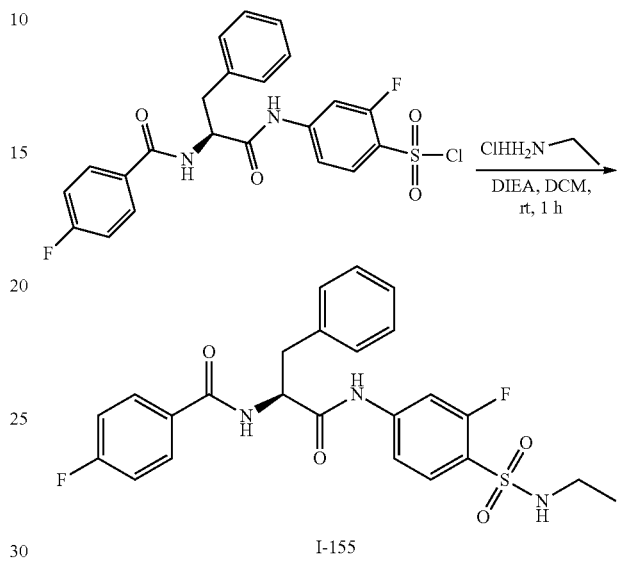

To a mixture of 84.65 mg ethanamine hydrochloride (1.045 mmol, 5.0 equiv) and 134.8 mg N,N-diisopropylethylamine (1.045 mmol, 5.00 equiv) in 10 mL dichloromethane was added 100 mg (S)-2-fluoro-4-(2-(4-fluorobenzamido)-3-phenylpropanamido)benzene-1-sulfonyl chloride (0.209 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH4HCO3+0.1% NH3—H2O) and ACN (33% ACN up to 54% in 7 min); UV detection at 254/220 nm. The product-containing fractions were combined and evaporated partially in vacuo and lyophilized overnight to afford 34.9 mg (S)-N-(1-(4-(N-ethylsulfamoyl)-3-fluorophenylamino)-1-oxo-3-phenylpropan-2-yl)-4-fluorobenzamide (I-155) as a white solid.

Using this general procedure for the preparation of I-155 and substituting the appropriate amine in the last step, the following compounds were prepared.

TABLE 16

Compounds prepared according to Example 74.

| Compound | Chemical Name | yield | MS | 1HNMR |
|---|---|---|---|---|
| I-155 | (S)-N-(1-(4-(N-ethylsulfamoyl)-3-fluorophenylamino)-1-oxo-3-phenylpropan-2-yl)-4-fluorobenzamide | 34% | MS (ESI+, m/z): Calcd for C24H23F2N3O4S: 487; found 488 [M + H]+; | 1H NMR (400 MHz, CD3OD) δ 7.76-7.72 (m, 2H), 7.66-7.62 (m, 2H), 7.24-7.05 (m, 8H), 4.82-4.78 (m, 1H), 3.21-3.02 (m, 2H), 2.88 (q, 2H), 1.00 (t, 3H). |

TABLE 16-continued

Compounds prepared according to Example 74.

| Compound | Chemical Name | yield | MS | 1HNMR |
|---|---|---|---|---|
| I-156 | (S)-N-(1-(4-(N-tert-butylsulfamoyl)-3-fluorophenylamino)-1-oxo-3-phenylpropan-2-yl)-4-fluorobenzamide | 35% | MS (ESI+, m/z): Calcd for C26H27F2N3O4S: 515; found 516 [M + H]+ | $^1$H NMR (400 MHz, CD$_3$OD) δ 7.88-7.84 (m, 2H), 7.80-7.72 (m, 2H), 7.35-7.17 (m, 8H), 4.94-4.90 (m, 1H), 3.30-3.15 (m, 2H), 1.21 (s, 9H). |

Example 75: (S)-N-(1-(4-(N-ethylsulfamoyl)-2-fluorophenylamino)-1-oxo-3-phenylpropan-2-yl)-4-fluorobenzamide, I-157

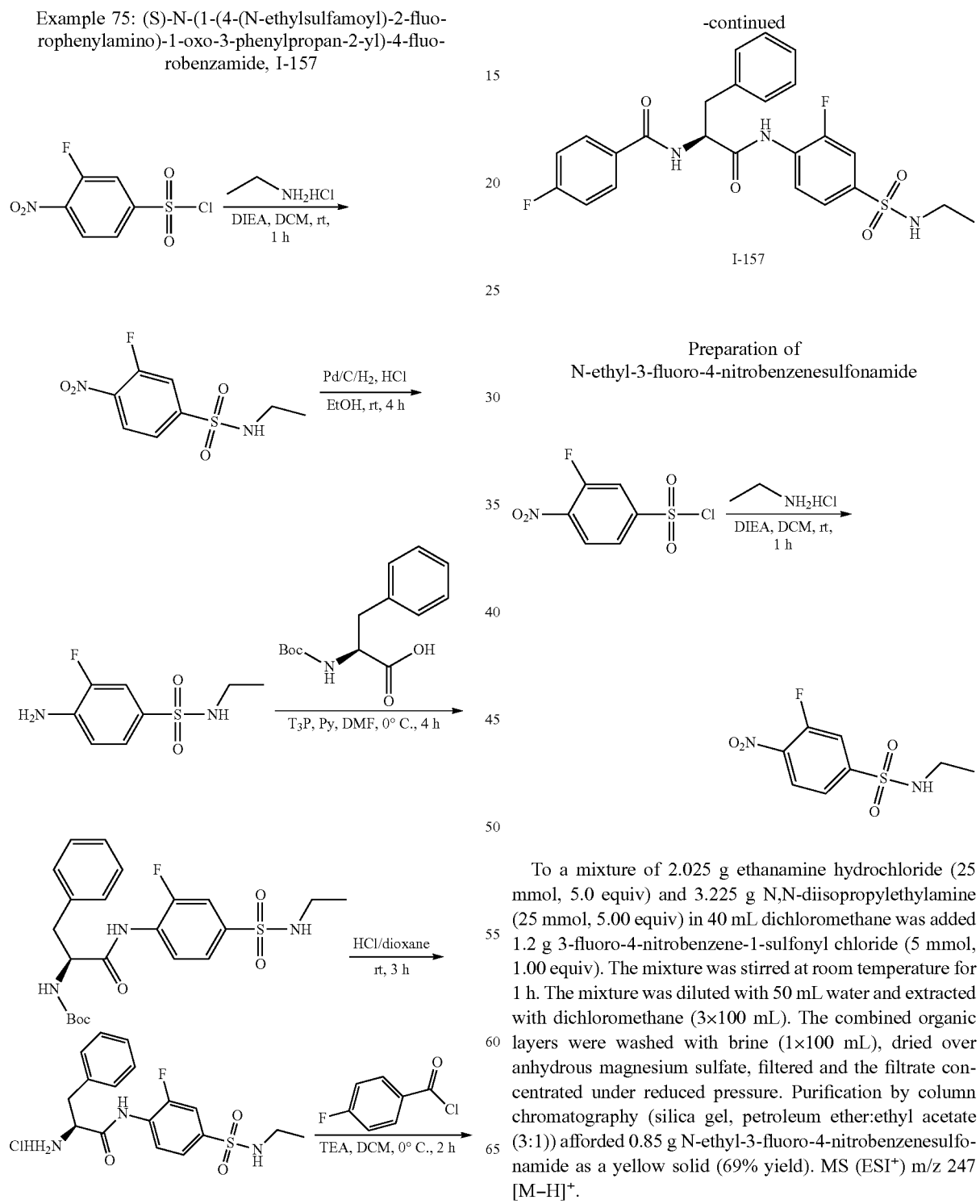

Preparation of N-ethyl-3-fluoro-4-nitrobenzenesulfonamide

To a mixture of 2.025 g ethanamine hydrochloride (25 mmol, 5.0 equiv) and 3.225 g N,N-diisopropylethylamine (25 mmol, 5.00 equiv) in 40 mL dichloromethane was added 1.2 g 3-fluoro-4-nitrobenzene-1-sulfonyl chloride (5 mmol, 1.00 equiv). The mixture was stirred at room temperature for 1 h. The mixture was diluted with 50 mL water and extracted with dichloromethane (3×100 mL). The combined organic layers were washed with brine (1×100 mL), dried over anhydrous magnesium sulfate, filtered and the filtrate concentrated under reduced pressure. Purification by column chromatography (silica gel, petroleum ether:ethyl acetate (3:1)) afforded 0.85 g N-ethyl-3-fluoro-4-nitrobenzenesulfonamide as a yellow solid (69% yield). MS (ESI+) m/z 247 [M−H]+.

Preparation of 4-amino-N-ethyl-3-fluorobenzenesulfonamide

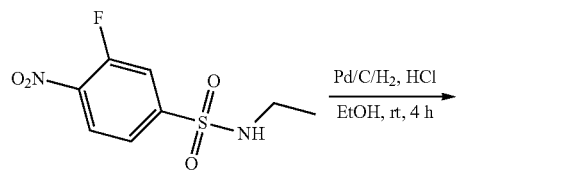

To a solution of 0.85 g N-ethyl-3-fluoro-4-nitrobenzenesulfonamide (3.43 mmol, 1 equiv) in 20 mL ethanol was added 1 mL hydrogen chloride and 200 mg palladium on carbon. To the above hydrogen (g) was introduced in. The resulting mixture was stirred at r.t for 2 h. The solid was filtered out. The filtrate was concentrated under vacuum to afforded 615 mg 4-amino-N-ethyl-3-fluorobenzenesulfonamide as a white solid (82% yield). MS (ESI$^+$) m/z 219 [M+H]$^+$.

Preparation of(S)-tert-butyl 1-(4-(N-ethylsulfamoyl)-2-fluorophenylamino)-1-oxo-3-phenylpropan-2-ylcarbamate

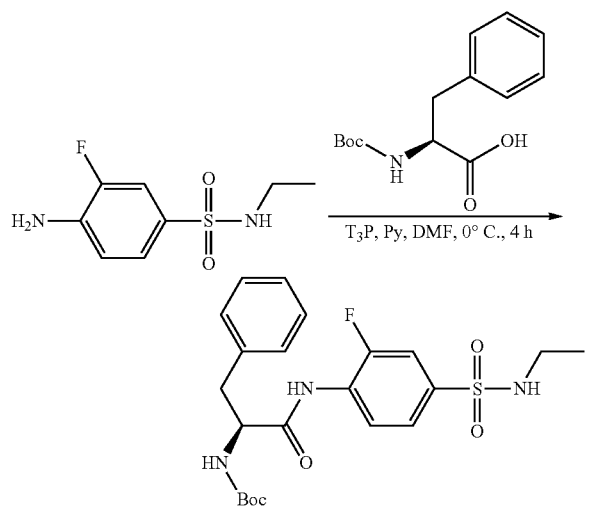

To a solution of 615 mg 4-amino-N-ethyl-3-fluorobenzenesulfonamide (2.82 mmol, 1.00 equiv), 747.3 mg (S)-2-(tert-butoxycarbonylamino)-3-phenylpropanoic acid (2.82 mmol, 1.00 equiv) and 2.23 g pyridine (28.2 mmol, 10.00 equiv) in 10 mL N,N-dimethylformamide was added dropwise a solution 7.28 g propanephosphonic acid cyclic anhydride in ethyl acetate (50%, 14.1 mmol, 5.00 equiv) at 0° C. The resulting mixture was stirred for 4 h at 0° C. The mixture was diluted with 100 mL water and extracted with ethyl acetate (3×100 mL). The combined organic layers were washed with brine (3×50 mL), dried over anhydrous magnesium sulfate, filtered and the filtrate concentrated in vacuo. Purification by column chromatography (silica gel, petroleum ether:ethyl acetate (1:1)) provided 735 mg (S)-tert-butyl 1-(4-(N-ethylsulfamoyl)-2-fluorophenylamino)-1-oxo-3-phenylpropan-2-ylcarbamate as a yellow solid (56% yield). MS (ESI$^+$) m/z 410 [M-56+H]$^+$.

Preparation of (S)-2-amino-N-(4-(N-ethylsulfamoyl)-2-fluorophenyl)-3-phenylpropanamide Hydrochloride

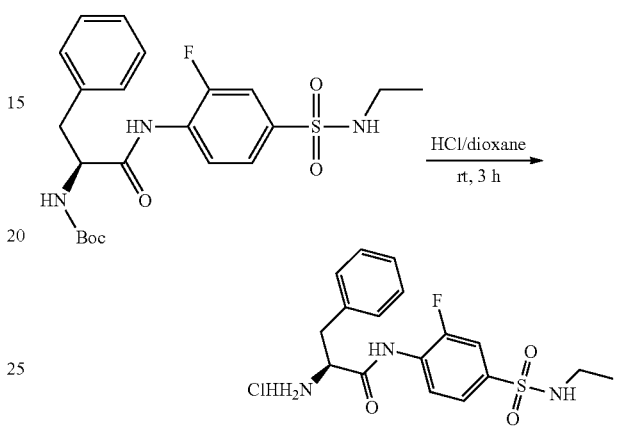

A mixture of 735 mg (S)-tert-butyl 1-(4-(N-ethylsulfamoyl)-2-fluorophenylamino)-1-oxo-3-phenylpropan-2-ylcarbamate (1.58 mmol, 1.00 equiv) in 10 mL hydrochloric acid in 1,4-dioxane (4.0 M) was stirred at room temperature for 3 h. The mixture was concentrated to afford 636 mg (S)-2-amino-N-(4-(N-ethylsulfamoyl)-2-fluorophenyl)-3-phenylpropanamide hydrochloride as a light yellow solid (100% yield). MS (ESI$^+$) m/z 366 [M+H]$^+$.

Preparation of (S)-N-(1-(4-(N-ethylsulfamoyl)-2-fluorophenylamino)-1-oxo-3-phenylpropan-2-yl)-4-fluorobenzamide (I-157)

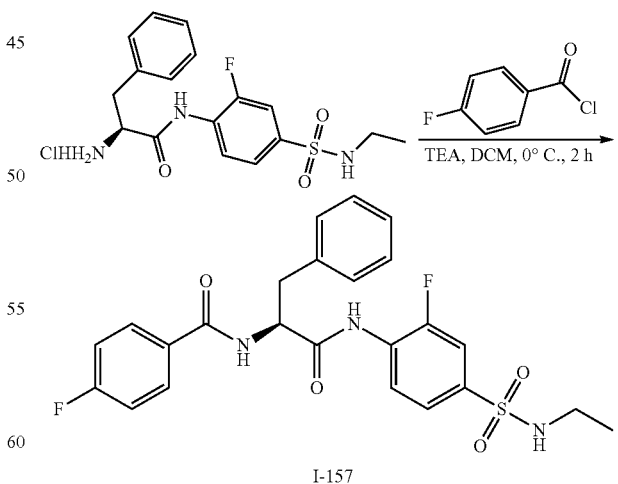

I-157

To a solution of 110 mg (S)-2-amino-N-(4-(N-ethylsulfamoyl)-2-fluorophenyl)-3-phenylpropanamide hydrochloride (0.27 mmol, 1.00 equiv) and 163.62 mg triethylamine (1.62 mmol, 6.00 equiv) in 10 mL dichloromethane was added dropwise 51.2 mg 4-fluorobenzoyl chloride (0.324 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (32% ACN up to 51% in 7 min); UV detection at 254/220 nm. The product-containing fractions were combined and evaporated partially in vacuo and lyophilized overnight to afford 40.8 mg (S)-N-(1-(4-(N-ethylsulfamoyl)-2-fluorophenylamino)-1-oxo-3-phenylpropan-2-yl)-4-fluorobenzamide (I-157) as a white solid (31% yield). MS (ESI, m/z) 488 [M+H]$^+$; $^1$H NMR (400 MHz, d$_6$-DMSO) δ 10.39 (s, 1H), 8.85 (d, 1H), 8.22 (t, 1H), 7.91-7.87 (m, 2H), 7.66-7.60 (m, 3H), 7.44 (d, 2H), 7.32-7.27 (m, 4H), 7.19 (t, 1H), 5.05-5.02 (m, 1H), 3.22-3.08 (m, 2H), 2.80 (q, 2H), 0.98 (t, 3H).

Example 76: (S)-N-(1-(4-(N-tert-butylsulfamoyl)-2-fluorophenylamino)-1-oxo-3-phenylpropan-2-yl)-4-fluorobenzamide, I-158

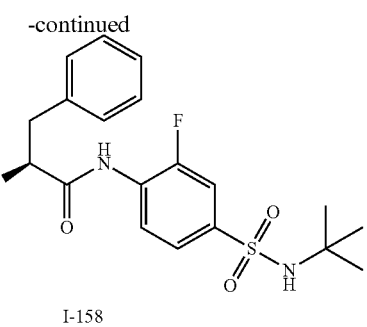

I-158

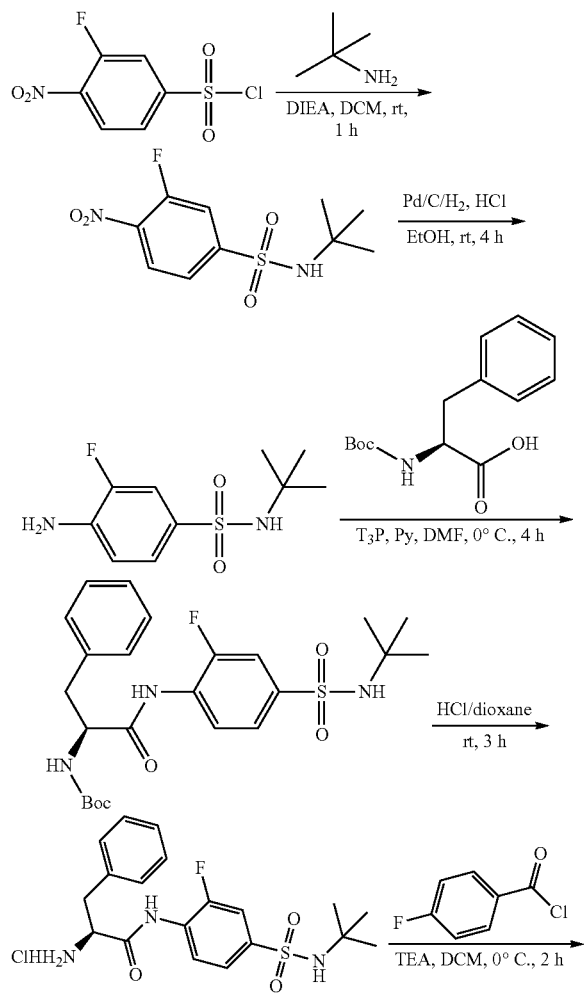

Preparation of
N-tert-butyl-3-fluoro-4-nitrobenzenesulfonamide

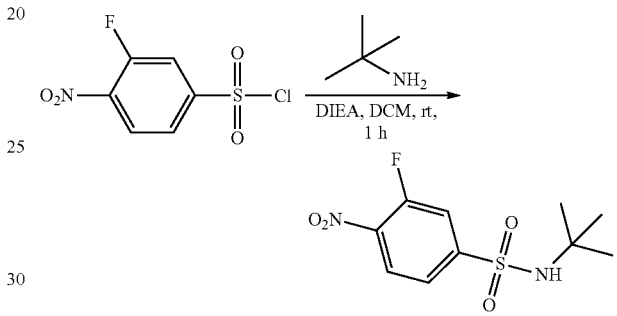

To a mixture of 1.825 g 2-methylpropan-2-amine (25 mmol, 5.0 equiv) and 3.225 g N,N-diisopropylethylamine (25 mmol, 5.00 equiv) in 40 mL dichloromethane was added 1.2 g 3-fluoro-4-nitrobenzene-1-sulfonyl chloride (5 mmol, 1.00 equiv). The mixture was stirred at room temperature for 1 h. The mixture was diluted with 50 mL water and extracted with dichloromethane (3×100 mL). The combined organic layers were washed with brine (1×100 mL), dried over anhydrous magnesium sulfate, filtered and the filtrate concentrated under reduced pressure. Purification by column chromatography (silica gel, petroleum ether:ethyl acetate (3:1)) afforded 0.925 g N-tert-butyl-3-fluoro-4-nitrobenzenesulfonamide as a yellow solid (67% yield). MS (ESI$^+$) m/z 277 [M+H]$^+$.

Preparation of
4-amino-N-tert-butyl-3-fluorobenzenesulfonamide

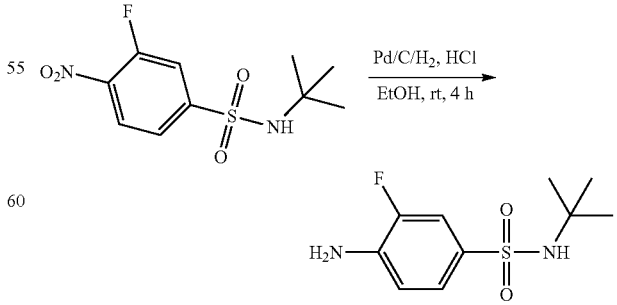

To a solution of 0.925 g N-tert-butyl-3-fluoro-4-nitrobenzenesulfonamide (3.35 mmol, 1 equiv) in 20 mL ethanol was added 1 mL hydrogen chloride and 200 mg palladium on carbon. To the above hydrogen (g) was introduced in. The resulting mixture was stirred at r.t for 2 h. The solid was filtered out. The filtrate was concentrated under vacuum to afforded 692 mg 4-amino-N-tert-butyl-3-fluorobenzene-sulfonamide as a white solid (84% yield). MS (ESI+) m/z 245 [M–H]+.

Preparation of (S)-tert-butyl 1-(4-(N-tert-butylsulfa-moyl)-2-fluorophenylamino)-1-oxo-3-phenylpropan-2-ylcarbamate

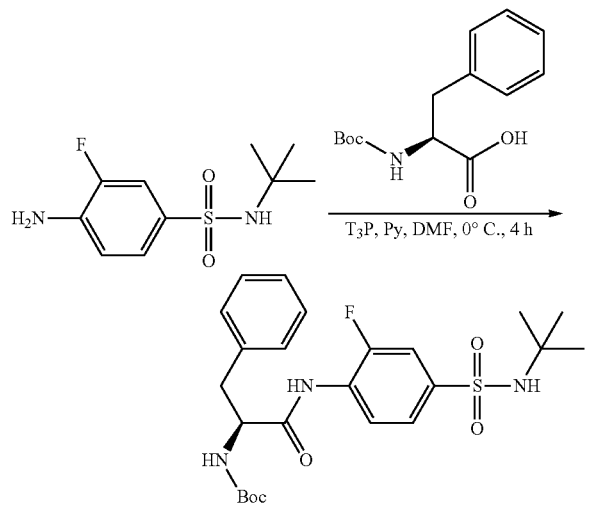

To a solution of 692 mg 4-amino-N-tert-butyl-3-fluo-robenzenesulfonamide (2.81 mmol, 1.00 equiv), 745.4 mg (S)-2-(tert-butoxycarbonylamino)-3-phenylpropanoic acid (2.81 mmol, 1.00 equiv) and 2.22 g pyridine (28.1 mmol, 10.00 equiv) in 10 mL N,N-dimethylformamide was added dropwise a solution 7.22 g propanephosphonic acid cyclic anhydride in ethyl acetate (50%, 14.05 mmol, 5.00 equiv) at 0° C. The resulting mixture was stirred for 4 h at 0° C. The mixture was diluted with 100 mL water and extracted with ethyl acetate (3×100 mL). The combined organic layers were washed with brine (3×50 mL), dried over anhydrous magnesium sulfate, filtered and the filtrate concentrated in vacuo. Purification by column chromatography (silica gel, petroleum ether:ethyl acetate (1:1)) provided 817 mg (S)-tert-butyl 1-(4-(N-tert-butylsulfamoyl)-2-fluorophe-nylamino)-1-oxo-3-phenylpropan-2-ylcarbamate as a yellow solid (59% yield). MS (ESI+) m/z 438 [M-56+H]+.

Preparation of (S)-2-amino-N-(4-(N-tert-butylsulfa-moyl)-2-fluorophenyl)-3-phenylpropanamide Hydrochloride

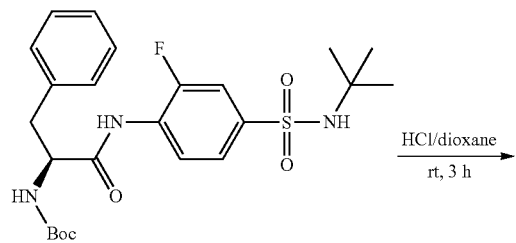

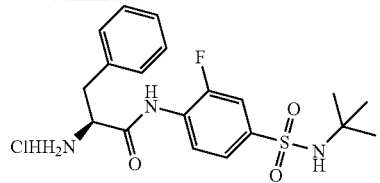

A mixture of 817 mg (S)-tert-butyl 1-(4-(N-tert-butylsul-famoyl)-2-fluorophenylamino)-1-oxo-3-phenylpropan-2-yl-carbamate (1.66 mmol, 1.00 equiv) in 10 mL hydrochloric acid in 1,4-dioxane (4.0 M) was stirred at room temperature for 3 h. The mixture was concentrated to afford 715 mg (S)-2-amino-N-(4-(N-tert-butylsulfamoyl)-2-fluorophenyl)-3-phenylpropanamide hydrochloride as a light yellow solid (100% yield). MS (ESI+) m/z 394 [M+H]+.

Preparation of (S)-N-(1-(4-(N-tert-butylsulfamoyl)-2-fluorophenylamino)-1-oxo-3-phenylpropan-2-yl)-4-fluorobenzamide (I-158)

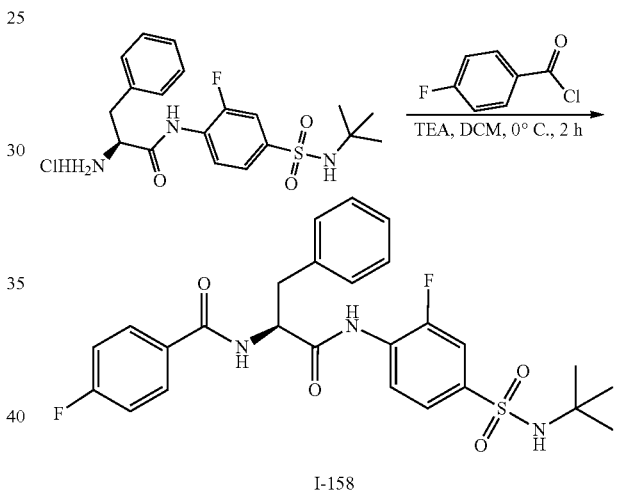

I-158

To a solution of 100 mg (S)-2-amino-N-(4-(N-tert-bu-tylsulfamoyl)-2-fluorophenyl)-3-phenylpropanamide hydrochloride (0.23 mmol, 1.00 equiv) and 139.38 mg triethyl-amine (1.38 mmol, 6.00 equiv) in 10 mL dichloromethane was added dropwise 43.6 mg 4-fluorobenzoyl chloride (0.276 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. The crude product was purified by Prep-HPLC with the following conditions: Column, YMC-Actus Triart C18, 30*250 mm, 5 um; Mobile Phase, water (10% NH4HCO3+0.1% NH3—H2O) and ACN (31% ACN up to 52% in 7 min); UV detection at 254/220 nm. The product-containing fractions were combined and evaporated partially in vacuo and lyophilized overnight to afford 41.7 mg (S)-N-(1-(4-(N-tert-butylsulfamoyl)-2-fluorophenylamino)-1-oxo-3-phenylpro-pan-2-yl)-4-fluorobenzamide (I-158) as a white solid (35% yield). MS (ESI, m/z) 514 [M–H]−; 1H NMR (400 MHz, CD3OD) δ 8.24 (d, 1H), 7.86-7.82 (m, 2H), 7.68-7.63 (m, 2H), 7.38-7.17 (m, 7H), 5.10-5.06 (m, 1H), 3.40-3.34 (m, 1H), 3.24-3.15 (m, 1H), 1.21 (s, 9H).

Example 77: (S)-4-fluoro-N-(1-(3-methoxy-4-(N-(1-methoxy-2-methylpropan-2-yl)sulfamoyl)phenylamino)-1-oxo-3-phenylpropan-2-yl)-N-methyl-benzamide, I-159

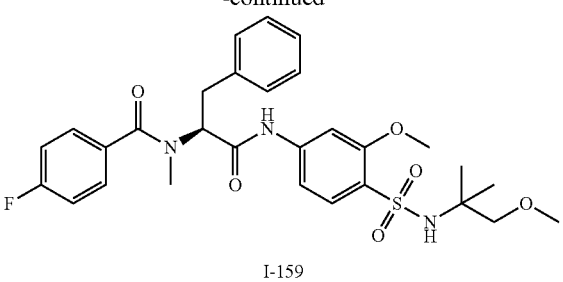

I-159

Preparation of (S)-tert-butyl 1-(4-(benzylthio)-3-methoxyphenylamino)-1-oxo-3-phenylpropan-2-yl (methyl)carbamate

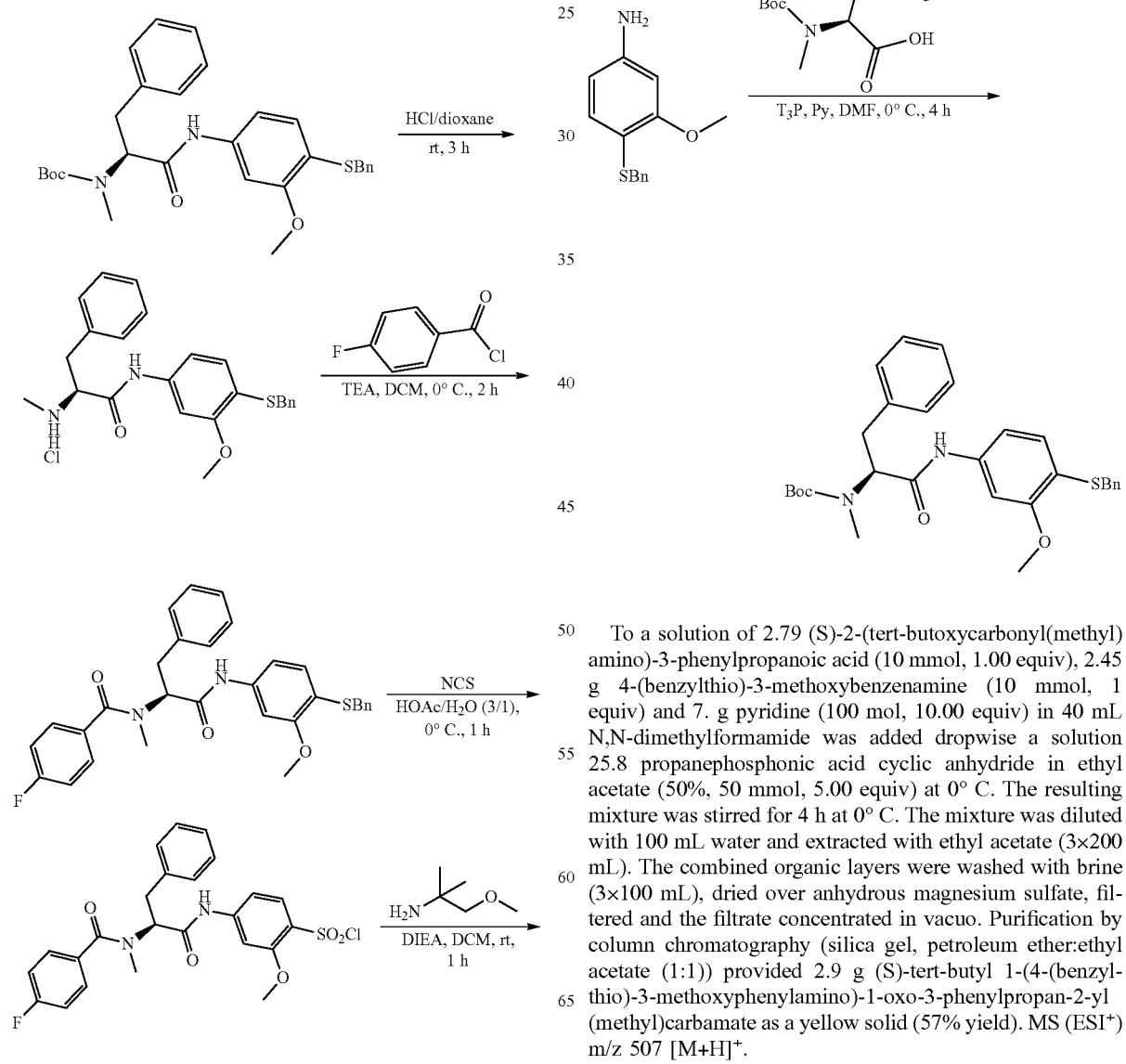

To a solution of 2.79 (S)-2-(tert-butoxycarbonyl(methyl)amino)-3-phenylpropanoic acid (10 mmol, 1.00 equiv), 2.45 g 4-(benzylthio)-3-methoxybenzenamine (10 mmol, 1 equiv) and 7. g pyridine (100 mol, 10.00 equiv) in 40 mL N,N-dimethylformamide was added dropwise a solution 25.8 propanephosphonic acid cyclic anhydride in ethyl acetate (50%, 50 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (1:1)) provided 2.9 g (S)-tert-butyl 1-(4-(benzylthio)-3-methoxyphenylamino)-1-oxo-3-phenylpropan-2-yl (methyl)carbamate as a yellow solid (57% yield). MS (ESI$^+$) m/z 507 [M+H]$^+$.

Preparation of (S)-N-(4-(benzylthio)-3-methoxyphenyl)-2-(methylamino)-3-phenylpropanamide Hydrochloride

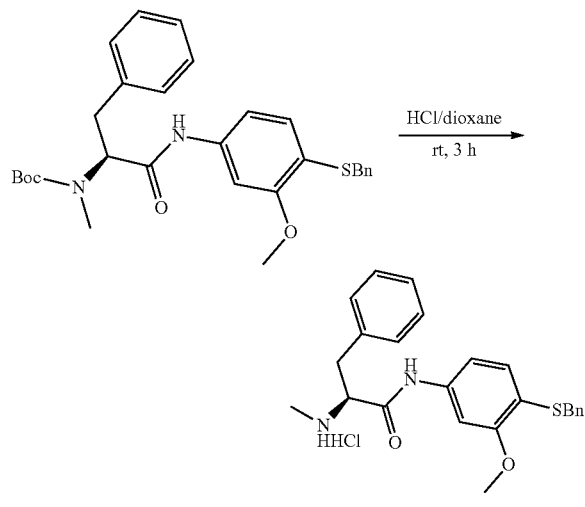

A mixture of 2.9 g (S)-tert-butyl 1-(4-(benzylthio)-3-methoxyphenylamino)-1-oxo-3-phenylpropan-2-yl(methyl)carbamate (5.73 mmol, 1.00 equiv) in 20 mL hydrochloric acid in 1,4-dioxane (4.0 M) was stirred at room temperature for 3 h. The mixture was concentrated to afford 2.55 g (S)-N-(4-(benzylthio)-3-methoxyphenyl)-2-(methylamino)-3-phenylpropanamide hydrochloride as a light yellow solid (100% yield). MS (ESI$^+$) m/z 407 [M+H]$^+$.

Preparation of (S)-N-(1-(4-(benzylthio)-3-methoxyphenylamino)-1-oxo-3-phenylpropan-2-yl)-4-fluoro-N-methylbenzamide

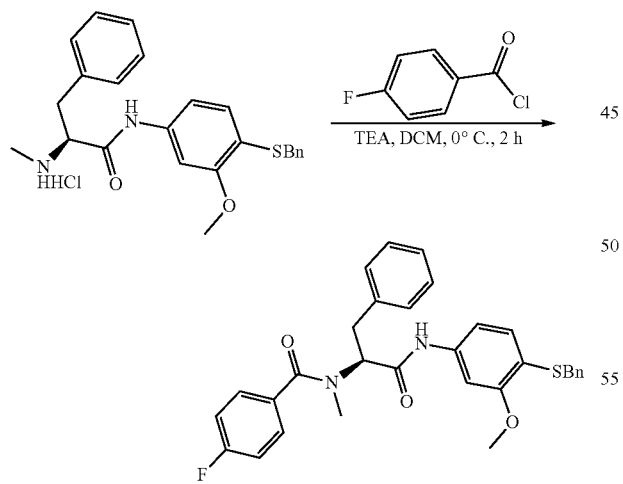

To a solution of 1.33 g (S)-N-(4-(benzylthio)-3-methoxyphenyl)-2-(methylamino)-3-phenylpropanamide hydrochloride (3.00 mmol, 1.00 equiv) and 1.818 g triethylamine (18.00 mmol, 6.00 equiv) in 20 mL dichloromethane was added dropwise 568.8 mg 4-fluorobenzoyl chloride (3.60 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1 g (S)-N-(1-(4-(benzylthio)-3-methoxyphenylamino)-1-oxo-3-phenylpropan-2-yl)-4-fluoro-N-methylbenzamide as a yellow solid (63% yield). MS (ESI$^+$) m/z 529 [M+H]$^+$.

Preparation of (S)-4-(2-(4-fluoro-N-methylbenzamido)-3-phenylpropanamido)-2-methoxybenzene-1-sulfonyl Chloride

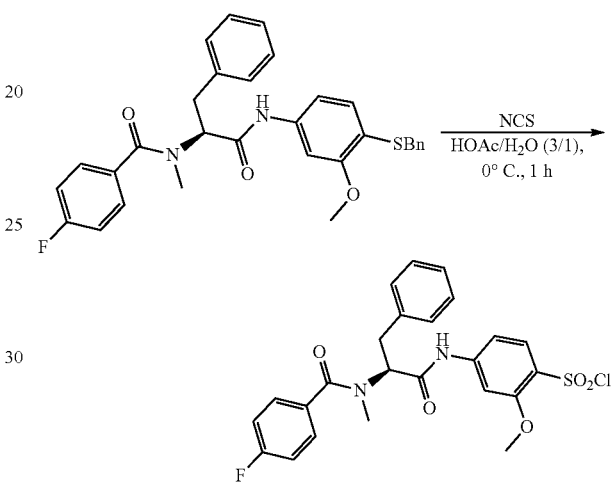

To a solution of 1 g (S)-N-(1-(4-(benzylthio)-3-methoxyphenylamino)-1-oxo-3-phenylpropan-2-yl)-4-fluoro-N-methylbenzamide (1.9 mmol, 1.00 equiv) in 6 mL acetic acid and 2 mL water was added 1.02 g N-chlorosuccinimide (7.6 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.55 g (S)-4-(2-(4-fluoro-N-methylbenzamido)-3-phenylpropanamido)-2-methoxybenzene-1-sulfonyl chloride as a white solid (57% yield). MS (ESI$^+$) m/z 505 and 507 [M+H]$^+$.

Preparation of (S)-4-fluoro-N-(1-(3-methoxy-4-(N-(1-methoxy-2-methylpropan-2-yl)sulfamoyl)phenylamino)-1-oxo-3-phenylpropan-2-yl)-N-methylbenzamide (I-159)

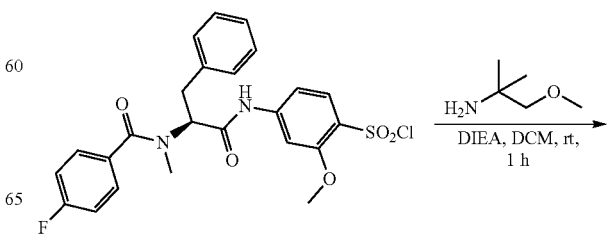

-continued

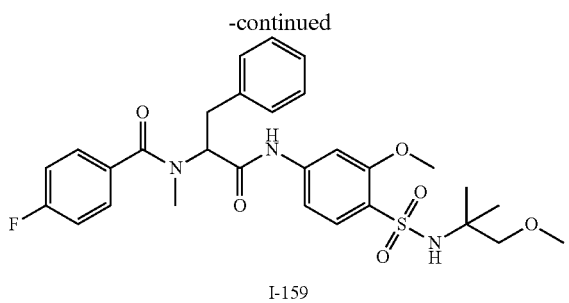

I-159

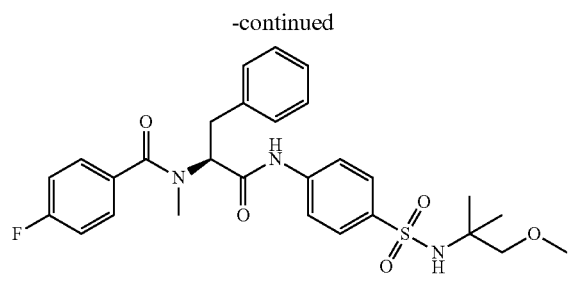

I-160

To a mixture of 226.6 mg 1-methoxy-2-methylpropan-2-amine (2.2 mmol, 5.0 equiv) and 283.8 mg N,N-diisopropylethylamine (2.2 mmol, 5.00 equiv) in 10 mL dichloromethane was added 220 mg (S)-4-(2-(4-fluorobenzamido)-3-phenylpropanamido)-3-methoxybenzene-1-sulfonyl chloride (0.44 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH$_4$HCO$_3$+0.1% NH$_3$—H$_2$O) and ACN (22% ACN up to 44% in 7 min); UV detection at 254/220 nm. The product-containing fractions were combined and evaporated partially in vacuo and lyophilized overnight to afford 52.6 mg (S)-4-fluoro-N-(1-(3-methoxy-4-(N-(1-methoxy-2-methylpropan-2-yl)sulfamoyl)phenylamino)-1-oxo-3-phenylpropan-2-yl)-N-methylbenzamide (I-159) as a white solid (21% yield). MS (ESI, m/z) 572 [M+H]$^+$; $^1$H NMR (300 MHz, CD$_3$OD) δ 7.77-7.69 (m, 2H), 7.37-6.90 (m, 10H), 5.50-4.78 (m, 1H), 3.99 (m, 3H), 3.45-3.34 (m, 1H), 3.24-2.95 (m, 9H), 1.13 (s, 6H).

Example 78. Preparation of (S)-4-fluoro-N-(1-(4-(N-(1-methoxy-2-methylpropan-2-yl)sulfamoyl) phenylamino)-1-oxo-3-phenylpropan-2-yl)-N-methylbenzamide, I-160

Synthesis Scheme:

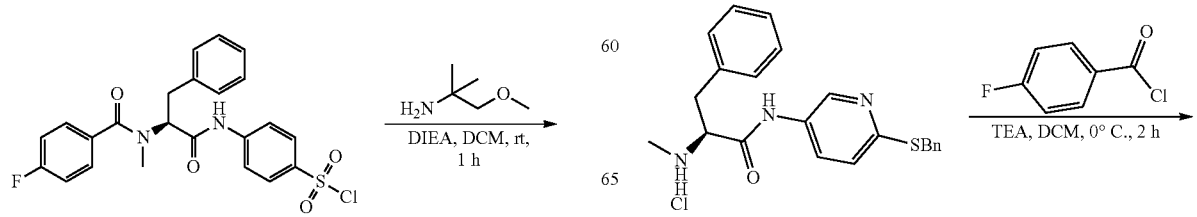

Using this general procedure for the preparation of Example 42 and substituting the appropriate amine in the last step, the following compounds were prepared.

TABLE 17

Compounds prepared according to Example 42.

| Compound | Chemical Name | yield | MS | 1HNMR |
|---|---|---|---|---|
| I-160 | (S)-4-fluoro-N-(1-(4-(N-(1-methoxy-2-methylpropan-2-yl)sulfamoyl) phenylamino)-1-oxo-3-phenylpropan-2-yl)-N-methylbenzamide | 27% | MS (ESI$^+$, m/z): Calcd for C28H32FN3O5S: 541; found 542 [M + H]$^+$; | $^1$H NMR (300 MHz, CD$_3$OD) δ 7.85 (d, 2H), 7.78 (d, 2H), 7.44-6.90 (m, 9H), 5.62-4.78 (m, 1H), 3.51-3.38 (m, 1H), 3.30-3.14 (m, 7H), 3.10-2.93 (m, 2H), 1.17 (s, 6H). |

Example 79: (S)-4-fluoro-N-(1-(6-(N-(1-methoxy-2-methylpropan-2-yl)sulfamoyl)pyridin-3-ylamino)-1-oxo-3-phenylpropan-2-yl)-N-methylbenzamide, I-161

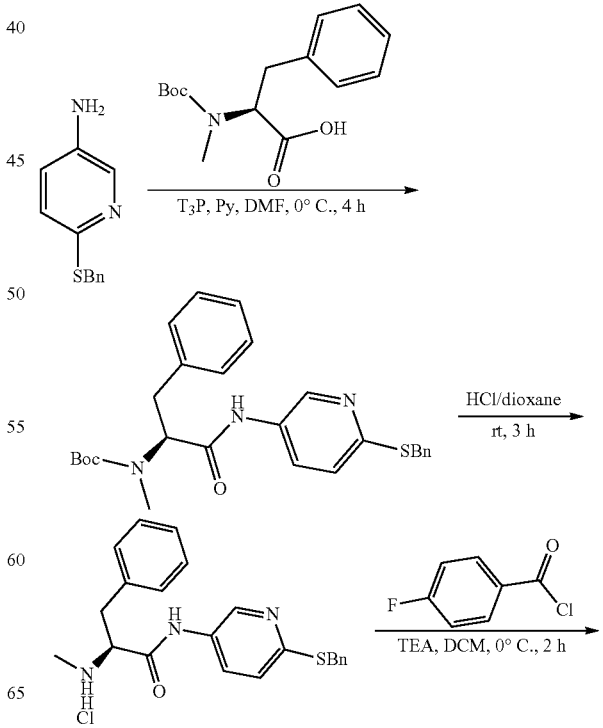

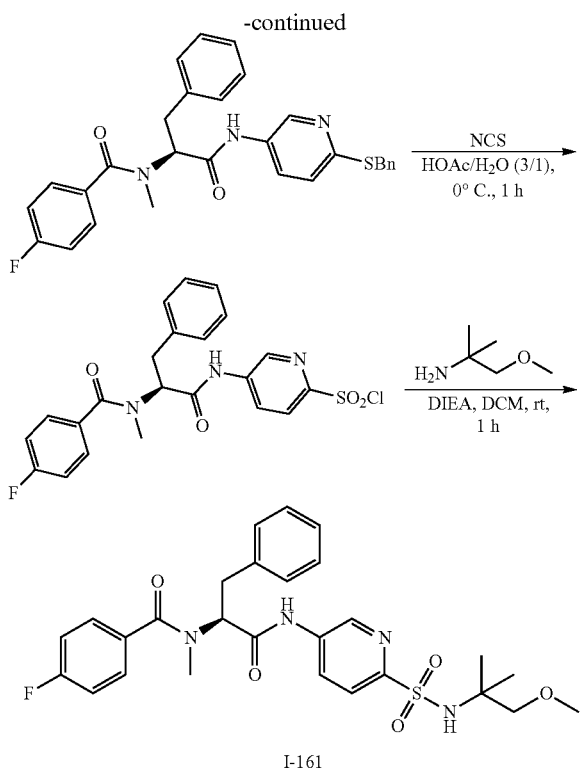

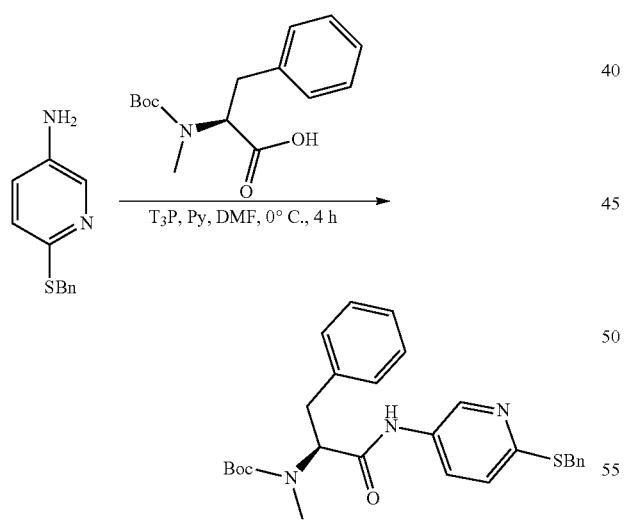

Preparation of (S)-tert-butyl 1-(6-(benzylthio)pyridin-3-ylamino)-1-oxo-3-phenylpropan-2-yl(methyl) carbamate To a solution of 2.79 (S)-2-(tert-butoxycarbonyl(methyl)amino)-3-phenylpropanoic acid (10 mmol, 1.00 equiv), 2.16 g 6-(benzylthio)pyridin-3-amine (10 mmol, 1 equiv) and 7. g pyridine (100 mol, 10.00 equiv) in 40 mL N,N-dimethylformamide was added dropwise a solution 25.8 propanephosphonic acid cyclic anhydride in ethyl acetate (50%, 50 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (1:1)) provided 2.77 g (S)-tert-butyl 1-(6-(benzylthio)pyridin-3-ylamino)-1-oxo-3-phenylpropan-2-yl(methyl)carbamate as a yellow solid (58% yield). MS (ESI$^+$) m/z 478 [M+H]$^+$.

Preparation of (S)-N-(6-(benzylthio)pyridin-3-yl)-2-(methylamino)-3-phenylpropanamide Hydrochloride

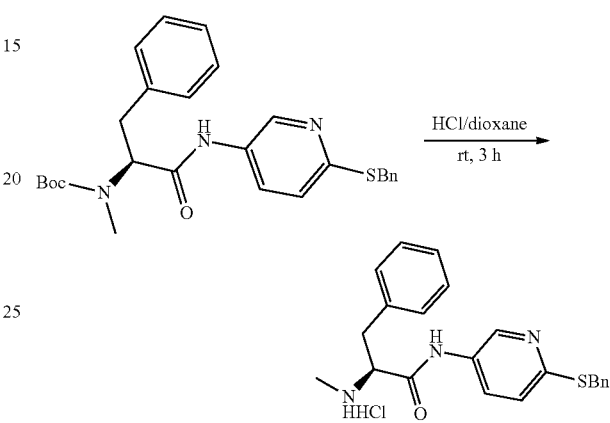

A mixture of 2.77 g (S)-tert-butyl 1-(6-(benzylthio)pyridin-3-ylamino)-1-oxo-3-phenylpropan-2-yl(methyl)carbamate (5.8 mmol, 1.00 equiv) in 20 mL hydrochloric acid in 1,4-dioxane (4.0 M) was stirred at room temperature for 3 h. The mixture was concentrated to afford 2.41 g (S)-N-(6-(benzylthio)pyridin-3-yl)-2-(methylamino)-3-phenylpropanamide hydrochloride as a light yellow solid (100% yield). MS (ESI$^+$) m/z 378 [M+H]$^+$.

Preparation of (S)-N-(1-(6-(benzylthio)pyridin-3-ylamino)-1-oxo-3-phenylpropan-2-yl)-4-fluoro-N-methylbenzamide

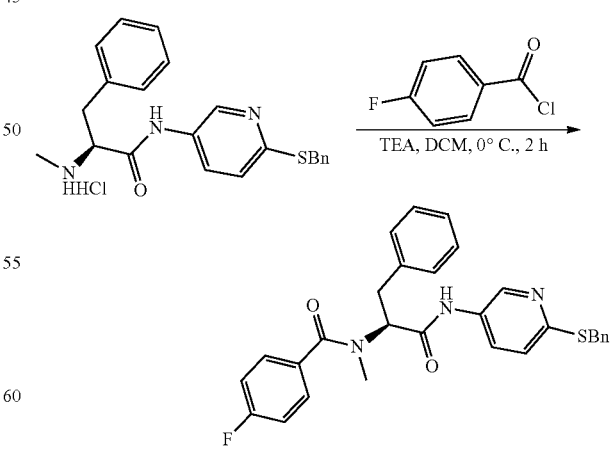

To a solution of 1.24 g (S)-N-(6-(benzylthio)pyridin-3-yl)-2-(methylamino)-3-phenylpropanamide hydrochloride (3.00 mmol, 1.00 equiv) and 1.818 g triethylamine (18.00 mmol, 6.00 equiv) in 20 mL dichloromethane was added dropwise 568.8 mg 4-fluorobenzoyl chloride (3.60 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 0.93 g (S)-N-(1-(6-(benzylthio)pyridin-3-ylamino)-1-oxo-3-phenylpropan-2-yl)-4-fluoro-N-methylbenzamide as a yellow solid (62% yield). MS (ESI⁺) m/z 500 [M+H]⁺.

Preparation of (S)-5-(2-(4-fluoro-N-methylbenzamido)-3-phenylpropanamido)pyridine-2-sulfonyl Chloride

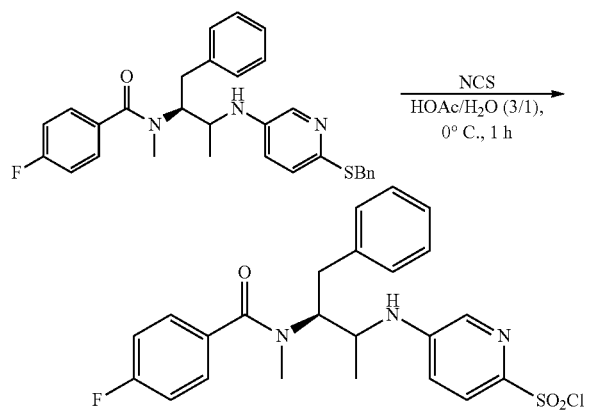

To a solution of 0.93 g (S)-N-(1-(6-(benzylthio)pyridin-3-ylamino)-1-oxo-3-phenylpropan-2-yl)-4-fluoro-N-methylbenzamide (1.86 mmol, 1.00 equiv) in 6 mL acetic acid and 2 mL water was added 1 g N-chlorosuccinimide (7.44 mmol, 4.00 equiv) at 0° C. The resulting mixture was stirred at 0° C. for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated to give 0.486 g (S)-5-(2-(4-fluoro-N-methylbenzamido)-3-phenylpropanamido)pyridine-2-sulfonyl chloride as a white solid (55% yield). MS (ESI⁺) m/z 476 and 478 [M+H]⁺.

Preparation of (S)-4-fluoro-N-(1-(6-(N-(1-methoxy-2-methylpropan-2-yl)sulfamoyl)pyridin-3-ylamino)-1-oxo-3-phenylpropan-2-yl)-N-methylbenzamide (I-161)

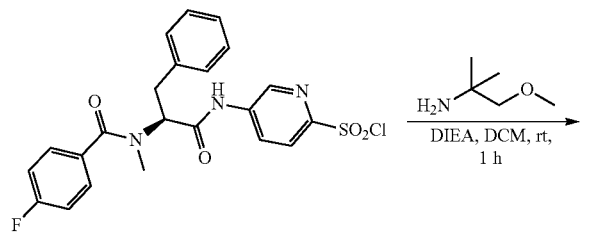

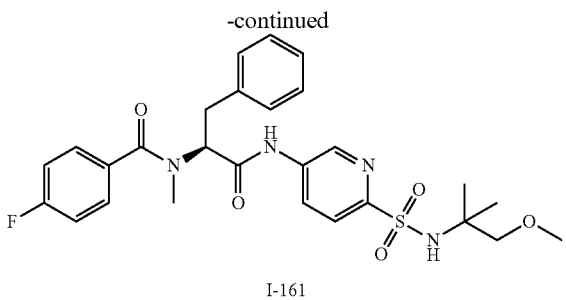

I-161

To a mixture of 118.45 mg 1-methoxy-2-methylpropan-2-amine (1.15 mmol, 5.0 equiv) and 148.35 mg N,N-diisopropylethylamine (1.15 mmol, 5.00 equiv) in 10 mL dichloromethane was added 110 mg (S)-4-(2-(4-fluorobenzamido)-3-phenylpropanamido)-3-methoxybenzene-1-sulfonyl chloride (0.23 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH₄HCO₃+ 0.1% NH₃—H₂O) and ACN (18% ACN up to 36% in 7 min); UV detection at 254/220 nm. The product-containing fractions were combined and evaporated partially in vacuo and lyophilized overnight to afford 12.5 mg (S)-4-fluoro-N-(1-(6-(N-(1-methoxy-2-methylpropan-2-yl)sulfamoyl)pyridin-3-ylamino)-1-oxo-3-phenylpropan-2-yl)-N-methylbenzamide (I-161) as a white solid (10% yield). MS (ESI, m/z) 543 [M+H]⁺; ¹H NMR (300 MHz, CD₃OD) δ 8.87 (s, 1H), 8.33 (dd, 1H), 8.01 (d, 1H), 7.37-7.10 (m, 9H), 5.60-4.78 (m, 1H), 3.45-3.34 (m, 1H), 3.24-2.95 (m, 9H), 1.18 (s, 6H).

Example 80. Synthesis of (S)-4-fluoro-N-(1-(4-(N-(2-methyl-1-morpholinopropan-2-yl)sulfamoyl)phenylamino)-1-oxo-3-phenylpropan-2-yl)benzamide (I-162) and (S)-4-fluoro-N-(1-(4-(N-(2-methyl-4-morpholinobutan-2-yl)sulfamoyl)phenylamino)-1-oxo-3-phenylpropan-2-yl)benzamide (I-163)

Synthesis Scheme 1

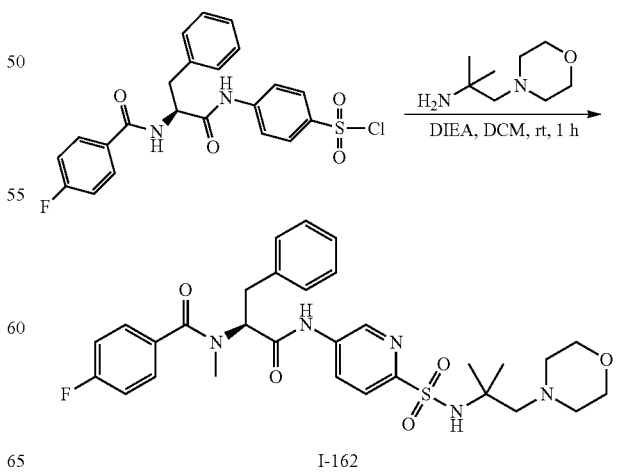

I-162

Synthesis Scheme 2:

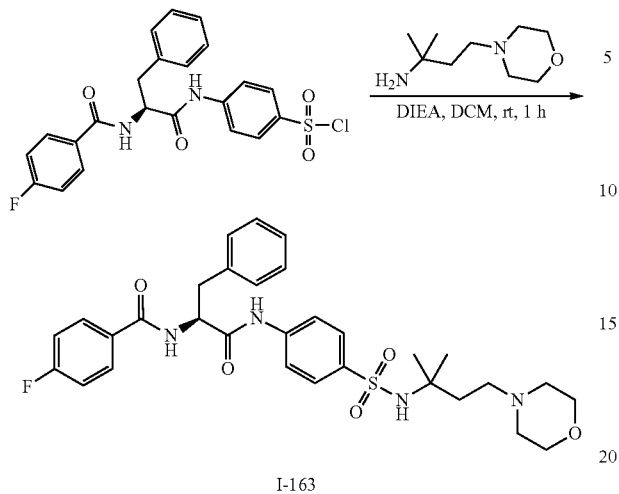

I-163

Using this general procedure for the preparation of Example 70 and substituting the appropriate amine in the last step, the following compounds were prepared.

TABLE 18

Compounds prepared according to Example 80.

| Compound | Chemical Name | yield | MS | 1HNMR |
|---|---|---|---|---|
| I-162 | (S)-4-fluoro-N-(1-(4-(N-(2-methyl-1-morpholinopropan-2-yl)sulfamoyl)phenylamino)-1-oxo-3-phenylpropan-2-yl)benzamide | 28% | MS (ESI$^+$, m/z): Calcd for C30H35FN4O5S: 582; found 583 [M + H]$^+$; | $^1$H NMR (300 MHz, CD$_3$OD) δ 7.87-7.80 (m, 4H), 7.71 (d, 2H), 7.35-7.15 (m, 7H), 4.95-4.90 (m, 1H), 3.72-3.65 (m, 4H), 3.30-3.13 (m, 2H), 2.62-2.55 (m, 4H), 2.37 (s, 2H), 1.13 (s, 6H). |
| I-163 | (S)-4-fluoro-N-(1-(4-(N-(2-methyl-4-morpholinobutan-2-yl)sulfamoyl)phenylamino)-1-oxo-3-phenylpropan-2-yl)benzamide | 26% | MS (ESI$^+$, m/z): Calcd for C31H37FN4O5S: 596; found 597 [M + H]$^+$ | $^1$H NMR (400 MHz, CD$_3$OD) δ 7.88-7.80 (m, 4H), 7.72 (d, 2H), 7.36-7.16 (m, 7H), 4.96-4.90 (m, 1H), 3.76-3.71 (m, 4H), 3.30-3.13 (m, 2H), 2.63-2.52 (m, 6H), 1.73 (t, 2H), 1.21 (s, 6H). |

Example 81: (S)-N-(4-(N-tert-butylsulfamoyl)phenyl)-2-(4-fluorophenylsulfonamido)-3-phenylpropanamide, I-165

Preparation of (S)-N-(4-(N-tert-butylsulfamoyl)phenyl)-2-(4-fluorophenylsulfonamido)-3-phenylpropanamide (I-165)

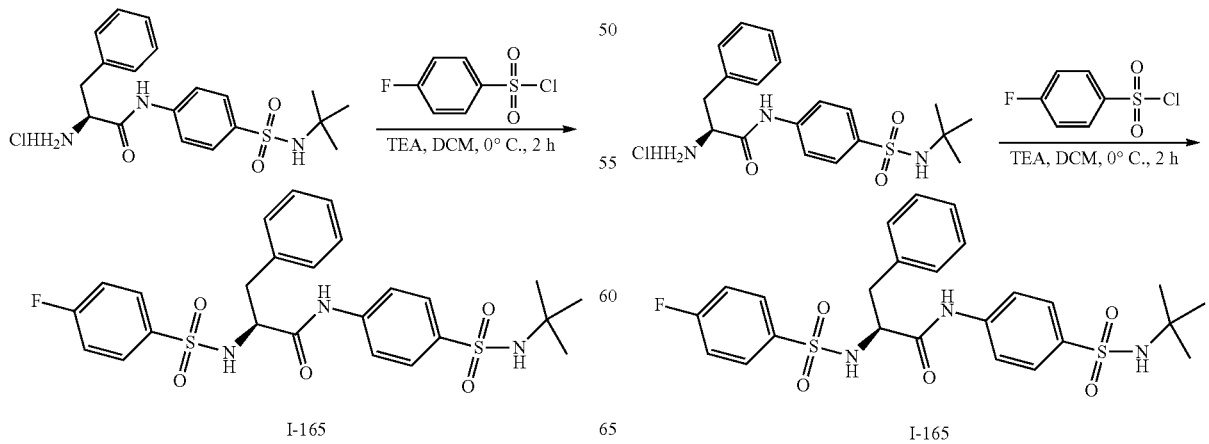

To a solution of 111.38 mg (S)-2-amino-N-(4-(N-tert-butylsulfamoyl)phenyl)-3-phenylpropanamide hydrochloride (0.27 mmol, 1.00 equiv) and 163.62 mg triethylamine (1.62 mmol, 6.00 equiv) in 10 mL dichloromethane was added dropwise 63.18 mg 4-fluorobenzene-1-sulfonyl chloride (0.324 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. The crude product was purified by Prep-HPLC with the following conditions: Column, YMC-Actus Triart C18, 30*250 mm, 5 um; Mobile Phase, water (10% $NH_4HCO_3$+0.1% $NH_3$—$H_2O$) and ACN (38% ACN up to 58% in 7 min); UV detection at 254/220 nm. The product-containing fractions were combined and evaporated partially in vacuo and lyophilized overnight to afford 21.7 mg (S)-N-(4-(N-tert-butylsulfamoyl)phenyl)-2-(4-fluorophenylsulfonamido)-3-phenylpropanamide (I-165) as a white solid (15% yield). MS (ESI, m/z) 532 [M−H]$^-$; $^1$H NMR (400 MHz, $d_6$-DMSO) δ 10.31 (s, 1H), 8.48 (d, 1H), 7.71 (d, 2H), 7.65-7.61 (m, 2H), 7.52 (d, 2H), 7.41 (s, 1H), 7.23-7.11 (m, 7H), 4.20-4.13 (m, 1H), 2.98-2.92 (m, 1H), 2.83-2.77 (m, 1H), 1.09 (s, 9H).

Example 82: (S)-N-(1-(4-(N-tert-butylsulfamoyl)-3-chlorophenylamino)-1-oxo-3-phenylpropan-2-yl)-4-fluorobenzamide, I-168

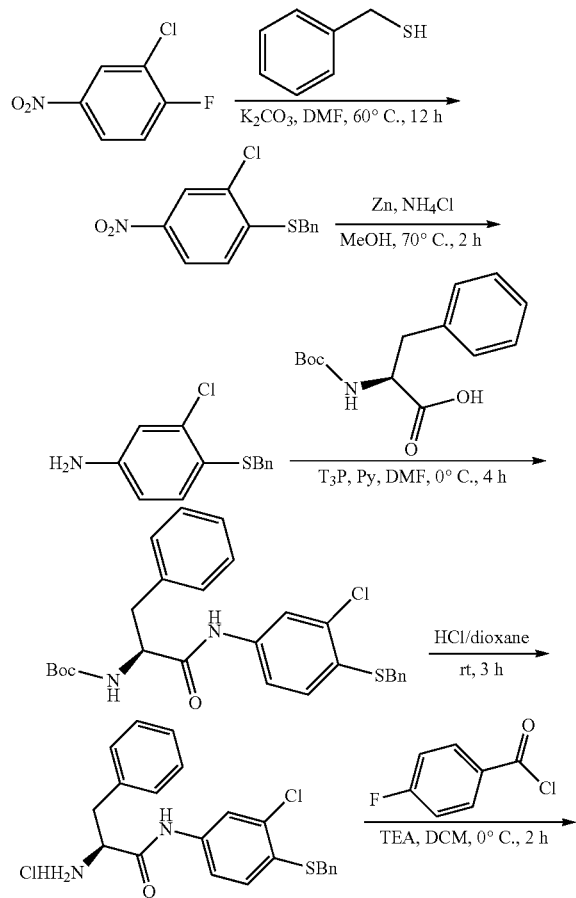

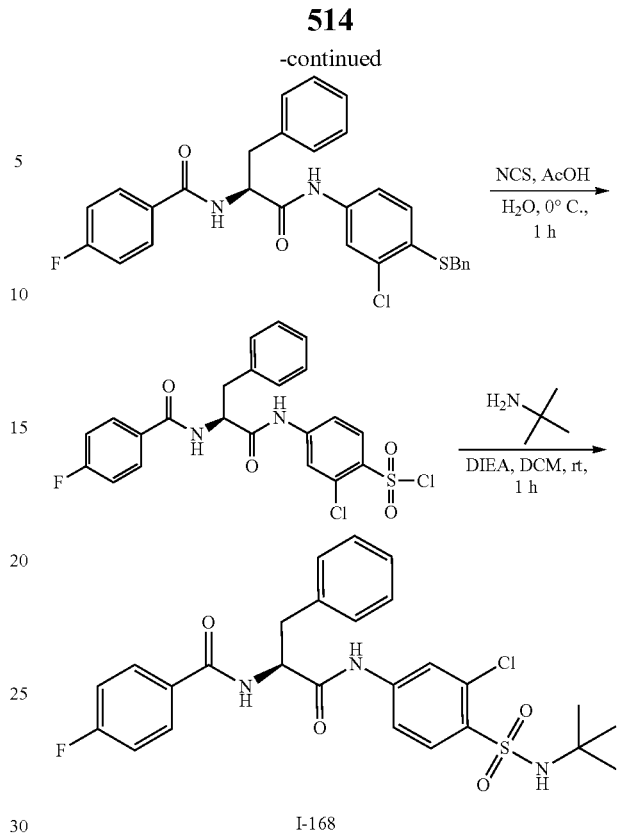

I-168

Preparation of benzyl(2-chloro-4-nitrophenyl)sulfane

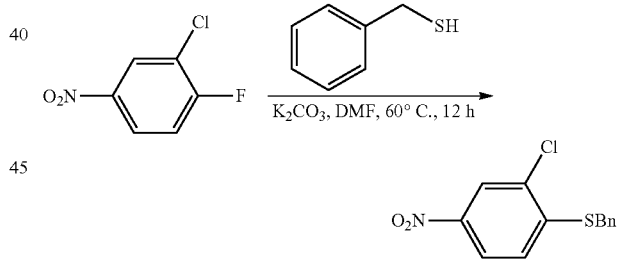

To a solution of 8.8 g 2-chloro-1-fluoro-4-nitrobenzene (50 mmol, 1.00 equiv) and 13.8 g potassium carbonate (100 mmol, 2.00 equiv) in 300 mL anhydrous N,N-dimethylformamide was added dropwise 7.44 g of phenylmethanethiol (60 mmol, 1.20 equiv) at room temperature. The resulting mixture was stirred for 12 h at 60° C. The mixture was cooled to room temperature, diluted with 500 mL water and extracted with ethyl acetate (3×500 mL). The combined organic layers were washed with brine (3×200 mL), dried over anhydrous magnesium sulfate, filtered and the filtrate was concentrated in vacuo. Purification by column chromatography (silica gel, petroleum ether:ethyl acetate (5:1)) afforded 8.54 g benzyl(2-chloro-4-nitrophenyl)sulfane as a yellow solid (61% yield). MS (ESI$^+$) m/z 280 and 282 [M+H]$^+$.

Preparation of 4-(benzylthio)-3-chlorobenzenamine

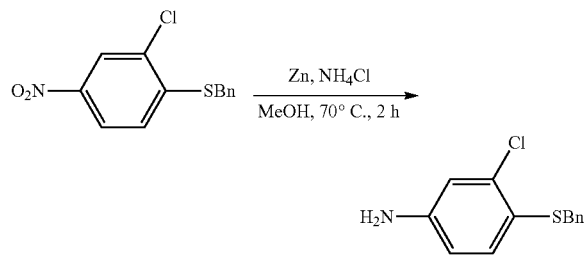

To a solution of 8.54 g benzyl(2-chloro-4-nitrophenyl)sulfane (30.5 mmol, 1.00 equiv) in 200 mL methanol was added 8.16 g ammonium chloride (152.5 mmol, 5.00 equiv) and 7.75 g zinc (122 mmol, 4.00 equiv) at room temperature. The resulting mixture was stirred for 2 h at 70° C. under nitrogen atmosphere. The mixture was cooled to room temperature, filtered and the filtrate concentrated in vacuo. The residue was diluted with 50 mL water, then adjusted to pH 9 with sodium bicarbonate (aq.). The mixture was extracted with ethyl acetate (3×200 mL). The combined organic layers were washed with brine (2×100 mL), dried over anhydrous magnesium sulfate, filtered and the filtrate concentrated in vacuo. Purification by column chromatography (silica gel, petroleum ether:ethyl acetate (2:1)) afforded 4.58 g 4-(benzylthio)-3-chlorobenzenamine as an orange oil (60% yield). MS (ESI$^+$) m/z 250 and 252 [M+H]$^+$.

Preparation of (S)-tert-butyl 1-(4-(benzylthio)-3-chlorophenylamino)-1-oxo-3-phenylpropan-2-ylcarbamate

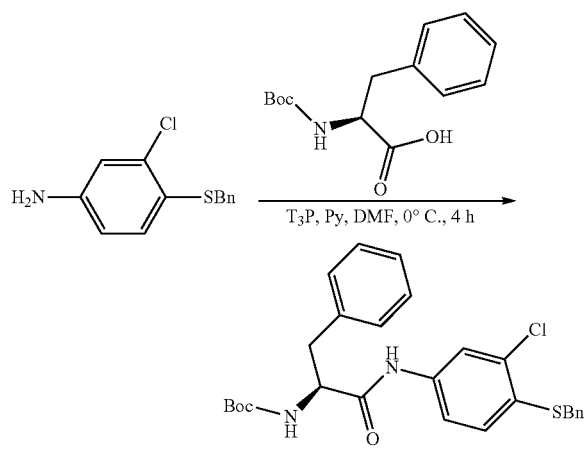

To a solution of 1.9 g (S)-2-(tert-butoxycarbonylamino)-3-phenylpropanoic acid (7.14 mmol, 1.00 equiv), 1.96 g 4-(benzylthio)-3-chlorobenzenamine (7.85 mmol, 1.10 equiv) and 5.64 g pyridine (71.40 mmol, 10.00 equiv) in 40 mL N,N-dimethylformamide was added dropwise a solution 18.42 g propanephosphonic acid cyclic anhydride in ethyl acetate (50%, 35.70 mmol, 5.00 equiv) at 0° C. The resulting mixture was stirred for 4 h at 0° C. The mixture was diluted with 100 mL water and extracted with ethyl acetate (3×200 mL). The combined organic layers were washed with brine (3×100 mL), dried over anhydrous magnesium sulfate, filtered and the filtrate concentrated in vacuo. Purification by column chromatography (silica gel, petroleum ether:ethyl acetate (3:1)) provided 2.26 g (S)-tert-butyl 1-(4-(benzylthio)-3-chlorophenylamino)-1-oxo-3-phenylpropan-2-ylcarbamate as a yellow solid (64% yield). MS (ESI$^+$) m/z 441 [M-56+H]$^+$.

Preparation of (S)-2-amino-N-(4-(benzylthio)-3-chlorophenyl)-3-phenylpropanamide Hydrochloride

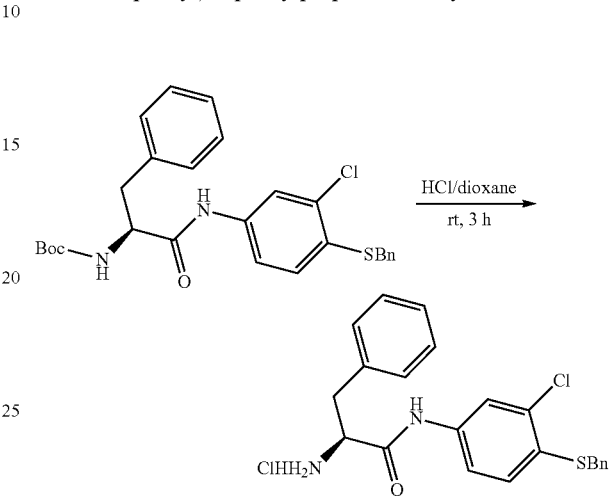

A mixture of 2.26 g (S)-tert-butyl 1-(4-(benzylthio)phenylamino)-1-oxo-3-(pyridin-2-yl)propan-2-ylcarbamate (4.56 mmol, 1.00 equiv) in 20 mL hydrochloric acid in 1,4-dioxane (4.0 M) was stirred at room temperature for 2 h. The mixture was concentrated to afford 2 g (S)-2-amino-N-(4-(benzylthio)-3-chlorophenyl)-3-phenylpropanamide hydrochloride as a light yellow solid (100% yield). MS (ESI$^+$) m/z 397 [M+H]$^+$.

Preparation of (S)-N-(1-(4-(benzylthio)-3-chlorophenylamino)-1-oxo-3-phenylpropan-2-yl)-4-fluorobenzamide

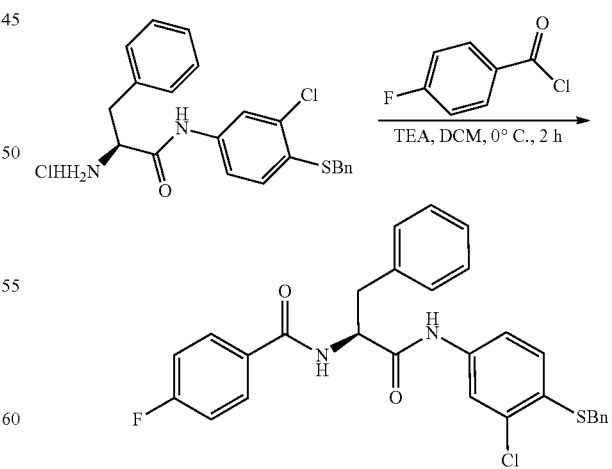

To a solution of 2 g (S)-2-amino-N-(4-(benzylthio)-3-chlorophenyl)-3-phenylpropanamide hydrochloride (4.56 mmol, 1.00 equiv) and 2.76 g triethylamine (27.36 mmol, 6.00 equiv) in 20 mL dichloromethane was added dropwise 865 mg 4-fluorobenzoyl chloride (5.47 mmol, 1.20 equiv) at 0° C. The resulting mixture was stirred for 2 h at 0° C. The resulting mixture was diluted with 20 mL water and extracted with dichloromethane (3×30 mL). The combined organic layers were washed with brine (1×30 mL), dried over anhydrous magnesium sulfate, filtered and the filtrate concentrated in vacuo. Purification by column chromatography (silica gel, petroleum ether:ethyl acetate (1:1)) afforded 1.488 g (S)-N-(1-(4-(benzylthio)-3-chlorophenylamino)-1-oxo-3-phenylpropan-2-yl)-4-fluorobenzamide as a yellow solid (63% yield). MS (ESI⁺) m/z 519 [M+H]⁺.

Preparation of (S)-2-chloro-4-(2-(4-fluorobenzamido)-3-phenylpropanamido)benzene-1-sulfonyl Chloride

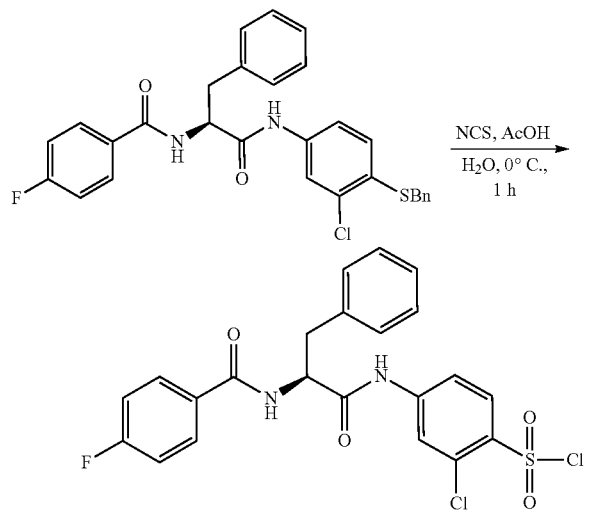

To a solution of 1.488 g (S)-N-(1-(4-(benzylthio)-3-chlorophenylamino)-1-oxo-3-phenylpropan-2-yl)-4-fluorobenzamide (2.87 mmol, 1.00 equiv) in 12 mL acetic acid and 4 mL water was added 1.53 g N-chlorosuccinimide (11.48 mmol, 4.00 equiv) at 0° C. The resulting mixture was stirred at 0° C. for 2 h. The mixture was diluted with 30 mL water and extracted with dichloromethane (3×50 mL). The combined organic layers were washed with brine (1×50 mL), dried over anhydrous magnesium sulfate, filtered and the filtrate concentrated to give 0.64 g (S)-2-chloro-4-(2-(4-fluorobenzamido)-3-phenylpropanamido)benzene-1-sulfonyl chloride as a white solid (45% yield). MS (ESI⁺) m/z 495 [M+H]⁺.

Preparation of (S)-N-(1-(4-(N-tert-butylsulfamoyl)-3-chlorophenylamino)-1-oxo-3-phenylpropan-2-yl)-4-fluorobenzamide (I-168)

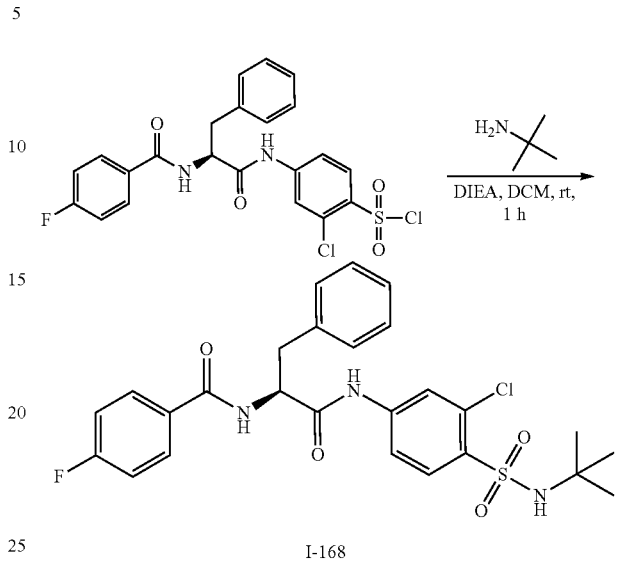

I-168

To a mixture of 73.73 mg 2-methylpropan-2-amine (1.01 mmol, 5.0 equiv) and 130.3 mg N,N-diisopropylethylamine (1.01 mmol, 5.00 equiv) in 10 mL dichloromethane was added 100 mg (S)-2-chloro-4-(2-(4-fluorobenzamido)-3-phenylpropanamido)benzene-1-sulfonyl chloride (0.202 mmol, 1.00 equiv). The mixture was stirred at room temperature for 1 h. The mixture was diluted with 10 mL water and extracted with dichloromethane (3×20 mL). The combined organic layers were washed with brine (1×30 mL), dried over anhydrous magnesium sulfate, filtered and the filtrate concentrated under reduced pressure. The crude product was purified by Prep-HPLC with the following conditions: Column, YMC-Actus Triart C18, 30*250 mm, 5 um; Mobile Phase, water (10% NH₄HCO₃+0.1% NH₃·H₂O) and ACN (32% ACN up to 46% in 7 min); UV detection at 254/220 nm. The product-containing fractions were combined and evaporated partially in vacuo and lyophilized overnight to afford 39.8 mg (S)-N-(1-(4-(N-tert-butylsulfamoyl)-3-chlorophenylamino)-1-oxo-3-phenylpropan-2-yl)-4-fluorobenzamide (I-168) as a white solid.

Using this general procedure for the preparation of I-168 and substituting the appropriate amine in the last step, the following compounds were prepared.

TABLE 19

Compounds prepared according to Example 82.

| Compound | Chemical Name | yield | MS | 1HNMR |
|---|---|---|---|---|
| I-168 | (S)-N-(1-(4-(N-tert-butylsulfamoyl)-3-chlorophenylamino)-1-oxo-3-phenylpropan-2-yl)-4-fluorobenzamide | 37% | MS (ESI⁺, m/z): Calcd for C26H27ClFN3O4S: 531; found 532 [M + H]⁺; | ¹H NMR (300 MHz, CD₃OD) δ 7.99-7.82 (m, 4H), 7.52 (dd, 1H), 7.34-7.15 (m, 7H), 4.93-4.88 (m, 1H), 3.27-3.13 (m, 2H), 1.19 (s, 9H). |
| I-169 | (S)-N-(1-(4-(N-bicyclo[1.1.1]pentan-1-ylsulfamoyl)-3-chlorophenylamino)-1-oxo-3-phenylpropan-2-yl)-4-fluorobenzamide | 38% | MS (ESI⁺, m/z): Calcd for C27H25ClFN3O4S: 541; found 542 [M + H]⁺ | ¹H NMR (300 MHz, d₆-DMSO) δ 10.71 (s, 1H), 8.88 (d, 1H), 8.69 (s, 1H), 8.00-7.88 (m, 4H), 7.65 (dd, 1H), 7.40-7.18 (m, 7H), 4.86-4.75 (m, 1H), 3.20-3.07 (m, 2H), 2.25 (s, 1H), 1.68 (s, 6H). |

TABLE 19-continued

Compounds prepared according to Example 82.

| Compound | Chemical Name | yield | MS | 1HNMR |
|---|---|---|---|---|
| I-170 | (S)-N-(1-(3-chloro-4-(N-oxetan-3-ylsulfamoyl)phenylamino)-1-oxo-3-phenylpropan-2-yl)-4-fluorobenzamide | 36% | MS (ESI+, m/z): Calcd for C25H23ClFN3O5S: 531; found 532 [M + H]+; | $^1$H NMR (400 MHz, $d_6$-DMSO) δ 10.79 (br s, 1H), 8.90 (d, 1H), 8.00 (s, 1H), 7.97-7.90 (m, 3H), 7.65 (dd, 1H), 7.45-7.40 (m, 2H), 7.35-7.27 (m, 4H), 7.24-7.18 (m, 1H), 4.86-4.78 (m, 1H), 4.56-4.50 (m, 2H), 4.45-4.35 (m, 3H), 3.25-3.05 (m, 2H). |
| I-171 | (S)-N-(1-(3-chloro-4-(N-(4-methoxy-2-methylbutan-2-yl)sulfamoyl)phenylamino)-1-oxo-3-phenylpropan-2-yl)-4-fluorobenzamide | 37% | MS (ESI+, m/z): Calcd for C28H31ClFN3O5S: 575; found 576 [M + H]+; | $^1$H NMR (400 MHz, CD$_3$OD) δ 7.97-7.95 (m, 2H), 7.88-7.84 (m, 2H), 7.54 (dd, 1H), 7.38-7.27 (m, 4H), 7.25-7.16 (m, 3H), 4.95-4.89 (m, 1H), 3.53 (t, 2H), 3.32 (s, 3H), 3.31-3.26 (dd, 1H),3.20-3.15 (dd, 1H), 1.80 (t, 2H), 1.18 (s, 6H). |

Example 83. Preparation of (S)-N-(1-(4-(N-(2-cyanopropan-2-yl)sulfamoyl)phenylamino)-1-oxo-3-phenylpropan-2-yl)-4-fluorobenzamide (I-172), (S)-4-fluoro-N-(1-(4-(N-(2-methylbut-3-yn-2-yl)sulfamoyl)phenylamino)-1-oxo-3-phenylpropan-2-yl)benzamide (I-173), 4-fluoro-N-((S)-1-oxo-3-phenyl-1-(4-(N-((S)-tetrahydrofuran-3-yl)sulfamoyl)phenylamino)propan-2-yl)benzamide (I-174), and 4-fluoro-N-((S)-1-oxo-3-phenyl-1-(4-(N-((R)-tetrahydrofuran-3-yl)sulfamoyl)phenylamino)propan-2-yl)benzamide (I-175)

Synthesis Scheme for I-172:

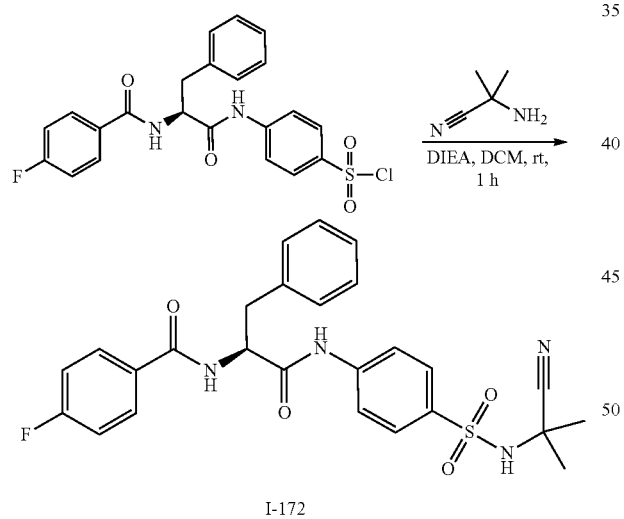

I-172

Synthesis Scheme for I-173:

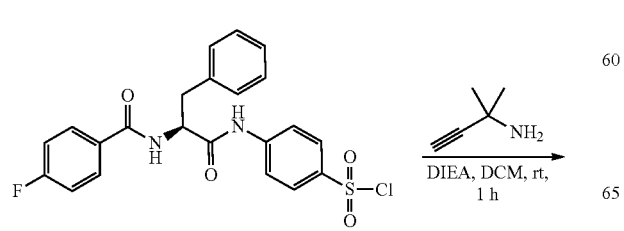

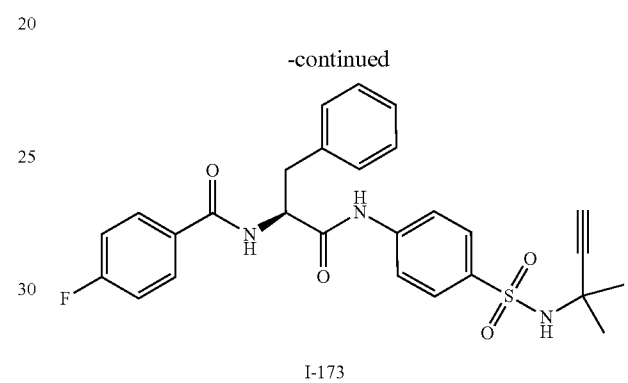

I-173

Synthesis Scheme for I-174:

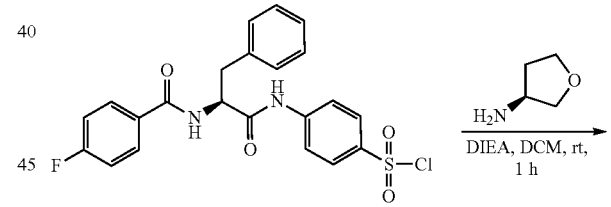

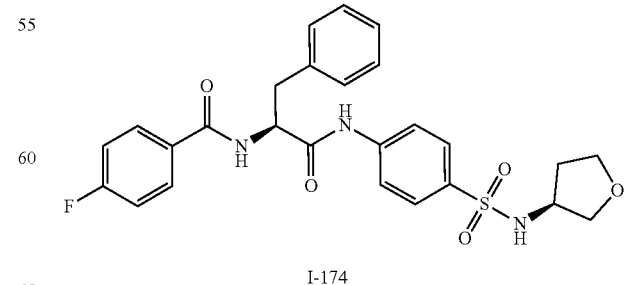

I-174

Synthesis Scheme for I-175:

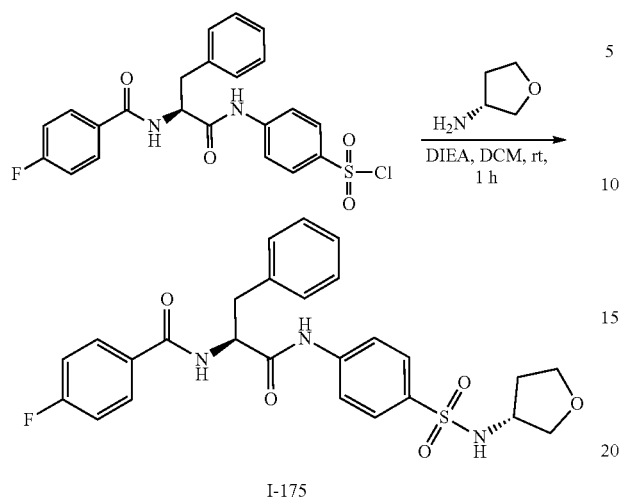

I-175

Using the general N-sulfonylation procedure described in Example 2a and substituting the appropriate amine in the last step, I-172, I-173, I-174, and I-175 were prepared.

TABLE 20

Compounds from Example 83 prepared according to Example 2a.

| Compound | Chemical Name | yield | MS | 1HNMR |
|---|---|---|---|---|
| I-172 | (S)-N-(1-(4-(N-(2-cyanopropan-2-yl)sulfamoyl)phenylamino)-1-oxo-3-phenylpropan-2-yl)-4-fluorobenzamide | 43% | MS (ESI$^+$, m/z): Calcd for C26H25FN4O4S: 508; found 509 [M + H]$^+$; | $^1$H NMR (400 MHz, CD$_3$OD) δ 7.87-7.84 (m, 4H), 7.80-7.75 (m, 2H), 7.37-7.28 (m, 4H), 7.25-7.17 (m, 3H), 4.97-4.93 (m, 1H), 3.31-3.15 (m, 2H), 1.61 (s, 6H). |
| I-173 | (S)-4-fluoro-N-(1-(4-(N-(2-methylbut-3-yn-2-yl)sulfamoyl)phenylamino)-1-oxo-3-phenylpropan-2-yl)benzamide | 44% | MS (ESI$^+$, m/z): Calcd for C27H26FN3O4S: 507; found 508 [M + H]$^+$ | $^1$H NMR (300 MHz, CD$_3$OD) δ 7.86-7.80 (m, 4H), 7.68 (d, 2H), 7.35-7.14 (m, 7H), 4.97-4.92 (m, 1H), 3.31-3.13 (m, 2H), 2.39 (s, 1H), 1.50 (s, 6H). |
| I-174 | 4-fluoro-N-((S)-1-oxo-3-phenyl-1-(4-(N-((S)-tetrahydrofuran-3-yl)sulfamoyl)phenylamino)propan-2-yl)benzamide | 46% | MS (ESI$^+$, m/z): Calcd for C26H26FN3O5S: 511; found 512 [M + H]$^+$; | $^1$H NMR (300 MHz, CD$_3$OD) δ 7.87-7.72 (m, 6H), 7.35-7.15 (m, 7H), 4.96-4.91 (m, 1H), 3.86-3.78 (m, 2H), 3.74-3.65 (m, 2H), 3.46-3.42 (m, 1H), 3.31-3.13 (m, 2H), 2.08-1.96 (m, 1H), 1.76-1.63 (m, 1H). |
| I-175 | 4-fluoro-N-((S)-1-oxo-3-phenyl-1-(4-(N-((R)-tetrahydrofuran-3-yl)sulfamoyl)phenylamino)propan-2-yl)benzamide | 47% | MS (ESI$^+$, m/z): Calcd for C26H26FN3O5S: 511; found 512 [M + H]$^+$; | $^1$H NMR (300 MHz, d$_6$-DMSO) δ 10.62 (s, 1H), 8.87 (d, 1H), 7.96-7.75 (m, 7H), 7.47-7.15 (m, 7H), 4.88-4.80 (m, 1H), 3.71-3.53 (m, 4H), 3.31-3.08 (m, 3H), 1.95-1.81 (m, 1H), 1.66-1.52 (m, 1H). |

Example 84. Dundee MALDI-TOF Mass Spectrometry Assay (IC$_{50}$)

Compounds were tested in a MALDI-TOF assay based on the paper by Ritorto et al. (Ritorto et al. Screening of DUB activity and specificity by MALDI-TOF mass spectrometry. *Nat. Commun.* 5:4763).

USP30 (25 ng/µl) tested against K48-linked diubiquitin (5.6 µM). USP30 was diluted in a buffer containing 40 mM Tris, 0.01% BSA, 1 mM DTT and K48 in 40 mM Tris, 0.01% BSA.

The compounds were pre-incubated with the USP30 for 5 mins at room temp before the K48 dimer addition. The assay mixture was then incubated for 45 mins at room temp. The assay was stopped by the addition of TFA to a final concentration of 2% (v/v).

Acidified samples of the DUB assays were mixed with 0.5 mM 15N-ubiquitin and then with one part of 2% (v/v) TFA and one part of 2,5 DHAP matrix solution (7.6 mg of 2,5 DHAP in 375 ml ethanol and 125 ml of an aqueous 12 mg ml 1 diammonium hydrogen citrate). Then 250 nl of these solutions were spotted onto an MTP AnchorChip 1,536 TF and this is analysed on the Bruker rapifleX MALDI-TOF.

Table 21 presents $IC_{50}$ values for the MALDI-TOF assay.

Table 21 shows the activity of selected compounds of this invention in the Dundee MALDI-TOF assay. The compound numbers correspond to the compound numbers in Table 1. Compounds having an activity designated as "A" provided an $IC_{50} \leq 0.05$ μM; compounds having an activity designated as "B" provided an $IC_{50}$ of >0.05-1.0 μM; compounds having an activity designated as "C" provided an $IC_{50}$ of 1.0 to 10.0 μM; compounds having an activity designated as "C+" provided an $IC_{50}$ of >1.0 μM; and compounds having an activity designated as "D" provided an $IC_{50} \geq 10.0$ μM.

TABLE 21

$IC_{50}$ results.

| Compound | Dundee $IC_{50}$ μM (avg in vitro MS assay) |
|---|---|
| I-1 | B |
| I-2 | B |
| I-3 | D |
| I-4 | B |
| I-5 | A |
| I-6 | A |
| I-7 | A |
| I-8 | A |
| I-9 | A |
| I-10 | A |
| I-11 | A |
| I-11 | B |
| I-12 | A |
| I-13 | A |
| I-15 | B |
| I-17 | C+ |
| I-18 | D |
| I-19 | B |
| I-22 | B |
| I-23 | A |
| I-24 | A |
| I-25 | A |
| I-26 | A |
| I-27 | A |
| I-28 | A |
| I-29 | C+ |
| I-30 | B |
| I-31 | B |
| I-32 | B |
| I-33 | B |
| I-34 | A |
| I-35 | B |
| I-35 | B |
| I-36 | C+ |
| I-41 | C |
| I-42 | C |
| I-44 | C+ |
| I-45 | C+ |
| I-46 | C+ |
| I-47 | C+ |
| I-48 | C+ |
| I-49 | C |
| I-50 | C |
| I-51 | C |
| I-51 | C |
| I-54 | C+ |
| I-57 | C+ |
| I-61 | A |
| I-62 | A |
| I-63 | B |
| I-64 | A |
| I-65 | B |
| I-66 | B |
| I-67 | A |
| I-68 | C+ |
| I-69 | C |
| I-70 | C |
| I-72 | C |
| I-73 | A |

TABLE 21-continued $IC_{50}$ results.

| Compound | Dundee $IC_{50}$ μM (avg in vitro MS assay) |
|---|---|
| I-74 | B |
| I-75 | B |
| I-76 | B |
| I-77 | B |
| I-78 | B |
| I-79 | B |
| I-80 | B |
| I-81 | B |
| I-82 | C+ |
| I-83 | C+ |
| I-84 | B |
| I-85 | B |
| I-87 | B |
| I-88 | A |
| I-89 | C |
| I-90 | D |
| I-91 | B |
| I-92 | C |
| I-93 | B |
| I-94 | B |
| I-95 | B |
| I-96 | B |
| I-97 | B |
| I-98 | B |
| I-99 | D |
| I-100 | C |
| I-101 | D |
| I-102 | B |
| I-104 | A |
| I-105 | B |
| I-106 | B |
| I-107 | A |
| I-108 | B |
| I-111 | B |
| I-112 | B |
| I-113 | B |
| I-114 | B |
| I-115 | A |
| I-116 | B |
| I-117 | A |
| I-118 | B |
| I-119 | B |
| I-120 | B |
| I-121 | B |
| I-122 | B |
| I-123 | B |
| I-124 | A |
| I-125 | A |
| I-126 | C |
| I-129 | C |
| I-130 | B |
| I-131 | B |
| I-132 | A |
| I-133 | C |
| I-134 | A |
| I-135 | B |
| I-136 | A |
| I-137 | A |
| I-138 | A |
| I-139 | B |
| I-140 | B |
| I-141 | B |
| I-142 | A |
| I-144 | B |
| I-146 | B |
| I-147 | A |
| I-148 | A |
| I-149 | A |
| I-150 | A |
| I-151 | A |
| I-152 | A |
| I-155 | A |
| I-156 | A |
| I-157 | B |

TABLE 21-continued

IC$_{50}$ results.

| Compound | Dundee IC$_{50}$ μM (avg in vitro MS assay) |
|---|---|
| I-158 | A |
| I-162 | A |

Example 85. Dundee MALDI-TOF Mass Spectrometry Assay (% DUB Activity Remaining at 1 μM)

Table 22 presents the Dundee MALDI-TOF values expressed as % DUB activity remaining at a compound concentration of 1 μM.

Table 22 shows the activity of selected compounds of this invention in the Dundee MALDI-TOF assay. The compound numbers correspond to the compound numbers in Table 1. Compounds having an activity designated as "A" provided an % activity remaining at 1 μM of 0-25%; compounds having an activity designated as "B" provided an % activity remaining at 1 μM of 25-50%; compounds having an activity designated as "C" provided an % activity remaining at 1 μM of 50-75%; and compounds having an activity designated as "D" provided an % activity remaining at 1 μM of >75%.

TABLE 22

% DUB activity remaining at 1 μM.

| Compound Number | Dundee % Activity at 1 μM (avg in vitro MS assay) |
|---|---|
| I-15 | B |
| I-17 | D |
| I-18 | C |
| I-19 | B |
| I-20 | D |
| I-21 | D |
| I-22 | A |
| I-26 | A |
| I-27 | A |
| I-28 | A |
| I-29 | D |
| I-35 | A |
| I-36 | D |
| I-41 | B |
| I-42 | D |
| I-43 | C |
| I-44 | D |
| I-45 | D |
| I-46 | D |
| I-47 | D |
| I-48 | D |
| I-49 | D |
| I-50 | C |
| I-51 | D |
| I-52 | D |
| I-53 | D |
| I-55 | D |
| I-57 | D |
| I-59 | D |
| I-60 | D |
| I-64 | A |
| I-65 | A |
| I-66 | A |
| I-68 | D |

TABLE 22-continued

% DUB activity remaining at 1 μM.

| Compound Number | Dundee % Activity at 1 μM (avg in vitro MS assay) |
|---|---|
| I-82 | D |
| I-83 | D |

Example 86. In Vitro USP30 Biochemical Assay

In vitro biochemical assay to establish the potency of compounds for USP30 inhibition: a 384-well plate assay using a fluorophore tagged substrate of USP30 was used for in vitro screening of compounds. Each compound was tested at 10 different concentrations (0.5 to 10,000 nM) in duplicate wells. Compounds were pre-incubated at 25° C. for 30 min in an assay buffer consisting of 20 mM Tris/HCl, pH8.0, 1 mM GSH, 0.01% Triton X-100, 0.03% BGG and 1.5 nM recombinant USP30 (amino acids 57-517 of the human sequence with a C-terminal 6-His tag). Following the pre-incubation, Ubiquitin-Rhodamine substrate dissolved in the assay buffer was added at the final concentration of 25 nM to each well and plates were incubated at 25° C. for an additional 75 minutes. The reaction was stopped by adding 10 mM citric acid and fluorescence was read using excitation wavelength 485 nm, emission of 535 nm. Data were analyzed using Graph Pad Prism software with a four-parameter (floating slope) fit to log concentration data to determine IC$_{50}$s.

Table 23 presents IC$_{50}$ values for the USP30 biochemical assay.

Table 23 shows the activity of selected compounds of this invention in the USP30 biochemical assay. The compound numbers correspond to the compound numbers in Table 1. Compounds having an activity designated as "A" provided an IC$_{50}$≤0.05 μM; compounds having an activity designated as "B" provided an IC$_{50}$ of >0.05-1.0 μM; compounds having an activity designated as "C" provided an IC$_{50}$ of 1.0 to 10.0 μM; and compounds having an activity designated as "D" provided an IC$_{50}$≥10.0 μM.

TABLE 23

IC$_{50}$ results.

| Compound | USP30 IC$_{50}$ μM (avg) |
|---|---|
| I-4 | C |
| I-5 | B |
| I-10 | A |
| I-11 | B |
| I-11 | B |
| I-13 | B |
| I-18 | D |
| I-19 | B |
| I-20 | D |
| I-21 | D |
| I-22 | C |
| I-23 | B |
| I-25 | A |
| I-26 | B |
| I-30 | B |
| I-33 | B |
| I-34 | A |
| I-35 | B |
| I-35 | C |
| I-41 | C |
| I-43 | C |
| I-50 | C |

TABLE 23-continued

IC$_{50}$ results.

| Compound | USP30 IC$_{50}$ μM (avg) |
| --- | --- |
| I-51 | C |
| I-52 | D |
| I-53 | D |
| I-55 | D |
| I-56 | D |
| I-59 | C |
| I-60 | D |
| I-64 | B |
| I-65 | B |
| I-70 | C |
| I-71 | D |
| I-72 | C |
| I-73 | B |
| I-74 | B |
| I-75 | B |
| I-76 | C |
| I-77 | B |
| I-78 | C |
| I-79 | C |
| I-80 | B |
| I-81 | B |
| I-84 | B |
| I-85 | A |
| I-86 | D |
| I-87 | B |
| I-88 | B |
| I-89 | D |
| I-90 | C |
| I-91 | B |
| I-92 | C |
| I-93 | A |
| I-94 | B |
| I-95 | B |
| I-96 | A |
| I-97 | B |
| I-98 | B |
| I-99 | D |
| I-100 | D |
| I-101 | D |
| I-102 | D |
| I-103 | D |
| I-104 | B |
| I-105 | B |
| I-106 | B |
| I-107 | A |
| I-108 | B |
| I-109 | C |
| I-110 | B |
| I-111 | B |
| I-112 | B |
| I-113 | B |
| I-114 | B |
| I-115 | B |
| I-116 | B |
| I-117 | B |
| I-118 | B |
| I-119 | B |
| I-120 | B |
| I-121 | B |
| I-122 | B |
| I-123 | B |
| I-124 | B |
| I-125 | B |
| I-126 | D |
| I-127 | D |
| I-128 | D |
| I-129 | C |
| I-130 | B |
| I-131 | B |
| I-132 | B |
| I-133 | B |
| I-134 | A |
| I-135 | C |
| I-136 | A |
| I-137 | A |
| I-138 | B |
| I-139 | B |
| I-140 | B |
| I-141 | B |
| I-142 | B |
| I-143 | C |
| I-144 | B |
| I-145 | C |
| I-146 | B |
| I-147 | B |
| I-148 | B |
| I-149 | B |
| I-150 | B |
| I-151 | B |
| I-152 | B |
| I-153 | B |
| I-154 | B |
| I-155 | B |
| I-156 | A |
| I-157 | B |
| I-158 | A |
| I-159 | C |
| I-160 | C |
| I-161 | c |
| I-162 | A |
| I-163 | A |
| I-165 | D |
| I-166 | B |
| I-167 | A |
| I-168 | A |
| I-169 | B |
| I-170 | B |
| I-171 | B |
| I-172 | B |
| I-173 | A |
| I-174 | A |
| I-175 | A |
| I-176 | B |
| I-177 | B |
| I-178 | A |
| I-179 | B |
| I-180 | B |
| I-181 | B |
| I-182 | A |
| I-183 | A |

Example 87. In-Cell Tom20 Loss Assay

To evaluate Tom20 loss following treatment with compounds and/or antimycin/oligomycin, a 96-well plate assay was performed on differentiated RenCell VM. These were seeded into laminin-coated 96-well plates at 5000 cells/well in normal growth medium (ReNcell NSC maintenance medium+20 ng/ml FDF-2 and 20 ng/ml EGF). After 3 days, growth medium was replaced with differentiation medium (ReNCell NSC medium+0.1 mM dibutyryl cAMP and 2 ng/ml GDNF). On days 1 and 4 following addition of differentiation medium, the media was removed and replaced with fresh differentiation medium. On the 7$^{th}$ day compounds or DMSO were added, and 1 hour later, some wells also received additions of oligomycin (1 uM and antimycin (1 uM). 20 h after compound addition, cells were fixed by adding formaldehyde to a final concentration of 3.700, incubated 20 minutes at room temperature, then washed with PBS. Blocking buffer (3% bovine serum albumin, 2% fetal bovine serum, 0.2% Triton X100 in PBS) was added to all wells for two hours, then removed and replaced with blocking buffer containing antibody against Tom20 overnight. After washing with PBS, secondary antibody (Donkey anti-mouse conjugated to Cy3) was added along with DAPI to mark nuclei, and incubated two hours. After again washing with PBS, cells were imaged using GE INCell 6000 at 40× and quantified using HCA-based quantification algorithm of fluorescence density×area normalized to the number of nuclei.

Table 24 shows the activity of selected compounds of this invention in the in-cell Tom20 loss assay. The compound numbers correspond to the compound numbers in Table 1. Compounds having an activity designated as "A" provided an $IC_{50} \leq 0.5$ µM; compounds having an activity designated as "B" provided an $IC_{50}$ of >0.5-1.0 µM; compounds having an activity designated as "C" provided an $IC_{50}$ of 1.0 to 10.0 M; and compounds having an activity designated as "D" provided an $IC_{50} \geq 10.0$ µM.

TABLE 24

In-cell Tom20 loss Assay results.

| Compound | Tom20 Loss $IC_{50}$ (µM) |
| --- | --- |
| I-11 | A |
| I-22 | D |
| I-34 | A |
| I-80 | C |
| I-93 | B |
| I-104 | A |
| I-107 | B |
| I-130 | D |
| I-137 | A |
| I-175 | A |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I':

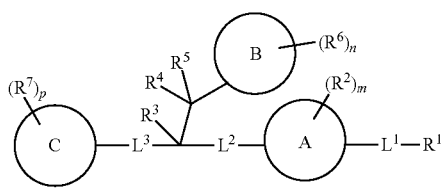

or a pharmaceutically acceptable salt thereof, wherein:
Ring A is phenyl, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;
$L^1$ is a $C_{1-3}$ bivalent hydrocarbon chain wherein one methylene unit of the chain is replaced by —C(O)N(R)—, —N(R)C(O)—, —S(O)—, —S(O)$_2$—, —S(O)N(R)—, —S(O)$_2$N(R)—, or —S(O)(R)=N—;
each R is independently hydrogen or an optionally substituted $C_{1-3}$ aliphatic group; or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur; or
an R group and $R^1$ on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur;
$R^1$ is an optionally substituted group selected from C1-6 aliphatic, a 3-8 membered saturated or partially unsaturated monocyclic carbocyclic ring, a 5-8 membered saturated or partially unsaturated bridged bicyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;
each $R^2$ is independently halogen, —CF$_3$, —CN, —C(O)NHR, —NO$_2$, —NHR, —NHC(O)R, —NHS(O)$_2$R, —N(R)$_2$, or —OR, or a $C_{1-6}$ aliphatic group; or
two $R^2$ on the same carbon are optionally taken together to form =O; or
two $R^2$ groups are optionally taken together with their intervening atoms to form a 5-8 membered partially unsaturated fused ring having 0-2 heteroatoms independently selected from nitrogen, oxygen, or sulfur;
$L^2$ is —C(O)N(R')—;
R' is hydrogen or a $C_{1-3}$ aliphatic group;
$L^3$ is —C(O)N(R")—;
R" is hydrogen or a $C_{1-3}$ aliphatic group;
$R^3$ is hydrogen or $C_{1-3}$ aliphatic;
$R^4$ is hydrogen;
$R^5$ is hydrogen;
Ring B is phenyl, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;
each $R^6$ is independently halogen, —CN, —NO$_2$, —NHR, —N(R)$_2$, —OR, or an optionally substituted $C_{1-6}$ aliphatic group; or:
two $R^6$ on the same carbon are optionally taken together to form =O;
an $R^6$ group and R' group are optionally taken together with their intervening atoms to form a 5-8 membered partially unsaturated fused ring having 0-2 heteroatoms, in addition to the nitrogen, independently selected from nitrogen, oxygen, or sulfur;
an $R^6$ group and $R^3$ group are optionally taken together with their intervening atoms to form a 5-8 membered partially unsaturated spiro-fused ring having 0-2 heteroatoms independently selected from nitrogen, oxygen, or sulfur; or
an $R^6$ group and R" group are optionally taken together with their intervening atoms to form a 5-8 membered partially unsaturated fused ring having 0-2 heteroatoms, in addition to the nitrogen, independently selected from nitrogen, oxygen, or sulfur;
Ring C is phenyl, a 3-8 membered saturated or partially unsaturated carbocyclic ring, a 4-7 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, or an 8-10 membered bicyclic aryl or heteroaryl ring having 0-3 heteroatoms independently selected from nitrogen, oxygen, or sulfur;

each R⁷ is independently halogen, —CN, —NO₂, —NHR, —N(R)₂, —OR, or an C$_{1-6}$ aliphatic group; or two R⁷ on the same carbon are optionally taken together to form =O; or an R⁷ group and R″ group are optionally taken together with their intervening atoms to form a 5-8 membered partially unsaturated fused ring having 0-2 heteroatoms, in addition to the nitrogen, independently selected from nitrogen, oxygen, or sulfur; and each of m, n, and p is independently 0, 1, 2, or 4;

provided that R¹ is other than isopropyl, t-butyl, 1-methylcyclopropyl, 1-fluoromethylcyclopropyl, 1-difluoromethylcyclopropyl, 1-trifluoromethylcyclopropyl, or 3-methyl-3-oxetanyl when L¹ is —S(O)₂N(R)—;

R¹ is other than ethyl when L¹ is —S(O)₂N(R)— and Ring A is naphthyl; and the compound is other than

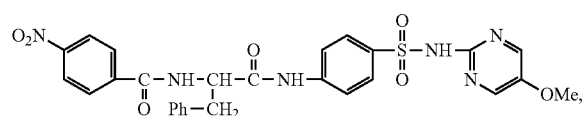

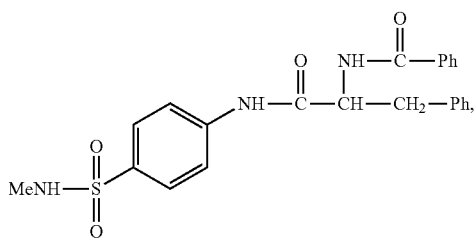

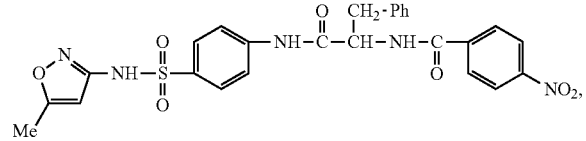

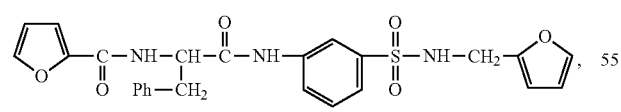

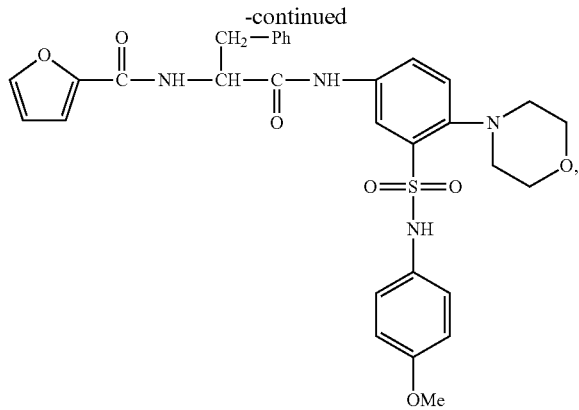

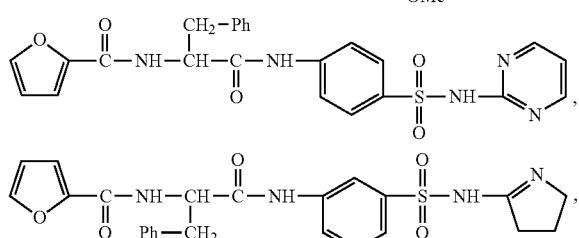

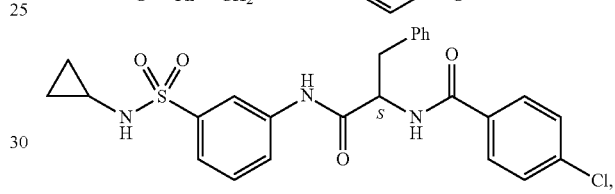

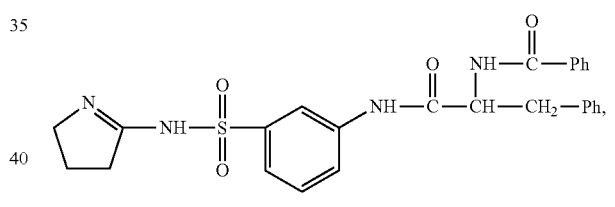

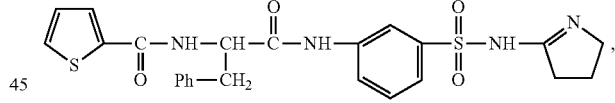

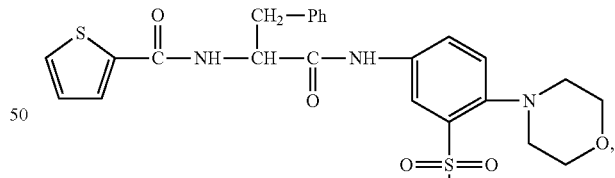

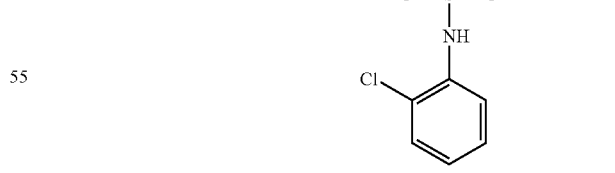

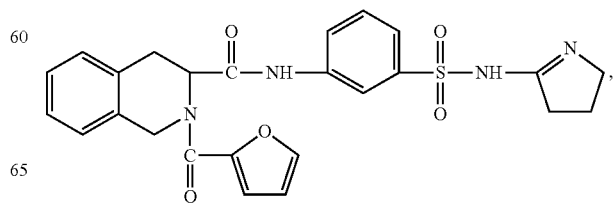

533
-continued
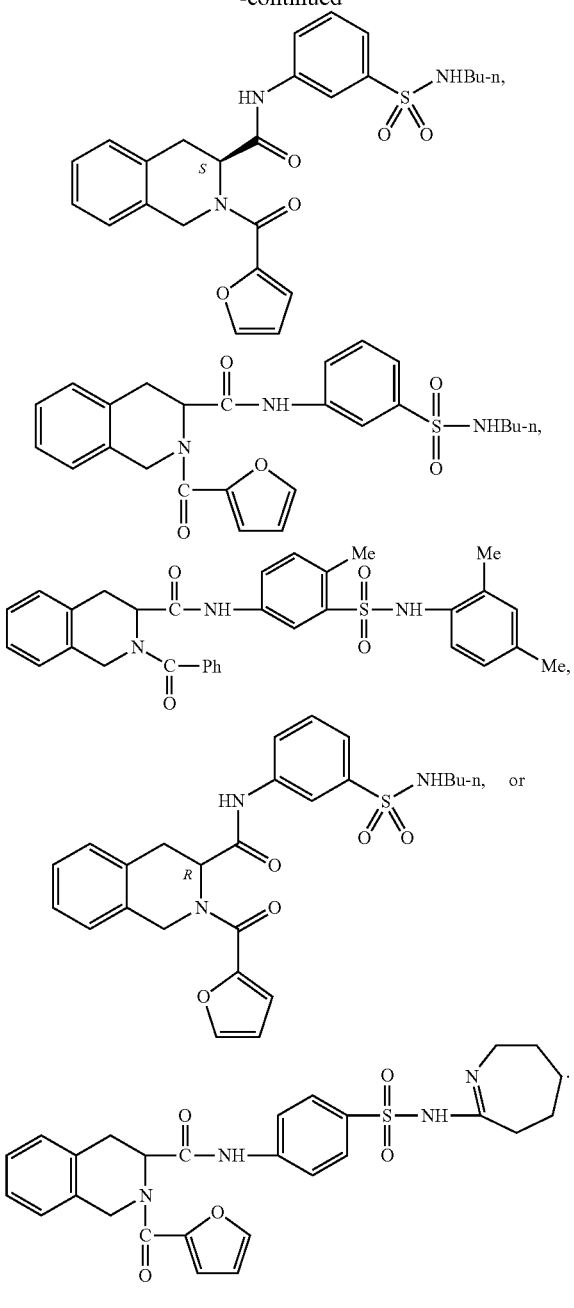
2. The compound of claim 1 of formula II:
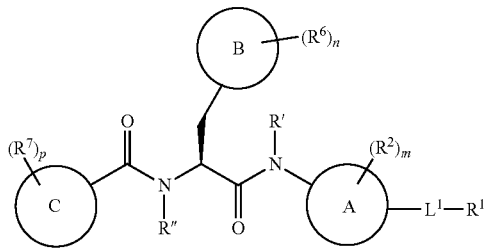
or a pharmaceutically acceptable salt thereof.
3. The compound of claim 1 of one of formulas III-a, III-b, III-c, or III-d:
III-a
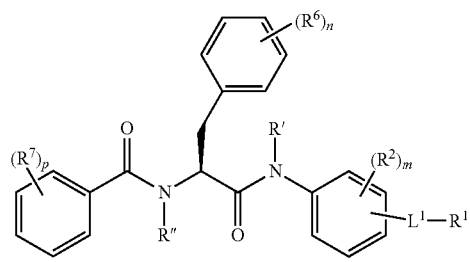
III-b
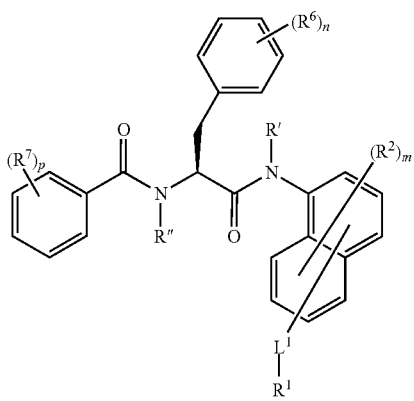
III-c
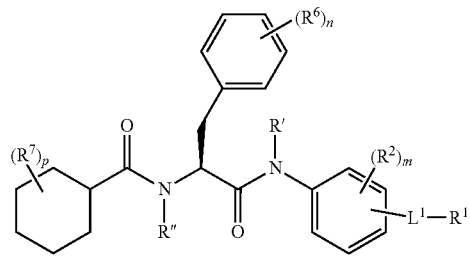
III-d
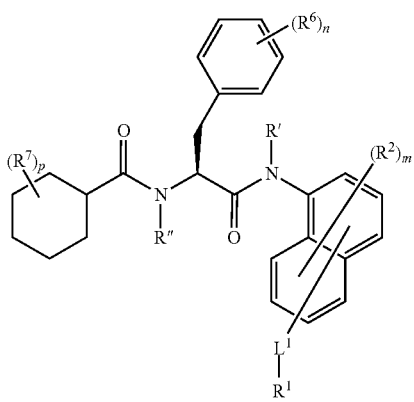
or a pharmaceutically acceptable salt thereof.
4. The compound of claim 1 where $L^1$ is —S(O)$_2$NH—, —C(O)NH—, —S(O)$_2$—, —S(O)(NH)—, —S(O)—, or —S(O)(N-t-Bu).

5. The compound of claim 1 of one of formulas IV-a, IV-b, IV-c, or IV-d:
6. The compound of claim 1 of one of formulas V-a, V-b, V-c, or V-d:
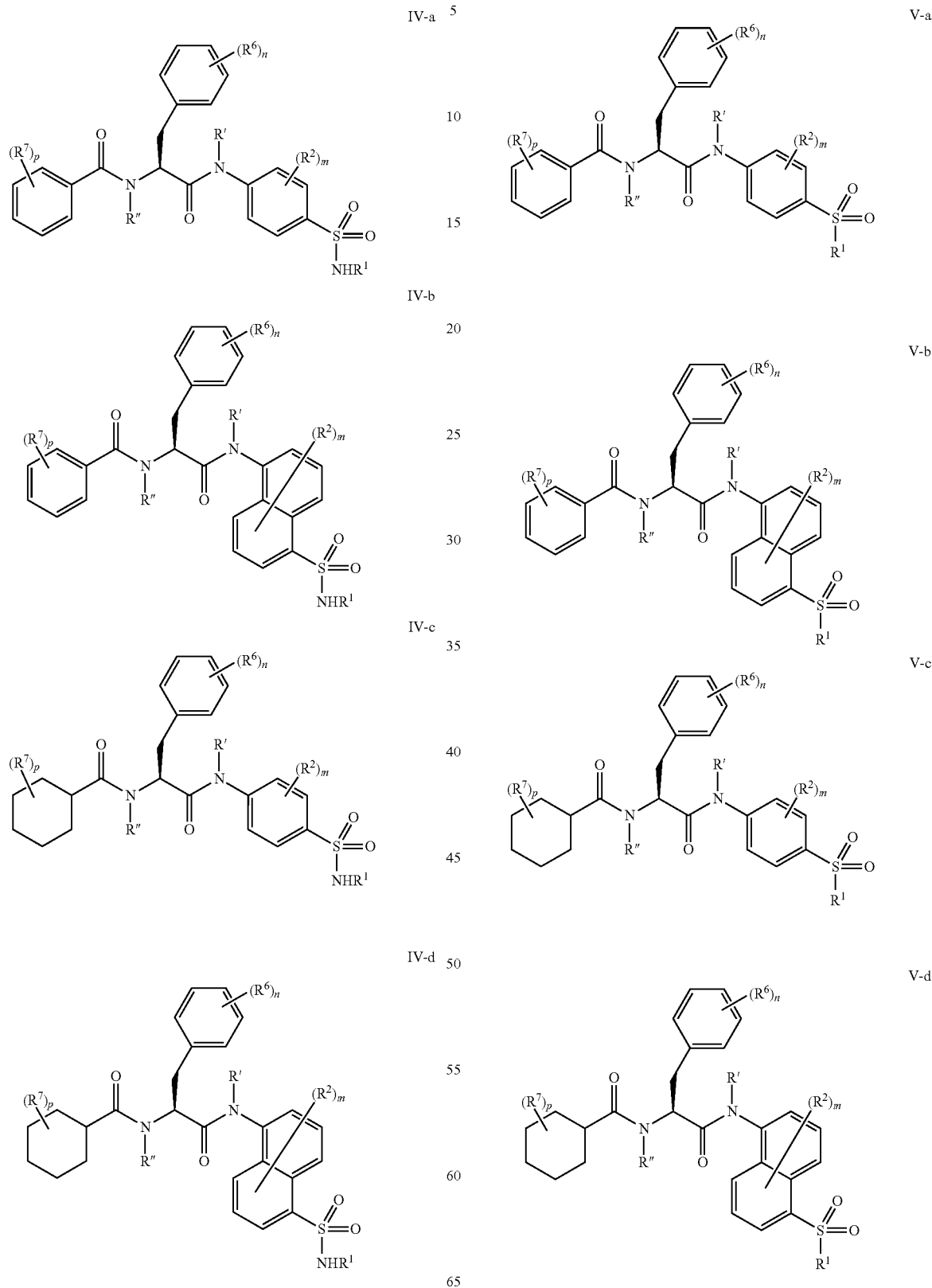
or a pharmaceutically acceptable salt thereof.
or a pharmaceutically acceptable salt thereof.

7. The compound of claim 1 of one of formulas VI-a, VI-b, VI-c, or VI-d:
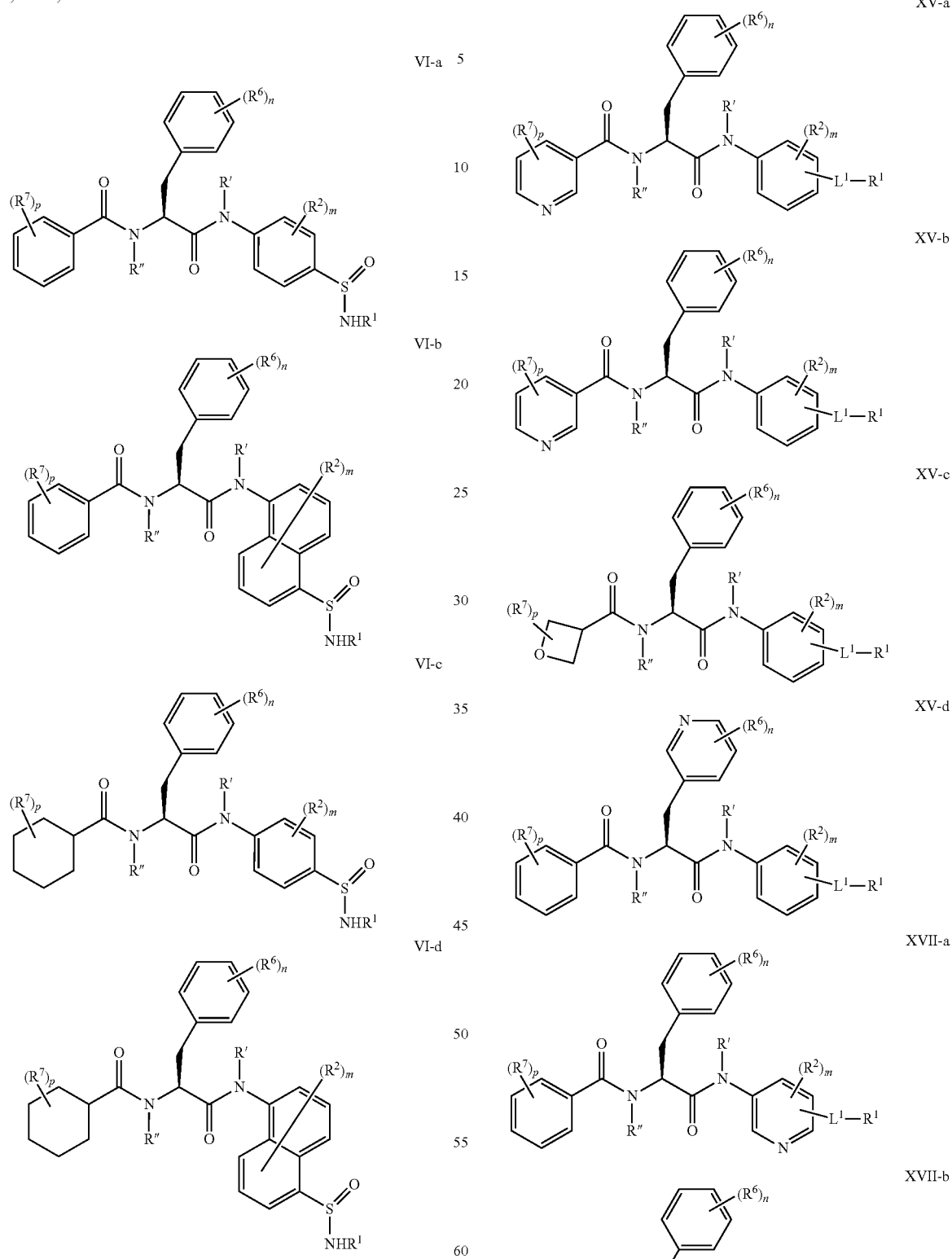
or a pharmaceutically acceptable salt thereof.
8. A compound of any one of formulas XV-a, XV-b, XV-c, XV-d, XVII-a, XVII-b, XVII-c, XVII-d, XIX-a, XIX-b, XIX-c, XIX-d, XXI, XXIII-a, XXIII-b, XXV-a, XXV-b, XXV-c, or XXV-d:

XVII-c
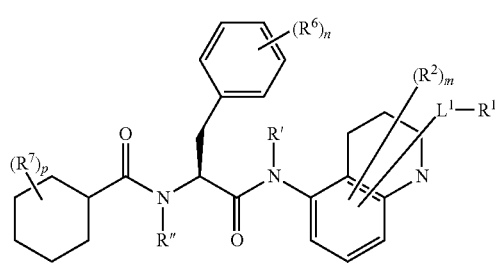
XVII-d
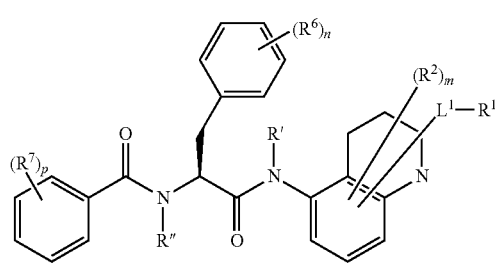
XIX-a
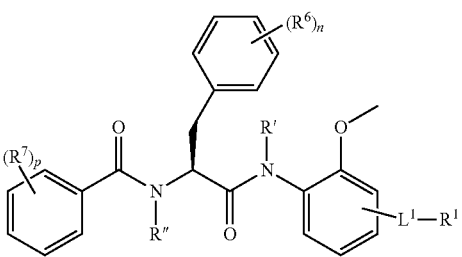
XIX-b
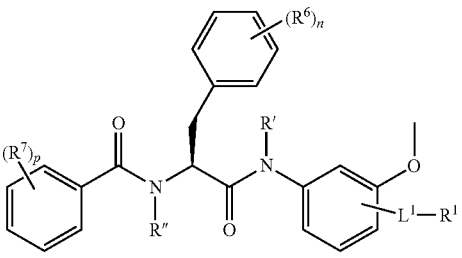
XIX-c
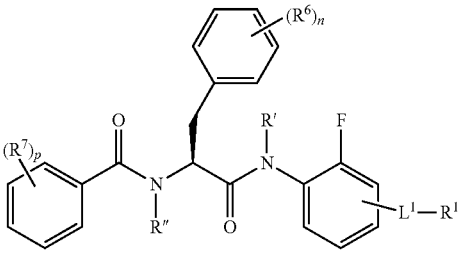
XIX-d
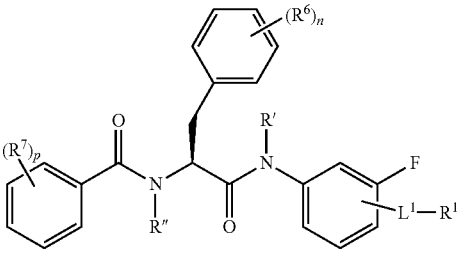
XXI
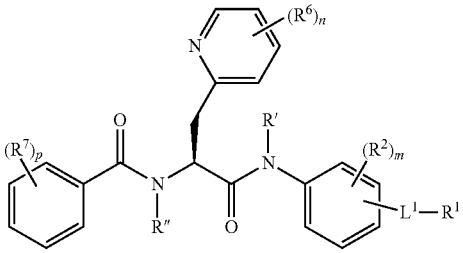
XXIII-a
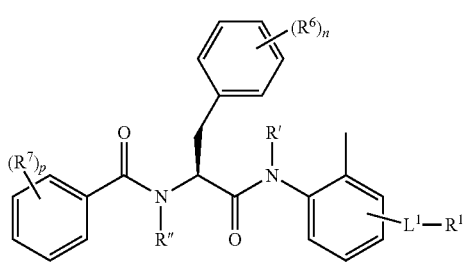
XXIII-b
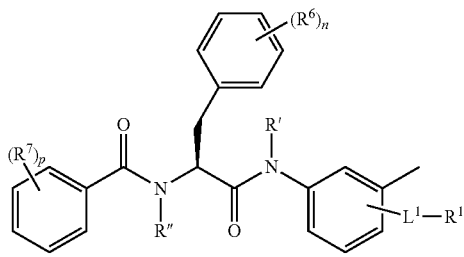
XXV-a
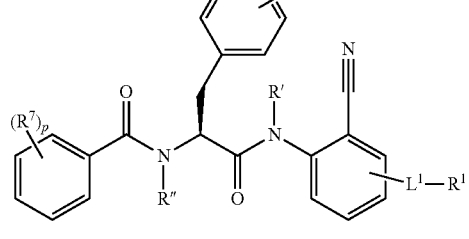
XXV-b
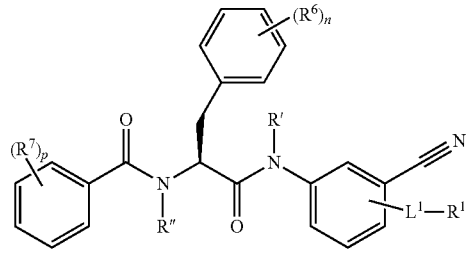
XXV-c
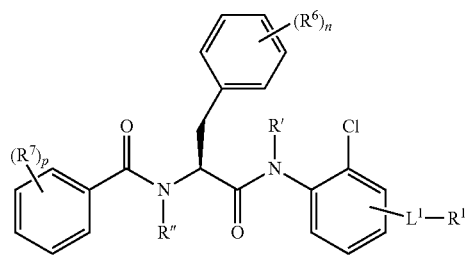

-continued

XXV-d

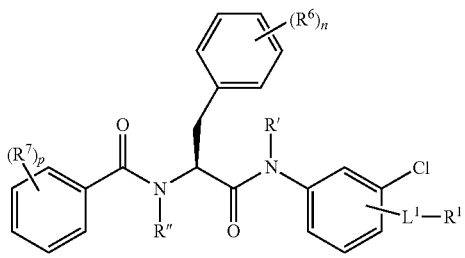

or a pharmaceutically acceptable salt thereof, wherein:

$L^1$ is a $C_{1-3}$ bivalent hydrocarbon chain wherein one methylene unit of the chain is replaced by —C(O)—, —C(O)N(R)—, —N(R)C(O)—, —S(O)—, —S(O)$_2$—, —S(O)N(R)—, —S(O)$_2$N(R)—, or —S(O)(R)=N—;

each R is independently hydrogen or an optionally substituted $C_{1-3}$ aliphatic group; or:
  two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur; or
  an R group and $R^1$ on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, or sulfur;

$R^1$ is an optionally substituted group selected from $C_{1-6}$ aliphatic, a 3-8 membered saturated or partially unsaturated monocyclic carbocyclic ring, a 5-8 membered saturated or partially unsaturated bridged bicyclic carbocyclic ring, phenyl, a 4-7 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

each $R^2$ is independently halogen, —CF$_3$, —CN, —C(O)NHR, —NO$_2$, —NHR, —NHC(O)R, —NHS(O)$_2$R, —N(R)$_2$, or —OR, or an optionally substituted $C_{1-6}$ aliphatic group; or
  two $R^2$ on the same carbon are optionally taken together to form =O; or
  two $R^2$ groups are optionally taken together with their intervening atoms to form a 5-8 membered partially unsaturated fused ring having 0-2 heteroatoms independently selected from nitrogen, oxygen, or sulfur;

R' is hydrogen or a $C_{1-3}$ aliphatic group;
R" is hydrogen or a $C_{1-3}$ aliphatic group;
each $R^6$ is independently halogen, —CN, —NO$_2$, —NHR, —N(R)$_2$, —OR, or an optionally substituted $C_{1-6}$ aliphatic group; or:
  two $R^6$ on the same carbon are optionally taken together to form =O;
  an $R^6$ group and R' group are optionally taken together with their intervening atoms to form a 5-8 membered partially unsaturated fused ring having 0-2 heteroatoms, in addition to the nitrogen, independently selected from nitrogen, oxygen, or sulfur; or an $R^6$ group and R" group are optionally taken together with their intervening atoms to form a 5-8 membered partially unsaturated fused ring having 0-2 heteroatoms, in addition to the nitrogen, independently selected from nitrogen, oxygen, or sulfur;

each $R^7$ is independently halogen, —CN, —NO$_2$, —NHR, —N(R)$_2$, —OR, or an $C_{1-6}$ aliphatic group; or
  two $R^7$ on the same carbon are optionally taken together to form =O; or
  an $R^7$ group and R" group are optionally taken together with their intervening atoms to form a 5-8 membered partially unsaturated fused ring having 0-2 heteroatoms, in addition to the nitrogen, independently selected from nitrogen, oxygen, or sulfur; and each of m, n, and p is independently 0, 1, 2, 3, or 4;

provided that $R^1$ is other than isopropyl, t-butyl, 1-methylcyclopropyl, 1-fluoromethylcyclopropyl, 1-difluoromethylcyclopropyl, 1-trifluoromethylcyclopropyl, or 3-methyl-3-oxetanyl when $L^1$ is —S(O)$_2$N(R)—.

9. The compound of claim 8 of any one of formulas XVI-a, XVI-b, XVI-c, XVI-d, XVIII-a, XVIII-b, XVIII-c, XVIII-d, XX-a, XX-b, XX-c, XX-d, XXII, XXIV-a, XXIV-b, XXVI-a, XXVI-b, XXVI-c, or XXVI-d:

XVI-a

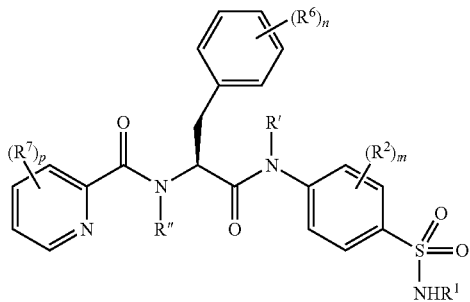

XVI-b

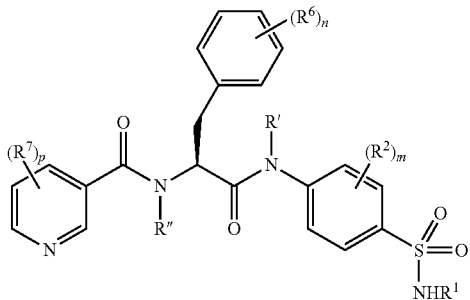

XVI-c

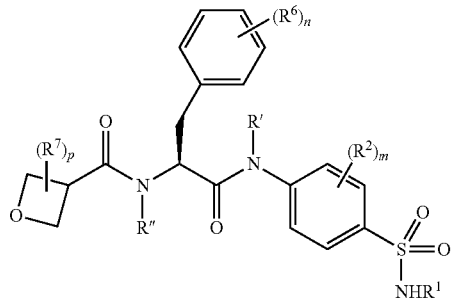

XVI-d
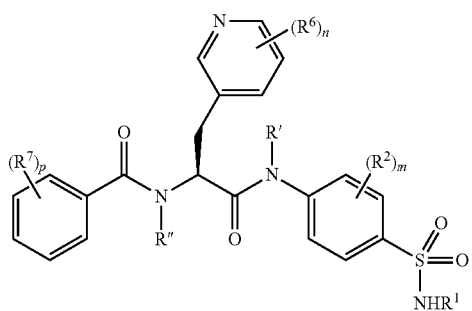
XVIII-a
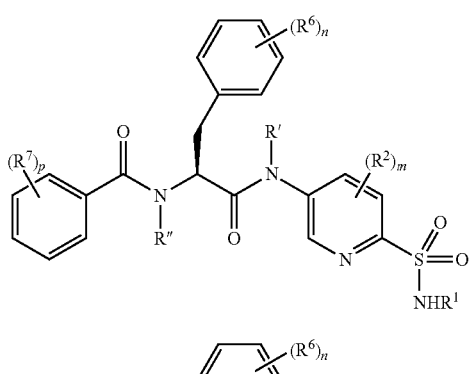
XVIII-b
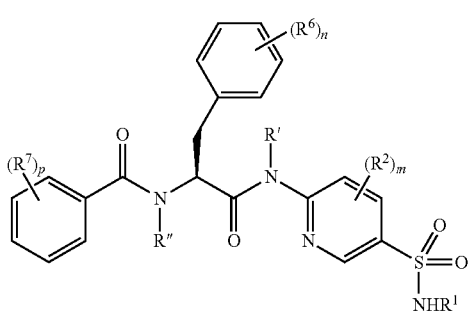
XVIII-c
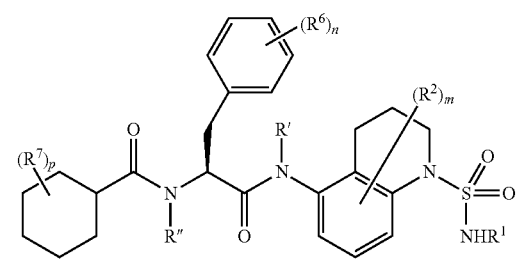
XVIII-d
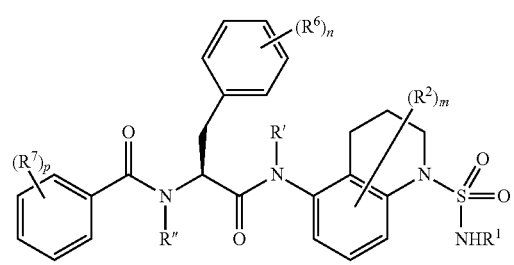
XX-a
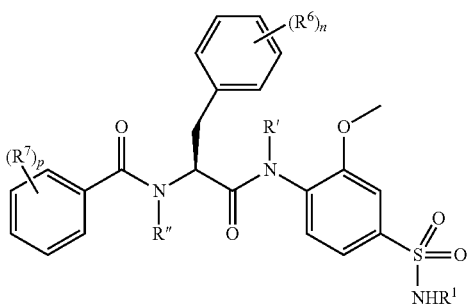
XX-b
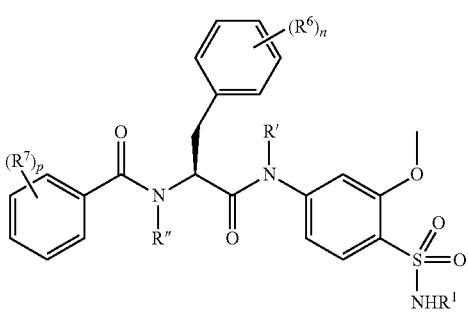
XX-c
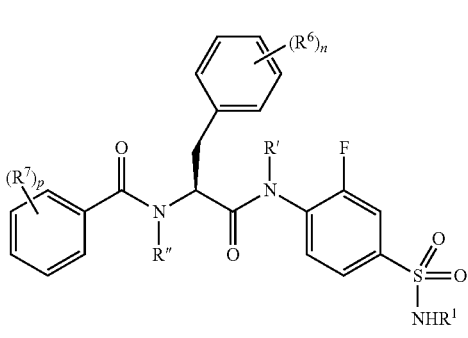
XX-d
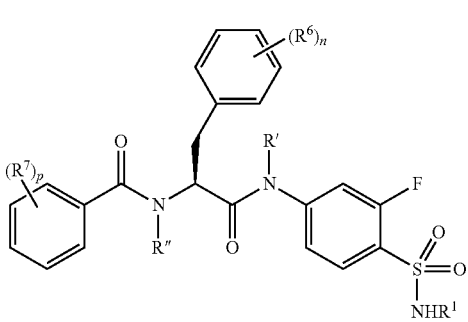
XXII
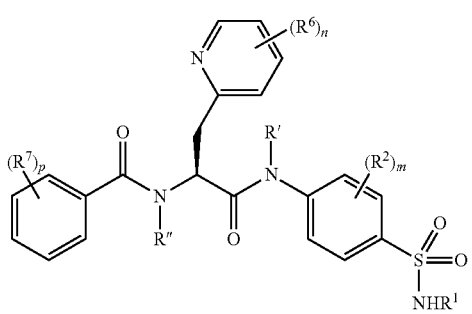

XXIV-a 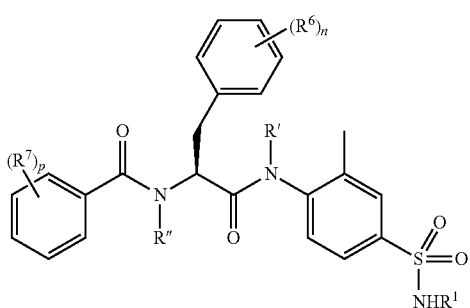

XXIV-b 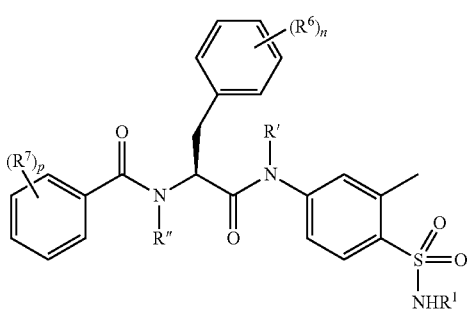

XXVI-a 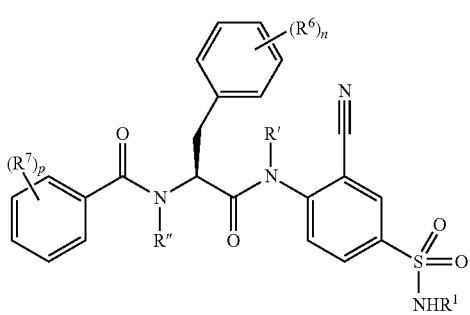

XXVI-b 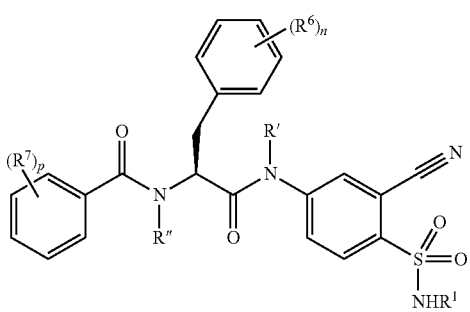

XXVI-c 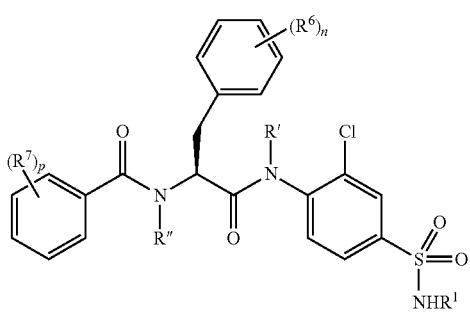

XXVI-d 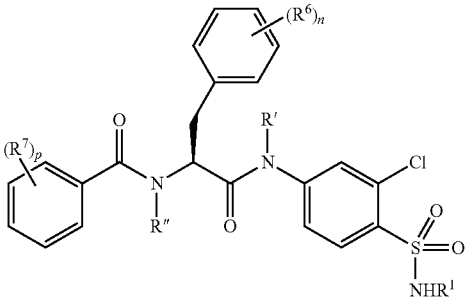

or a pharmaceutically acceptable salt thereof.

10. The compound of claim 1, wherein at least one $R^2$ is fluoro, methyl, or methoxy.

11. The compound of claim 1, wherein m is 0, 1, 2, or 3.

12. The compound of claim 1, wherein p is 0, 1, 2, or 3.

13. The compound of claim 1, wherein at least one $R^7$ is fluoro.

14. A pharmaceutical composition comprising a compound according to claim 1, or a pharmaceutically acceptable salt thereof, and a pharmaceutically acceptable carrier, adjuvant, or vehicle.

15. A method of inhibiting USP30 in a biological sample comprising contacting the sample with the compound of claim 1, or a pharmaceutically acceptable salt thereof.

16. A method of treating an USP30-mediated disorder, disease, or condition in a patient comprising administering to said patient the pharmaceutical composition of claim 14.

17. The method of claim 16, wherein the disorder is selected from the group consisting of a neurodegenerative disease; mitochondrial myopathy, encephalopathy, lactic acidosis, stroke-like episodes (MELAS) syndrome; Leber's hereditary optic neuropathy (LHON); neuropathy ataxia; retinitis pigmentosa-maternally inherited Leigh syndrome (NARP-MILS); Danon disease; ischemic heart disease leading to myocardial infarction; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; coenzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial recessive ataxia syndrome; mitochondrial cytopathy; mitochondrial DNA depletion syndrome; myoneurogastrointestinal disorder and encephalopathy; Pearson syndrome; pyruvate carboxylase deficiency; pyruvate dehydrogenase deficiency; POLG mutations; medium/short-chain 3-hydroxyacyl-CoA dehydrogenase (M/SCHAD) deficiency; and very long-chain acyl-CoA dehydrogenase (VLCAD) deficiency.

18. The compound of claim 1, wherein Ring B is phenyl, and Ring C is phenyl or a 3-8 membered saturated carbocyclic ring.

19. The compound of claim 18, wherein Ring A is phenyl, L¹ is —S(O)₂N(R)—, and R¹ is a 4-7 membered saturated or partially unsaturated heterocyclic ring having 1-2 heteroatoms independently selected from nitrogen, oxygen, or sulfur.
20. A compound selected from:
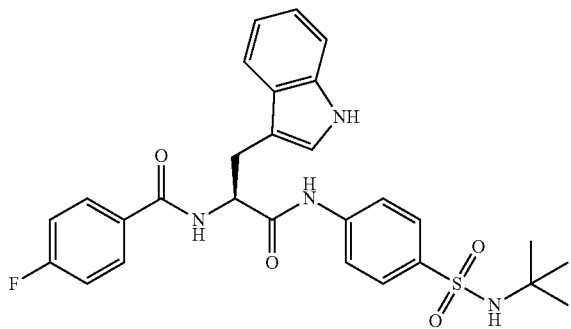
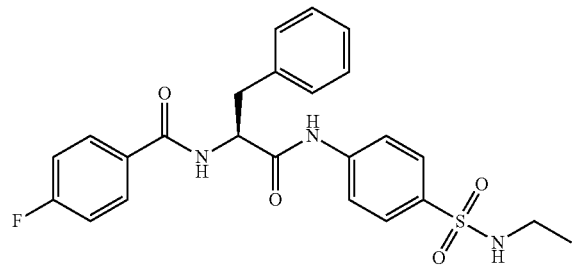
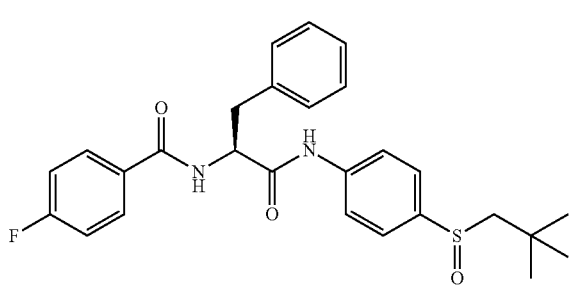

I-10
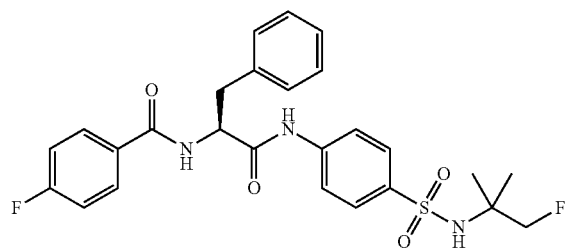
I-15
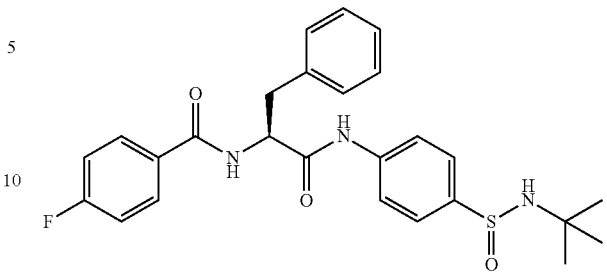
I-11
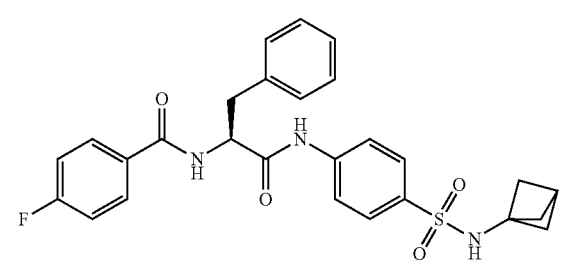
I-16
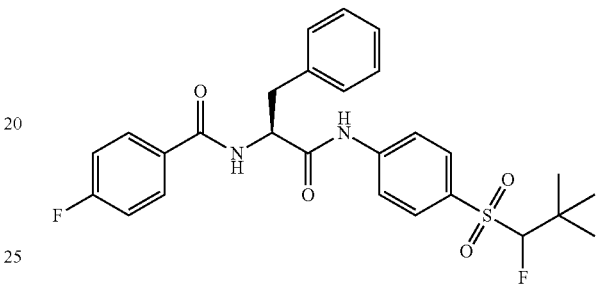
I-12
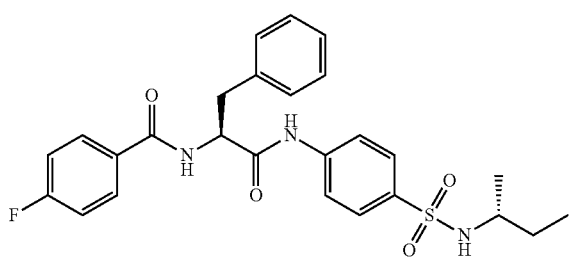
I-17
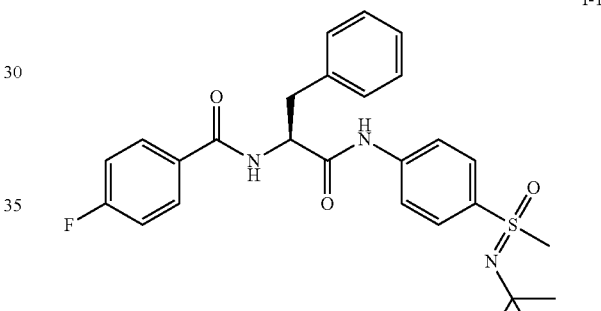
I-13
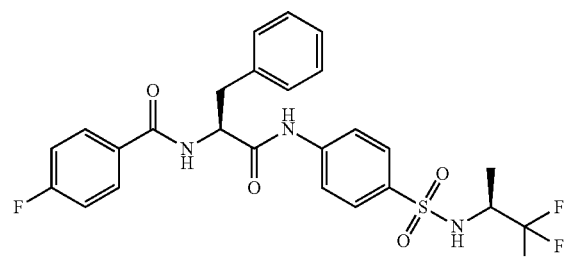
I-18
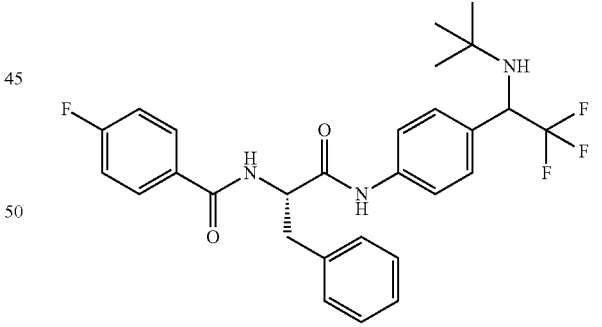
I-14
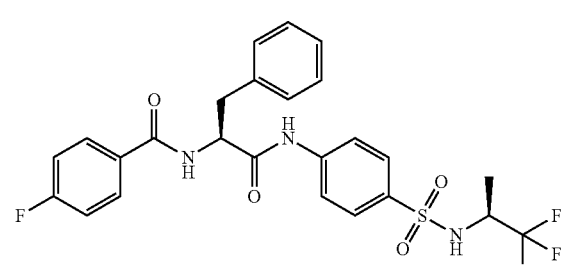
I-19
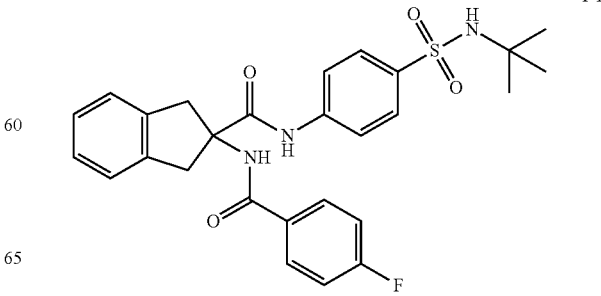

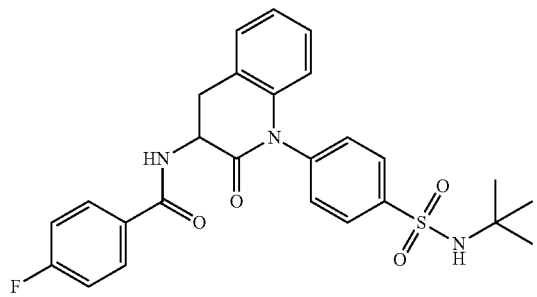
I-20
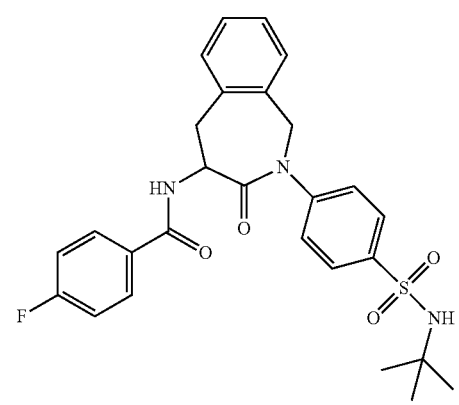
I-21
I-22
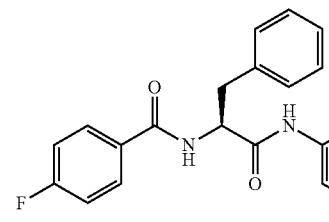
I-24
I-25
I-26
I-27
I-28
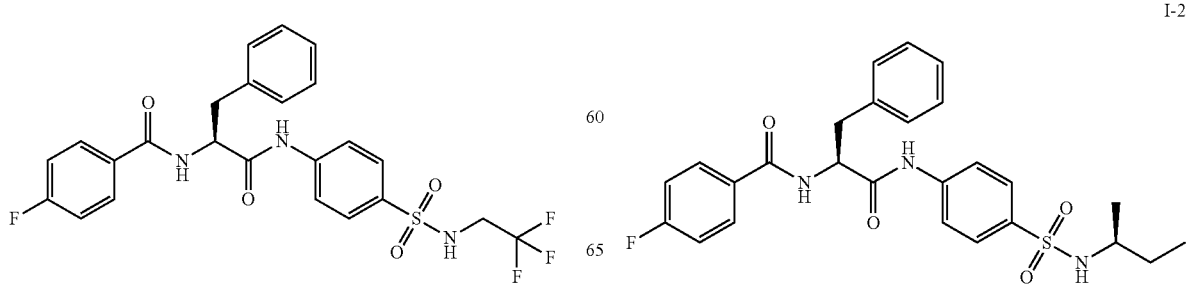
I-23

I-29
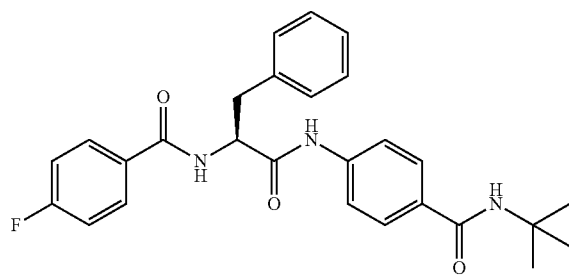
I-34
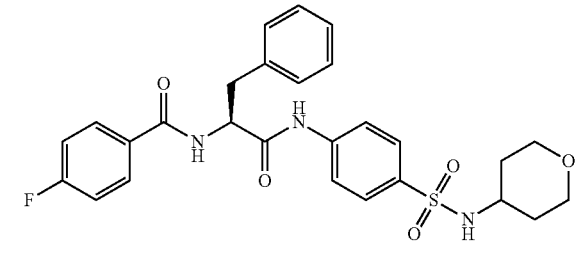
I-30
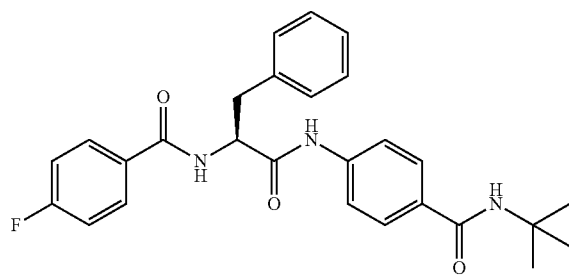
I-35
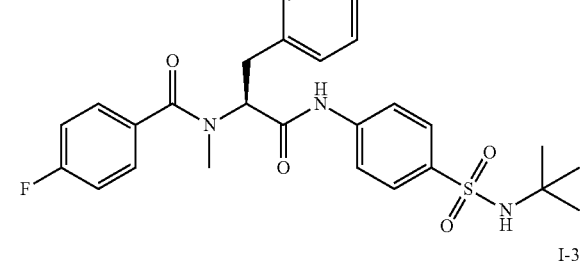
I-31
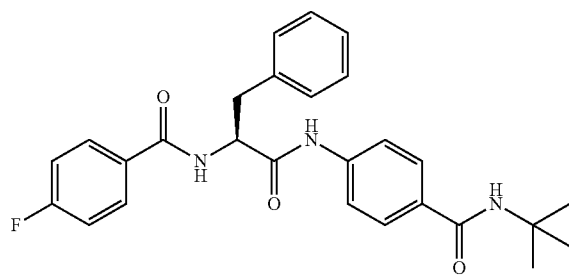
I-36
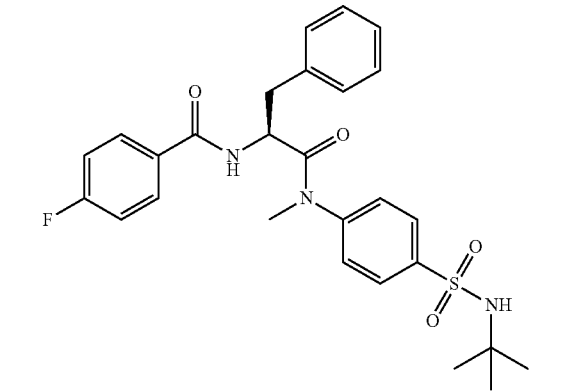
I-32
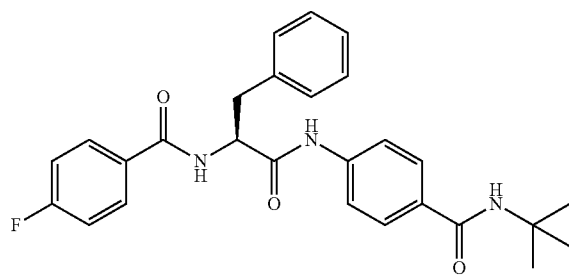
I-37
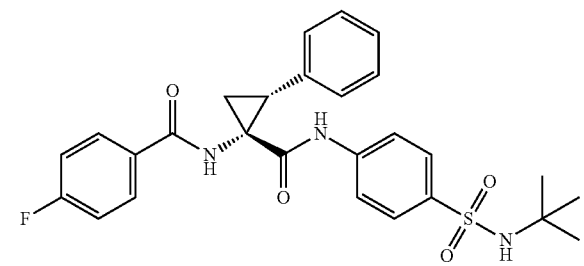
I-33
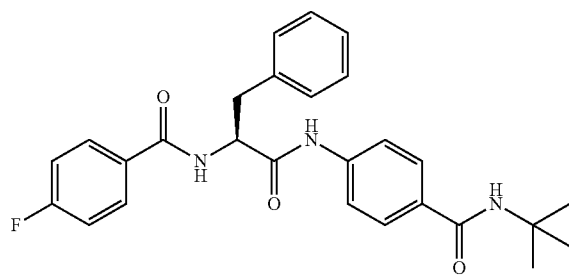
I-38
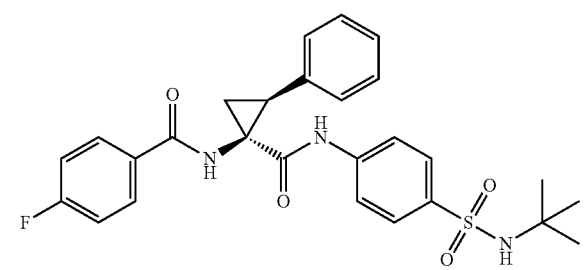

I-39
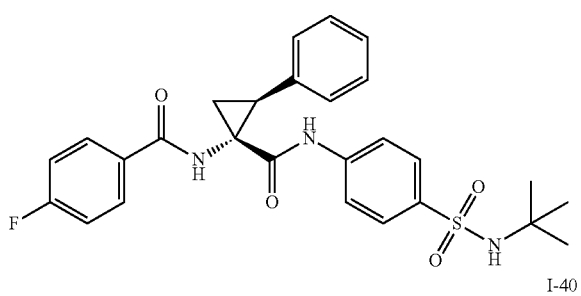
I-40
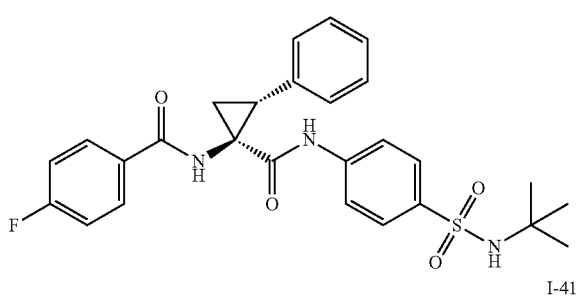
I-41
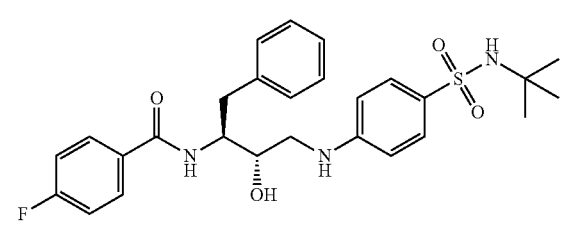
I-42
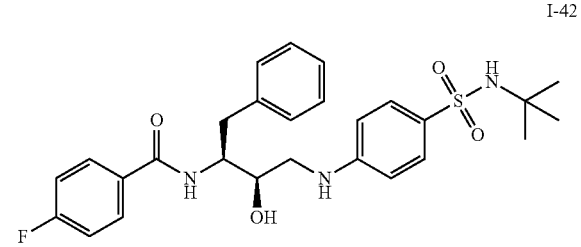
I-43
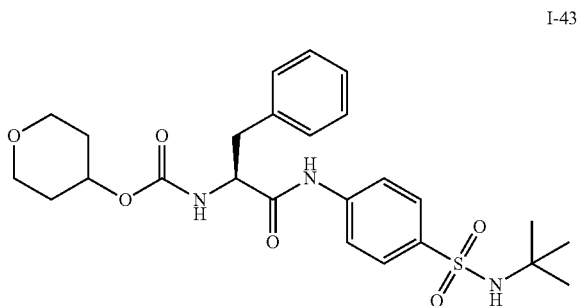
I-44
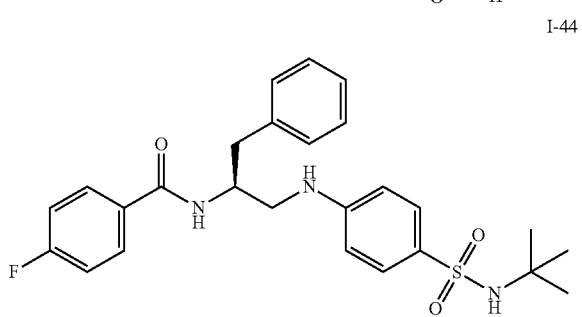
I-45
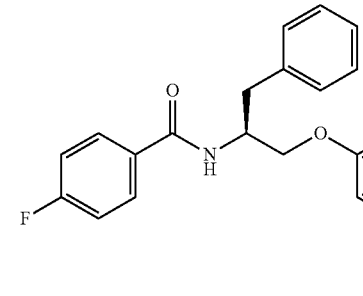
I-46
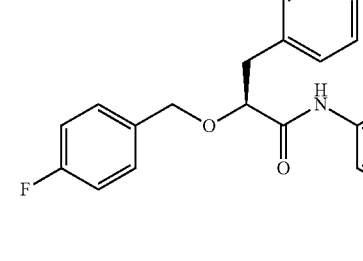
I-47
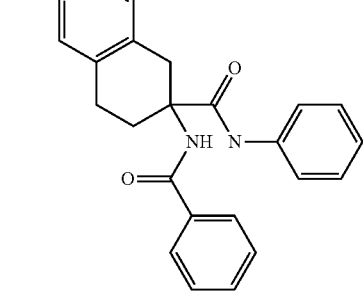
I-48
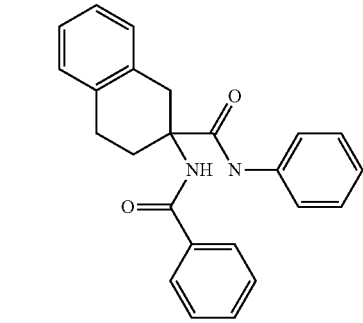

I-50
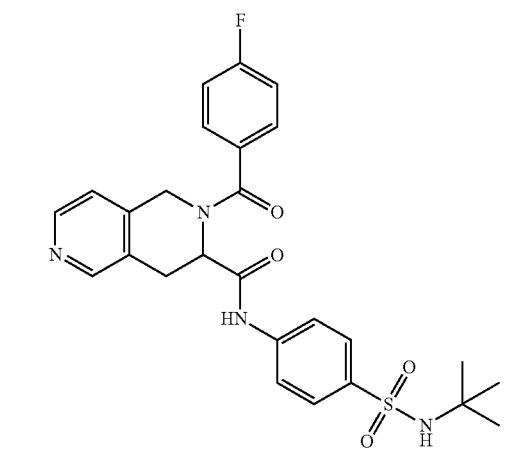
I-51
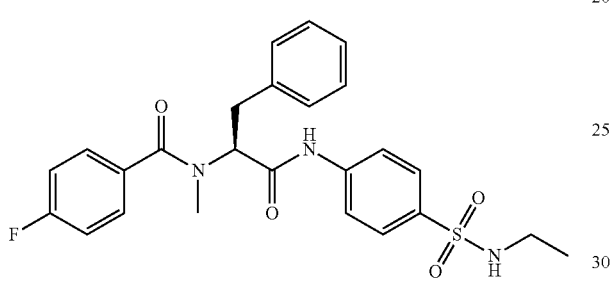
I-52
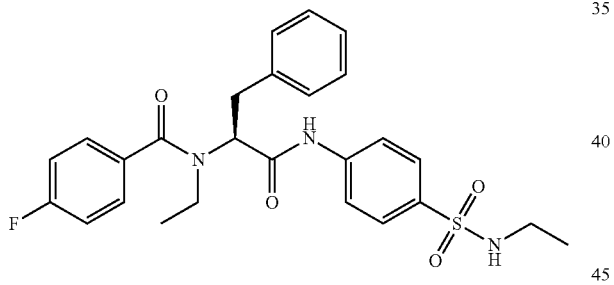
I-53
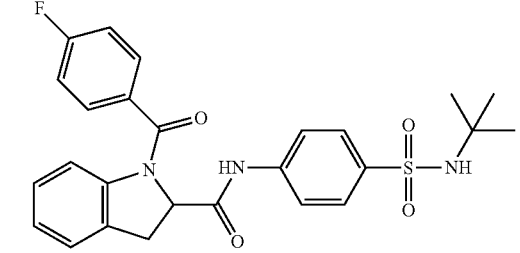
I-54
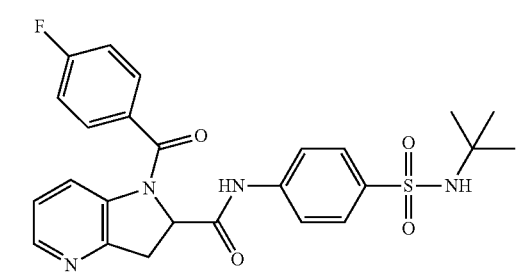
I-55
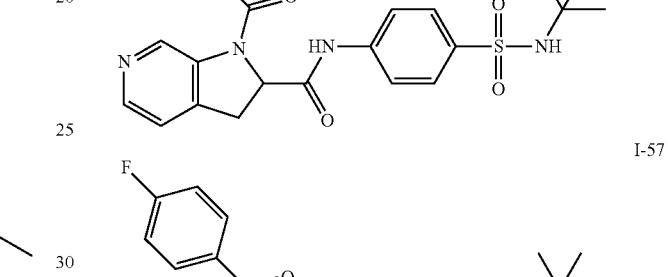
I-56
I-57
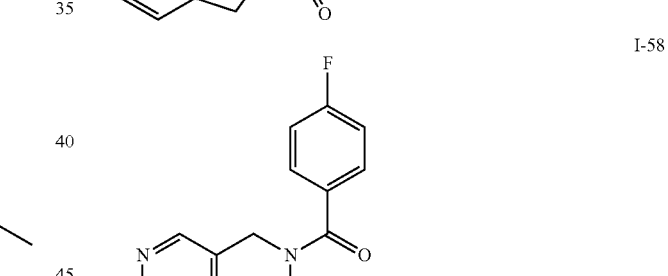
I-58
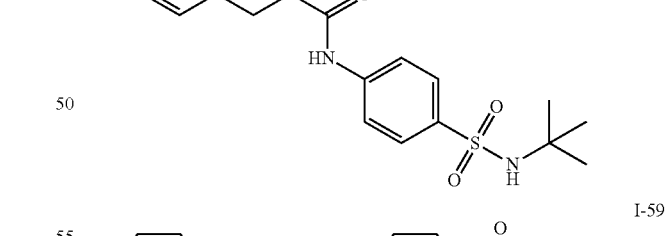
I-59
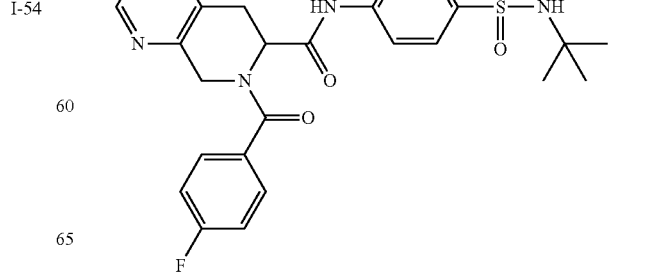

I-60
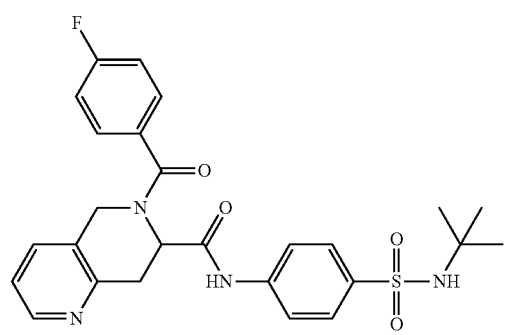
I-61
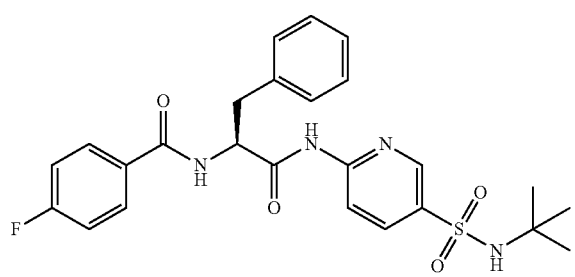
I-62
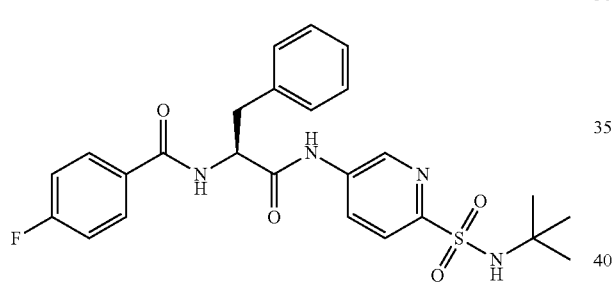
I-63
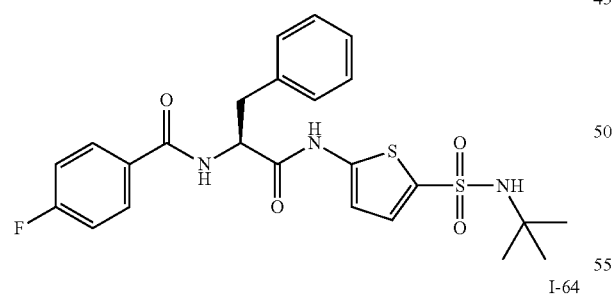
I-64
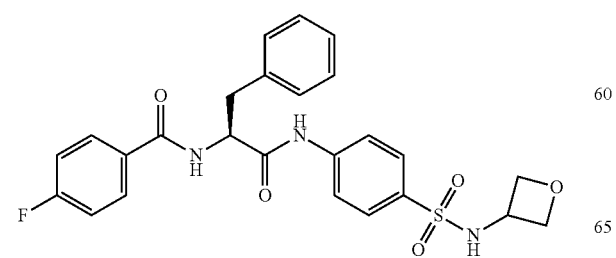
I-65
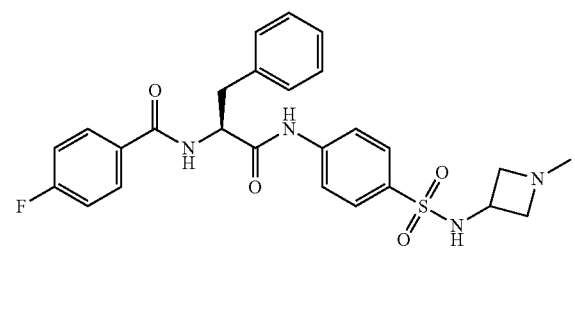
I-66
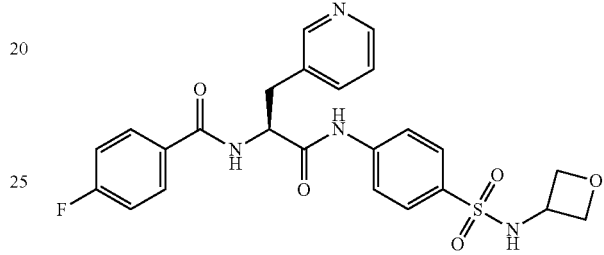
I-67
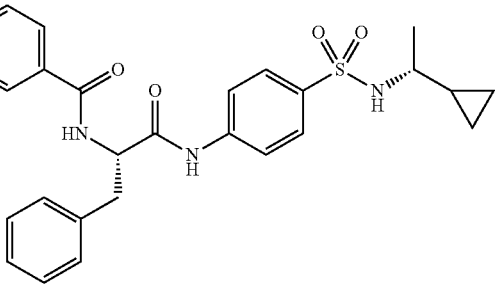
I-68
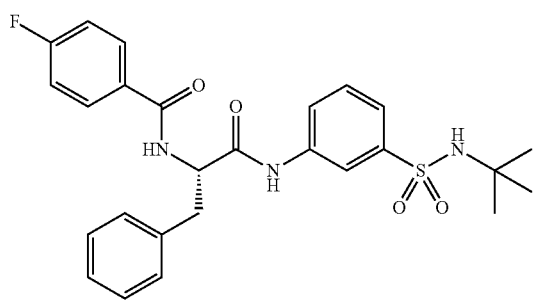
I-69
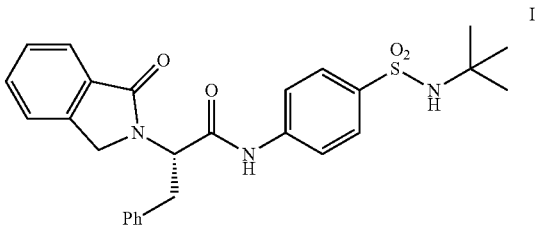

I-70
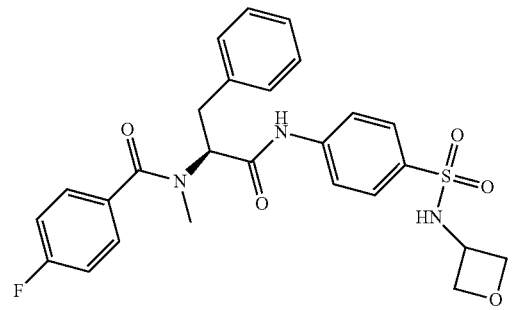
I-75
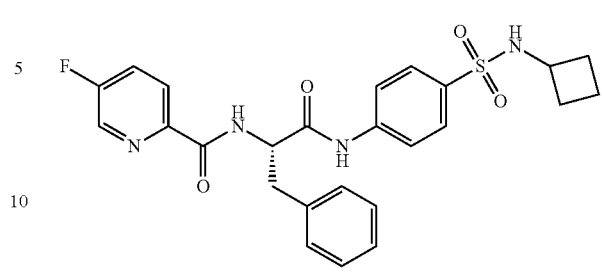
I-71
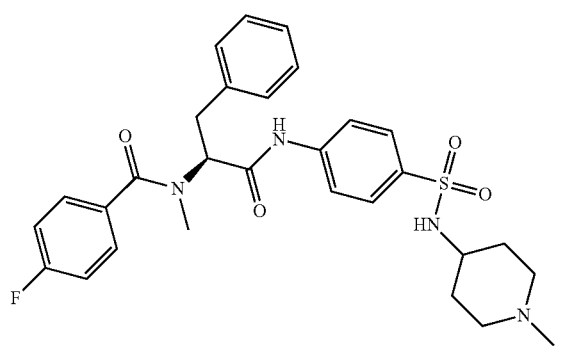
I-76
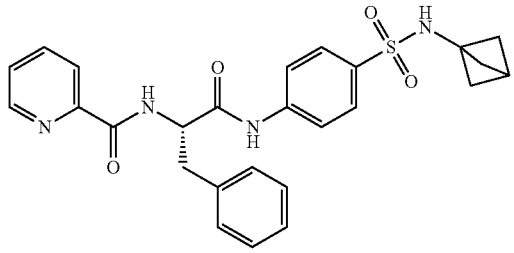
I-72
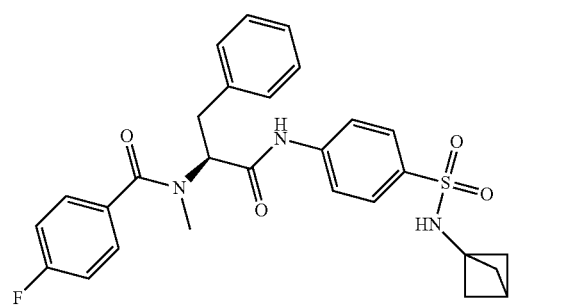
I-77
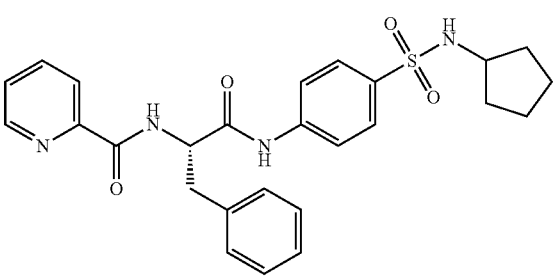
I-73
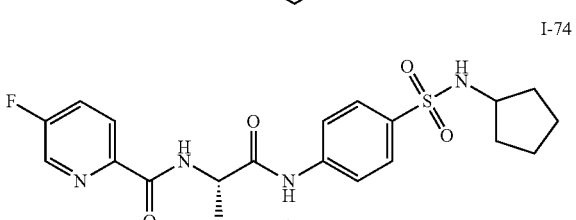
I-78
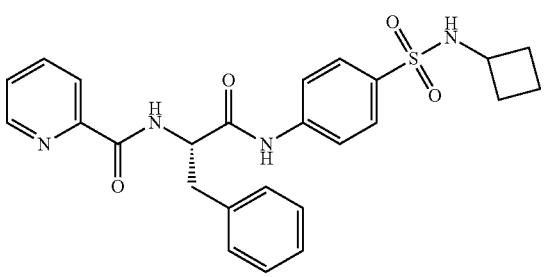
I-74
I-79
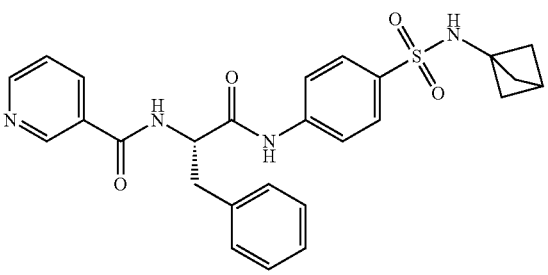

I-80
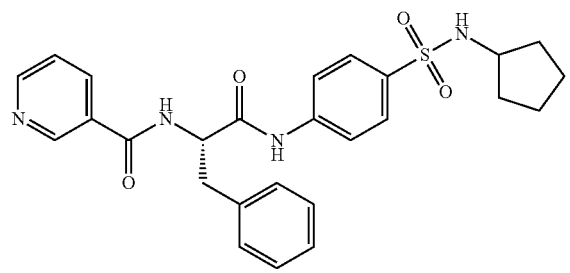
I-85
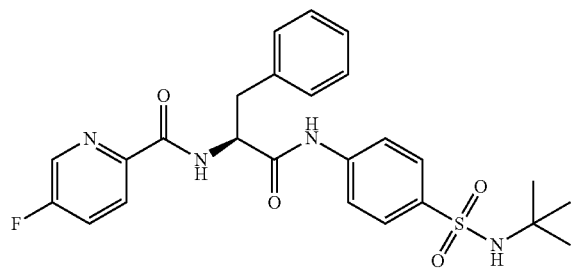
I-81
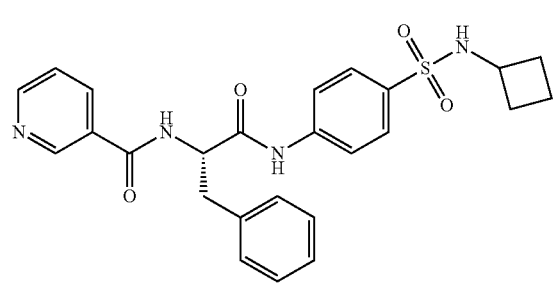
I-86
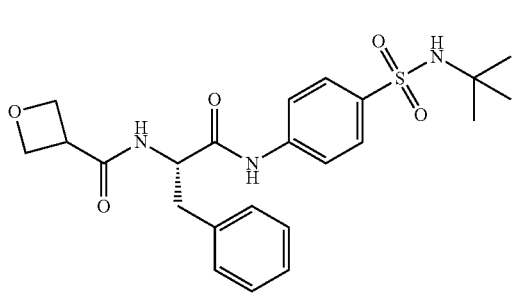
I-82
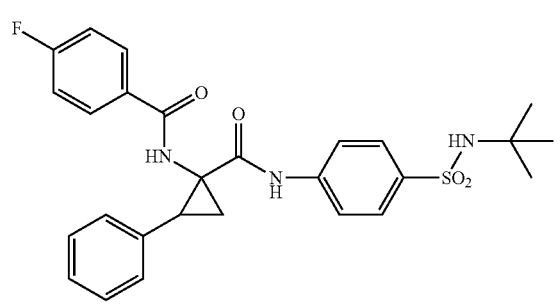
I-87
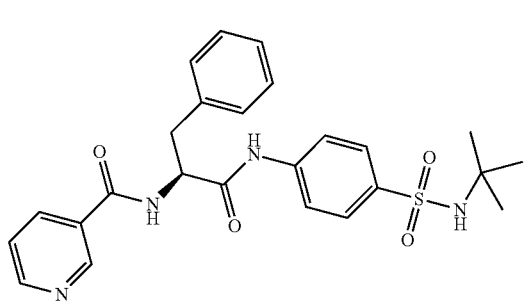
I-83
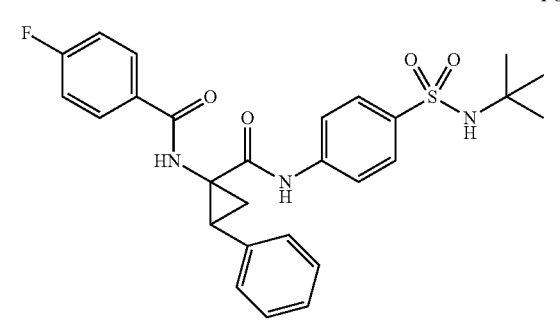
I-88
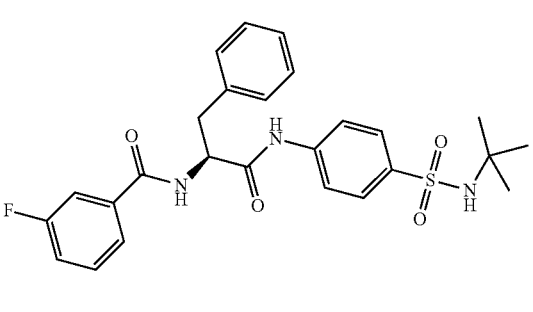
I-84
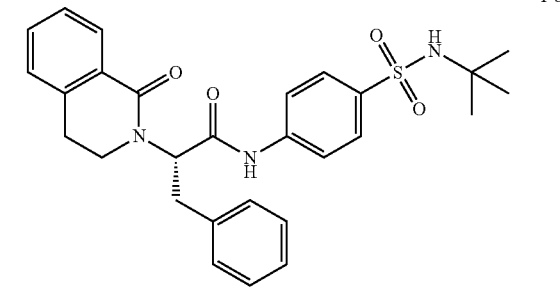
I-89
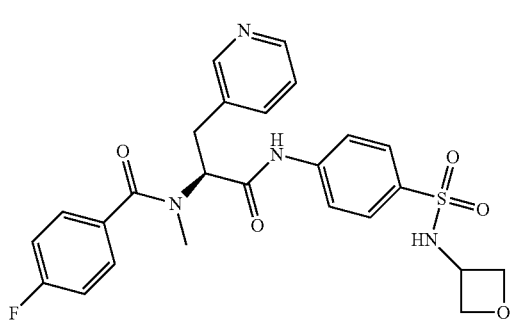

I-90
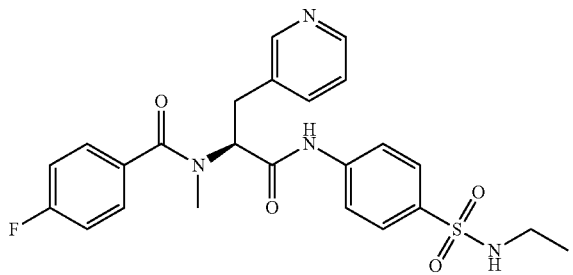
I-91
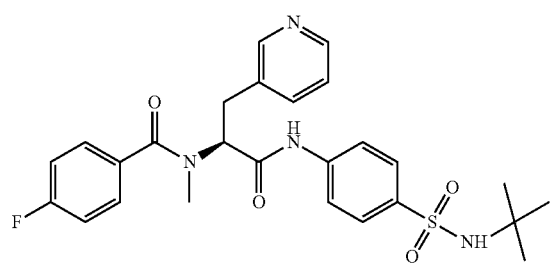
I-92
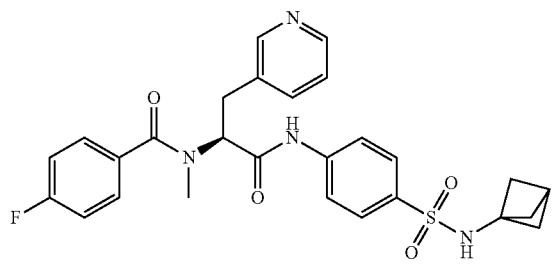
I-93
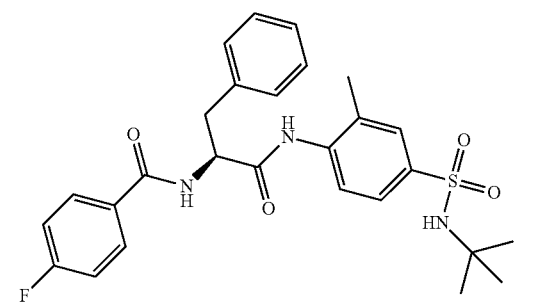
I-94
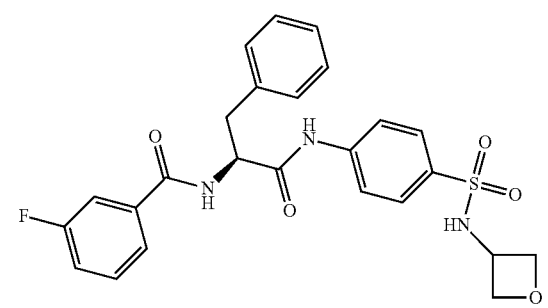
I-95
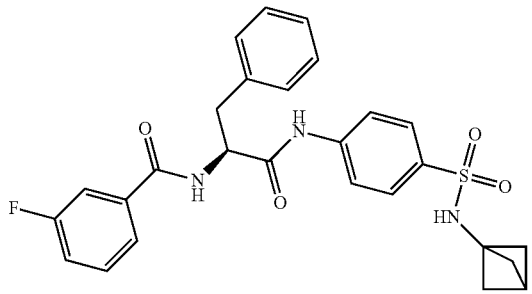
I-96
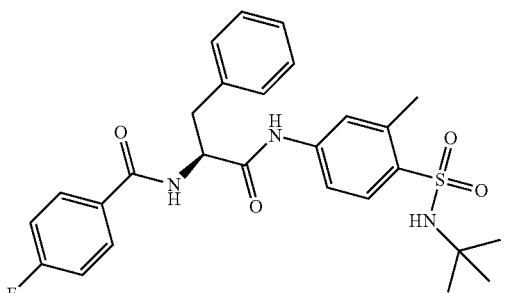
I-97
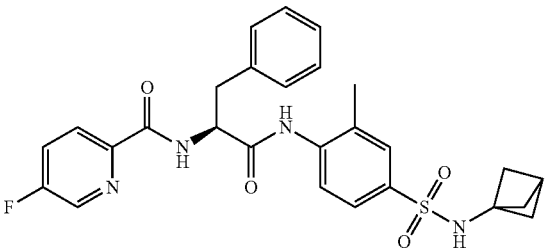
I-98
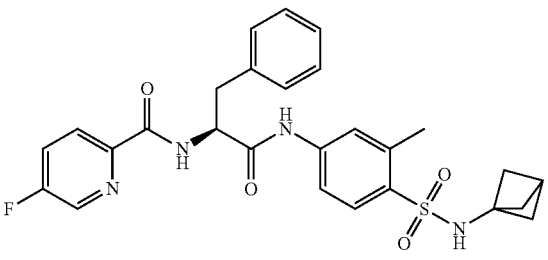
I-99
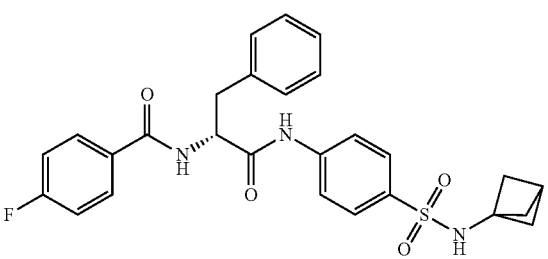

I-100
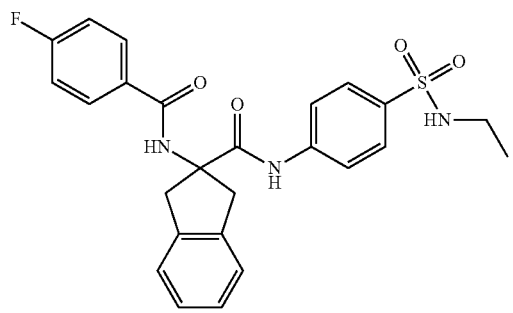
I-101
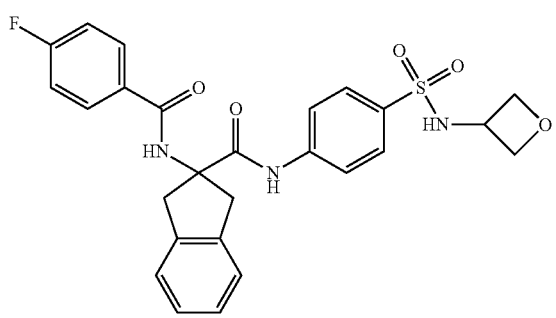
I-102
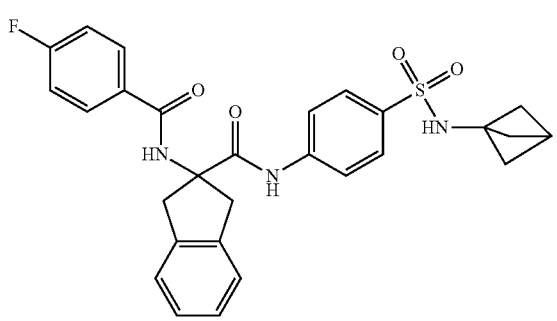
I-103
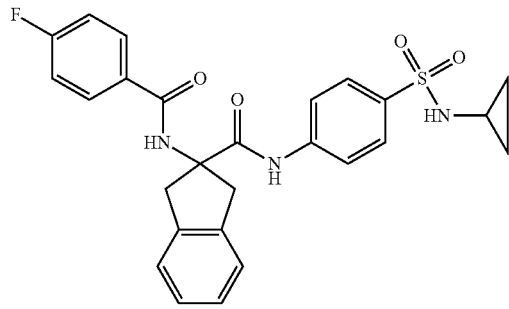
I-104
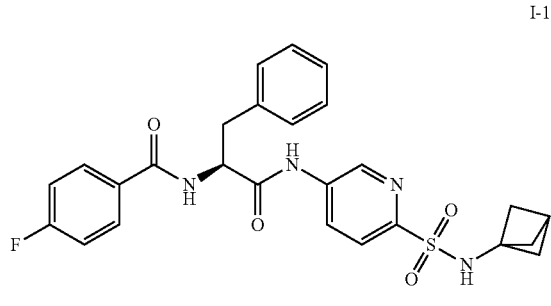
I-105
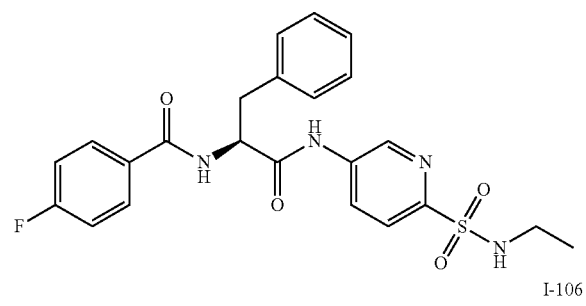
I-106
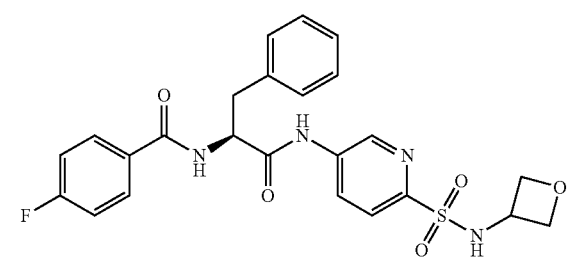
I-107
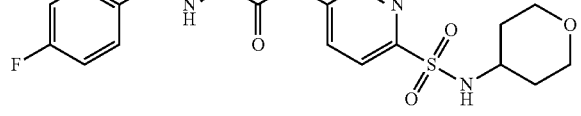
I-108
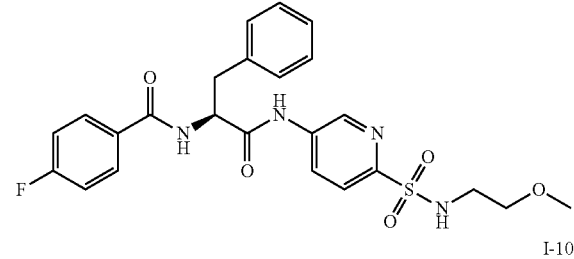
I-109
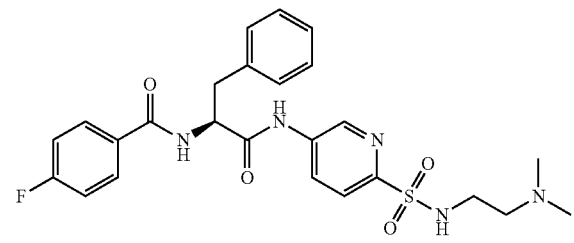
I-110
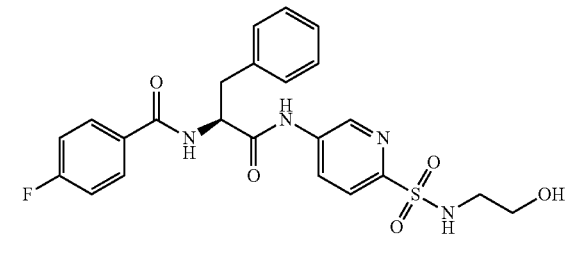

569
-continued
I-111
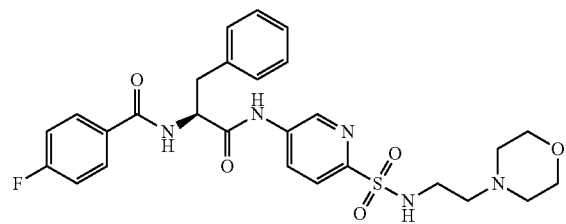
I-112
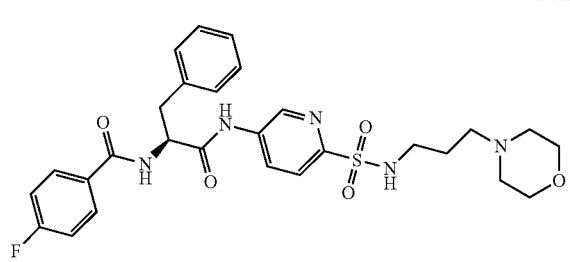
I-113
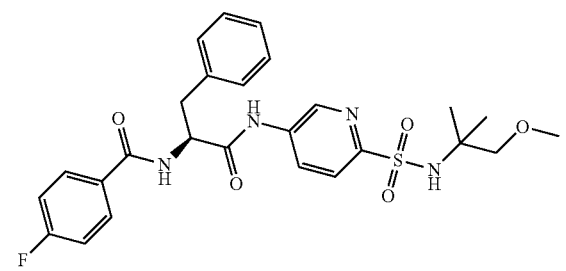
I-114
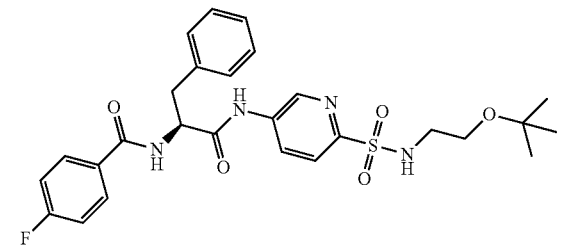
I-115
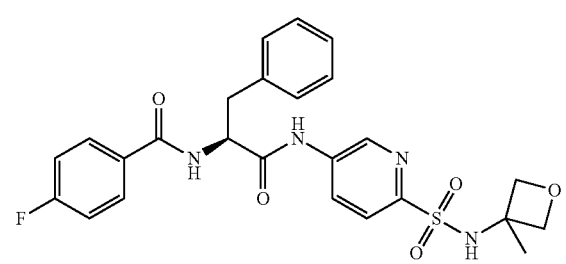
570
-continued
I-116
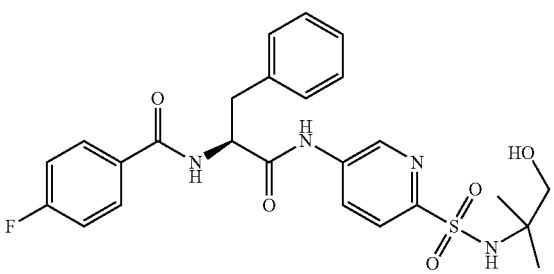
I-117
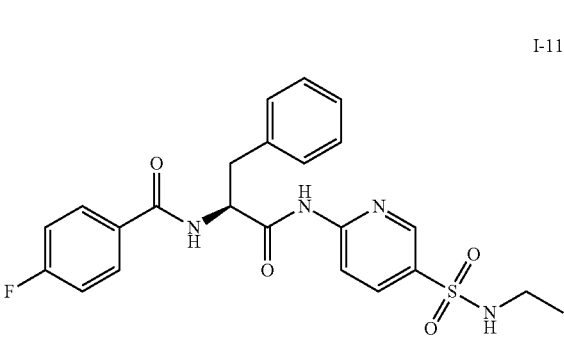
I-118
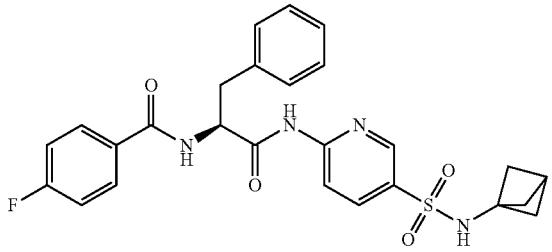
I-119
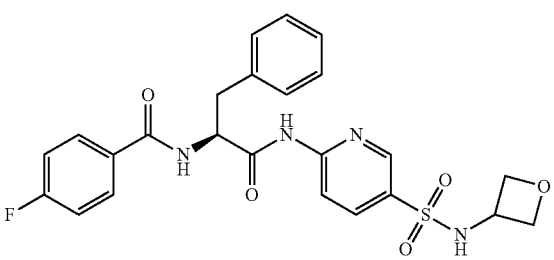
I-120
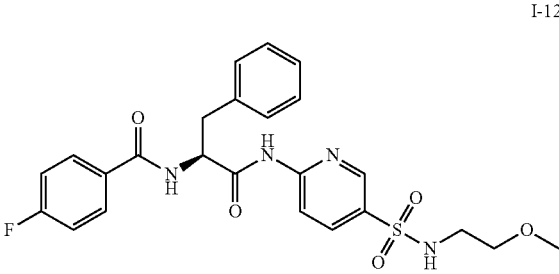

I-121
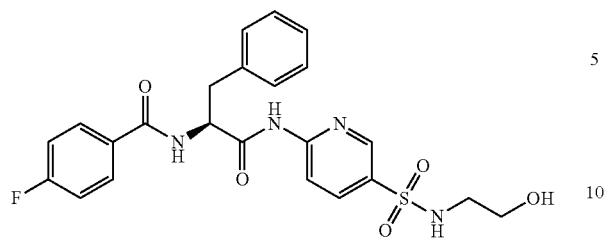
I-122
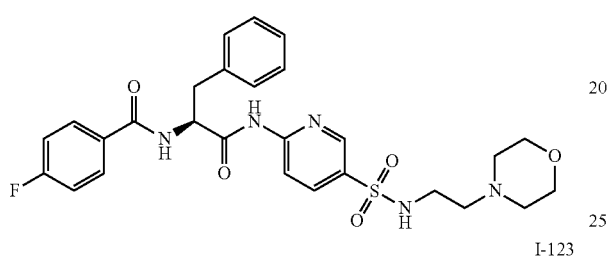
I-123
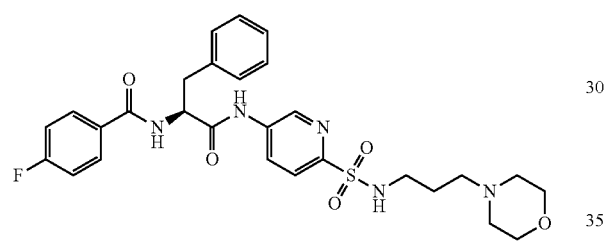
I-124
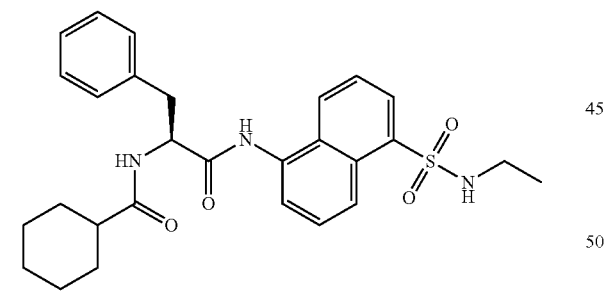
I-125
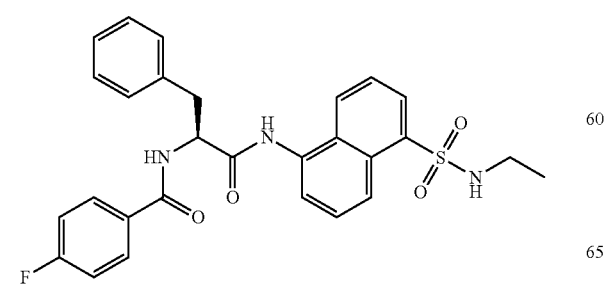
I-126
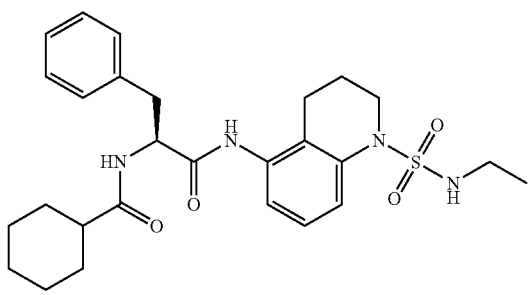
I-127
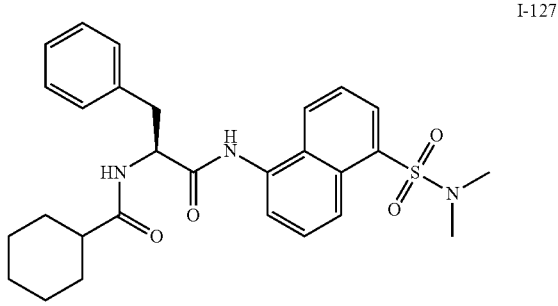
I-128
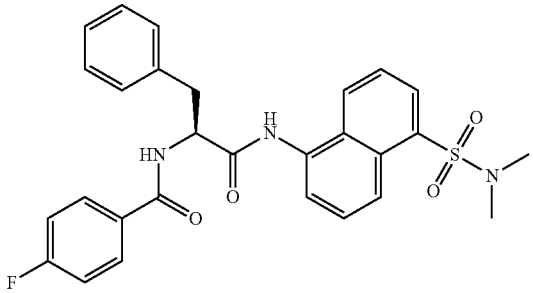
I-129
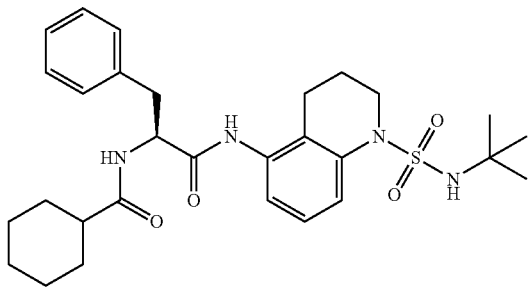
I-130
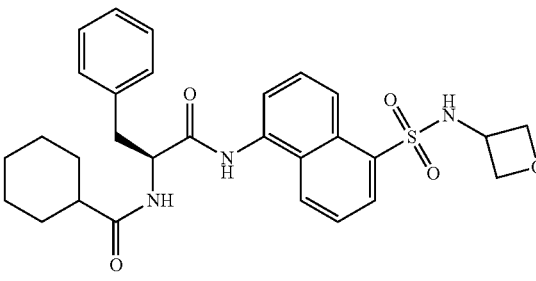

573
-continued
I-131
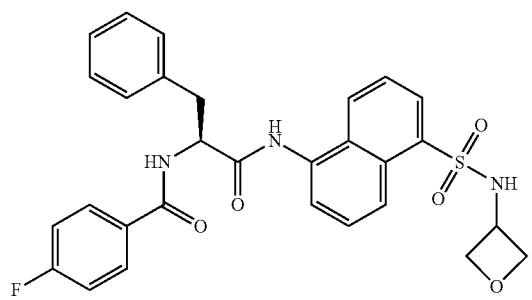
I-132
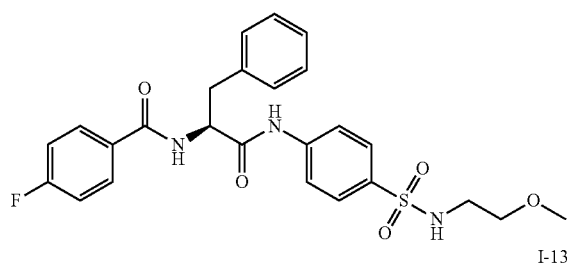
I-133
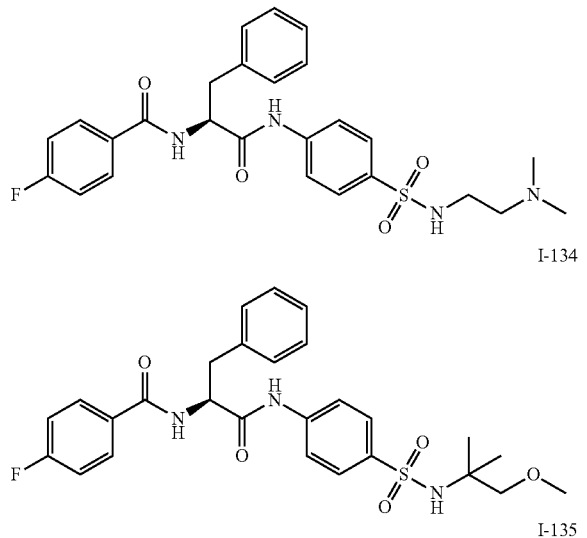
I-134
I-135
I-136
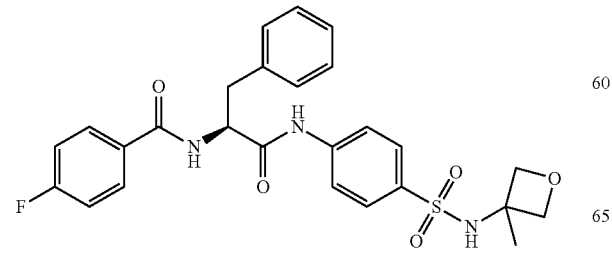
574
-continued
I-137
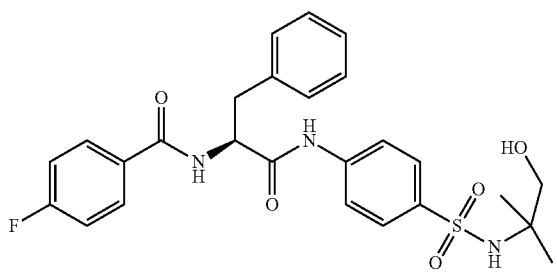
I-138
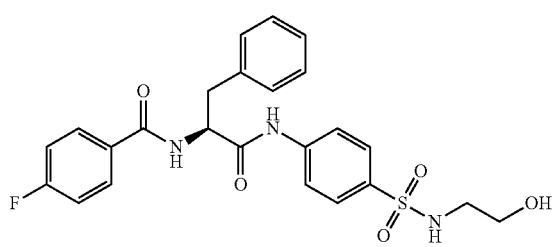
I-139
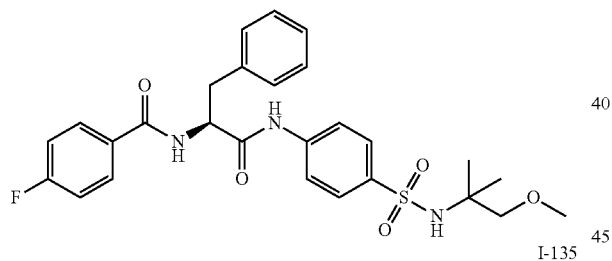
I-140
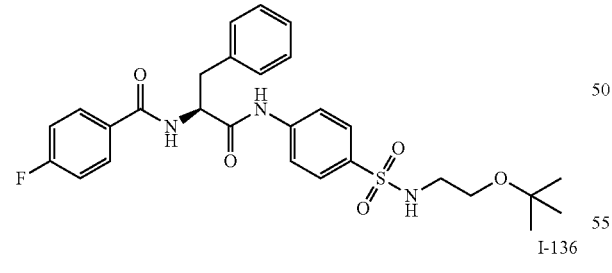
I-141
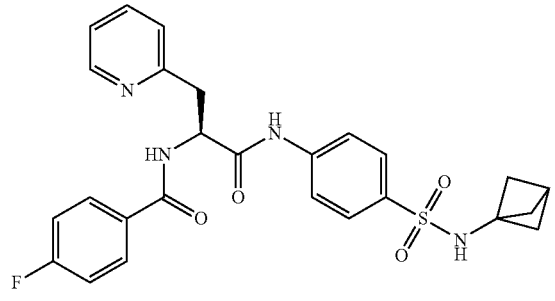

I-142
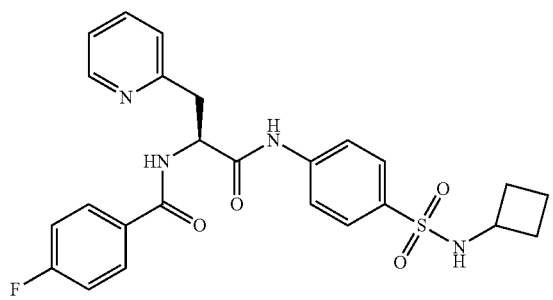
I-143
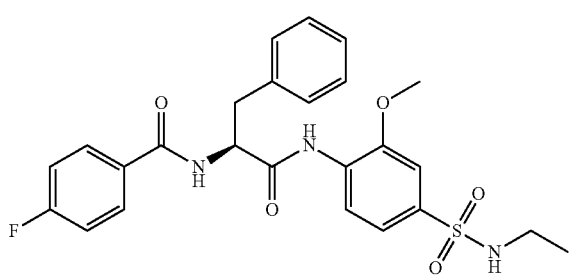
I-144
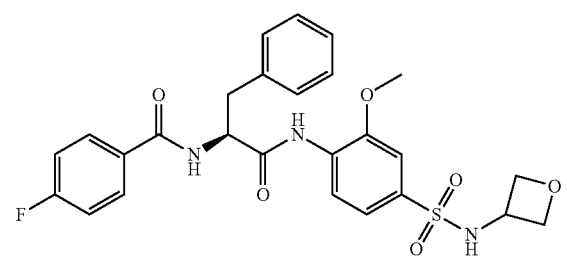
I-145
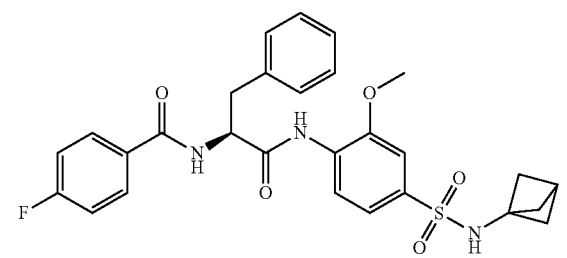
I-146
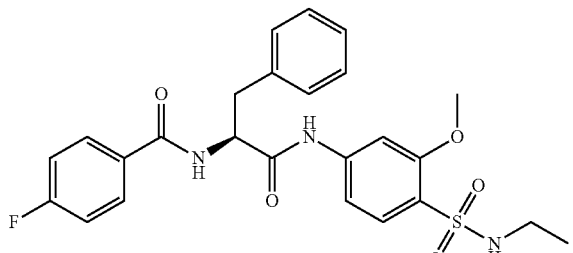
I-147
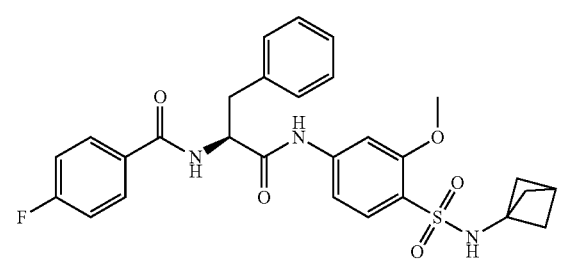
I-148
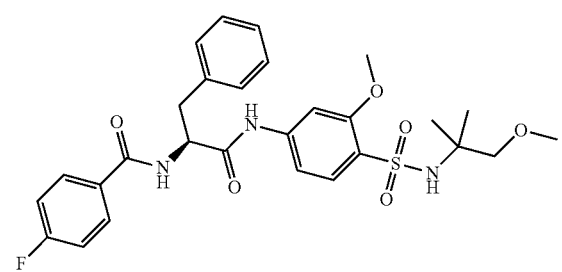
I-149
I-150
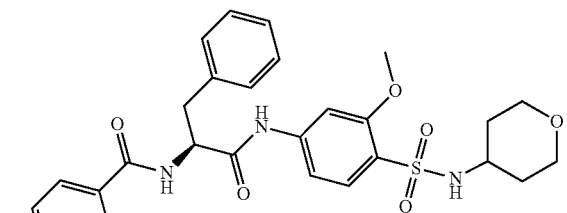
I-151

577
-continued
I-152
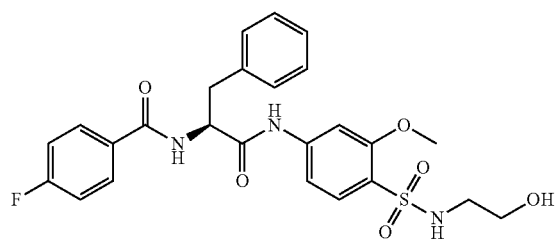
I-153
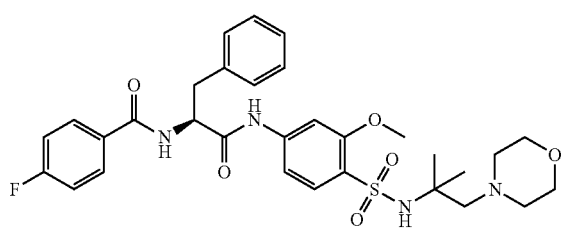
I-154
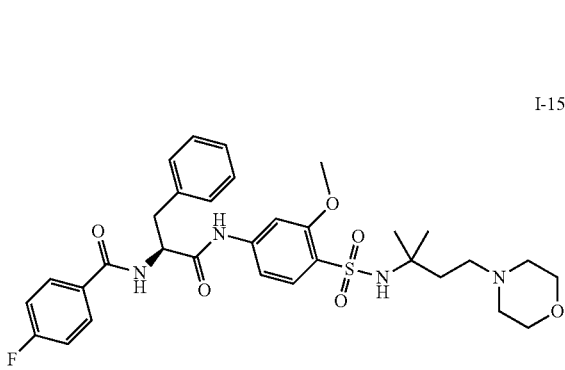
I-155
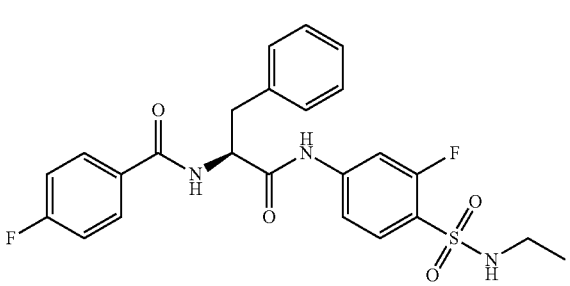
I-156
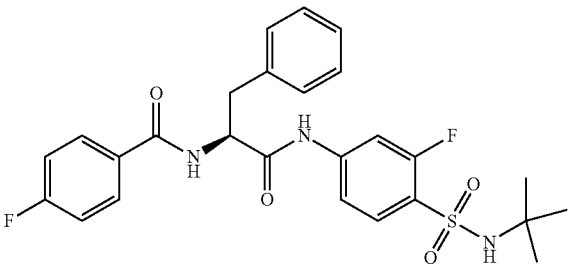
578
-continued
I-157
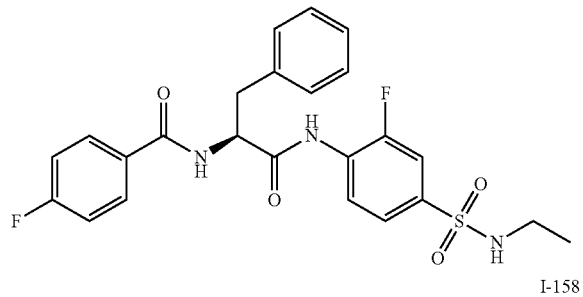
I-158
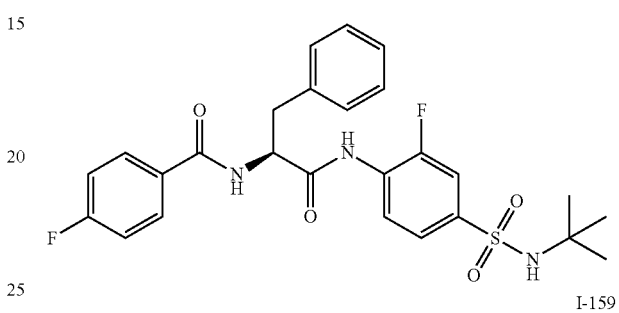
I-159
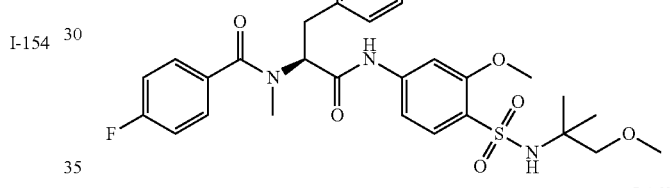
I-160
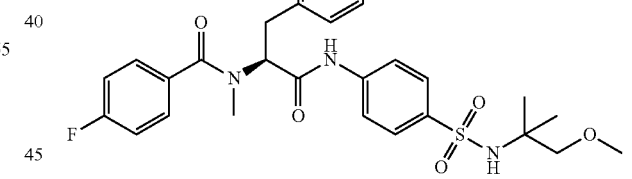
I-161
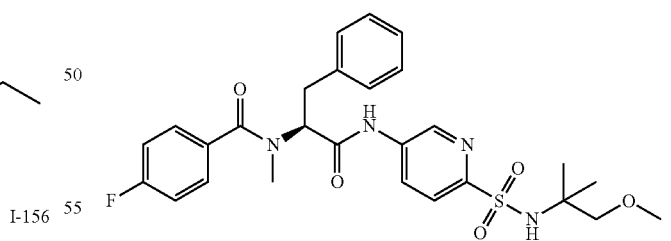
I-162
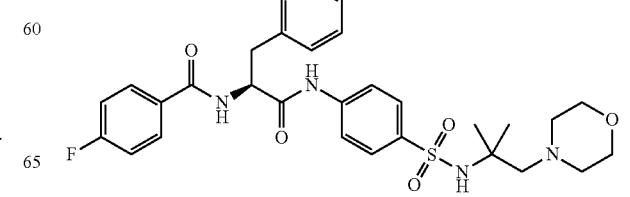

I-163
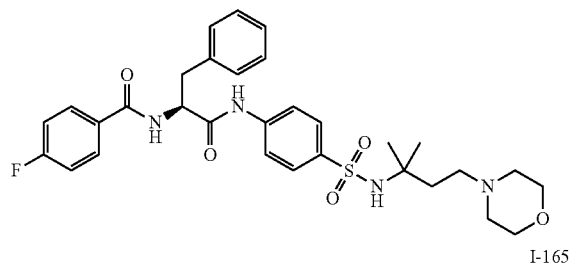
I-170
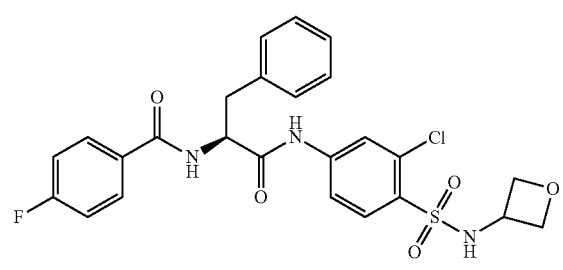
I-165
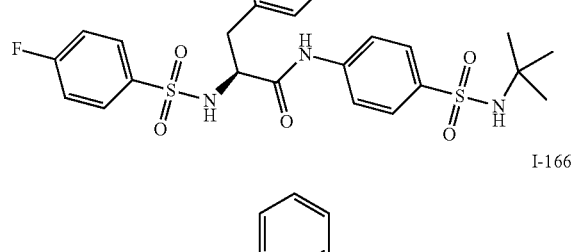
I-171
I-166
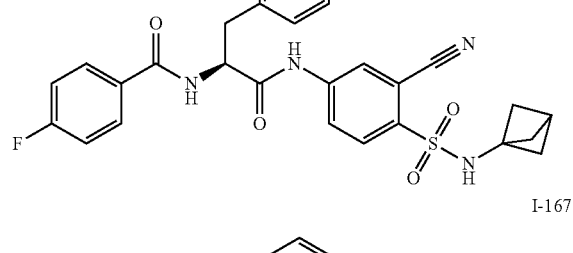
I-172
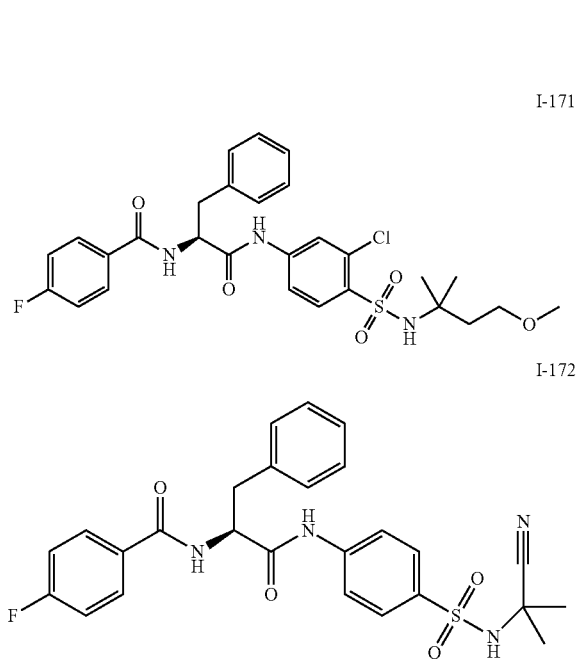
I-167
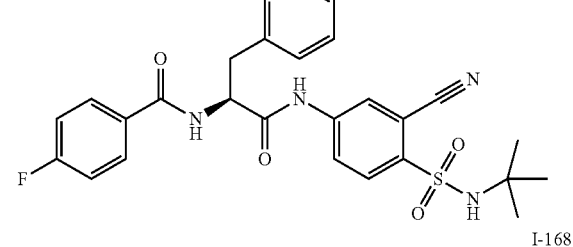
I-168
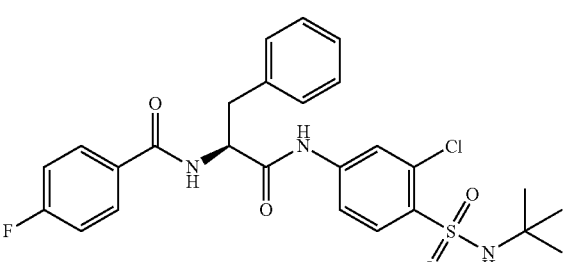
I-173
I-169
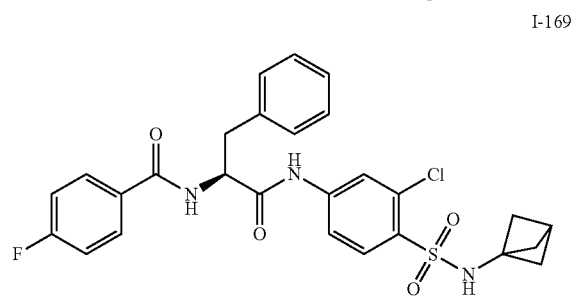
I-174
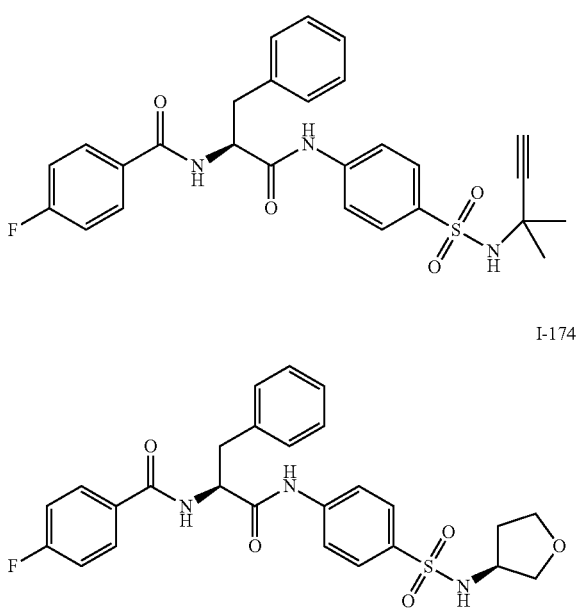

I-175
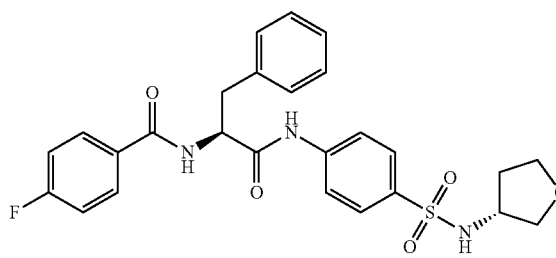
I-176
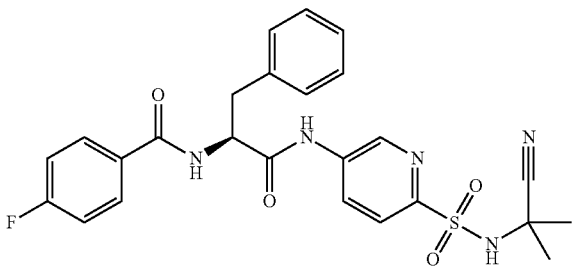
I-177
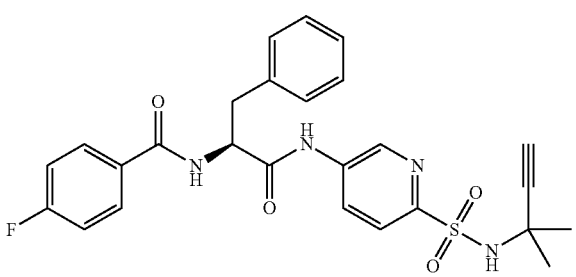
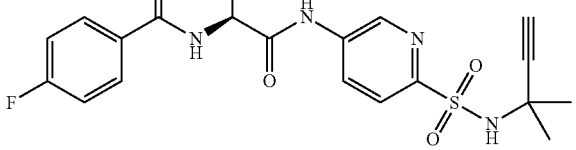
I-178
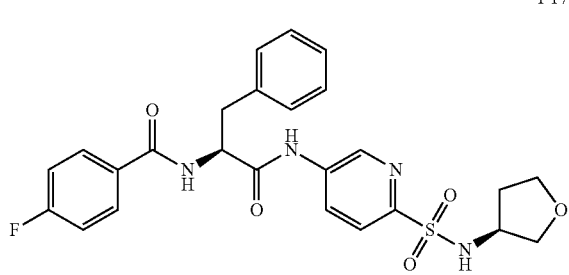
I-179
I-180
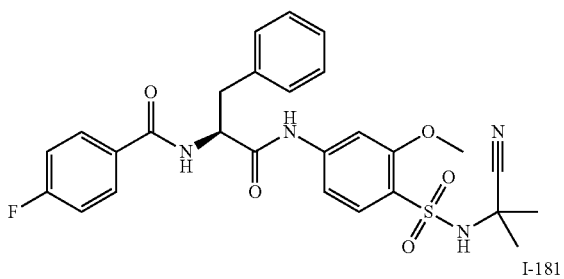
I-181
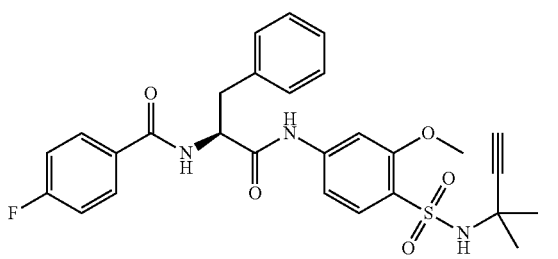
I-182
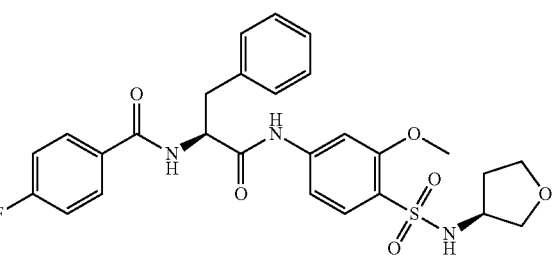
I-183
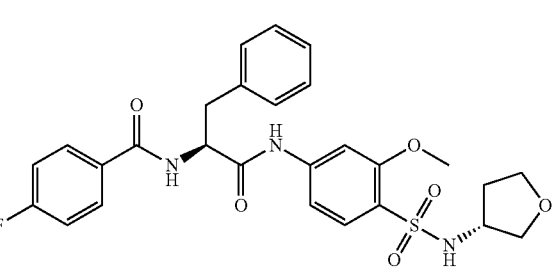
or a pharmaceutically acceptable salt thereof.
21. The compound of claim 20, wherein the compound is
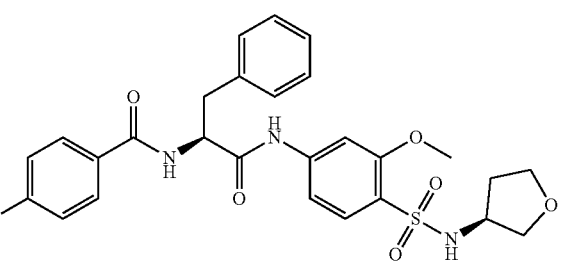
or a pharmaceutically acceptable salt thereof.
* * * * *